(12) United States Patent
Ranganath Rao et al.

(10) Patent No.: US 9,278,915 B2
(45) Date of Patent: Mar. 8, 2016

(54) AGONISTS OF GPR40

(75) Inventors: Jagannath Madanahalli Ranganath Rao, Bangalore (IN); Nagarajan Arumugam, Bangalore (IN); Mohd Mudabbir Ansari, Akola (IN); Chandrasekhar Gudla, Pradesh (IN); Shanmugam Pachiyappan, Cheyyar (IN); Manivannan Ramalingam, Nadu Salem (IN); Jenson George, Ernakulam (IN); George Fernanda Arul, Trichy (IN); Kenchegowda Bommegowda, Y, Mandya (IN); Sathesh Kumar Angupillai, Tamil Nadu (IN); Ramamoorthy Kottamalai, Tamil Nadu (IN); Pradeep Jidugu, Guntur (IN); Shivanageshwara Rao, D, Guntur (IN)

(73) Assignee: CONNEXIOS LIFE SCIENCES PVT LTD, Bangalore (IN)

( * ) Notice: Subject to any disclaimer, the term of this patent is extended or adjusted under 35 U.S.C. 154(b) by 116 days.

(21) Appl. No.: 13/811,825

(22) PCT Filed: Jul. 20, 2011

(86) PCT No.: PCT/IN2011/000479
§ 371 (c)(1),
(2), (4) Date: Jun. 3, 2013

(87) PCT Pub. No.: WO2012/011125
PCT Pub. Date: Jan. 26, 2012

(65) Prior Publication Data
US 2013/0237571 A1  Sep. 12, 2013

Related U.S. Application Data

(60) Provisional application No. 61/389,508, filed on Oct. 4, 2010.

(30) Foreign Application Priority Data

Jul. 23, 2010   (IN) .......................... 2110/CHE/2010

(51) Int. Cl.
| | |
|---|---|
| C07C 251/36 | (2006.01) |
| C07C 251/52 | (2006.01) |
| C07C 255/52 | (2006.01) |
| C07C 255/61 | (2006.01) |
| C07C 257/06 | (2006.01) |
| C07C 317/32 | (2006.01) |
| C07C 251/48 | (2006.01) |
| C07C 255/41 | (2006.01) |
| C07D 209/14 | (2006.01) |
| C07D 213/53 | (2006.01) |
| C07D 213/64 | (2006.01) |
| C07D 213/74 | (2006.01) |
| C07D 249/04 | (2006.01) |

(Continued)

(52) U.S. Cl.
CPC ............ *C07C 257/06* (2013.01); *C07C 251/48* (2013.01); *C07C 251/52* (2013.01); *C07C 255/41* (2013.01); *C07C 255/61* (2013.01); *C07C 317/32* (2013.01); *C07D 209/14* (2013.01); *C07D 213/53* (2013.01); *C07D 213/64* (2013.01); *C07D 213/74* (2013.01); *C07D 249/04* (2013.01); *C07D 249/08* (2013.01); *C07D 257/04* (2013.01); *C07D 261/08* (2013.01); *C07D 263/32* (2013.01); *C07D 271/10* (2013.01); *C07D 277/64* (2013.01); *C07D 307/79* (2013.01); *C07D 307/80* (2013.01); *C07D 333/22* (2013.01); *C07D 333/58* (2013.01); *C07D 401/04* (2013.01); *C07D 487/04* (2013.01); *C07F 9/4015* (2013.01); *C07F 9/4056* (2013.01); *C07C 2101/02* (2013.01); *C07C 2101/14* (2013.01)

(58) Field of Classification Search
CPC ............ C07C 2101/16; C07C 2101/14; C07C 251/48; C07C 251/36; C07C 257/06; C07C 251/52; C07C 255/41; C07C 255/61; C07C 317/32; C07D 209/14; C07D 213/53; C07D 213/64; C07D 213/74; C07D 249/04; C07D 249/08; C07D 257/04; C07D 261/08; C07D 263/32; C07D 271/10; C07D 277/64; C07D 307/79; C07D 307/80; C07D 333/22; C07D 333/58; C07D 401/04; C07D 487/04; C07F 9/4056

See application file for complete search history.

(56) References Cited

U.S. PATENT DOCUMENTS

| 5,484,786 A | 1/1996 | Dellaria et al. |
|---|---|---|
| 5,516,795 A | 5/1996 | Dellaria et al. |
| 2007/0276138 A1* | 11/2007 | Brooks et al. .................. 544/174 |

FOREIGN PATENT DOCUMENTS

| EP | 0 280 240 A2 | 8/1988 |
|---|---|---|
| EP | 1176139 A1 * | 1/2002 |

(Continued)

OTHER PUBLICATIONS

International Search Report of PCT/IN2011/000479 dated Dec. 22, 2011.

*Primary Examiner* — Kendra D Carter
(74) *Attorney, Agent, or Firm* — Hauptman Ham, LLP

(57) ABSTRACT

The present invention relates to compounds that have the ability to modulate the activity of GPR40 and are therefore useful in the treatment of GPR40 related disorders. In addition the invention relates to the compounds, methods for their preparation, pharmaceutical compositions containing the compounds and the uses of these compounds in the treatment of certain disorders related to GPR40 activity.

17 Claims, No Drawings

(51) Int. Cl.
*C07D 249/08* (2006.01)
*C07D 257/04* (2006.01)
*C07D 261/08* (2006.01)
*C07D 263/32* (2006.01)
*C07D 271/10* (2006.01)
*C07D 277/64* (2006.01)
*C07D 307/79* (2006.01)
*C07D 333/22* (2006.01)
*C07D 333/58* (2006.01)
*C07D 401/04* (2006.01)
*C07D 487/04* (2006.01)
*C07F 9/40* (2006.01)
*C07D 307/80* (2006.01)

(56) References Cited

FOREIGN PATENT DOCUMENTS

WO 00/01704 A2 1/2000
WO 2009/038204 A1 3/2009

* cited by examiner

AGONISTS OF GPR40

RELATED APPLICATIONS

This application is a 35 U.S.C. 371 national stage entry of PCT/IN2011/00479, entitled "Agonists of GPR40," which was filed on Jul. 20, 2011, and claims priority to Indian Patent Application No. 2110/CHE/2010, which was filed on Jul. 23, 2010, and U.S. Provisional Application No. 61/389,508, which was filed on Oct. 4, 2010.

FIELD OF THE INVENTION

The present invention relates to compounds that have the ability to modulate the activity of GPR40 and are therefore useful in the treatment of GPR40 related disorders. In addition the invention relates to the compounds, methods for their preparation, pharmaceutical compositions containing the compounds and the uses of these compounds in the treatment of certain disorders related to GPR40 activity.

BACKGROUND OF THE INVENTION

The G-protein-coupled receptor GPR40 functions as a receptor for long-chain free fatty acids (FFAs) in the body. As such is implicated in a large number of metabolic conditions in the body. For example it has been alleged that a GPR40 agonist promotes insulin secretion whilst a GPR40 antagonist inhibits insulin secretion and so depending upon the circumstances the agonist and the antagonist may be useful as therapeutic agents for a number of insulin related conditions such as type 2 diabetes, obesity, impaired glucose tolerance, insulin resistance, neurodegenerative diseases and the like.

Diabetes is typically a chronic disease that occurs either when the pancreas does not produce enough insulin or when the body cannot effectively use the insulin it produces to regulate blood glucose levels. Hyperglycaemia, or raised blood sugar, is a common outcome of uncontrolled diabetes and over time leads to adverse physiological changes to those suffering from the disease, especially to the nervous system and the cardiovascular system.

The World Health Organisation (WHO) estimates that more than 220 million people worldwide suffer from diabetes. In 2005, an estimated 1.1 million people died from diabetes (although the actual number is likely to be much larger as this figure does not include people who have died from diabetic complications such as heart disease or kidney failure). Of all diabetes deaths, almost 80% occur in low- and middle-income countries, almost 50% in people under the age of 70 years and approximately 55% in women. The WHO further predicts that diabetes deaths will have doubled between 2005 and 2030 unless urgent preventive steps are taken to curb or reverse this epidemic. Whilst at least a part of the diabetic epidemic can be attributed to genetic factors, the primary driver is the rapid epidemiological transition associated with changes in dietary patterns and decreased physical activity, as evident from the higher prevalence of diabetes in the urban population.

Whilst a healthy diet, regular physical activity, maintaining a normal body weight and avoiding tobacco use can prevent or delay the onset of the disease, there are currently no effective therapeutic strategies for the prophylaxis or treatment of diabetes.

The pathogenesis of type 2 diabetes is characterized by beta cell dysfunction and progressive insulin resistance with compensatory hyperinsulinemia, followed by declining insulin secretion and increasing hyperglycemia. The long-term adaptation of the beta cell mass to rising glucose concentration is achieved mainly by increasing the number of beta cells through hyperplasia and neogenesis (Bonner-Weir S, 2002; Rhodes C J, 2005).

Type 2 diabetes is also characterized by elevated plasma levels of long-chain FFAs, which further impair beta cell insulin secretion. Normally, FFAs provide essential fuel to the beta cell, but become toxic when chronically present at elevated levels. In the endocrine pancreas, short-term exposure of beta cells to dietary fatty acids potentiates glucose-induced insulin release (Haber E P et al., 2003, Yaney G C and Crokey B E, 2003), while long term exposure impairs insulin secretion and induces secretary failures (lipotoxicity; Lee Y et al., 1994, Unger R H, 2002) and beta cell apoptosis (lipoapoptosis; Shimabukuro M et al., 1998, Lupi R et al., 2002).

There is increasing evidence that lipids can also serve as extracellular ligands for a specific class of receptors and thus act as "nutritional sensors" (Nolan C J et al., 2006). The discovery of these receptors suggested that lipids, specifically, free fatty acids (FFAs), can regulate cell function. Recently, free fatty acids (FFAs) have been demonstrated as ligands for orphan G protein-coupled receptors (GPCRs) and have been proposed to play a critical role in physiological glucose homeostasis (Rayasam G V et al., 2007).

GPR40, GPR120, GPR41 and GPR43 exemplify a growing number of GPCRs that have been shown to be activated by free fatty acids (Kotarsky K et al., 2003, Brown A J et al., 2003). GPR40 and GPR120 are activated by medium to long-chain free fatty acids whereas short-chain fatty acids activate GPR41 and GPR43 (Kotarsky K et al., 2003, Nilsson N E et al., 2003, Brown A J et al., 2003).

Each GPR displays a characteristic tissue distribution. GPR40 is preferentially expressed in pancreatic beta cells (Salehi A et al., 2005). The gene encoding GPR40 is located downstream of CD22 on chromosome 19q13.1 (Sawzdargo M et al., 1997) close to a region that has shown linkage to elevated serum triglycerides in families with type 2 diabetes (Elbein S C and Hasstedt S J, 2002). Two polymorphisms, an Arg211His substitution and a rare Asp175Asn mutation have been identified in the GPR40 gene (Haga H et al., 2002). Lately, GPR40 expression was also seen in omental adipose tissue and pancreatic alpha cells (Fodgren E et al., 2007).

It is well established that fatty acids function acutely to maintain basal insulin secretion and to 'prime' the islet β-cells to respond to glucose following a prolonged fasting (Gravena C et al., 2002). Furthermore the finding that activation of the receptor resulted in elevation of intracellular $Ca^{2+}$ via coupling to $G\alpha_{q/11}$, leading to activation of PKC suggested a possible role for GPR40 in insulin secretion (Poitout V 2003, Fujiwara K et al., 2005, Schnell S et al., 2007). Down-regulation of GPR40 expression in the mouse insulinoma cell lines resulted in a decrease in the ability of fatty acids to potentiate insulin secretion (Itoh Y et al., 2003, Shapiro H et al., 2005). GPR40 was shown to play a role not only in fatty acid modulation of insulin secretion, but also in GSIS after high-fat feeding (Kebede M et al., 2008).

To investigate the role of GPR40 on metabolism, several groups have studied the phenotype of GPR40 knock out or GPR40 over-expression in different rodent models. GPR40−/− mice on HFD became as obese as their wild type (WT) counterparts but were protected from obesity-induced hyperinsulinemia, glucose-intolerance, hepatic steatosis, hypertriglyceridemia and increased hepatic glucose output (Steneberg P et al., 2005). Another group investigating the effect of chow diet on GPR40−/− mice showed the lack of loss of acute palmitate stimulated GSIS (50% reduction) in isolated islets. On the other hand, these islets did not show any effect on inhibition of GSIS after 72 hr of exposure to palmitate or oleate, compared to WT (Latour M G et al., 2007). In another study, when GPR40 was specifically over-expressed in pancreatic beta cells, the transgenic mice become glucose intolerant, lost first-phase insulin secretion and finally became diabetic. Beta cell morphology was also affected in these mice (Steneberg P et al., 2005).

Though the above mention observations favour antagonism of GPR40 as a control of diabetes, another set of studies proved the opposite. A comprehensive study with a series of potent and selective agonists for GPR40 showed that these compounds significantly enhanced GSIS in wild type but not in GPR40−/− mice. They also showed lowering of blood glucose in streptozotocin-induced diabetic rats and high fat diet induced obese mice. These compounds didn't seem to mediate the chronic toxic effect of free fatty acids on islets (Tan C P et al., 2008). In another recent report, it has been shown that though GPR40 is required for insulin secretion in response to FFA GPR40−/− mice were not protected from high fat diet induced insulin resistance or hepatic steatosis (Lan H et al., 2008).

As fatty acids potentiate insulin secretion in a glucose-sensitive manner it is conceivable that if the effects of fatty acids on insulin secretion are mediated at least in part through GPR40, a small-molecule GPR40 agonist may act as a glucose-sensitive secretagogue (Briscoe C P et al., 2006).

It has recently been shown that GPR40 is expressed in endocrine cells of the gastrointestinal tract, including cells expressing the incretin hormones GLP-1 and GIP, and that GPR40 mediates FFA-stimulated incretin secretion (Edfalk S et al., 2008, Parker H E et al., 2009).

It is well established that acute exposure to FFAs stimulates insulin secretion, whereas chronic exposure impairs beta-cell function and induces apoptosis. It was observed that oleic acid, action of which was mediated at least in part through GPR40, could protect NIT-1 cells from palmitate-induced lipoapoptosis. Moreover, it was found that oleic acid promoted the activation of extracellular signal-regulated protein kinase-MAPK pathway mainly via GPR40, which increased the expression of early growth response gene-1, leading to the anti-lipoapoptotic effect on NIT-1 cells. It was suggested that GPR40 might be implicated in the control of beta-cell mass plasticity (Zhang Y et al., 2007).

Clinical studies have shown that total body fat mass is related to both bone density and fracture risk and that fat ingestion reduces bone turnover. These effects are at least partially mediated by endocrine mechanisms, but it is possible that lipids might act directly on bone. Receptors known to bind fatty acids were found to be expressed in osteoblastic (GPR120) and osteoclastic (GPR40, 41, 43, 120) cells. A synthetic GPR 40/120 agonist mimicked the inhibitory effects of fatty acids on osteoclastogenesis (Cornish J et al., 2008).

GPR40 was recently identified in neurons throughout the brain. Recent studies show that polyunsaturated fatty acids (PUFA) are capable of improving hippocampal long-term potentiation, learning ability of aged rats, and cognitive function of humans with memory deficits. It is probable that certain PUFA may act, as endogenous ligands, on GPR40 on the neuronal cell surface (Yamashima T, 2008).

In another study involving adult monkeys showed that the GPR40 protein increased significantly in the second week after global cerebral ischemia as compared with the control. This data suggest that GPR40 might have a role in regulating adult hippocampal neurogenesis in primates (Ma D et al., 2007; 2008).

Accordingly compounds that modulate GPR40 are expected to have useful therapeutic properties especially in relation to metabolic conditions such as diabetes, obesity, hyperglycemia, glucose intolerance, insulin resistance, hyperinsulemia, hypercholesteremia, hypertension, hyperlipoproteinemia, hyperlipidemia, hypertriglyceridemia, dyslipedemia, metabolic syndrome X, atherosclerosis, diabetic neuropathy, diabetic retinopathy, and hypoglycemia, Compounds of this type may also be useful in the treatment of cognitive disorders, osteoporosis, inflammatory disorders, cardiovascular disease, kidney disease, ketoacidosis, thrombotic disorders, nephropathy, sexual dysfunction, dermatopathy, dyspepsia, cancer and edema. As such there is significant interest in the development of compounds with this mode of action.

OBJECTS OF INVENTION

The principal object of the invention is to provide compounds that are modulators of GPR40 receptor activity. These compounds would be expected to be useful in the treatment of GPR40 related conditions.

A further object is to provide a pharmaceutical composition containing a compound that is a modulator of GPR40 receptor activity and a pharmaceutically acceptable excipient, diluent or carrier.

A further object is to provide a method of prevention or treatment of a condition associated with GPR40 receptor function in a mammal.

SUMMARY OF INVENTION

The present invention provides compounds of formula (I):

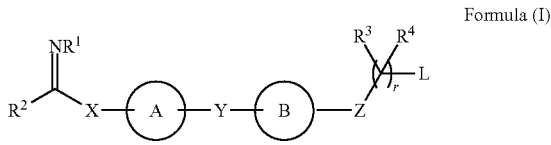

Formula (I)

wherein:
ring A is selected from the group consisting of optionally substituted $C_3$-$C_{12}$cycloalkyl, optionally substituted $C_2$-$C_{12}$heterocycloalkyl, an optionally substituted $C_6$-$C_{10}$arylfused$C_3$-$C_6$cycloalkyl, an optionally substituted $C_1$-$C_{18}$heteroarylfused$C_3$-$C_6$cycloalkyl, optionally substituted $C_6$-$C_{10}$arylfused$C_2$-$C_{12}$heterocycloalkyl, optionally substituted $C_1$-$C_{18}$heteroarylfused $C_2$-$C_{12}$heterocycloalkyl, optionally substituted $C_6$-$C_{18}$aryl and optionally substituted $C_1$-$C_{18}$heteroaryl;

ring B is an optionally substituted $C_6$-$C_{18}$aryl group, optionally substituted $C_6$-$C_{10}$arylfused$C_2$-$C_{12}$heterocycloalkyl or an optionally substituted $C_1$-$C_{18}$heteroaryl group;

X is a bond or a linking moiety containing from 1 to 8 atoms in the normal chain;

Y is a bond or a linking moiety containing from 1 to 8 atoms in the normal chain;

Z is a bond or is selected from the group consisting of optionally substituted $C_6$-$C_{18}$aryl, and optionally substituted $C_1$-$C_{18}$heteroaryl, —C(=O)—, —C(=NR$^1$)—, —(CR$^5$R$^6$)—, —(CR$^5$R$^6$)O—, —(CR$^5$R$^6$)S—, —(CR$^5$R$^6$)NR'— or is a heteroatomic group selected from the group consisting of S, O, P and NR" where R" is selected from the group consisting of H, optionally substituted $C_1$-$C_{12}$alkyl, optionally substituted $C_2$-$C_{10}$heteroalkyl, optionally substituted $C_3$-$C_{12}$cycloalkyl, optionally substituted $C_6$-$C_{18}$aryl, and optionally substituted $C_1$-$C_{18}$heteroaryl;

L is a group capable of releasing a cation or a salt thereof;

$R^1$ is selected from the group consisting of H, $OR^7$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_1$-$C_{12}$alkyloxy, optionally substituted $C_1$-$C_{12}$haloalkyloxy, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl, $R^2$ is H or a ring selected from the group consisting of an optionally substituted $C_3$-$C_{12}$cycloalkyl, optionally substituted $C_2$-$C_{12}$heterocycloalkyl, an optionally substituted $C_6$-$C_{10}$arylfused$C_3$-$C_6$cycloalkyl, an optionally substituted $C_1$-$C_{18}$heteroarylfused$C_3$-$C_6$cycloalkyl, optionally substituted $C_6$-$C_{10}$arylfused$C_2$-$C_{12}$heterocycloalkyl, optionally substituted $C_1$-$C_{18}$heteroarylfused $C_2$-$C_{12}$heterocycloalkyl, optionally substituted $C_6$-$C_{18}$aryl and optionally substituted $C_1$-$C_{18}$heteroaryl;

each $R^3$, $R^4$, $R^5$ and $R^6$ is independently selected from the group consisting of H, halogen, CN, —$NO_2$, SH, $CF_3$, OH, $CO_2H$, $CONH_2$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_1$-$C_{12}$alkyloxy, optionally substituted $C_1$-$C_{12}$haloalkyloxy, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$ heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl, or any two of $R^3$, $R^4$, $R^5$ and $R^6$ when taken together with the atoms to which they are attached may form an optionally substituted cyclic moiety or a double or triple bond between the atoms to which they are attached;

$R^7$ is selected from the group consisting of H, optionally substituted $C_1$-$C_{12}$alkyl, optionally substituted $C_2$-$C_{12}$alkenyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, and optionally substituted $C_1$-$C_{18}$heteroaryl;

r is an integer selected from the group consisting of 0, 1 and 2;

or a pharmaceutically acceptable salt, N-oxide, or prodrug thereof.

As with any group of structurally related compounds which possess a particular utility, certain embodiments of variables of the compounds of the Formula (I), are particularly useful in their end use application.

The moiety L may be any moiety or group that is capable of releasing a cation or a salt thereof. There are many potential groups of this type as would be apparent to a skilled addressee in the art. In some embodiments L is selected from the group consisting of —$CO_2H$, —$SO_3H$, —$PO_3H$, —$SO_2NH_2$, —$CONHSO_2CH_3$, and tetrazol-5-yl. In some embodiments L is $CO_2H$ or a salt thereof.

In the compounds of the invention r is an integer selected from the group consisting of 0, 1 and 2. In some embodiments r is 0. In some embodiments r is 1. In some embodiments r is 2.

In some embodiments L is $CO_2H$ and r is 1. This provides compounds of formula (II).

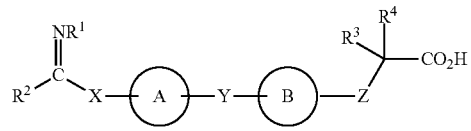

Formula (II)

or a pharmaceutically acceptable salt or prodrug thereof where $R^1$, $R^2$, $R^3$, $R^4$, A, B, X, Y, and Z are as defined above.

In some embodiments each $R^3$ and $R^4$ is independently selected from the group consisting of H, halogen, CN, —$NO_2$, SH, $CF_3$, $OCF_3CH_3$, and $CH_2CH_3$. In some embodiments $R^3$ and $R^4$ are H.

In some embodiments Z is —C(=O)—. In some embodiments Z is —C(=$NR^1$)—. In some embodiments Z is —($CR^5R^5$)—. In some embodiments Z is —($CR^5R^6$)— where $R^5$ is H such that Z is $CHR^6$.

In some embodiments each $R^5$ and $R^6$ is independently selected from the group consisting of H, halogen, CN, —$NO_2$, SH, $CF_3$, $OCF_3CH_3$, and $CH_2CH_3$. In some embodiments each $R^5$ is H and $R^6$ is cyano.

In some embodiments $R^5$ or $R^6$ when taken together with one of $R^3$ and $R^4$ and the atoms to which they are attached forms a cyclic moiety. In some embodiments the cyclic moiety is a cyclopropyl group.

In some embodiments L is $CO_2H$, r is 1, Z is —($CR^5R^6$)— and each of $R^3$, $R^4$ and $R^5$ is H. This provides compounds of formula (III).

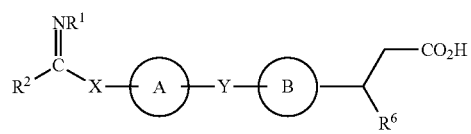

Formula (III)

or a pharmaceutically acceptable salt or prodrug thereof where $R^1$, $R^2$, $R^6$, A, B, X, and Y are as defined above.

In some embodiments L is $CO_2H$, r is 1, Z is —($CR^5R^6$)— and each of $R^3$, $R^4$, $R^5$ and $R^6$ is H. This provides compounds of formula (IIIa).

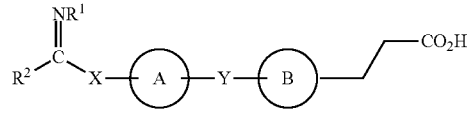

Formula (IIIa)

or a pharmaceutically acceptable salt or prodrug thereof where $R^1$, $R^2$, A, B, X, and Y are as defined above.

In some embodiments ring A and ring B are independently selected from the group consisting of optionally substituted $C_6$-$C_{18}$aryl and optionally substituted $C_1$-$C_{18}$ heteroaryl and may be monocyclic, bicyclic or polycyclic moieties. In certain embodiments each of A and B is a monocyclic or bicyclic moiety. In certain embodiments each of A and B are a monocyclic moiety.

In certain embodiments ring B is selected from the group consisting of:

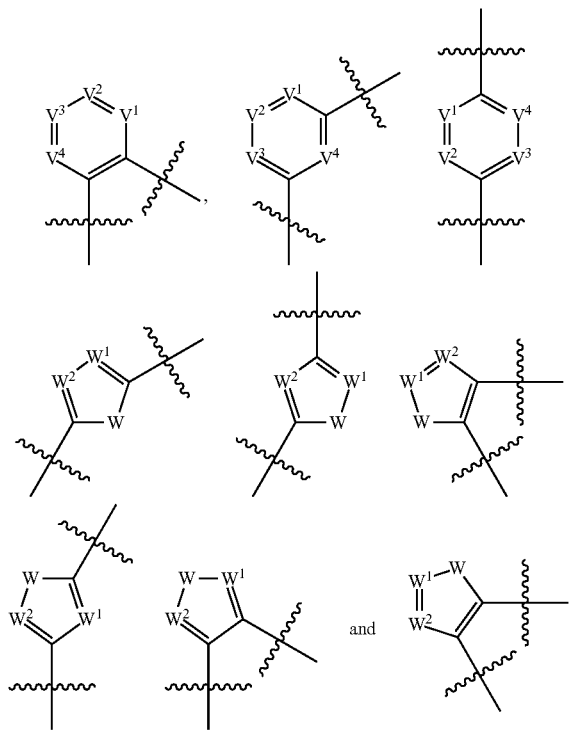

wherein $V^1$, $V^2$, $V^3$ and $V^4$ are each independently selected from the group consisting of N, and $C(R^8)$;

W is selected from the group consisting of O, S and $NR^8$;

$W^1$ and $W^2$ are each independently selected from the group consisting of N and $CR^8$;

wherein each $R^8$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^7$, $SO_3H$, $SO_2NR^7R^7$, $SO_2R^{10}$, $SONR^7R^7$, $SOR^7$, $COR^7$, COOH, $COOR^7$, $CONR^7R^7$, $NR^7COR^7$, $NR^7COOR^7$, $NR^7SO_2R^7$, $NR^7CONR^7R^7$, $NR^7R^7$, and acyl.

In some embodiments ring B is an optionally substituted phenyl group. The group may be unsubstituted or may be substituted with one or more optional substituents. A wide variety of optional substituents may be used as defined above. Examples of particularly suitable optional substituents include, but are not limited to OH, F, Br, Cl, methyl, CN, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, phenoxy, hydroxy, methoxy, ethoxy, pyrrol-1-yl, and 3,5-dimethyl-pyrazol-1-yl.

In some embodiments ring B is an optionally substituted phenyl group of the formula IV:

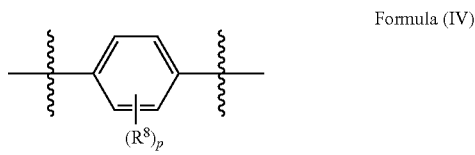

Formula (IV)

each $R^8$ is independently selected from the group consisting of H, halogen, OH, $NH_2$, $NO_2$, CN, $C_1$-$C_{12}$alkyl, $C_1$-$C_{12}$haloalkyl, $C_1$-$C_{12}$alkoxyl, and $C_1$-$C_{12}$haloalkoxyl, wherein p is an integer selected from the group consisting of 0, 1, 2, 3 and 4.

In the compounds of the invention p is an integer selected from the group consisting of 0, 1, 2, 3 and 4. In some embodiments p is 0. In some embodiments p is 1. In some embodiments p is 2. In some embodiments p is 3. In some embodiments p is 4.

$R^8$ may be selected from a wide range of possible substituents as discussed above. In some embodiments each $R^8$ is independently selected from the group consisting of H, halogen, OH, $NO_2$, CN, $C_1$-$C_{12}$alkyl, $C_1$-$C_{12}$haloalkyl, $C_1$-$C_{12}$alkoxyl, and $C_1$-$C_{12}$haloalkoxyl. Exemplary $R^8$ substituents include F, Cl, Br, I, $CH_3$, $CH_2CH_3$, OH, $OCH_3$, $CF_3$, $OCF_3$, $NO_2$, $NH_2$, and CN.

In some embodiments L is $CO_2H$, r is 1, Z is —$(CR^5R^6)$— and each of $R^3$, $R^4$, $R^5$ is H and ring B is an optionally substituted phenyl group of formula (IV). This provides compounds of formula (IVa).

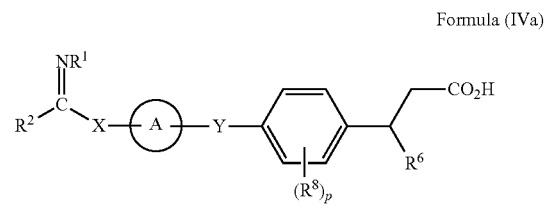

Formula (IVa)

or a pharmaceutically acceptable salt or prodrug thereof where $R^1$, $R^2$, $R^6$, $R^8$, A, p, X, and Y are as defined above.

In some embodiments L is $CO_2H$, r is 1, Z is —$(CR^5R^6)$— and each of $R^3$, $R^4$, $R^5$ and $R^6$ is H and ring B is an optionally substituted phenyl group of formula (IV). This provides compounds of formula (IVb).

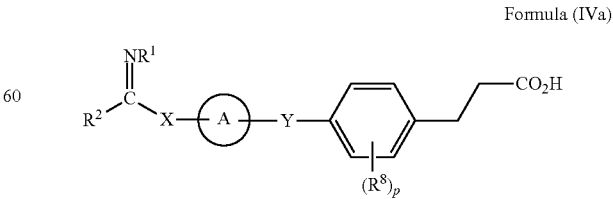

Formula (IVa)

or a pharmaceutically acceptable salt or prodrug thereof where $R^1$, $R^2$, $R^8$, A, p, X, and Y are as defined above.

In certain embodiments ring A is selected from the group consisting of:

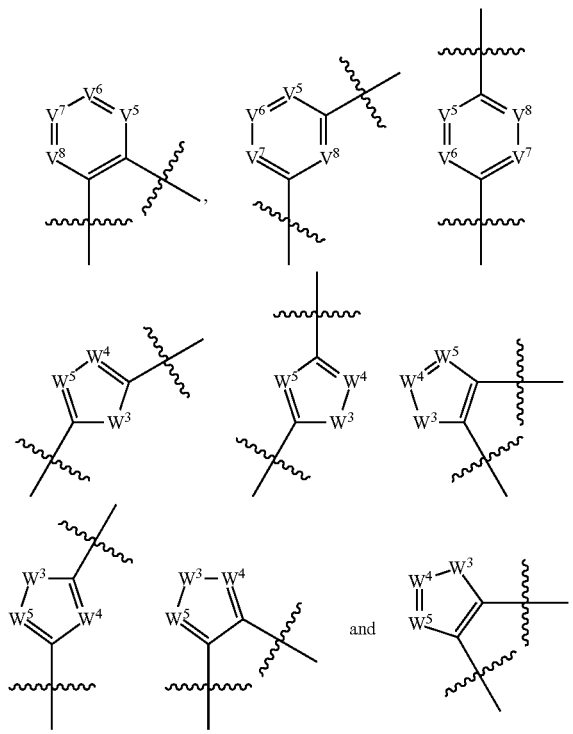

wherein $V^5$, $V^6$, $V^7$ and $V^8$ are each independently selected from the group consisting of N, and $C(R^9)$;

$W^3$ is selected from the group consisting of O, S and $NR^9$;

$W^4$ and $W^5$ are each independently selected from the group consisting of N and $CR^9$;

wherein each $R^9$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_1$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^7$, $SO_3H$, $SO_2NR^7R^7$, $SO_2R^7$, $SONR^7R^7$, $SOR^7$, $COR^7$, COOH, $COOR^7$, $CONR^7R^7$, $NR^7COR^7$, $NR^7COOR^7$, $NR^7SO_2R^7$, $NR^7CONR^7R^7$, $NR^7R^7$, and acyl.

In some embodiments ring A is an optionally substituted phenyl group. The group may be unsubstituted or may be substituted with one or more optional substituents. A wide variety of optional substituents may be used as defined above. Examples of particularly suitable optional substituents include, but are not limited to OH, F, Br, Cl, methyl, CN, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, phenoxy, hydroxy, methoxy, ethoxy, pyrrol-1-yl, and 3,5-dimethyl-pyrazol-1-yl.

In some embodiments ring A is an optionally substituted phenyl group. In some embodiments ring A is an optionally substituted phenyl group selected from the group consisting of formula (Va) and formula (Vb):

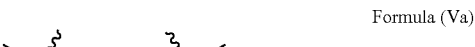

Formula (Va)

Formula (Vb)

wherein each $R^9$ is independently selected from the group consisting of H, halogen, OH, $NH_2$, $NO_2$, CN, $C_1$-$C_{12}$alkyl, $C_1$-$C_{12}$haloalkyl, $C_1$-$C_{12}$alkoxyl, and $C_1$-$C_{12}$haloalkoxyl;

wherein q is an integer selected from the group consisting of 0, 1, 2, 3 and 4.

In certain embodiments ring A is an optionally substituted phenyl group of the formula:

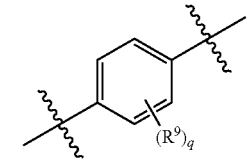

wherein $R^9$ and q are as defined above.

In the compounds of the invention q is an integer selected from the group consisting of 0, 1, 2, 3 and 4. In some embodiments q is 0. In some embodiments q is 1. In some embodiments q is 2. In some embodiments q is 3. In some embodiments q is 4.

$R^9$ may be selected from a wide range of possible substituents as discussed above. In some embodiments each $R^9$ is independently selected from the group consisting of H, halogen, OH, $NO_2$, CN, $C_1$-$C_{12}$alkyl, $C_1$-$C_{12}$haloalkyl, $C_1$-$C_{12}$alkoxyl, and $C_1$-$C_{12}$haloalkoxyl. Exemplary $R^9$ substituents include F, Cl, Br, I, $CH_3$, $CH_2CH_3$, OH, $OCH_3$, $CF_3$, $OCF_3$, $NO_2$, $NH_2$, and CN.

In some embodiments L is $CO_2H$, r is 1, Z is —$(CR^5R^6)$— and each of $R^3$, $R^4$, $R^5$ is H, ring B is an optionally substituted phenyl group of formula (IV) and ring A is an optionally substituted phenyl group of formula (Va). This provides compounds of formula (Vc).

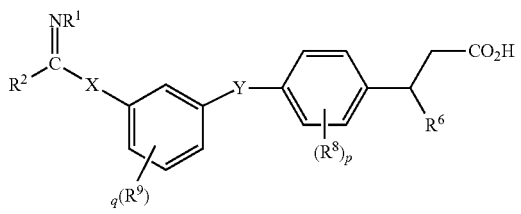

Formula (Vc)

or a pharmaceutically acceptable salt or prodrug thereof where $R^1$, $R^2$, $R^6$, $R^8$, $R^9$, q, p, X, and Y are as defined above.

In some embodiments L is $CO_2H$, r is 1, Z is —$(CR^5R^6)$— and each of $R^3$, $R^4$, $R^5$ and $R^6$ is H, ring B is an optionally substituted phenyl group of formula (IV) and ring A is an optionally substituted phenyl group of formula (Va). This provides compounds of formula (Vd).

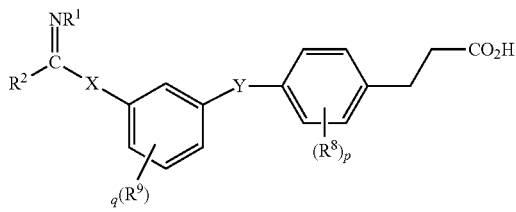

Formula (Vd)

or a pharmaceutically acceptable salt or prodrug thereof where $R^1$, $R^2$, $R^8$, $R^9$, q, p, X, and Y are as defined above.

In some embodiments L is $CO_2H$, r is 1, Z is —$(CR^5R^6)$— and each of $R^3$, $R^4$, $R^5$ is H, ring B is an optionally substituted phenyl group of formula (IV) and ring A is an optionally substituted phenyl group of formula (Vb). This provides compounds of formula (Ve).

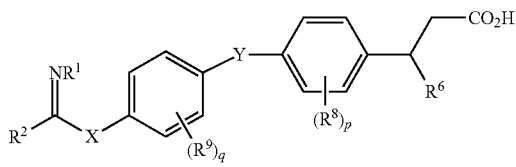

Formula (Ve)

or a pharmaceutically acceptable salt or prodrug thereof where $R^1$, $R^2$, $R^6$, $R^8$, $R^9$, q, p, X, and Y are as defined above.

In some embodiments L is $CO_2H$, r is 1, Z is —$(CR^5R^6)$— and each of $R^3$, $R^4$, $R^5$ and $R^6$ is H, ring B is an optionally substituted phenyl group of formula (IV) and ring A is an optionally substituted phenyl group of formula (Vb). This provides compounds of formula (Vf).

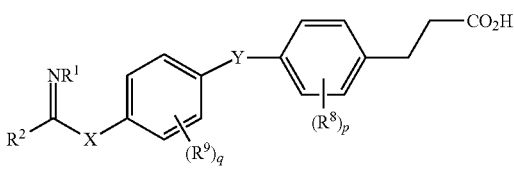

Formula (Vf)

or a pharmaceutically acceptable salt or prodrug thereof where $R^1$, $R^2$, $R^8$, $R^9$, q, p, X, and Y are as defined above.

In the compounds of the invention X and Y are independently chosen such that they are a bond or there are between 1 and 8 atoms in the normal chain.

In some embodiments Y is selected from the group consisting of:
(a) a bond
(b) —O—
(c) —S—
(d) —S(=O)—
(e) —S(=O)$_2$—
(f) —N($R^{10}$)—,
(g) —C($R^{10}$)$_2$—,
(h) —C($R^{10}$)$_2$O—
(i) —C($R^{10}$)$_2$N($R^{10}$)—
(j) —C(=$R^{11}$)
(k) —O$C_{1-5}$alkyl-,
(l) —$C_{1-5}$alkylO—,
(m) —$C_{1-5}$alkylO$C_{1-5}$alkyl,
(n) —N($R^{10}$)$C_{1-5}$alkyl-,
(o) —$C_{1-5}$alkylN($R^{10}$)—;
(p) —$C_{1-5}$alkylN($R^{10}$)$C_{1-5}$alkyl-,
(q) —N($R^{10}$)CO—,
(r) —N($R^{10}$)CO$C_{1-5}$alkyl-,
(s) —$C_{1-5}$alkylN($R^{10}$)CO—,
(t) —$C_{1-5}$alkylN($R^{10}$)CO$C_{1-5}$alkyl-,
(u) —CON($R^{10}$)—,
(v) —$C_{1-5}$alkylCON($R^{10}$)—,
(w) —CON($R^{10}$)$C_{1-5}$alkyl-,
(x) —$C_{1-5}$alkylCON($R^{10}$)$C_{1-5}$alkyl-,
(y) —$SO_2$N($R^{10}$)—
(z) —N($R^{10}$)$SO_2$
(aa) —$C_{1-5}$alkyl-wherein each of the alkyl moieties can be further optionally substituted, wherein $R^{10}$ is selected from the group consisting of H, optionally substituted $C_1$-$C_{12}$alkyl, optionally substituted $C_2$-$C_{10}$heteroalkyl optionally substituted $C_3$-$C_{12}$cycloalkyl, optionally substituted $C_6$-$C_{18}$aryl, and optionally substituted $C_1$-$C_{18}$heteroaryl, or two $R^{10}$ when taken together may form a cyclic moiety;

wherein $R^{11}$ is selected from the group consisting of: O, S, $NR^{12}$ and $C(R^{13}R^{14})$;

wherein each $R^{12}$ is selected from the group consisting of H, $OR^{15}$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_1$-$C_{12}$alkyloxy, optionally substituted $C_1$-$C_{12}$haloalkyloxy, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, and optionally substituted $C_1$-$C_{18}$heteroaryl;

each $R^{13}$ and $R^{14}$ is independently selected from the group consisting of H, halogen, OH, $NO_2$, CN, SH, $NH_2$, $CF_3$, OCF$_3$, optionally substituted C$_1$-C$_{12}$alkyl, optionally substituted C$_1$-C$_{12}$haloalkyl optionally substituted C$_2$-C$_{12}$alkenyl, optionally substituted C$_2$-C$_{12}$alkynyl, optionally substituted C$_2$-C$_{12}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$heterocycloalkenyl, optionally substituted C$_6$-C$_{18}$aryl, optionally substituted C$_1$-C$_{18}$heteroaryl, optionally substituted C$_1$-C$_{12}$alkyloxy, optionally substituted C$_2$-C$_{12}$alkenyloxy, optionally substituted C$_2$-C$_{12}$alkynyloxy, optionally substituted C$_1$-C$_{10}$heteroalkyloxy, optionally substituted C$_3$-C$_{12}$cycloalkyloxy, optionally substituted C$_3$-C$_{12}$cycloalkenyloxy, optionally substituted C$_2$-C$_{12}$heterocycloalkyloxy, optionally substituted C$_2$-C$_{12}$heterocycloalkenyloxy, optionally substituted C$_6$-C$_{18}$aryloxy, optionally substituted C$_1$-C$_1$heteroaryloxy, optionally substituted C$_1$-C$_{12}$alkylamino, SR$^{15}$, SO$_3$H, SO$_2$NR$^{15}$R$^{16}$, SO$_2$R$^{15}$, SONR$^{15}$R$^{16}$, SOR$^{15}$, COR$^{15}$, COOH, COOR$^{16}$, CONR$^{15}$R$^{16}$, NR$^{15}$COR$^{16}$, NR$^{15}$COOR$^{16}$, NR$^{15}$SO$_2$R$^{16}$, NR$^{15}$CONR$^{16}$R$^{17}$, NR$^{15}$R$^{16}$, and acyl;

each R$^{15}$, R$^{16}$ and R$^{17}$ is independently selected from the group consisting of H, optionally substituted C$_1$-C$_{12}$alkyl, optionally substituted C$_2$-C$_{10}$heteroalkyl optionally substituted C$_1$-C$_{12}$haloalkyl, optionally substituted C$_3$-C$_{12}$cycloalkyl, optionally substituted C$_6$-C$_{18}$aryl, and optionally substituted C$_1$-C$_{18}$heteroaryl.

In some embodiments Y is selected from the group consisting of:
(a) —C$_{1-5}$alkylO—,
(b) —C$_{1-5}$alkylN(R$^{10}$)—;
(c) —N(R$^{10}$)—, and
(d) —CON(R$^{10}$)—,
wherein R$^{10}$ is as defined above.

In some embodiments Y is selected from the group consisting of —CH$_2$NH—, —CH$_2$O—, —NH—, —CONH—, —SO$_2$NH—, and —CH$_2$CH$_2$NH—. In some embodiments Y is —CH$_2$NH—. In some embodiments Y is —CH$_2$O—. In some embodiments Y is —NH—. In some embodiments Y is —CONH—. In some embodiments Y is —SO$_2$NH—. In some embodiments Y is —CH$_2$CH$_2$NH—.

In some embodiments Y is selected from —CH$_2$NH— and —CH$_2$O—.

In some embodiments L is CO$_2$H, r is 1, Z is —(CR$^5$R$^6$)— and each of R$^3$, R$^4$, R$^5$ is H, ring B is an optionally substituted phenyl group of formula (IV), ring A is an optionally substituted phenyl group of formula (Va) and Y is —CH$_2$NH—. This provides compounds of formula (VI).

Formula (VI)

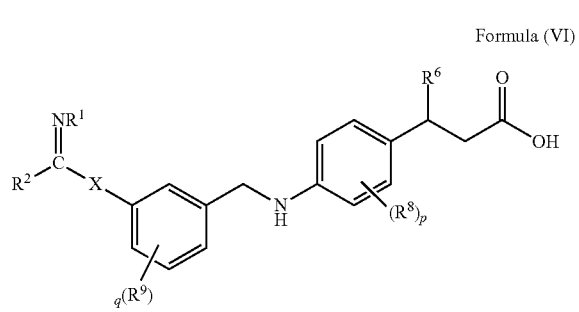

or a pharmaceutically acceptable salt or prodrug thereof where R$^1$, R$^2$, R$^6$, R$^8$, R$^9$, q, p, and X, are as defined above.

In some embodiments L is CO$_2$H, r is 1, Z is —(CR$^5$R$^6$)— and each of R$^3$, R$^4$, R$^5$ and R$^6$ is H, ring B is an optionally substituted phenyl group of formula (IV), ring A is an optionally substituted phenyl group of formula (Va) and Y is —CH$_2$NH—. This provides compounds of formula (VIa).

Formula (VIa)

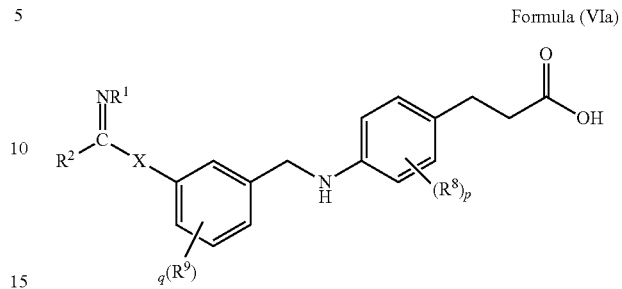

or a pharmaceutically acceptable salt or prodrug thereof where R$^1$, R$^2$, R$^8$, R$^9$, q, p, and X, are as defined above.

In some embodiments L is CO$_2$H, r is 1, Z is —(CR$^5$R$^6$)— and each R$^3$, R$^4$, R$^5$ is H, ring B is an optionally substituted phenyl group of formula (IV), ring A is an optionally substituted phenyl group of formula (Vb) and Y is —CH$_2$NH—. This provides compounds of formula (VIb).

Formula (VIb)

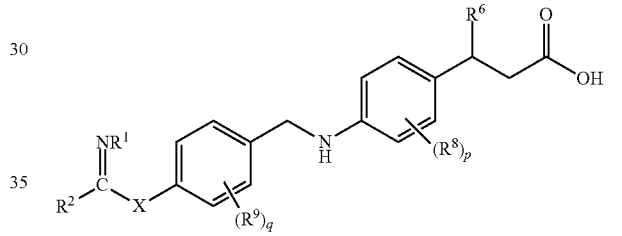

or a pharmaceutically acceptable salt or prodrug thereof where R$^1$, R$^2$, R$^6$, R$^8$, R$^9$, q, p, and X, are as defined above.

In some embodiments L is CO$_2$H, r is 1, Z is —(CR$^5$R$^6$)— and each of R$^3$, R$^4$, R$^5$ and R$^6$ is H, ring B is an optionally substituted phenyl group of formula (IV), ring A is an optionally substituted phenyl group of formula (Vb) and Y is —CH$_2$NH—. This provides compounds of formula (VIc).

Formula (VIc)

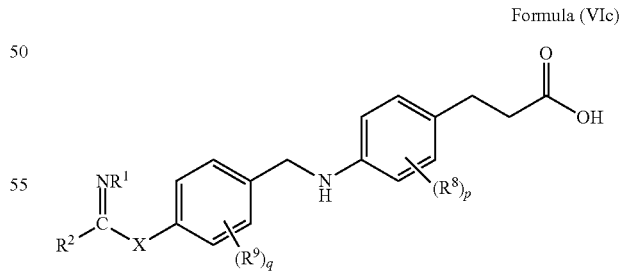

or a pharmaceutically acceptable salt or prodrug thereof where R$^1$, R$^2$, R$^8$, R$^9$, q, p, and X, are as defined above.

In some embodiments L is CO$_2$H, r is 1, Z is —(CR$^5$R$^6$)— and each of R$^3$, R$^4$, R$^5$ is H, ring B is an optionally substituted phenyl group of formula (IV), ring A is an optionally substituted phenyl group of formula (Va) and Y is —CH$_2$O—. This provides compounds of formula (VId).

Formula (VId)

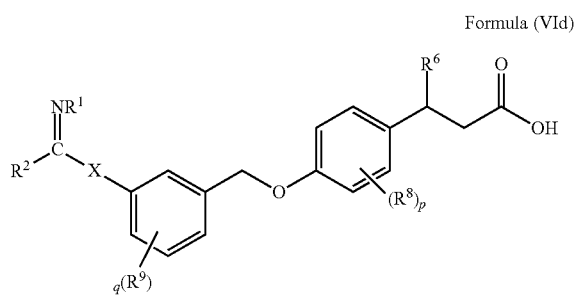

or a pharmaceutically acceptable salt or prodrug thereof where $R^1$, $R^2$, $R^6$, $R^8$, $R^9$, q, p, and X, are as defined above.

In some embodiments L is $CO_2H$, r is 1, Z is —$(CR^5R^6)$— and each of each $R^3$, $R^4$, $R^5$ and $R^6$ is H, ring B is an optionally substituted phenyl group of formula (IV), ring A is an optionally substituted phenyl group of formula (Va) and Y is —$CH_2O$—. This provides compounds of formula (VIe).

Formula (VIe)

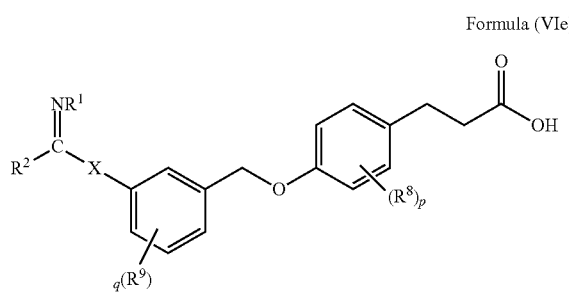

or a pharmaceutically acceptable salt or prodrug thereof where $R^1$, $R^2$, $R^8$, $R^9$, q, p, and X, are as defined above.

In some embodiments L is $CO_2H$, r is 1, Z is —$(CR^5R^6)$— and each of $R^3$, $R^4$, $R^5$ is H, ring B is an optionally substituted phenyl group of formula (IV), ring A is an optionally substituted phenyl group of formula (Vb) and Y is —$CH_2O$—. This provides compounds of formula (VIf).

Formula (VIf)

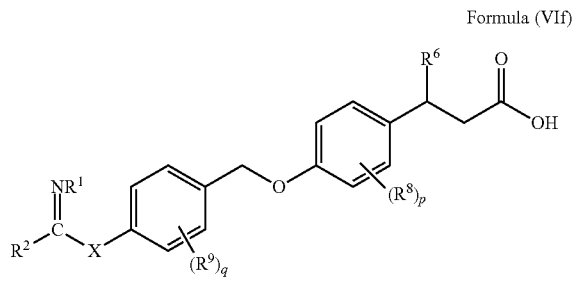

or a pharmaceutically acceptable salt or prodrug thereof where $R^1$, $R^2$, $R^6$, $R^8$, $R^9$, q, p, and X, are as defined above.

In some embodiments L is $CO_2H$, r is 1, Z is —$(CR^5R^6)$— and each of $R^3$, $R^4$, $R^5$ and $R^6$ to is H, ring B is an optionally substituted phenyl group of formula (IV), ring A is an optionally substituted phenyl group of formula (Vb) and Y is —$CH_2O$—. This provides compounds of formula (VIg)

Formula (VIg)

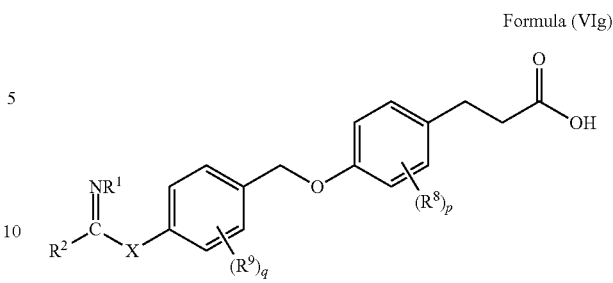

or a pharmaceutically acceptable salt or prodrug thereof where $R^1$, $R^2$, $R^8$, $R^9$, q, p, and X, are as defined above.

In some embodiments X is selected from the group consisting of:
(a) a bond
(b) —O—
(c) —S—
(d) —S(=O)—
(e) —S(=O)$_2$—
(f) —N($R^{18}$)—,
(g) C($R^{18}$)$_2$—
(h) —C(=$R^{19}$)
(i) —O$C_{1-5}$alkyl-,
(j) —$C_{1-5}$alkylO—,
(k) —$C_{1-5}$alkylO$C_{1-5}$alkyl,
(l) —N($R^{18}$)$C_{1-5}$alkyl-,
(m) —$C_{1-5}$alkylN($R^{18}$)—;
(n) —$C_{1-5}$alkylN($R^{18}$)$C_{1-5}$alkyl-,
(o) —N($R^{18}$)CO—,
(p) —N($R^{18}$)CO$C_{1-5}$alkyl-,
(q) —$C_{1-5}$alkylN($R^{18}$)CO—,
(r) —$C_{1-5}$alkylN($R^{18}$)CO$C_{1-5}$alkyl-,
(s) —CON($R^{18}$)—,
(t) —$C_{1-5}$alkylCON($R^{18}$)—,
(u) —CON($R^{18}$)$C_{1-5}$alkyl-,
(v) —$C_{1-5}$alkylCON($R^{18}$)$C_{1-5}$alkyl-,
(w) —$SO_2$N($R^{18}$)—
(x) —N($R^{18}$)$SO_2$
(y) —$C_{1-5}$alkyl-
wherein each of the alkyl moieties can be further optionally substituted,
wherein $R^{18}$ is selected from the group consisting of H, optionally substituted $C_1$-$C_{12}$alkyl, optionally substituted $C_2$-$C_{10}$heteroalkyl optionally substituted $C_3$-$C_{12}$cycloalkyl, optionally substituted $C_6$-$C_{18}$aryl, and optionally substituted $C_1$-$C_{18}$heteroaryl;
wherein $R^{19}$ is selected from the group consisting of: O, S, N$R^{20}$ and C($R^{21}R^{22}$);
wherein each $R^{20}$ is selected from the group consisting of H, O$R^{23}$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_1$-$C_{12}$alkyloxy, optionally substituted $C_1$-$C_{12}$haloalkyloxy, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$ heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl;
each $R^{21}$ and $R^{22}$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_1$heteroaryloxy, optionally substituted $C_1$-$C_{12}$alkylamino, $SR^{24}$, $SO_3H$, $SO_2NR^{24}R^{25}$, $SO_2R^{24}$, $SONR^{24}R^{25}$, $SOR^{24}$, $COR^{24}$, COOH, $COOR^{24}$, $CONR^{24}R^{25}$, $NR^{24}COR^{25}$, $NR^{24}COOR^{25}$, $NR^{24}SO_2R^{25}$, $NR^{24}CONR^{24}R^{25}$, $NR^{24}R^{25}$, and acyl;

each $R^{23}$, $R^{24}$ and $R^{25}$ is independently selected from the group consisting of H, optionally substituted $C_1$-$C_{12}$alkyl, optionally substituted $C_2$-$C_{10}$heteroalkyl optionally substituted $C_3$-$C_{12}$cycloalkyl, optionally substituted $C_6$-$C_{18}$aryl, and optionally substituted $C_1$-$C_{18}$heteroaryl.

In some embodiments X is selected from the group consisting of a bond, O and $CH_2O$. In some embodiments X is a bond. In some embodiments X is O. In some embodiments X is $CH_2O$.

In some embodiments L is $CO_2H$, r is 1, Z is —$(CR^5R^6)$— and each of $R^3$, $R^4$, $R^5$ is H, ring B is an optionally substituted phenyl group of formula (IV), ring A is an optionally substituted phenyl group of formula (Vb), X is $CH_2O$. and Y is —$CH_2O$—. This provides compounds of formula (VIIf)

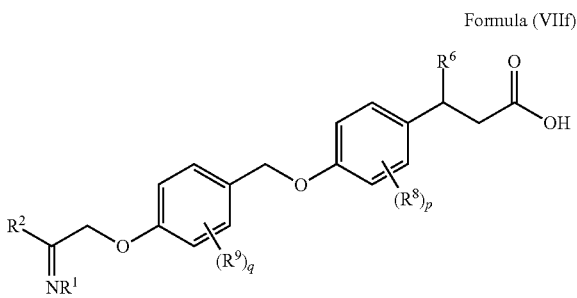

Formula (VIIf)

or a pharmaceutically acceptable salt or prodrug thereof where $R^1$, $R^2$, $R^6$, $R^8$, $R^9$, q, and p are as defined above.

In some embodiments L is $CO_2H$, r is 1, Z is —$(CR^5R^6)$— and each of $R^3$, $R^4$, $R^5$ and $R^6$ is H, ring B is an optionally substituted phenyl group of formula (IV), ring A is an optionally substituted phenyl group of formula (Vb), X is —$CH_2O$— and Y is —$CH_2O$—. This provides compounds of formula (VIIg).

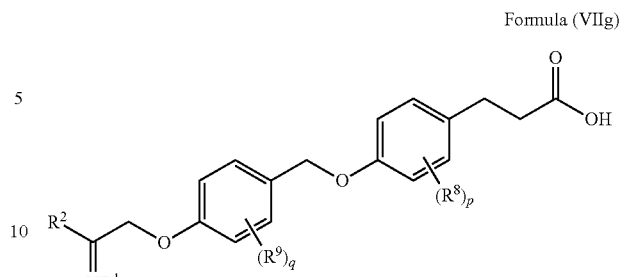

Formula (VIIg)

or a pharmaceutically acceptable salt or prodrug thereof where $R^1$, $R^2$, $R^8$, $R^9$, q, and p, are as defined above.

In some embodiments $R^1$ is $OR^7$. In some embodiments $R^7$ is selected from the group consisting of H, optionally substituted $C_1$-$C_{12}$alkyl, optionally substituted $C_2$-$C_{10}$heteroalkyl and optionally substituted $C_1$-$C_{12}$haloalkyl.

In some embodiments $R^7$ is optionally substituted $C_1$-$C_{12}$alkyl. In some embodiments $R^7$ is selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, hexyl, heptyl, and octyl.

In some embodiments $R^7$ is an optionally substituted $C_2$-$C_{12}$heteroalkyl group. In some embodiments the $C_2$-$C_{12}$heteroalkyl group is selected from the group consisting of hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. Examples of possible values of $R^2$ as $C_2$-$C_{12}$heteroalkyl include hydroxymethyl, hydroxyethyl, hydroxypropyl, hydroxybutyl, hydroxypentyl, methoxymethyl, 2-methoxyethyl, 3-methoxypropyl, 2-ethoxyethyl, 3-ethoxypropyl, aminomethyl, 2-aminoethyl, 3-aminopropyl, 4-aminobutyl, 5 aminopentyl, methylaminomethyl, 2-methylaminoethyl, 3-methylaminopropyl, 4-methylaminobutyl, 5-methylaminopentyl, ethylaminomethyl, 2-ethylaminoethyl, 3-ethylaminopropyl, 4-ethylaminobutyl, 5-ethylaminopentyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl and 5-diethylaminopentyl.

In some embodiments $R^1$ is selected from the group consisting of H, methoxy; difluoromethoxy; trifluoromethyloxy; ethoxy; 2-cyclopropyl-ethoxy; 2,2,2-trifluoro-ethoxy; 2-(N, N-dimethyl amino) ethoxy; isopropoxy; cyclopropyloxy; and 2-propynyloxy.

In some embodiments $R^2$ is H or is selected from the group consisting of optionally substituted $C_6$-$C_{18}$aryl and optionally substituted $C_1$-$C_{18}$heteroaryl.

In some embodiments $R^2$ is an optionally substituted $C_1$-$C_{18}$heteroaryl group. In some embodiments the optionally substituted $C_1$-$C_{18}$heteroaryl group is a monocyclic heteroaryl group. In some embodiments the optionally substituted $C_1$-$C_{18}$heteroaryl group is a bicyclic heteroaryl group.

In some embodiments $R^2$ is an optionally substituted 5-membered heteroaryl ring. Examples of groups of this type include 2-furan; 3-furan; 2-thiophene; 3-thiophene; 1-pyrrole; 2-pyrrole; 3-pyrrole; 2-oxazole; 4-oxazole; 5-oxazole, 2-thiazole; 4-thiazole; 5-thiazole 1-imidazole; 2-imidazole; 4-imidazole; 5-imidazole; 1-pyrazole; 3-pyrazole; 4-pyrazole; 5-pyrazole; 3-isoxazole; 4-isoxazole; 5-isoxazole; 3-isothiazole; 4-isothiazole; 5-isothiazole; 4-(1,2,3-oxadiazole); 5-(1,2,3-oxadiazole); 3-(1,2,4-oxadiazole); 5-(1,2,4- oxadiazole); 1-(1,2,3-triazole); 4-(1,2,3-triazole); 5-(1,2,3-triazole); 1-(1,2,4-triazole); 3-(1,2,4-triazole); 5-(1,2,4-triazole); 3-(1,2,4-thiadiazole); 5-(1,2,4-thiadiazole); 2-(1,3,4-thiadiazole), 1-tetrazole, and 5-tetrazole.

In some embodiments $R^2$ is an optionally substituted $C_6$-$C_{18}$aryl group. In one embodiment $R^2$ is an optionally substituted phenyl group. The substituents may be located at any substitutable position around the aryl ring available for substitution as would be clear to a skilled addressee. Examples of suitable optionally substituted phenyl compounds include, but are not limited to, 2-methoxy-phenyl, 3-methoxy-phenyl, 4-methoxy-phenyl, 2-trifluoromethyl-phenyl, 3-trifluoromethyl-phenyl, 4-trifluoromethyl-phenyl, 2-chloro-phenyl, 3-chloro-phenyl, 4-chloro-phenyl, 4-bromo-phenyl, 2-fluoro-phenyl, 3-fluoro-phenyl, 4-fluoro-phenyl, 4-hydroxy-phenyl, 4-phenyl-phenyl, 4-methyl-phenyl, 2,4-dichloro-phenyl, 3,4-dichloro-phenyl, 2,5-dichloro-phenyl, 2,6-difluoro-phenyl, 2-chloro-6-fluoro-phenyl, 3-fluoro-4-chloro-phenyl, 3-methyl-4-chloro-phenyl, 3-chloro-4-fluoro-phenyl, 3-chloro-4-methyl-phenyl, 2-hydroxy-phenyl, 3-hydroxy-phenyl, 4-hydroxy-phenyl, 4-ethoxy-phenyl, 3-phenoxy-phenyl, 4-phenoxy-phenyl, 2-methyl-phenyl, 3-methyl-phenyl, 4-methyl-phenyl, 4-isopropyl-phenyl, 4-cyano-phenyl, 3,4-dimethyl-phenyl, 2,4-dimethyl-phenyl, 4-t-butyl-phenyl, 2,4-dimethoxy-phenyl, and 3,4-methylenedioxy-phenyl.

In some embodiments $R^2$ is an optionally substituted phenyl group of the formula (IIX):

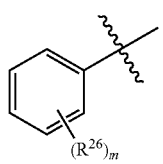

Formula (IIX)

wherein each $R^{26}$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_1$ alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_8$-$C_{18}$aryloxy, optionally substituted $C_1$-$C_{18}$heteroaryloxy, optionally substituted $C_1$-$C_{12}$alkylamino, $SR^7$, $SO_3H$, $SO_2NR^7R^7$, $SO_2R^7$, $SONR^7R^7$, $SOR^7$, $COR^7$, COOH, $COOR^7$, $CONR^7R^7$, $NR^7COR^7$, $NR^7COOR^7$, $NR^7SO_2R^7$, $NR^7CONR^7R^7$, $NR^7R^7$, and acyl; and m is an integer selected from the group consisting of 0, 1, 2, 3, 4 and 5.

In some embodiments L is $CO_2H$, r is 1, Z is —$(CR^5R^6)$— and each of $R^3$, $R^4$, $R^5$ is H, ring B is an optionally substituted phenyl group of formula (IV), ring A is an optionally substituted phenyl group of formula (Vb), X is $CH_2O$—, Y is —$CH_2O$— and $R^2$ is an optionally substituted phenyl group of the formula (IIX): This provides compounds of formula (IIXf).

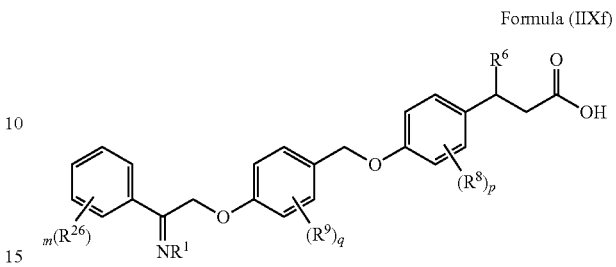

Formula (IIXf)

or a pharmaceutically acceptable salt or prodrug thereof where $R^1$, $R^6$, $R^8$, $R^9$, $R^{26}$, m, q, and p are as defined above.

In some embodiments L is $CO_2H$, r is 1, Z is —$(CR^5R^6)$— and each of $R^3$, $R^4$, $R^5$ and $R^6$ is H, ring B is an optionally substituted phenyl group of formula (IV), ring A is an optionally substituted phenyl group of formula (Vb), X is $CH_2O$—, Y is —$CH_2O$— and $R^2$ is an optionally substituted phenyl group of the formula (IIX): This provides compounds of formula (IIXg).

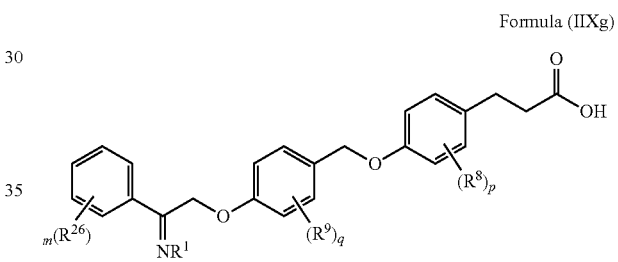

Formula (IIXg)

or a pharmaceutically acceptable salt or prodrug thereof where $R^1$, $R^8$, $R^9$, $R^{26}$, m, q, and p, are as defined above.

As a result of the presence of the Oximino double bond the compounds of the invention may exist as either the E or Z geometrical isomer. In some embodiments the compounds are in the E geometric form. In some embodiments the isomers are in the Z geometric form.

Many if not all of the variables discussed above may be optionally substituted. If the variable is optionally substituted then in some embodiments each optional substituent is independently selected from the group consisting of halogen, =, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)$R^a$, —C(=O)$OR^a$, C(=O)$NR^aR^b$, $C(=NOH)R^a$, $C(=NR^a)NR^bR^c$, $NR^aR^b$, $NR^aC(=O)R^b$, $NR^aC(=O)OR^b$, $NR^aC(=O)NR^bR^c$, $NR^aC(=NR^b)NR^cR^d$, $NR^aSO_2R^b$, —$SR^a$, $SO_2NR^aR^b$, —$OR^a$, $OC(=O)NR^aR^b$, $OC(=O)R^a$ and acyl, wherein $R^a$, $R^b$, $R^c$ and $R^d$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_1$-$C_{10}$ heteroalkyl, $C_3$-$C_{12}$cycloalkyl, $C_3$-$C_{12}$cycloalkenyl, $C_1$-$C_{12}$heterocycloalkyl, $C_1$-$C_{12}$ heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: F, Cl, Br, =O, =S, —CN, —$NO_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —$C(O)OR^a$, COOH, SH, and acyl.

In some embodiments each optional substituent is independently selected from the group consisting of: F, Br, Cl, =O, =S, —CN, methyl, trifluoro-methyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, —$NO_2$, phenoxy, hydroxy, methoxy, trifluoro-methoxy, ethoxy, and methylenedioxy.

Alternatively, two optional substituents on the same moiety when taken together may be joined to form a fused cyclic substituent attached to the moiety that is optionally substituted. Accordingly the term optionally substituted includes a fused ring such as a cycloalkyl ring, a heterocycloalkyl ring, an aryl ring or a heteroaryl ring.

In addition to compounds of formula I, the embodiments disclosed are also directed to pharmaceutically acceptable salts, pharmaceutically acceptable N-oxides, pharmaceutically acceptable prodrugs, and pharmaceutically active metabolites of such compounds, and pharmaceutically acceptable salts of such metabolites.

The invention also relates to pharmaceutical compositions including a compound of the invention and a pharmaceutically acceptable carrier, diluent or excipient.

In a further aspect the present invention provides a method of prevention or treatment of a condition associated with GPR40 receptor function in a mammal, the method comprising administering an effective amount of a compound of the invention.

In yet an even further aspect the invention provides the use of a compound of the invention in the preparation of a medicament for the treatment of a condition associated with GPR40 receptor function.

In yet an even further aspect the invention provides the use of a compound of the invention in the treatment of a condition associated with GPR40 receptor function.

In some embodiments the condition is selected from the group consisting of cognitive disorders, osteoporosis, inflammatory disorders, diabetes, obesity, hyperglycemia, glucose to intolerance, insulin resistance, hyperinsulemia, hypercholesteremia, hypertension, hyperlipoproteinemia, hyperlipidemia, hypertriglyceridemia, dyslipedemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In some embodiments the condition is diabetes. In some embodiments the condition is type II diabetes.

These and other teachings of the invention are set forth herein.

DETAILED DESCRIPTION OF THE INVENTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —$C(=O)$OH, —$C(=O)R^a$, —$C(=O)OR^a$, $C(=O)NR^aR^b$, $C(=NOH)R^a$, $C(=NR^a)NR^bR^c$, $NR^aR^b$, $NR^aC(=O)R^b$, $NR^aC(=O)OR^b$, $NR^aC(=O)NR^bR^c$, $NR^aC(=NR^b)NR^cR^d$, $NR^aSO_2R^b$, —$SR^a$, $SO_2NR^aR^b$, —$OR^aC(=O)NR^aR^b$, $OC(=O)R^a$ and acyl, wherein $R^a$, $R^b$, $R^c$ and $R^d$ are each independently selected from the group consisting of H, optionally substituted $C_1$-$C_{12}$alkyl, optionally substituted $C_1$-$C_{12}$haloalkyl, optionally substituted $C_2$-$C_{12}$alkenyl, optionally substituted $C_2$-$C_{12}$alkynyl, optionally substituted $C_2$-$C_{10}$ heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, $C_2$-$C_{12}$ heterocycloalkenyl, optionally substituted $C_6$-$C_{18}$aryl, optionally substituted $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an R—C(=O)—NH— group in which the R group may be an alkyl, cycloalkyl, heterocycloalkyl, aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. The alkenyl group is preferably a 1-alkenyl group. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are C$_1$-C$_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a C$_1$-C$_{12}$ alkyl, more preferably a C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means an Alkyl-NH— group, in which alkyl is as defined herein. "Dialkylamino" means a (alkyl)$_2$N— group, in which each alkyl may be the same or different and are each as defined herein for alkyl. The alkyl group is preferably a C$_1$-C$_6$alkyl group. The group may be a terminal group or a bridging group. If the group is a terminal group it is bonded to the remainder of the molecule through the nitrogen atom.

"Alkylaminocarbonyl" refers to a group of the formula (Alkyl)$_x$(H)$_y$NC(=O)— in which alkyl is as defined herein, x is 1 or 2, and the sum of X+Y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a C$_1$-C$_6$alkyloxy. Examples include, but are not limited to, methoxy and ethoxy. The group may be a terminal group or a bridging group.

"Alkyloxyalkyl" refers to an alkyloxy-alkyl- group in which the alkyloxy and alkyl moieties are as defined herein. The group may be a terminal group or a bridging group. If the group is a terminal group it is bonded to the remainder of the molecule through the alkyl group.

"Alkyloxyaryl" refers to an alkyloxy-aryl- group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a C$_1$-C$_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl- group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroaryl" refers to an alkyloxy-heteroaryl- group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl- group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a C$_1$-C$_6$ alkyl group. Exemplary alkylsulfinyl groups include, but are not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a C$_1$-C$_6$alkyl group. Examples include, but are not limited to, methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are C$_1$-C$_6$alkynyloxy groups. The group may be a terminal group or a bridging group. If the group is a terminal group it is bonded to the remainder of the molecule through the oxygen atom.

"Aminoalkyl" means an NH$_2$-alkyl- group in which the alkyl group is as defined herein. The group may be a terminal group or a bridging group. If the group is a terminal group it is bonded to the remainder of the molecule through the alkyl group.

"Aminosulfonyl" means an $NH_2—S(=O)_2—$ group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl- group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl- group in which the aryl and alkyl moieties are as defined herein. Preferred arylalkyl groups contain a $C_{1-5}$alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. di-arylamino means a group of formula $(aryl)_2N$— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl- group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-$S(=O)_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl- group in which the cycloalkyl and alkyl moieties are as defined herein. Exemplary monocycloalkylalkyl groups include cyclopropylm ethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl- group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl-group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$ alkyl, optionally substituted $C_3$-$C_{12}$ cycloalkyl, optionally substituted $C_6$-$C_{18}$ aryl, and optionally substituted $C_1$-$C_{18}$ heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to a heteroalkyl-O— group in which heteroalkyl is as defined herein. Preferably the heteroalkyloxy is a $C_2$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl- group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl- group in which the heteroaryl and heteroalkyl moieties are as defined herein. The group may be a terminal group or a bridging group. If the group is a terminal group it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl group as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. A heterocycloalkyl group typically is a $C_2$-$C_{12}$heterocycloalkyl group. The group may be a terminal group or a bridging group.

"Heterocycloalkylalkyl" refers to a heterocycloalkyl-alkyl- group in which the heterocycloalkyl and alkyl moieties are as defined herein. Exemplary heterocycloalkylalkyl groups include (2-tetrahydrofuryl)methyl, (2-tetrahydrothiofuranyl)methyl. The group may be a terminal group or a bridging group. If the group is a terminal group it is bonded to the remainder of the molecule through the alkyl group.

"Heterocycloalkylalkenyl" refers to a heterocycloalkyl-alkenyl- group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl- group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$ Heterocycloalkenyloxy. The group may be a terminal group or a bridging group. If the group is a terminal group it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art. For those compounds where there is the possibility of geometric isomerism the applicant has drawn the isomer that the compound is thought to be although it will be appreciated that the other isomer may be the correct structural assignment.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propanoic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007).

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Specific compounds of the invention include the following:

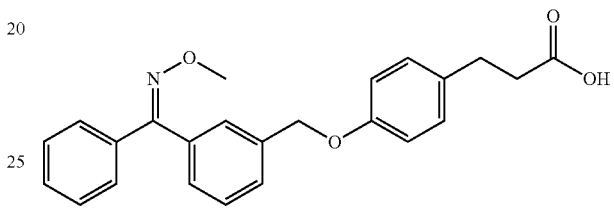

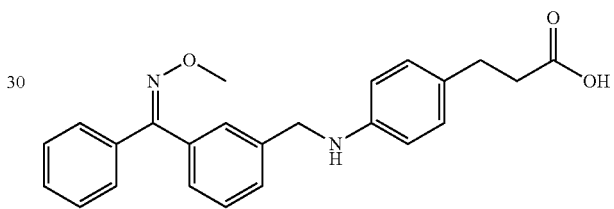

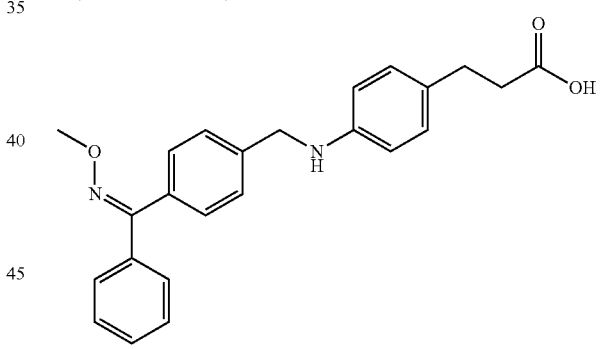

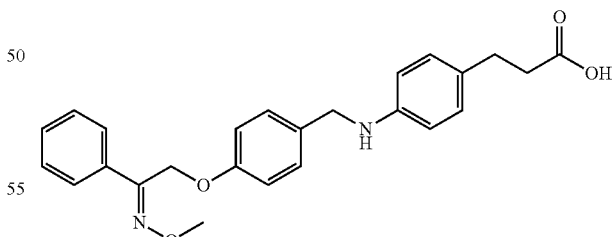

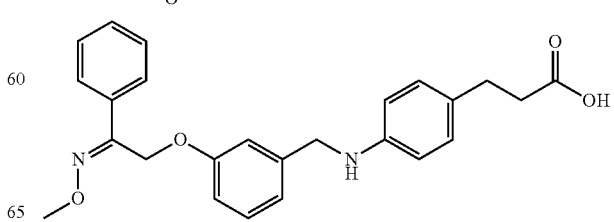

31
-continued
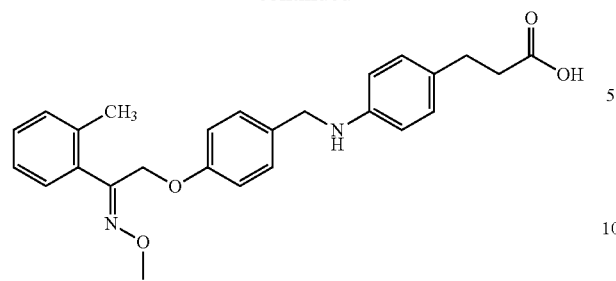
32
-continued
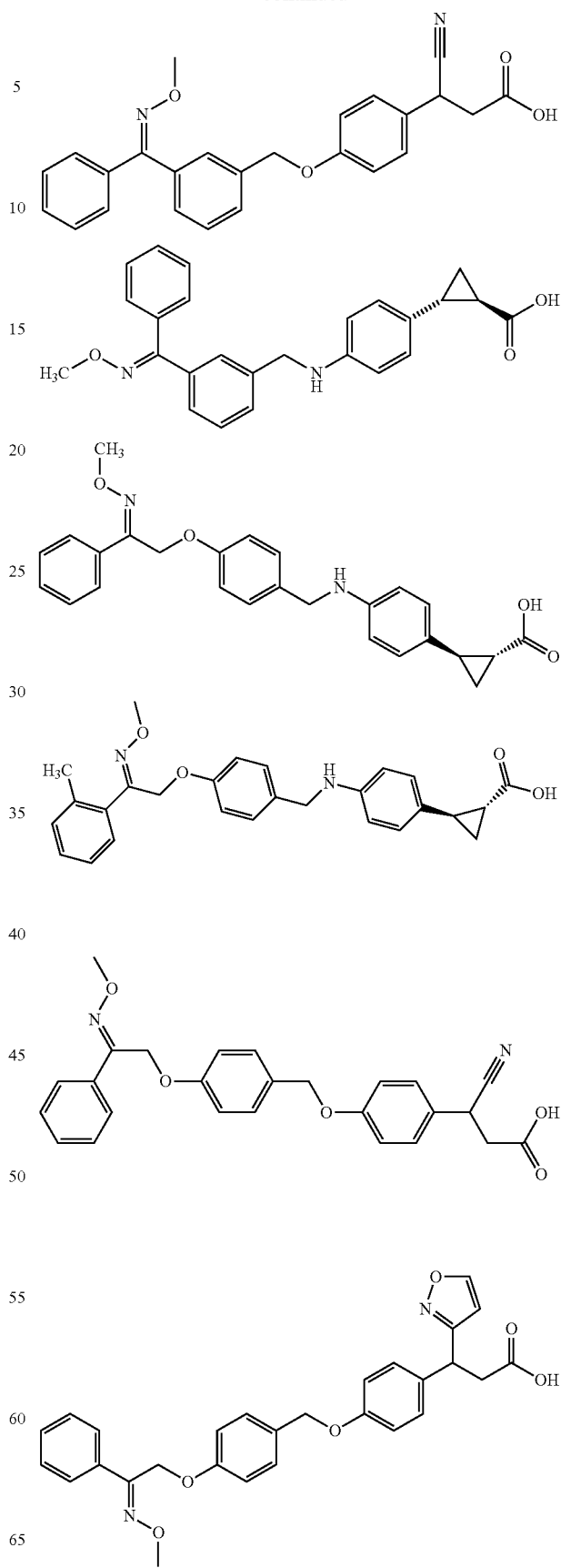

33
-continued
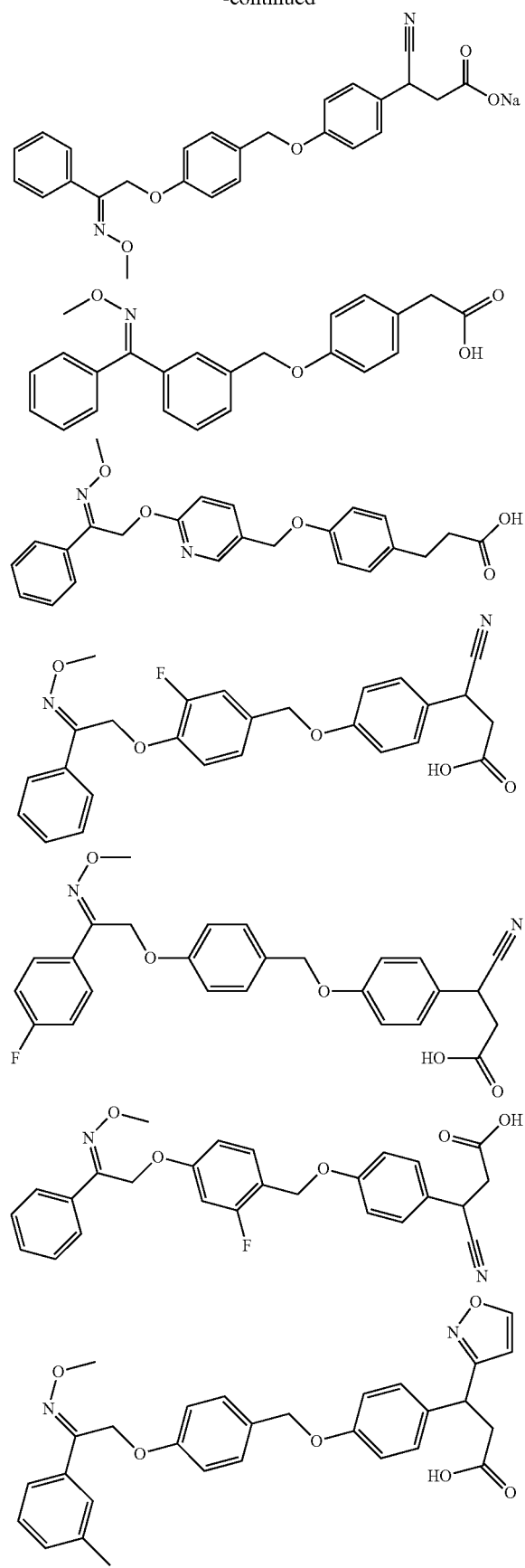
34
-continued
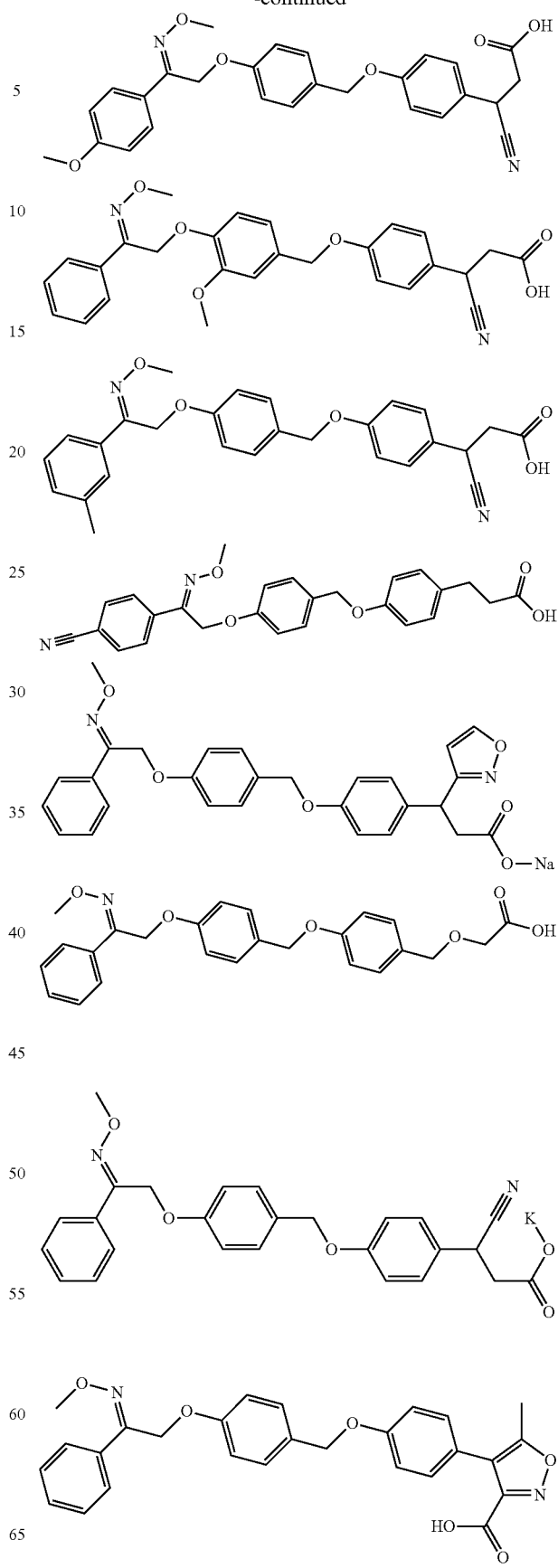

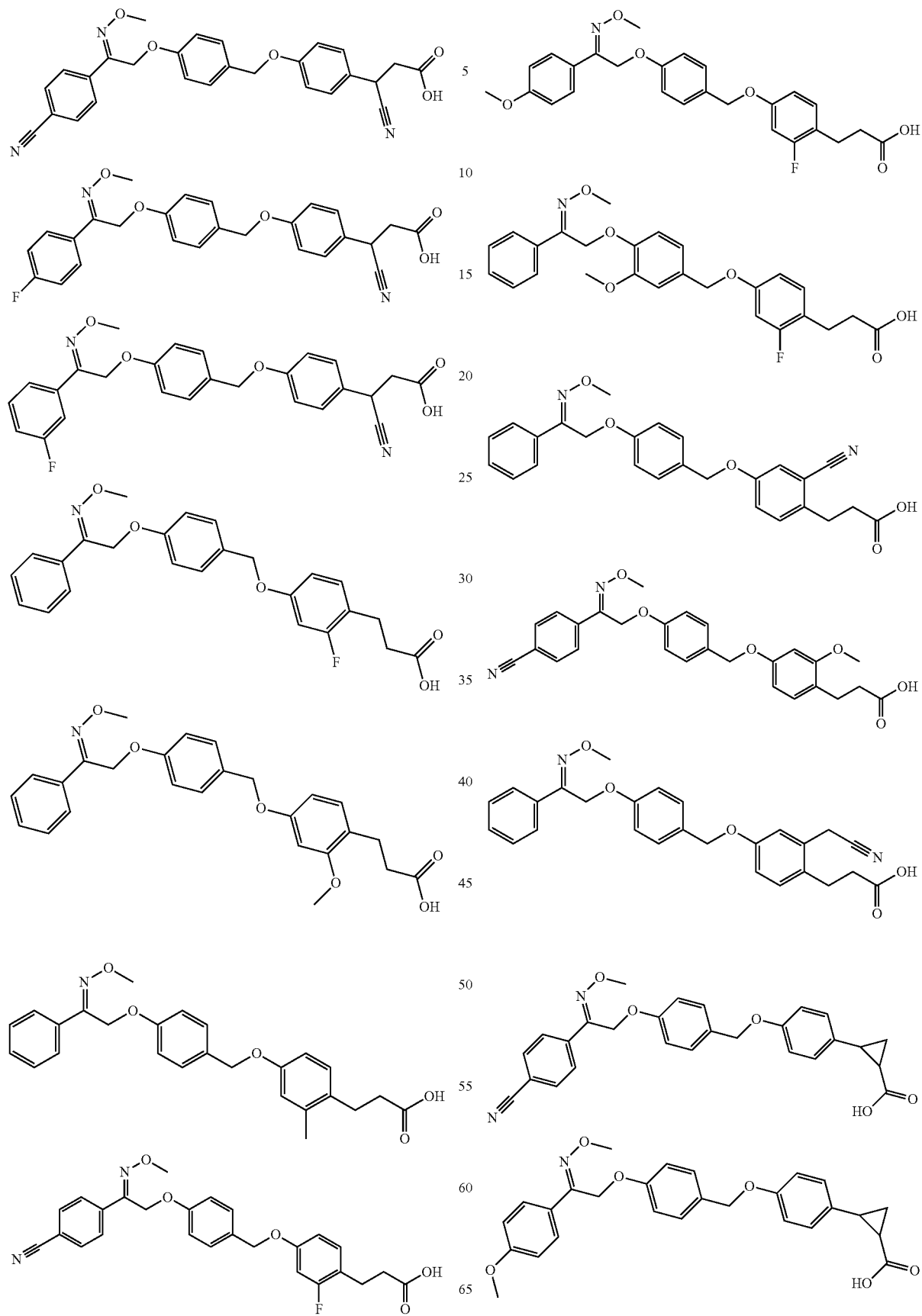

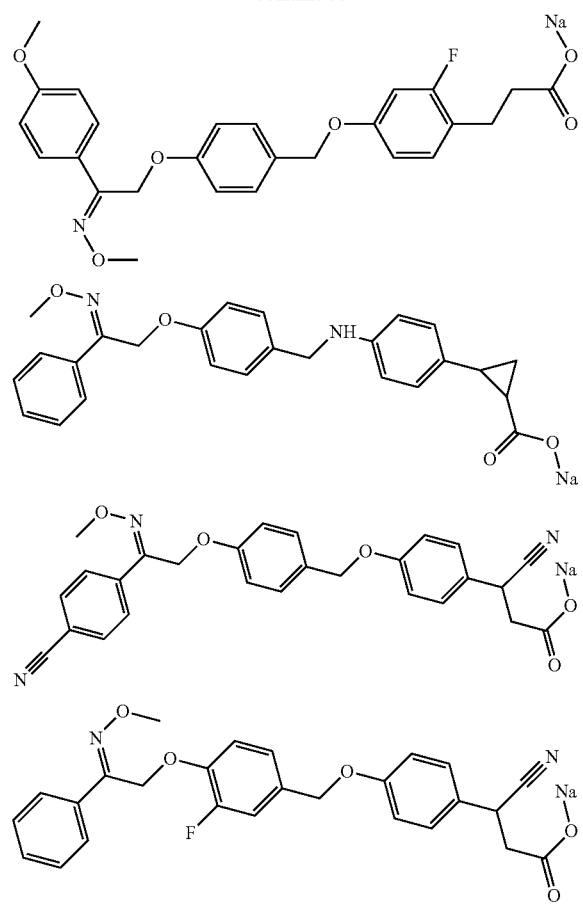
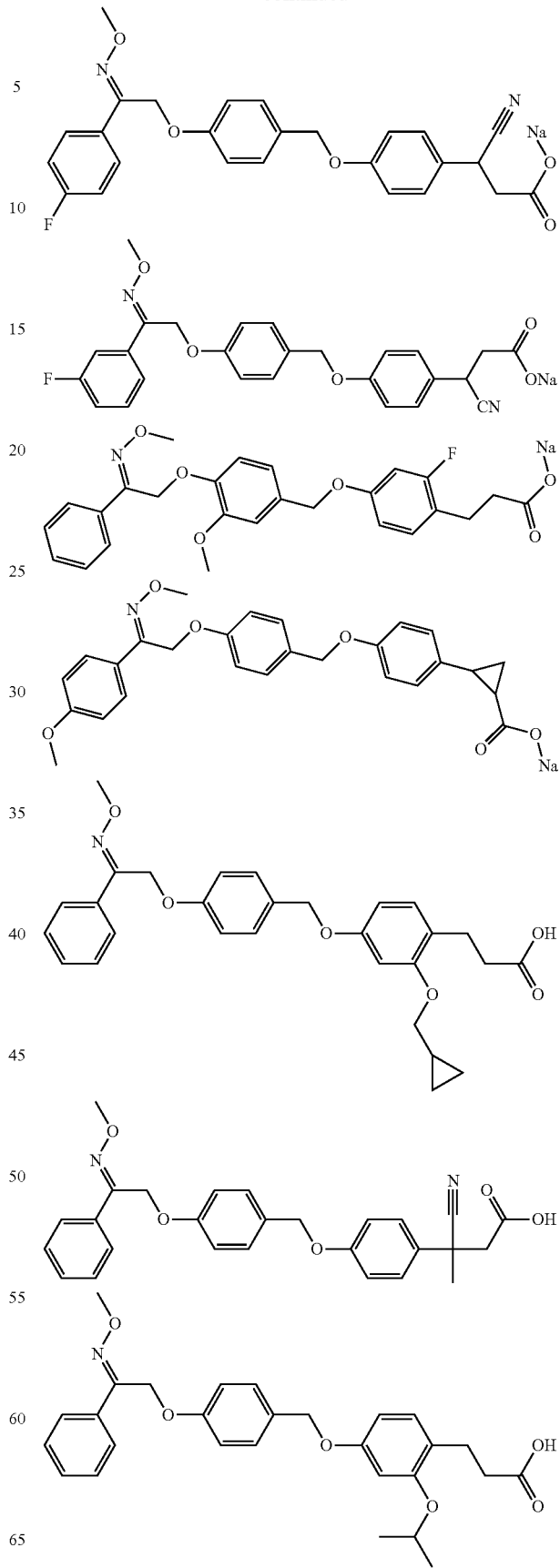

39
-continued
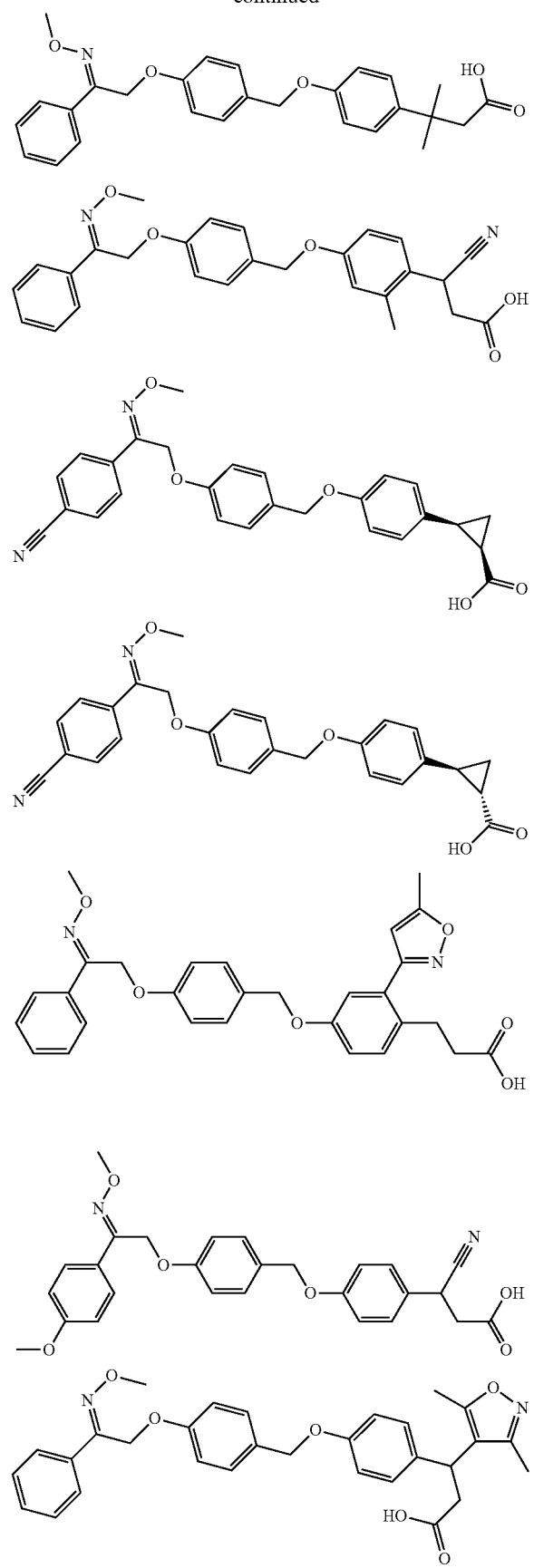
40
-continued
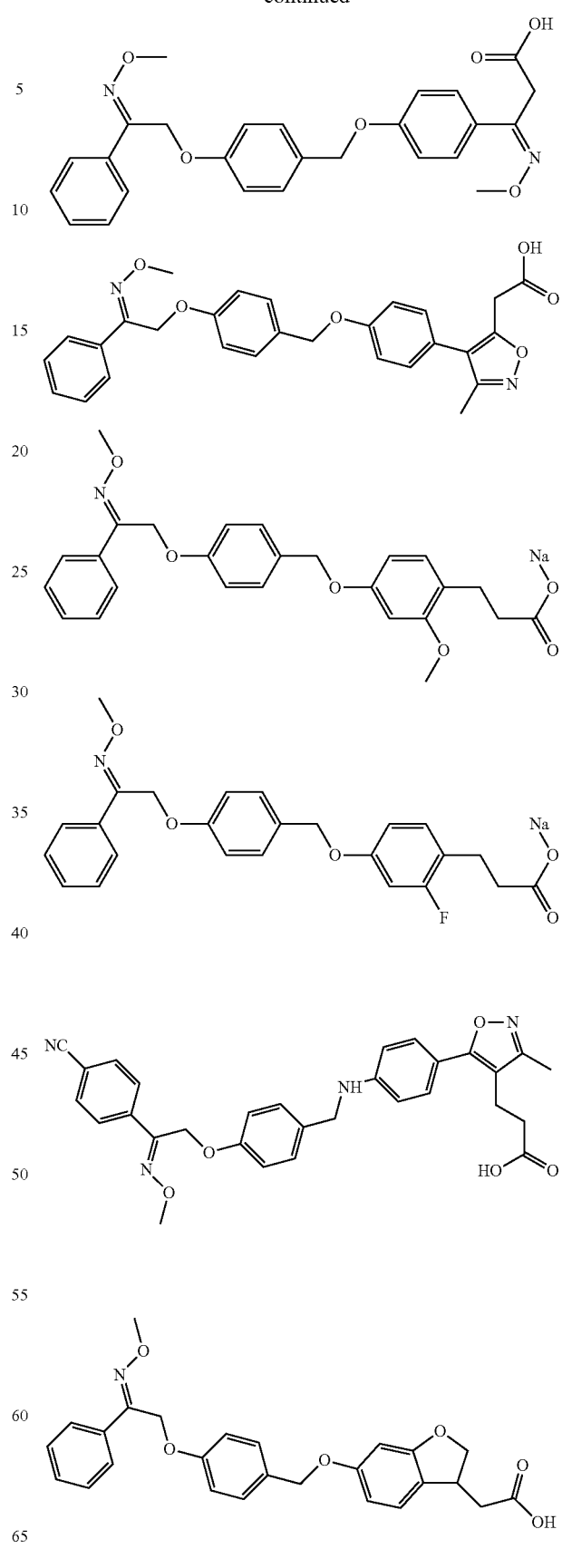

41
-continued
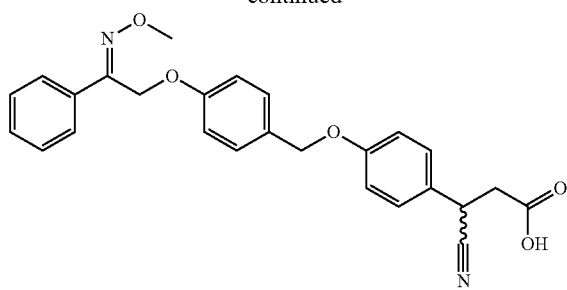
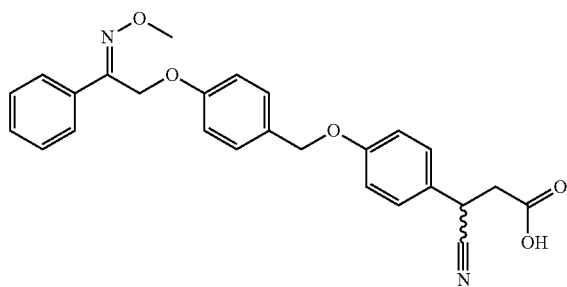
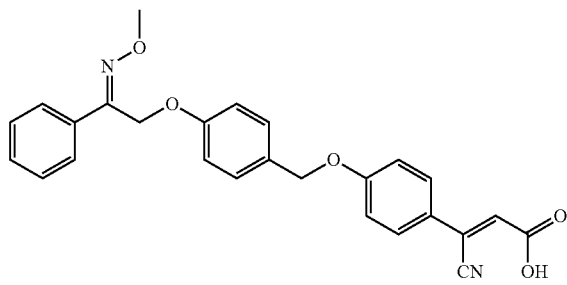
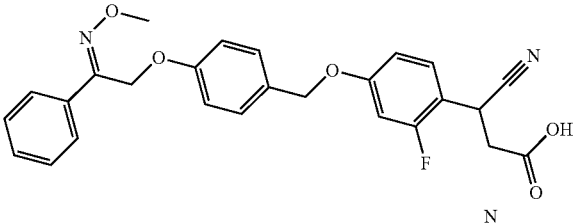
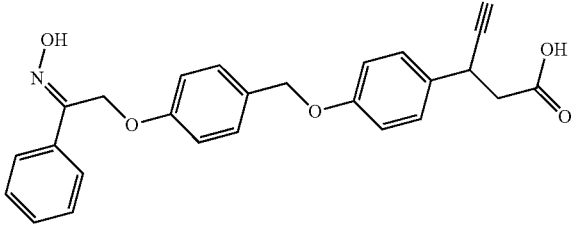
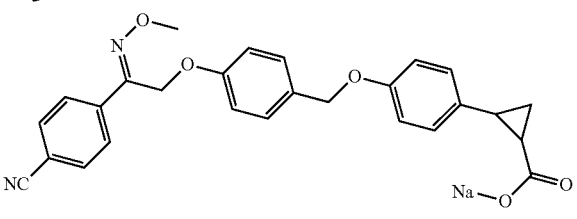
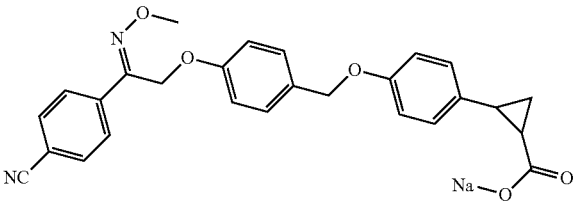
42
-continued
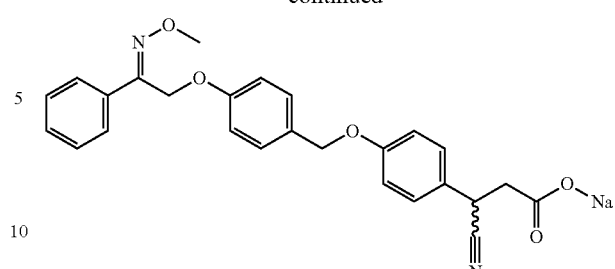
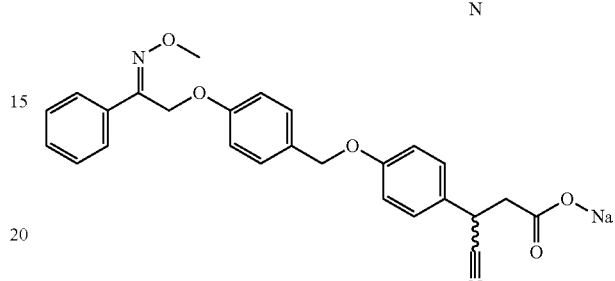
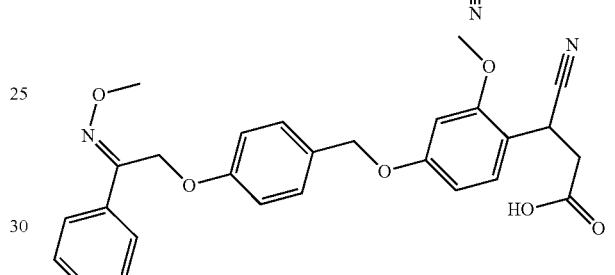
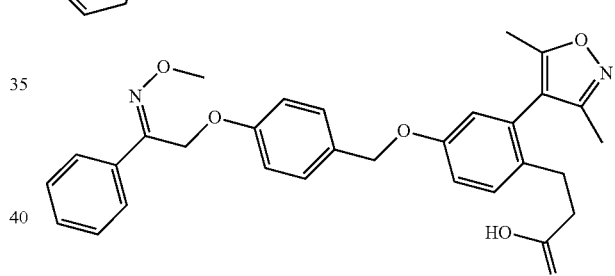
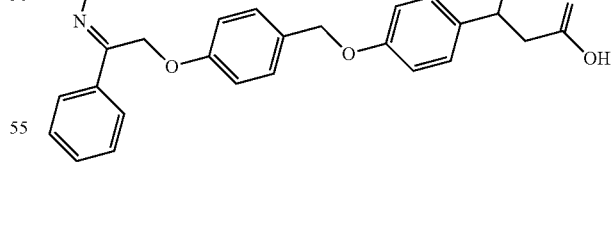
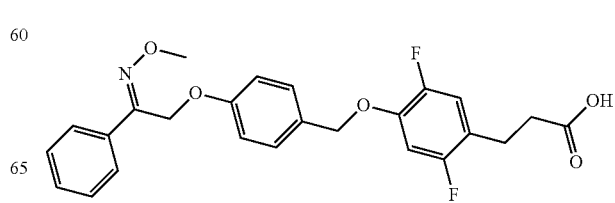

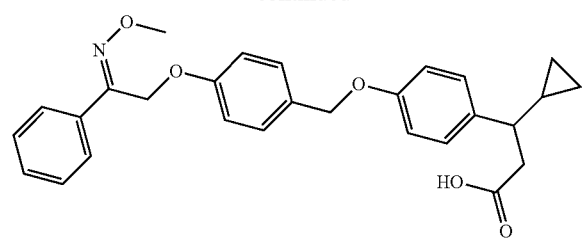
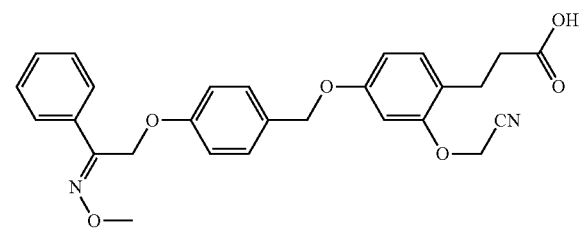
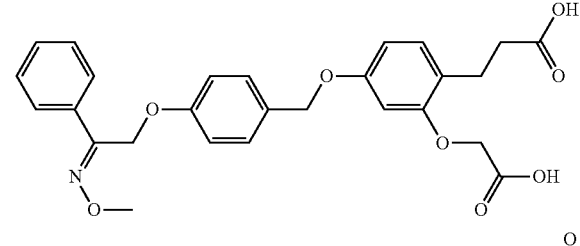
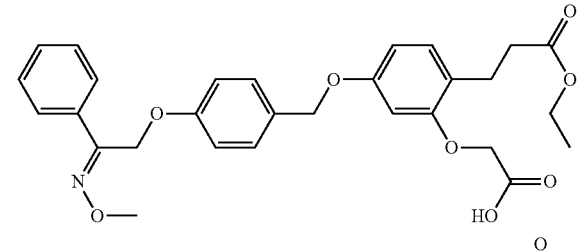
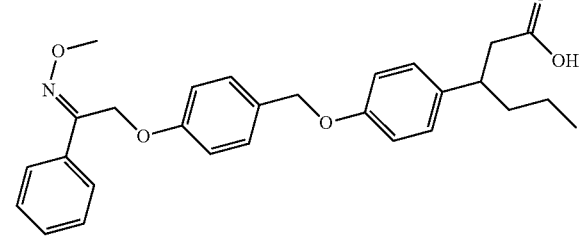
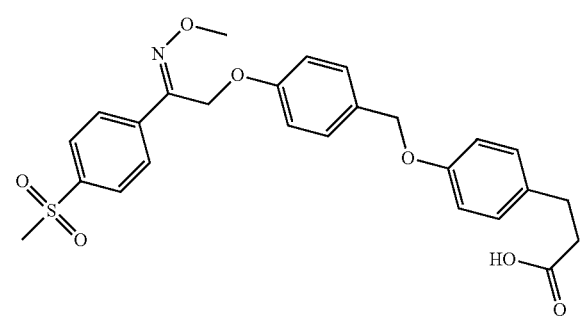
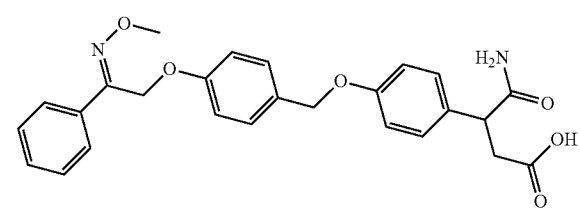
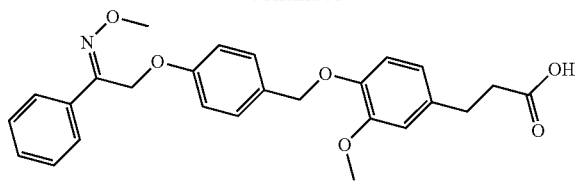
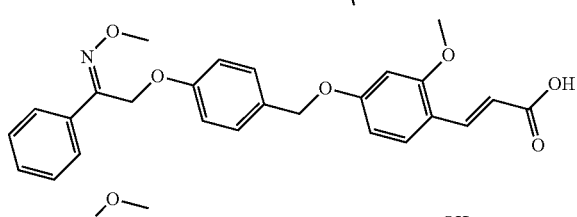
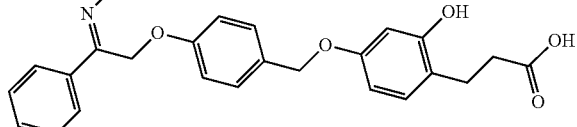
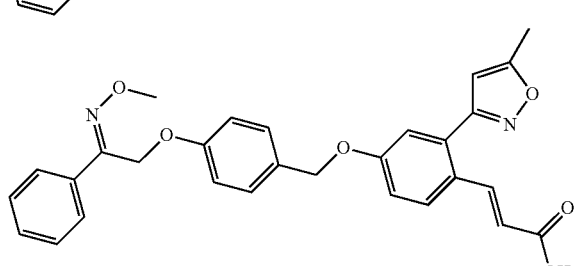
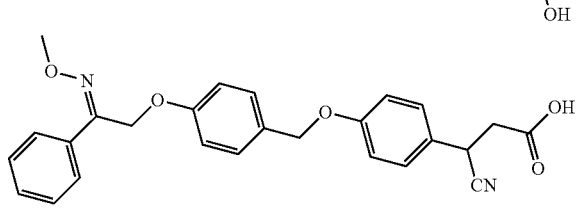
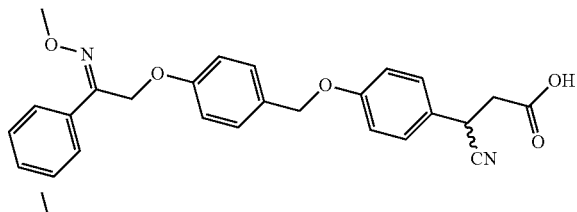
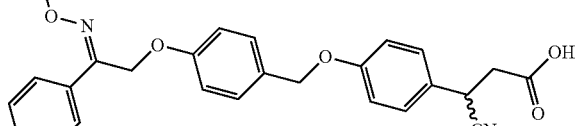
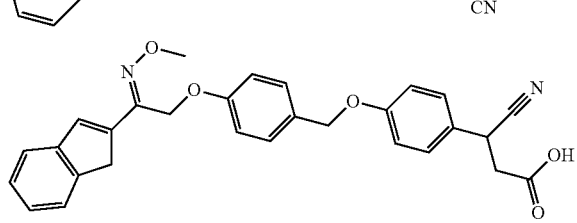
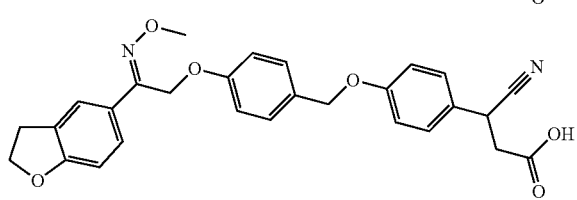

45
-continued
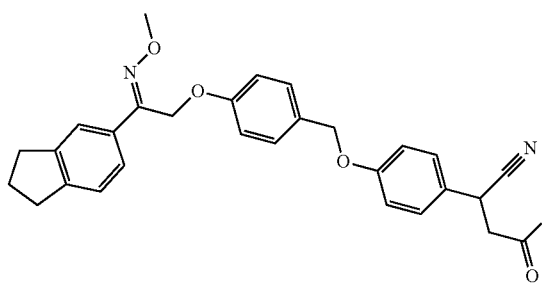
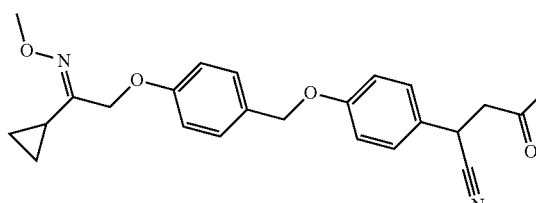
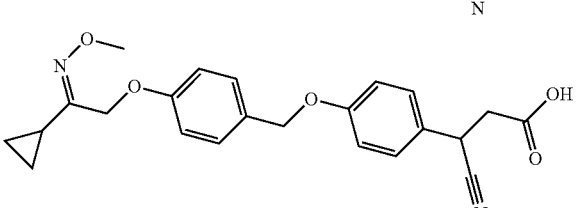
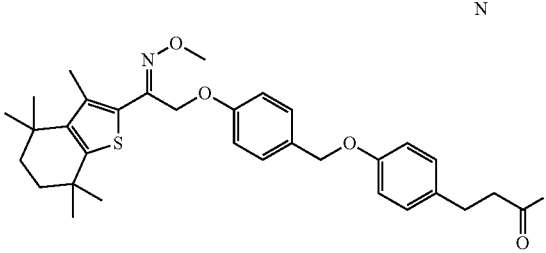
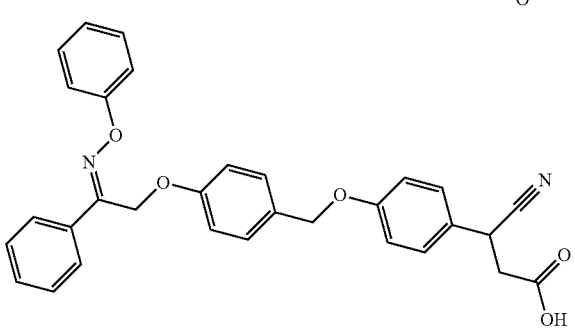
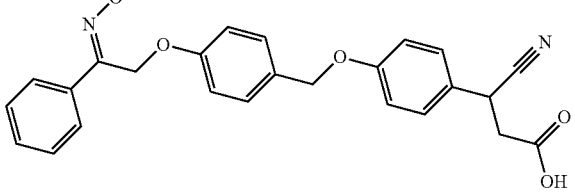
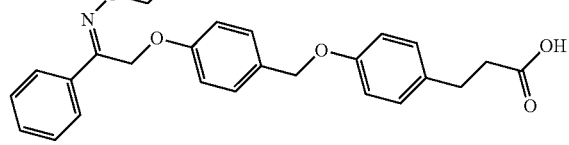
46
-continued
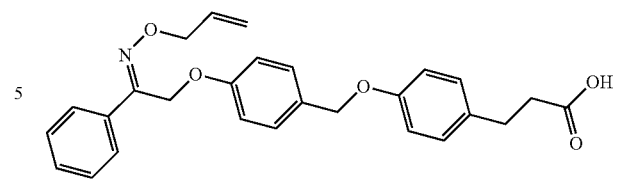
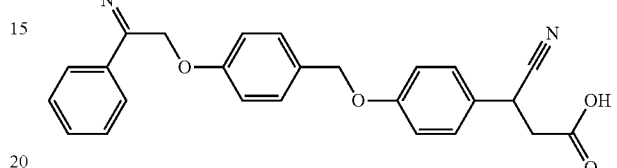
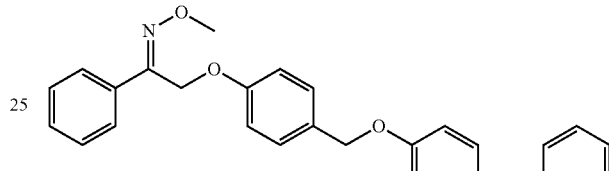
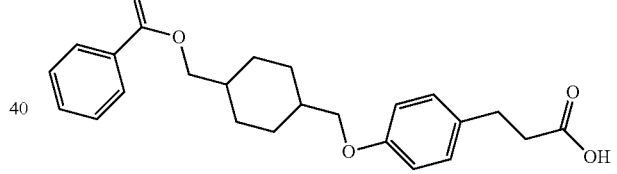
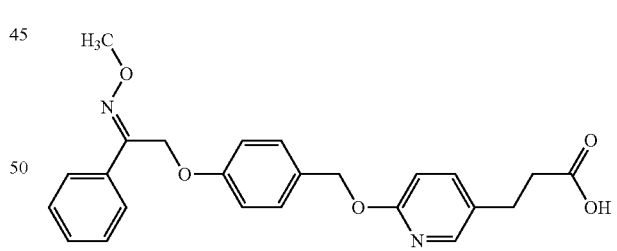
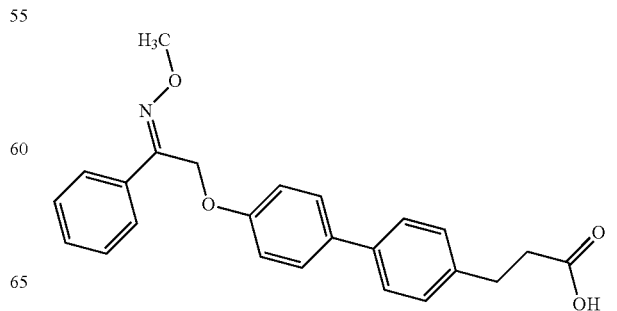

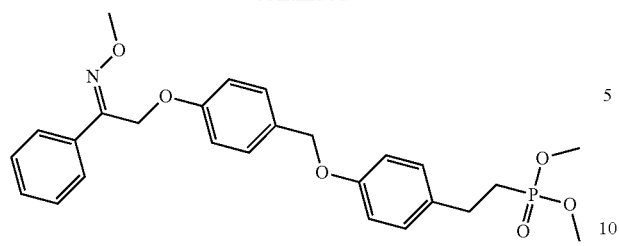
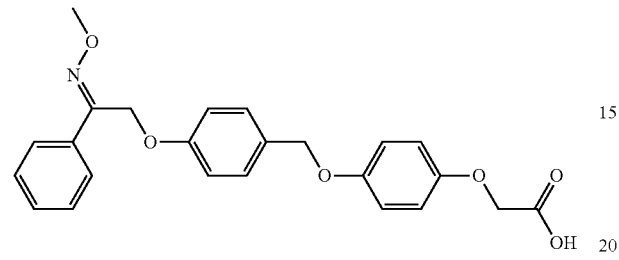
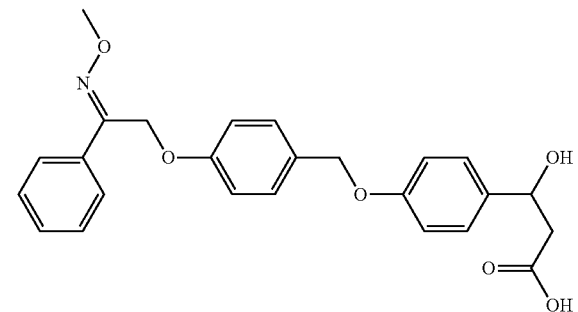
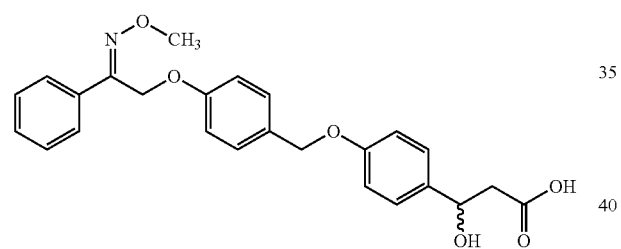
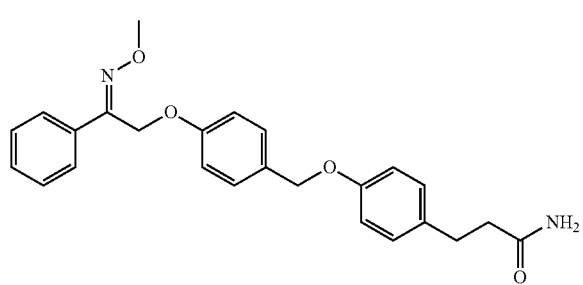
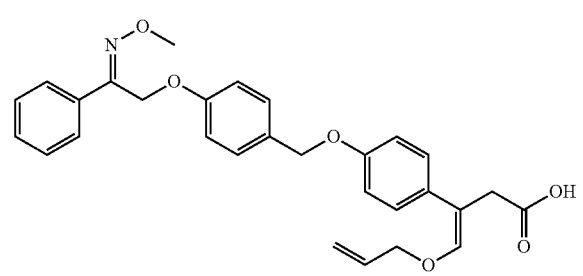

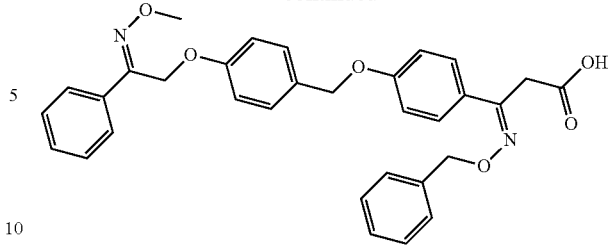
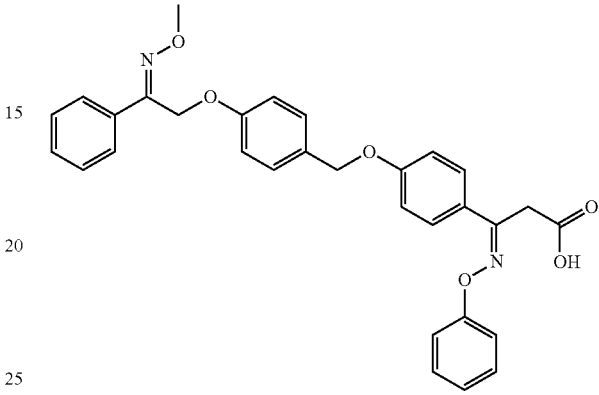
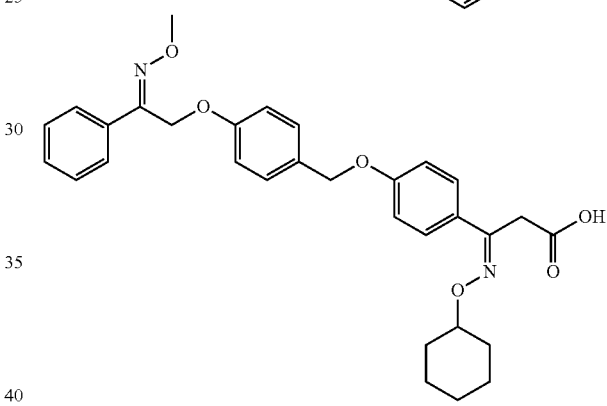

or a geometric isomer or a pharmaceutically acceptable salt or prodrug thereof.

The compounds have the ability to activate GPR40 receptor. The ability to activate GPR40 receptor activity may be a result of the compounds acting directly and solely on the GPR40 receptor to modulate/potentiate biological activity. However, it is understood that the compounds may also act at least partially on other factors associated with GPR40 receptor activity.

The activation of GPR40 receptor may be carried out in any of a number of well known ways in the art. For example if activation of the GPR40 receptor in vitro is desired an appropriate amount of the compound may be added to a solution containing the GPR40 receptor. In circumstances where it is desired to activate the GPR40 receptor in a mammal, the activation of the GPR40 receptor typically involves administering the compound to a mammal containing the GPR40 receptor.

Accordingly the compounds may find a multiple number of applications in which their ability to activate GPR40 receptor of the type mentioned above can be utilised.

Accordingly compounds of the invention would be expected to have useful therapeutic properties especially in relation to metabolic conditions such as diabetes, obesity, hyperglycemia, glucose intolerance, insulin resistance, hyperinsulemia, hypercholesteremia, hypertension, hyperlipoproteinemia, hyperlipidemia, hypertriglyceridemia, dyslipedemia, metabolic syndrome X, atherosclerosis, diabetic neuropathy, diabetic retinopathy, and hypoglycemia.

Compounds of the invention may also be useful in the treatment of cognitive disorders, osteoporosis, inflammatory disorders, cardiovascular disease, kidney disease, ketoacidosis, thrombotic disorders, nephropathy, sexual dysfunction, dermatopathy, dyspepsia, cancer and edema. As such there is significant interest in the development of compounds with this mode of action.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the activator compound may be selectively toxic or more toxic to rapidly proliferating cells, e.g. cancerous tumours, than to normal cells.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, $19^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in some embodiments the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

Synthesis of Compounds of the Invention

The agents of the various embodiments may be prepared using the reaction routes and synthesis schemes as described below, employing the techniques available in the art using starting materials that are readily available. The preparation of particular compounds of the embodiments is described in detail in the following examples, but the artisan will to recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, $3^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

The symbols, abbreviations and conventions in the processes, schemes, and examples are consistent with those used in the contemporary scientific literature. Specifically but not meant as limiting, the following abbreviations may be used in the examples and throughout the specification.

g (grams)
L (liters)
Hz (Hertz)
mol (moles)
RT (room temperature)
min (minutes)
MeOH (methanol)
$CHCl_3$ (chloroform)
DCM (dichloromethane)
DMSO (dimethylsulfoxide)
EtOAc (ethyl acetate)
mg (milligrams)
mL (milliliters)
psi (pounds per square inch)
mM (millimolar)
MHz (megahertz)
h (hours)
TLC (thin layer chromatography)
EtOH (ethanol)
$CDCl_3$ (deuterated chloroform)
HCl (hydrochloric acid)
DMF (N,N-dimethylformamide)
THF (tetrahydro furan)
$K_2CO_3$ (potassium carbonate)
$Na_2SO_4$ (sodium sulfate)
RM (Reaction Mixture)

Unless otherwise indicated, all temperatures are expressed in ° C. (degree centigrade). All reactions conducted at room temperature unless otherwise mentioned.

All the solvents and reagents used are commercially available and purchased from Sigma Aldrich, Fluka, Acros, Spectrochem, Alfa Aesar, Avra, Qualigens, Merck, Rankem and Leonid Chemicals.

¹H NMR spectra were recorded on a Bruker AV 300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on single quadruple 6120 LCMS from Agilent technologies, using either atmospheric chemical ionization (APCI) or Electrospray ionization (ESI) or in the combination of these two sources.

All samples were run on SHIMADZU system with an LC-20 AD pump, SPD-M20A diode array detector, SIL-20A auto sampler.

Synthetic Scheme 1

One scheme for making certain compounds of the invention is shown in scheme 1 below. Thus using standard techniques the brominated diphenyl ketone (intermediate 1) and the 3-(4-hydroxy-phenyl)methyl propionate (intermediate 2) were produced and reacted to produce intermediate 3. The methyl group of the acid is then removed followed by reaction with an appropriate amine to form the corresponding oxime. By variation of the starting materials used to make intermediates 1 and 2 and the identity of the amine used to make the final oxime a wide variety of compounds of the invention can be made using this methodology. As a general rule all oximes containing an oxygen in the Y group can be made using this approach or a variation thereof.

Scheme 1:

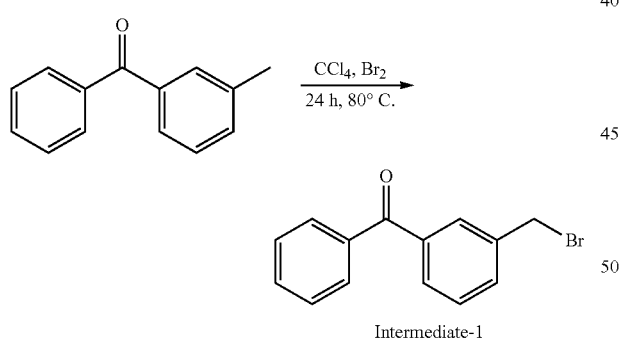

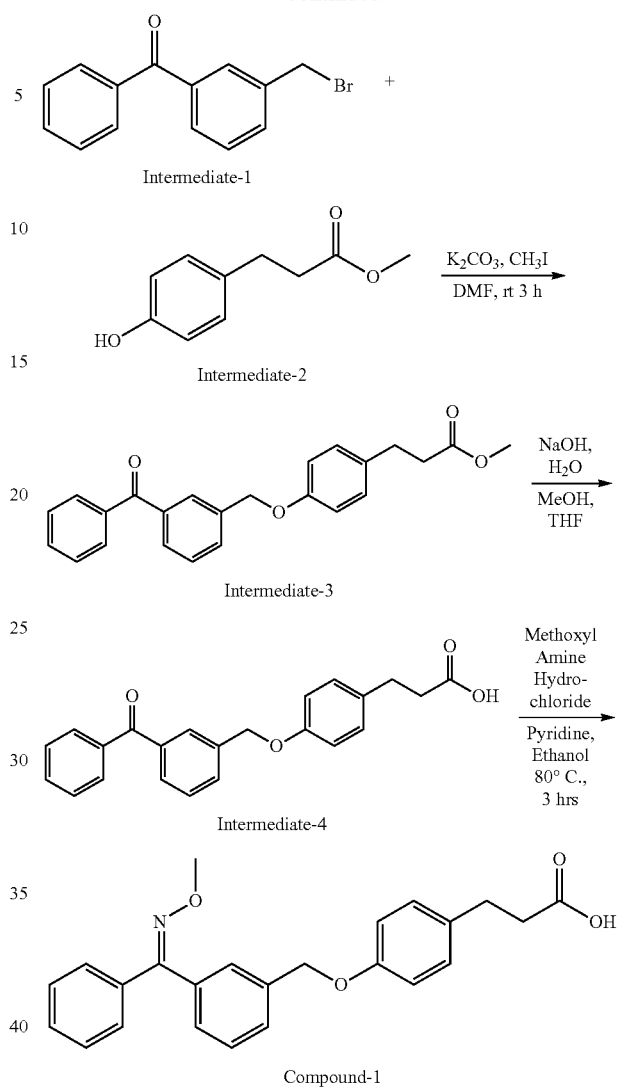

Example 1

3-[4-({3-[(E,Z)-(methoxyimino)(phenyl)methyl]benzyl}oxy)phenyl]propanoic acid (1)

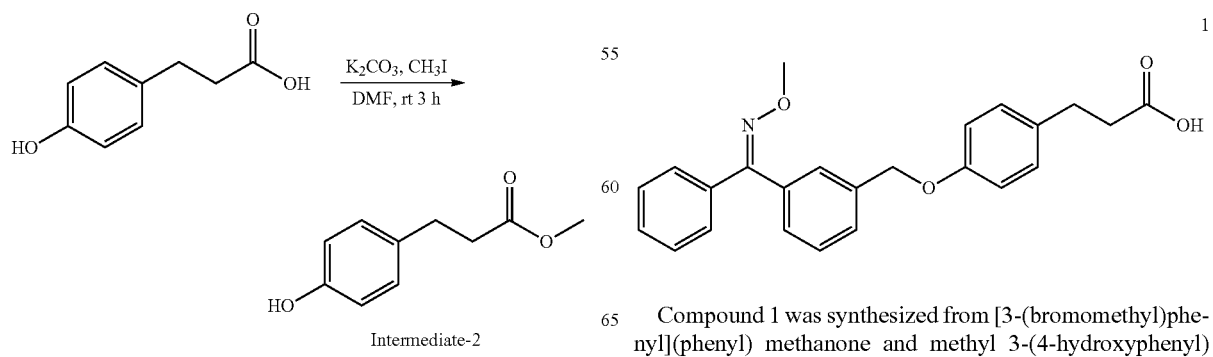

Compound 1 was synthesized from [3-(bromomethyl)phenyl](phenyl) methanone and methyl 3-(4-hydroxyphenyl)propanoate by following the procedure in Scheme 1.

Intermediate 1: [3-(Bromomethyl)phenyl](phenyl)methanone

To a 1000 mL RB flask fitted with magnetic stirrer, was charged with 375 mL of $CCl_4$. The solvent was cooled to 0° C. and to the stirred solvent was added phenyl-m-tolyl-methanone (15.0 g, 76.45 mmol) followed by the addition of bromine (24.43 g, 152.9 mmol) at 0° C. and the mixture was allowed to stir at the same temperature for 30 minutes. The resulting solution was refluxed at 80° C. for 24 h. After completion of the reaction (reaction monitored by TLC), RM was cooled to 10° C. and quenched with the addition of solid sodium bicarbonate (15 g, 178.57 mmol). The organic layer was washed with saturated sodium bicarbonate solution (300 mL×2) and saturated brine solution (300 mL). The organic layer was dried over anhydrous $Na_2SO_4$ and the solvent was removed under reduced pressure to get the product as a white solid (6.8 g, Yield: 32.3%): $^1H$ NMR (300 MHz, $CDCl_3$): δ 7.74-7.76 (m, 2H), 7.71-7.72 (t, 2H), 7.51-7.67 (m, 2H), 7.40-7.45 (m, 3H), 4.46 (s, 2H).

Intermediate 2: Methyl 3-(4-hydroxyphenyl)propanoate

To a 1000 mL RB flask fitted with magnetic stirrer was charged 250 mL of DMF, 3-(4-Hydroxy-phenyl)-propanoic acid (25.0 g, 150.43 mmol) and $K_2CO_3$ (41.58 g, 300.87 mmol). The resulting mixture was stirred at RT for 30 minutes. Methyl Iodide (25.627 g, 180.51 mmol) was added to the resulting mixture which was precooled to 0° C. The resulting mixture was stirred at RT for 3 h. After completion of the reaction (reaction monitored by TLC), the solvent was removed under reduced pressure and the crude mass was dissolved in ethyl acetate (250 mL). The organic layer was washed with water (250 mL), saturated sodium bicarbonate solution (250 mL×2), and saturated brine solution (250 mL). The organic layer was dried over anhydrous $Na_2SO_4$ and the solvent was removed under reduced pressure. The product was obtained as yellow color oil (26 g, Yield: 95.9%): MS (ESI, 120 eV): m/z=178.9 $(M-H)^+$; $^1H$ NMR (300 MHz, $CDCl_3$): δ 6.97-7.00 (d, 2H), 6.66-6.69 (d, 2H), 4.94 (s, 1H), 3.59 (s, 3H), 2.78-2.83 (t, 2H), 2.50-2.55 (t, 2H).

Intermediate 3: Methyl 3-{4-[(3-benzoylbenzyl)oxy]phenyl}propanoate

To a 250 mL RB flask fitted with magnetic stirrer was charged 45 mL of DMF. To the stirred solvent was added 3-(4-Hydroxy-phenyl)-propanoic acid methyl ester (4.5 g, 16.35 mmol) followed by $K_2CO_3$ (6.78 g, 49.074 mmol) and the resulting mixture stirred at room temperature for 30 minutes. (3-bromomethyl-phenyl)-phenyl-methanone (2.94 g, 16.35 mmol) was added to the above mixture and stirring continued at RT for 24 h. After completion of the reaction (reaction monitored by TLC), reaction solvent was removed under reduced pressure. The crude compound was purified by column chromatography on silica gel (100/200 mesh) using petroleum ether (60-80) and ethyl acetate as eluent which yielded the product as yellow color oil (5.1 g, Yield: 83.3%): MS (ESI, 120 eV): m/z=375.1 $(M+H)^+$; $^1H$ NMR (300 MHz, $CDCl_3$): δ 7.68 (s, 1H), 7.62-7.66 (d, 3H), 7.57-7.59 (d, 1H), 7.53 (m, 1H), 7.45-7.50 (m, 3H), 7.11-7.13 (d, 2H), 6.88-6.90 (d, 2H), 5.10 (s, 2H), 3.66 (s, 3H), 2.85-2.92 (m, 2H), 2.56-2.62 (m, 2H).

Intermediate 4: 3-{4-[(3-Benzoylbenzyl)oxy]phenyl}propanoic acid

To a 100 mL RB flask fitted with magnetic stirrer was charged 15 mL of THF, 1.0 mL water, and 1.0 mL methanol. To the stirred solvent mixture was added [4-(3-benzoyl-benzyloxy)-phenyl]-propanoic acid methyl ester (1.5 g, 4.0064 mmol) followed by the addition of sodium hydroxide (0.480 g, 12.02 mmol). The resulting solution was stirred at RT for 15 h. After completion of the reaction (reaction monitored by TLC), RM was diluted with 10 mL of water and washed with 40 mL DCM (50 mL×2). Then the aqueous layer was acidified to pH 6 using conc. HCl and extracted with DCM (75 mL×3). The DCM layer was washed with water (75 mL), dried over anhydrous $Na_2SO_4$ and the solvent was removed under reduced pressure. The product was obtained as white solid (1.4 g, yield: 97.2%): MS (ESI, 120 eV): m/z=361.1 $(M+H)^+$; $^1H$ NMR (300 MHz, $CDCl_3$): δ 12.09 (s, 1H), 7.80 (s, 1H), 7.66-7.73 (m, 5H), 7.56-7.58 (d, 3H), 7.13-7.16 (m, 2H), 6.90-6.93 (d, 2H), 5.18 (s, 2H), 2.72-2.77 (t, 2H), 2.42-2.45 (m, 2H).

Compound 1: 3-[4-({3-[(E,Z)-Methoxyimino)(phenyl)methyl]benzyl}oxy)phenyl]propanoic acid To a 100 mL RB flask fitted with magnetic stirrer along with reflux condenser was charged with 42 mL of ethanol, and 8.4 mL of pyridine. To the stirred solvent mixture was added 3-[4-(3-benzoyl-benzyloxy)-phenyl]-propanoic acid (1.4 g, 3.884 mmol) followed by methoxyl amine hydrochloride (1.62 g, 19.422 mmol). The resulting solution was refluxed at 80° C. for 3 h. After completion of the reaction (reaction monitored by TLC), solvent was removed under reduced pressure and the resulting crude mass was taken in dichloromethane (100 mL). The organic layer was washed with water (100 mL×3) and saturated brine solution (100 mL). The organic layer was dried over anhydrous $Na_2SO_4$ and the solvent was removed under reduced pressure. The product was obtained as white solid (1.1 g, Yield: 72.8%); Purity: 98.3%.

Synthetic Scheme 2

An alternative scheme for making certain compounds of the invention is shown in scheme 2 below. Thus using standard techniques the brominated diphenyl ketone (intermediate 1) and the 3-(4-amino-phenyl)propanoic acid were produced and reacted to produce intermediate 5. This is then followed by reaction with an appropriate amine to form the corresponding oxime. By variation of the starting materials used to make intermediate 1 and the identity of the propanoic acid used and the identity of the amine used to make the final oxime a wide variety of compounds of the invention can be made using this methodology. As a general rule all oximes containing a nitrogen in the Y group can be made using this approach or a variation thereof.

Scheme 2:

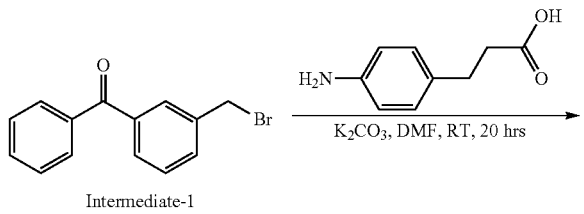

Intermediate-1

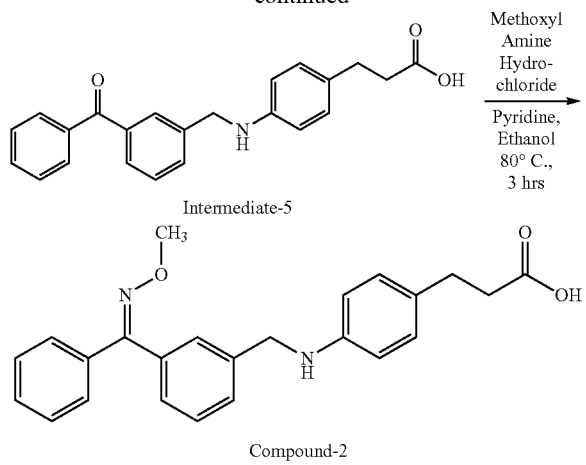

Example 2

3-[4-({3-[(E,Z)-(Methoxyimino)(phenyl)methyl]benzyl}amino)phenyl]propanoic acid (2)

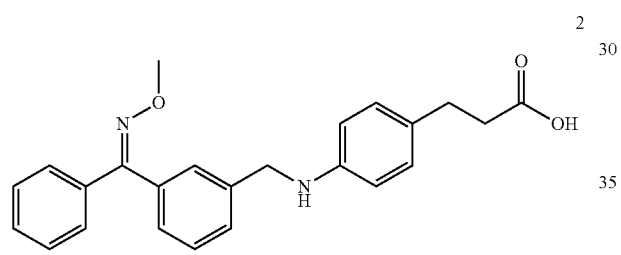

Compound 2 was synthesized from [3-(bromomethyl)phenyl](phenyl) methanone and 3-(4-aminophenyl)propanoic acid by following the procedure described in Scheme 2.

Intermediate 5: 3-{4-[(3-Benzoylbenzyl)amino]phenyl}propanoic acid

To a 250 mL RB flask fitted with magnetic stirrer was charged 25 mL of DMF. To the stirred solvent was added 3-(4-Amino-phenyl)-propanoic acid (0.6 g, 3.635 mmol) followed by $K_2CO_3$ (1.507 g, 10.905 mmol) and the mixture stirred at RT for 30 minutes. To the resulting mixture was added (3-bromomethyl-phenyl)-phenyl-methanone (1.0 g, 3.635 mmol) and the stirring continued at RT for further 20 h. After completion of the reaction (reaction monitored by TLC), solvent was removed under reduced pressure, and the resulting crude compound was dissolved in water (15 mL). This aqueous layer was acidified with saturated citric acid solution in water (1.5 g in 3 mL water) to pH 5. The compound was obtained after extracting the residue with diethyl ether (100 mL×3). The combined ether layer was washed with saturated brine solution (50 mL). The organic layer was dried over anhydrous $Na_2SO_4$ and the solvent was removed under reduced pressure. The crude mass thus obtained was purified by column chromatography on silica gel (100/200 mesh), using petroleum ether (60-80) and ethyl acetate as eluent. The product was obtained as brown sticky solid (0.3 g, Yield: 22.9%): MS (ESI, 120 eV): m/z=360.1 (M+H)$^+$; $^1$H NMR (300 MHz, DMSO-d$_6$): δ 12.04 (s, 1H), 7.72 (s, 1H), 7.64-7.68 (t, 4H), 7.57-7.60 (d, 1H), 7.48-7.54 (m, 3H), 6.89-6.91 (d, 2H), 6.46-6.49 (d, 2H), 6.18-6.22 (t, 1H), 4.32-4.34 (d, 2H), 2.61-2.66 (d, 2H), 2.38-2.43 (d, 2H).

Compound 2: 3-[4-({3-[(E,Z)-(Methoxyimino)(phenyl)methyl]benzyl}amino)phenyl]propanoic acid To a 100 mL RB flask fitted with magnetic stirrer and reflux condenser charged with 9 mL of ethanol and 1.8 mL of pyridine. To the stirred solution was added 3-[4-(3-benzoyl-benzylamino)-phenyl]-propanoic acid (0.3 g, 0.834 mmol) followed by methoxylamine hydrochloride (0.348 g, 4.173 mmol). The resulting solution was refluxed at 82° C. for 3 h. After completion of the reaction (reaction monitored by TLC), solvent was removed under reduced pressure and the resulting crude mass was taken in dichloromethane (50 mL). The organic layer was then washed with water (50 mL×3), saturated brine solution (50 mL). The organic layer was dried over anhydrous $Na_2SO_4$ and the solvent was removed under reduced pressure. The resulting crude was purified by column chromatography on silica gel (100/200 mesh), using petroleum ether (60-80) and ethyl acetate as eluent, gave product as white solid (0.1 g, Yield: 31.3%); purity: 97.1%.

Example 3

3-[4-({4-[(E,Z)-(Methoxyimino)(phenyl)methyl]benzyl}amino)phenyl]propanoic acid (3)

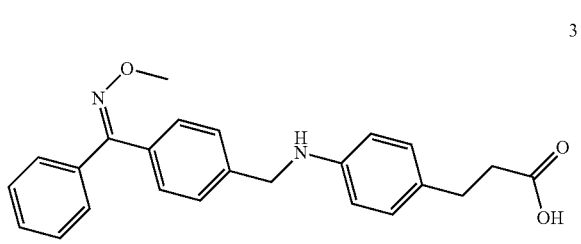 [SMILES: CO/N=C(/c1ccccc1)c1ccc(CNc2ccc(CCC(=O)O)cc2)cc1]

Compound 3 was synthesized from [4-(bromomethyl)phenyl](phenyl) methanone (0.65 g, 2.1 mmol) and 3-(4-aminophenyl)propanoic acid (0.25 g, 1.4 mmol) by following the similar procedure described in Scheme 2. (0.006 g, Yield: 1.5%); purity: 87.98%.

Synthetic Scheme 3

An alternative scheme for making certain compounds of the invention is shown in scheme 3 below and finds application for the synthesis of compounds in which X is other than a bond. Thus using standard techniques the brominated oxime (intermediate 6) and an appropriately substituted hydroxyl aldehyde are reacted to produce intermediate 7. This is then reacted with an appropriate 3-(4-amino-phenyl)methyl propionate to produce intermediate 8 which can be smoothly demethylated to produce compound 4. By variation of the starting materials used to make intermediate 6 and the identity of hydroxyl aldehyde and the propanoic acid derivative a wide variety of compounds of the invention can be made using this methodology.

Scheme 3:

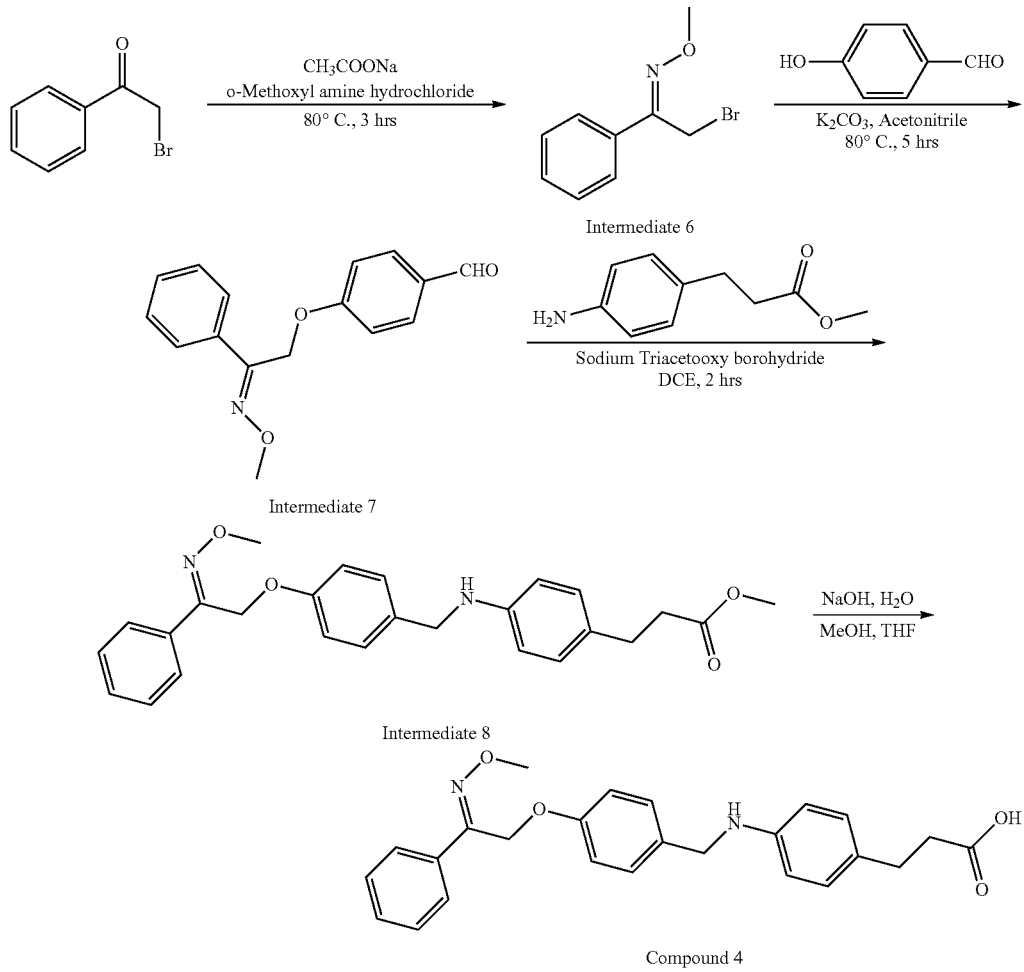

Example 4

3-{4-[(4-{[(2Z)-2-(Methoxyimino)-2-phenylethyl]oxy}benzyl)amino]phenyl}propanoic acid (4)

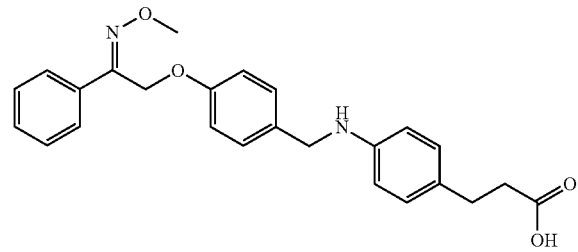

Compound 4 was synthesized from 4-{[(2Z)-2-(methoxyimino)-2-phenylethyl]oxy}benzaldehyde and methyl 3-(4-aminophenyl)propanoate by following the procedure described in Scheme 3.

Intermediate 6:
(1Z)-2-Bromo-N-methoxy-1-phenylethanimine

To a 100 mL RB flask fitted with magnetic stirrer was charged 20 mL of Acetic acid. To the stirred solvent was added 2-bromo acetophenone (1 g, 5 mmol) and sodium acetate (0.49 g, 5.97 mmol). The resulting mixture was stirred for 5 min, o-methoxylamine hydrochloride (0.4 g, 4.79 mmol) was added to the above mixture and the RM heated at 80° C. and stirred at the same temperature for 3 h. After completion of the reaction (reaction monitored by TLC), RM was poured into water (15 mL) and extracted with ethyl acetate (100 mL). The organic layer was washed with saturated brine solution (50 mL) and dried over anhydrous $Na_2SO_4$. The solvent was removed under reduced pressure and the residue purified by column chromatography on silica gel (100/200 mesh), using petroleum ether (60-80) and ethyl acetate to obtain the title compound (0.6 g, Yield: 52.6%): MS (ESI, 120 eV): m/z=228.1 $(M+H)^+$; $^1H$ NMR (300 MHz, $CDCl_3$): δ 7.62-7.64 (m, 2H), 7.32-7.34 (m, 3H), 4.28 (s, 2H), 4.02 (s, 3H).

Intermediate 7: 4-{[(2Z)-2-(Methoxyimino)-2-phenylethyl]oxy}benzaldehyde

To a 100 mL RB flask fitted with magnetic stirrer was charged 20 mL of acetonitrile. To the stirred solvent was added 4-hydroxy-benzaldehyde (0.21 g, 1.72 mmol) and K$_2$CO$_3$ (0.46 g, 3.33 mmol). Then it was stirred for 5 min. 2-Bromo-1-phenyl-ethanone o-methyl-oxime (0.4 g, 1.7 mmol) was added. Then RM was heated to 80° C. and stirred at this temperature for 5 h. After completion of the reaction (reaction monitored by TLC), RM was concentrated by removal of the acetonitrile, water (10 mL) was added, and the mixture was extracted with ethyl acetate (20 mL×2). The organic layer washed with saturated brine solution (20 mL) and dried over anhydrous Na$_2$SO$_4$ and evaporated to dryness to get the title compound (0.4 g, Yield: 87.5%): MS (ESI, 120 eV): m/z=270.1 (M+H)$^+$; $^1$H NMR (300 MHz, CDCl$_3$): δ 9.80 (s, 1H), 7.72-7.75 (d, 2H), 7.655-7.59 (m, 2H), 7.27-7.29 (m, 3H), 6.92-6.95 (d, 2H), 5.22 (s, 2H), 4.01 (s, 3H).

Intermediate 8: Methyl 3-{4-[(4-{[(2Z)-2-(methoxy-imino)-2-phenylethyl]oxy}benzyl)amino]phenyl}propanoate To a 50 mL RB flask fitted with magnetic stirrer was charged 5 mL of dichloroethane. To the stirred solvent was added 4-(2-methoxyimino-2-phenyl-ethoxy)-benzaldehyde (0.4 g, 1.5 mmol), 3-(4-amino-phenyl)-propanoic acid methyl ester (0.27 g, 1.5 mmol). RM was cooled to 0° C. and sodium triacetoxyborohydride (0.47 g, 2.25 mmol) was added portion wise over a period of 15 minutes. The reaction mixture was stirred at RT for 2 h. The RM was quenched with NaHCO$_3$ solution (40 mL 10% solution in water) and extracted with ethyl acetate (20 mL×2). The organic layer washed with saturated brine solution (25 mL), dried over anhydrous Na$_2$SO$_4$ and evaporated in vacuum to dryness. The resulting crude compound was purified by column chromatography on silica gel (100/200 mesh), using petroleum ether (60-80) and ethyl acetate as eluent to give the product (0.450 g, Yield: 69.4%): MS (ESI, 120 eV): m/z=433.1 (M+H)$^+$.

Compound 4: 3-{4-[(4-{[(2Z)-2-(Methoxyimino)-2-phenylethyl]oxy}benzyl)amino]phenyl}propanoic acid To a 25 mL RB flask fitted with magnetic stirrer was charged 1:2 mL of methanol:THF. To the stirred solvent, was added 3-{4-[4-(2-methoxyimino-2-phenyl-ethoxy)-benzyl amino]-phenyl}-propanoic acid methyl ester (0.4 g, 0.92 mmol). To the stirred solution, NaOH (0.074 g, 1.85 mmol) in water (1 mL) was added. The resulting solution was stirred at RT for 3 h. After completion of the reaction (reaction monitored by TLC), the solvents and water were evaporated under reduced pressure. The residue was diluted with 1 mL of water, cooled to 0° C., then acidified with 1N HCl, and extracted with ethyl acetate (15 mL×2). The organic layer was washed with water (20 mL) and saturated brine solution (20 mL) and dried over anhydrous Na$_2$SO$_4$. The organic layer was evaporated under reduced pressure. The product was obtained as colorless solid (0.32 g, yield: 84.2%): purity: 94.09%:

Example 5

3-{4-[(3-{[(2Z)-2-(Methoxyimino)-2-phenylethyl]oxy}benzyl)amino]phenyl}propanoic acid (5)

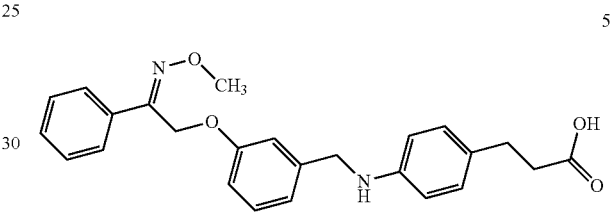

Compound 5 was synthesized from 3-{[(2Z)-2-(methoxyimino)-2-phenylethyl]oxy}benzaldehyde (0.27 g, 1.0 mmol) and 3-(4-aminophenyl)propanoic acid (0.179 g, 1 mmol) by following the similar procedure described in Scheme 3. (0.04 g, yield: 9.6%); purity: 98.54%.

Scheme 4:

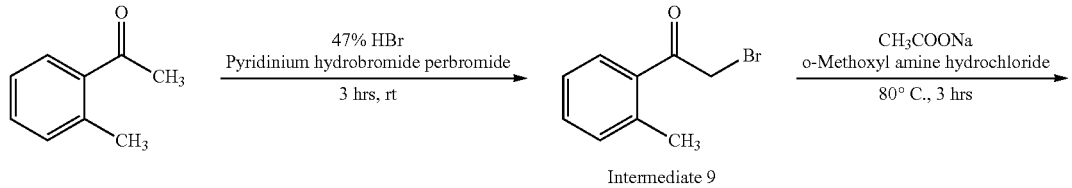

Intermediate 9

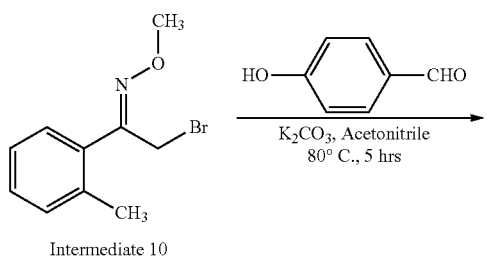

Intermediate 10

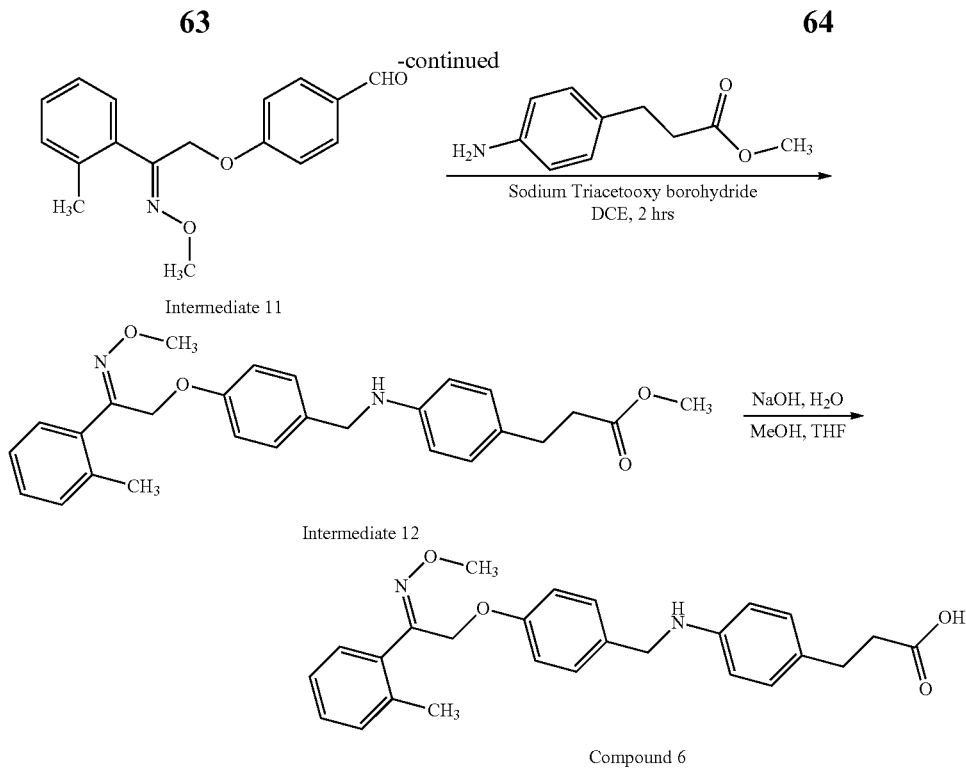

Intermediate 11

Intermediate 12

Compound 6

Example 6

3-{4-[(4-{[(2Z)-2-(Methoxyimino)-2-(2-methylphenyl)ethyl]oxy}benzyl)amino]phenyl}propanoic acid (6)

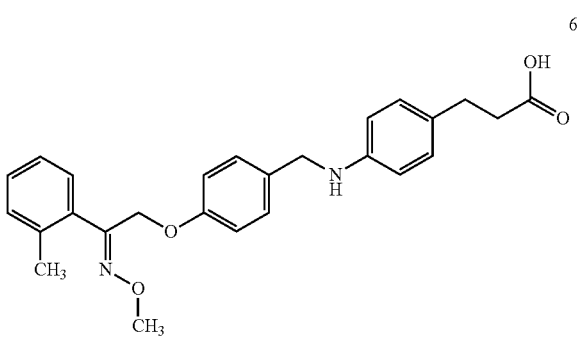 [SMILES: CO/N=C(\COc1ccc(CNc2ccc(CCC(=O)O)cc2)cc1)c1ccccc1C]

Compound 6 was synthesized from 4-{[(2Z)-2-(methoxyimino)-2-(2-methylphenyl)ethyl]oxy}benzaldehyde and 3-(4-aminophenyl)propanoic acid by following the procedure described in Scheme 4

Intermediate 9: 2-Bromo-1-(2-methylphenyl)ethanone

To a 250 mL RB flask fitted with magnetic stirrer was charged 60 mL of Acetic acid. To the stirred solvent was added 1-o-tolyl-ethanone (3.0 g, 22.35 mmol) RM cooled to 0° C. was added 47% hydrobromic acid (9.7 mL, 178.63 mmol), pyridinium hydro bromide per bromide (8.6 g, 26.89 mmol) slowly. The resulting mixture was stirred at RT for 3 h. The RM was then quenched with 10% sodium bicarbonate solution in water (150 mL) at 0° C. and extracted with ethyl acetate (75 mL×2). The organic layer was washed with saturated brine solution (50 mL) and dried over anhydrous $Na_2SO_4$ and evaporated to dryness. The crude compound thus obtained was purified by column chromatography on silica gel (100/200 mesh), using petroleum ether (60-80) and ethyl acetate (ratio) as eluent to give the product (2.50 g, yield: 52.5%)

Intermediate 10: (1Z)-2-Bromo-N-methoxy-1-(2-methylphenyl)ethanimine

Procedure is as same as described for intermediate 6 in scheme 3.

Intermediate 11: 4-{[(2Z)-2-(Methoxyimino)-2-(2-methylphenyl)ethyl]oxy}benzaldehyde Procedure is as same as described for intermediate 7 in scheme 3.

Intermediate 12: Methyl 3-{4-[(4-{[(2Z)-2-(methoxyimino)-2-(2-methylphenyl)ethyl]oxy}benzyl)amino]phenyl}propanoate Procedure is as same as described for intermediate 8 in scheme 3.

Compound 6: 3-{4-[(4-{[(2Z)-2-(Methoxyimino)-2-(2-methylphenyl)ethyl]oxy}benzyl)amino]phenyl}propanoic acid Compound 6 was synthesized from 4-{[(2Z)-2-(methoxyimino)-2-(2-methylphenyl)ethyl]oxy}benzaldehyde and 3-(4-aminophenyl)propanoic acid by following the procedure described in Scheme 3 (0.10 g, yield: 5.5%); purity: 97.84%.

Scheme 5:

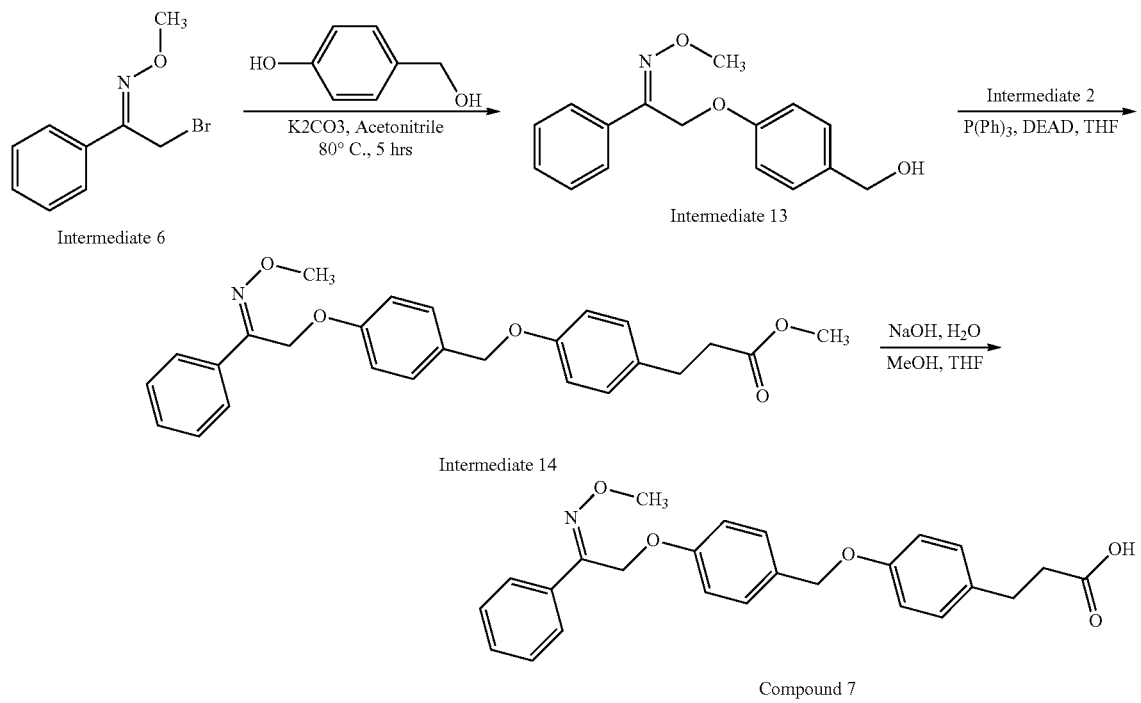

Example 7

3-{4-[(4-{[(2Z)-2-(Methoxyimino)-2-phenylethyl]oxy}benzyl)oxy]phenyl}propanoic acid (7)

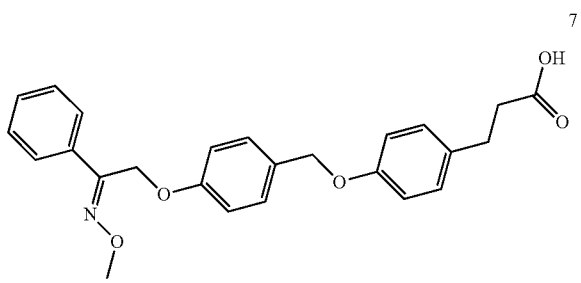 [SMILES: CO/N=C(\COc1ccc(COc2ccc(CCC(=O)O)cc2)cc1)c1ccccc1]

Compound 7 was synthesized from (4-{[(2Z)-2-(methoxyimino)-2-phenylethyl]oxy}phenyl)methanol and methyl 3-(4-hydroxyphenyl)propanoate by following the procedure described in Scheme 5

Intermediate 13: (4-{[(2Z)-2-(Methoxyimino)-2-phenylethyl]oxy}phenyl)methanol To a 100 mL RB flask fitted with magnetic stirrer was charged 20 mL of acetonitrile. To the stirred solvent was added 4-Hydroxy-benzylalcohol (0.27 g, 2.175 mmol) and $K_2CO_3$ (0.4 g, 2.89 mmol). Then it was stirred for 5 min. 2-Bromo-1-phenyl-ethanone o-methyl-oxime (0.5 g, 2 mmol) was added. Then RM heated 80° C. for 5 h. After completion of the reaction (reaction monitored by TLC), the RM was concentrated in vacuum to remove the acetonitrile. To the residue was then added 10 mL of water and extracted with ethyl acetate (15 mL×2). The organic layer was washed with saturated brine solution (15 mL), dried over anhydrous $Na_2SO_4$ and evaporated to dryness gave the titled compound (0.5 g, yield: 92.2%); $^1$H NMR (300 MHz, DMSO-$d_6$): δ 7.61-7.64 (m, 2H), 7.38-7.40 (t, 3H), 7.18-7.21 (d, 2H), 6.83-6.86 (d, 2H), 5.20 (s, 2H), 5.02-5.06 (t, 1H), 4.38-4.39 (d, 2H), 3.99 (s, 3H).

Intermediate 14: Methyl 3-{4-[(4-{[(2Z)-2-(methoxyimino)-2-phenylethyl]oxy}benzyl)oxy]phenyl}propanoate To a 50 mL RB flask fitted with magnetic stirrer was charged dry THF (5.0 mL) and 2-(4-hydroxymethyl-phenoxy)-1-phenyl-ethanone o-methyl-oxime (0.25 g, 0.9 mmol). To the above mixture 3-(4-hydroxy-phenyl)-propanoic acid methyl ester (0.16 g, 0.889 mmol) was added and the resulting mixture stirred at 0° C. for 5 min. Triphenyl phosphine (0.3 g, 1.3 mmol) was added to the mixture and stirred at 0° C. for 15 min followed by the addition of diethylazadicarboxylate (0.23 g, 1.32 mmol). After stirring the resulting mixture at RT for 10 h, the RM was evaporated to remove the THF. The residue was diluted with water (15 mL) and extracted with ethyl acetate (15 mL×2). The organic layer was washed with saturated brine solution (15 mL) and dried over anhydrous $Na_2SO_4$. Concentration of the solvent and purification of the resulting residue by column chromatography on silica gel (100/200 mesh), using petroleum ether (60-80) and ethyl acetate (ratio) as eluent, gave the product (0.09 g, yield: 23.4%): MS (ESI, 120 eV): m/z=434.2 (M+H)$^+$; $^1$H NMR (300 MHz, DMSO-$d_6$): δ 7.62-7.64 (m, 2H), 7.38-7.40 (t, 3H), 7.32-7.34 (d, 2H), 7.09-7.12 (d, 2H), 6.86-6.92 (t, 4H), 5.20-5.22 (d, 2H), 4.93-4.95 (d, 2H), 3.97-3.99 (t, 3H), 3.55-3.56 (d, 3H), 2.74-2.79 (t, 2H), 2.55-2.59 (t, 2H).

Compound 7: 3-{4-[(4-{[(2Z)-2-(Methoxyimino)-2-phenylethyl]oxy}benzyl)oxy]phenyl}propanoic acid To a 25 mL RB flask fitted with magnetic stirrer was charged 2 mL of methanol and 1 mL of THF. To the stirred solvent, was added 3-{4-[4-(2-methoxyimino-2-phenyl-ethoxy)-benzyloxy]-phenyl}-propanoic acid methyl ester (0.085 g, 0.19 mmol). To the stirred solution, NaOH (0.015 g, 0.375 mmol) in water (1 mL) was added. The resulting solution was stirred at RT for 3 h. After completion of the reaction (reaction monitored by TLC), the solvent was evaporated under reduced pressure. The RM was diluted with 1 mL of water, cooled to 0° C., then acidified with 1N HCl (5 mL), and extracted with ethyl acetate (10 mL×2), organic layer was given water (5 mL) and saturated brine solution wash (5 mL), dried over anhydrous Na$_2$SO$_4$ and evaporated to dryness to yield colorless solid (0.050 g, yield: 63.3%); purity: 97.65%.

Scheme 6:

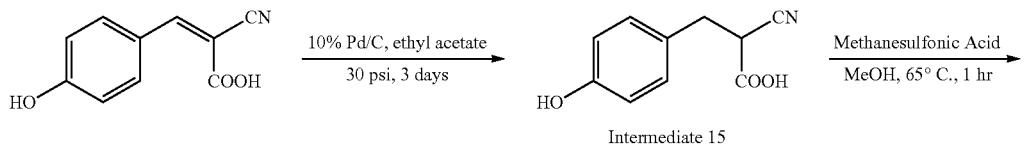

Intermediate 15

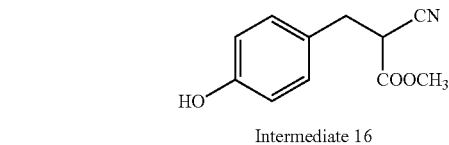

Intermediate 16

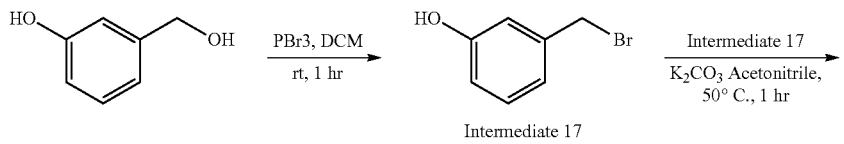

Intermediate 17

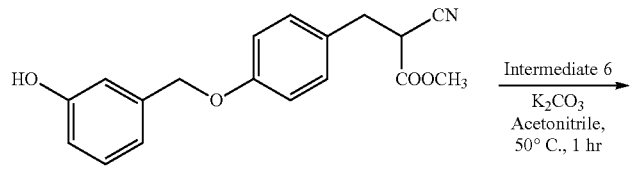

Intermediate 18

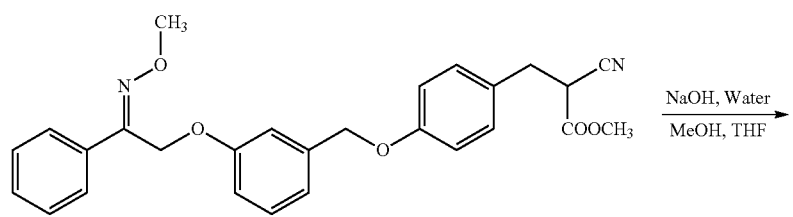

Intermediate 19

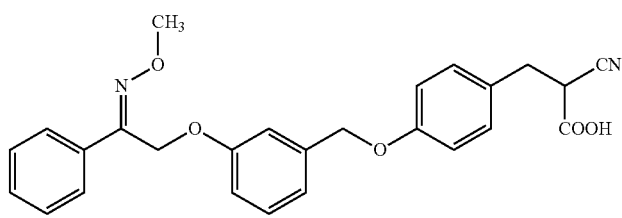

Compound 8

Example 8

2-Cyano-3-{4-[(3-{[(2E,2Z)-2-(methoxyimino)-2-phenylethyl]oxy}benzyl)oxy]phenyl}propanoic acid (8)

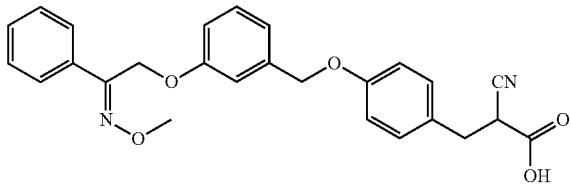

Compound 8 was synthesized from methyl 2-cyano-3-(4-hydroxyphenyl)propanoate and (3-{[(2E,2Z)-2-(methoxyimino)-2-phenylethyl]oxy}phenyl) methanol by following the procedure described in Scheme 6

Intermediate 15: 2-Cyano-3-(4-hydroxyphenyl)propanoic acid

To a 250 mL par shaker flask was charged 2-cyano-3-(4-hydroxy-phenyl)-acrylic acid (0.5 g, 2.6 mmol) in ethyl acetate (10 mL) and the solution was purged with nitrogen for 10 minutes. Then 10% palladium on carbon (0.07 g) was added under nitrogen atmosphere. After addition, the mixture was hydrogenated at 30 psi for 3 days. After completion of the reaction (monitored by TLC), the RM was filtered through celite bed and the residue was washed thoroughly with methanol (15 mL). After filtration, the filtrate was concentrated to distill off the solvent and dried under vacuum. The product was obtained as yellow liquid 0.5 g, yield: 98.9%): MS (ESI, 120 eV): m/z=192.1 (M+H)$^+$; $^1$H NMR (300 MHz, DMSO-d$_6$): δ 7.07-7.10 (d, 2H), 6.70-6.72 (d, 2H), 4.17-4.21 (t, 1H), 2.92-3.09 (m, 2H).

Intermediate 16: Methyl 2-cyano-3-(4-hydroxyphenyl)propanoate

To a 25 mL RB flask fitted with magnetic stirrer was charged 10 mL of methanol. To the stirred solvent was added 2-cyano-3-(4-hydroxy-phenyl)-propanoic acid (0.5 g, 2.62 mmol), followed by methanesulfonic aid (0.5 mL, 7.69 mmol). After addition, the RM was refluxed at 65° C. for 1 h. After 1 h, the solvent was evaporated, water (20 mL) was added and the organic layer was extracted with ethyl acetate (15 mL×2). The organic layer was dried over anhydrous Na$_2$SO$_4$ and the solvent was removed under reduced pressure. The product was obtained as brown liquid. (0.3 g, yield: 55.8%): MS (ESI, 120 eV): m/z=204.1 (M–H)$^+$.

Intermediate 17: 3-(Bromomethyl)phenol

To a 50 mL RB flask fitted with magnetic stirrer was charged 15 mL of dichloromethane. To the stirred solvent was added 3-hydroxymethyl-phenol (0.5 g, 4.03 mmol). The RM was brought to 0° C. and phosphorous tribromide (1.6 g, 0.56 mL, 6.04 mmol) was added drop wise. After addition, the RM was stirred at RT for 1 h. After 1 h, the RM was diluted with dichloromethane (25 mL) and the organic layer was washed with water (20 mL). The organic layer was dried over anhydrous Na$_2$SO$_4$ and the solvent was removed under reduced pressure. The product was obtained as brown solid. (0.65 g, yield: 86.3%); MS (ESI, 120 eV): m/z=187.0 (M+H)$^+$; $^1$H NMR (300 MHz, CDCl$_3$): δ 7.10-7.15 (t, 1H), 6.86-6.89 (d, 1H), 6.80 (d, 1H), 6.67-6.71 (m, 1H), 4.35-4.36 (d, 2H), 3.80-3.94 (bro s, 1H).

Intermediate 18: Methyl 2-cyano-3-{4-[(3-hydroxy-benzyl)oxy]phenyl}propanoate To a 50 mL RB flask fitted with magnetic stirrer was charged 10 mL of acetonitrile. To the stirred solvent was added 2-cyano-3-(4-hydroxy-phenyl)-propanoic acid methyl ester (0.3 g, 1.57 mmol), followed by K$_2$CO$_3$ (0.65 g, 4.71 mmol) and 3-bromomethyl-phenol (0.294 g, 1.57 mmol). After addition, the RM was heated at 50° C. for 1 h. After 1 h, the RM was concentrated to distill off the solvent, water (20 mL) was added and the aqueous layer was extracted with ethyl acetate (15 mL×2). The organic layer was dried over anhydrous Na$_2$SO$_4$. The solvent was removed under reduced pressure. The product was obtained as yellow liquid. (0.32 g, yield: 65.44%); MS (ESI, 120 eV): m/z=310.0 (M–H)$^+$.

Intermediate 19: Methyl 2-cyano-3-{4-[(3-{[(2E,2Z)-2-(methoxyimino)-2-phenylethyl]oxy}benzyl)oxy]phenyl}propanoate To a 50 mL RB flask fitted with magnetic stirrer was charged 10 mL of acetonitrile. To the stirred solvent was added 2-cyano-3-[4-(3-hydroxy-benzyloxy)-phenyl]-propanoic acid methyl ester (0.32 g, 1.027 mmol), followed by K$_2$CO$_3$ (0.425 g, 3.081 mmol). Then 2-bromo-1-phenyl-ethanone o-methyl-oxime (0.234 g, 1.027 mmol) was added. After addition, the RM was heated at 50° C. for 1 h. After 1 h, the RM was concentrated; water (20 mL) was added and extracted with ethyl acetate (15 mL×2). The organic layer was dried over anhydrous Na$_2$SO$_4$. The solvent was removed under reduced pressure. The product was obtained as pale yellow liquid. (0.07 g, yield: 14.85%); MS (ESI, 120 eV): m/z=459.1 (M+H)$^+$.

Compound 8: 2-Cyano-3-{4-[(3-{[(2E,2Z)-2-(methoxyimino)-2-phenylethyl]oxy}benzyl)oxy]phenyl}propanoic acid To a 10 mL RB flask fitted with magnetic stirrer was charged 3 mL of THF. To the stirred solvent was added 2-cyano-3-{4-[3-(2-methoxyimino-2-phenyl-ethoxy)-benzyloxy]-phenyl}-propanoic acid methyl ester (0.07 g, 0.152 mmol) and methanol (3 mL). The RM was brought to 0° C. and sodium hydroxide (0.03 g) in water (1 mL) was added drop wise. Then the reaction was stirred at RT for 1 h. After 1 h, the solvents were evaporated and the crude was dissolved in minimum amount of water (2 mL) and the aqueous layer was washed with ether (5 mL×2). The aqueous layer was acidified to pH 3 with 1N hydrochloric acid. The aqueous layer was extracted with ethyl acetate (5 mL×2). The organic layer was washed with saturated brine solution (5 mL) and dried over anhydrous Na$_2$SO$_4$. The solvent was removed under reduced pressure, solid obtained as pale yellow semi-solid. (0.015 g, yield: 22.1%); purity: 85.1%.

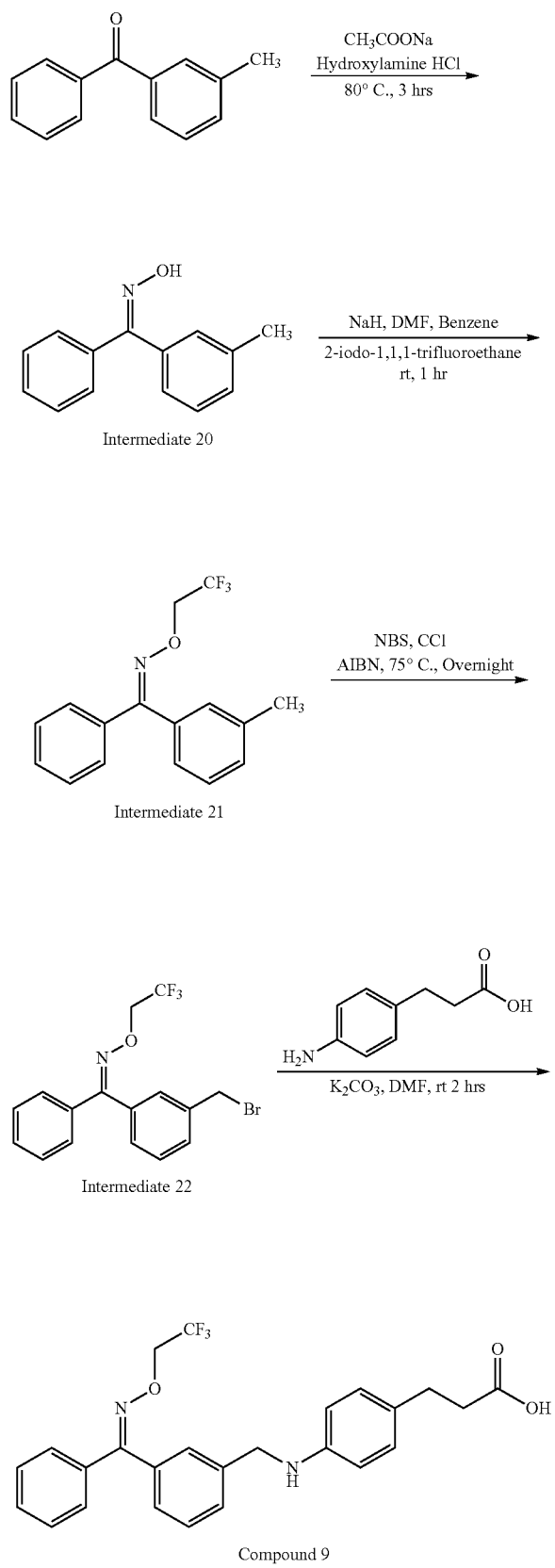

Example 9

3-{4-[(3-{(E,Z)-Phenyl[(2,2,2-trifluoroethoxy)imino]methyl}benzyl)amino]phenyl}propanoic acid (9)

Compound 9 was synthesized from (E,Z)-1-[3-(bromomethyl)phenyl]-1-phenyl-N-(2,2,2-trifluoroethoxy) methanimine and 3-(4-aminophenyl) propanoic acid by following the procedure described in Scheme 7.

Intermediate 20: (E,Z)-N-Hydroxy-1-(3-methylphenyl)-1-phenylmethanimine

To a 100 mL RB flask fitted with magnetic stirrer was charged 20 mL of acetic acid. To the stirred solvent was added (3-methylphenyl) (phenyl) methanone (2 g, 10 mmol) and sodium acetate (1.06 g, 1.3 eq). Then it was stirred for 5 min, hydroxylamine hydrochloride (0.89 g, 1.2 eq) was added. The RM heated 80° C. for 3 h. After completion of the reaction (reaction monitored by TLC), RM poured into water (75 mL) and extracted with ethyl acetate (50 mL×2). The organic layer was washed with saturated brine solution (40 mL), dried over anhydrous $Na_2SO_4$ and evaporated to dryness and purified by silica gel (100/200 mesh), using petroleum ether (60-80) and ethyl acetate gave title compound (1.6 g, yield: 74.4%); MS (ESI, 120 eV): m/z=212.1 $(M+H)^+$; $^1H$ NMR (300 MHz, DMSO-$d_6$): δ 11.27-11.28 (d, 1H), 7.04-7.48 (m, 9H), 2.27-2.33 (d, 3H).

Intermediate 21: (E,Z)-1-(3-Methylphenyl)-1-phenyl-N-(2,2,2-trifluoroethoxy)methanimine To a 50 mL RB flask fitted with magnetic stirrer was charged 5 mL of DMF. To the stirred solvent was added sodium hydride (60%) at 0° C., followed by (Z)—N-hydroxy-1-(3-methylphenyl)-1-phenylmethanimine (0.6 g, 2.8 mmol), in 1:1 mixture of DMF and benzene, at 0° C. and stirred at 0° C. for 30 min. 2-Iodo-1,1,1-trifluoroethane (0.71 g, 3.4 mmol) was added and the resulting mixture was stirred at RT for 1 h. After completion of the reaction (reaction monitored by TLC), RM poured into water (5 mL) extracted with ethyl acetate (15 mL×2). The organic layer washed with saturated brine solution (15 mL), dried over anhydrous $Na_2SO_4$, evaporated to dryness and purified by column chromatography on silica gel (100/200 mesh), using petroleum ether (60-80) and ethyl acetate, gave the title compound (0.23 g, yield: 28.1%): MS (ESI, 120 eV): m/z=294.1 $(M+H)^+$; $^1H$ NMR (300 MHz, $CDCl_3$): δ 7.06-7.39 (m, 9H), 4.41-4.49 (q, 2H), 2.26-2.30 (d, 3H).

Intermediate 22: (E,Z)-1-[3-(Bromomethyl)phenyl]-1-phenyl-N-(2,2,2-trifluoroethoxy)methanimine To a 100 mL RB flask fitted with magnetic stirrer was charged with 50 mL of $CCl_4$, added (E,Z)-1-(3-methylphenyl)-1-phenyl-N-(propan-2-yloxy)methanimine (0.22 g, 0.7 mmol), N-bromosuccinimide (0.14 g, 0.8 mmol) and AIBN (0.011 g, 0.07 mmol). The resulting mixture was refluxed at 75° C. for 8 h. After completion of the reaction (reaction monitored by TLC), RM was quenched with ice cold water (5 mL) and extracted with chloroform (10 mL×2). The organic layer was washed with saturated brine solution (10 mL), dried over anhydrous $Na_2SO_4$, purified by column chromatography, using petroleum ether (60-80) and ethyl acetate gave the product (0.175 g, yield: 67.3%): MS (ESI, 120 eV): m/z=372.0 $(M+H)^+$; $^1H$ NMR (300 MHz, $CDCl_3$): δ 7.19-7.46 (m, 9H), 4.39-4.50 (m, 4H).

Compound 9: 3-{4-[(3-{(E,Z)-Phenyl[(2,2,2-trifluoroethoxy)imino]methyl}benzyl)amino]phenyl}propanoic acid To a 100 mL RB flask fitted with magnetic stirrer was charged 5 mL of DMF. To the stirred solvent was added 3-(4-amino-phenyl)-propanoic acid (0.068 g, 0.41 mmol) and $K_2CO_3$ (0.15 g, 1.085 mmol). Then it was stirred for 15 min. (E,Z)-1-[3-(bromomethyl)phenyl]-1-phenyl-N-(propan-2-yloxy)methanimine (0.17 g, 0.45 mmol) was added. Then RM stirred at RT for 2 h. After completion of the reaction (reaction monitored by TLC), RM evaporated to remove the DMF, then added water (5 mL) extracted with ethyl acetate (5 mL×2). The organic layer was washed with saturated brine solution (5 mL), dried over anhydrous $Na_2SO_4$, evaporated to dryness and purified by prep TLC using 30% ethyl acetate in petroleum ether (60-80) yielded the title compound (0.020 g, yield: 10.7%); purity: 95.01%:

Example 10

3-{4-[(3-{(E,Z)-Phenyl[(propan-2-yloxy)imino]methyl}benzyl)amino]phenyl}propanoic acid (10)

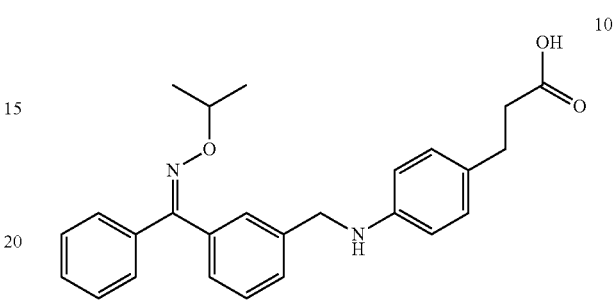

Compound 10 was synthesized from (E,Z)-1-[3-(bromomethyl)phenyl]-1-phenyl-N-(propan-2-yloxy)methanimine (0.38 g, 1.14 mmol) and 3-(4-aminophenyl)propanoic acid (0.17 g, 1.02 mmol) by following the similar procedure described in Scheme 7. (0.02 g, Yield: 4.2%); Purity: 87.98%.

Scheme 8:

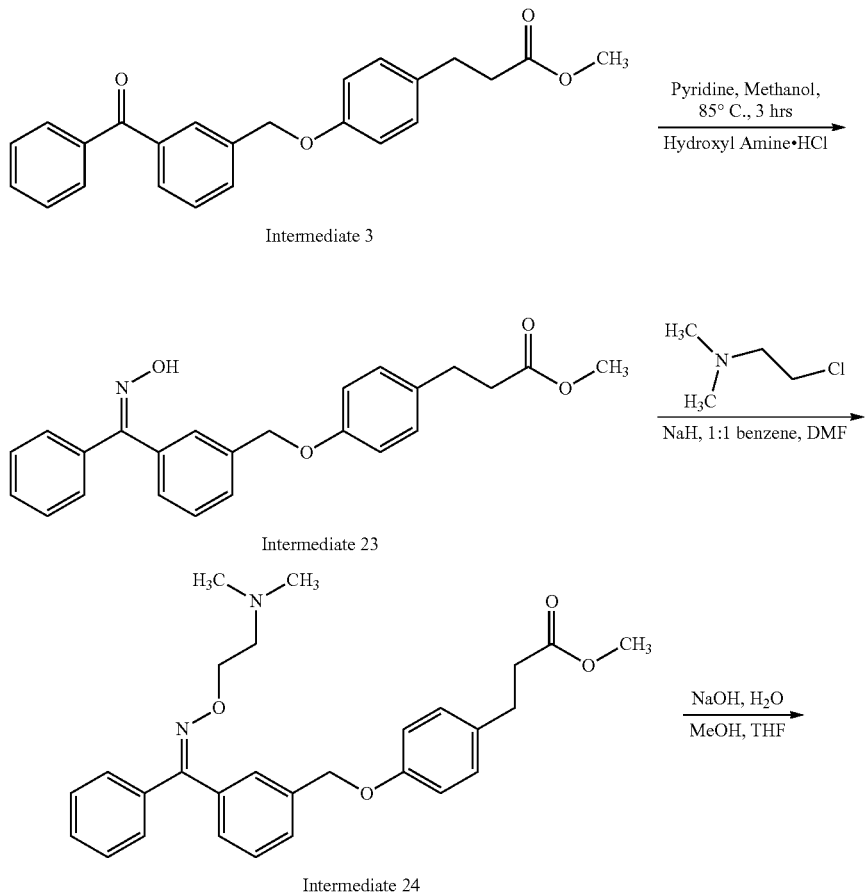

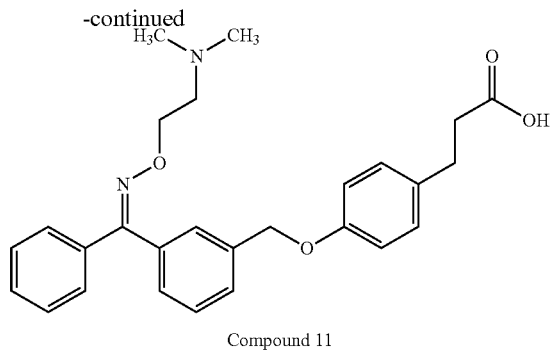

Compound 11

Example 11

3-[4-({3-[(E,Z)-{[2-(Dimethylamino)ethoxy]imino}(phenyl)methyl]benzyl}oxy)phenyl]propanoic acid (11)

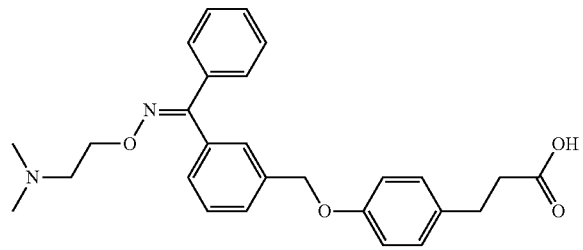

11

Compound 11 was synthesized from 2-chloro-N,N-dimethylethanamine and methyl 3-[4-({3-[(Z)-(hydroxy imino)(phenyl)methyl]benzyl}oxy)phenyl]propanoate by following the procedure described in Scheme 8.

Intermediate 23: Methyl 3-[4-({3-[(E,Z)-(hydroxy imino)(phenyl)methyl]benzyl}oxy)phenyl]propanoate To a 100 mL RB flask fitted with magnetic stirrer and reflux condenser was charged with 35 mL of ethanol and 7.8 mL of pyridine. To the stirred solution was added 3-[4-(3-Benzoyl-benzyloxy)-phenyl]-propanoic acid methyl ester (1.31 g, 3.498 mmol) followed by hydroxylamine hydrochloride (1.2 g, 17.494 mmol). The resulting solution was refluxed at 85° C. for 3 h. After completion of the reaction (reaction monitored by TLC), reaction solvent was removed under reduced pressure and the resulting crude mass was taken in dichloromethane (100 mL). The organic layer was washed with water (100 mL×2) and saturated brine solution (100 mL). The organic layer was dried over anhydrous Na$_2$SO$_4$ and the solvent was removed under reduced pressure. The resulting crude compound was purified by column chromatography on silica gel (100/200 mesh), using petroleum ether (60-80) and ethyl acetate (ratio) as eluent. The product was obtained as yellow syrup (1.05 g, yield: 78.4%): MS (ESI, 120 eV): m/z=390.2 (M+H)$^+$; $^1$H NMR (300 MHz, CDCl$_3$): δ 11.36-11.37 (s, 1H), 7.46-7.49 (m, 4H), 7.36-7.43 (m, 2H), 7.25-7.33 (m, 3H), 7.10-7.13 (m, 2H), 6.85-6.92 (m, 2H), 5.05-5.09d, 2H), 3.56 (s, 3H), 2.72-2.79 (m, 2H), 2.55-2.60 (m, 2H).

Intermediate 24: Methyl 3-[4-({3-[(E,Z)-{[2-(dimethylamino)ethoxy]imino}(phenyl)methyl]benzyl}oxy)phenyl]propanoate To a 100 mL RB flask fitted with magnetic stirrer and reflux condenser charged with NaH (0.051 g, 1.28 mmol) and 6 mL of DMF was added under nitrogen atmosphere. The RM was cooled to 0° C. and to the stirred mass was added 3-{4-[3-(hydroxy imino-phenyl-methyl)-benzyloxy]-phenyl}propanoic acid methyl ester (0.5 g, 1.28 mmol), in a 1:1 benzene, DMF mixture (4 mL). The resulting mixture was then stirred for 15 minutes and was added 2-chloro-N,N-dimethyl ethyl amine hydrochloride (0.20 g, 1.41 mmol) at 0° C. The resulting solution was heated at 45° C. for 3 h. After completion of the reaction (reaction monitored by TLC), reaction solvent was removed under reduced pressure. The resulting crude mass was taken in diethyl ether (100 mL), washed with water (50 mL×2) and saturated brine solution (50 mL). The organic layer was dried over anhydrous Na$_2$SO$_4$ and the solvent was removed under reduced pressure. The resulting crude compound was purified by column chromatography on silica gel (100/200 mesh), using petroleum ether (60-80) and ethyl acetate as eluent. The product was obtained as yellow syrup (0.175 g, yield: 29.7%): MS(ESI, 120 eV): m/z=461.2 (M+H)$^+$; $^1$H NMR (300 MHz, CDCl$_3$): δ 7.39-7.41 (m, 2H), 7.31-7.36 (m, 4H), 7.24-7.28 (m, 3H), 7.02-7.05 (d, 2H), 6.78-6.84 (m, 2H), 4.93-4.97 (d, 2H), 4.25-4.28 (t, 2H), 3.59 (s, 3H), 2.79-2.85 (t, 2H), 2.66-2.67 (d, 2H), 2.50-2.55 (t, 2H), 2.18-2.28 (m, 6H).

Compound 11: 3-[4-({3-[(E,Z)-{[2-(Dimethylamino)ethoxy]imino}(phenyl)methyl]benzyl}oxy)phenyl]propanoic acid To a 50 mL RB flask fitted with magnetic stirrer was charged 3 mL of THF, 0.5 mL water, and 0.5 mL methanol. To the stirred solvent was added 3-(4-{3-[(2-dimethylamino-ethoxyimino)-phenyl-methyl]-benzyloxy}phenyl)-propanoic acid methyl ester (0.1 g, 0.217 mmol) followed by the addition of sodium hydroxide (0.026 g, 0.651 mmol). The resulting solution was stirred at RT for 15 h. After completion of the reaction (reaction monitored by TLC), RM was diluted with 10 mL of water and washed with dichloride methane (20 mL×2). The aqueous layer was acidified to pH 3 with concentrated hydrochloric acid and extracted with DCM (75 mL×3). The DCM layer was dried over anhydrous Na$_2$SO$_4$ and the solvent was removed under reduced pressure. The product was obtained as white solid (0.045 g, yield: 15.5%, purity: 85.01%).

Scheme 9:

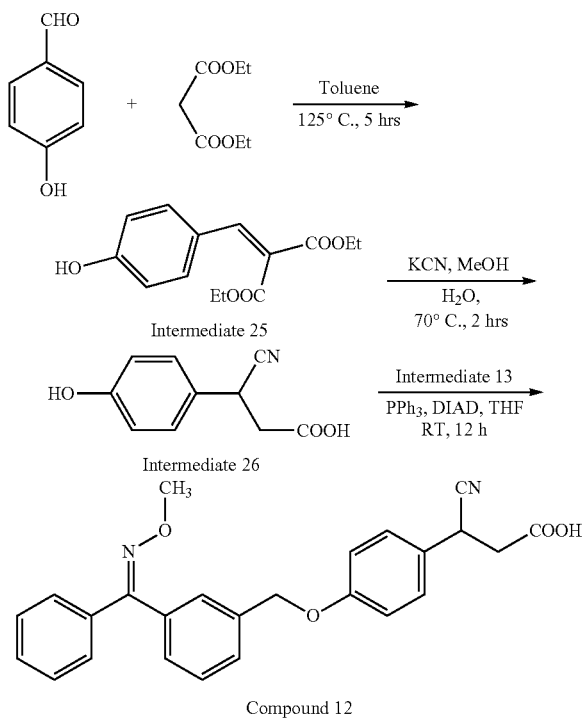

Compound 12

Example 12

3-Cyano-3-[4-({3-[(E,Z)-(methoxyimino)(phenyl)methyl]benzyl}oxy)phenyl]propanoic acid (12)

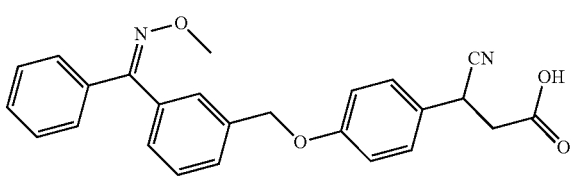

12

Compound 12 was synthesized from 3-cyano-3-(4-hydroxyphenyl)propanoic acid and (1E,1Z)-2-bromo-N-methoxy-1-phenylethanimine by following the procedure described in Scheme 9.

Intermediate 25: Diethyl (4-hydroxybenzylidene)propanedioate

To a 100 mL RB flask fitted with magnetic stirrer was charged with piperidine (0.426 g, 0.5 mL, 5 mmol) and acetic acid (0.3 g, 0.3 mL, 5 mmol). To this, toluene (25 mL) was added, followed by 4-hydroxybenzaldehyde (2 g, 16.4 mmol) and diethyl malonate (3.15 g, 19.7 mmol). The RM was heated at 125° C., by fitted with a dean-stark's apparatus for 5 h. After 5 h, the RM was concentrated; water (50 mL) was added and extracted with ethyl acetate (50 mL×2)). The organic layer was washed with saturated brine solution (50 mL). The organic layer was dried over anhydrous $Na_2SO_4$ and the solvent was removed under reduced pressure. The product was obtained as yellow solid. (2 g, yield: 46.2%); MS (ESI, 120 eV): m/z=263.1 (M−H)$^+$; $^1$H NMR (300 MHz, DMSO-d$_6$): δ 10.27 (s, 1H), 7.58 (s, 1H), 7.36-7.38 (d, 2H), 6.81-6.84 (d, 2H), 4.17-4.32 (m, 4H), 4.06-4.14 (q, 1H), 1.21-1.26 (t, 6H).

Intermediate 26: 3-Cyano-3-(4-hydroxyphenyl)propanoic acid

To a 25 mL RB flask fitted with magnetic stirrer was charged with methanol (6 mL) and water (1 mL). To the stirred solvent was added 2-(4-hydroxy-benzylidene)-malonic acid diethyl ester (1 g, 3.8 mmol), followed by potassium cyanide (0.492 g, 7.6 mmol). The RM was heated at 70° C. for 2 h. The RM was concentrated, diluted with saturated $NaHCO_3$ solution (50 mL) and washed with ethyl acetate (50 mL×2). The aqueous layer was acidified to pH 3 with 1N hydrochloric acid and extracted with ethyl acetate (50 mL×2). The organic layer was washed with water (50 mL) and saturated brine solution (50 mL). The organic layer was dried over anhydrous $Na_2SO_4$ and the solvent was removed under reduced pressure. The product was obtained as brown liquid. (0.6 g, yield: 72.3%); MS (ESI, 120 eV): m/z=190.0 (M−H)$^+$; $^1$H NMR (300 MHz, DMSO-d$_6$): δ 12.69 (s, 1H), 9.58 (s, 1H), 7.22-7.24 (d, 2H), 6.75-6.78 (d, 2H), 4.28-4.40 (m, 1H), 2.77-3.12 (m, 2H).

Compound 12: 3-Cyano-3-[4-({3-[(E,Z)-(methoxyimino)(phenyl)methyl]benzyl}oxy)phenyl]propanoic acid To a 25 mL RB flask fitted with magnetic stirrer was charged ethanol (3 mL). To the stirred solvent was added 3-cyano-3-(4-hydroxy-phenyl)-propanoic acid (0.1 g, 0.52 mmol), (3-bromomethyl-phenyl)-phenyl-methanone o-methyl-oxime (0.159 g, 0.52 mmol) and sodium hydroxide (0.03 g, 0.75 mmol) in water (1 mL). The RM was stirred at RT for 8 h. The RM was concentrated, water (10 mL) was added and extracted with ethyl acetate (15 mL×2). The organic layer was dried over anhydrous $Na_2SO_4$ and the solvent was removed under reduced pressure. The product was obtained as pale yellow solid (0.017 g, yield: 7.8%); Purity: 94.19%.

Scheme 10:

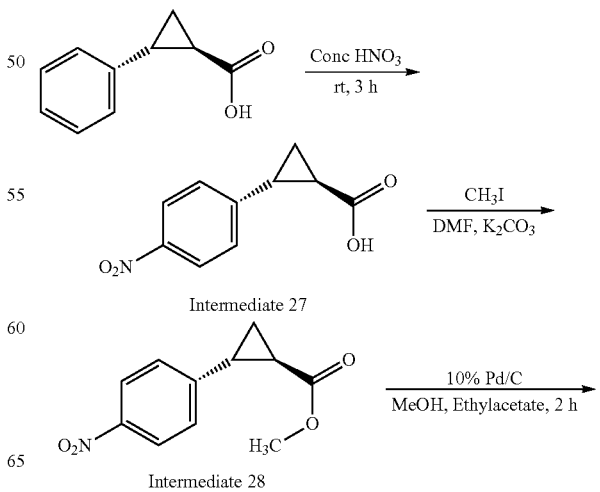

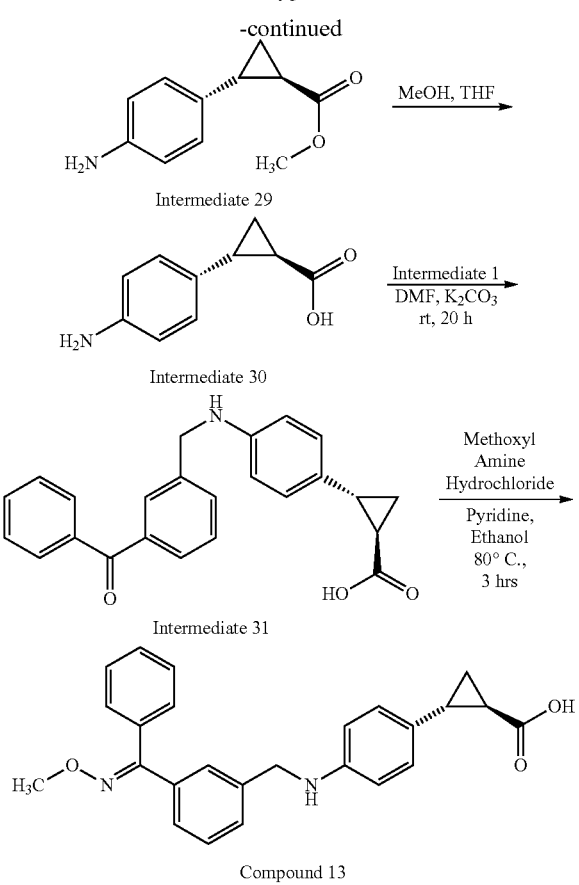

Example 13

(1R,2R)-2-[4-({3-[(E,Z)-(Methoxyimino)(phenyl)methyl]benzyl}amino)phenyl]cyclopropanecarboxylic acid (13)

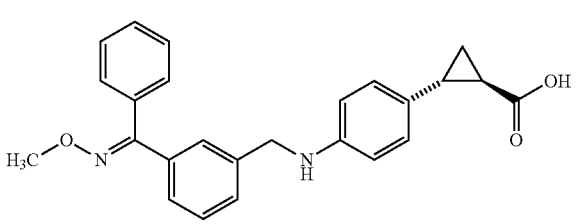

Compound 13 was prepared by using (1R,2R)-2-{4-[(3-benzoylbenzyl)amino]phenyl}cyclopropane carboxylic acid (0.5 g, 1.3 mmol), and methoxylamine hydrochloride (0.56 g, 6.7 mmol) by following the procedure described in Scheme 10.

Intermediate 27: (1R,2R)-2-(4-Nitrophenyl)cyclopropanecarboxylic acid

To a 1000 mL RB flask fitted with magnetic stirrer was charged with 150 mL of $HNO_3$, cooled to 0° C., was added (1R,2R)-2-phenylcyclopropanecarboxylic acid (15 g, 92.593 mmol) portion wise for half an hour, RM brought to RT and stirred for 3 h. After the completion of reaction, RM was poured into ice cold water, stirred for 30 min and filtered off the product and dried under vacuum. The obtained product was white color solid (15 g, yield: 78.2%).

Intermediate 28: Methyl (1R,2R)-2-(4-nitrophenyl)cyclopropanecarboxylate

To a 500 mL RB flask fitted with magnetic stirrer was charged with 120 mL of DMF. To the stirred solvent was added (1R,2R)-2-(4-nitrophenyl)cyclo propane carboxylic acid (15 g, 72 mmol), $K_2CO_3$ (29 g, 217 mmol) and methyl iodide (5.5 mL, 86 mmol), stirred at RT for 8 h. The RM was poured into water (100 mL) and extracted with ethyl acetate (150 mL×2). The organic layer was washed with saturated $NaHCO_3$ solution (50 mL), water (50 mL) and saturated brine solution (50 mL). The organic layer was dried over anhydrous $Na_2SO_4$ and the solvent was removed under reduced pressure. The product was obtained as pale yellow color liquid (14 g, yield: 87.9%). MS (ESI, 120 eV): m/z=206.1 (M−H)$^+$.

Intermediate 29: Methyl (1R,2R)-2-(4-aminophenyl)cyclopropanecarboxylate

To a 1000 mL parr hydrogenater flask with methanol (70 mL) and ethyl acetate (70 mL), was added methyl (1R,2R)-2-(4-nitrophenyl)cyclo propane carboxylate (14 g, 63.3 mmol) and 10% Pd/C (2 g) under $N_2$ atmosphere. The RM was hydrogenated at 40 psi for 5 h. RM was diluted with ethyl acetate (100 mL), filtered through celite bed to remove Pd/C and evaporated to dryness under reduced pressure. The crude was purified by flash column chromatography on silica gel (230/400 mesh), to give the product (4 g, yield: 33.1%). MS (ESI, 120 eV): m/z=192.1 (M+H)$^+$; $^1$H NMR (300 MHz, $CDCl_3$): δ 6.83-6.86 (d, 2H), 6.58-6.61 (d, 2H), 3.63 (s, 3H), 2.36-2.39 (m, 1H), 1.69-1.75 (m, 1H), 1.42-1.49 (m, 1H), 1.14-1.20 (m, 1H).

Intermediate 30: (1R,2R)-2-(4-Aminophenyl)cyclopropanecarboxylic acid

To a 25 mL RB flask fitted with magnetic stirrer was charged 5 mL of methanol: and 5 mL of THF. To the stirred solvent, was added methyl (1R,2R)-2-(4-aminophenyl)cyclo propane carboxylate (1 g, 5.23 mmol) and NaOH (0.627 g, 15.69 mmol) in water (3 mL). The resulting solution was stirred at RT for 3 h. After completion of the reaction (reaction monitored by TLC), solvent was removed under reduced pressure. The RM was diluted with 3 mL of water, cooled to 0° C., then acidified to pH 3 with 1N HCl, and extracted with ethyl acetate (50 mL×2). The organic layer was washed water (50 mL), and saturated brine solution (30 mL). The organic layer was dried over anhydrous $Na_2SO_4$ and the solvent was removed under reduced pressure. The product was obtained as white color solid (0.9 g, yield: 97.2%).

Intermediate 31: (1R,2R)-2-{4-[(3-Benzoylbenzyl)amino]phenyl}cyclopropane carboxylic acid It was prepared from (1R,2R)-2-(4-aminophenyl)cyclopropane carboxylic acid (0.7 g, 3.9 mmol) and [3-(bromomethyl)phenyl](phenyl)methanone (0.9 g, 3.2 mmol) by following the procedure described in Scheme 2 for Intermediate 5. (0.5 g, Yield: 39%). MS (ESI, 120 eV): m/z=372.0 (M+H)$^+$.

Compound 13: (1R,2R)-2-[4-({3-[(E,Z)-(Methoxy-imino)(phenyl)methyl]benzyl}amino)phenyl]cyclopropanecarboxylic acid It was prepared from (1R,2R)-2-{4-[(3-benzoylbenzyl)amino]phenyl}cyclopropanecarboxylic acid (0.5 g, 1.3 mmol), and methoxylamine hydrochloride (0.56 g, 6.7 mmol) by following the procedure described in Scheme 2 for Compound 2 (0.01 g, yield: 1.9%); purity: 94.46% (48.37%: 44.56%).

Example 14

(1R,2R)-2-{4-[(4-{[(2E,2Z)-2-(Methoxyimino)-2-phenylethyl]oxy}benzyl)amino]phenyl}cyclopropanecarboxylic acid (14)

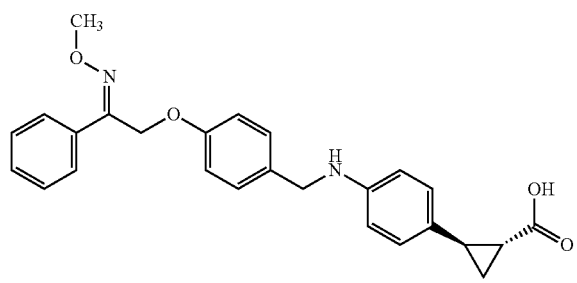

14

Compound 14 was synthesized from methyl (1R,2R)-2-(4-aminophenyl)cyclo propane carboxylate (0.3 g, 1.5 mmol) and 4-{[(2)-2-(methoxyimino)-2-phenylethyl]oxy}benzaldehyde (0.4 g, 1.5 mmol) by following the procedure described in Scheme 10 (0.15 g, yield: 23.8%); purity: 95.4%.

Example 15

(1R,2R)-2-{4-[(4-{[(2Z)-2-(Methoxyimino)-2-(2-methylphenyl)ethyl]oxy}benzyl)amino]phenyl}cyclopropanecarboxylic acid (15)

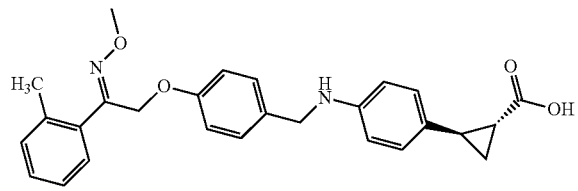

15

Compound 15 was synthesized from methyl (1R,2R)-2-(4-aminophenyl)cyclopropane carboxylate (0.18 g, 0.9 mmol) and 4-{[(2Z)-2-(methoxyimino)-2-(2-methylphenyl)ethyl]oxy}benzaldehyde (0.31 g, 1.1 mmol) by following the procedure described in Scheme 3 (0.12 g, yield: 28%); Purity: 91.26%.

Example 16

3-Cyano-3-{4-[(4-{[(2Z)-2-(methoxyimino)-2-phenylethyl]oxy}benzyl)oxy]phenyl}propanoic acid (16)

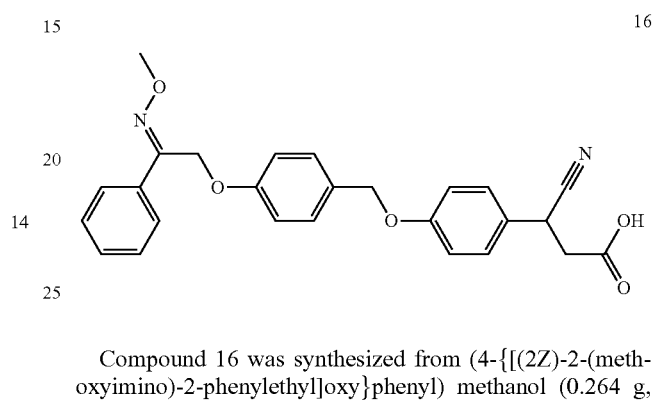

16

Compound 16 was synthesized from (4-{[(2Z)-2-(methoxyimino)-2-phenylethyl]oxy}phenyl) methanol (0.264 g, 0.98 mmol) and methyl 3-cyano-3-(4-hydroxyphenyl)propanoate (0.2 g, 0.98 mmol) by following the procedure described in Scheme 5 (0.15 g, yield: 34.7%); Purity: 98.2%:

Scheme 11:

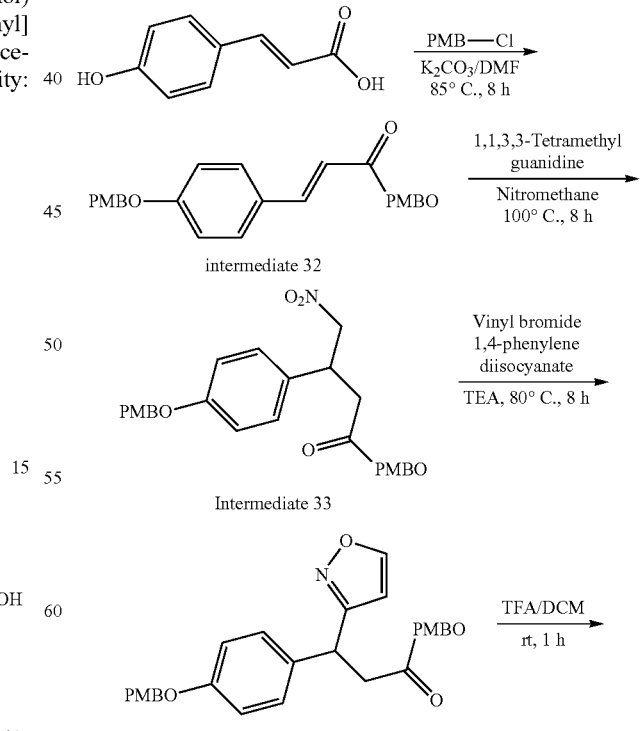

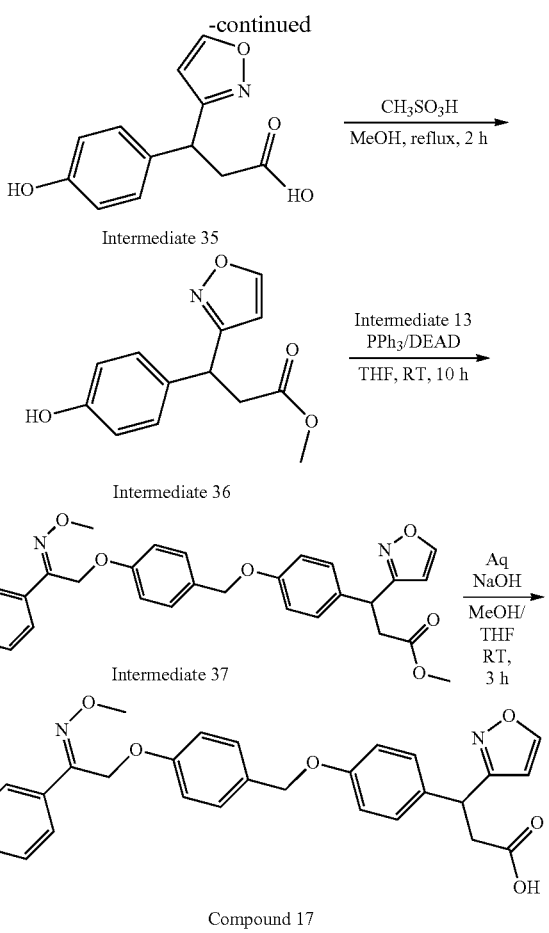

Example 17

3-{4-[(4-{[(2Z)-2-(methoxyimino)-2-phenylethyl]oxy}benzyl)oxy]phenyl}-3-(1,2-oxazol-3-yl)propanoic acid (17)

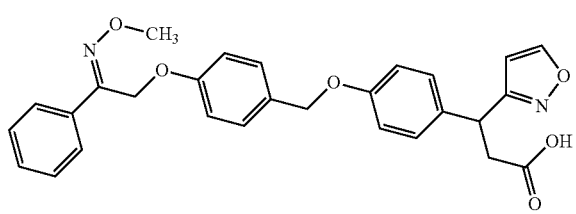

Compound 17 was prepared by using methyl 3-(4-hydroxyphenyl)-3-(1,2-oxazol-3-yl)propanoate and (4-{[(2Z)-2-(Methoxyimino)-2-phenylethyl]oxy}phenyl) methanol by following the procedure described in Scheme 11.

Intermediate 32: 4-methoxybenzyl (2Z)-3-{4-[(4-methoxybenzyl)oxy]phenyl}prop-2-enoate To a 250 mL RB flask fitted with magnetic stirrer was charged with 25 mL of DMF. To the stirred solvent were added (2Z)-3-(4-hydroxyphenyl)prop-2-enoic acid (2 g, 12.18 mmol), $K_2CO_3$ (6.67 g, 48.73 mmol) and 1-(chloro methyl)-4-methoxybenzene (3.81 g, 24.36 mmol), stirred at 85° C. for 8 h under nitrogen atmosphere. The RM was concentrated by removal of solvent. The crude was dissolved in ethyl acetate (100 mL). The organic layer was washed with water (50 mL) and saturated brine solution (50 mL). The organic layer was dried over anhydrous $Na_2SO_4$ and the solvent was removed under reduced pressure. The product was obtained as white color solid (4.5 g, yield: 91.83%). MS (ESI, 120 eV): m/z=403 (M−H)$^+$; $^1$H NMR (300 MHz, CDCl$_3$): δ 7.55-7.60 (d, 1H), 7.35-7.38 (d, 2H), 7.25-7.28 (dd, 4H), 6.81-6.88 (m, 5H), 5.09 (s, 2H), 4.92 (s, 2H), 3.73 (s, 6H).

Intermediate 33: 4-methoxybenzyl 3-{4-[(4-methoxybenzyl)oxy]phenyl}-4-nitrobutanoate To a 500 mL RB flask fitted with magnetic stirrer was charged with 10 mL of nitro ethane. To the stirred solvent was added 4-methoxybenzyl (2E,2Z)-3-{4-[(4-methoxybenzyl)oxy]phenyl}prop-2-enoate (1 g, 2.47 mmol) and 1,1,3,3-tetramethyl guanidine (0.14 g, 1.28 mmol), stirred at RT for 8 h, then increased the temperature to 50° C. and stirred for 3 h and then at 100° C. for 8 h. The RM was concentrated by removal of solvent and the crude was dissolved in ethyl acetate (100 mL). The organic layer was washed with water (50 mL) and saturated brine solution (50 mL). The organic layer was dried over anhydrous $Na_2SO_4$ and the solvent was removed under reduced pressure. The crude was purified by column chromatography on silica gel (100/200 mesh), the product obtained as pale yellow color solid (0.4 g, yield: 58.82%). $^1$H NMR (300 MHz, CDCl$_3$): δ 7.26-7.29 (d, 2H), 7.09-7.12 (d, 2H), 7.01-7.04 (d, 2H), 6.76-6.86 (m, 6H), 4.91 (s, 2H), 4.87 (s, 2H), 4.46-4.62 (m, 2H), 3.83-3.88 (t, 1H), 3.74 (s, 3H), 3.72 (s, 3H), 2.66-2.69 (d, 2H).

Intermediate 34: 4-methoxybenzyl 3-{4-[(4-methoxybenzyl)oxy]phenyl}-3-(1,2-oxazol-3-yl)propanoate To a 50 mL RB flask fitted with magnetic stirrer was charged with 3 mL of triethyl amine. To this, added 4-methoxybenzyl 3-{4-[(4-methoxybenzyl)oxy]phenyl}-4-nitrobutanoate (0.25 g, 0.537 mmol) and followed by addition of vinyl bromide (4 ml), 1,4-phenylene diisocyanate (0.3 g, 1.87 mmol), refluxed at 85° C. for 8 h. The RM was cooled to RT, solid was precipitated. The solid was removed by filtration and the filtrate was evaporated under reduced pressure. The product obtained as a brown color gummy material (0.1 g, yield: 40.2%). $^1$H NMR (300 MHz, CDCl$_3$): δ 8.17-8.18 (d, 1H), 7.25-7.28 (d, 2H), 7.05-7.11 (t, 4H), 6.75-6.85 (m, 6H), 5.97-5.98 (d, 1H), 4.92 (s, 2H), 4.86 (s, 2H), 4.46-4.52 (t, 1H), 3.73 (s, 3H), 3.72 (s, 3H), 3.18-3.26 (q, 1H), 2.85-2.93 (q, 1H).

Intermediate 35: 3-(4-hydroxyphenyl)-3-(1,2-oxazol-3-yl)propanoic acid

To a 100 mL RB flask fitted with magnetic stirrer was charged 30 mL of DCM. To the stirred solvent, was added 4-methoxybenzyl 3-{4-[(4-methoxybenzyl)oxy]phenyl}-3-(1,2-oxazol-3-yl) propanoate (3 g, 6.33 mmol) and cooled to 0° C., to this added 30 mL of trifluoroacetic acid drop wise. The resulting solution was stirred at RT for 1 h. After completion of the reaction (reaction monitored by TLC), solvent was removed under reduced pressure. The RM was diluted with 30 mL of methanol, solid was precipitated. The solid was removed by filtration and the filtrate was evaporated under reduced pressure. The product obtained as a gummy material (1.48 g, yield: 99%). MS (ESI, 120 eV): m/z=234.2 (M+H)+, $^1$H NMR (300 MHz, CDCl$_3$): δ 8.23 (d, 1H), 6.98-7.01 (d, 2H), 6.67-6.70 (d, 4H), 6.04-6.05 (d, 1H), 4.42-4.47 (t, 1H), 3.07-3.15 (q, 1H), 2.75-2.83 (q, 1H).

Intermediate 36: methyl 3-(4-hydroxyphenyl)-3-(1,2-oxazol-3-yl)propanoate

To a 100 mL RB flask fitted with magnetic stirrer was charged 20 mL of methanol. To the stirred solvent added 3-(4-hydroxyphenyl)-3-(1,2-oxazol-3-yl) propanoic acid (1.48 g, 6.34 mmol) and cooled to 0° C., added 1 mL of methanesulfonic acid. The resulting mixture was stirred at reflux temperature for 2 h. After completion of the reaction (reaction monitored by TLC), the solvent was removed under reduced pressure and the crude mass was dissolved in ethyl acetate (25 mL). The organic layer was washed with water (50 mL), saturated brine solution (50 mL). The organic layer was dried over anhydrous Na$_2$SO$_4$ and the solvent was removed under reduced pressure. The product was obtained as pale yellow color oil (0.69 g, Yield: 44%): MS (ESI, 120 eV): m/z=248.9 (M+H)+; $^1$H NMR (300 MHz, CDCl$_3$): δ 8.20 (s, 1H), 7.01-7.04 (d, 2H), 6.66-6.69 (d, 2H), 6.00 (d, 1H), 5.56 (bro s, 1H), 4.46-4.51 (t, 1H), 3.56 (s, 3H), 3.17-3.25 (q, 1H), 2.83-2.91 (q, 1H).

Intermediate 37: methyl 3-{4-[(4-{[(2Z)-2-(methoxyimino)-2-phenylethyl]oxy}benzyl)oxy]phenyl}-3-(1,2-oxazol-3-yl)propanoate To a 50 mL RB flask fitted with magnetic stirrer was charged dry THF (5.0 mL) and methyl 3-(4-hydroxyphenyl)-3-(1,2-oxazol-3-yl)propanoate (0.18 g, 0.74 mmol). To the above mixture (4-{[(2Z)-2-(methoxyimino)-2-phenylethyl]oxy}phenyl)methanol (0.2 g, 0.74 mmol) was added and the resulting mixture stirred at 0° C. for 5 min. Triphenyl phosphine (0.25 g, 0.96 mmol) was added to the mixture and stirred at 0° C. for 15 min followed by the addition of diisopropylazadicarboxylate (0.19 g, 0.96 mmol). After stirring the resulting mixture at RT for 10 h, the RM was evaporated to remove the THF. The residue was diluted with water (15 mL) and extracted with ethyl acetate (15 mL×2). The organic layer was washed with saturated brine solution (15 mL) and dried over anhydrous Na$_2$SO$_4$. Concentration of the solvent and purification of the resulting residue by column chromatography on silica gel (100/200 mesh), using petroleum ether (60-80) and ethyl acetate (ratio) as eluant, gave the product (0.1 g, yield: 27.47%): MS (ESI, 120 eV): m/z=501.1 (M+H)+; $^1$H NMR (300 MHz, CDCl$_3$): δ 8.20 (d, 1H), 7.57-7.60 (t, 2H), 7.22-7.28 (m, 5H), 7.07-7.10 (d, 2H), 6.81-6.85 (m, 4H), 5.99-6.00 (d, 1H), 5.12 (s, 2H), 4.85 (s, 2H), 4.47-4.52 (t, 1H), 3.98 (s, 3H), 3.56 (s, 3H), 3.18-3.26 (q, 1H), 2.82-2.90 (q, 1H).

Compound 17: 3-{4-[(4-{[(2Z)-2-(methoxyimino)-2-phenylethyl]oxy}benzyl)oxy]phenyl}-3-(1,2-oxazol-3-yl)propanoic acid To a 25 mL RB flask fitted with magnetic stirrer was charged 2 mL of methanol and 2 mL of THF. To the stirred solvent, was added methyl 3-{4-[(4-{[(2Z)-2-(methoxyimino)-2-phenylethyl]oxy}benzyl)oxy]phenyl}-3-(1,2-oxazol-3-yl)propanoate (0.1 g, 0.2 mmol) and NaOH (0.03 g, 0.6 mmol) in water (1 mL). The resulting solution was stirred at RT for 3 h. to After completion of the reaction (reaction monitored by TLC), solvent was removed under reduced pressure. The RM was diluted with 2 mL of water, cooled to 0° C., then acidified to pH 3 with 1N HCl, and extracted with ethyl acetate (15 mL×2). The organic layer was washed water (20 mL), and saturated brine solution (20 mL). The organic layer was dried over anhydrous Na$_2$SO$_4$ and the solvent was removed under reduced pressure. The product was obtained as white color solid (0.015 g, yield: 15.5%), Purity: 97.68%.

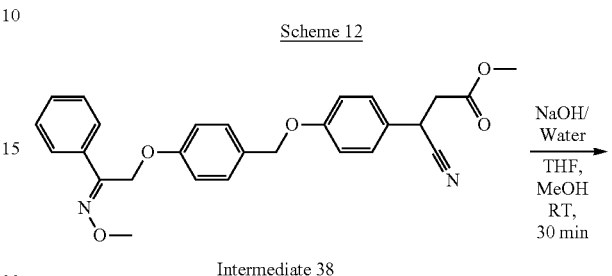

Example 18

Sodium 3-cyano-3-{4-[(4-{[(2Z)-2-(methoxyimino)-2-phenylethyl]oxy}benzyl)oxy]phenyl}propanoate (18)

Compound 18 was synthesized from (4-{[(2Z)-2-(methoxyimino)-2-phenylethyl]oxy}phenyl)methanol (0.264 g, 0.98 mmol) and methyl 3-cyano-3-(4-hydroxyphenyl)propanoate (0.2 g, 0.98 mmol) by following the procedure described in Scheme 5. (0.15 g, yield: 34.7%); Purity: 99.9%.

Example 19

[4-({3-[(E,Z)-(Methoxyimino)(phenyl)methyl]benzyl}oxy)phenyl]acetic acid (19)

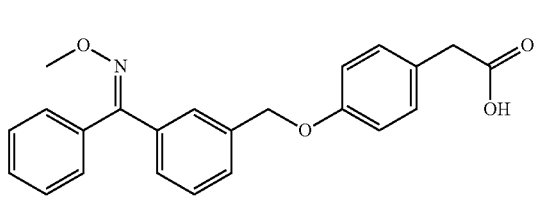

Compound 19 was prepared by using (E,Z)-1-[3-(bromomethyl)phenyl]-N-methoxy-1-phenylmethanimine (1.0 g, 3.635 mmol) and (4-hydroxyphenyl)acetic acid (0.553 g, 3.635 mmol) by following the procedure described in scheme 1. The product was obtained as colorless liquid (0.1 g, Yield: 30.84%); Purity: 94.3%.

Example 20

3-{4-[(6-{[(2Z)-2-(Methoxyimino)-2-phenylethyl]oxy}pyridin-3-yl)methoxy]phenyl}propanoic acid (20)

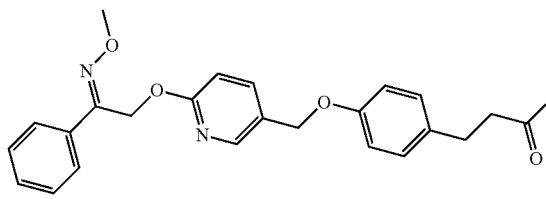

Compound 20 was prepared by using (2Z)-2-(methoxyimino)-2-phenylethyl]oxy}pyridin-3-yl) methanol (0.34 g, 1.248 mmol) and methyl 3-(4-hydroxyphenyl)propanoate (0.23 g, 1.248 mmol) and in place of DEAD used DIAD as a reagent by following the procedure described in scheme 5. The product was obtained as white colour solid (0.08 g, Yield: 45.93%); Purity: 84.8%.

Scheme 13

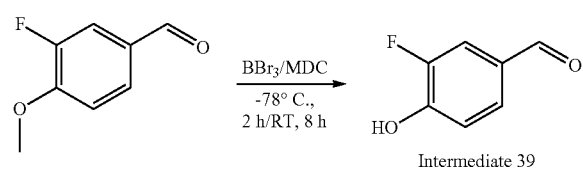

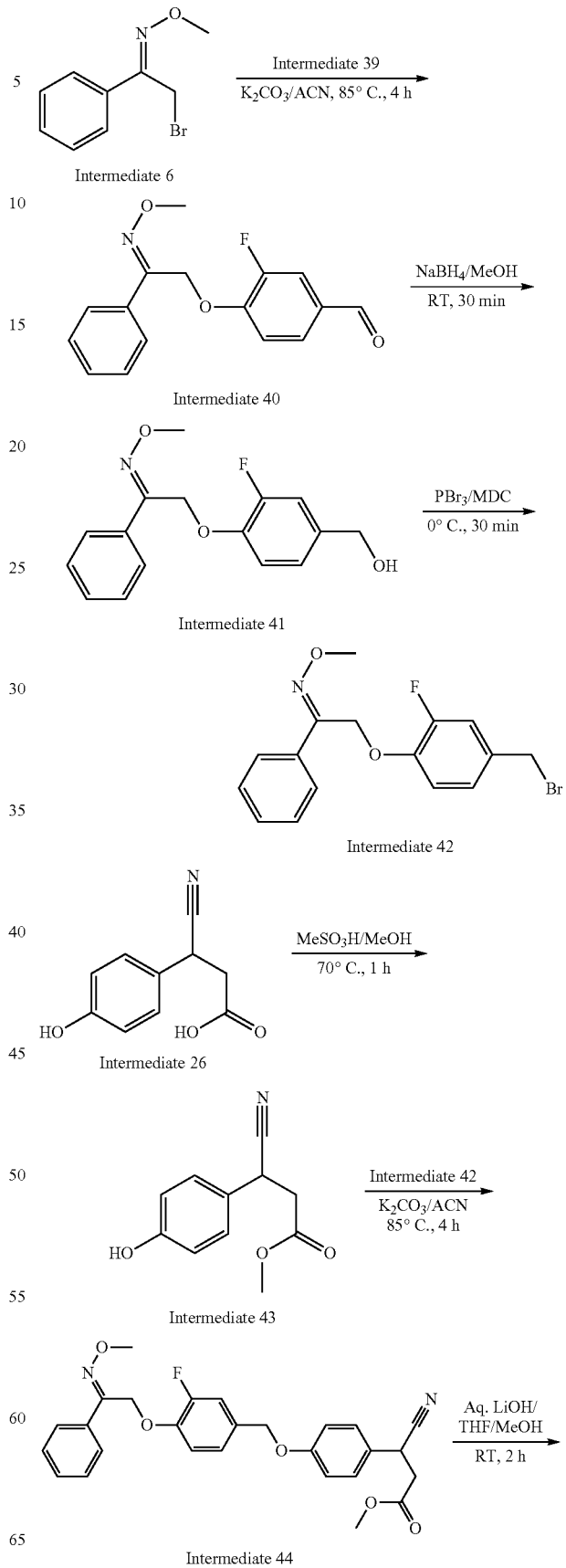

-continued

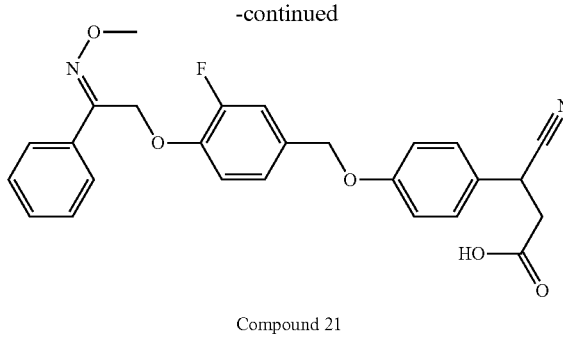

Compound 21

Example 21

3-Cyano-3-{4-[(3-fluoro-4-{[(2E,2Z)-2-(methoxy-imino)-2-phenylethyl]oxy}benzyl)oxy]phenyl}propanoic acid (21)

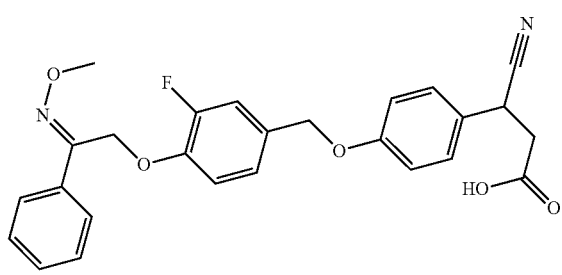

Compound 21 was prepared by using methyl 3-cyano-3-(4-hydroxyphenyl)-propanoate and (1E,1Z)-2-[4-(bromomethyl)-2-fluorophenoxy]-N-methoxy-1-phenylethanimine by following the procedure described in scheme 13.

Intermediate 39: 3-Fluoro-4-hydroxybenzaldehyde

To a 25 mL RB flask fitted with magnetic stirrer was charged with 20 mL of dichloromethane. To the stirred solvent was added 3-fluoro-4-methoxybenzaldehyde (2 g, 12.97 mmol). The reaction mixture was cooled to −78° C. and boron tribromide (51 mL) was added drop wise, stirred for 2 h at the same temperature and stirred at RT about 16 h. The reaction mixture was quenched with $NaHCO_3$ solution at 0° C. by slow addition. The reaction mixture was concentrated to distill off the solvent; ethyl acetate (20 mL) was added. The organic layer was washed with saturated $NaHCO_3$ solution (20 mL), followed by brine solution (20 mL). The organic layer was dried over anhydrous $Na_2SO_4$ and the solvent was removed under reduced pressure. The product was obtained as white solid (1.0 g, yield: 54.94%). $^1H$ NMR (300 MHz, $CDCl_3$): δ 9.77 (s, 1H), 7.54-7.59 (m, 1H), 7.08-7.12 (t, 1H), 6.40 (s, 1H).

Intermediate 40: 3-Fluoro-4-{[(2E,2Z)-2-(methoxy-imino)-2-phenylethyl]oxy}benzaldehyde To a 250 mL RB flask fitted with magnetic stirrer was charged with 75 mL of acetonitrile. To the stirred solvent were added (1E,1Z)-2-bromo-1-phenylethanone O-methyloxime (1.1 g, 5.0 mmol), potassium carbonate (2.3 g, 15.00 mmol). At 0° C., 3-fluoro-4-hydroxybenzaldehyde (0.7 g, 5.0 mmol) in acetonitrile (10 mL) was added drop wise and stirred at 85° C. for 4 h under nitrogen atmosphere. The RM was filtered through sintered funnel and washed with ethyl acetate. The filtrate was concentrated to distill off the solvent. Water (30 mL) was added and extracted with ethyl acetate (20 mL×3). The organic layer was washed with water (30 mL) and saturated brine solution (30 mL). The organic layer was dried over anhydrous $Na_2SO_4$ and the solvent was removed under reduced pressure. The crude material was purified by silica gel column chromatography using ethyl acetate and petroleum ether as elutants. The product was obtained as yellow liquid (1 g, yield: 72%). $^1H$ NMR (300 MHz, $CDCl_3$): δ 9.86 (s, 1H), 7.78-7.81 (d, 1H), 7.64-7.68 (m, 3H), 7.40-7.45 (m, 4H), 5.45 (s, 2H), 4.03 (s, 3H).

Intermediate 41: (1E,1Z)-2-[2-Fluoro-4-(hydroxymethyl)phenoxy]-1-phenylethanone O-methyloxime To a 25 mL RB flask fitted with magnetic stirrer was charged with 4 mL of methanol. To the stirred solvent was added 3-fluoro-4-{[(2E,2Z)-2-(methoxyimino)-2-phenyl-ethyl]oxy}benzaldehyde (0.83 g, 2.89 mmol). The reaction mixture was brought to 0° C. and sodium borohydride (0.16 g, 4.33 mmol) was added portion wise. The reaction mixture was allowed to stirred for 30 minutes. Then, the reaction mixture was concentrated to distill off the solvent. Water (10 mL) was added and extracted with ethyl acetate (10 mL×3). The organic layer was washed with water (50 mL) and saturated brine solution (10 mL). The organic layer was dried over anhydrous $Na_2SO_4$ and the solvent was removed under reduced pressure. The product was obtained as colorless liquid (0.7 g, yield: 84.34%). $^1H$ NMR (300 MHz, $CDCl_3$): δ 7.60-7.63 (m, 2H), 7.27-7.29 (m, 3H), 6.89-6.98 (m, 3H), 5.19 (s, 2H), 4.49 (s, 2H), 3.97 (s, 3H).

Intermediate 42: (1E,1Z)-2-[4-(Bromomethyl)-2-fluorophenoxy]-1-phenyl ethanone O-methyloxime To a 25 mL RB flask fitted with magnetic stirrer was charged with (3-fluoro-4-{[(2E,2Z)-2-(methoxyimino)-2-phenylethyl]oxy}phenyl)methanol (0.45 g, 1.55 mmol) and DCM (4 mL). To the stirring solution, phosphorous tribromide (0.5 mL, 3 eq) was added at 0° C. and stirred for 30 minutes under nitrogen atmosphere. The RM was poured into water (5 mL) and extracted with ethyl acetate (20 mL). The organic layer was washed with water (10 mL) and saturated brine solution (10 mL). The organic layer was dried over anhydrous $Na_2SO_4$ and the solvent was removed under reduced pressure. The product was obtained as colorless liquid (0.24 g, yield: 44.44%). $^1H$ NMR (300 MHz, $CDCl_3$): δ 7.60-7.63 (m, 2H), 7.27-7.29 (m, 3H), 6.98-7.02 (m, 2H), 6.86-6.91 (t, 1H), 5.19 (s, 2H), 4.33 (s, 2H), 3.97 (s, 3H).

Intermediate 43: Methyl 3-cyano-3-(4-hydroxyphenyl)propanoate

To a 50 mL RB flask fitted with magnetic stirrer was charged with methanol (15 mL). To the stirred solvent was added 3-cyano-3-(4-hydroxyphenyl)propanoic acid (0.6 g, 3.1 mmol), followed by the addition of methanesulfonic acid (1 mL). The reaction mixture was refluxed for 1 h. After completion of the reaction, the reaction mixture was concentrated to distill off the solvent. Water (10 mL) was added and extracted with ethyl acetate (25 mL). The organic layer was washed with water (5 mL) and saturated brine solution (5 mL). The organic layer was dried over anhydrous Na₂SO₄ and the solvent was removed under reduced pressure. The product was obtained as pale yellow liquid (0.6 g, yield: 93.3%). ¹H NMR (300 MHz, CDCl₃): δ 7.13-7.15 (d, 2H), 6.75-6.78 (d, 2H), 4.14-4.19 (t, 1H), 3.65 (s, 3H), 2.89-2.97 (m, 1H), 2.71-2.79 (m, 1H).

Intermediate 44: Methyl 3-cyano-3-{4-[(3-fluoro-4-{[2E,(2Z)-2-(methoxyimino)-2-phenylethyl]oxy}benzyl)oxy]phenyl}propanoate To a 250 mL RB flask fitted with magnetic stirrer was charged with 2 mL of acetonitrile. To the stirred solvent were added (1E,1Z)-2-[4-(bromomethyl)-2-fluorophenoxy]-N-methoxy-1-phenylethanimine (0.24 g, 0.68 mmol), potassium carbonate (0.28 g, 2.0 mmol) at 0° C., was added drop wise methyl 3-cyano-3-(4-hydroxyphenyl)propanoate (0.14 g, 0.68 mmol) in acetonitrile (2 mL) and stirred at 85° C. for 4 h under nitrogen atmosphere. The RM was filtered through sintered funnel and washed with ethyl acetate. The filtrate was concentrated to distill off the solvent. The residue was extracted with ethyl acetate (10 mL). The organic layer was washed with water (5 mL) and saturated brine solution (5 mL). The organic layer was dried over anhydrous Na₂SO₄ and the solvent was removed under reduced pressure. The crude material was purified by silica gel column chromatography (ethyl acetate:hexane=5:95-30:70). The product was obtained as yellow liquid (0.18 g, yield: 56.25%). ¹H NMR (300 MHz, CDCl₃): δ 7.64-7.67 (m, 2H), 7.35-7.41 (m, 5H), 7.18-7.28 (m, 3H), 6.99-7.02 (d, 2H), 5.30 (s, 2H), 5.01 (s, 2H), 4.42-4.47 (q, 1H), 3.99-4.06 (s, 3H), 3.62 (s, 3H), 3.07-3.16 (q, 1H), 2.90-2.97 (q, 1H).

Compound 21: 3-Cyano-3-{4-[(3-fluoro-4-{[(2E,2Z)-2-(methoxyimino)-2-phenylethyl]oxy}benzyl)oxy]phenyl}propanoic acid To a 10 mL RB flask fitted with magnetic stirrer was charged with 2 mL of tetrahydrofuran. To the stirred solvent were added methyl 3-cyano-3-{4-[(3-fluoro-4-{[(2E,2Z)-2-(methoxyimino)-2-phenylethyl]oxy}benzyl)oxy]phenyl}propanoate (0.1 g, 0.21 mmol) and methanol (2 mL). The reaction mixture was brought to 0° C. and Lithium hydroxide (0.03 g, 1.2 mmol) in water (2 mL) was added drop wise. The reaction mixture was stirred at room temperature for 2 h. After completion of the reaction, the reaction mixture was concentrated to distill off the solvent. The obtained salt was dissolved in water (1 mL) was added and to extracted with ether (5 mL). The aqueous layer was acidified with 1N HCl to make pH 3 and extracted with ether (5 mL). The organic layer was washed with brine (5 mL) dried the solvent under anhydrous Na₂SO₄ and concentrated to give a gummy solid (0.09 g, yield: 92.73%). MS (ESI, 120 eV): m/z=463.1 (M+H)⁺; HPLC purity: 89.53%.

Example 22

3-Cyano-3-{4-[(4-{[(2E,2Z)-2-(4-fluorophenyl)-2-(methoxyimino)ethyl]oxy}benzyl)oxy]phenyl}propanoic acid (22)

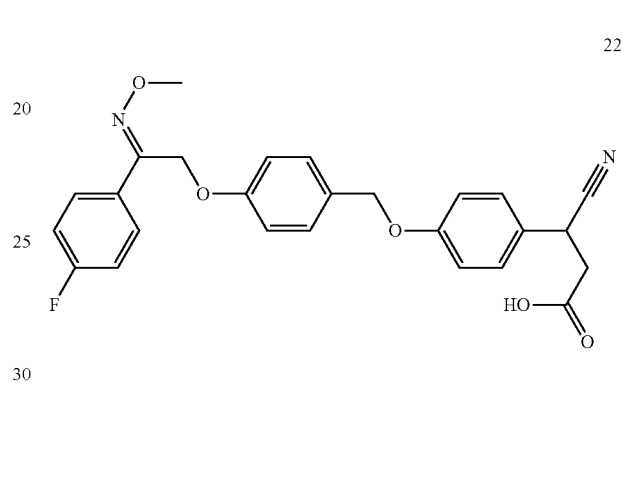

Compound 22 was synthesized from (1E,1Z)-1-(4-fluorophenyl)-2-[4-(hydroxymethyl)-phenoxy]-ethanone O-methyloxime (0.212 g, 0.731 mmol) and methyl 3-cyano-3-(4-hydroxyphenyl)propanoate (0.1 g, 0.487 mmol) by following the procedure described in scheme 13 (0.02 g, yield: 44%); Purity: 98.58%.

Example 23

3-Cyano-3-{4-[(2-fluoro-4-{[(2E,2Z)-2-(methoxyimino)-2-phenylethyl]oxy}benzyl)oxy]phenyl}propanoic acid (23)

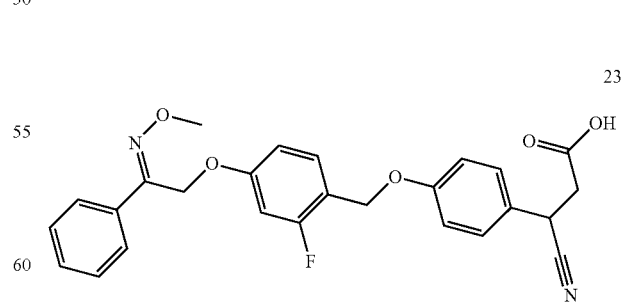

Compound 23 was synthesized from (1E,1Z)-2-[3-fluoro-4-(hydroxymethyl)-phenoxy]-1-phenylethanone O-methyloxime (0.14 g, 0.397 mmol) and methyl 3-cyano-3-(4-hydroxyphenyl)propanoate (0.0815 g, 0.397 mmol) by

Example 24

3-{4-[(4-{[(2E,2Z)-2-(Methoxyimino)-2-(3-methylphenyl)ethyl]oxy}benzyl)oxy]phenyl}-3-(1,2-oxazol-3-yl)propanoic acid (24)

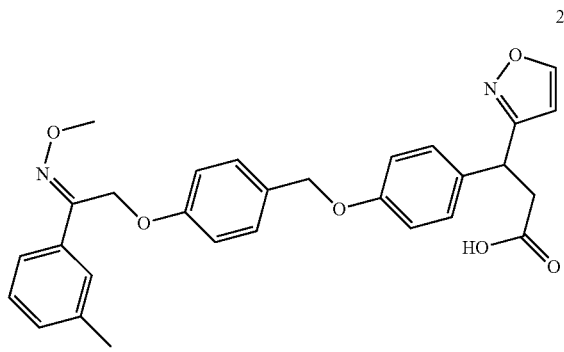

Compound 24 was synthesized from (1E,1Z)-2-[4-(bromomethyl)phenoxy]-N-methoxy-1-(3-methylphenyl)ethanimine (0.2 g, 0.5 mmol) and methyl 3-(4-hydroxyphenyl)-3-(1,2-oxazol-3-yl)propanoate (0.14 g, 0.56 mmol), in place of DEAD, used DIAD as a coupling agent by following the procedure described in scheme 11 and 13 (0.04 g, yield: 14.0%); Purity: 96.74%.

Example 25

3-Cyano-3-{4-[(4-{[(2E,2Z)-2-(methoxyimino)-2-(4-methoxyphenyl)ethyl]oxy}benzyl)oxy]phenyl}propanoic acid (25)

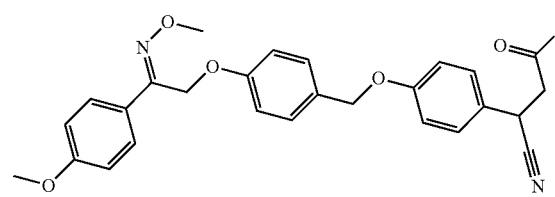

Compound 25 was synthesized from (1E,1Z)-2-[4-(hydroxymethyl)-phenoxy]-1-(4-methoxyphenyl)-ethanone O-methyloxime (0.2 g, 0.66 mmol) and methyl 3-cyano-3-(4-hydroxyphenyl)propanoate (0.136 g, 0.66 mmol) and in place of DEAD, used DIAD as a coupling agent by following the procedure described in scheme 11 (0.0038 g, yield: 3.01%); Purity: 89.41%.

Example 26

3-Cyano-3-{4-[(3-methoxy-4-{[(2Z)-2-(methoxyimino)-2-phenylethyl]oxy}benzyl)oxy]phenyl}propanoic acid (26)

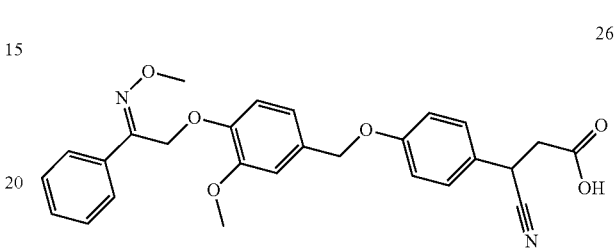

Compound 2b was synthesized from (1Z)-2-[4-(hydroxymethyl)-2-methoxyphenoxy]-1-phenylethanone O-methyloxime (0.2 g, 0.66 mmol) and methyl 3-cyano-3-(4-hydroxyphenyl)propanoate (0.136 g, 0.66 mmol) by following the procedure described in scheme 11 (0.0032 g, yield: 7.77%); Purity: 95.56%.

Example 27

3-Cyano-3-{4-[(4-{[(2E,2Z)-2-(methoxyimino)-2-(3-methylphenyl)ethyl]oxy}benzyl)oxy]phenyl}propanoic acid (27)

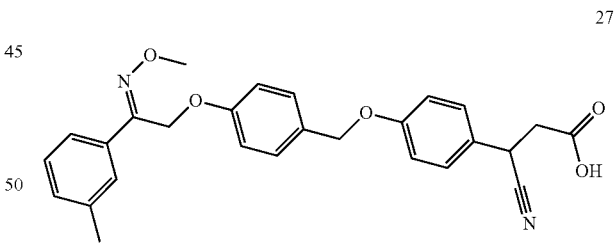

Compound 27 was synthesized from (1E,1Z)-2-[4-(bromomethyl) phenoxy]-N-methoxy-1-(3-methylphenyl)ethanimine (0.2 g, 0.5 mmol) and methyl 3-(4-hydroxy phenyl)-3-(1,2-oxazol-3-yl)propanoate (0.14 g, 0.56 mmol), in place of DEAD, used DIAD as a coupling agent. Then the hydrolysis of Methyl 3-{4-[(4-{[(2E,2Z)-2-(methoxyimino)-2-(3-methylphenyl)ethyl]oxy}benzyl)oxy]phenyl}-3-(1,2-oxazol-3-yl)propanoate (0.150 g, 1.0 eq) with aqueous solution of NaOH (60 mg, 2.5 eq), by following the procedure described in scheme 11 and 13 (0.04 mg, 14.0%); Purity: 96.2%.

Example 28

3-{4-[(4-{[(2E,2Z)-2-(4-Cyanophenyl)-2-(methoxy-imino)ethyl]oxy}benzyl)oxy]phenyl}propanoic acid (28)

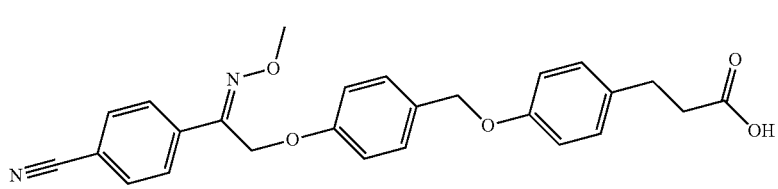

Compound 28 was synthesized from 4-{(1E,1Z)-2-[4-(hydroxymethyl)-phenoxy]-N-methoxyethanimidoyl}benzonitrile (0.26 g, 0.668 mmol) and methyl 3-(4-hydroxyphenyl)propanoate (0.144 g, 0.802 mmol) by following the procedure described in scheme 13 (0.098 g, yield: 84%); Purity: 93.06%.

Example 29

Sodium 3-{4-[(4-{[(2Z)-2-(methoxyimino)-2-phenylethyl]oxy}benzyl)oxy]phenyl}-3-(1,2-oxazol-3-yl)propanoate (29)

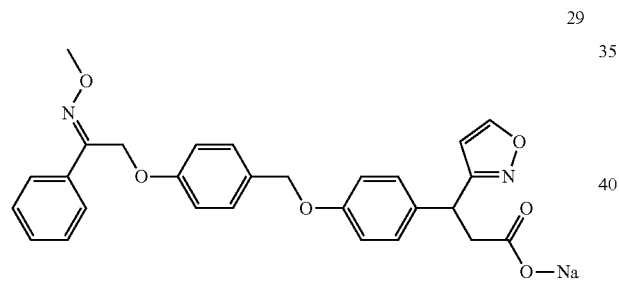

Compound 29 was synthesized from 3-{4-[(4-{[(2Z)-2-(methoxyimino)-2-phenylethyl]oxy}benzyl)oxy]phenyl}-3-(1,2-oxazol-3-yl)propanoic acid (0.07 g, 0.14 mmol) and sodium hydroxide (0.0057 g, 0.14 mmol) by following the procedure described in scheme 12 (0.052 g, yield: 71.2%); Purity: 99.00%.

Scheme 14

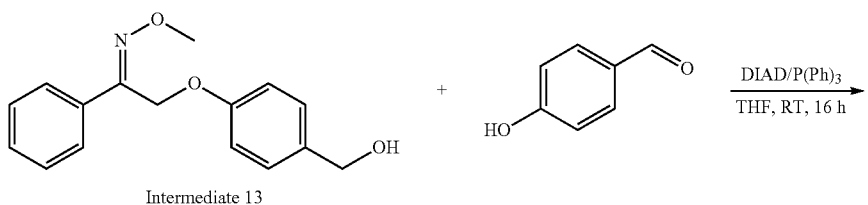

Intermediate 13

-continued

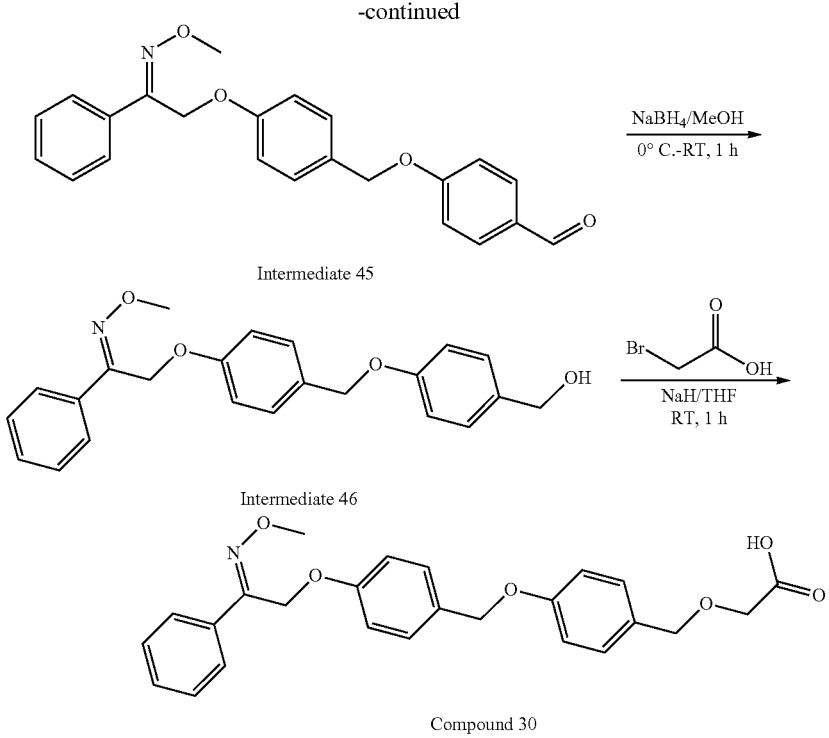

Intermediate 45

Intermediate 46

Compound 30

Example 30

({4-[(4-{[(2E,2Z)-2-(Methoxyimino)-2-phenylethyl]oxy}benzyl)oxy]benzyl}oxy)acetic acid (30)

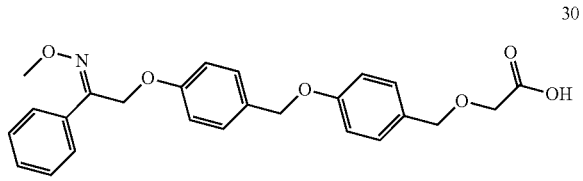 [SMILES: CO/N=C(/COc1ccc(COc2ccc(COCC(=O)O)cc2)cc1)c1ccccc1]

Compound 30 was synthesized from {4-[(4-{[(2E,2Z)-2-(methoxyimino)-2-phenylethyl]oxy}benzyl)oxy]phenyl}methanol (0.1 g, 0.26 mmol) and bromoacetic acid (0.022 g, 0.15 mmol) by following the procedure described in scheme 14 (0.01 g, yield: 6.25%); Purity: 59.30%.

Intermediate 45: 4-[(4-{[(2E,2Z)-2-(Methoxyimino)-2-phenylethyl]oxy}benzyl)oxy]benzaldehyde To a 50 mL RB flask fitted with magnetic stirrer was charged dry THF (5.0 mL) and (4-{[(2E,2Z)-2-(methoxyimino)-2-phenylethyl]oxy}phenyl)methanol (1.5 g, 5.5 mmol), to the above mixture 4-hydroxybenzaldehyde (0.81 g, 6.6 mmol) was added and the resulting mixture stirred at 0° C. for 5 min. Triphenyl phosphine (1.88 g, 7.15 mmol) was added to the mixture and stirred at 0° C. for 15 min followed by the addition of Diisopropylazadicarboxylate (1.44 g, 7.15 mmol). After stirring the resulting mixture at RT for 16 h, the RM was evaporated to remove the THF. The residue was diluted with water (50 mL) and extracted with ethyl acetate (150 mL×2). The organic layer was washed with saturated brine solution (50 mL) and dried over anhydrous $Na_2SO_4$. The concentration of the solvent under reduced pressure gave the product (0.7 g, yield: 35.0%).

Intermediate 46: {4-[(4-{[(2E,2Z)-2-(Methoxyimino)-2-phenylethyl]oxy}benzyl)oxy]phenyl}methanol To a 50 mL RB flask fitted with magnetic stirrer was charged 10 mL of Methanol. To the stirred solvent was added 4-[(4-{[(2E,2Z)-2-(methoxyimino)-2-phenylethyl]oxy}benzyl)oxy]benzaldehyde (0.7 g, 1.86 mmol), RM was cooled to 0° C. and sodium borohydride (0.105 g, 2.79 mmol) was added portion wise over a period of 15 minutes. The reaction mixture was stirred at RT for 1 h. The RM was quenched with $NaHCO_3$ solution (40 mL 10% solution in water) and extracted with ethyl acetate (20 mL×2). The organic layer washed with saturated brine solution (25 mL), dried over anhydrous $Na_2SO_4$ and removed the solvent under reduced pressure to yield the product (0.7 g, Yield: 100.0%).

Compound 30: ({4-[(4-{[(2E,2Z)-2-(Methoxyimino)-2-phenylethyl]oxy}benzyl)oxy]benzyl}oxy) acetic acid To a 25 mL RB flask fitted with magnetic stirrer was charged with 12 mL THF. To the stirred solvent was added sodium hydride (0.015 g, 0.6 mmol) was added portion wise at 0° C. and stirred at same temperature for 30 minutes. Then {4-[(4-{[(2E,2Z)-2-(methoxyimino)-2-phenyl ethyl]oxy}benzyl)oxy]phenyl}methanol (0.1 g, 0.26 mmol) in tetrahydrofuran (3 mL) was added drop wise. The reaction mixture was stirred at RT for 13 h. The reaction mixture was quenched with water at 0° C., acidified and extracted with ethyl acetate. The organic layer was washed with water and brine solution. The organic layer was dried over anhydrous Na$_2$SO$_4$ and the solvent was removed under reduced pressure. The product was obtained as white solid (0.01 g, yield 6.25%).

Example 31

Potassium 3-cyano-3-{4-[(4-{[(2Z)-2-(methoxy-imino)-2-phenylethyl]oxy}benzyl)oxy]phenyl}propanoate (31)

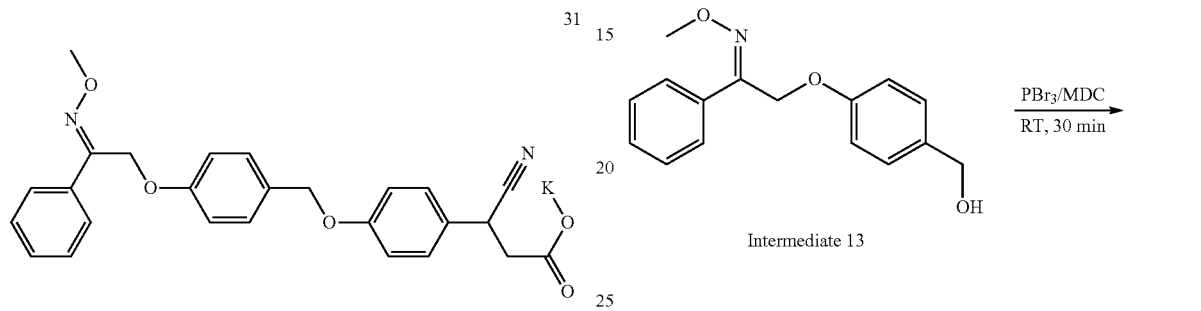

Compound 31 was synthesized from ethyl 3-cyano-3-{4-[(4-{[(2Z)-2-(methoxyimino)-2-phenylethyl]oxy}benzyl)oxy]phenyl}propanoate (0.5 g, 1.06 mmol) and potassium hydroxide (0.093 g, 1.66 mmol) by following the procedure described in Scheme 12 (0.4 g, yield: 78.34%); Purity: 99.27%.

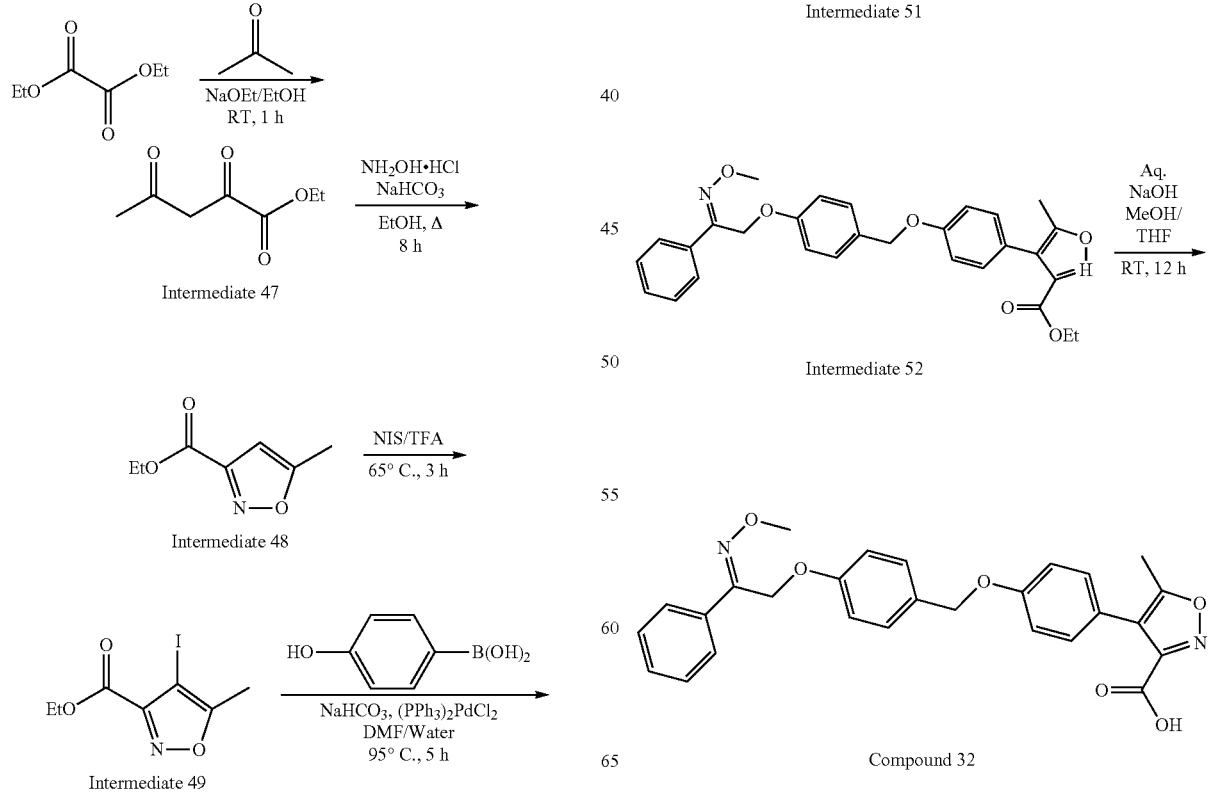

Example 32

4-{4-[(4-{[(2E,2Z)-2-(Methoxyimino)-2-phenylethyl]oxy}benzyl)oxy]phenyl}-5-methyl-1,2-oxazole-3-carboxylic acid (32)

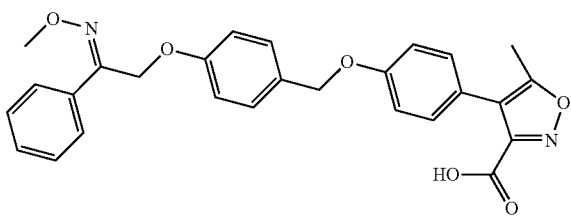

Compound 32 was prepared by using ethyl 4-(4-hydroxyphenyl)-5-methyl-1,2-oxazole-3-carboxylate and (1E,1Z)-2-[3-(bromomethyl)phenoxy]-1-phenylethanone O-methyloxime by following the procedure described in scheme 15.

Intermediate 47: Ethyl 2,4-dioxopentanoate

To a 100 mL two neck RB flask fitted with magnetic stirrer was charged with 25 mL of ethanol. To the stirred solvent was added sodium metal pieces (0.86 g, 37 mmol) slowly at 0° C. under nitrogen atmosphere and stirred for 30 minutes at room temperature. After 30 minutes, diethyl oxalate (5 g, 34.2 mmol) in acetone (10 mL) was added drop wise. During addition, the reaction mixture was changed to yellow color. After addition, thick mass was observed, was added ethanol (10 mL) to the reaction mixture and stirred at room temperature for 1 h. Then, the reaction mixture was filtered; the solids were dissolved in ice-cold water (50 mL), acidified with concentrated sulfuric acid and extracted with ethyl acetate (100 mL). The organic layer was concentrated under reduced pressure and the solvent traces were removed by triturated with n-hexane. The product was obtained as brown liquid (3.2 g, yield: 59.2%). $^1$H NMR (300 MHz, DMSO-$d_6$): δ 5.46 (s, 2H), 4.02-4.09 (q, 2H), 1.89 (s, 3H), 1.18-1.22 (t, 3H).

Intermediate 48: Ethyl 5-methyl-1,2-oxazole-3-carboxylate

To a 100 mL RB flask fitted with a condenser and a magnetic stirrer was charged with 10.5 mL of ethanol. To the stirred solvent were added ethyl 2,4-dioxopentanoate (2.5 g, 15 mmol), hydroxylamine hydrochloride (1.09 g, 15 mmol) and sodium bicarbonate (1.32 g, 15 mmol). After addition, the reaction mixture was refluxed at 80° C. for 8 h under nitrogen atmosphere. After completion of the reaction, the solvent was evaporated from the reaction mixture. Ethyl acetate (50 mL) was added; organic layer was washed with water (50 mL), followed by brine solution (25 mL). The organic layer was dried over anhydrous $Na_2SO_4$ and the solvent was removed under reduced pressure. The product was obtained as a colorless liquid (1 g, yield: 40.08%). $^1$H NMR (300 MHz, CDCl$_3$): δ 6.34 (s, 1H), 4.33-4.40 (q, 2H), 2.43 (s, 3H), 1.32-1.37 (t, 3H).

Intermediate 49: Ethyl 4-iodo-5-methyl-1,2-oxazole-3-carboxylate

To a 25 mL RB flask fitted with a magnetic stirrer was charged with 1 mL of TFA. To the stirred solvent were added ethyl 5-methyl-1,2-oxazole-3-carboxylate (0.1 g, 0.6 mmol) and N-iodosuccinimide (0.289 g, 1.2 mmol). After addition, the reaction mixture was heated at 65° C. for 3 h. After completion of the reaction, the reaction mixture was diluted with ethyl acetate (10 mL), the organic layer was washed with saturated NaHCO$_3$ solution (10 mL), thiosulfate solution (10 mL), water (25 mL) and finally with brine solution (10 mL). The organic layer was dried over anhydrous Na$_2$SO$_4$ and the solvent was removed under reduced pressure. The product was obtained as a brown liquid (0.12 g, yield: 66.2%). $^1$H NMR (300 MHz, CDCl$_3$): δ 4.36-4.43 (q, 2H), 2.49 (s, 3H), 1.34-1.39 (t, 3H).

Intermediate 50: Ethyl 4-(4-hydroxyphenyl)-5-methyl-1,2-oxazole-3-carboxylate To a 25 mL RB flask fitted with a magnetic stirrer was charged with DMF (2.5 mL). To the stirred solvent were added 4-hydroxyphenylboronic acid (0.2 g, 0.7 mmol), ethyl 4-iodo-5-methyl-1,2-oxazole-3-carboxylate (0.116 g, 0.8 mmol), sodium bicarbonate (0.18 g, 2.1 mmol) and water (0.08 mL) under argon atmosphere. After addition, the reaction mixture was purged with argon for 15 minutes. To this bis(triphenylphosphine)palladium (II) chloride (0.05 g, 0.07 mmol) was added and purged with argon for 10 minutes. After addition, the reaction mixture was heated at 95° C. for 5 h under argon atmosphere. After completion of the reaction, the reaction mixture was quenched with water (10 mL) and extracted with ethyl acetate (10 mL). The organic layer was washed with water (5 mL) and brine solution (5 mL). The organic layer was dried over anhydrous Na$_2$SO$_4$ and the solvent was removed under reduced pressure. The crude was purified through silica gel column chromatography using ethyl acetate and petroleum ether as elutants. The product was obtained as an off white solid (0.1 g, yield: 57%). $^1$H NMR (300 MHz, CDCl$_3$): δ 7.10-7.13 (d, 2H), 6.80-6.82 (d, 2H), 5.14 (s, 1H), 4.25-4.32 (q, 2H), 2.36 (s, 3H), 1.23-1.28 (t, 3H).

Intermediate 51: (1E,1Z)-2-[4-(Bromomethyl)phenoxy]-1-phenylethanone O-methyloxime To a 50 mL RB flask fitted with magnetic stirrer was charged with 10 mL of dichloromethane. To the stirred solvent was added (1E,1Z)-2-[4-(hydroxymethyl) phenoxy]-1-phenylethanone O-methyloxime (0.5 g, 1.84 mmol). At 0° C., phosphorous tribromide (0.746 g, 2.76 mmol) was added drop wise and stirred at room temperature for 30 minutes. After completion of the reaction, the reaction mixture was poured into water (25 mL) and extracted with dichloromethane (50 mL). The organic layer was washed with water (25 mL) and saturated brine solution (25 mL). The organic layer was dried over anhydrous Na$_2$SO$_4$ and the solvent was removed under reduced pressure. The product was obtained as yellowish gummy solid (0.4 g, yield: 65%).

Intermediate 52: Ethyl 4-{4-[(4-{[(2E,2Z)-2-(methoxyimino)-2-phenylethyl]oxy}benzyl)oxy]phenyl}-5-methyl-1,2-oxazole-3-carboxylate To a 25 mL RB flask fitted with magnetic stirrer was charged with 5 mL of acetonitrile. To the stirred solvent were added ethyl 4-(4-hydroxyphenyl)-5-methyl-1,2-oxazole-3-carboxylate (0.1 g, 0.4 mmol), potassium carbonate (0.178 g, 1.2 mmol). The reaction mixture was brought to 0° C., (1Z)-2-[4-(bromomethyl)phenoxy]-1-phenylethanone O-methyloxime (0.143 g, 0.4 mmol) in acetonitrile (2 mL) was added drop wise and stirred at 70° C. for 2 h. The reaction mixture was concentrated to distill off the solvent diluted with water (10 mL) was added and extracted with ethyl acetate (10 mL). The organic layer was washed with water (5 mL) and saturated brine solution (5 mL). The organic layer was dried over anhydrous $Na_2SO_4$ and the solvent was removed under reduced pressure. The crude material was purified by silica gel column chromatography using ethyl acetate and petroleum ether as elutants. The product was obtained as white solid (0.11 g, yield: 54%). $^1$H NMR (300 MHz, $CDCl_3$): δ 7.59-7.62 (m, 2H), 7.26-7.34 (m, 5H), 7.14-7.17 (d, 2H), 6.92-6.95 (d, 2H), 6.85-6.88 (d, 2H), 5.14 (s, 2H), 4.93 (s, 2H), 4.24-4.31 (q, 2H), 3.99 (s, 3H), 2.36 (s, 3H), 1.21-1.26 (t, 3H).

Compound 32: 4-{4-[(4-{[(2E,2Z)-2-(Methoxyimino)-2-phenylethyl]oxy}benzyl)oxy]phenyl}-5-methyl-1,2-oxazole-3-carboxylic acid To a 10 mL RB flask fitted with magnetic stirrer was charged with 3 mL of tetrahydrofuran. To the stirred solvent were added methyl 4-{4-[(4-{[(2E,2Z)-2-(methoxyimino)-2-phenylethyl]oxy}benzyl)oxy]phenyl}-5-methyl-1,2-oxazole-3-carboxylate (0.11 g, 0.2 mmol), ethanol (3 mL) and sodium hydroxide (0.035 g, 0.9 mmol) in water (0.5 mL). The reaction mixture was stirred at room temperature overnight. After completion of the reaction, the solvent was removed, the sodium salt was washed with diethyl ether (5 mL); the aqueous layer was acidified with 1N HCl to pH 2.0 and extracted with ethyl acetate (5 mL). The organic layer was dried over anhydrous $Na_2SO_4$ and the solvent was removed under reduced pressure. The crude was purified through silica gel column chromatography using methanol and dichloromethane as elutants. The product was obtained as pale yellow sticky solid (0.045 g, yield: 38.8%).

Example 33

3-Cyano-3-{4-[(4-{[(2E,2Z)-2-(4-cyanophenyl)-2-(methoxyimino)ethyl]oxy}benzyl)oxy]phenyl}propanoic acid (33)

33

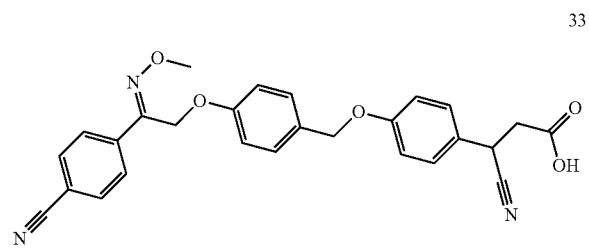 [SMILES: CO/N=C(\COc1ccc(COc2ccc(C(C#N)CC(=O)O)cc2)cc1)c1ccc(C#N)cc1]

Compound 33 was synthesized from 4-{(1E,1Z)-2-[4-(hydroxymethyl)phenoxy]-N-methoxyethanimidoyl}benzonitrile (0.328 g, 0.9 mmol) and methyl 3-cyano-3-(4-hydroxyphenyl)propanoate (0.2 g, 0.9 mmol) by following the procedure described in scheme 18 (0.04 g, yield: 13.73%); Purity: 78.04%.

Example 34

3-Cyano-3-{4-[(4-{[(2Z)-2-(4-fluorophenyl)-2-(methoxyimino)ethyl]oxy}benzyl)oxy]phenyl}propanoic acid (34)

34

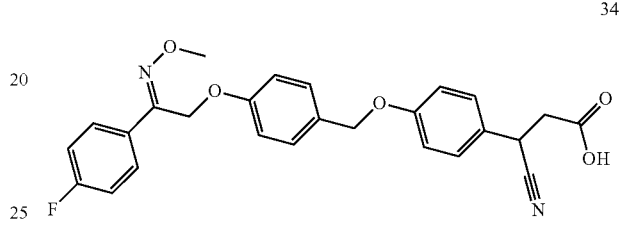

Compound 34 was synthesized from (1Z)-1-(4-fluorophenyl)-2-[4-(hydroxymethyl)phenoxy]ethanone O-methyloxime (0.4 g, 1.46 mmol) and methyl 3-cyano-3-(4-hydroxyphenyl)propanoate (0.3 g, 1.46 mmol) by following the procedure described in scheme 18 (0.06 g, yield: 15.46%); Purity: 95.29%.

Example 35

3-Cyano-3-{4-[(4-{[(2Z)-2-(3-fluorophenyl)-2-(methoxyimino)ethyl]oxy}benzyl)oxy]phenyl}propanoic acid (35)

35

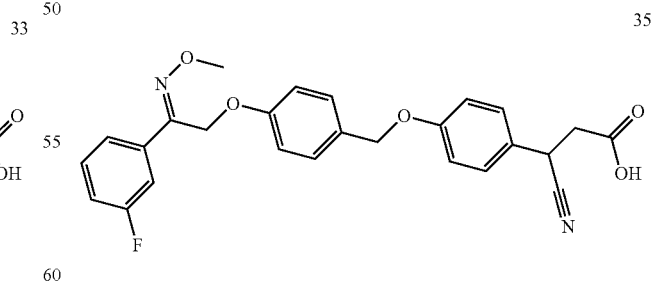

Compound 35 was synthesized from (1Z)-1-(3-fluorophenyl)-2-[4-(hydroxymethyl)phenoxy]ethanone O-methyloxime (0.5 g, 1.8 mmol) and methyl 3-cyano-3-(4-hydroxyphenyl)propanoate (0.372 g, 1.8 mmol) by following the procedure described in scheme 18 (0.1 g, yield: 18.73%); Purity: 95.1%.

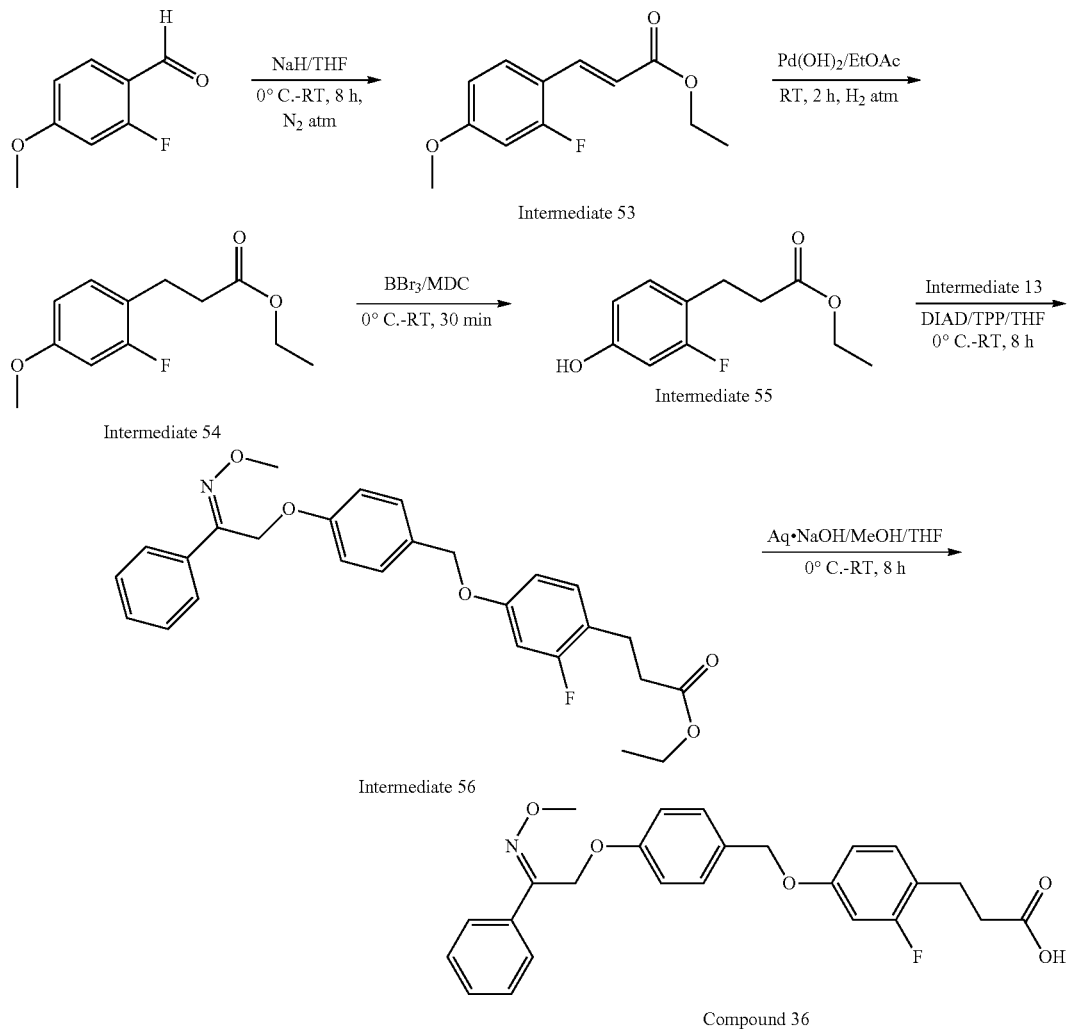

Scheme 16

Example 36

3-{2-Fluoro-4-[(4-{[(2Z)-2-(methoxyimino)-2-phenylethyl]oxy}benzyl)oxy]phenyl}propanoic acid (36)

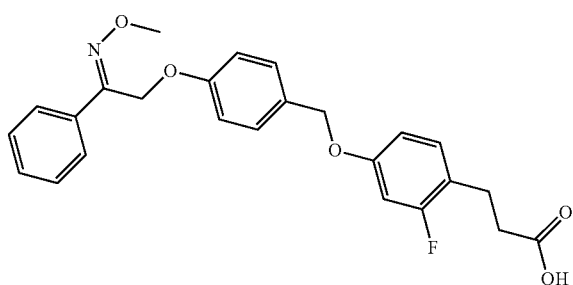

36

Compound 36 was prepared by using methyl 3-cyano-3-(4-hydroxyphenyl)propanoate and (1Z)-2-[4-(bromomethyl)-2-fluorophenoxy]-1-phenylethanone O-methyloxime by following the procedure described in scheme 16 (0.186 g, yield: 65.97%). Purity: 98.88%.

Intermediate 53: Ethyl (2Z)-3-(2-fluoro-4-methoxyphenyl) acrylate

To a 100 mL RB flask fitted with magnetic stirrer was charged with 25 mL of tetrahydrofuran. To the stirred solvent was added sodium hydride (0.39 g, 16.2 mmol) portion wise at 0° C., followed by triethyl phosphonoacetate (2.9 g, 12.9 mmol). The reaction mixture was stirred at 0° C. for 30 minutes. To the stirring solution, 2-fluoro-4-methoxybenzaldehyde (1 g, 6.4 mmol) in tetrahydrofuran (2 mL) was added drop wise and stirred at room temperature overnight. After completion of the reaction, the reaction mixture was poured into ice and extracted with ethyl acetate (50 mL). The organic layer was washed with water (25 mL) and saturated brine solution (25 mL). The organic layer was dried over anhydrous $Na_2SO_4$ and the solvent was removed under reduced pressure. The crude material was purified by silica gel column chromatography using ethyl acetate and petroleum ether as eluants. The product was obtained as colorless oil (1.2 g, yield:

82.49%). $^1$H NMR (300 MHz, CDCl$_3$): δ 7.65-7.70 (d, 1H), 7.35-7.41 (t, 1H), 6.54-6.66 (m, 2H), 6.31-6.37 (d, 1H), 4.15-4.22 (q, 2H), 3.76 (s, 3H), 1.24-1.29 (t, 3H).

Intermediate 54: Ethyl 3-(2-fluoro-4-methoxyphenyl)propanoate

To a 500 mL parr shaker flask was charged with ethyl (2E,2Z)-3-(2-fluoro-4-methoxyphenyl) prop-2-enoate (0.5 g, 2.2 mmol) and ethyl acetate (15 mL) and purged with nitrogen for 10 minutes. Palladium hydroxide (20%) was added and kept for hydrogenation at 50 psi for 2 h. After completion of the reaction, the reaction mixture was filtered through celite, washed thoroughly with ethyl acetate (25 mL) and concentrated to distill off the solvent. The product was obtained as brown solid (0.462 g, yield: 91.58%). $^1$H NMR (300 MHz, CDCl$_3$): δ 7.00-7.06 (t, 1H), 6.50-6.56 (m, 2H), 4.01-4.09 (q, 2H), 3.70 (s, 3H), 2.81-2.86 (t, 2H), 2.49-2.54 (t, 2H), 1.14-1.19 (t, 3H).

Intermediate 55: Ethyl 3-(2-fluoro-4-hydroxyphenyl)propanoate

To a 25 mL RB flask fitted with magnetic stirrer was charged with 10 mL of dichloromethane. To the stirred solvent was added ethyl 3-(2-fluoro-4-methoxyphenyl)propanoate (0.45 g, 2 mmol). The reaction mixture was cooled to 0° C. and boron tribromide (0.45 mL) was added drop wise. After stirred for 30 minutes, the reaction mixture was quenched with ethanol (1 mL) at 0° C. by slow addition. The reaction mixture was concentrated to distill off the solvent; ethyl acetate (10 mL) was added. The organic layer was washed with saturated NaHCO$_3$ solution (10 mL), followed by brine solution (10 mL). The organic layer was dried over anhydrous Na$_2$SO$_4$ and the solvent was removed under reduced pressure. The product was obtained as colorless oil (0.421 g, yield: 99.75%). $^1$H NMR (300 MHz, CDCl$_3$): δ 6.93-6.99 (t, 1H), 6.43-6.48 (m, 2H), 5.54 (s, 1H), 4.02-4.09 (q, 2H), 2.79-2.85 (t, 2H), 2.50-2.55 (t, 2H), 1.14-1.19 (t, 3H).

Intermediate 56: Ethyl 3-{2-fluoro-4-[(4-{[(2Z)-2-(methoxyimino)-2-phenylethyl]oxy}benzyl)oxy]phenyl}propanoate To a 50 mL RB flask fitted with magnetic stirrer was charged with tetrahydrofuran (10 mL). To the stirred solvent were added (4-{[(2E,2Z)-2-(methoxyimino)-2-phenylethyl]oxy}phenyl) methanol (0.524 g, 1.93 mmol), ethyl 3-(2-fluoro-4-hydroxyphenyl)propanoate (0.41 g, 1.93 mmol) and triphenylphosphine (0.608 g, 2.32 mmol) under argon atmosphere. The reaction mixture was cooled to 0° C., diisopropylazocarboxylate (0.43 g, 2.12 mmol) was added drop wise. The reaction mixture was stirred at room temperature overnight under argon atmosphere. After completion of the reaction, the reaction mixture was concentrated; water (10 mL) was added and extracted with ethyl acetate (25 mL). The organic layer was washed with brine solution (10 mL). The crude material was purified by silica gel column chromatography using ethyl acetate and petroleum ether as elutants. The product was obtained as white solid (0.324 g, yield: 36.02%). MS (ESI, 120 eV): m/z=466.2 (M+H)$^+$; $^1$H NMR (300 MHz, CDCl$_3$): δ 7.58-7.61 (m, 2H), 7.27-7.29 (m, 3H), 7.22-7.25 (m, 2H), 6.99-7.05 (m, 1H), 6.83-6.86 (d, 2H), 6.55-6.61 (m, 2H), 5.13 (s, 2H), 4.85 (s, 2H), 4.01-4.08 (q, 2H), 3.99 (s, 3H), 2.80-2.85 (t, 2H), 2.48-2.54 (t, 2H), 1.14-1.18 (t, 3H).

Compound 36: 3-{2-Fluoro-4-[(4-{[(2Z)-2-(methoxyimino)-2-phenylethyl]oxy}benzyl)oxy]phenyl}propanoic acid To a 10 mL RB flask fitted with magnetic stirrer was charged with 1 mL of tetrahydrofuran. To the stirred solvent were added ethyl 3-{2-fluoro-4-[(4-{[(2e,2Z)-2-(methoxyimino)-2-phenylethyl]oxy}benzyl)oxy]phenyl}propanoate (0.3 g, 0.64 mmol) and methanol (2 mL). The reaction mixture was brought to 0° C. and sodium hydroxide (0.13 g, 3.2 mmol) in water (1 mL) was added drop wise. The reaction mixture was stirred overnight. After completion of the reaction, the reaction mixture was concentrated to distill off the solvent. Water (1 mL) was added and extracted with ether (5 mL). The aqueous layer was acidified with 1N HCl to make pH 3 and extracted with ether (5 mL). The organic layer was washed with brine solution (5 mL), the solvent was distilled off and dried. The product was obtained as off white solid (0.186 g, yield: 65.97%). MS (ESI, 120 eV): m/z=438.1 (M+H)$^+$; HPLC purity: 98.88%;

Example 37

3-{2-Methoxy-4-[(4-{[(2Z)-2-(methoxyimino)-2-phenylethyl]oxy}benzyl)oxy]phenyl}propanoic acid (37)

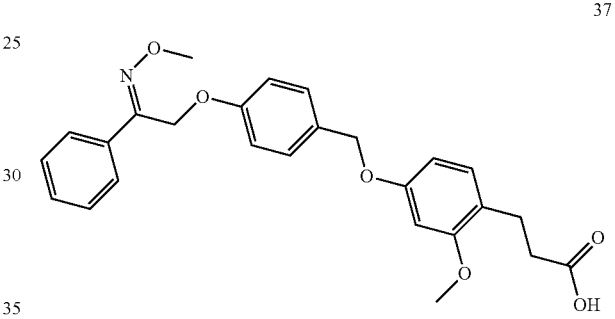

Compound 37 was synthesized from (1Z)-2-[4-(hydroxymethyl)phenoxy]-1-phenylethanone O-methyloxime (0.4 g, 1.197 mmol) and methyl 3-(4-hydroxy-2-methoxyphenyl)propanoate (0.268 g, 1.197 mmol) by following the procedure described in scheme 13 (0.2 g, yield: 89%); Purity: 99.31%.

Example 38

3-{(4-[(4-{[(2Z)-2-(Methoxyimino)-2-phenylethyl]oxy}benzyl)oxy]-2-methylphenyl}propanoic acid (38)

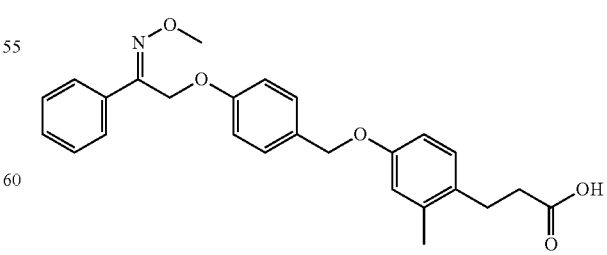

Compound 38 was synthesized from (1Z)-2-[4-(hydroxymethyl)phenoxy]-1-phenylethanone O-methyloxime (0.45 g, 1.7 mmol) and methyl 3-(4-hydroxy-2-methylphenyl)propanoate (0.34 g, 1.7 mmol) by following the procedure described in scheme 15 (0.003 g, yield: 8.0%); Purity: 98.24%.

Example 39

3-{(4-[(4-{[(2Z)-2-(4-Cyanophenyl)-2-(methoxyimino)ethyl]oxy}benzyl)oxy]-2-fluorophenyl}propanoic acid (39)

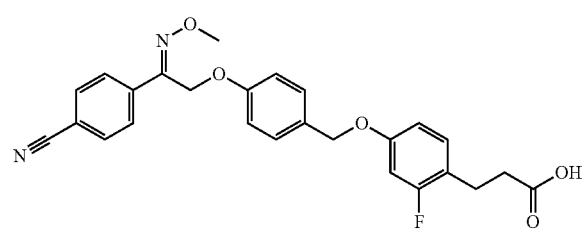

Compound 39 was synthesized from 4-{(1Z)-2-[4-(hydroxymethyl)-phenoxy]-N-methoxyethanimidoyl}benzonitrile (0.4 g, 1.4 mmol) and methyl 3-(2-fluoro-4-hydroxyphenyl)propanoate (0.3 g, 1.4 mmol) by following the procedure described in scheme 13 (0.074 g, yield: 50.19%); Purity: 93.47%.

Example 40

3-{2-Fluoro-4-[(4-{[(2Z)-2-(methoxyimino)-2-(4-methoxyphenyl)ethyl]oxy}benzyl)oxy]phenyl}propanoic acid (40)

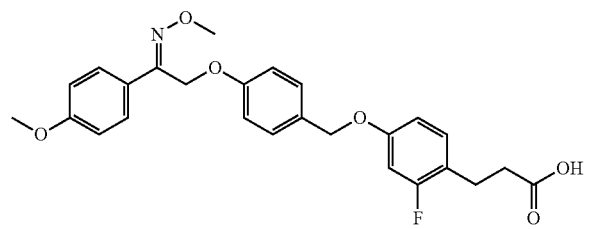

Compound 40 was synthesized from (1Z)-2-[4-(hydroxymethyl)phenoxy]-1-(4-methoxyphenyl)ethanone O-methyloxime (0.25 g, 0.84 mmol) and methyl 3-(2-fluoro-4-hydroxyphenyl)propanoate (0.2 g, 0.94 mmol) by following the procedure described in scheme 18 (0.1 g, yield: 71.00%); Purity: 98.10%.

Example 41

3-{2-Fluoro-4-[(3-methoxy-4-{[(2E,2Z)-2-(methoxyimino)-2-phenylethyl]oxy}benzyl)oxy]phenyl}propanoic acid (41)

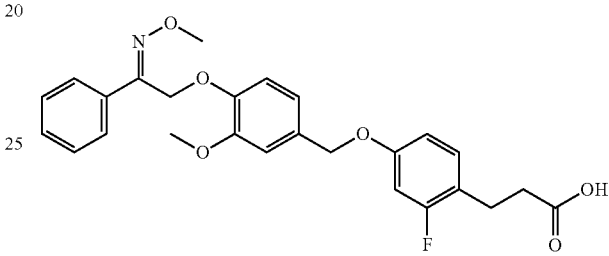

Compound 41 was synthesized from (1E,1Z)-2-[4-(hydroxymethyl)-2-methoxyphenoxy]-1-phenylethanone O-methyloxime (0.464 g, 1.54 mmol) and methyl 3-(2-fluoro-4-hydroxyphenyl)propanoate (0.327 g, 1.54 mmol) by following the procedure described in scheme 11 (0.13 g, yield: 47.00%); Purity: 89.09%.

Example 42

3-{2-Cyano-4-[(4-{[(2E,2Z)-2-(methoxyimino)-2-phenylethyl]oxy}benzyl)oxy]phenyl}propanoic acid (42)

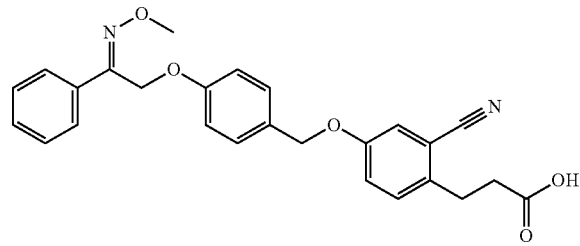

Compound 42 was synthesized from (1E,1Z)-2-[4-(hydroxymethyl)phenoxy]-1-phenylethanone O-methyloxime (0.034 g, 0.1 mmol) and methyl 3-(2-cyano-4-hydroxyphenyl)propanoate (0.026 g, 0.2 mmol) by following the procedure described in scheme 18 (0.0025 g, yield: 12.89%); Purity: 76.00%.

Example 43

3-{4-[(4-{[(2Z)-2-(4-Cyanophenyl)-2-(methoxyimino)ethyl]oxy}benzyl)oxy]-2-methoxyphenyl}propanoic acid (43)

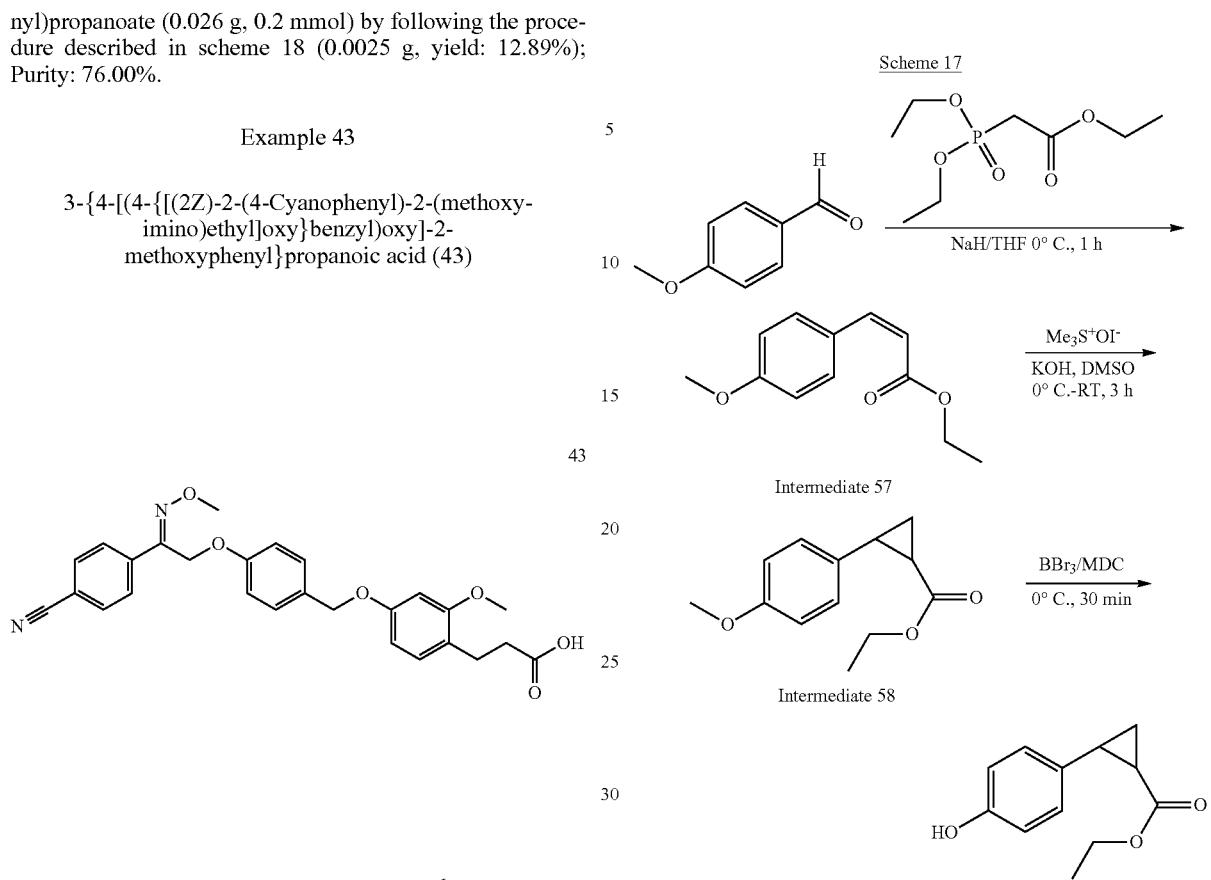

Compound 43 was synthesized from 4-{(1Z)-2-[4-(hydroxymethyl)-phenoxy]-N-methoxyethanimidoyl}benzonitrile (0.563 g, 1.9 mmol) and methyl 3-(4-hydroxy-2-methoxyphenyl)propanoate (0.4 g, 1.9 mmol) by following the procedure described in scheme 18 (0.27 g, yield: 71.5%); Purity: 94.96%.

Example 44

3-{2-(Cyanomethyl)-4-[(4-{[(2Z)-2-(methoxyimino)-2-phenylethyl]oxy}benzyl)oxy]phenyl}propanoic acid (44)

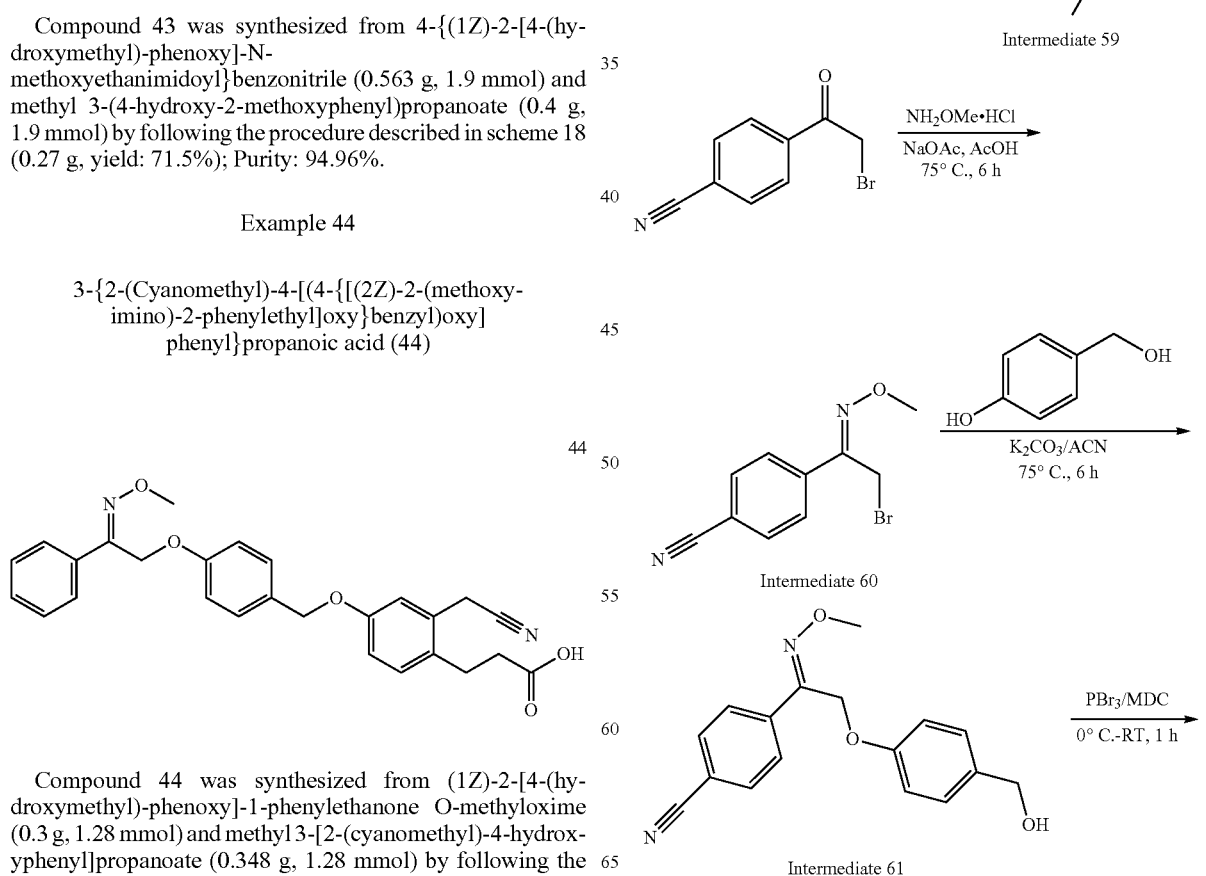

Compound 44 was synthesized from (1Z)-2-[4-(hydroxymethyl)-phenoxy]-1-phenylethanone O-methyloxime (0.3 g, 1.28 mmol) and methyl 3-[2-(cyanomethyl)-4-hydroxyphenyl]propanoate (0.348 g, 1.28 mmol) by following the procedure described in scheme 18 (0.1 g, yield: 71.00%); Purity: 92.72%.

Scheme 17

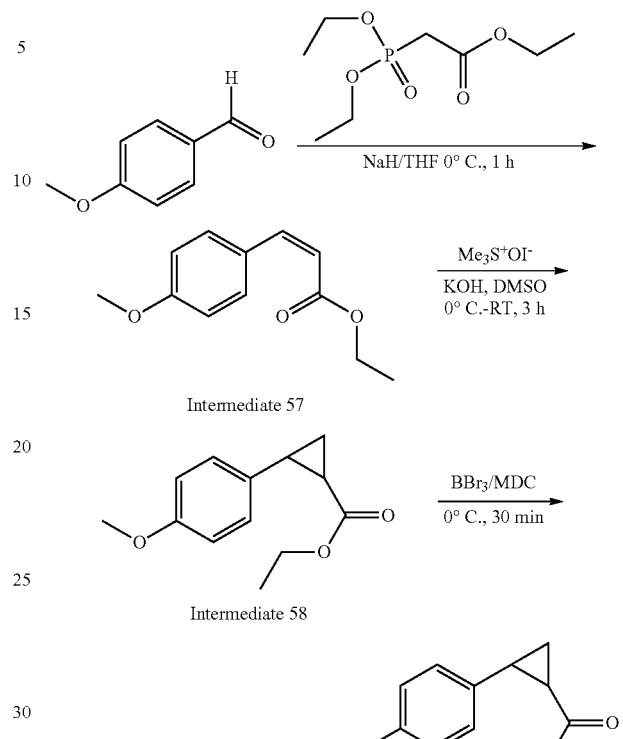

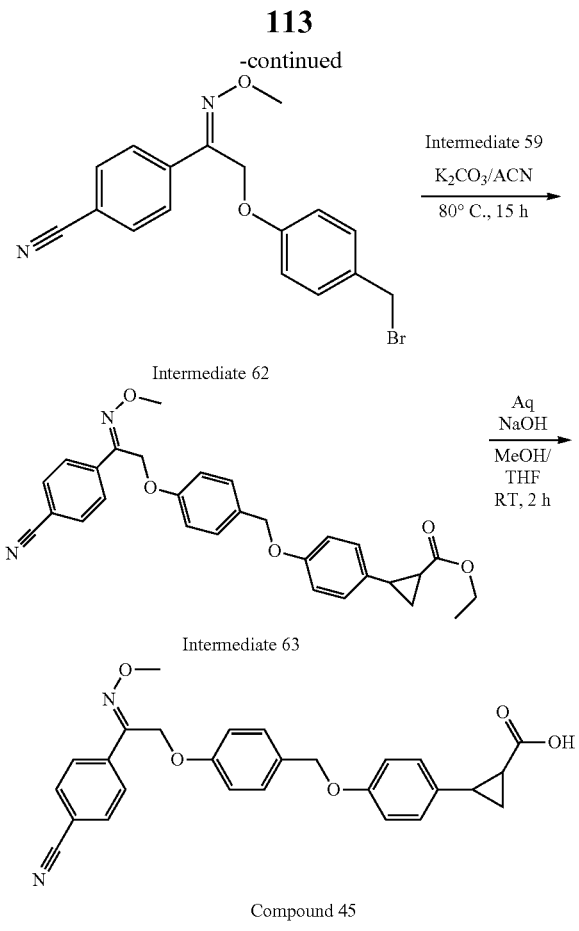

Example 45

2-{4-[(4-{[(2Z)-2-(4-Cyanophenyl)-2-(methoxyimino)ethyl]oxy}benzyl)oxy]phenyl}cyclopropanecarboxylic acid (45)

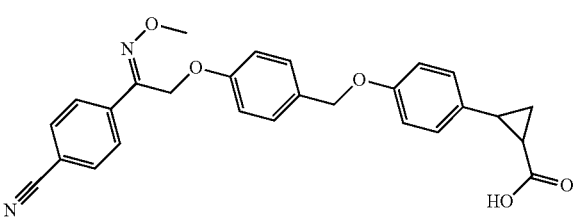

Compound 45 was prepared from ethyl 2-(4-hydroxyphenyl)cyclopropanecarboxylate (0.1 g, 0.48 mmol), and 4-{(1Z)-2-[4-(bromomethyl) phenoxy]-N-methoxyethanimidoyl}benzonitrile (0.175 g, 0.48 mmol) by following the procedure described in scheme 17.

Intermediate 57: Ethyl (2Z)-3-(4-methoxyphenyl)prop-2-enoate

To a 500 mL RB flask fitted with magnetic stirrer was charged with 160 mL of tetrahydrofuran. To the stirred solvent was added ethyl phosphonoacetate (16.5 g, 73.6 mmol) under argon atmosphere. The reaction mixture was cooled to 0° C. and sodium hydride (2.65 g, 110 mmol) was added portion wise, stirred for 15 minutes at the same temperature. Then 4-methoxybenzaldehyde (5 g, 36.0 mmol) in tetrahydrofuran (30 mL) was added drop wise. The reaction mixture was stirred at 0° C. for 1 h. The reaction mixture was quenched with water at 0° C. by slow addition, stirred for 10 minutes. The layers were separated; ethyl acetate (50 mL) was added to the aqueous layer and extracted the layers. The organic layer was washed with brine solution (50 mL). The organic layer was dried over anhydrous $Na_2SO_4$ and the solvent was removed under reduced pressure. The product was obtained as pale yellow semi-solid (7.4 g, yield: 98.76%). $^1H$ NMR (300 MHz, $CDCl_3$): δ 7.54-7.60 (d, 1H), 7.39-7.42 (d, 2H), 6.82-6.85 (d, 2H), 6.21-6.26 (d, 1H), 4.15-4.22 (q, 2H), 3.76 (s, 3H), 1.24-1.28 (t, 3H).

Intermediate 58: Ethyl 2-(4-methoxyphenyl)cyclopropanecarboxylate

To a 50 mL RB flask fitted with magnetic stirrer was charged with 14 mL of dimethylsulfoxide. To the stirred solvent was added trimethylsulfoxonium iodide (1.53 g, 6.93 mmol). The reaction mixture was cooled to 0° C. and powdered potassium hydroxide (0.42 g, 7.49 mmol) was added portion wise, stirred for 10 minutes at room temperature. Then ethyl (2Z)-3-(4-methoxyphenyl)-acrylate (1.3 g, 6.31 mmol) was added. The reaction mixture was stirred at room temperature for 3 h. The reaction mixture was quenched with water and diethyl ether was added. The layers were separated and the organic layer was washed with brine solution (50 mL). The organic layer was dried over anhydrous $Na_2SO_4$ and the solvent was removed under reduced pressure. The crude material was purified by silica gel column chromatography using ethyl acetate and petroleum ether as elutant. The product was obtained as pale pink solid (0.6 g, yield: 43.22%). $^1H$ NMR (300 MHz, $CDCl_3$): δ 6.95-6.98 (d, 2H), 6.74-6.77 (d, 2H), 4.06-4.13 (q, 2H), 3.72 (s, 3H), 2.38-2.44 (m, 1H), 1.72-1.78 (m, 1H), 1.43-1.61 (m, 2H), 1.25-1.29 (t, 3H).

Intermediate 59: Ethyl 2-(4-hydroxyphenyl)cyclopropanecarboxylate

To a 50 mL RB flask fitted with magnetic stirrer was charged with 20 mL of dichloromethane. To the stirred solvent was added ethyl 2-(4-methoxyphenyl)cyclopropanecarboxylate (0.9 g, 4 mmol). The reaction mixture was cooled to 0° C. and boron tribromide (0.9 mL) was added drop wise, stirred for 30 minutes at the same temperature. The reaction mixture was quenched by the addition of ethanol drop wise at 0° C. The reaction mixture was concentrated to distill off the solvent; water was added to the crude and extracted with ethyl acetate. The organic layer was washed with saturated solution of $NaHCO_3$ (25 mL), followed by brine solution (25 mL). The organic layer was dried over anhydrous $Na_2SO_4$ and the solvent was removed under reduced pressure. The product was obtained as pale yellow liquid (0.3 g, yield: 35.6%). $^1H$ NMR (300 MHz, DMSO-$d_6$): δ 9.27 (s, 1H), 6.94-6.97 (d, 2H), 6.64-6.67 (d, 2H), 4.05-4.12 (q, 2H), 2.28-2.36 (m, 1H), 1.75-1.80 (m, 1H), 1.35-1.41 (m, 2H), 1.15-1.28 (t, 3H).

Intermediate 60: 4-[(1Z)-2-Bromo-N-methoxyethanimidoyl]-benzonitrile

To a 1 L RB flask fitted with magnetic stirrer was charged with 300 mL of acetic acid. To the stirred solvent were added 4-(bromoacetyl)-benzonitrile (40 g, 178 mmol), O-methoxylamine hydrochloride (22.36 g, 267 mmol), followed by sodium acetate (21.96 g, 267 mmol). The reaction mixture was heated at 75° C. for 6 h. The reaction mixture was basified to pH 8 using saturated solution of NaHCO$_3$ (500 mL). The aqueous layer was extracted with ethyl acetate (250 mL×3), the organic layer was washed with water (200 mL), followed by brine solution (100 mL). The organic layer was dried over anhydrous Na$_2$SO$_4$ and the solvent was removed under reduced pressure. The crude material was purified by silica gel column chromatography using ethyl acetate and petroleum ether as elutant. The product was obtained as pale yellow oil (19 g, yield: 42.06%). $^1$H NMR (300 MHz, CDCl$_3$): δ 7.75-7.78 (d, 2H), 7.61-7.64 (d, 2H), 4.46 (s, 2H), 4.06 (s, 3H).

Intermediate 61: 4-{(1Z)-2-[4-(Hydroxymethyl)-phenoxy]-N-methoxyethanimidoyl}-benzonitrile To a 500 mL RB flask fitted with mechanical stirrer was charged with 200 mL of acetonitrile. To the stirred solvent were added 4-[(1E,1Z)-2-bromo-N-methoxyethanimidoyl]-benzonitrile (19 g, 75 mmol), 4-(hydroxymethyl)-phenol (9.31 g, 75 mmol), followed by potassium carbonate (31.1 g, 225 mmol). The reaction mixture was heated at 75° C. for 6 h. The reaction mixture was filtered through sintered funnel and washed with ethyl acetate (100 mL). The filtrate was concentrated to distill off the solvent; water (100 mL) was added and extracted with ethyl acetate (100 mL×2). The organic layer was washed with water (100 mL), followed by brine solution (50 mL). The organic layer was dried over anhydrous Na$_2$SO$_4$ and the solvent was removed under reduced pressure. The crude material was purified by silica gel column chromatography using ethyl acetate and petroleum ether as elutant. The product was obtained as yellow liquid (12.2 g, yield: 54.83%). $^1$H NMR (300 MHz, CDCl$_3$): δ 7.71-7.74 (d, 2H), 7.55-7.57 (d, 2H), 7.19-7.21 (d, 2H), 6.79-6.81 (d, 2H), 5.14 (s, 2H), 4.53-4.55 (d, 2H), 4.02 (s, 3H).

Intermediate 62: 4-{(1Z)-2-[4-(Bromomethyl)phenoxy]-N-methoxyethanimidoyl}benzonitrile To a 25 mL RB flask fitted with magnetic stirrer was charged with 50 mL of dichloromethane. To the stirred solvent was added 4-{(1E,1Z)-2-[4-(hydroxymethyl) phenoxy]-N-methoxyethanimidoyl}benzonitrile (0.2 g, 6.0 mmol) at 0° C., phosphorous tribromide (0.1 mL, 9.0 mmol) was added drop wise and stirred at room temperature for 1 h. After completion of the reaction, the reaction mixture was poured into water (10 mL) and extracted with dichloromethane (20 mL). The organic layer was washed with water (25 mL) and saturated brine solution (20 mL). The organic layer was dried over anhydrous Na$_2$SO$_4$ and the solvent was removed under reduced pressure. The product was obtained as yellowish gummy solid (0.2 g, yield: 90.9%).

Intermediate 63: Ethyl 2-{4-[(4-{[(2Z)-2-(4-cyanophenyl)-2-(methoxyimino)ethyl]oxy}benzyl)oxy]phenyl}cyclopropanecarboxylate To a 25 mL RB flask fitted with magnetic stirrer was charged with 5 mL of acetonitrile. To the stirred solvent were added ethyl 2-(4-hydroxy phenyl)cyclopropanecarboxylate (0.1 g, 0.48 mmol), potassium carbonate (0.2 g, 1.4 mmol). The reaction mixture was brought to 0° C., 4-{(1E,1Z)-2-[4-(bromomethyl)phenoxy]-N-methoxyethanimidoyl}benzonitrile (0.175 g, 0.48 mmol) in acetonitrile (5 mL) was added drop wise and stirred at 70° C. for 15 h. The reaction mixture was concentrated to distill off the solvent diluted with water (10 mL) was added and extracted with ethyl acetate (10 mL). The organic layer was washed with water (5 mL) and saturated brine solution (5 mL). The organic layer was dried over anhydrous Na$_2$SO$_4$ and the solvent was removed under reduced pressure. The crude material was purified by silica gel column chromatography using ethyl acetate and petroleum ether as elutants. The product was obtained as white solid (0.19 g, yield: 82.6%).

Compound 45: 2-{4-[(4-{[(2Z)-2-(4-Cyanophenyl)-2-(methoxyimino)ethyl]oxy}benzyl)oxy]phenyl}cyclopropanecarboxylic acid To a 50 mL RB flask fitted with magnetic stirrer was charged with 30 mL of tetrahydrofuran. To the stirred solvent was added ethyl 2-{4-[(4-{[(2E,2Z)-2-(4-cyanophenyl)-2-(methoxyimino)ethyl]oxy}benzyl)oxy]phenyl}cyclopropanecarboxylate (0.07 g, 0.16 mmol) in methanol (5 mL). The reaction mixture was cooled to 0° C. and sodium hydroxide (0.7 g, 0.8 mmol) in water (5 mL) was added drop wise and stirred for 4 h. The reaction mixture was concentrated to distill off the solvent; ethyl acetate (10 mL) was added and stirred for 10 minutes. The organic layer was removed and the crude was acidified with saturated solution of citric acid to make pH 6. The obtained solids were filtered and dried. The product was obtained as white solid (0.012 g, yield: 18.5%). MS (ESI, 120 eV): m/z=455.1 (M−H)$^+$; HPLC purity: 97.19%; $^1$H NMR (300 MHz, DMSO-d$_6$): δ 7.80-7.89 (m, 4H), 7.32-7.35 (d, 2H), 7.05-7.08 (d, 2H), 6.87-6.91 (m, 4H), 5.27 (s, 2H), 4.97 (s, 2H), 4.04 (s, 3H), 2.27-2.35 (m, 1H), 1.67-1.73 (m, 1H), 1.23-1.41 (m, 2H).

Example 46

2-{4-[(4-{[(2Z)-2-(Methoxyimino)-2-(4-methoxyphenyl)ethyl]oxy}benzyl)oxy]phenyl}cyclopropanecarboxylic acid (46)

46

Compound 46 was synthesized from (1Z)-2-[4-(hydroxymethyl)phenoxy]-1-(4-methoxyphenyl)ethanone O-methyloxime (0.146 g, 0.48 mmol) and ethyl 2-(4-hydroxyphenyl)cyclopropanecarboxylate (0.1 g, 0.4 mmol) by following the procedure described in scheme 18 (0.01 g, yield: 13.26%); Purity: 92.24%.

Example 47

Sodium 3-{2-fluoro-4-[(4-{[(2Z)-2-(methoxyimino)-2-(4-methoxyphenyl)ethyl]oxy}benzyl)oxy]phenyl}propanoate (47)

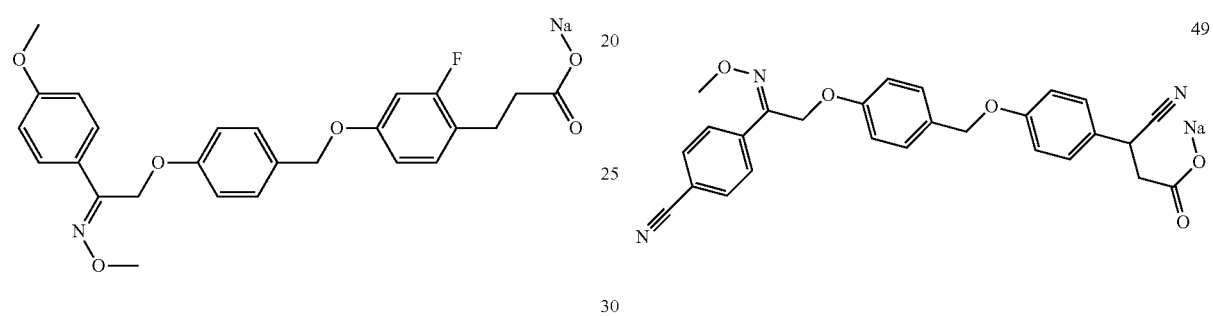

Compound 47 was synthesized from sodium hydroxide (0.007 g, 0.18 mmol) and 3-{2-fluoro-4-[(4-{[(2Z)-2-(methoxyimino)-2-(4-methoxyphenyl)ethyl]oxy}benzyl)oxy]phenyl}propanoic acid (0.087 g, 0.18 mmol) by following the procedure described in scheme 12 (0.07 g, yield: 79.00%); Purity: 99.79%.

Example 48

Sodium 2-{4-[(4-{[(2E,2Z)-2-(methoxyimino)-2-phenylethyl]oxy}benzyl)amino]phenyl}cyclopropanecarboxylate (48)

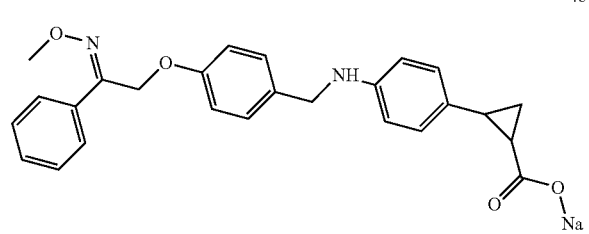

Compound 48 was synthesized from 2-{4-[(4-{[(2E,2Z)-2-(methoxyimino)-2-phenylethyl]oxy}benzyl)amino]phenyl}cyclopropanecarboxylic acid (0.093 g, 0.216 mmol) and sodium hydroxide (0.0086 g, 0.216 mmol) by following the procedure described in scheme 12 (0.075 g, yield: 81.50%); Purity: 91.51%.

Example 49

Sodium 3-cyano-3-{4-[(4-{[(2E,2Z)-2-(4-cyanophenyl)-2-(methoxyimino)ethyl]oxy}benzyl)oxy]phenyl}propanoate (49)

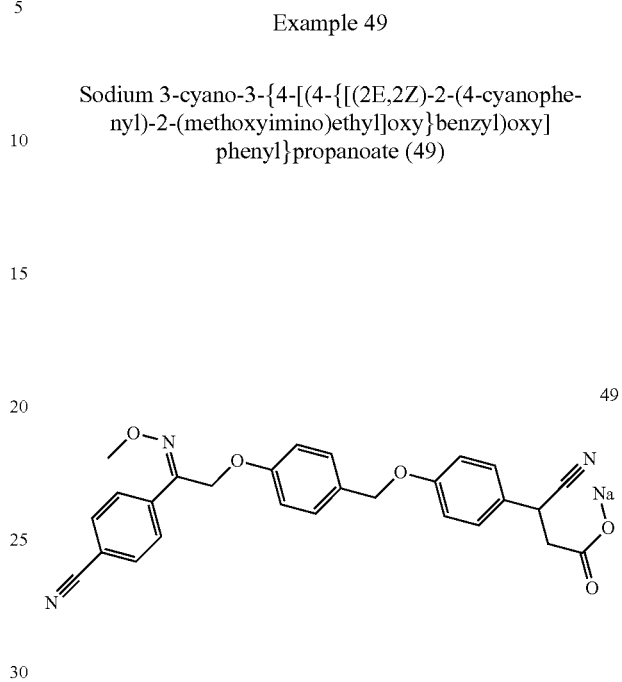

Compound 49 was synthesized from 3-cyano-3-{4-[(4-{[(2E,2Z)-2-(4-cyanophenyl)-2-(methoxyimino)ethyl]oxy}benzyl)oxy]phenyl}propanoic acid (1.5 g, 3 mmol) and sodium hydroxide (0.3 g, 1M solution) by following the procedure described in scheme 12 (0.51 g, yield: 34.40%); Purity: 98.20%.

Example 50

Sodium 3-cyano-3-{4-[(3-fluoro-4-{[(2Z)-2-(methoxyimino)-2-phenylethyl]oxy}benzyl)oxy]phenyl}propanoate (50)

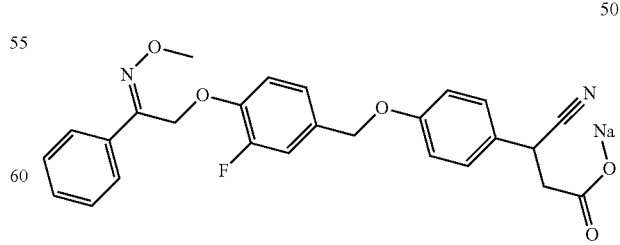

Compound 50 was synthesized from 3-cyano-3-{4-[(3-fluoro-4-{[(2Z)-2-(methoxyimino)-2-phenylethyl]oxy}benzyl)oxy]phenyl}propanoic acid (0.08 g, 0.0002 mmol) sodium hydroxide (0.01 g, 1M solution) by following the procedure described in scheme 12 (0.072 g, yield: 82.76%); Purity: 88.00%.

Example 51

Sodium 2-{4-[(4-{[(2Z)-2-(4-cyanophenyl)-2-(methoxyimino)ethyl]oxy}benzyl)oxy]phenyl}cyclopropanecarboxylate (51)

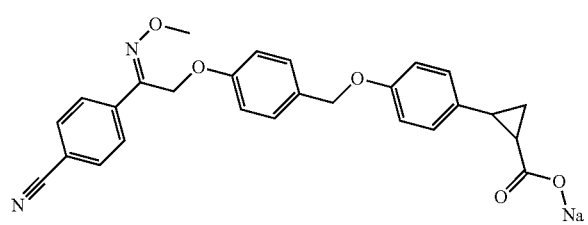

51

Compound 51 was synthesized from sodium hydroxide (0.04 g, 0.96 mmol) and 2-{4-[(4-{[(2Z)-2-(4-cyanophenyl)-2-(methoxyimino)ethyl]oxy}benzyl)oxy]phenyl}cyclopropanecarboxylic acid (0.22 g, 0.48 mmol) by following the procedure described in scheme 12 (0.15 g, yield: 72.40%); Purity: 90.60%.

Example 52

Sodium 3-{(4-[(4-{[(2Z)-2-(4-cyanophenyl)-2-(methoxyimino)ethyl]oxy}benzyl)oxy]-2-fluorophenyl}propanoate (52)

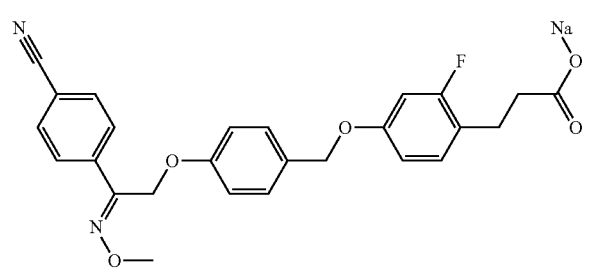

52

Compound 52 was synthesized from 3-{4-[(4-{[(22)-2-(4-cyanophenyl)-2-(methoxyimino)ethyl]oxy}benzyl)oxy]-2-fluorophenyl}propanoic acid (0.06 g, 0.12 mmol) and sodium hydroxide (0.0049 g, 0.12 mmol) by following the procedure described in scheme 12 (0.046 g, yield: 85.2%); Purity: 88.58%.

Example 53

Sodium 3-cyano-3-{4-[(4-{[(2E)-2-(methoxyimino)-2-phenylethyl]oxy}benzyl)oxy]phenyl}propanoate (53)

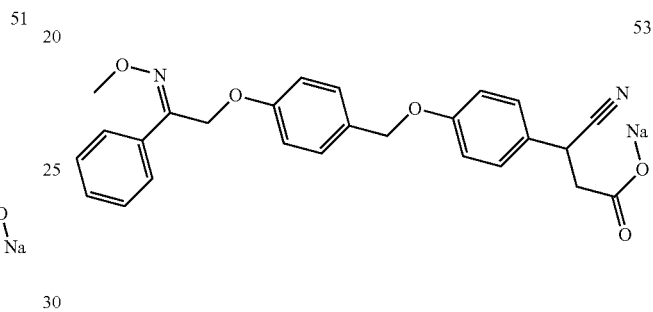

53

Compound 53 was synthesized from sodium hydroxide (0.05 g, 1.27 mmol) and ethyl 3-cyano-3-{4-[(4-{[(2E)-2-(methoxyimino)-2-phenylethyl]oxy}benzyl)oxy]phenyl}propanoate (0.3 g, 0.64 mmol) by following the procedure described in scheme 12 (0.2 g, yield: 67.38%); Purity: 89.99%.

Example 54

Sodium 3-cyano-3-{4-[(4-{[(2Z)-2-(4-fluorophenyl)-2-(methoxyimino)ethyl]oxy}benzyl)oxy]phenyl}propanoate (54)

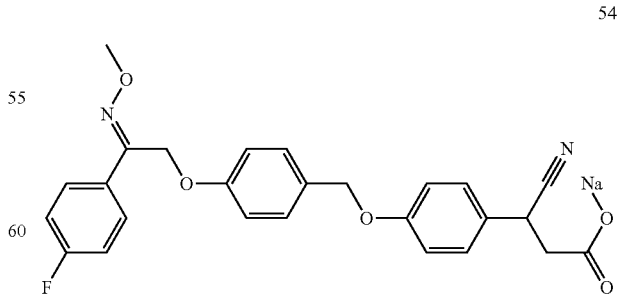

54

Compound 54 was synthesized from sodium hydroxide (0.067 g, 1.6 mmol) and 3-cyano-3-{4-[(4-{[(2Z)-2-(4-fluorophenyl)-2-(methoxyimino)ethyl]oxy}benzyl)oxy]

phenyl}propanoic acid (0.4 g, 0.8 mmol) by following the procedure described in scheme 12 (0.3 g, yield: 73.84%); Purity: 96.50%.

Example 55

Sodium 3-cyano-3-{4-[(4-{[(2Z)-2-(3-fluorophenyl)-2-(methoxyimino)ethyl]oxy}benzyl)oxy]phenyl}propanoate (55)

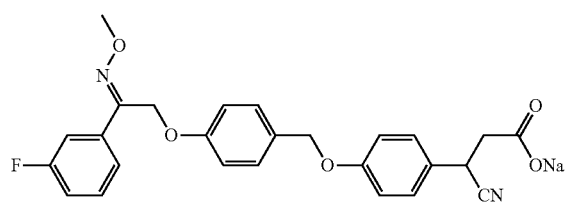

Compound 55 was synthesized from 3-cyano-3-{4-[(4-{[(2Z)-2-(3-fluorophenyl)-2-(methoxyimino)ethyl]oxy}benzyl)oxy]phenyl}propanoic acid (0.55 g, 1.2 mmol) and sodium hydroxide (0.092 g, 2.3 mmol) by following the procedure described in scheme 12 (0.4 g, yield: 71.59%); Purity: 96.74%.

Example 56

Sodium 3-{2-fluoro-4-[(3-methoxy-4-{[(2Z)-2-(methoxyimino)-2-phenylethyl]oxy}benzyl)oxy]phenyl}propanoate (56)

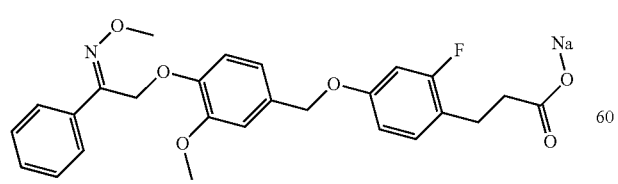

Compound 56 was synthesized from 3-{2-fluoro-4-[(3-methoxy-4-{[(2Z)-2-(methoxyimino)-2-phenylethyl]oxy}benzyl)oxy]phenyl}propanoic acid (0.3 g, 0.6 mmol) and sodium hydroxide (0.072 g, 1.8 mmol) by following the procedure described in scheme 12 (0.085 g, yield: 30.00%); Purity: 90.03%.

Example 57

Sodium 2-{4-[(4-{[(2Z)-2-(methoxyimino)-2-(4-methoxyphenyl)ethyl]oxy}benzyl)oxy]phenyl}cyclopropanecarboxylate (57)

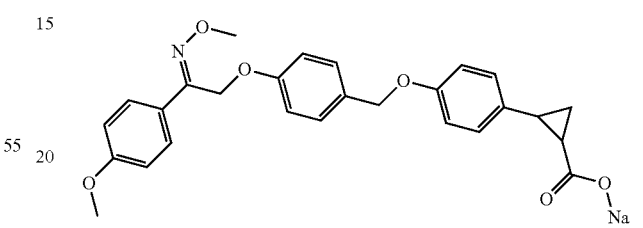

Compound 57 was synthesized from 2-{4-[(4-{[(2Z)-2-(methoxyimino)-2-(4-methoxyphenyl)ethyl]oxy}benzyl)oxy]phenyl}cyclopropanecarboxylic acid (0.08 g, 0.2 mmol) and sodium hydroxide (0.013 g, 0.3 mmol) by following the procedure described in scheme 12 (0.022 g, yield: 27.84%); Purity: 98.61%.

Example 58

3-{2-(Cyclopropylmethoxy)-4-[(4-{[(2Z)-2-(methoxyimino)-2-phenylethyl]oxy}benzyl)oxy]phenyl}propanoic acid (58)

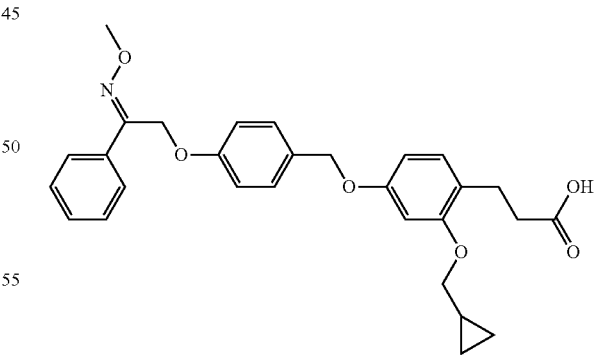

Compound 58 was synthesized from (1Z)-2-[4-(hydroxymethyl)phenoxy]-1-phenylethanone O-methyloxime (0.656 g, 2.4 mmol) and methyl 3-[2-(cyclopropylmethoxy)-

4-hydroxyphenyl]propanoate (0.6 g, 2.4 mmol) by following the procedure described in scheme 18 (0.04 g, yield: 4.20%); Purity: 98.15%.

Example 59

3-Cyano-3-{4-[(4-{[(2Z)-2-(methoxyimino)-2-phenylethyl]oxy}benzyl)oxy]phenyl}butanoic acid (59)

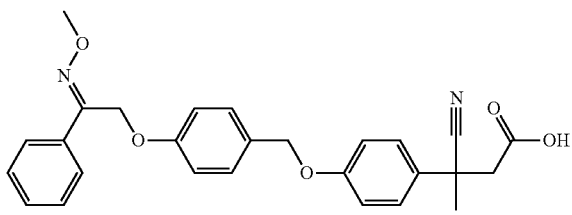

Compound 59 was synthesized from (1Z)-2-[4-(hydroxymethyl)phenoxy]-1-phenylethanone O-methyloxime (2.34 g, 8.66 mmol) and ethyl 3-cyano-3-(4-hydroxyphenyl)butanoate (2.4 g, 9.6 mmol) by following the procedure described in scheme 18 (0.15 g, yield: 57.47%); Purity: 98.34%.

Example 60

3-{4-[(4-{[(2Z)-2-(Methoxyimino)-2-phenylethyl]oxy}benzyl)oxy]-2-(propan-2-yloxy)phenyl}propanoic acid (60)

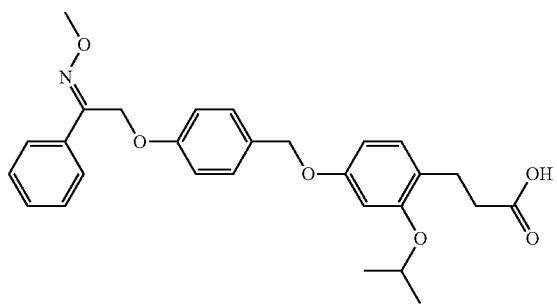

Compound 60 was synthesized from (1Z)-2-[4-(hydroxymethyl)phenoxy]-1-phenylethanone O-methyloxime (0.268 g, 0.99 mmol) and ethyl 3-(4-hydroxy-2-isopropoxyphenyl)propanoate (0.25 g, 0.99 mmol) by following the procedure described in scheme 15 (0.04 g, yield: 13.73%); Purity: 97.21%.

Example 61

3-{4-[(4-{[(2E,2Z)-2-(Methoxyimino)-2-phenylethyl]oxy}benzyl)oxy]phenyl}-3-methylbutanoic acid (61)

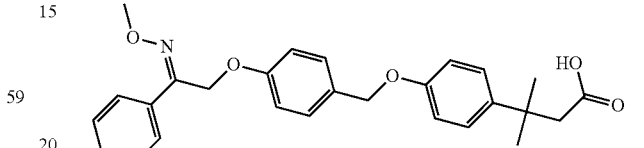

Compound 61 was synthesized from (1E,1Z)-2-[4-(hydroxymethyl)phenoxy]-1-phenylethanone O-methyloxime (0.128 g, 0.47 mmol) and methyl 3-(4-hydroxyphenyl)-3-methylbutanoate (0.11 g, 0.52 mmol) by following the procedure described in scheme 18 (0.001 g, yield: 1.04%); Purity: 65.13%.

Example 62

3-Cyano-3-{4-[(4-{[(2Z)-2-(methoxyimino)-2-phenylethyl]oxy}benzyl)oxy]-2-methylphenyl}propanoic acid (62)

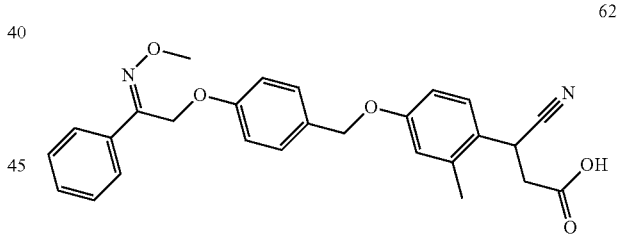

Compound 62 was synthesized from (1Z)-2-[4-(hydroxymethyl)phenoxy]-1-phenylethanone O-methyloxime (0.5 g, 1.85 mmol) and methyl 3-cyano-3-(4-hydroxy-2-methylphenyl)propanoate (0.404 g, 1.85 mmol) by following the procedure described in scheme 18 (0.65 g, yield: 95.69%); Purity: 93.64%.

Scheme 18

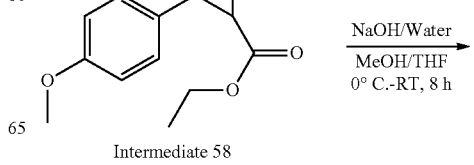

Intermediate 58

-continued

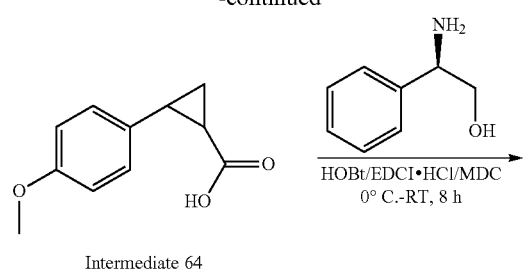
Intermediate 64

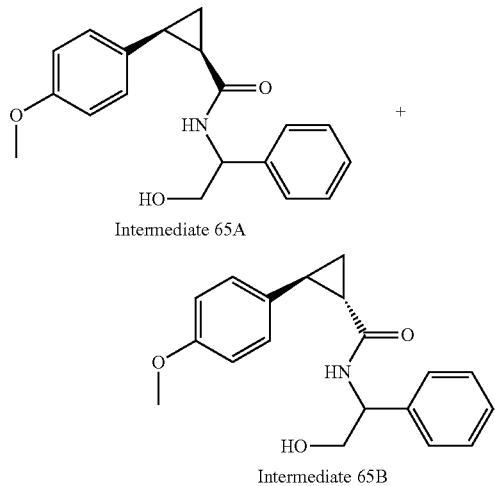
Intermediate 65A

Intermediate 65B

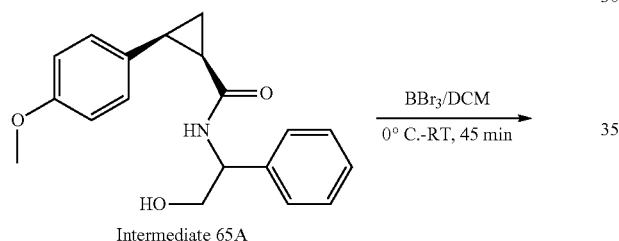
Intermediate 65A

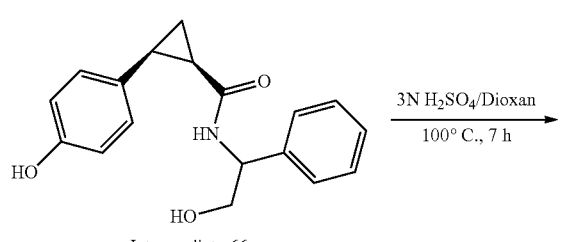
Intermediate 66

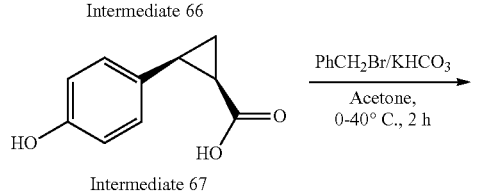
Intermediate 67

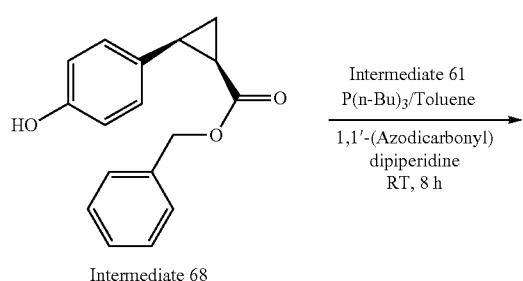
Intermediate 68

-continued

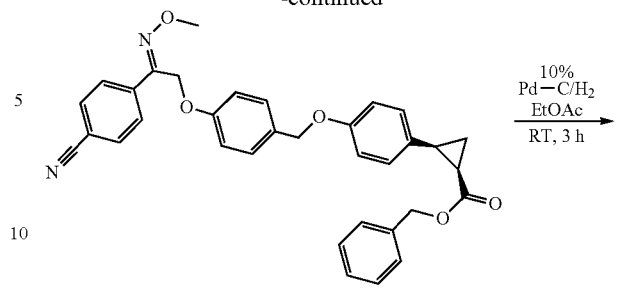
Intermediate 69

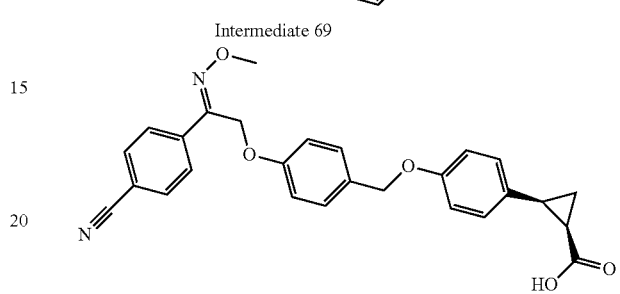
Compound 63

Example 63

(1R,2S)-2-{4-[(4-{[(2Z)-2-(4-Cyanophenyl)-2-(methoxyimino)ethyl]oxy}benzyl)oxy]phenyl}cyclopropanecarboxylic acid (63)

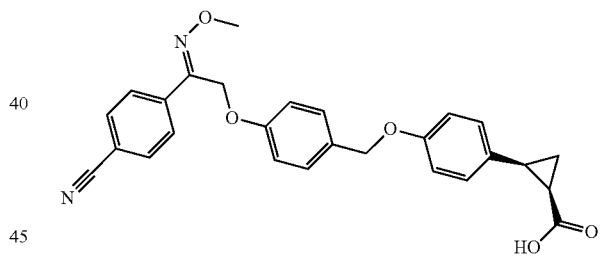

Compound 63 was prepared by using benzyl (1R,2S)-2-(4-hydroxyphenyl)cyclopropanecarboxylate and 4-{(1E,1Z)-2-[4-(hydroxymethyl)phenoxy]-N-methoxyethanimidoyl}benzonitrile by following the procedure described in scheme 17.

Intermediate 64:
2-(4-Methoxyphenyl)cyclopropanecarboxylic acid

To a 100 mL RB flask fitted with magnetic stirrer was charged with 20 mL of tetrahydrofuran. To the stirred solvent was added ethyl 2-(4-methoxyphenyl)cyclopropanecarboxylate (8 g, 36 mmol). The reaction mixture was cooled to 0° C. and sodium hydroxide (2.1 g, 54 mmol) in water (5 mL) was added drop wise, followed by ethanol (10 mL). The reaction mixture was stirred for 8 h at room temperature. The reaction mixture was concentrated to distill off the solvent; the crude was acidified with 1N hydrochloric acid to make acidic pH and extracted with ethyl acetate (50 mL). The layers were separated; the organic layer was washed with brine solution (20 mL). The organic layer was dried over Na$_2$SO$_4$ and the solvent was removed under reduced pressure. The product was obtained as off white solid (6.5 g, yield: 94.2%). $^1$H NMR (300 MHz, CDCl$_3$): δ 6.96-6.99 (d, 2H), 6.74-6.77 (d, 2H), 3.71 (s, 3H), 2.46-2.53 (m, 1H), 1.72-1.78 (m, 1H), 1.52-1.58 (m, 1H), 1.27-1.32 (m, 1H).

Intermediate 65A and 65B: (1R,2S)-N-(2-Hydroxy-1-phenylethyl)-2-(4-methoxyphenyl)cyclopropanecarboxamide To a 250 mL RB flask fitted with magnetic stirrer was charged with 70 mL of dichloromethane. To the stirred solvent were added 2-(4-methoxyphenyl)cyclopropanecarboxylic acid (4.5 g, 33 mmol), D-(−)-α-phenylglycinol (3.2 g, 50 mmol). The reaction mixture was brought to 0° C., followed by the addition of N-(3-dimethylaminopropyl)-N-ethylcarbodiimide hydrochloride (6.7 g, 50 mmol), N-hydroxybenzotriazole (3.1 g, 33 mmol) and the reaction mixture was allowed to stir at room temperature for 8 h. The reaction mixture was diluted with dichloromethane (100 mL) and washed with water (100 mL). The organic layer was washed with brine solution (25 mL). The organic layer was dried over Na$_2$SO$_4$ and the solvent was removed under reduced pressure. The product was obtained as white solid (2 g, yield: 27.44%).

Intermediate 66: (1R,2S)-2-(4-Hydroxyphenyl)-N-(2-hydroxy-1-phenylethyl)cyclopropanecarboxamide To a 250 mL RB flask fitted with magnetic stirrer was charged with 100 mL of dichloromethane. To the stirred solvent was added (1R,2S)—N-(2-hydroxy-1-phenylethyl)-2-(4-methoxyphenyl)cyclopropanecarboxamide (1.9 g, 6 mmol). The reaction mixture was brought to 0° C. and boron tribromide (0.86 mL, 9 mmol) was added drop wise. The reaction mixture was allowed to stir at room temperature for 45 minutes. The reaction mixture was quenched with ethanol (5 mL), the reaction mixture was concentrated to distill off the solvent; water (25 mL) was added and extracted with ethyl acetate (25 mL). The organic layer was washed with saturated NaHCO$_3$ solution (10 mL) and brine solution (10 mL). The organic layer was dried over Na$_2$SO$_4$ and the solvent was removed under reduced pressure. The product was obtained as white solid (0.55 g, yield: 58.7%). $^1$H NMR (300 MHz, DMSO-d$_6$): δ 9.20 (s, 1H), 8.47-8.50 (d, 1H), 7.21-7.30 (m, 5H), 6.88-6.91 (d, 2H), 6.63-6.66 (d, 2H), 4.86-4.90 (t, 2H), 3.52-3.56 (t, 2H), 2.05-2.11 (m, 1H), 1.87-1.93 (m, 1H), 1.24-1.29 (m, 1H), 1.04-1.10 (m, 1H).

Intermediate 67: (1R,2S)-2-(4-Hydroxyphenyl)cyclopropanecarboxylic acid

To a 100 mL RB flask fitted with magnetic stirrer was charged with 22 mL of dioxan. To the stirred solvent were added (1R,2S)-2-(4-hydroxyphenyl)-N-(2-hydroxy-1-phenylethyl)cyclopropanecarboxamide (0.75 g, 2.52 mmol) and 3N sulfuric acid (22 mL). The reaction mixture was heated at 100° C. for 7 h. The reaction mixture was poured into ice and extracted with ethyl acetate (25 mL). The organic layer was washed with brine solution (25 mL). The organic layer was dried over Na$_2$SO$_4$ and the solvent was removed under reduced pressure. The product was obtained as pale yellow oil (0.51 g, yield: 100%). $^1$H NMR (300 MHz, DMSO-d$_6$): δ 12.20 (s, 1H), 9.25 (s, 1H), 6.93-6.96 (d, 2H), 6.64-6.67 (d, 2H), 2.24-2.31 (m, 1H), 1.63-1.68 (m, 1H), 1.31-1.37 (m, 1H), 1.20-1.26 (m, 1H).

Intermediate 68: Benzyl (1R,2S)-2-(4-hydroxyphenyl)cyclopropane carboxylate

To a 100 mL RB flask fitted with magnetic stirrer was charged with 50 mL of acetone. To the stirred solvent was added (1R,2S)-2-(4-hydroxyphenyl)cyclopropanecarboxylic acid (0.51 g, 2.86 mmol). The reaction mixture was brought to 0° C., potassium bicarbonate (0.28 g, 2.8 mmol), stirred for 10 minutes, benzyl bromide (0.3 mL, 2.8 mmol) was added drop wise. The reaction mixture was heated at 40° C. for 2 h. The reaction mixture was concentrated to distill off the solvent; water (25 mL) was added and extracted with ethyl acetate (25 mL). The organic layer was washed with brine solution (25 mL). The organic layer was dried over Na$_2$SO$_4$ and the solvent was removed under reduced pressure. The product was obtained as pale yellow liquid (0.44 g, yield: 57.2%). $^1$H NMR (300 MHz, CDCl$_3$): δ 7.30 (s, 4H), 7.19 (s, 1H), 6.89-6.92 (d, 2H), 6.66-6.68 (d, 2H), 5.08 (s, 2H), 4.89 (s, 1H), 2.41-2.48 (m, 1H), 1.78-1.84 (m, 1H), 1.49-1.56 (m, 1H), 1.17-1.24 (m, 1H).

Intermediate 69: Benzyl (1R,2S)-2-{4-[(4-{[(2E,2Z)-2-(4-cyanophenyl)-2-(methoxyimino)ethyl]oxy}benzyl)oxy]phenyl}cyclopropanecarboxylate To a 100 mL RB flask fitted with magnetic stirrer was charged with 20 mL of toluene. To the stirred solvent were added benzyl (1R,2S)-2-(4-hydroxyphenyl)cyclopropanecarboxylate (0.44 g, 1.6 mmol) and 4-{(1E,1Z)-2-[4-(hydroxymethyl)phenoxy]-N-methoxyethanimidoyl}benzonitrile (0.43 g, 1.4 mmol). The reaction mixture was brought to 0° C.; tributylphosphine (0.61 mL, 2.4 mmol) was added and stirred for 10 minutes. To that, 1,1-(azodicarbonyl)dipiperidine (0.62 g, 2.4 mmol) in toluene (2 mL) was added drop wise. The reaction mixture was stirred at room temperature for 8 h. The reaction mixture was diluted with ethyl acetate (25 mL) and washed with water (25 mL). The organic layer was washed with brine solution (25 mL). The organic layer was dried over Na$_2$SO$_4$ and the solvent was removed under reduced pressure. The product was obtained as pale yellow oil (0.64 g, yield: 71.4%).

Compound 63: (1R,2S)-2-{4-[(4-{[(2Z)-2-(4-Cyanophenyl)-2-(methoxyimino)ethyl]oxy}benzyl)oxy]phenyl}cyclopropanecarboxylic acid To a 250 mL RB flask fitted with a magnetic stirrer was charged with 20 mL of ethyl acetate. To the stirred solvent was added benzyl (1R,2S)-2-{4-[(4-{[(2E,2Z)-2-(4-cyanophenyl)-2-(methoxyimino)ethyl]oxy}benzyl)oxy]phenyl}cyclopropanecarboxylate (0.64 g, 1.17 mmol). The reaction mixture was purged with nitrogen for 10 minutes. Then 10% palladium on carbon (0.07 g) was added and stirred under hydrogen atmosphere for 3 h. After 3 h, the reaction mixture was filtered through celite and washed with ethyl acetate (50 mL). The filtrate was concentrated to distill off the solvent and dried under vacuum. The product was obtained as white solid (0.19 g, yield: 37.7%). MS (ESI, 120 eV): m/z=455.1 (M−H)$^+$; HPLC purity: 94.6%; $^1$H NMR (300 MHz, DMSO-d$_6$): δ 12.11 (br s, 1H), 7.80-7.89 (m, 4H), 7.32-7.35 (d, 2H), 7.05-7.08 (d, 2H), 6.87-6.91 (m, 4H), 5.27 (s, 2H), 4.97 (s, 2H), 2.27-2.35 (m, 1H), 1.67-1.73 (m, 1H), 1.33-1.39 (m, 1H).

Example 64

(1S,2S)-2-{4-[(4-{[(2E,2Z)-2-(4-Cyanophenyl)-2-(methoxyimino)ethyl]oxy}benzyl)oxy]phenyl}cyclopropanecarboxylic acid (64)

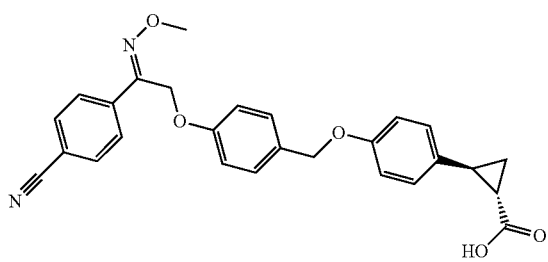

Compound 64 was synthesized from benzyl (1S,2S)-2-(4-hydroxyphenyl)cyclopropanecarboxylate (0.6 g, 2.2 mmol) and 4-{(1E,1Z)-2-[4-(hydroxymethyl)phenoxy]-N-methoxyethanimidoyl}benzonitrile (0.66 g, 2.2 mmol) by following the procedure described in scheme 18 (0.2 g, yield: 39.91%); Purity: 89.14%.

Example 65

3-{4-[(4-{[(2Z)-2-(Methoxyimino)-2-phenylethyl]oxy}benzyl)oxy]-2-(5-methyl-1,2-oxazol-3-yl)phenyl}propanoic acid

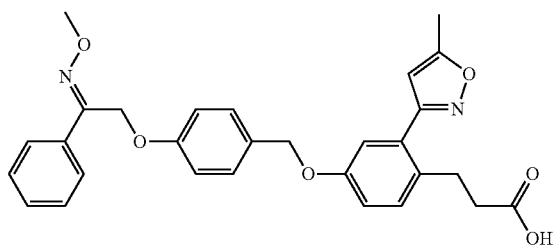

Compound 65 was synthesized from (4-{[(2Z)-2-(methoxyimino)-2-phenylethyl]oxy}phenyl)methanol (0.0012 g, 0.0439 mmol) and methyl 3-[4-hydroxy-2-(5-methyl-1,2-oxazol-3-yl)phenyl]propanoate (0.0015 g, 0.0549 mmol) by following the procedure described in scheme 18 (0.006 g, yield: 10.20%); Purity: 96.94%.

Example 66

3-Cyano-3-{4-[(4-{[(2Z)-2-(methoxyimino)-2-(4-methoxyphenyl)ethyl]oxy}benzyl)oxy]phenyl}propanoic acid

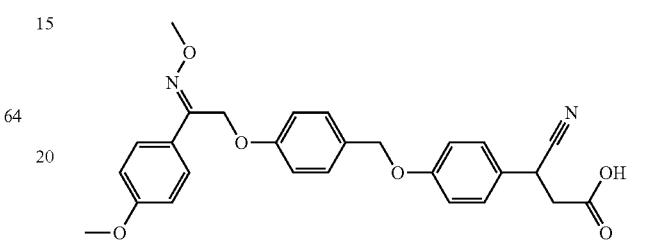

Compound 66 was synthesized from (4-{[(2Z)-2-(methoxyimino)-2-(4-methoxyphenyl)ethyl]oxy}phenyl)methanol (0.33 g, 0.9 mmol) and methyl 3-cyano-3-(4-hydroxyphenyl)propanoate (0.21 g, 0.9 mmol) by following the procedure described in scheme 13 (0.3 g, yield: 89.28%); Purity: 85%.

Scheme 19

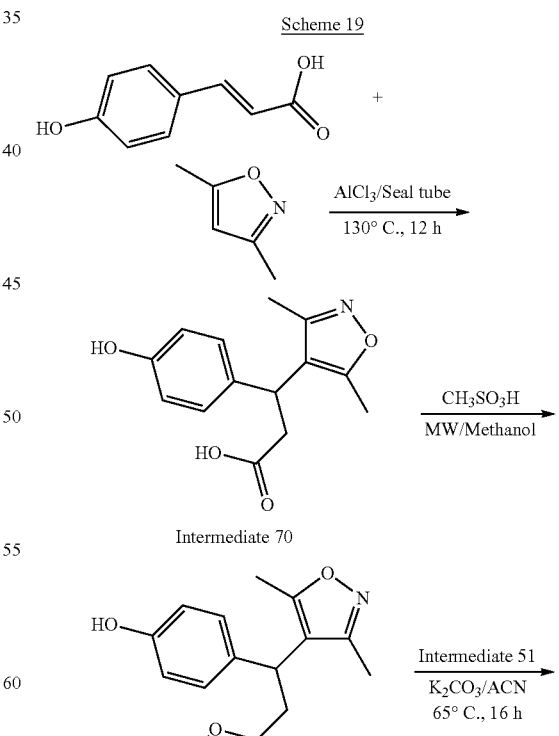

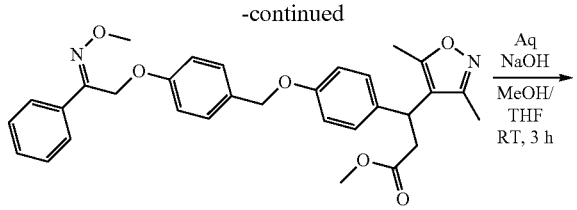

Intermediate 72

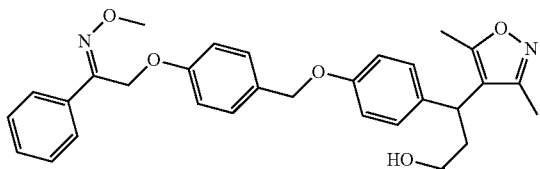

Compound 67

Example 67

3-(3,5-Dimethyl-1,2-oxazol-4-yl)-3-{4-[(4-{[(2E, 2Z)-2-(methoxyimino)-2-phenylethyl]oxy}benzyl) oxy]phenyl}propanoic acid

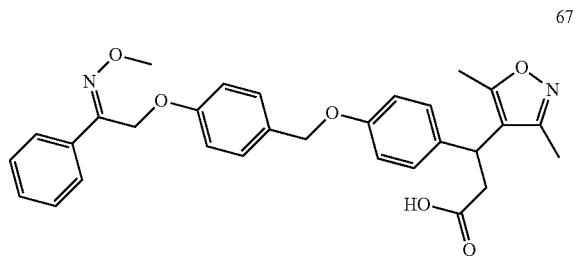 [SMILES: CO/N=C(\COc1ccc(COc2ccc(C(CC(=O)O)c3c(C)noc3C)cc2)cc1)c1ccccc1]

Compound 67 was synthesized from (1E,1Z)-2-[4-(bromomethyl)phenoxy]-N-methoxy-1-phenylethanimine (0.121 g, 0.363 mmol) and methyl 3-(3,5-dimethyl-1,2-oxazol-4-yl)-3-(4-hydroxyphenyl)propanoate (0.1 g, 0.363 mmol) by following the procedure described in scheme 18 (0.01 g, yield: 5.4%).

Intermediate 70: 3-(3,5-Dimethyl-1,2-oxazol-4-yl)-3-(4-hydroxyphenyl)propanoic acid To a 50 mL sealed was charged with (2E)-3-(4-hydroxyphenyl)prop-2-enoic acid (3.0 g, 0.018 mmol) and 3,5-dimethyl-1,2-oxazole (3.54 g, 0.054 mmol) and heated at 130° C. for 16 h. The reaction mixture diluted with water (10 mL) was added and extracted with DCM (20 mL). The combined extract was dried over anhydrous $Na_2SO_4$ and the solvent was removed under reduced pressure. The crude material was taken for next step with out purification (1.0 g, yield: 20.96%).

Intermediate 71: Methyl 3-(3,5-dimethyl-1,2-oxazol-4-yl)-3-(4-hydroxyphenyl)propanoate To a 25 mL RB flask fitted with magnetic stirrer was charged 20 mL of methanol. To the stirred solvent was added 3-(3,5-Dimethyl-1,2-oxazol-4-yl)-3-(4-hydroxyphenyl)propanoic acid (1.0 g, 6.1 mmol), followed by methanesulfonic acid (1.16 g, 12.0 mmol). After addition, the RM was refluxed at 65° C. for 1 h. After 1 h, the solvent was evaporated, water (20 mL) was added and the organic layer was extracted with ethyl acetate (15 mL×2). The organic layer was dried over anhydrous $Na_2SO_4$ and the solvent was removed under reduced pressure. The product was obtained as brown liquid. (0.2 g, yield: 18.72%).

Intermediate 72: Methyl 3-(3,5-dimethyl-1,2-oxazol-4-yl)-3-{4-[(4-{[(2E,2Z)-2-(methoxyimino)-2-phenylethyl]oxy}benzyl)oxy]phenyl}propanoate To a 25 mL RB flask fitted with magnetic stirrer was charged with 5 mL of acetonitrile. To the stirred solvent were added methyl 3-(3,5-dimethyl-1,2-oxazol-4-yl)-3-(4-hydroxyphenyl)propanoate (0.1 g, 0.363 mmol), potassium carbonate (0.15 g, 1.09 mmol). The reaction mixture was brought to 0° C., (1E,1Z)-2-[4-(bromomethyl)phenoxy]-N-methoxy-1-phenylethanimine (0.121 g, 0.363 mmol) in acetonitrile (2 mL) was added drop wise and stirred at 65° C. for 14 h. The reaction mixture was concentrated to distill off the solvent diluted with water (10 mL) was added and extracted with ethyl acetate (10 mL). The organic layer was washed with water (5 mL) and saturated brine solution (5 mL). The organic layer was dried over anhydrous $Na_2SO_4$ and the solvent was removed under reduced pressure. The crude material was purified by silica gel column chromatography using ethyl acetate and petroleum ether as elutants. The product was obtained as white solid (0.19 g, yield: 100.00%).

Compound 67: 3-(3,5-Dimethyl-1,2-oxazol-4-yl)-3-{4-[(4-{[(2E,2Z)-2-(methoxyimino)-2-phenylethyl]oxy}benzyl)oxy]phenyl}propanoic acid To a 10 mL RB flask fitted with magnetic stirrer was charged with 3 mL of tetrahydrofuran. To the stirred solvent were added Methyl 3-(3,5-dimethyl-1,2-oxazol-4-yl)-3-{4-[(4-{[(2E,2Z)-2-(methoxyimino)-2-phenylethyl]oxy}benzyl)oxy]phenyl}propanoate (0.19 g, 0.36 mmol), methanol (3 mL) and sodium hydroxide (0.030 g, 0.75 mmol) in water (1.0 mL). The reaction mixture was stirred at room temperature overnight. After completion of the reaction, the solvent was removed, the sodium salt was washed with diethyl ether (5 mL); the aqueous layer was acidified with 1N HCl to pH 2.0 and extracted with ethyl acetate (5 mL). The organic layer was dried over anhydrous $Na_2SO_4$ and the solvent was removed under reduced pressure. The crude was purified through silica gel column chromatography using methanol and dichloromethane as elutants. The product was obtained as pale yellow sticky solid (0.01 g, yield: 5.4%).

Scheme 20

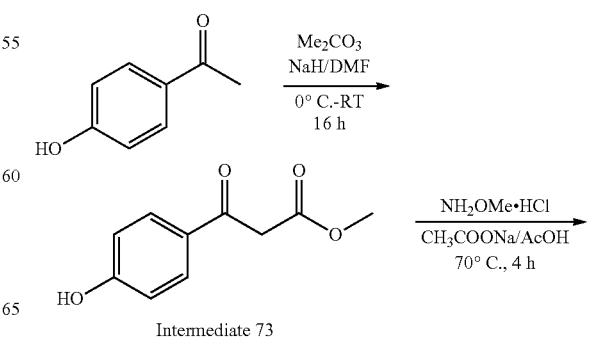

Intermediate 73

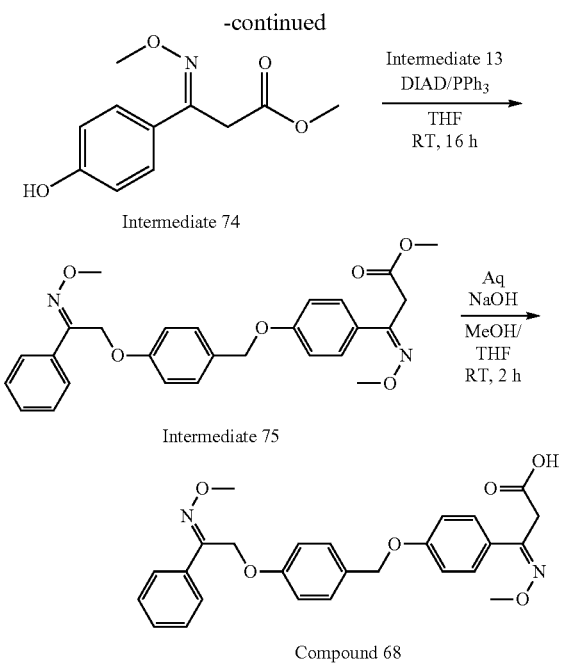

Example 68

(3E,3Z)-3-(Methoxyimino)-3-{4-[(4-{[(2Z)-2-(methoxyimino)-2-phenylethyl]oxy}benzyl)oxy]phenyl}propanoic acid

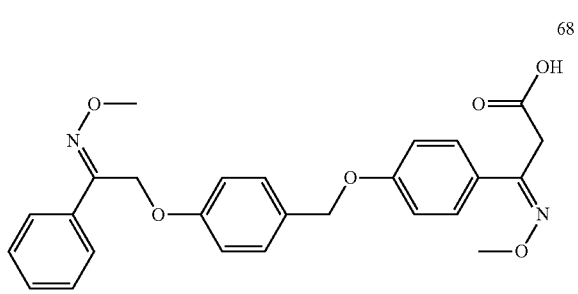 [SMILES: CO/N=C(\COc1ccc(COc2ccc(/C(CC(=O)O)=N\OC)cc2)cc1)c1ccccc1]

Compound 68 was synthesized from (4-{[(2Z)-2-(methoxyimino)-2-phenylethyl]oxy}phenyl)methanol (0.24 g, 0.89 mmol) and methyl (3E,3Z)-3-(4-hydroxyphenyl)-3-(methoxyimino) propanoate (0.2 g, 0.89 mmol) by following the procedure described in scheme 20 (0.02 g, yield: 25.76%); Purity: 96.32%.

Intermediate 73: Methyl 3-(4-hydroxyphenyl)-3-oxopropanoate

To a 250 mL RB flask fitted with magnetic stirrer was charged with sodium hydride (3.5 g, 147 mmol). At 0 deg C., 100 mL of DMF was added slowly with stirring. To the stirred solvent were added 1-(4-hydroxyphenyl)ethanone (5 g, 36 mmol) and dimethylcarbonate (15.5 g, 170 mmol), stirred at room temperature overnight. The RM was poured into water (100 mL) and extracted with ethyl acetate (100 mL). The organic layer was washed with water (50 mL) and saturated brine solution (50 mL). The organic layer was dried over anhydrous $Na_2SO_4$ and the solvent was removed under reduced pressure. The crude material was purified by silica gel column chromatography using ethyl acetate and petroleum ether as elutants. The product was obtained as pale yellow oil (3.4 g, yield: 47.66%). MS (ESI, 120 eV): m/z=195 (M+H)$^+$; $^1$H NMR (300 MHz, CDCl$_3$): δ 7.79-7.82 (d, 2H), 6.81-6.84 (d, 2H), 6.21 (br s, 1H), 3.90 (s, 2H), 3.69 (s, 3H).

Intermediate 74: Methyl (3E,3Z)-3-(4-hydroxyphenyl)-3-(methoxyimino)propanoate To a 50 mL RB flask fitted with magnetic stirrer was charged with 10 mL of acetic acid. To the stirred solvent were added methyl 3-(4-hydroxyphenyl)-3-oxopropanoate (0.5 g, 2.6 mmol), sodium acetate (0.31 g, 3.8 mmol) and O-methylhydroxylamine hydrochloride (0.32 g, 3.8 mmol), stirred at 70° C. for 4 h. The RM was poured into water (50 mL) and extracted with ethyl acetate (50 mL). The organic layer was washed with water (25 mL) and saturated brine solution (25 mL). The organic layer was dried over anhydrous $Na_2SO_4$ and the solvent was removed under reduced pressure. The product was obtained as white solid (0.35 g, yield: 60.86%). MS (ESI, 120 eV): m/z=224 (M+H)$^+$; $^1$H NMR (300 MHz, CDCl3): δ 7.43-7.46 (d, 2H), 6.71-6.74 (d, 2H), 5.45 (s, 1H), 3.91 (s, 3H), 3.68 (s, 2H), 3.63 (s, 3H).

Intermediate 75: Methyl (3E,3Z)-3-(methoxyimino)-3-{4-[(4-{[(2Z)-2-(methoxy imino)-2-phenylethyl]oxy}benzyl)oxy]phenyl}propanoate To a 50 mL RB flask fitted with magnetic stirrer was charged with 10 mL of tetrahydrofuran. To the stirred solvent were added methyl (3E,3Z)-3-(4-hydroxyphenyl)-3-(methoxyimino)propanoate (0.2 g, 0.89 mmol), (1E,1Z)-2-[4-(hydroxymethyl)phenoxy]-1-phenylethanone (0.24 g, 0.89 mmol) and triphenylphosphine (0.34 g, 1.34 mmol). The reaction mixture was cooled to 0° C. and diisopropylazocarboxylate (0.27 g, 13.4 mmol) was added drop wise and stirred at room temperature overnight. The RM was poured into water (25 mL) and extracted with ethyl acetate (50 mL). The organic layer was washed with water (50 mL) and saturated brine solution (50 mL). The organic layer was dried over anhydrous Na2SO4 and the solvent was removed under reduced pressure. The crude material was purified by silica gel column chromatography using ethyl acetate and petroleum ether as elutants. The product was obtained as colorless oil (0.08 g, yield: 18.74%). MS (ESI, 120 eV): m/z=477 (M+H)$^+$; $^1$H NMR (300 MHz, CDCl$_3$): δ 7.58-7.61 (m, 2H), 7.49-7.52 (d, 2H), 7.26-7.29 (m, 4H), 7.23 (s, 1H), 6.83-6.89 (t, 4H), 5.13 (s, 2H), 4.92 (s, 2H), 3.99 (s, 3H), 3.91 (s, 3H), 3.68 (s, 2H), 3.62 (s, 3H).

Compound 68: (3E,3Z)-3-(Methoxyimino)-3-{4-[(4-{[(2Z)-2-(methoxyimino)-2-phenylethyl]oxy}benzyl)oxy]phenyl}propanoic acid To a 10 mL RB flask fitted with magnetic stirrer was charged with 4 mL of tetrahydrofuran. To the stirred solvent were added methyl (3E,3Z)-3-(methoxyimino)-3-{4-[(4-{[(2E,2Z)-2-(methoxyimino)-2-phenylethyl]oxy}benzyl)oxy]phenyl}propanoate (0.08 g, 0.16 mmol) and methanol (2 mL). Then the reaction mixture was cooled to 0° C. and sodium hydroxide (0.13 g, 0.33 mmol) in water (1 mL) was added and stirred for 1 hour. The RM was concentrated to distill off the solvent, the crude was washed with ether, acidified with 1N HCl and extracted with ethyl acetate (5 mL). The crude was purified by preparative TLC using to methanol and chloroform as elutants. The product was obtained as off white solid (0.02 g, yield: 25.76%).

Scheme 21

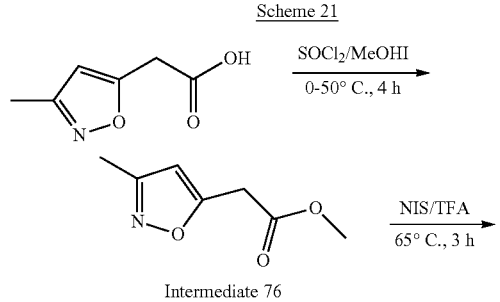

Intermediate 76

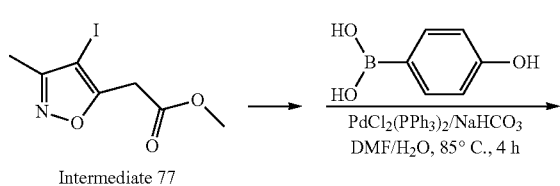

Intermediate 77

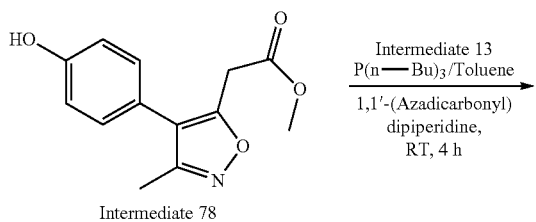

Intermediate 78

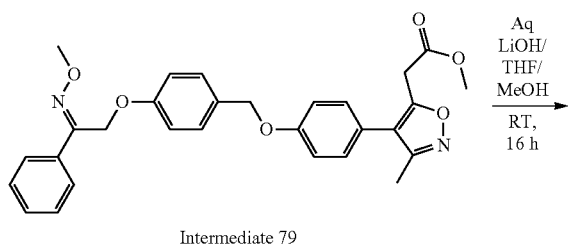

Intermediate 79

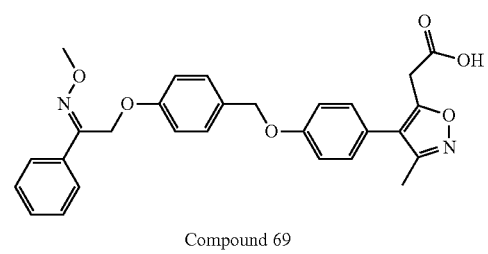

Compound 69

Example 69

(4-{(4-[(4-{[(2Z)-2-(Methoxyimino)-2-phenylethyl]oxy}benzyl)oxy]phenyl}3-methyl-1,2-oxazol-5-yl) acetic acid

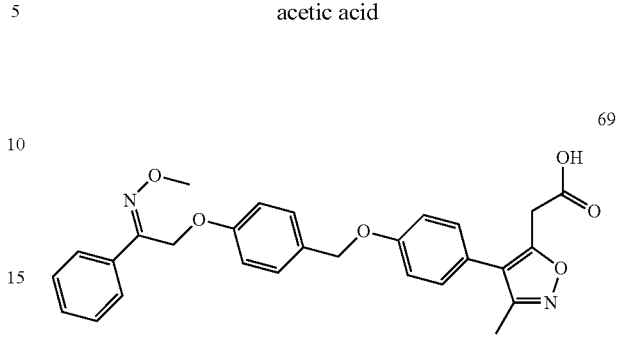

Compound 69 was synthesized from (4-{[(2Z)-2-(methoxyimino)-2-phenylethyl]oxy}phenyl) methanol (0.329 g, 1.2 mmol) and methyl [4-(4-hydroxyphenyl)-3-methyl-1,2-oxazol-5-yl]acetate (0.3 g, 1.2 mmol) by following the procedure described in scheme 21 (0.32 g, yield: 70.2%); Purity: 96.43%.

Intermediate 76: Methyl (3-methyl-1,2-oxazol-5-yl)acetate

To a 50 mL RB flask fitted with magnetic stirrer was charged with 10 mL of methanol. To the stirred solvent was added (3-methyl-1,2-oxazol-5-yl)acetic acid (1 g, 7 mmol), was added drop wise $SOCl_2$ (1.25 g, 10.5 mmol) to the reaction mixture at 0° C. and stirred at 50° C. for 4 h. After completion of the reaction, the reaction mixture was concentrated to distill off the solvent; water (25 mL) was added and extracted with ethyl acetate (25 mL). The organic layer was washed with saturated $NaHCO_3$ solution (10 mL) and brine solution (10 mL). The organic layer was dried over anhydrous $Na_2SO_4$ and the solvent was removed under reduced pressure. The product was obtained as brown liquid (1 g, yield: 92%). $^1H$ NMR (300 MHz, $CDCl_3$): δ 6.03 (s, 1H), 3.73 (d, 2H), 3.69 (s, 3H), 2.23 (s, 3H).

Intermediate 77: Methyl (4-iodo-3-methyl-1,2-oxazol-5-yl)acetate

To a sealed tube fitted with magnetic stirrer was charged methyl (3-methyl-1,2-oxazol-5-yl)acetate (0.9 g, 5.8 mmol) and N-iodosuccinimide (2.61 g, 11.6 mmol) in 10 mL trifluoroacetic acid. The reaction mixture was heated at 65° C. for 3 h. The RM was quenched with $NaHCO_3$ solution (25 mL) and extracted with ethyl acetate (30 mL). The organic layer was washed with water (30 mL) and saturated brine solution (30 mL). The organic layer was dried over anhydrous $Na_2SO_4$ and the solvent was removed under reduced pressure. The product was obtained as brown solid (1.18 g, yield: 72.4%).

Intermediate 78: Methyl [4-(4-hydroxyphenyl)-3-methyl-1,2-oxazol-5-yl]acetate To a 50 mL two neck RB flask fitted with magnetic stirrer was charged with 5 mL of DMF. To the stirred solvent were added methyl (4-iodo-3-methyl-1,2-oxazol-5-yl)acetate (0.7 g, 2.5 mmol), (4-hydroxyphenyl)boronic acid (0.34 g, 2.5 mmol) and 1 mL of aqueous NaHCO3 solution (0.62 g, 7.47 mmol) under argon atmosphere. After purging the argon gas about 10 minutes was added bis-(triphenylphosphine) palladium(II)chloride (0.21 g, 0.3 mmol) and heated at 85° C. for 4 h. The RM was filtered through celite and washed with cold water and extracted with ethyl acetate (25 mL). The organic layer was washed with water (20 mL) and saturated brine solution (20 mL). The organic layer was dried over anhydrous Na$_2$SO$_4$ and the solvent was removed under reduced pressure. The crude material was purified by silica gel column chromatography using ethyl acetate and petroleum ether as eluents. The product was obtained as brown solid (0.4 g, yield: 66.6%). $^1$H NMR (300 MHz, CDCl$_3$): δ 7.07-7.10 (d, 2H), 6.84-6.86 (d, 2H), 5.82 (s, 1H), 3.69 (s, 2H), 3.66 (s, 3H), 2.21 (s, 3H).

Intermediate 79: Methyl (4-{4-[(4-{[(2Z)-2-(methoxyimino)-2-phenylethyl]oxy}benzyl)oxy]phenyl}-3-methyl-1,2-oxazol-5-yl)acetate To a 50 mL two neck RB flask fitted with magnetic stirrer was charged with 15 mL of toluene. To the stirred solvent were added methyl [4-(4-hydroxyphenyl)-3-methyl-1,2-oxazol-5-yl]acetate (0.3 g, 1.21 mmol), (1Z)-2-[4-(hydroxymethyl)phenoxy]-1-phenylethanone O-methyloxime (0.33 g, 1.21 mmol) and tri-(n-butyl)phosphine (0.39 g, 1.94 mmol) under nitrogen atmosphere. The reaction mixture was cooled to 0° C. and 1,1'-(azodicarbonyl)-dipiperidine (0.49 g, 1.94 mmol) was added portion wise and stirred at room temperature for 2 h. After completion of the reaction, the reaction mixture was poured into water (20 mL) and extracted with ethyl acetate (25 mL). The organic layer was dried over anhydrous Na$_2$SO$_4$ and the solvent was removed under reduced pressure. The crude material was purified by silica gel column chromatography using ethyl acetate and petroleum ether as eluents. The product was obtained as colorless oil (0.47 g, yield: 77%). $^1$H NMR (300 MHz, CDCl$_3$): δ 7.57-7.61 (m, 2H), 7.26-7.30 (m, 5H), 7.11-7.14 (d, 2H), 6.94-6.97 (d, 2H), 6.85-6.88 (d, 2H), 5.14 (s, 2H), 4.93 (s, 2H), 3.99 (s, 3H), 3.68 (s, 2H), 3.65 (s, 3H), 2.20 (s, 3H).

Compound 69: (4-{4-[(4-{[(2Z)-2-(Methoxyimino)-2-phenylethyl]oxy}benzyl)oxy]phenyl}-3-methyl-1,2-oxazol-5-yl)acetic acid To a 25 mL RB flask fitted with magnetic stirrer was charged with tetrahydrofuran (5 mL). To the stirred solvent were added Methyl (4-{4-[(4-{[(2Z)-2-(methoxyimino)-2-phenylethyl]oxy}benzyl)oxy]phenyl}-3-methyl-1,2-oxazol-5-yl)acetate (0.47 g, 0.94 mmol), methanol (3 mL) and lithium hydroxide (0.07 g, 0.94 mmol) in water (3 mL). After addition, the reaction mixture was stirred at room temperature overnight. The reaction mixture was concentrated to distill off the solvent; the crude was washed with diethyl ether (5 mL). Water (1 mL) was added and the aqueous layer was acidified with saturated citric acid solution to make pH 6. The aqueous layer was extracted with ethyl acetate (5 mL). The organic layer was dried over anhydrous Na$_2$SO$_4$ and the solvent was removed under reduced pressure. The product was obtained as white solid (0.32 g, yield: 70.2%).

Example 70

Sodium 3-{2-methoxy-4-[(4-{[(2Z)-2-(methoxyimino)-2-phenylethyl]oxy}benzyl)oxy]phenyl}propanoate

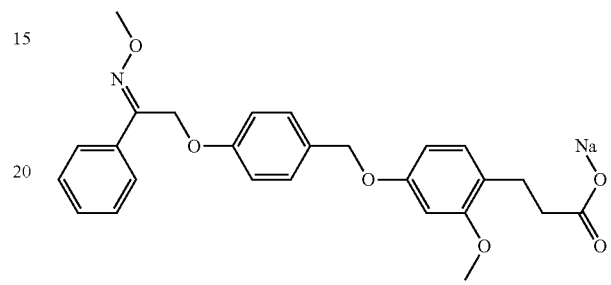

Compound 70 was synthesized 3-{2-methoxy-4-[(4-{[(2Z)-2-(methoxyimino)-2-phenylethyl]oxy}benzyl)oxy]phenyl}propanoic acid (0.204 g, 0.45 mmol) and sodium hydroxide [0.45 mL (1M, solution), 0.45 mmol] by following the procedure described in scheme 12 (0.15 g, yield: 71.43%); Purity: 99.11%.

Example 71

Sodium 3-{2-fluoro-4-[(4-{[(2Z)-2-(methoxyimino)-2-phenylethyl]oxy}benzyl)oxy]phenyl}propanoate

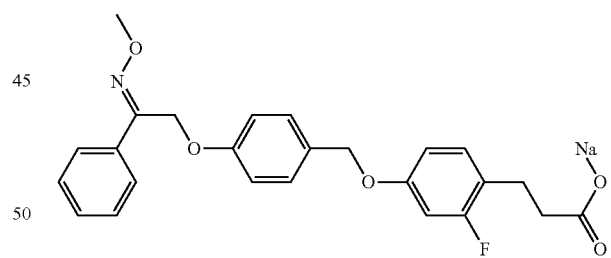

Compound 71 was synthesized from 3-{2-fluoro-4-[(4-{[(2Z)-2-(methoxyimino)-2-phenylethyl]oxy}benzyl)oxy]phenyl}propanoic acid (0.102 g, 0.233 mmol) and sodium hydroxide [0.233 mL, 1M solution, 0.233 mmol] by following the procedure described in scheme 12 (0.06 g, yield: 56.07%); Purity: 98.81%.

Scheme 22

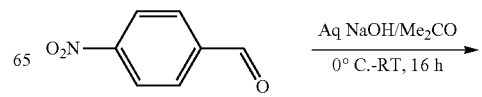

-continued

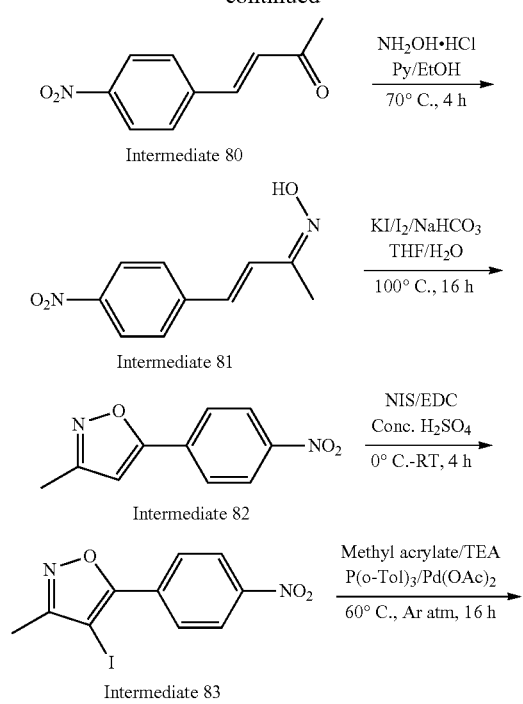

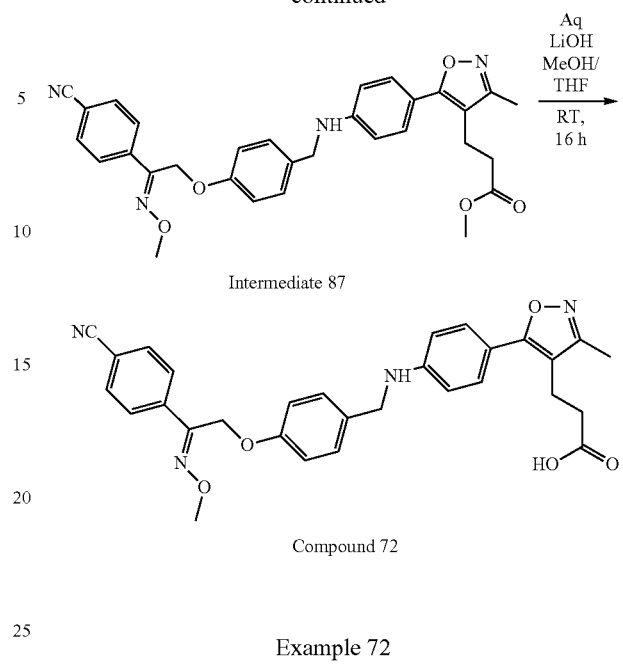

Intermediate 87

Compound 72

Example 72

3-(5-{4-[(4-{[(2E,2Z)-2-(4-Cyanophenyl)-2-(methoxyimino)ethyl]oxy}benzyl)amino]phenyl}-3-methyl-1,2-oxazol-4-yl)propanoic acid (72)

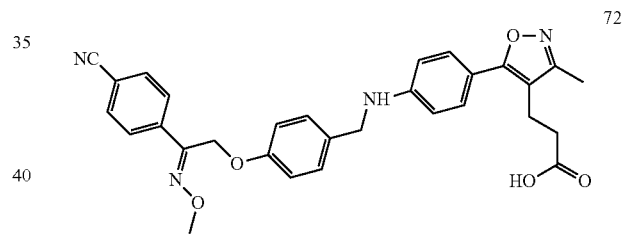

Compound 72 was synthesized from 4-[(1E,1Z)-2-(4-formylphenoxy)-N-methoxyethanimidoyl]benzonitrile (0.158 g, 0.54 mmol) and methyl 3-[5-(4-aminophenyl)-3-methyl-1,2-oxazol-4-yl]propanoate (0.14 g, 0.54 mmol) by following the procedure described in scheme 22 (0.0056 g, yield: 33.84%); Purity: 87.65%.

Intermediate 80: (3E,3Z)-4-(4-Nitrophenyl) but-3-en-2-one

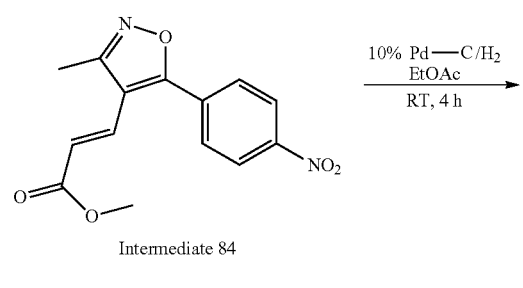

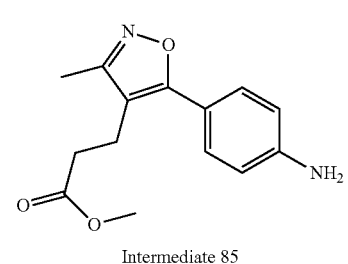

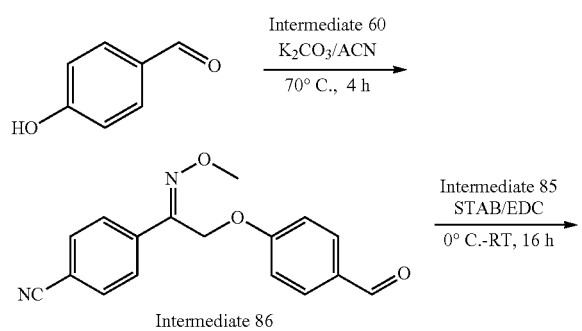

To a 100 mL RB flask fitted with magnetic stirrer was charged with 100 mL of acetone. To the stirred solvent were added 4-nitrobenzaldehyde (10 g, 66.2 mmol) followed by 4N NaOH solution (10 mL) at 0° C. The reaction mixture was stirred at room temperature overnight. The reaction mixture was concentrated to distill off the solvent. Water (25 mL) was added and extracted with ethyl acetate (25 mL). The organic layer was washed with saturated brine solution. The organic layer was dried over anhydrous $Na_2SO_4$ and the solvent was removed under reduced pressure. The crude material was purified by silica gel column chromatography using ethyl acetate and petroleum ether as eluents. The product was obtained as yellow solid (2.5 g, yield: 19.75%). $^1H$ NMR (300

MHz, CDCl$_3$): δ 8.18-8.21 (d, 2H), 7.62-7.65 (d, 2H), 7.44-7.49 (d, 1H), 6.73-6.78 (d, 1H), 2.36 (s, 3H).

Intermediate 81: (2Z,3E)-4-(4-Nitrophenyl) but-3-en-2-one oxime

To a 100 mL RB flask fitted with magnetic stirrer was charged with 10 mL of ethanol. To the stirred solvent were added (2Z,3E)-4-(4-nitrophenyl)but-3-en-2-one (0.5 g, 2.62 mmol), hydroxylamine hydrochloride (0.27 g, 3.93 mmol) and pyridine (0.828 g, 10.47 mmol) and stirred at 70° C. for 4 h under nitrogen atmosphere. The RM was poured into water (50 mL) and extracted with ethyl acetate (50 mL). The organic layer was washed with 1N HCl solution (25 mL) and saturated brine solution (25 mL). The organic layer was dried over anhydrous Na2SO4 and the solvent was removed under reduced pressure. The product was obtained as yellow solid (0.516 g, yield: 95.7%). MS (ESI, 120 eV): m/z=207.1 (M+H)$^+$; $^1$H NMR (300 MHz, DMSO-d$_6$): δ 11.49 (s, 1H), 8.19-8.22 (d, 2H), 7.84-7.87 (d, 2H), 7.10 (s, 2H), 2.02 (s, 3H).

Intermediate 82: 3-Methyl-5-(4-nitrophenyl)-1,2-oxazole

To a 100 mL RB flask fitted with magnetic stirrer was charged with 20 mL of tetrahydrofuran and water (10 mL). To the stirred solvent were added (2Z,3E)-N-hydroxy-4-(4-nitrophenyl)but-3-en-2-imine (0.5 g, 2.42 mmol), potassium iodide (0.81 g, 4.85 mmol), iodine (1.23 g, 4.49 mmol) and NaHCO3 (0.81 g, 9.7 mmol). The mixture was stirred at 100° C. overnight under nitrogen atmosphere. The reaction mixture was cooled, poured into water and extracted with ethyl acetate. The organic layer was washed with water (25 mL), sodium thiosulphate solution (30 mL) and saturated brine solution (30 mL). The organic layer was dried over anhydrous Na2SO4 and the solvent was removed under reduced pressure. The crude material was purified by silica gel column chromatography using ethyl acetate and petroleum ether as eluents. The product was obtained as yellow solid (0.31 g, yield: 62.6%). MS (ESI, 120 eV): m/z=205.1 (M+H)$^+$; $^1$H NMR (300 MHz, CDCl$_3$): δ 8.24-8.27 (t, 2H), 7.85-7.87 (t, 2H), 6.49 (s, 1H), 2.33 (s, 3H).

Intermediate 83: 4-Iodo-3-methyl-5-(4-nitrophenyl)-1,2-oxazole

To a 100 mL RB flask fitted with magnetic stirrer was charged with 10 mL of 1,2-dichloroethane. To the stirring solution were added 3-methyl-5-(4-nitrophenyl)-1,2-oxazole (0.27 g, 1.30 mmol), N-iodosuccinimide (0.28 g, 1.24 mmol), followed by concentrated H$_2$SO$_4$ (0.2 mL) at 0° C. and stirred at room temperature for 4 h. The reaction mixture was poured into water (30 mL) and extracted with ethyl acetate (50 mL). The organic layer was washed with sodium thiosulphate solution (30 mL), water (30 mL) and saturated brine solution (10 mL). The organic layer was dried over anhydrous Na$_2$SO$_4$ and the solvent was removed under reduced pressure. The product was obtained as yellow solid (0.40 g, yield: 93.7%). $^1$H NMR (300 MHz, CDCl$_3$): δ 8.29-8.32 (dd, 2H), 8.18-8.21 (dd, 2H), 2.33 (s, 3H).

Intermediate 84: Methyl (2E,2Z)-3-[3-methyl-5-(4-nitrophenyl)-1,2-oxazol-4-yl]acrylate To a 100 mL 3-neck RB flask fitted with magnetic stirrer was charged with triethylamine (15 mL). To the stirred solvent were added 4-iodo-3-methyl-5-(4-nitrophenyl)-1,2-oxazole (0.35 g, 1.06 mmol) and methyl acrylate (0.2 mL, 2.12 mmol) under argon atmosphere. After purged for 15 minutes tri-o-tolylphosphine (0.032 g, 0.11 mmol) and palladium(II) acetate (0.024 g, 0.11 mmol) were added to the reaction mixture. The reaction mixture was heated at 60° C. overnight under argon atmosphere. The reaction mixture was filtered through celite and washed with ethyl acetate and the solvent was removed under reduced pressure. The crude material was purified by silica gel column chromatography using ethyl acetate and petroleum ether as eluents. The product was obtained as pale yellow solid (0.175 g, yield: 57.4%). $^1$H NMR (300 MHz, CDCl$_3$): δ 8.25-8.28 (d, 1H), 7.85-7.88 (d, 1H), 7.80-7.83 (d, 2H), 7.57-7.62 (d, 1H), 6.26-6.32 (d, 1H), 3.76 (s, 3H) 2.44 (s, 3H).

Intermediate 85: Methyl 3-[5-(4-aminophenyl)-3-methyl-1,2-oxazol-4-yl]propanoate]

To the hydrogenation flask was charged with ethyl acetate (15 mL) and methyl (2E,2Z)-3-[3-methyl-5-(4-nitrophenyl)-1,2-oxazol-4-yl]prop-2-enoate (0.17 g, 0.59 mmol) followed by 10% Pd/C (0.2 g). The hydrogen flask was kept for hydrogenation for 4 h at 60 psi. The reaction mixture was filtered through celite, washed with ethyl acetate and the solvent was removed under reduced pressure to distill off the solvent. The product was obtained as yellow solid (0.148 g, yield: 97%). MS (ESI, 120 eV): m/z=261.0 (M+H)$^+$; $^1$H NMR (300 MHz, CDCl$_3$): δ 7.41-7.43 (d, 2H), 6.66-6.69 (d, 2H), 3.60 (s, 3H), 2.80-2.85 (t, 2H), 2.44-2.49 (t, 2H), 2.22 (s, 3H).

Intermediate 86: 4-[(1E,1Z)-2-(4-Formylphenoxy)-N-methoxyethanimidoyl]benzonitrile To a 100 mL RB flask fitted with magnetic stirrer was charged with 20 mL of acetonitrile. To the stirred solvent were added 4-hydroxybenzaldehyde (0.7 g, 5.7 mmol) and potassium carbonate (2.4 g, 17.1 mmol). The reaction mixture was cooled to 0° C. and 4-[(1E,1Z)-2-bromo-N-methoxyethanimidoyl]benzonitrile (1.45 g, 5.7 mmol) in acetonitrile (5 mL) was added drop wise. After addition, the reaction mixture was stirred at 80° C. for 3 h. The reaction mixture was filtered through sintered funnel, washed with ethyl acetate (10 mL). The filtrate was washed with water (20 mL) and brine solution (10 mL). The organic layer was dried over anhydrous Na$_2$SO$_4$ and the solvent was removed under reduced pressure. The crude material was purified by silica gel column chromatography using ethyl acetate and petroleum ether as eluents. The product was obtained as white solid (0.7 g, yield: 42%). $^1$H NMR (300 MHz, CDCl$_3$): δ 9.82 (s, 1H), 7.70-7.77 (m, 4H), 7.56-7.59 (d, 2H), 6.91-6.94 (d, 2H), 5.23 (s, 2H), 4.05 (s, 3H).

Intermediate 87: Methyl 3-(5-{4-[(4-{[(2E,2Z)-2-(4-cyanophenyl)-2-(methoxy imino)ethyl]oxy}benzyl)amino]phenyl}-3-methyl-1,2-oxazol-4-yl)propanoate To a 100 mL RB flask fitted with magnetic stirrer was charged with 10 mL of 1,2-dichloroethane. To the stirred solvent were added 4-[(1E,1Z)-2-(4-formylphenoxy)-N-methoxyethanimidoyl]benzonitrile (0.158 g, 0.54 mmol) and methyl 3-[5-(4-aminophenyl)-3-methyl-1,2-oxazol-4-yl]propanoate (0.14 g, 0.54 mmol). The reaction mixture was cooled to 0° C. and sodium triacetoxyborohydride (0.29 g, 1.35 mmol) was added portion wise. After addition, the reaction mixture was stirred at room temperature overnight. The reaction mixture was poured into water (10 mL) and extracted with dichloromethane (20 mL). The organic layer was washed with water (20 mL) and brine solution (10 mL). The organic layer was dried over anhydrous Na$_2$SO$_4$ and the solvent was removed under reduced pressure. The crude material was purified by silica gel column chromatography using ethyl acetate and petroleum ether as eluents. The product was obtained as yellow gummy solid (0.017 g, yield: 5.9%). $^1$H NMR (300 MHz, CDCl$_3$): δ 7.71-7.74 (d, 2H), 7.55-7.58 (d, 2H), 7.41-7.44 (d, 2H), 7.18-7.20 (d, 2H), 6.78-6.81 (d, 2H), 6.58-6.61 (d, 2H), 5.13 (s, 2H), 4.23 (s, 2H), 4.02 (s, 3H), 3.59 (s, 3H), 2.79-2.84 (t, 2H), 2.43-2.48 (t, 2H), 2.21 (s, 3H).

Compound 72: 3-(5-{4-[(4-{[(2E,2Z)-2-(4-Cyanophenyl)-2-(methoxyimino)ethyl]oxy}benzyl)amino]phenyl}-3-methyl-1,2-oxazol-4-yl)propanoic acid To a 25 mL RB flask fitted with magnetic stirrer was charged with 3 mL of tetrahydrofuran. To the stirred solvent were added methyl 3-(5-{4-[(4-{[(2E,2Z)-2-(4-cyanophenyl)-2-(methoxyimino)ethyl]oxy}benzyl)amino]phenyl}-3-methyl-1,2-oxazol-4-yl)propanoate (0.017 g, 0.03 mmol), methanol (0.5 mL) and lithium hydroxide (0.003 g, 0.13 mmol) in water (0.5 mL). After addition, the reaction mixture was stirred at room temperature overnight. The reaction mixture was concentrated to distill off the solvent; the crude was washed with diethyl ether (5 mL). Water (1 mL) was added and the aqueous layer was acidified with saturated citric acid solution to make pH 6. The aqueous layer was extracted with ethyl acetate (5 mL). The organic layer was dried over anhydrous Na$_2$SO$_4$ and the solvent was removed under reduced pressure. The crude material was purified by preparative TLC using methanol and chloroform as eluents. The product was obtained as yellow solid (0.0056 g, yield: 33.84%), 2H), 6.74-6.78 (t, 1H), 6.66-6.69 (d, 2H), 5.24 (s, 2H), 4.23-4.25 (d, 2H), 4.06 (s, 3H), 2.72-2.77 (t, 2H), 2.40-2.45 (t, 2H), 2.20 (s, 3H).

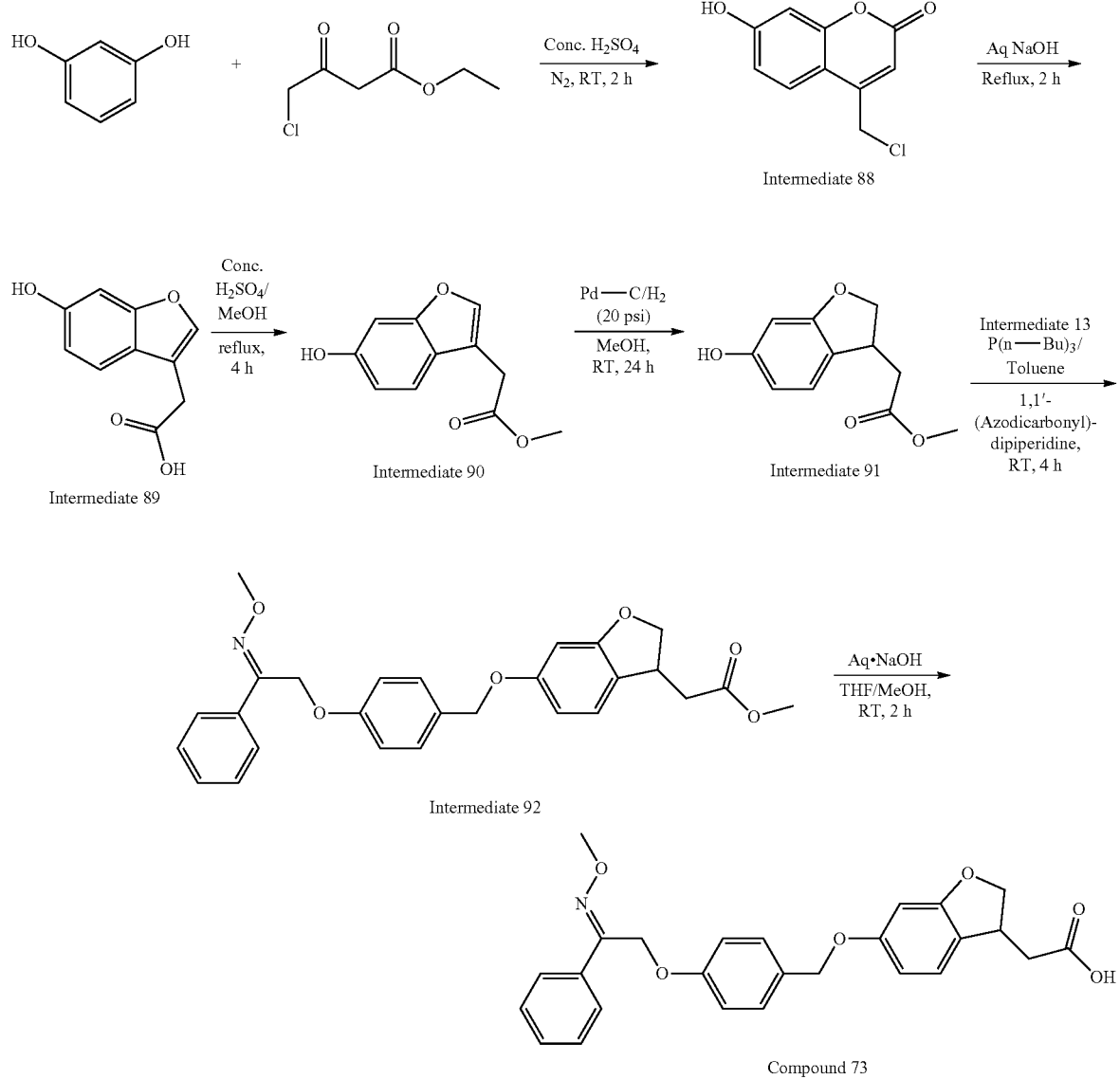

Scheme 23

Example 73

{6-[(4-{[(2Z)-2-(Methoxyimino)-2-phenylethyl]oxy}benzyl)oxy]-2,3-dihydro-1-benzofuran-3-yl}acetic acid

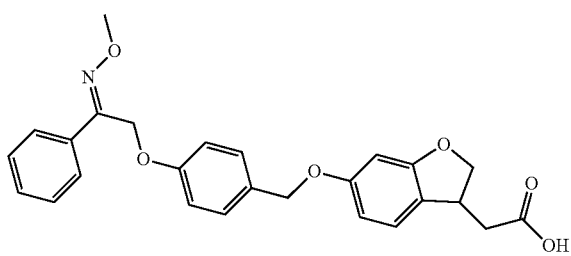

Compound 73 was synthesized from (4-{[(2Z)-2-(methoxyimino)-2-phenylethyl]oxy}phenyl)methanol (0.26 g, 0.96 mmol) and methyl (6-hydroxy-2,3-dihydro-1-benzofuran-3-yl)acetate (0.20 g, 0.96 mmol) by following the procedure described in scheme 23 (0.001 g, yield: 5.0%); Purity: 97.09%.

Intermediate 88: 4-(Chloromethyl)-7-hydroxy-2H-chromen-2-one

To a 250 mL RB flask fitted with magnetic stirrer was charged with Ethyl 4-chloroacetoacetate (22.12 g, 134.9 mmol) was dissolved in concentrated sulfuric acid (48 mL) at 0° C., and resorcinol (14.0 g, 127.3 mmol) was added portionwise. The mixture was stirred at room temperature for 2 h. The reaction mixture was poured into ice-water, and the resulting solid was collected by filtration, washed with water, and dried to give 4-(chloromethyl)-7-hydroxy-2H-chromen-2-one (21.0 g, 75.6%) as a beige solid.

Intermediate 89: (6-Hydroxy-1-benzofuran-3-yl)acetic acid

A mixture of the obtained 4-(chloromethyl)-7-hydroxy-2H-chromen-2-one (21.0 g, 21.0 mmol) and 1 M aqueous sodium hydroxide solution (1 L) was stirred at reflux for 2 h. The reaction mixture was acidified with concentrated sulfuric acid and extracted with ethyl acetate. The extract was washed with brine, dried over anhydrous sodium sulphate and concentrated to give (6-Hydroxy-1-benzofuran-3-yl)acetic acid (18.0 g, 93.75%).

Intermediate 90: Methyl (6-hydroxy-1-benzofuran-3-yl)acetate

The obtained crystals of (6-Hydroxy-1-benzofuran-3-yl)acetic acid suspended in methanol (100 mL), and to the suspension was added concentrated $H_2SO_4$ (10 mL), and the mixture was stirred at reflux for 4 h. After evaporation of the solvent, the residue was diluted with ether and subsequently washed with water, saturated sodium hydrogen carbonate solution, and brine, dried over anhydrous sodium sulphate and concentrated to give methyl (6-hydroxy-1-benzofuran-3-yl)acetate. The crude material has been purified by column chromatography to obtain the solid (11.23 g, 58%).

Intermediate 91: Methyl (6-hydroxy-2,3-dihydro-1-benzofuran-3-yl)acetate

The obtained Methyl (6-hydroxy-1-benzofuran-3-yl)acetate (6 g, 29.13 mmol) was hydrogenated on 10% Palladium on carbon (1 g in 1 mL of water) in methanol (60 mL) under hydrogen atmosphere (20 psi) about 24 h. The catalyst was removed by filtration and the filtrate was concentrated. The residue was purified by silica gel column chromatography to give a solid (2.9 g, 47.93%).

Intermediate 92: Methyl {6-[(4-{[(2Z)-2-(methoxyimino)-2-phenyl ethyl]oxy}benzyl)oxy]-2,3-dihydro-1-benzofuran-3-yl}acetate To a 50 mL two neck RB flask fitted with magnetic stirrer was charged with 5 mL of toluene. To the stirred solvent were added (4-{[(2E,2Z)-2-(methoxyimino)-2-phenylethyl]oxy}phenyl)methanol (0.26 g, 0.96 mmol) acetate and methyl (6-hydroxy-2,3-dihydro-1-benzofuran-3-yl)acetate (0.20 g, 0.96 mmol) and tri-(n-butyl)phosphine (0.25 g, 1.2 mmol) under nitrogen atmosphere. The reaction mixture was cooled to 0° C. and 1,1'-(azodicarbonyl)-dipiperidine (0.30 g, 1.2 mmol) was added portion wise and stirred at room temperature for 2 h. After completion of the reaction, the reaction mixture was poured into water (10 mL) and extracted with ethyl acetate (15 mL). The organic layer was dried over anhydrous $Na_2SO_4$ and the solvent was removed under reduced pressure. The crude material was purified by silica gel column chromatography using ethyl acetate and petroleum ether as eluents. The product was obtained as colorless oil (0.21 g, yield: 53.1%).

Compound 73: {6-[(4-{[(2Z)-2-(Methoxyimino)-2-phenylethyl]oxy}benzyl)oxy]-2,3-dihydro-1-benzofuran-3-yl}acetic acid To a 25 mL RB flask fitted with magnetic stirrer was charged with 5 mL of tetrahydrofuran. To the stirred solvent was added methyl {6-[(4-{[(2E,2Z)-2-(methoxyimino)-2-phenylethyl]oxy}benzyl)oxy]-2,3-dihydro-1-benzofuran-3-yl}acetate (0.2 g, 0.43 mmol) in methanol (5 mL). The reaction mixture was cooled to 0° C. and sodium hydroxide (0.035 g, 0.86 mmol) in water (5 mL) was added drop wise and stirred for 2 h. The reaction mixture was concentrated to distill off the solvent; ethyl acetate (10 mL) was added and stirred for 10 minutes. The organic layer was removed and the crude was acidified with saturated solution of citric acid to make pH 6. The obtained solids were filtered and dried. The product was obtained as white solid (0.01 g, yield: 5.0%).

Scheme 24
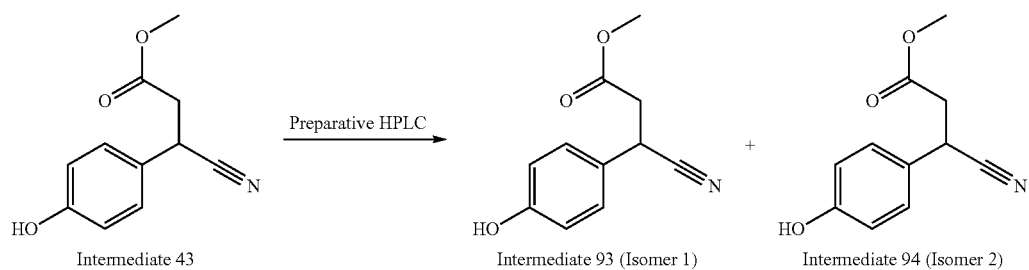
Intermediate 43 → Intermediate 93 (Isomer 1) + Intermediate 94 (Isomer 2)
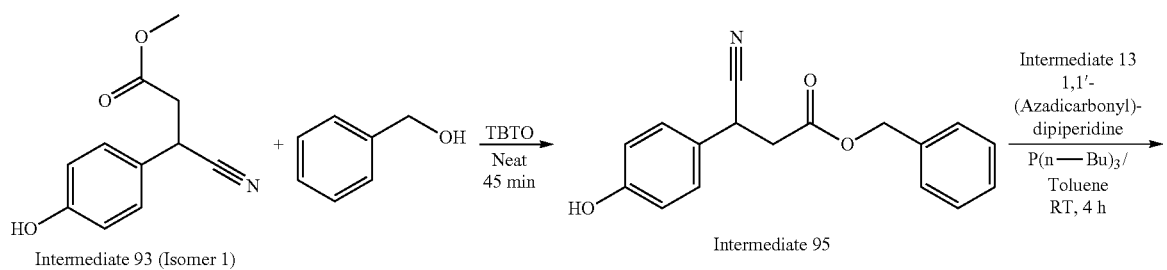
Intermediate 93 (Isomer 1) → Intermediate 95
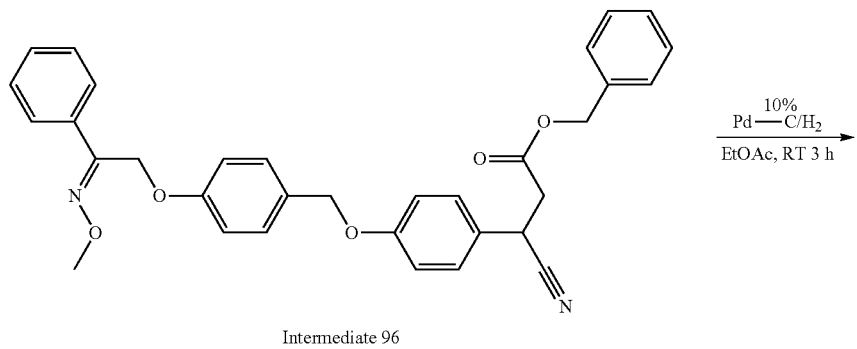
Intermediate 96
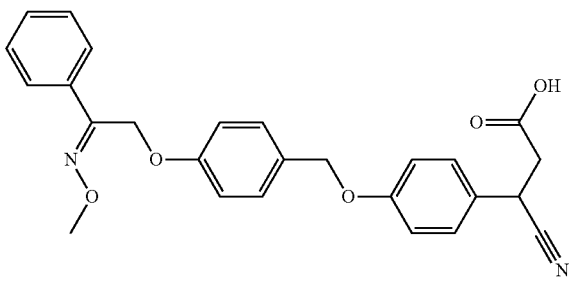
Compound 74

Example 74

(+)-3-Cyano-3-{4-[(4-{[(2Z)-2-(methoxyimino)-2-phenylethyl]oxy}benzyl)oxy]phenyl}propanoic acid (74)

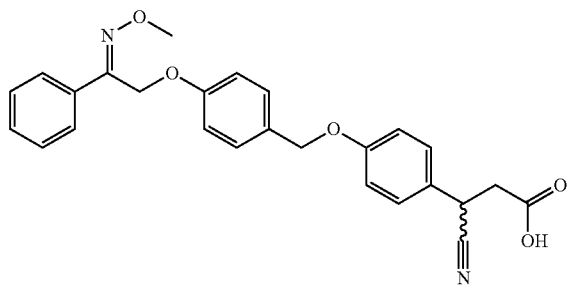

Compound 74 was synthesized from (4-{[(2Z)-2-(methoxyimino)-2-phenylethyl]oxy}phenyl)methanol (0.04 g, 2.2 mmol) and benzyl 3-cyano-3-(4-hydroxyphenyl)propanoate (0.66 g, 2.2 mmol) by following the procedure described in scheme 24 (0.2 g, yield: 39.91%); Purity: 98.51%.

Intermediate 93 (Isomer 1): (+)-Methyl 3-cyano-3-(4-hydroxyphenyl)propanoate Methyl 3-cyano-3-(4-hydroxyphenyl)propanoate was resolved using normal phase preparative HPLC [CHIRAL-PAK IC (250*4.6) mm, Mobile phase: hexanes:IPA:TFA (80:20:0.1, v/v/v), Flow rate: 1.0 mL/min; Column temp.: 25° C.; The isomer methyl 3-cyano-3-(4-hydroxyphenyl)propanoate (+ve) (retention time 10.22 min) was thus obtained with a 99.34 ee.

Intermediate 94 (Isomer 2): (−)-Methyl 3-cyano-3-(4-hydroxyphenyl)propanoate Methyl 3-cyano-3-(4-hydroxyphenyl)propanoate was resolved using normal phase preparative HPLC [CHIRAL-PAK IC (250*4.6) mm, Mobile phase: hexanes:IPA:TFA (80:20:0.1, v/v/v), Flow rate: 1.0 mL/min; Column temp.: 25° C.; The isomer methyl 3-cyano-3-(4-hydroxyphenyl)propanoate (−ve) (retention time 12.75 min) was thus obtained 98.03% ee.

Intermediate 95: Benzyl 3-cyano-3-(4-hydroxyphenyl)propanoate

To the microwave vial was charged with isomer methyl 3-cyano-3-(4-hydroxyphenyl)propanoate (+ve) (0.5 g, 2.4 mmole) & benzyl alcohol (0.5 mL, 4.8 mmol), was added tributyltinoxide (0.03 g, 5% W/W). Temperature was set 90° C. & energy is fixed at 250 W for 30 mins. After completion of the reaction (monitored by TLC), the RM mixture was extracted with ethyl acetate. The organic layer was washed with water and saturated brine solution, dried over anhydrous Na2SO4 and evaporated to dryness gave the titled compound (0.040 g, yield: 6.0%).

Intermediate 96: (+)-Benzyl 3-cyano-3-{4-[(4-{[(2Z)-2-(methoxyimino)-2-phenyl ethyl]oxy}benzyl)oxy]phenyl}propanoate To a 50 mL RB flask fitted with magnetic stirrer was charged Toluene (20 mL). To the stirred solvent was added 2-(4-Hydroxymethyl-phenoxy)-1-phenyl-ethanone O-methyl-oxime (0.039 g, 0.14 mmol) and benzyl 3-cyano-3-(4-hydroxyphenyl)propanoate (0.04 g, 0.14 mmol) at 0° C. for 5 min. Then added tributylphosphine (0.043 g, 0.2 mmol) stirred at 0° C. for 15 min, was added 1,1′aza(dicarbonyl) dipiperidine (0.054 g, 0.2 mmol), this resulting mass stirred at RT for 16 h. The solvent removed, the residue was extracted with ethyl acetate. The organic layer washed with water and brine solution and dried by anhydrous sodium sulphate to and evaporated, purified by 100-200 silica column using pet-ether and ethylacetate. The product obtained as a colourless oily liquid (0.06 g, 79.00%)

Compound 74: (+)-3-Cyano-3-{4-[(4-{[(2Z)-2-(methoxyimino)-2-phenylethyl]oxy}benzyl)oxy]phenyl}propanoic acid (+ve)

To a 500 mL parr hydrogenater flask with ethyl acetate (15 mL), was added benzyl 3-cyano-3-{4-[(4-{[(2E,2Z)-2-(methoxyimino)-2-phenyl ethyl]oxy}benzyl)oxy] phenyl}propanoate (0.06 g, 0.1 mmol) and 10% Pd/C (0.006 g) under N2 atmosphere. The RM was hydrogenated for 16 h. The RM was diluted with ethyl acetate (10 mL), filtered through celite bed to remove Pd/C and evaporated to dryness under reduced pressure. The crude was purified by flash column chromatography on silica gel (100/200 mesh), to give the product (0.0097 g, yield: 18.00%).

Example 75

(−)-3-Cyano-3-{4-[(4-{[(2Z)-2-(methoxyimino)-2-phenylethyl]oxy}benzyl)oxy]phenyl}propanoic acid

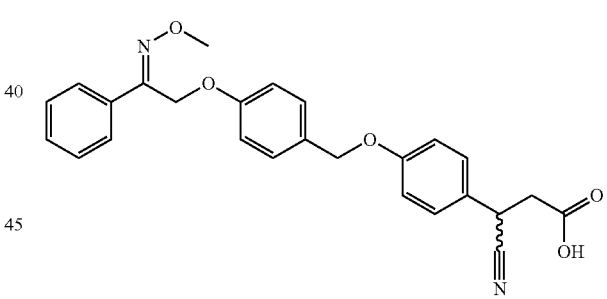

Compound 75 was synthesized from benzyl 3-cyano-3-(4-hydroxyphenyl)propanoate (0.27 g, 0.95 mmol) obtained from Intermediate 96, then it has been coupled with (4-{[(22)-2-(methoxyimino)-2-phenylethyl]oxy}phenyl)methanol (0.26 g, 0.95 mmol) by following the procedure described in scheme 24 (0.08 g, yield: 88.89%); Purity: 89.58%

Scheme 25

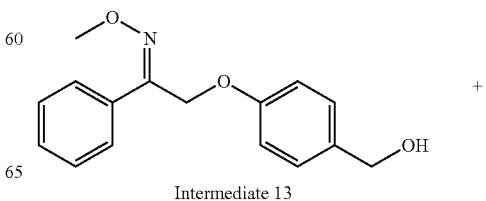

Intermediate 13

+

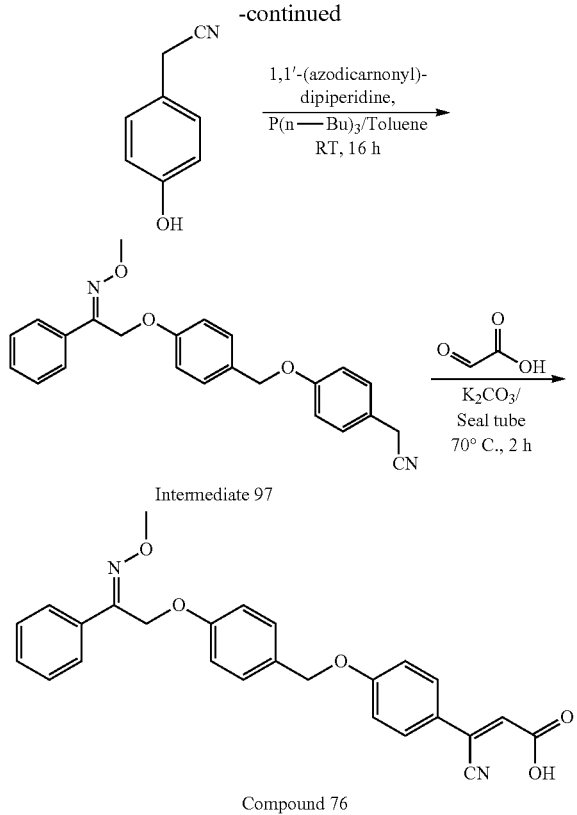

Intermediate 97

Compound 76

Example 76

(2Z)-3-Cyano-3-{4-[(4-{[(2Z)-2-(methoxyimino)-2-phenylethyl]oxy}benzyl)oxy]phenyl}prop-2-enoic acid

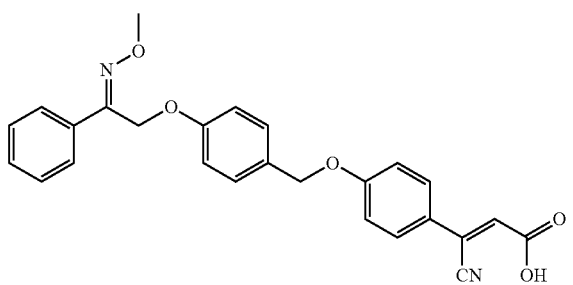

Compound 76 was synthesized from (4-{[(2Z)-2-(methoxyimino)-2-phenylethyl]oxy}phenyl)methanol (0.18 g, 0.47 mmol) and oxoacetic acid (0.064 g, 0.70 mmol) by following the procedure described in scheme 25 (0.012 g, yield: 5.8%); Purity: 96.28%%.

Intermediate 97: {4-[(4-{[(2Z)-2-(Methoxyimino)-2-phenylethyl]oxy}benzyl)oxy]phenyl}acetonitrile To a 50 mL RB flask fitted with magnetic stirrer was charged dry Toluene. To the stirred solvent was added 2-(4-Hydroxymethyl-phenoxy)-1-phenyl-ethanone O-methyl-oxime (0.20 g, 0.74 mmol) and (4-hydroxyphenyl)acetonitrile (0.098 g, 0.74 mmol) at 0° C. for 5 min. Then added tributylphosphine (0.0.24 g, 1.2 mmol) stirred at 0° C. for 15 min, was added 1,1'aza(dicarbonyl)dipiperidine (0.303 g, 1.2 mmol), this resulting mass stirred at RT for 16 h, The solvent removed, the residue was extracted with ethyl acetate. The organic layer washed with water and brine solution and dried by anhydrous sodium sulphate and evaporated, purified by 100-200 silica column using pet-ether and ethylacetate. The product obtained as a colourless oily liquid (0.18 g, 60.00%)

Compound 76: (2Z)-3-Cyano-3-{4-[(4-{[(2E,2Z)-2-(methoxyimino)-2-phenylethyl]oxy}benzyl)oxy]phenyl}prop-2-enoic acid To a 50 mL sealed tube with magnetic stirrer was charged with methanol (5 mL). To the stirred solvent were added {4-[(4-{[(2E,2Z)-2-(methoxyimino)-2-phenylethyl]oxy}benzyl)oxy]phenyl}acetonitrile (0.18 g, 0.47 mmol), potassium carbonate (0.26 g, 1.9 mmol) and oxoacetic acid (0.064 g, 0.70 mmol) under nitrogen atmosphere. The reaction mixture was heated at 70° C. for 2 h. Then removed the solvent under reduced pressure, obtained residue was dissolved in water (10 mL), washed with diethyl ether (20 mL). The aqueous layer was acidified with 1N HCl, extracted with ethyl acetate, washed water and brine solution. The organic layer was dried over anhydrous $Na_2SO_4$ and the solvent was removed under reduced pressure to obtain the product (0.012 g, yield: 5.80%).

Example 77

3-Cyano-3-{2-fluoro-4-[(4-{[(2Z)-2-(methoxyimino)-2-phenylethyl]oxy}benzyl)oxy]phenyl}propanoic acid

77

Compound 77 was synthesized from (4-{[(2Z)-2-(methoxyimino)-2-phenylethyl]oxy}phenyl)methanol (0.607 g, 2.24 mmol) and methyl 3-cyano-3-(2-fluoro-4-hydroxyphenyl)propanoate (0.5 g, 2.24 mmol) by following the procedure described in scheme 18 (0.2 g, yield: 95.4%); Purity: 95.68%.

Example 78

3-Cyano-3-{4-[(4-{[(2E,2Z)-2-(hydroxyimino)-2-phenylethyl]oxy}benzyl)oxy]phenyl}propanoic acid Compound 78 was synthesized from 2-[4-(hydroxymethyl)phenoxy]-1-phenylethanone (0.5 g, 2.06 mmol) and methyl 3-cyano-3-(4-hydroxyphenyl)propanoate (0.452 g, 2.06 mmol) by following the procedure described in scheme 8 (0.023 g, 15.00%); Purity: 68.90%.

Example 79

Sodium 2-{4-[(4-{[(2Z)-2-(4-cyanophenyl)-2-(methoxyimino)ethyl]oxy}benzyl)oxy]phenyl}cyclopropanecarboxylate (Enantiomer-1)

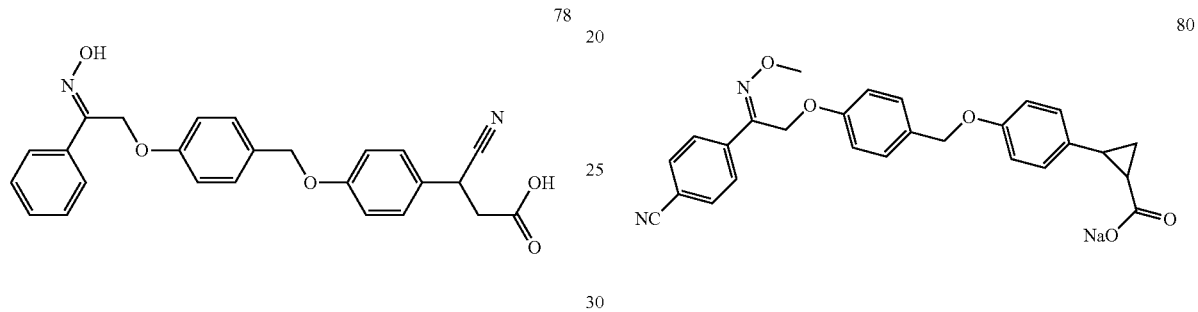

Compound 79 was synthesized from 2-{4-[(4-{[(2Z)-2-(4-cyanophenyl)-2-(methoxyimino)ethyl]oxy}benzyl)oxy]phenyl}cyclopropanecarboxylic acid (0.1 g, 2.4 mmol) and sodiumbicarbonate (0.25 mL, 2.4 mmol) by following the procedure described in scheme 12 (0.095 g, yield: 90.56%); Purity: 89.00%.

Example 80

Sodium 2-{4-[(4-{[(2Z)-2-(4-cyanophenyl)-2-(methoxyimino)ethyl]oxy}benzyl)oxy]phenyl}cyclopropanecarboxylate (Enantiomer-2)

Compound 80 was synthesized from 2-{4-[(4-{[(2Z)-2-(4-cyanophenyl)-2-(methoxyimino)ethyl]oxy}benzyl)oxy]phenyl}cyclopropanecarboxylic acid (0.026 g, 0.0567 mmol) and sodium bicarbonate [(0.06 mL, 1M solution) by following the procedure described in scheme 12 (0.0051 g, yield: 18.89%); Purity: 96.10%.

Example 81

(+)-Sodium 3-cyano-3-{4-[(4-{[(2Z)-2-(methoxyimino)-2-phenylethyl]oxy}benzyl)oxy]phenyl}propanoate

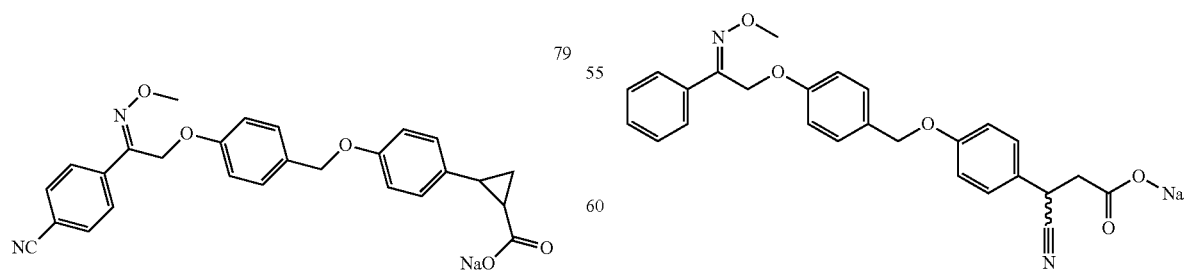

Compound 81 was synthesized from 3-cyano-3-{4-[(4-{[(2Z)-2-(methoxyimino)-2-phenylethyl]oxy}benzyl)oxy]phenyl}propanoic acid (0.78 g, 1.75 mmol) and NaHCO₃ solution (1.75 mL, 1M solution) by following the procedure described in scheme 12 (0.58 g, yield: 70.00%); Purity: 89.10%.

Example 82

(−)-Sodium 3-cyano-3-{4-[(4-{[(2E,2Z)-2-(methoxyimino)-2-phenylethyl]oxy}benzyl)oxy]phenyl}propanoate

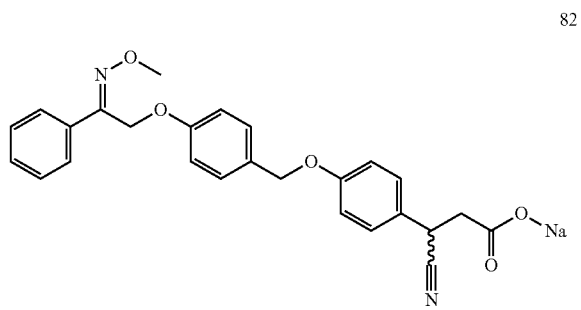

Compound 82 was synthesized from enantiomerically pure 3-cyano-3-{4-[(4-{[(2Z)-2-(methoxyimino)-2-phenylethyl]oxy}benzyl)oxy]phenyl}propanoic acid (0.45 g, 1.0135 mmol) and sodium bicarbonate [1.0 mL, 1.0135 mmol), the solvent was removed reduced pressure at 25° C. by following the procedure described in scheme 12 (0.312 g, yield: 95.74%); Purity: 98.88%. Optical rotation: −1.74 (25° C., Water)

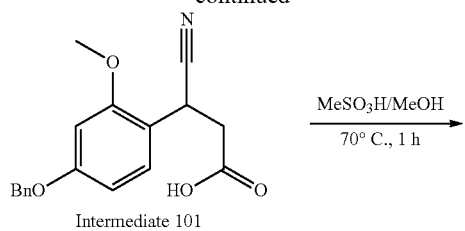

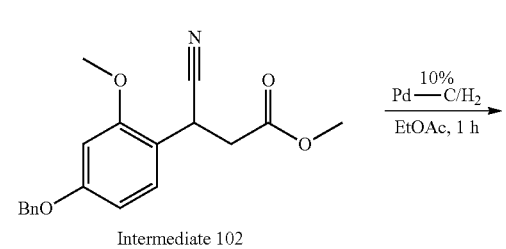

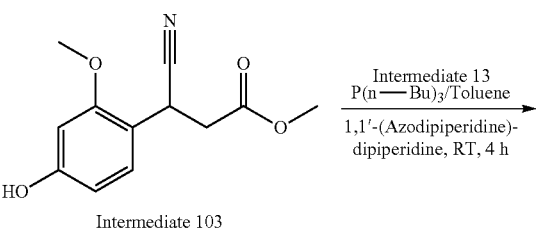

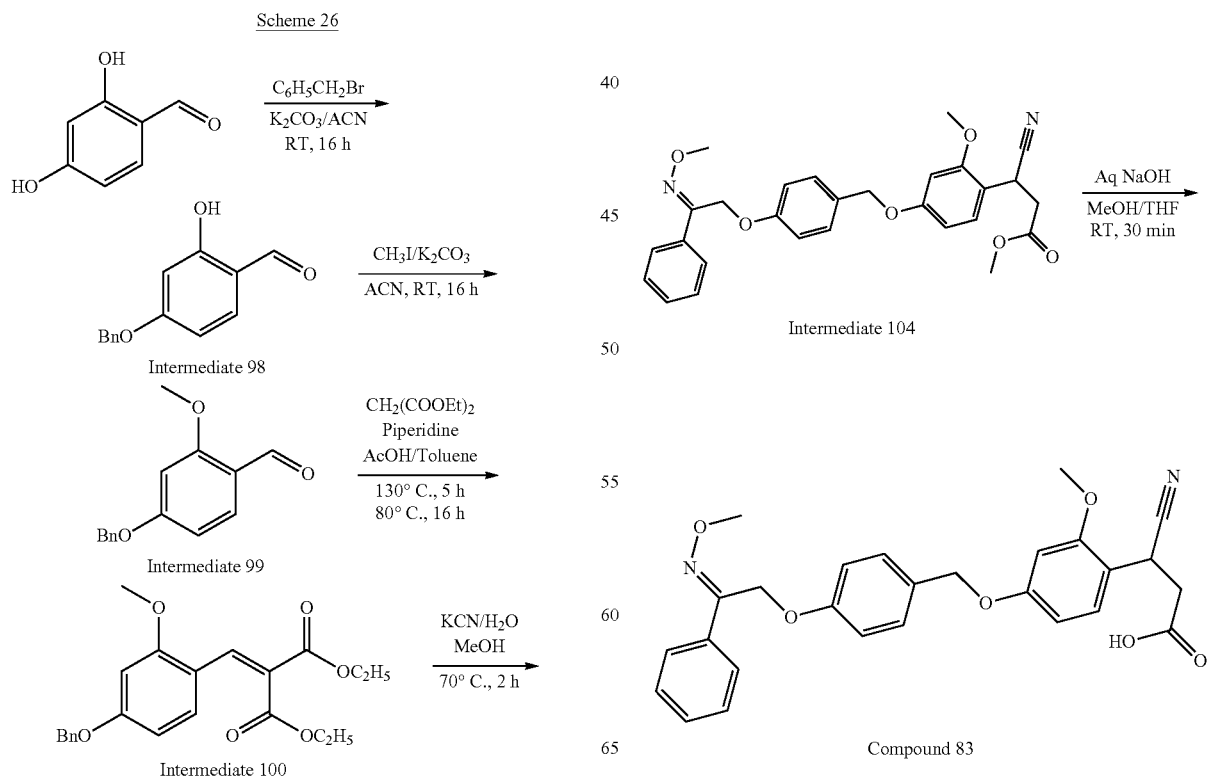

Example 83

3-Cyano-3-{2-methoxy-4-[(4-{[(2Z)-2-(methoxyimino)-2-phenylethyl]oxy}benzyl)oxy]phenyl}propanoic acid

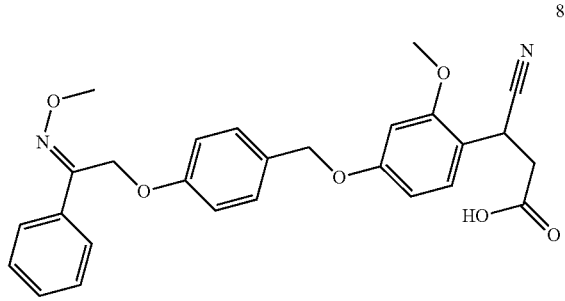

Compound 83 was synthesized from (4-{[(2Z)-2-(methoxyimino)-2-phenylethyl]oxy}phenyl)methanol (0.231 g, 0.85 mmol) and methyl 3-cyano-3-(4-hydroxy-2-methoxyphenyl)propanoate (0.2 g, 0.85 mmol) by following the procedure described in scheme 26 (0.0.01 g, yield: 6.86%); Purity: 95.70%.

Intermediate 98: 4-(Benzyloxy)-2-hydroxybenzaldehyde

To a 250 mL RB flask fitted with magnetic stirrer was charged with 30 mL of acetonitrile. To the stirred solvent were added 2,4-dihydroxybenzaldehyde (8.0 g, 57.0 mmol), potassium carbonate (15.77 g, 114.0 mmol). The reaction mixture was brought to 0° C., was added benzyl bromide (9.905 g, 57.0 mmol) in acetonitrile (100 mL) drop wise and stirred at room temperature for 3 h. The reaction mixture was concentrated to distill off the solvent. The residue was extracted with ethyl acetate (80 mL). The organic layer was washed with water (50 mL) and saturated brine solution (50 mL). The organic layer was dried over anhydrous $Na_2SO_4$ and the solvent was removed under reduced pressure. The product obtained as a white solid (4.0 g, yield: 30.77%).

Intermediate 99: 4-(Benzyloxy)-2-methoxybenzaldehyde

To a 100 mL RB flask fitted with magnetic stirrer was charged with 10 mL of acetonitrile. To the stirred solvent were added 4-(benzyloxy)-2-hydroxybenzaldehyde (1.0 g, 4.38 mmol), potassium carbonate (1.21 g, 8.76 mmol). The reaction mixture was brought to 0° C., was added methyl iodide (1.135 g, 8.76 mmol) in acetonitrile (5 mL) drop wise and stirred at room temperature for 16 h. The reaction mixture was concentrated to distill off the solvent. The residue was extracted with ethyl acetate (50 mL). The organic layer was washed with water (40 mL) and saturated brine solution (40 mL). The organic layer was dried over anhydrous $Na_2SO_4$ and the solvent was removed under reduced pressure. The product obtained as a white solid (1.06 g, yield: 100.0%).

Intermediate 100: Diethyl [4-(benzyloxy)-2-methoxybenzylidene]propanedioate

To a 100 mL RB flask fitted with magnetic stirrer was charged with piperidine (0.108 g, 0.13 mL, 1.35 mmol) and acetic acid (0.081 g, 0.08 mL, 1.35 mmol). To this, toluene (20 mL) was added, followed by 4-(benzyloxy)-2-methoxybenzaldehyde (1.1 g, 4.5 mmol) and diethyl malonate (0.87 g, 5.5 mmol). The RM was heated at 125° C., by fitted with a dean-stark's apparatus for 5 h. After 5 h, the RM was concentrated; water (50 mL) was added and extracted with ethyl acetate (50 mL×2)). The organic layer was washed with saturated brine solution (50 mL). The organic layer was dried over anhydrous $Na_2SO_4$ and the solvent was removed under reduced pressure. The product was obtained as yellow solid. (0.775 g, yield: 44.2%).

Intermediate 101: 3-[4-(Benzyloxy)-2-methoxyphenyl]-3-cyanopropanoic acid

To a 25 mL RB flask fitted with magnetic stirrer was charged with methanol (20 mL) and water (5 mL). To the stirred solvent was added diethyl [4-(benzyloxy)-2-methoxybenzylidene]propanedioate (0.775 g, 2.02 mmol), followed by potassium cyanide (0.262 g, 4.04 mmol). The RM was heated at 70° C. for 2 h. The RM was concentrated, diluted with saturated $NaHCO_3$ solution (50 mL) and washed with ethyl acetate (50 mL×2). The aqueous layer was acidified to pH 3 with 1N hydrochloric acid and extracted with ethyl acetate (50 mL×2). The organic layer was washed with water (50 mL) and saturated brine solution (50 mL). The organic layer was dried over anhydrous $Na_2SO_4$ and the solvent was removed under reduced pressure. The product was obtained as brown liquid. (0.62 g, yield: 100.0%).

Intermediate 102: Methyl 3-[4-(benzyloxy)-2-methoxyphenyl]-3-cyanopropanoate To a 25 mL RB flask fitted with magnetic stirrer was charged with methanol (10 mL). To the stirred solvent was added 3-[4-(benzyloxy)-2-methoxyphenyl]-3-cyanopropanoic acid (0.62 g, 2.56 mmol) and methane sulfonic acid (1 mL), it was heated at 65° C. for 2 h. The RM was concentrated, extracted with ethyl acetate (50 mL×2). The organic layer was washed with water (50 mL) and saturated brine solution (50 mL). The organic layer was dried over anhydrous $Na_2SO_4$ and the solvent was removed under reduced pressure. The product was obtained as brown liquid. (0.65 g, yield: 100.0%).

Intermediate 103: Methyl 3-cyano-3-(4-hydroxy-2-methoxyphenyl)propanoate

To a 500 mL parr hydrogenater flask with ethyl acetate (15 mL), was added methyl 3-cyano-3-(4-hydroxy-2-methoxyphenyl)propanoate (0.65 g, 2.0 mmol) and 10% Pd/C (0.1 g) under $N_2$ atmosphere. The RM was hydrogenated for 1 h. The RM was diluted with ethyl acetate (10 mL), filtered through celite bed to remove Pd/C and evaporated to dryness under reduced pressure. The crude was purified by flash column chromatography on silica gel (100/200 mesh), to give the product (0.2 g, yield: 42.50%).

Intermediate 104: Methyl 3-cyano-3-{2-methoxy-4-[(4-{[(2Z)-2-(methoxyimino)-2-phenylethyl]oxy}benzyl)oxy]phenyl}propanoate To a 50 mL RB flask fitted with magnetic stirrer was charged with 15 mL of toluene. To the stirred solvent were added (4-{[(2E,2Z)-2-(methoxyimino)-2-phenylethyl]oxy}phenyl)methanol (0.23 g, 0.85 mmol), methyl 3-cyano- 3-(4-hydroxy-2-methoxyphenyl)propanoate (0.2 g, 0.85 mmol). The reaction mixture was cooled to 0° C.; tributylphosphine (0.22 g, 1.1 mmol) was added and stirred for 10 minutes. To the stirring solution, 1,1'-(azodicarbonyl)dipiperidine (0.28 g, 1.1 mmol) in toluene (2 mL) was added drop wise at the same temperature and stirred at room temperature for 4 h. The reaction mixture was diluted with water (10 mL) and extracted with ethyl acetate (15 mL×2). The organic layer was washed with water (10 mL), followed by brine solution (10 mL). The organic layer was dried over anhydrous $Na_2SO_4$ and the solvent was removed under reduced pressure. The crude material was purified by silica gel column chromatography using ethyl acetate and petroleum ether as elutant. The product was obtained as colorless oil (0.15 g, yield: 36.60%).

Compound 83: 3-Cyano-3-{2-methoxy-4-[(4-{[(22Z)-2-(methoxyimino)-2-phenylethyl]oxy}benzyl)oxy]phenyl}propanoic acid To a 50 mL RB flask fitted with magnetic stirrer was charged with 5 mL of tetrahydrofuran. To the stirred solvent was added methyl 3-cyano-3-{2-methoxy-4-[(4-{[(2E,2Z)-2-(methoxyimino)-2-phenylethyl]oxy}benzyl)oxy]phenyl}propanoate (0.15 g, 0.31 mmol) in methanol (5 mL). The reaction mixture was cooled to 0° C. and sodium hydroxide (0.037 g, 0.29 mmol) in water (5 mL) was added drop wise and stirred for 30 h. The reaction mixture was concentrated to distill off the solvent; ethyl acetate (10 mL) was added and stirred for 10 minutes. The organic layer was removed and the crude was acidified with saturated solution of citric acid to make pH 6. The obtained solids were filtered and dried. The product was obtained as white solid (0.01 g, yield: 6.86%).

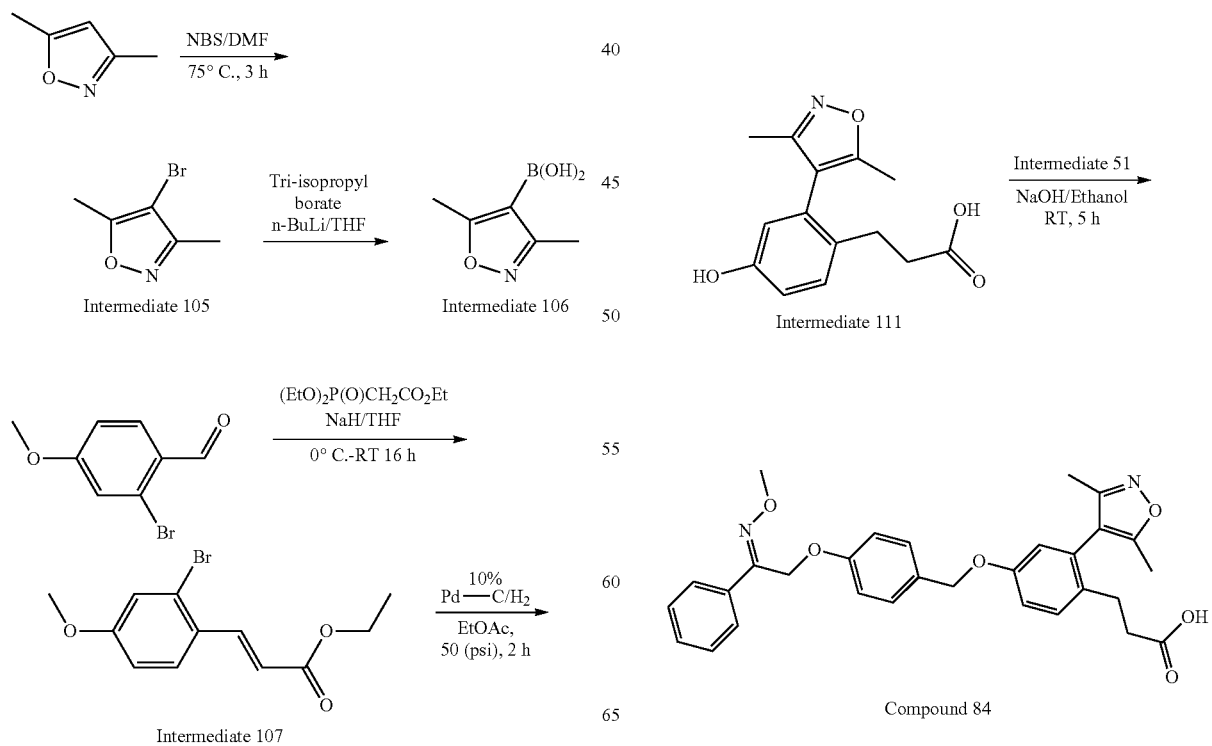

Scheme 27

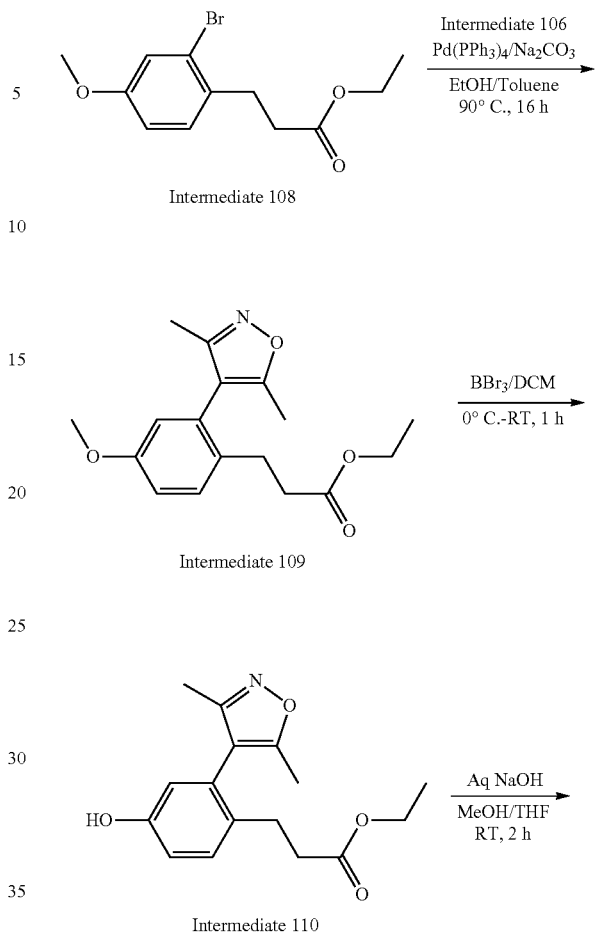

Example 84

3-{2-(3,5-Dimethyl-1,2-oxazol-4-yl)-4-[(4-{[(2E, 2Z)-2-(methoxyimino)-2-phenylethyl]oxy}benzyl) oxy]phenyl}propanoic acid

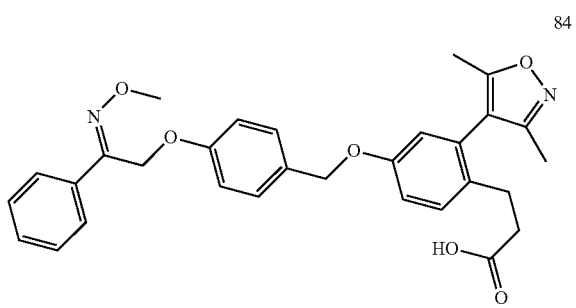 [SMILES: CO/N=C(\COc1ccc(COc2ccc(CCC(=O)O)c(-c3c(C)noc3C)c2)cc1)c1ccccc1]

Compound 84 was synthesized from 3-[2-(3,5-dimethyl-1,2-oxazol-4-yl)-4-hydroxyphenyl]propanoic acid (0.04 g, 0.15 mmol) and (1E,1Z)-2-[4-(bromomethyl)phenoxy]-N-methoxy-1-phenylethanimine (0.051 g, 0.15 mmol) by following the procedure described in scheme 27 ((0.04 g, yield: 6.20%). Purity: 80.10%.

Intermediate 105: 4-Bromo-3,5-dimethyl-1,2-oxazole

To a 250 mL RB flask fitted with a magnetic stirrer was charged with DMF (53 mL). To the stirred solvent were added 3,5-dimethyl-1,2-oxazole (5.3 g, 54.57 mmol) and N-iodosuccinimide (11.659 g, 65.49 mol), after addition, the reaction mixture was heated at 75° C. for 3 h. After completion of the reaction, the reaction mixture was diluted with ethyl acetate (100 mL), the organic layer was washed with saturated NaHCO$_3$ solution (100 mL), thiosulfate solution (100 mL), water (200 mL) and finally with brine solution (100 mL). The organic layer was dried over anhydrous Na$_2$SO$_4$ and the solvent was removed under reduced pressure to obtain the product (6.1 g, yield: 63.4%).

Intermediate 106: (3,5-Dimethyl-1,2-oxazol-4-yl) boronic acid

To a 500 mL three RB flask fitted with magnetic stirrer was charged 4-bromo-3,5-dimethyl-1,2-oxazole (4.0 g, 22.7 mmol) in THF (40 mL), cooled −78° C. To the stirred solvent was added n-butyl lithium (28.4 mL, 1.6M solution, 45.0 mmol) drop wise and stirred at −65° C. about 30 minutes. The RM was brought to −78° C., was added tri-isopropyl borate (12.81 g, 68.0 mmol), once the temperature to reached room temperature and stirred about 16 h. Then removed the solvent under reduced pressure and quenched with saturated NH$_4$Cl solution and extracted with ethyl acetate. The organic layer was washed with water, dried over anhydrous Na$_2$SO$_4$ and removed the solvent under reduced pressure. The obtained crude material was purified by silica gel column chromatography to obtain white solid. (0.4 g, yield: 12.5%).

Intermediate 107: Ethyl (2E,2Z)-3-(2-bromo-4-methoxyphenyl)prop-2-enoate

To a 250 mL RB flask fitted with magnetic stirrer was charged with 12 mL of ethyl acetate. To the stirred solvent was added ethyl phosphonoacetate (2.5 g, 11.0 mmol) under nitrogen atmosphere. The reaction mixture was cooled to 0° C. and sodium hydride (0.401 g, 16.0 mmol) was added portion wise, stirred for 1 h at the same temperature. Then 2-bromo-4-methoxybenzaldehyde (1.2 g, 5.5 mmol) in tetrahydrofuran (10 mL) was added drop wise. The reaction mixture was stirred at RT for 16 h. The reaction mixture was quenched with water at 0° C. by slow addition, stirred for 10 minutes. The layers were separated; ethyl acetate (50 mL) was added to the aqueous layer and extracted the layers. The organic layer was washed with brine solution (50 mL). The organic layer was dried over anhydrous Na$_2$SO$_4$ and the solvent was removed under reduced pressure. The product was obtained as pale yellow semi-solid (0.29 g, yield: 18.50%).

Intermediate 108: Ethyl 3-(2-bromo-4-methoxyphenyl)propanoate

To a 500 mL parr hydrogenater flask with ethyl acetate (10 mL), was added ethyl (2E)-3-(2-bromo-4-methoxyphenyl)prop-2-enoate (0.2 g, 0.7 mmol) and 10% Pd/C (0.05 g) under Nitrogen atmosphere. The RM was hydrogenated at pressure (50 psi) for 1 h. Then RM was diluted with ethyl acetate (10 mL), filtered through celite bed to remove Pd/C and evaporated to dryness under reduced pressure. The crude was purified by flash column chromatography on silica gel (100/200 mesh), to give the product (0.18 g, yield: 90.00%).

Intermediate 109: Ethyl 3-[2-(3,5-dimethyl-1,2-oxazol-4-yl)-4-methoxy phenyl]propanoate To a 25 mL RB flask fitted with a magnetic stirrer was charged with Toluene (1 mL). To the stirred solvent were added (3,5-dimethyl-1,2-oxazol-4-yl)boronic acid (0.059 g, 0.42 mmol), ethyl 3-(2-bromo-4-methoxyphenyl)propanoate (0.08 g, 0.28 mmol), sodium bicarbonate (0.5 mL, 2M solution) in ethanol (1 mL) under argon atmosphere. After addition, the reaction mixture was purged with argon for 15 minutes. To the reaction mixture was added tetrakis (triphenylphosphine) palladium (0) (0.016 g, 0.01 mmol) and purged with argon for 10 minutes. After addition, the reaction mixture was heated at 95° C. for 5 h under argon atmosphere. After completion of the reaction, the reaction mixture was quenched with water (10 mL) and extracted with ethyl acetate (10 mL). The organic layer was washed with water (5 mL) and brine solution (5 mL). The organic layer was dried over anhydrous Na$_2$SO$_4$ and the solvent was removed under reduced pressure. The crude product (0.08 g, yield: 94.10%) was taken for next step with out purification.

Intermediate 110: Ethyl 3-[2-(3,5-dimethyl-1,2-oxazol-4-yl)-4-hydroxy phenyl]propanoate To a 25 mL RB flask fitted with magnetic stirrer was charged with 10 mL of dichloromethane. To the stirred solvent was added ethyl 3-[2-(3,5-dimethyl-1,2-oxazol-4-yl)-4-methoxy phenyl]propanoate (0.120 g, 0.4 mmol). The reaction mixture was cooled to 0° C. and boron tribromide (0.099 g, 0.4 mmol) was added drop wise. After stirred for 30 minutes, the reaction mixture was quenched with ethanol (1 mL) at 0° C. by slow addition. The reaction mixture was concentrated to distill off the solvent; ethyl acetate (10 mL) was added. The organic layer was washed with saturated NaHCO$_3$ solution (10 mL), followed by brine solution (10 mL). The organic layer was dried over anhydrous Na$_2$SO$_4$ and the solvent was removed under reduced pressure. The product was obtained as colorless oil (0.1 g, yield: 90.90%).

Intermediate 111: 3-[2-(3,5-Dimethyl-1,2-oxazol-4-yl)-4-hydroxyphenyl]propanoic acid To a 10 mL RB flask fitted with magnetic stirrer was charged with 3 mL of tetrahydrofuran. To the stirred solvent were added ethyl 3-[2-(3,5-dimethyl-1,2-oxazol-4-yl)-4-hydroxy phenyl]propanoate (0.10 g, 0.35 mmol), ethanol (3 mL) and sodium hydroxide (0.015 g, 0.0.35 mmol) in water (0.5 mL). The reaction mixture was stirred at room 16 h. After completion of the reaction, the solvent was removed, the sodium salt was washed with diethyl ether (5 mL); the aqueous layer was acidified with 1N HCl to pH 2.0 and extracted with ethyl acetate (5 mL). The organic layer was dried over anhydrous $Na_2SO_4$ and the solvent was removed under reduced pressure to obtain the product (0.04 g, yield: 44.4%).

Compound 84: 3-{2-(3,5-Dimethyl-1,2-oxazol-4-yl)-4-[(4-{[(2E,2Z)-2-(methoxyimino)-2-phenylethyl]oxy}benzyl)oxy]phenyl}propanoic acid To a 25 mL RB flask fitted with magnetic stirrer was charged with 5 mL of acetonitrile. To the stirred solvent were added 3-[2-(3,5-dimethyl-1,2-oxazol-4-yl)-4-hydroxyphenyl]propanoic acid (0.04 g, 0.15 mmol), sodium hydroxide (0.019 g, 0.4 mmol). The reaction mixture was brought to 0° C., (1E,1Z)-2-[4-(bromomethyl) phenoxy]-N-methoxy-1-phenylethanimine (0.051 g, 0.15 mmol) in ethanol (2 mL) was added drop wise and stirred at RT for 5 h. After completion of the reaction, the solvent was removed, the sodium salt was washed with diethyl ether (5 mL); the aqueous layer was acidified with 1N HCl to pH 2.0 and extracted with ethyl acetate (5 mL). The organic layer was dried over anhydrous $Na_2SO_4$ and the solvent was removed under reduced pressure to obtain the product (0.006 g, yield: 6.2%).

Scheme 28

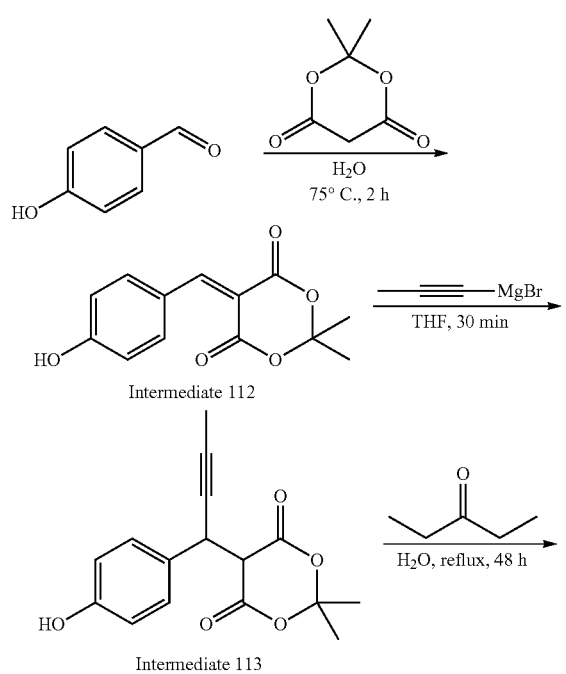

Intermediate 112

Intermediate 113

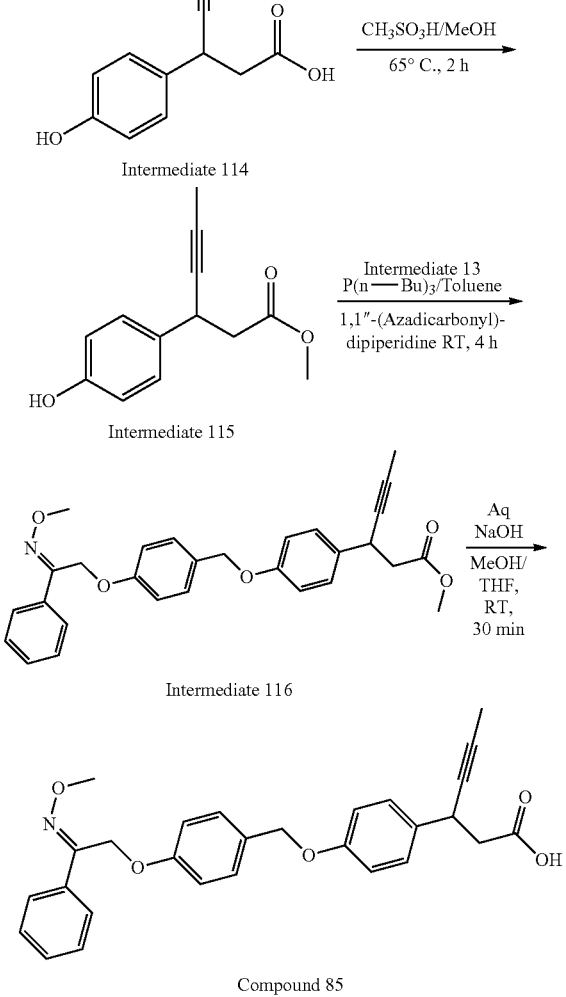

Intermediate 114

Intermediate 115

Intermediate 116

Compound 85

Example 85

3-{4-[(4-{[(2Z)-2-(Methoxyimino)-2-phenylethyl]oxy}benzyl)oxy]phenyl}hex-4-ynoic acid (85)

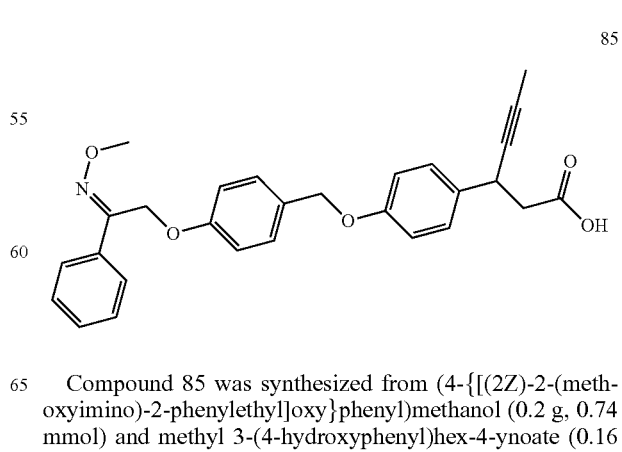

Compound 85 was synthesized from (4-{[(2Z)-2-(methoxyimino)-2-phenylethyl]oxy}phenyl)methanol (0.2 g, 0.74 mmol) and methyl 3-(4-hydroxyphenyl)hex-4-ynoate (0.16 g, 0.74 mmol) by following the procedure described in scheme 28 (0.03 g, yield: 20.59%); Purity: 98.37%.

Intermediate 112: 5-(4-Hydroxybenzylidene)-2,2-dimethyl-1,3-dioxane-4,6-dione

To a 500 mL RB flask fitted with magnetic stirrer was charged with water (160 mL). To the stirred solvent was added 4-hydroxybenzaldehyde (25.0 g, 122.12 mmol) and 2,2-dimethyl-1,3-dioxane-4,6-dione (25.0 g), it was heated at 75° C. for 2 h. The RM was cooled to obtain the solid, filtered and was washed with water, then dried to obtain the product (34.0, yield: 83.74%).

Intermediate 113: 5-[1-(4-Hydroxyphenyl)but-2-yn-1-yl]-2,2-dimethyl-1,3-dioxane-4,6-dione To a 250 mL 3-necked RB flask fitted with magnetic stirrer was charged with bromo(prop-1-yn-1-yl)magnesium (42.5 mL, 211 mmol) in THF (30 mL). To the RM was added slowly 5-(4-hydroxybenzylidene)-2,2-dimethyl-1,3-dioxane-4,6-dione (5.0 g, 100.8 mmol) in THF (20 mL) under nitrogen atmosphere. The RM was stirred at room temperature about 30 minutes. The reaction mixture was diluted with NH$_4$Cl solution and hexane. The aqueous layer was acidified with KHSO$_4$ solution to adjust the pH 2 and extracted with ethyl acetate, washed with water, then dried to obtain the product (5.8 g, yield: 100.0%).

Intermediate 114: 3-(4-Hydroxyphenyl)hex-4-ynoic acid

To a 250 mL 3-necked RB flask fitted with magnetic stirrer was charged with 5-[1-(4-hydroxyphenyl)but-2-yn-1-yl]-2,2-dimethyl-1,3-dioxane-4,6-dione (5.8 g, 20.13 mmol) in diethyl ketone was added water (13 mL), the reaction mixture was heated to refluxed for 48 h. The RM was acidified with 1N HCl and extracted with ethyl acetate. The organic layer was washed with water, dried over anhydrous sodium sulphat. Finally removal of solvent under reduced pressure to obtain the product (4.11 g, yield: 100.0%).

Intermediate 115: Methyl 3-(4-hydroxyphenyl)hex-4-ynoate

To a 250 mL RB flask fitted with magnetic stirrer was charged with methanol (10 mL). To the stirred solvent was added 3-(4-Hydroxyphenyl)hex-4-ynoic acid (0.62 g, 20.14 mmol) and methane sulfonic acid (3 mL), it was heated at 65° C. for 2 h. The RM was concentrated, extracted with ethyl acetate (50 mL×2). The organic layer was washed with water (50 mL) and saturated brine solution (50 mL). The organic layer was dried over anhydrous Na$_2$SO$_4$ and the solvent was removed under reduced pressure to obtain the product. (0.4 g, yield: 90.9%).

Intermediate 116: Methyl 3-{4-[(4-{[(2Z)-2-(methoxyimino)-2-phenylethyl]oxy}benzyl)oxy]phenyl}hex-4-ynoate To a 50 mL RB flask fitted with magnetic stirrer was charged with 15 mL of toluene. To the stirred solvent were added (4-{[(2E,2Z)-2-(methoxyimino)-2-phenylethyl]oxy}phenyl)methanol (0.2 g, 0.74 mmol), methyl 3-(4-hydroxyphenyl)hex-4-ynoate (0.16 g, 0.74 mmol). The reaction mixture was cooled to 0° C.; tributylphosphine (0.195 g, 0.96 mmol) was added and stirred for 10 minutes. To the stirring solution, 1,1'-(azodicarbonyl)dipiperidine (0.242 g, 0.96 mmol) in toluene (2 mL) was added drop wise at the same temperature and stirred at room temperature for 4 h. The reaction mixture was diluted with water (10 mL) and extracted with ethyl acetate (15 mL×2). The organic layer was washed with water (10 mL), followed by brine solution (10 mL). The organic layer was dried over anhydrous Na$_2$SO$_4$ and the solvent was removed under reduced pressure. The crude material was purified by silica gel column chromatography using ethyl acetate and petroleum ether as elutant. The product was obtained as colorless oil (0.15 g, yield: 42.86%).

Compound 85: 3-{4-[(4-{[(2Z)-2-(Methoxyimino)-2-phenylethyl]oxy}benzyl)oxy]phenyl}hex-4-ynoic acid To a 50 mL RB flask fitted with magnetic stirrer was charged with 5 mL of tetrahydrofuran. To the stirred solvent was added Methyl 3-{4-[(4-{[(2E,2Z)-2-(methoxyimino)-2-phenylethyl]oxy}benzyl)oxy]phenyl}hex-4-ynoate (0.15 g, 0.32 mmol) in methanol (5 mL). The reaction mixture was cooled to 0° C. and sodium hydroxide (0.025 g, 0.64 mmol) in water (5 mL) was added drop wise and stirred for 30 h. The reaction mixture was concentrated to distill off the solvent; ethyl acetate (10 mL) was added and stirred for 10 minutes. The organic layer was removed and the crude was acidified with saturated solution of citric acid to make pH 6. The obtained solids were filtered and dried. The product was obtained as white solid (0.03 g, yield: 20.59%).

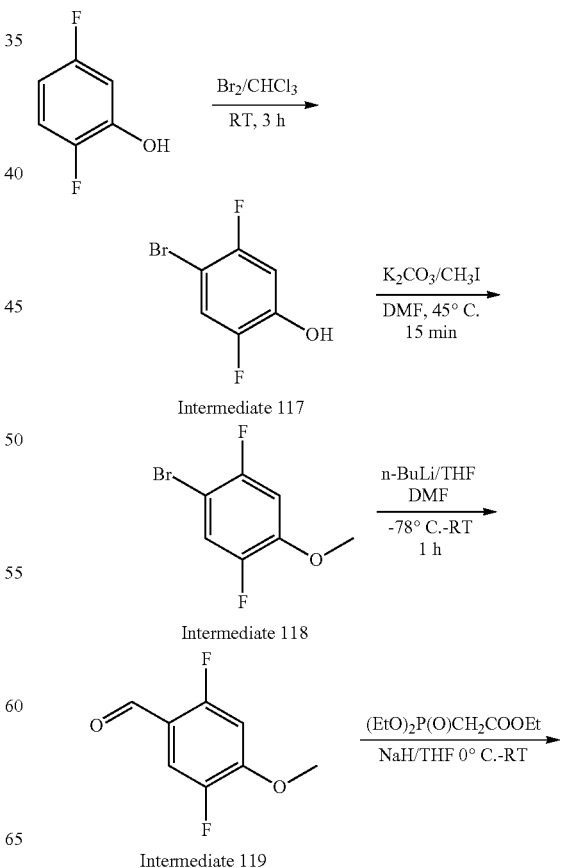

Scheme 29

-continued

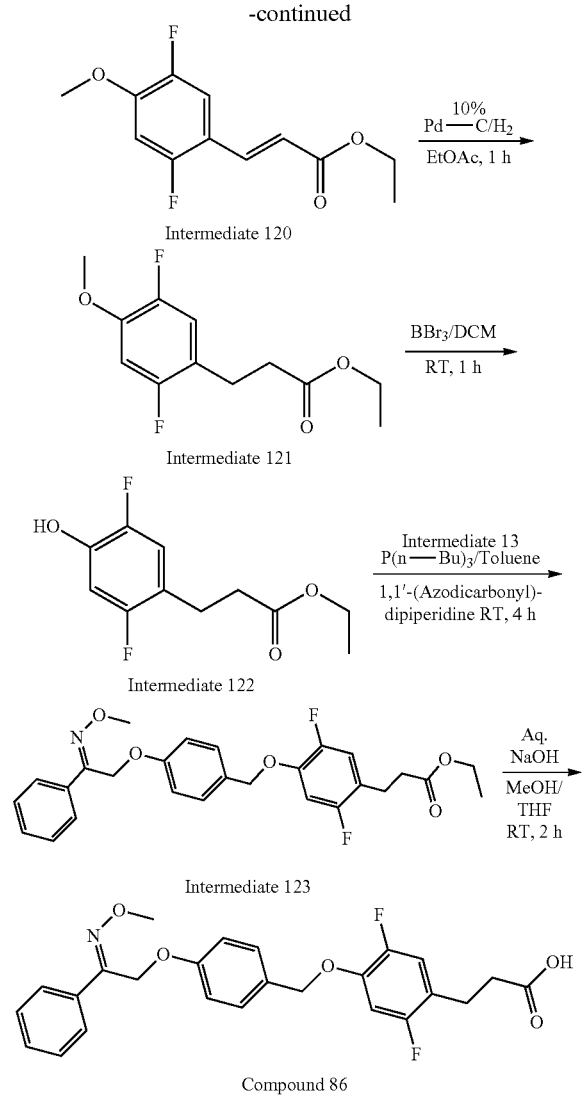

Example 86

3-{2,5-Difluoro-4-[(4-{[(2Z)-2-(methoxyimino)-2-phenylethyl]oxy}benzyl)oxy]phenyl}propanoic acid (86)

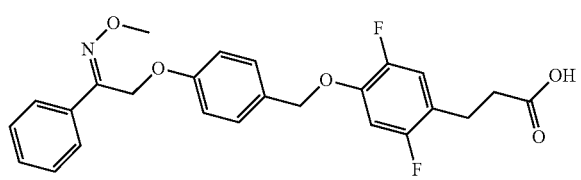

Compound 86 was synthesized from (4-{[(2Z)-2-(methoxyimino)-2-phenylethyl]oxy}phenyl)methanol (0.053 g, 0.109 mmol) and (0.05 g, 1.25 mmol) by following the procedure described in scheme 29 (0.008 g, yield: 16.00%); Purity: 94.64%.

Intermediate 117: 4-Bromo-2,5-difluorophenol

To a 250 mL RB flask fitted with magnetic stirrer was charged with 100 mL of CHCl$_3$. To the stirred solvent were added 2,5-difluorophenol (5.0 g, 38.4 mmol), bromine (6.14 g, 38.4 mmol), at 0° C. and stirred at room temperature for 3 h. The reaction mixture was quenched with sodium thio sulphate solution (20 mL) and extracted with ethyl acetate (15 mL×2). The organic layer was washed with water (50 mL), followed by brine solution (20 mL). The organic layer was dried over anhydrous Na$_2$SO$_4$ and the solvent was removed under reduced pressure to obtain product (6.5 g, yield: 81.05%).

Intermediate 118: 1-Bromo-2,5-difluoro-4-methoxybenzene

To a 100 mL RB flask fitted with magnetic stirrer was charged with 20 mL of DMF. To the stirred solvent were added 4-Bromo-2,5-difluorophenol (2.0 g, 9.6 mmol), K$_2$CO$_3$ (3.98 g, 28.8 mmol) and methyl iodide (1.63 g, 11.53 mmol), stirred at 45° C. for 15 minutes under nitrogen atmosphere. The RM was quenched with water, extracted with ethyl acetate (100 mL). The organic layer was washed with water (50 mL) and saturated brine solution (50 mL). The organic layer was dried over anhydrous Na$_2$SO$_4$ and the solvent was removed under reduced pressure. The product was obtained as white color solid (1.2 g, yield: 56.07%).

Intermediate 119: 2,5-Difluoro-4-methoxybenzaldehyde

To a 250 mL three RB flask fitted with magnetic stirrer was charged 1-Bromo-2,5-difluoro-4-methoxybenzene (1.0 g, 4.5 mmol) in 10 mL of THF, cooled –78° C. To the stirred solvent was added n-butyl lithium (3.09 mL, 1.6M solution, 4.95 mmol) drop wise and stirred at same temperature, was added DMF (0.375 g, 5.13 mmol), once the temperature to reached room temperature and stirred about 16 h. Then reaction mixture was quenched with ice-cold water and extracted with ethyl acetate. The organic layer was washed with water, dried over anhydrous Na$_2$SO$_4$. The removal of solvent under reduced pressure to obtain liquid product (0.77 g, yield: 100.0%).

Intermediate 120: Ethyl (2Z)-3-(2,5-difluoro-4-methoxyphenyl) prop-2-enoate

To a 100 mL RB flask fitted with magnetic stirrer was charged with 10 mL of tetrahydrofuran. To the stirred solvent was added sodium hydride (0.23 g, 9.86 mmol) portion wise at 0° C., followed by triethyl phosphonoacetate (1.66 g, 7.4 mmol). The reaction mixture was stirred at 0° C. for 30 minutes. To the stirring solution, 2,5-Difluoro-4-methoxybenzaldehyde (2.3 g, 7.2 mmol) in tetrahydrofuran (2 mL) was added drop wise and stirred at room temperature overnight. After completion of the reaction, the reaction mixture was poured into ice and extracted with ethyl acetate (25 mL). The organic layer was washed with water (25 mL) and saturated brine solution (25 mL). The organic layer was dried over anhydrous Na$_2$SO$_4$ and the solvent was removed under reduced pressure. The crude material was purified by silica gel column chromatography using ethyl acetate and petroleum ether as elutants. The product was obtained as colorless oil (0.1 g, yield: 8.4%).

Intermediate 121: Ethyl 3-(2,5-difluoro-4-methoxyphenyl)propanoate

To a 500 mL parr shaker flask was charged with Ethyl (2E)-3-(2,5-difluoro-4-methoxyphenyl)prop-2-enoate (0.1 g, 0.41 mmol), ethyl acetate (5 mL). To the reaction mixture was added 10% Pd—C (20%) and kept for hydrogenation using bladder 1 h. After completion of the reaction, the reaction mixture was filtered through celite, washed thoroughly with ethyl acetate (20 mL) and concentrated to distill off the solvent. The product was obtained as brown solid (0.080 g, yield: 80.0%).

Intermediate 122: Ethyl 3-(2,5-difluoro-4-hydroxyphenyl)propanoate

To a 25 mL RB flask fitted with magnetic stirrer was charged with 3 mL of dichloromethane. To the stirred solvent was added Ethyl 3-(2,5-difluoro-4-methoxyphenyl)propanoate (0.08 g, 0.327 mmol). The reaction mixture was cooled to 0° C. and boron tribromide (0.04 mL, 0.425 mmol) was added drop wise. After stirred for 30 minutes, the reaction mixture was quenched with ethanol (1 mL) at 0° C. by slow addition. The reaction mixture was concentrated to distill off the solvent; ethyl acetate (10 mL) was added. The organic layer was washed with saturated $NaHCO_3$ solution (10 mL), followed by brine solution (10 mL). The organic layer was dried over anhydrous $Na_2SO_4$ and the solvent was removed under reduced pressure. The product was obtained as colorless oil (0.06 g, yield: 80.0%).

Intermediate 123: Ethyl 3-{2,5-difluoro-4-[(4-{[(2Z)-2-(methoxyimino)-2-phenylethyl]oxy}benzyl)oxy]phenyl}propanoate To a 100 mL RB flask fitted with magnetic stirrer was charged with 2 mL of toluene. To the stirred solvent were added (4-{[(2E,2Z)-2-(methoxyimino)-2-phenylethyl]oxy}phenyl)methanol (0.0529 g, 0.195 mmol) and Ethyl 3-(2,5-difluoro-4-hydroxyphenyl)propanoate (1.0 g, 5.0 mmol). The reaction mixture was brought to 0° C.; tributylphosphine (0.057 g, 0.282 mmol) was added and stirred for 10 minutes. To the reaction mixture was added 1,1-(azodicarbonyl)dipiperidine (0.71 g, 0.282 mmol) in toluene (2 mL) was added drop wise. The reaction mixture was stirred at room temperature for 4 h. The reaction mixture was diluted with ethyl acetate (10 mL) and washed with water (25 mL). The organic layer was washed with brine solution (25 mL). The organic layer was dried over $Na_2SO_4$ and the solvent was removed under reduced pressure. The crude material was purified by silica gel column chromatography using ethyl acetate and petroleum ether as elutants to obtain the product (0.048 g, 48.0%).

Compound 86: 3-{2,5-Difluoro-4-[(4-{[(22)-2-(methoxyimino)-2-phenyl ethyl]oxy}benzyl)oxy]phenyl}propanoic acid To a 10 mL RB flask fitted with magnetic stirrer was charged with 3 mL of tetrahydrofuran. To the stirred solvent were added ethyl 3-{2,5-difluoro-4-[(4-{[(2E,2Z)-2-(methoxyimino)-2-phenylethyl]oxy}benzyl)oxy]phenyl}propanoate (0.053 g, 0.109 mmol) and methanol (3.0 mL). The reaction mixture was brought to 0° C. and sodium hydroxide (0.05 g, 1.25 mmol) in water (1 mL) was added drop wise. The reaction mixture was stirred overnight. After completion of the reaction, the reaction mixture was concentrated to distill off the solvent. The obtained salt was dissolved in water (1 mL) and extracted with ether (5 mL). The aqueous layer was acidified with 1N HCl to make pH 3 and extracted with ethyl acetater (15 mL). The organic layer was dried over $Na_2SO_4$ and the solvent was removed under reduced pressure to yield the product (0.008 g, 16.00%).

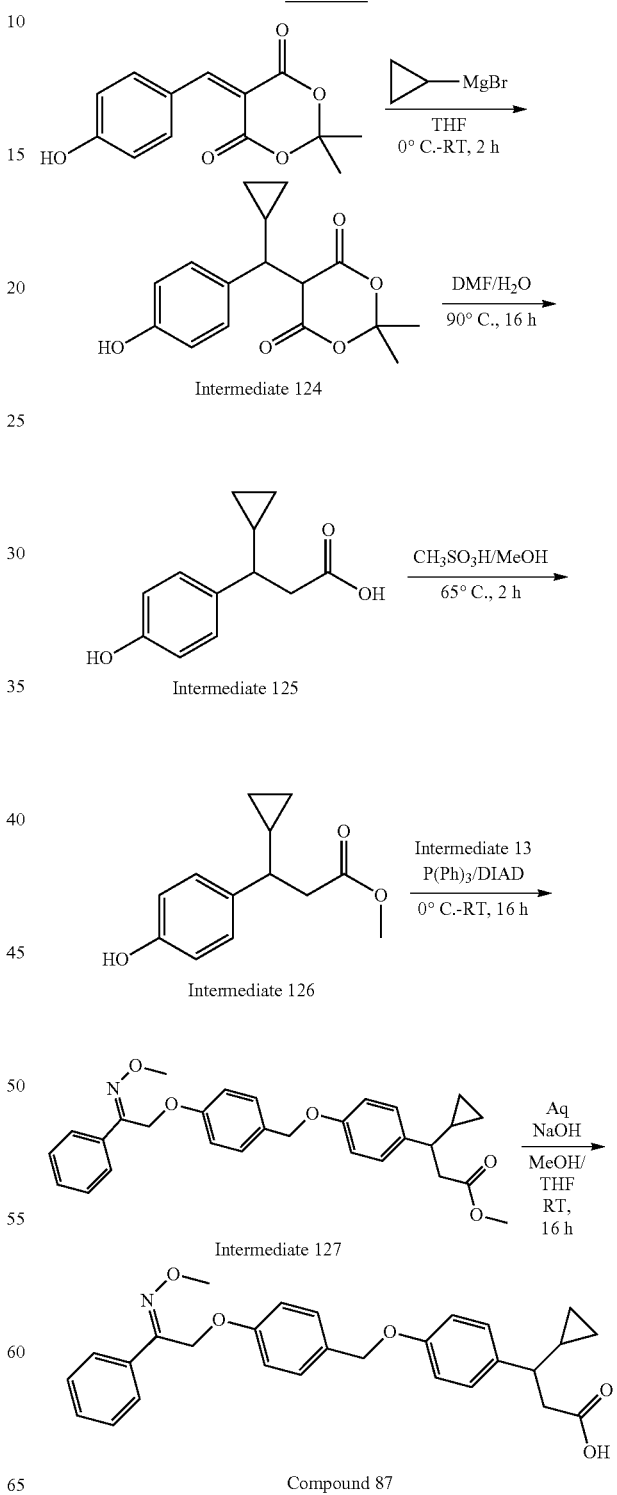

Scheme 30

Example 87

3-Cyclopropyl-3-{4-[(4-{[(2Z)-2-(methoxyimino)-2-phenyl ethyl]oxy}benzyl)oxy]phenyl}propanoic acid (87)

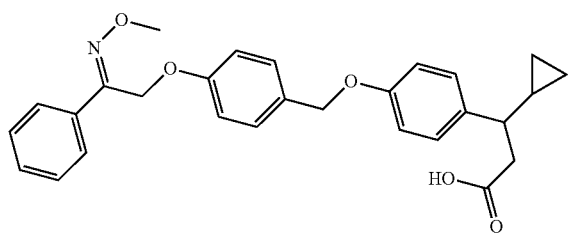

Compound 87 was synthesized from (4-{[(2Z)-2-(methoxyimino)-2-phenylethyl]oxy}phenyl)methanol (0.22 g, 0.8146 mmol) and methyl 3-cyclopropyl-3-(4-hydroxyphenyl)propanoate (0.2 g, 0.9082 mmol) by following the procedure described in scheme 30 (0.04 g, yield: 22.90%); Purity: 98.07%.

Intermediate 124: 5-[Cyclopropyl(4-hydroxyphenyl)methylidene]-2,2-dimethyl-1,3-dioxane-4,6-dione To a 250 mL RB flask fitted with magnetic stirrer was charged 6 mL of dry THF under argon atmosphere. To the stirred solvent was added 5-(4-hydroxybenzylidene)-2,2-dimethyl-1,3-dioxane-4,6-dione (0.6 g, 2.41 mmol). The resulting mixture was cooled to 0° C. and was added cyclopropylmagnesium bromide (25 mL, 0.5 M in THF, 7.25 mmol). The resulting mixture was stirred at ambient temperatures for 2 h. Then, the reaction mass was quenched with 20 mL of 1N HCl then, ethyl acetate (50 mL) was added, stirred well and the layers were separated. The organic layer was washed with water (100 mL×3), brine solution. Then the organic layer was dried over anhydrous $Na_2SO_4$. The solvent was removed under reduced pressure, and the resulting crude compound is purified by column chromatography on silica gel (60-120 meshes) using petroleum ether (60-80) and ethyl acetate as eluent. The product was obtained as yellow solid. Yield: 42.76% (0.3 g) MS (ESI, 120 ev): m/z=291.1 (M+1). (300 MHz, DMSO-$d_6$): δ 9.16 (s, 1H), 6.95-6.98 (d, 2H), 6.53-6.56 (d, 2H), 4.42-4.43 (d, 1H), 2.54-2.59 (m, 1H), 1.61 (s, 4H), 1.29 (s, 3H), 0.40-0.49 (m, 2H), 0.23-0.28 (m, 1H), 0.03-0.01 (m, 1H).

Intermediate 125: 3-Cyclopropyl-3-(4-hydroxyphenyl)propanoic acid

To a 100 mL RB flask fitted with magnetic stirrer was charged DMF (10 mL) and water (2 mL). To the stirred solvent was added 5-[cyclopropyl(4-hydroxyphenylmethylidene]-2,2-dimethyl-1,3-dioxane-4,6-dione (0.3 g). The resulting mixture was stirred at 90° C. for 15 h. After completion of the reaction (reaction monitored by TLC), solvent from the reaction mass was removed under reduced pressure and the resulting crude mass was taken in 4N NaOH (50 mL). The aqueous layer was washed with ether (100 mL×3). Then the aqueous layer was acidified using 3N HCl (50 ml) and was extracted using DCM (100 mL×3). The combined DCM layer was washed with saturated brine solution (100 mL). Then the organic layer was dried over anhydrous $Na_2SO_4$. Solvent was removed under reduced pressure. The product was obtained as brown syrup Yield: 75.01% (160 mg) $^1$H NMR (300 MHz, DMSO-$d_6$): δ 11.93 (s, 1H), 9.14 (s, 1H), 7.01-7.04 (d, 2H), 6.64-6.66 (d, 2H), 2.53-2.60 (m, 2H), 2.14-2.22 (m, 1H), 0.93-0.95 (m, 1H), 0.45-0.47 (m, 1H), 0.27-0.30 (m, 1H), 0.16-0.19 (m, 1H), 0.05-0.07 (m, 1H).

Intermediate 126: Methyl 3-cyclopropyl-3-(4-hydroxyphenyl)propanoate

To a 100 mL RB flask fitted with magnetic stirrer and reflux condenser was charged with 5 mL of Methanol. To the stirred solvent was added 3-cyclopropyl-3-(4-hydroxyphenyl)propanoic acid (160 mg, 0.7759 mmol) followed by the addition of Methane sulfonic acid (74.56 mg, 0.7759 mmol). The resulting mixture was stirred at 65° C. for 2 h. After completion of the reaction (reaction monitored by TLC), solvent from the reaction mass was removed under reduced pressure and the resulting crude mass was taken in ethyl acetate (50 mL) and was washed with water (100 mL×3), sodium bicarbonate solution (100 mL×3), saturated brine solution (100 mL). Then the organic layer was dried over anhydrous $Na_2SO_4$. The solvent was removed under reduced pressure. The product was obtained as brown syrup. yield: 98.0% (0.23 g, crude) (300 MHz, DMSO-$d_6$): δ 9.16 (s, 1H), 7.01-7.04 (d, 2H), 6.64-6.67 (d, 2H), 3.49 (s, 3H), 2.63-2.68 (m, 2H), 2.14-2.22 (m, 1H), 0.93-0.97 (m, 1H), 0.45-0.49 (m, 1H), 0.26-0.33 (m, 1H), 0.13-0.17 (m, 1H), 0.04-0.07 (m, 1H).

Intermediate 127: Methyl 3-cyclopropyl-3-{4-[(4-{[(2Z)-2-(methoxyimino)-2-phenylethyl]oxy}benzyl)oxy]phenyl}propanoate To a 100 mL RB flask fitted with magnetic stirrer was charged with 10 mL of THF. To the stirred solvent was (4-{[(2E,2Z)-2-(methoxyimino)-2-phenylethyl]oxy}phenyl)methanol (220.7 mg, 0.8146 mmol) followed by the addition of methyl 3-cyclopropyl-3-(4-hydroxyphenyl)propanoate (0.2 g, 0.9082 mmol). The resulting mixture was to cooled to 0° C. and was added triphenyl phosphene (0.3 g, 1.18 mmol) followed by DIAD (0.24 g, 1.18 mmol). The resulting mixture was stirred at ambient temperature for 15 h. After Then, solvent from the reaction mass was removed under reduced pressure and the resulting crude mass was taken in ethyl acetate (50 mL) and was washed with water (100 mL×3), saturated brine solution (100 mL). Then the organic layer was dried over 3 g of anhydrous $Na_2SO_4$. Solvent was removed under reduced pressure, and the resulting crude compound is purified by column chromatography on silica gel (60-120 meshes) using Petroleum ether (60-80) and ethyl acetate as eluent. The product was obtained as yellow syrup. Yield: 46.8 (0.18 g) MS (ESI, 120 ev): m/z=474.1 (M+H)$^+$. $^1$H NMR (300 MHz, CDCl$_3$): δ 7.57-7.60 (m, 2H), 7.24-7.27 (m, 5H), 7.04-7.07 (d, 2H), 6.79-6.84 (m, 4H), 5.11 (s, 2H), 4.84 (s, 2H), 3.96 (s, 3H), 3.50 (s, 3H), 2.60-2.65 (m, 2H), 2.20-2.28 (m, 1H), 1.33-1.35 (m, 2H), 0.45-0.50 (m, 1H), 0.31-0.35 (m, 1H), 0.13-0.18 (m, 1H), 0.04-0.08 (m, 1H)

Compound 87: 3-Cyclopropyl-3-{4-[(4-{[(2Z)-2-(methoxyimino)-2-phenylethyl]oxy}benzyl)oxy]phenyl}propanoic acid To a 100 mL RB flask fitted with magnetic stirrer was charged 10 mL of THF and 1 mL of methanol To the stirred solvent was methyl 3-cyclopropyl-3-{4-[(4-{[(2E,2Z)-2-(methoxyimino)-2-phenylethyl]oxy}benzyl)oxy]

phenyl}propanoate (180 mg, 0.38 mmol), to the resulting mixture was added sodium hydroxide (0.0456 g, 1.1404 mmol) in water (1 mL). The resulting mixture was stirred at ambient temperatures for 15 h. After completion of the reaction (reaction monitored by TLC), solvent from the reaction mass was removed under reduced pressure and the resulting crude mass was taken in water (50 mL). The aqueous layer was washed with ether (100 mL×3). Then the aqueous layer was acidified using 3N HCl (50 mL) and was extracted using DCM (100 mL×3). The combined DCM layer was washed with saturated brine solution (100 mL). Then the organic layer was dried over anhydrous Na$_2$SO$_4$, solvent was removed under reduced pressure. The resulting crude mass was purified by Prep TLC. The product was obtained as white solid. Yield: 22.9% (40 mg). MS (ESI, 120 ev): m/z=460.1 (M+1).

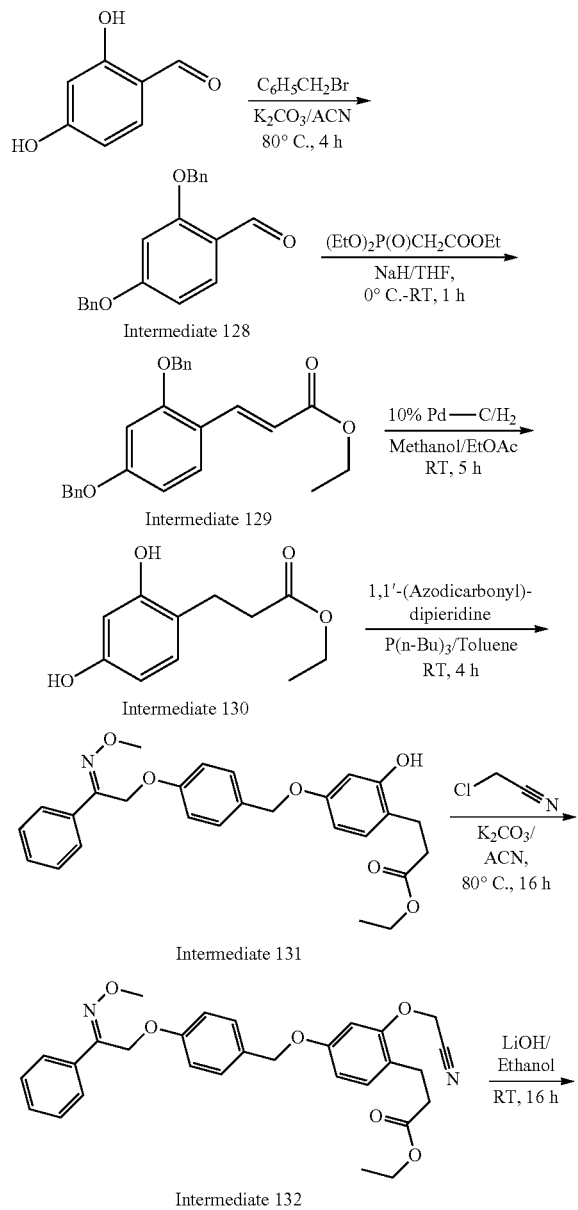

Scheme 31

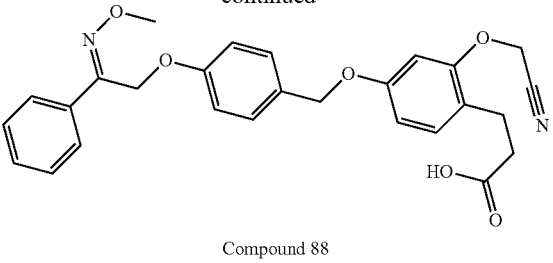

Compound 88

Example 88

3-{2-(Cyanomethoxy)-4-[(4-{[(2Z)-2-(methoxy-imino)-2-phenylethyl]oxy}benzyl)oxy]phenyl}propanoic acid (88)

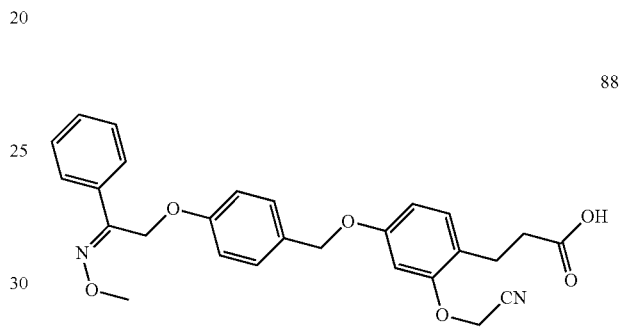

Compound 88 was synthesized from (4-{[(2Z)-2-(methoxyimino)-2-phenylethyl]oxy}phenyl)methanol (1.0 g, 5.0 mmol) and ethyl 3-(2,4-dihydroxy phenyl)propanoate (1.16 g, 4.0 mmol) by following the procedure described in scheme 31 (0.0031 g, yield: 8.16%).

Intermediate 128: 2,4-Bis(benzyloxy)benzaldehyde

To a 250 mL RB flask fitted with magnetic stirrer was charged 100 mL of acetonitrile. To the stirred solvent was added 2,4-dihydroxybenzaldehyde (10.0 g, 72.0 mmol) and K$_2$CO$_3$ (19.87 g, 144.0 mmol). Then it was stirred for 15 min, slowly was added benzylbromide (12.38 g, 72.0 mmol), the RM was heated to 80° C. for 3 h. Then, the solvent was removed under reduced pressure and the compound was extracted with ethyl acetate (50 mL×3). The organic layer washed with water and saturated brine solution and dried over anhydrous Na$_2$SO$_4$ and evaporated to dryness to get the crude product. The crude material was purified by silica gel column chromatography using ethyl acetate and petroleum ether as elutants to obtain the product (2.3 g, yield: 10.03%).

Intermediate 129: Ethyl (2E)-3-[2,4-bis(benzyloxy)phenyl]prop-2-enoate

To a 100 mL RB flask fitted with magnetic stirrer was charged with 25 mL of tetrahydrofuran. To the stirred solvent was added sodium hydride (0.35 g, 14.0 mmol) portion wise at 0° C., followed by triethyl phosphonoacetate (3.23 g, 14.0 mmol). The reaction mixture was stirred at 0° C. for 30 minutes. To the stirring solution, 2,4-bis(benzyloxy)benzaldehyde (2.3 g, 7.2 mmol) in tetrahydrofuran (2 mL) was added drop wise and stirred at room temperature 16 h. After completion of the reaction, the reaction mixture was poured into ice and extracted with ethyl acetate (50 mL). The organic layer was washed with water (25 mL) and saturated brine solution (25 mL). The organic layer was dried over anhydrous Na₂SO₄ and the solvent was removed under reduced pressure. The crude material was purified by silica gel column chromatography using ethyl acetate and petroleum ether as elutants. The product was obtained as colourless oil (2.3 g, yield: 82.14%).

Intermediate 130: Ethyl 3-(2,4-dihydroxyphenyl)propanoate

To a 500 mL parr shaker flask was charged with ethyl (2E)-3-[2,4-bis(benzyloxy)phenyl]prop-2-enoate (2.3 g, 5.92 mmol), ethyl acetate (10 mL) and methanol (10 mL). To the reaction mixture was added palladium hydroxide (20%) and kept for hydrogenation at 50 psi for 2 h. After completion of the reaction, the reaction mixture was filtered through celite, washed thoroughly with ethyl acetate (25 mL) and concentrated to distill off the solvent. The product was obtained as brown solid (1.2 g, yield: 96.8%).

Intermediate 131: Ethyl 3-{2-hydroxy-4-[(4-{[(2Z)-2-(methoxyimino)-2-phenylethyl]oxy}benzyl)oxy]phenyl}propanoate To a 100 mL RB flask fitted with magnetic stirrer was charged with 20 mL of toluene. To the stirred solvent were added (4-{[(2E,2Z)-2-(methoxyimino)-2-phenylethyl]oxy}phenyl)methanol (1.16 g, 4.0 mmol) and ethyl 3-(2,4-dihydroxyphenyl)propanoate (1.0 g, 5.0 mmol). The reaction mixture was brought to 0° C.; tributylphosphine (1.5 g, 7.0 mmol) was added and stirred for 10 minutes. To the reaction mixture was added 1,1-(azodicarbonyl)dipiperidine (1.2 g, 5.0 mmol) in toluene (2 mL) drop wise. The reaction mixture was stirred at room temperature for 8 h. The reaction mixture was diluted with ethyl acetate (25 mL) and washed with water (25 mL). The organic layer was washed with brine solution (25 mL). The organic layer was dried over Na₂SO₄ and the solvent was removed under reduced pressure. The crude material was purified by silica gel column chromatography using ethyl acetate and petroleum ether as elutants. The product was obtained as colourless oil (0.15 g, 6.48%).

Intermediate 132: Ethyl 3-{2-(cyanomethoxy)-4-[(4-{[(2Z)-2-(methoxyimino)-2-phenylethyl]oxy}benzyl)oxy]phenyl}propanoate To a 25 mL RB flask fitted with magnetic stirrer was charged with 2 mL of acetonitrile. To the stirred solvent were added ethyl 3-{2-hydroxy-4-[(4-{[(2E,2Z)-2-(methoxyimino)-2-phenylethyl]oxy}benzyl)oxy]phenyl}propanoate (0.1 g, 0.2 mmol), potassium carbonate (0.055 g, 0.4 mmol). The reaction mixture was brought to 0° C., was added chloroacetonitrile (0.024 g, 3.0 mmol) in acetonitrile (20 mL) drop wise and stirred at 80° C. temperature for 16 h. The reaction mixture was concentrated to distill off the solvent. The obtained residue was dissolved in water and extracted with ethyl acetate (20 mL). The organic layer was washed with water (10 mL) and saturated brine solution (10 mL). The organic layer was dried over anhydrous Na₂SO₄ and the solvent was removed under reduced pressure. The crude material was purified by silica gel column chromatography using ethyl acetate and petroleum ether as elutants to obtain product (0.05 g, yield: 50.0%).

Compound 88: 3-{2-(Cyanomethoxy)-4-[(4-{[(2Z)-2-(methoxyimino)-2-phenylethyl]oxy}benzyl)oxy]phenyl}propanoic acid To a 10 mL RB flask fitted with magnetic stirrer was charged with 1 mL of tetrahydrofuran. To the stirred solvent were added ethyl 3-{2-(cyanomethoxy)-4-[(4-{[(2E,2Z)-2-(methoxyimino)-2-phenylethyl]oxy}benzyl)oxy]phenyl}propanoate (0.04 g, 0.079 mmol) and ethanol (0.5 mL). The reaction mixture was brought to 0° C. and lithium hydroxide (0.0057 g, 0.23 mmol) in water (1 mL) was added drop wise. The reaction mixture was stirred overnight. After completion of the reaction, the reaction mixture was concentrated to distill off the solvent. The salt was dissolved in water (1 mL) and extracted with ether (5 mL). The aqueous layer was acidified with 1N HCl to make pH 3 and extracted with ether (5 mL). The organic layer was washed with brine solution (5 mL), the solvent was distilled off and dried. The crude material was purified by silica gel column chromatography using ethyl acetate and petroleum ether as elutants to obtain product (0.0031 g, yield: 8.16%).

Example 89

3-{2-(Carboxymethoxy)-4-[(4-{[(2E,2Z)-2-(methoxyimino)-2-phenylethyl]oxy}benzyl)oxy]phenyl}propanoic acid (89)

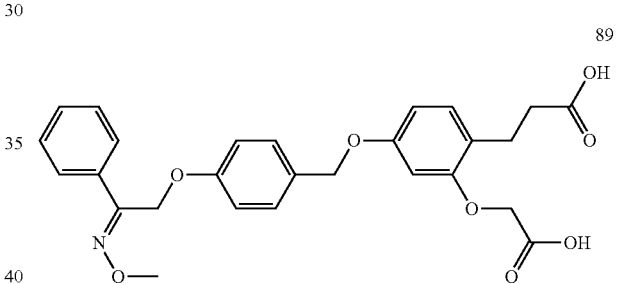

Compound 89 was synthesized from (4-{[(2Z)-2-(methoxyimino)-2-phenylethyl]oxy}phenyl)methanol (1.0 g, 5.0 mmol) and ethyl 3-(2,4-dihydroxy phenyl)propanoate (1.16 g, 4.0 mmol) by following the procedure described in scheme 31 (0.006 g, yield: 15.38%).

Example 90

{2-(3-Ethoxy-3-oxopropyl)-5-[(4-{[(2E,2Z)-2-(methoxyimino)-2-phenylethyl]oxy}benzyl)oxy]phenoxy}acetic acid (9190)

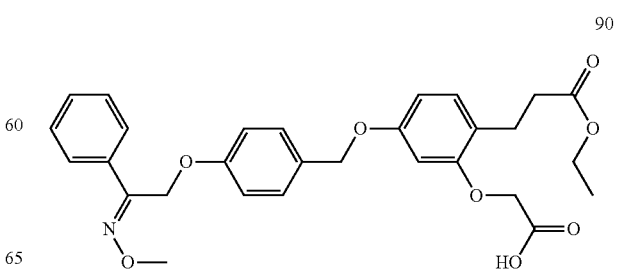

Compound 90 was synthesized from (4-{[(2Z)-2-(methoxyimino)-2-phenylethyl]oxy}phenyl)methanol (1.0 g, 5.0 mmol) and ethyl 3-(2,4-dihydroxyphenyl)propanoate (1.16 g, 4.0 mmol) by following the procedure described in scheme 31 (0.0008 g, yield: 19.28%).

Example 91

3-{4-[(4-{[(2Z)-2-(Methoxyimino)-2-phenylethyl]oxy}benzyl)oxy]phenyl}hexanoic acid (91)

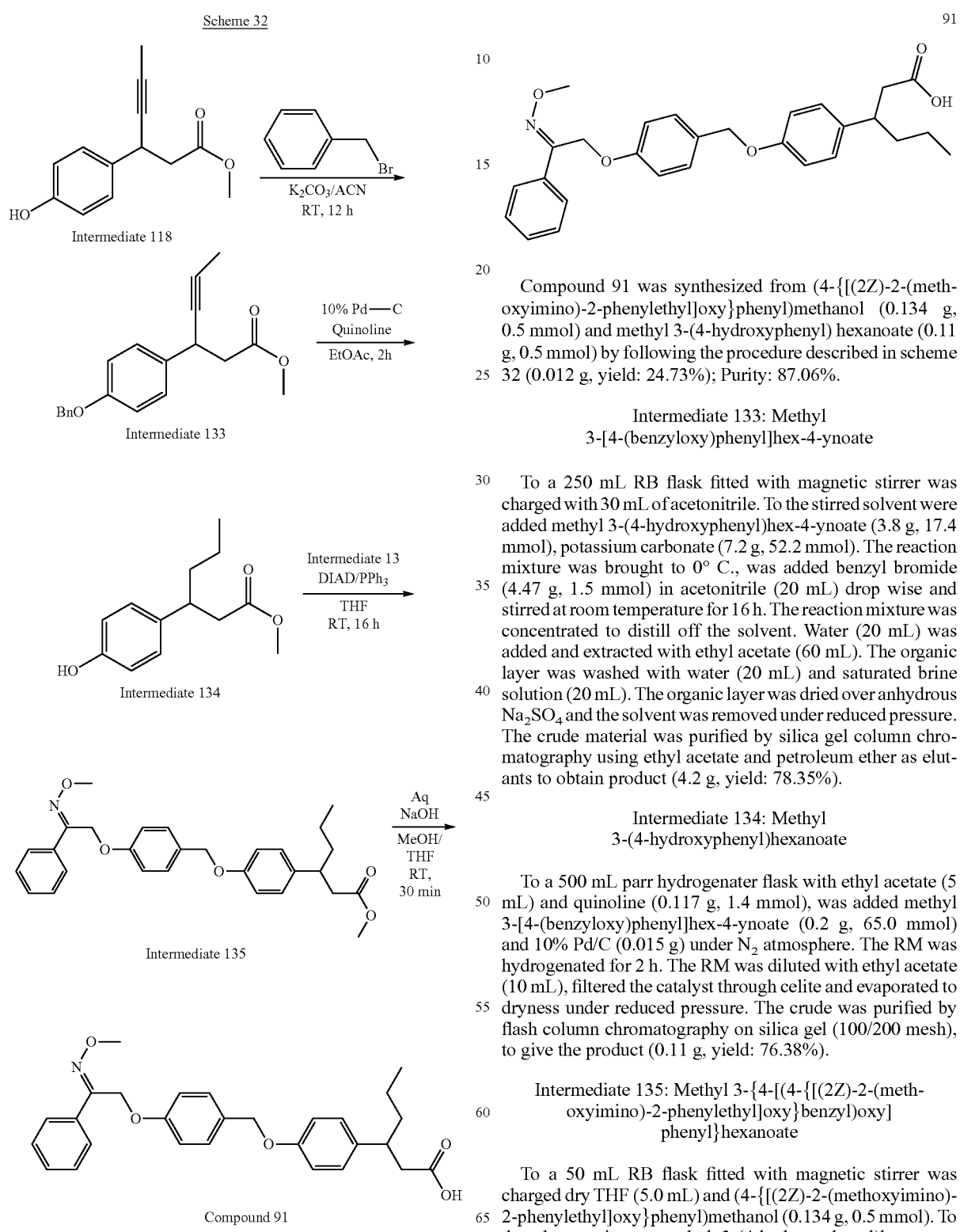

Compound 91 was synthesized from (4-{[(2Z)-2-(methoxyimino)-2-phenylethyl]oxy}phenyl)methanol (0.134 g, 0.5 mmol) and methyl 3-(4-hydroxyphenyl) hexanoate (0.11 g, 0.5 mmol) by following the procedure described in scheme 32 (0.012 g, yield: 24.73%); Purity: 87.06%.

Intermediate 133: Methyl 3-[4-(benzyloxy)phenyl]hex-4-ynoate

To a 250 mL RB flask fitted with magnetic stirrer was charged with 30 mL of acetonitrile. To the stirred solvent were added methyl 3-(4-hydroxyphenyl)hex-4-ynoate (3.8 g, 17.4 mmol), potassium carbonate (7.2 g, 52.2 mmol). The reaction mixture was brought to 0° C., was added benzyl bromide (4.47 g, 1.5 mmol) in acetonitrile (20 mL) drop wise and stirred at room temperature for 16 h. The reaction mixture was concentrated to distill off the solvent. Water (20 mL) was added and extracted with ethyl acetate (60 mL). The organic layer was washed with water (20 mL) and saturated brine solution (20 mL). The organic layer was dried over anhydrous Na$_2$SO$_4$ and the solvent was removed under reduced pressure. The crude material was purified by silica gel column chromatography using ethyl acetate and petroleum ether as elutants to obtain product (4.2 g, yield: 78.35%).

Intermediate 134: Methyl 3-(4-hydroxyphenyl)hexanoate

To a 500 mL parr hydrogenater flask with ethyl acetate (5 mL) and quinoline (0.117 g, 1.4 mmol), was added methyl 3-[4-(benzyloxy)phenyl]hex-4-ynoate (0.2 g, 65.0 mmol) and 10% Pd/C (0.015 g) under N$_2$ atmosphere. The RM was hydrogenated for 2 h. The RM was diluted with ethyl acetate (10 mL), filtered the catalyst through celite and evaporated to dryness under reduced pressure. The crude was purified by flash column chromatography on silica gel (100/200 mesh), to give the product (0.11 g, yield: 76.38%).

Intermediate 135: Methyl 3-{4-[(4-{[(2Z)-2-(methoxyimino)-2-phenylethyl]oxy}benzyl)oxy]phenyl}hexanoate To a 50 mL RB flask fitted with magnetic stirrer was charged dry THF (5.0 mL) and (4-{[(2Z)-2-(methoxyimino)-2-phenylethyl]oxy}phenyl)methanol (0.134 g, 0.5 mmol). To the above mixture methyl 3-(4-hydroxyphenyl)hexanoate (0.11 g, 0.5 mmol) was added and the resulting mixture stirred at 0° C. for 5 min. Triphenyl phosphine (0.17 g, 0.65 mmol) was added to the mixture and stirred at 0° C. for 15 min followed by the addition of diethylazadicarboxylate (0.13 g, 0.65 mmol). After stirring the resulting mixture at RT for 16 h, the RM was evaporated to remove the THF. The residue was diluted with water (15 mL) and extracted with ethyl acetate (15 mL×2). The organic layer was washed with saturated brine solution (15 mL) and dried over anhydrous Na$_2$SO$_4$. Concentration of the solvent and purification of the resulting residue by column chromatography on silica gel (100/200 mesh), using petroleum ether and ethyl acetate as eluent, gave the product (0.05 g, yield: 21.74%)

Compound 91: 3-{4-[(4-{[(2Z)-2-(Methoxyimino)-2-phenylethyl]oxy}benzyl)oxy]phenyl}hexanoic acid To a 25 mL RB flask fitted with magnetic stirrer was charged with 3 mL of tetrahydrofuran. To the stirred solvent were added methyl 3-{4-[(4-{[(2Z)-2-(methoxyimino)-2-phenylethyl]oxy}benzyl)oxy]phenyl}hexanoate (0.017 g, 0.03 mmol), methanol (0.5 mL) and sodium hydroxide (0.013 g, 0.32 mmol) in water (0.5 mL). After addition, the reaction mixture was stirred at room temperature 30 minutes. The reaction mixture was concentrated to distill off the solvent; the crude was washed with diethyl ether (5 mL). The salt was dissolved in water (1 mL) and the aqueous layer was acidified with saturated citric acid to solution to make pH 6. The aqueous layer was extracted with ethyl acetate (5 mL). The organic layer was dried over anhydrous Na$_2$SO$_4$ and the solvent was removed under reduced pressure. The crude material was purified by preparative TLC using methanol and chloroform as eluents. The product was obtained as white semi solid (0.012 g, yield: 24.73%). MS (ESI, 120 ev): m/z=462.1 (M+H)$^+$.

Example 92

3-(4-{[4-({(2Z)-2-(Methoxyimino)-2-[4-(methylsulfonyl)phenyl]ethyl}oxy)benzyl]oxy}phenyl)propanoic acid (92)

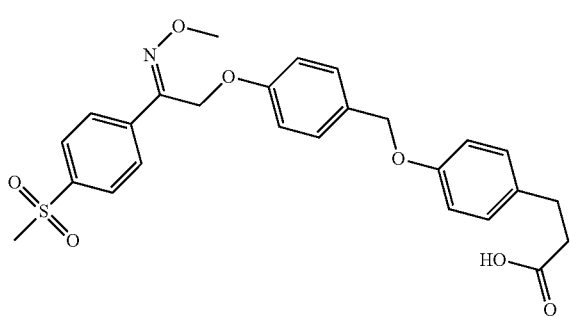

Compound 92 was synthesized from [4-({(2Z)-2-(methoxyimino)-2-[4-(methylsulfonyl)phenyl]ethyl}oxy)phenyl]methanol (0.57 g, 1.63 mmol) and methyl 3-(4-hydroxyphenyl)propanoate (0.293 g, 1.63 mmol) by following the procedure described in scheme 5 (0.2 g, yield: 39.91%); Purity: 96.52%.

Scheme 33

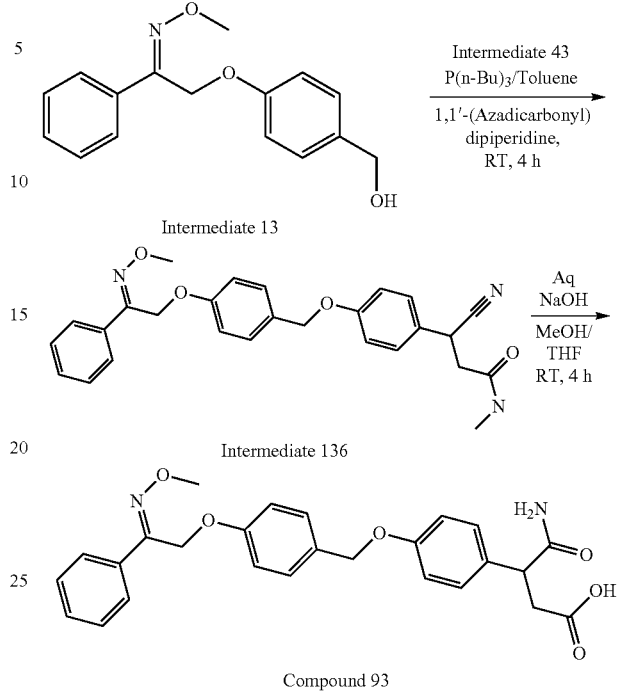

Example 93

4-Amino-3-{4-[(4-{[(2Z)-2-(methoxyimino)-2-phenylethyl]oxy}benzyl)oxy]phenyl}-4-oxobutanoic acid (93)

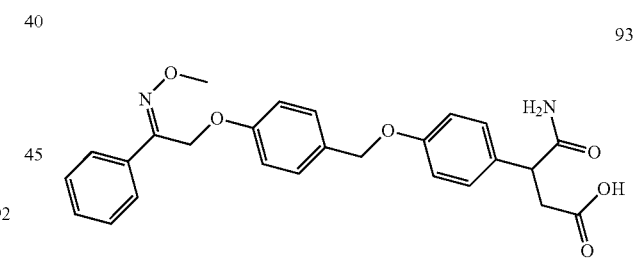

Compound 93 was synthesized from (4-{[(2Z)-2-(methoxyimino)-2-phenylethyl]oxy}phenyl)methanol (30.93 g, 114.0 mmol) and methyl 3-cyano-3-(4-hydroxyphenyl)propanoate (26.0 g, 127.0 mmol) by following the procedure described in scheme 33 (2.1 g, yield: 9.05%); Purity: 96.52%.

Intermediate 136: Methyl 3-cyano-3-{4-[(4-{[(2Z)-2-(methoxyimino)-2-phenylethyl]oxy}benzyl)oxy]phenyl}propanoate To a 500 mL 3-necked RB flask fitted with magnetic stirrer was charged with 100 mL of toluene. To the stirred solvent were added (4-{[(2E,2Z)-2-(methoxyimino)-2-phenylethyl]oxy}phenyl)methanol (30.93 g, 114.0 mmol) and methyl 3-cyano-3-(4-hydroxyphenyl)propanoate (26.0 g, 127.0 mmol). The reaction mixture was brought to 0° C., tributylphosphine (33.35 g, 4.26 mmol) was added and stirred for 20 minutes. To the reaction mixture was added 1,1-(azodicarbonyl)dipiperidine (41.56 g, 5.53 mmol) in toluene (50 mL) was added drop wise. The reaction mixture was stirred at room temperature for 4 h. The reaction mixture was diluted with ethyl acetate (250 mL) and washed with water. Finally the organic layer was washed with brine solution and dried over $Na_2SO_4$ and the solvent was removed under reduced pressure. The crude material was purified by silica gel column chromatography using ethyl acetate and petroleum ether as elutants. The product was obtained as colourless oil (45.0 g, 86.09%).

Compound 93: 4-Amino-3-{4-[(4-{[(2Z)-2-(methoxyimino)-2-phenyl ethyl]oxy}benzyl)oxy]phenyl}-4-oxobutanoic acid To a 500 mL RB flask fitted with magnetic stirrer was charged with 115 mL of tetrahydrofuran. To the stirred solvent were added methyl 3-cyano-3-{4-[(4-{[(2E,2Z)-2-(methoxyimino)-2-phenyl ethyl]oxy}benzyl)oxy]phenyl}propanoate (23.0 g, 0.502 mmol), methanol (115 mL) and sodium hydroxide (25.0 mL, 4N solution). Then, the reaction mixture was stirred at room temperature 2 h. The reaction mixture was concentrated to distill off the solvent; the crude was washed with ethyl acetate (100 mL). To the residue, was added water (50 mL) was added and the aqueous layer was acidified with saturated 1N NaOH solution to make pH 6. The aqueous layer was extracted with ethyl acetate (200 mL). The organic layer was dried over anhydrous $Na_2SO_4$ and the solvent was removed under reduced pressure. The crude material (5.0 g) was purified by crystallization with ethyl acetate (30.0 mL) and methanol (20.0 mL) mixture. The product was obtained as a white solid (2.1 g, yield: 9.05%).

Example 94

3-{3-Methoxy-4-[(4-{[(2Z)-2-(methoxyimino)-2-phenylethyl]oxy}benzyl)oxy]phenyl}propanoic acid (94)

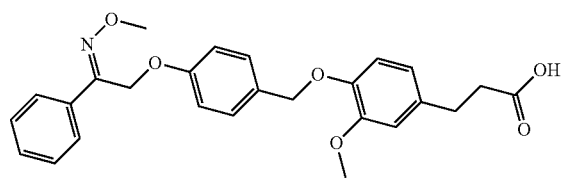

94

Compound 94 was synthesized from (4-{[(2Z)-2-(methoxyimino)-2-phenylethyl]oxy}phenyl)methanol (0.12 g, 0.446 mmol) and ethyl 3-(4-hydroxy-3-methoxyphenyl)propanoate (0.1 g, 0.446 mmol) by following the procedure described in scheme 16 (0.06 g, yield: 47.62%); Purity: 98.66%.

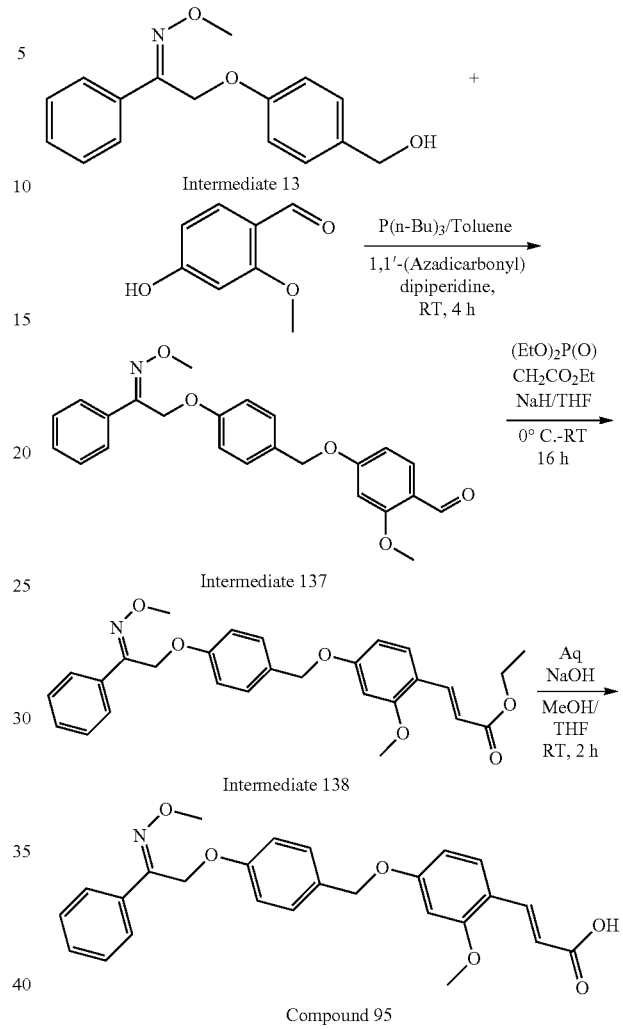

Scheme 34

Example 95

(2E,2Z)-3-{2-Methoxy-4-[(4-{[(2Z)-2-(methoxyimino)-2-phenylethyl]oxy}benzyl)oxy]phenyl}prop-2-enoic acid (95)

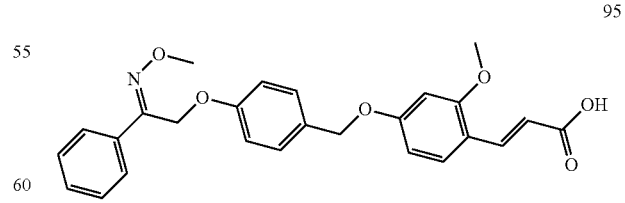

95

Compound 95 was synthesized from (4-{[(2Z)-2-(methoxyimino)-2-phenylethyl]oxy}phenyl)methanol (0.8 g, 2.95 mmol) and (2E,2Z)-3-(4-hydroxy-2-methoxyphenyl)prop-2-enoic acid (0.5 g, 3.28 mmol) by following the procedure described in scheme 34 (0.3 g, yield: 25.0%); Purity: 89.76%.

Intermediate 137: 2-Methoxy-4-[(4-{[(2Z)-2-(methoxyimino)-2-phenylethyl]oxy}benzyl)oxy]benzaldehyde To a 100 mL RB flask fitted with magnetic stirrer was charged with 20 mL of toluene. To the stirred solvent were added (4-{[(2E,2Z)-2-(methoxyimino)-2-phenylethyl]oxy}phenyl)methanol (0.8 g, 2.95 mmol) and 4-hydroxy-2-methoxybenzaldehyde (0.5 g, 3.28 mmol). The reaction mixture was brought to 0° C.; tributylphosphine (0.86 g, 4.26 mmol) was added and stirred for 10 minutes. To the reaction mixture was added 1,1-(azodicarbonyl)dipiperidine (1.39 g, 5.53 mmol) in toluene (2 mL) was added drop wise. The reaction mixture was stirred at room temperature for 16 h. The reaction mixture was diluted with ethyl acetate (25 mL) and washed with water (25 mL). The organic layer was washed with brine solution (25 mL). The organic layer was dried over Na$_2$SO$_4$ and the solvent was removed under reduced pressure. The crude material was purified by silica gel column chromatography using ethyl acetate and petroleum ether as elutants. The product was obtained as colourless oil (0.3 g, 25.0%).

Intermediate 138: Ethyl (2E,2Z)-3-{2-methoxy-4-[(4-{[(2Z)-2-(methoxyimino)-2-phenylethyl]oxy}benzyl)oxy]phenyl}prop-2-enoate To a 100 mL RB flask fitted with magnetic stirrer was charged with 10 mL of tetrahydrofuran. To the stirred solvent was added sodium hydride (0.035 g, 1.47 mmol) portion wise at 0° C., followed by triethyl phosphonoacetate (0.25 g, 1.1 mmol). The reaction mixture was stirred at 0° C. for 30 minutes. To the stirred solution, was added drop wise 2-methoxy-4-[(4-{[(2E,2Z)-2-(methoxyimino)-2-phenylethyl]oxy}benzyl)oxy]benzaldehyde (0.3 g, 0.739 mmol) in tetrahydrofuran (2 mL) and stirred at room temperature 16 h. After completion of the reaction, the reaction mixture was poured into ice and extracted with ethyl acetate (50 mL). The organic layer was washed with water (25 mL) and saturated brine solution (25 mL). The organic layer was dried over anhydrous Na$_2$SO$_4$ and the solvent was removed under reduced pressure. The crude material was purified by silica gel column chromatography using ethyl acetate and petroleum ether as elutants. The product was obtained as colorless oil (0.3 g, yield: 8.5%).

Compound 95: (2E,2Z)-3-{2-Methoxy-4-[(4-{[(2Z)-2-(methoxyimino)-2-phenyl ethyl]oxy}benzyl)oxy]phenyl}prop-2-enoic acid To a 25 mL RB flask fitted with magnetic stirrer was charged with 3 mL of tetrahydrofuran. To the stirred solvent were added ethyl (2E,2Z)-3-{2-methoxy-4-[(4-{[(2E,2Z)-2-(methoxyimino)-2-phenylethyl]oxy}benzyl)oxy]phenyl}prop-2-enoate (0.3 g, 0.63 mmol), methanol (3.0 mL) and sodium hydroxide (5.0 mL, 2N solution) in water (0.5 mL). After addition, the reaction mixture was stirred at room temperature 2 h. The reaction mixture was concentrated to distill off the solvent; the crude was washed with ethyl acetate (25 mL). To the residue, was added water (1 mL) was added and the aqueous layer was acidified with saturated citric acid solution to make pH 6. The aqueous layer was extracted with ethyl acetate (20 mL). The organic layer was dried over anhydrous Na$_2$SO$_4$ and the solvent was removed under reduced pressure. The crude material was purified by preparative TLC using methanol and chloroform as eluents. The product was obtained as a white semi solid (0.2 g, yield: 71.42%).

Example 96

3-{2-Hydroxy-4-[(4-{[(2Z)-2-(methoxyimino)-2-phenylethyl]oxy}benzyl)oxy]phenyl}propanoic acid (96)

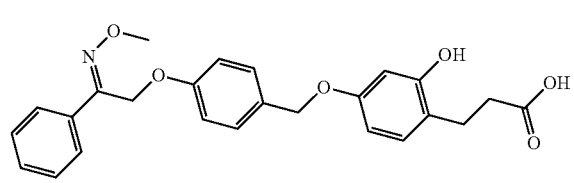

96

Compound 96 was synthesized from ethyl 3-{2-(cyanomethoxy)-4-[(4-{[(2Z)-2-(methoxyimino)-2-phenylethyl]oxy}benzyl)oxy]phenyl}propanoate (Intermediate 134, 0.1 g, 0.199 mmol) and Pd—C (0.02 g), followed by hydrolysis described in scheme 16 (0.005 g, yield: 36.0%); Purity: 93.97%.

Example 97

(2E,2Z)-3-{4-[(4-{[(2Z)-2-(Methoxyimino)-2-phenylethyl]oxy}benzyl)oxy]-2-(5-methyl-1,2-oxazol-3-yl)phenyl}prop-2-enoic acid

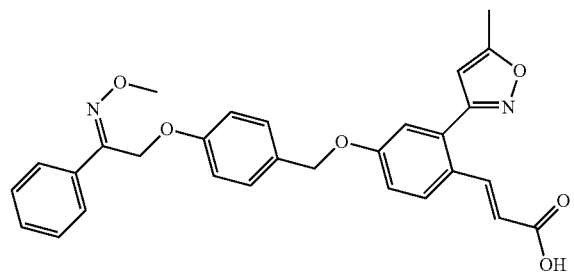

97

Compound 97 was synthesized from (4-{[(2Z)-2-(methoxyimino)-2-phenylethyl]oxy}phenyl)methanol (0.02 g, 0.0545 mmol) and methyl (2E)-3-[4-hydroxy-2-(5-methyl-1,2-oxazol-3-yl)phenyl]prop-2-enoate (0.012 g, 0.0436 mmol)

by following the procedure described in scheme 18 (0.008 g, yield: 13.70%); Purity: 95.32%.

Example 98

3-Cyano-3-{4-[(4-{[(2E)-2-(methoxyimino)-2-phenylethyl]oxy}benzyl)oxy]phenyl}propanoic acid (Racemate) (98)

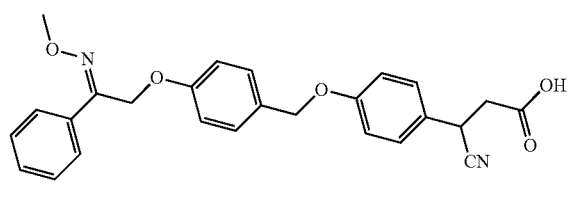

98

Compound 98 was synthesized from (4-{[(2E)-2-(methoxyimino)-2-phenylethyl]oxy}phenyl)methanol (0.55 g, 2.03 mmol) and methyl 3-cyano-3-(4-hydroxyphenyl)propanoate (0.46 g, 2.22 mmol) by following the procedure described in scheme 5 (0.008 g, yield: 30.1%); Purity: 93.18%.

Example 99

3-Cyano-3-{4-[(4-{[(2E)-2-(methoxyimino)-2-phenylethyl]oxy}benzyl)oxy]phenyl}propanoic acid (Enantiomer-1) (99)

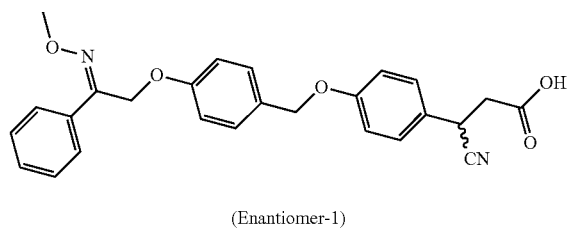

99
(Enantiomer-1)

Compound 99 was synthesized from (3-cyano-3-{4-[(4-{[(2E)-2-(methoxyimino)-2-phenylethyl]oxy}benzyl)oxy] phenyl}propanoic acid (compound 98) by chiral preparative HPLC. (0.008 g, yield: 15%); Purity: 84.93%; Chiral Purity: 98%.

Example 100

3-Cyano-3-{4-[(4-{[(2E)-2-(methoxyimino)-2-phenylethyl]oxy}benzyl)oxy]phenyl}propanoic acid (Enantiomer-2) (100)

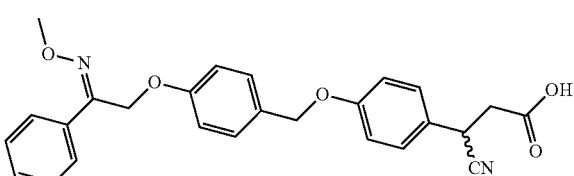

100 (Enantiomer-2)

Compound 100 was synthesized from (3-cyano-3-{4-[(4-{[(2E)-2-(methoxyimino)-2-phenylethyl]oxy}benzyl)oxy] phenyl}propanoic acid (compound 98) by chiral preparative HPLC. (0.008 g, yield: 15%); Purity: 92.37%; Chiral Purity: 95%.

Example 101

3-Cyano-3-{4-[(4-{[(2Z)-2-(1H-inden-2-yl)-2-(methoxyimino)ethyl]oxy}benzyl)oxy] phenyl}propanoic acid (101)

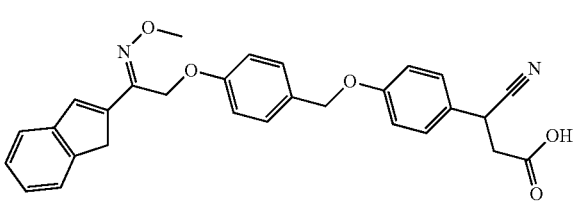

101

Compound 101 was synthesized from (4-{[(2Z)-2-(1H-inden-2-yl)-2-(methoxyimino)ethyl]oxy}phenyl)methanol (0.079 g, 0.4 mmol) and methyl 3-cyano-3-(4-hydroxyphenyl)propanoate (0.11 g, 0.4 mmol) by following the procedure described in scheme 5 (0.008 g, yield: 20.5%); Purity: 97.17%.

Example 102

3-Cyano-3-{4-[(4-{[(2Z)-2-(2,3-dihydro-1-benzofuran-5-yl)-2-(methoxyimino)ethyl]oxy}benzyl)oxy]phenyl}propanoic acid (102)

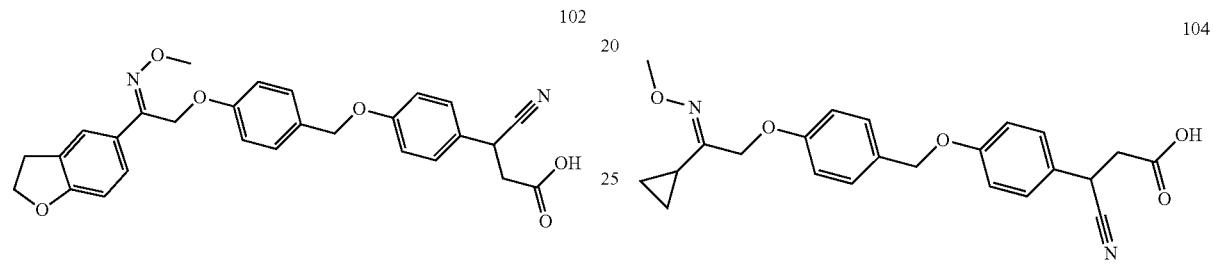

102

Compound 102 was synthesized from ((4-{[(2Z)-2-(2,3-dihydro-1-benzofuran-5-yl)-2-(methoxyimino)ethyl]oxy}phenyl)methanol (0.330 g, 1.0 mmol) and methyl 3-cyano-3-(4-hydroxyphenyl)propanoate (0.216 g, 1.0 mmol) by following the procedure described in scheme 5 (0.008 g, yield: 56.2%); Purity: 94.55%.

Example 103

3-Cyano-3-{4-[(4-{[(2Z)-2-(2,3-dihydro-1H-inden-5-yl)-2-(methoxyimino)ethyl]oxy}benzyl)oxy]phenyl}propanoic acid (103)

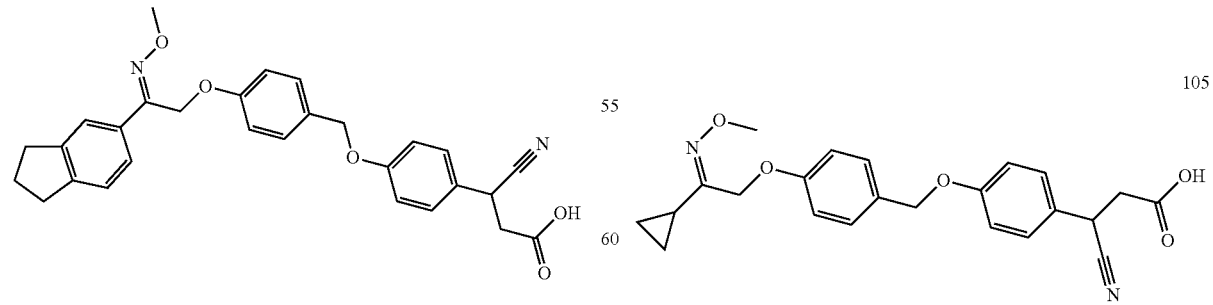

103

Compound 103 was synthesized from (4-{[(2Z)-2-(2,3-dihydro-1H-inden-5-yl)-2-(methoxyimino)ethyl]oxy}phenyl)methanol (0.25 g, 0.8 mmol) and methyl 3-cyano-3-(4-hydroxyphenyl)propanoate (0.214 g, 1.04 mmol) by following the procedure described in scheme 5 (0.008 g, yield: 38.4%); Purity: 95.42%.

Example 104

3-Cyano-3-{4-[(4-{[(2E)-2-cyclopropyl-2-(methoxyimino)ethyl]oxy}benzyl)oxy]phenyl}propanoic acid (104)

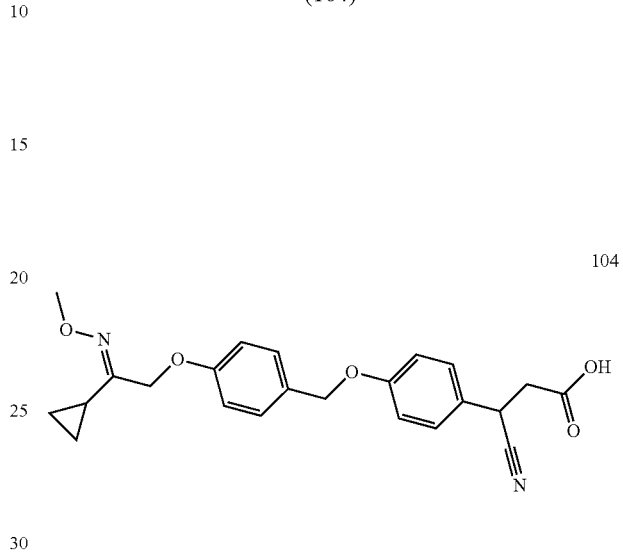

104

Compound 104 was synthesized from (4-{[(2E)-2-cyclopropyl-2-(methoxyimino)ethyl]oxy}phenyl)methanol (0.5 g, 2.12 mmol) and methyl 3-cyano-3-(4-hydroxyphenyl)propanoate (0.44 g, 2.12 mmol) by following the procedure described in scheme 5 (0.008 g, yield: 44.24%); Purity: 85.80%.

Example 105

3-Cyano-3-{4-[(4-{[(2Z)-2-cyclopropyl-2-(methoxyimino)ethyl]oxy}benzyl)oxy]phenyl}propanoic acid (105)

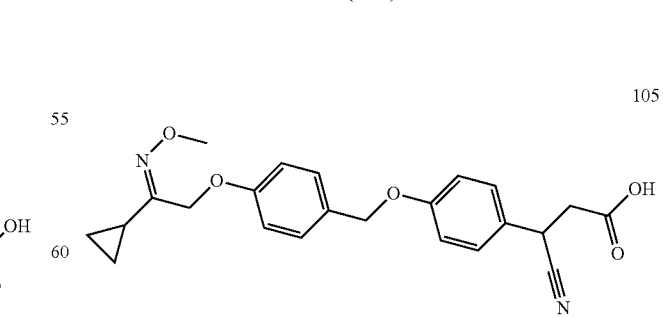

105

Compound 105 was synthesized from (4-{[(2Z)-2-cyclopropyl-2-(methoxyimino)ethyl]oxy}phenyl)methanol (0.5 g, 2.12 mmol) and methyl 3-cyano-3-(4-hydroxyphenyl)propanoate (0.44 g, 2.12 mmol) by following the procedure described in scheme 5 (0.008 g, yield: 56.32%); Purity: 84.26%.

Example 106

3-{4-[(4-{[(2E)-2-(Methoxyimino)-2-(3,4,4,7,7-pentamethyl-4,5,6,7-tetrahydro-1-benzothiophen-2-yl)ethyl]oxy}benzyl)oxy]phenyl}propanoic acid (106)

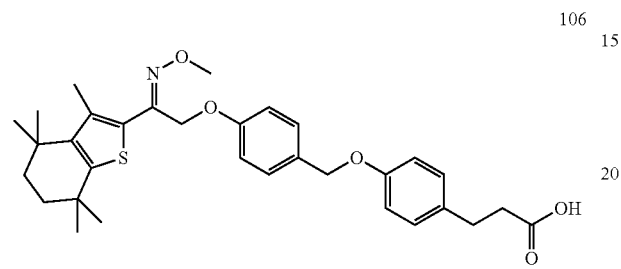

Compound 106 was synthesized from (4-{[(2E)-2-(methoxyimino)-2-(3,4,4,7,7-pentamethyl-4,5,6,7-tetrahydro-1-benzothiophen-2-yl)ethyl]oxy}phenyl)methanol (0.3 g, 0.7 mmol) and methyl 3-(4-hydroxyphenyl)propanoate (0.135 g, 0.7 mmol) by following the procedure described in scheme 5 (0.008 g, yield: 2.16%); Purity: 97.59%.

Scheme 35:

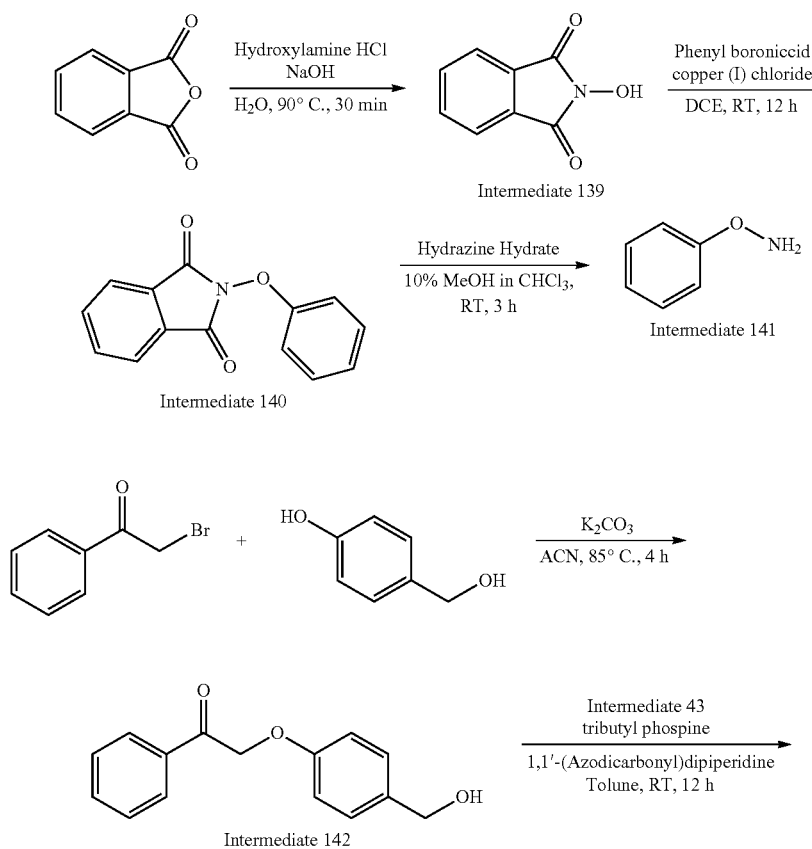

-continued
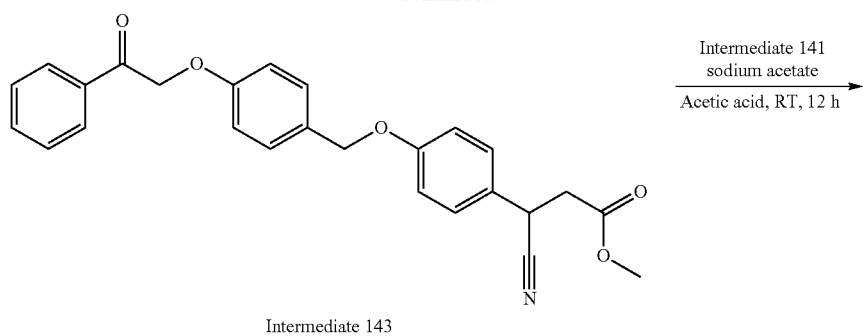
Intermediate 143
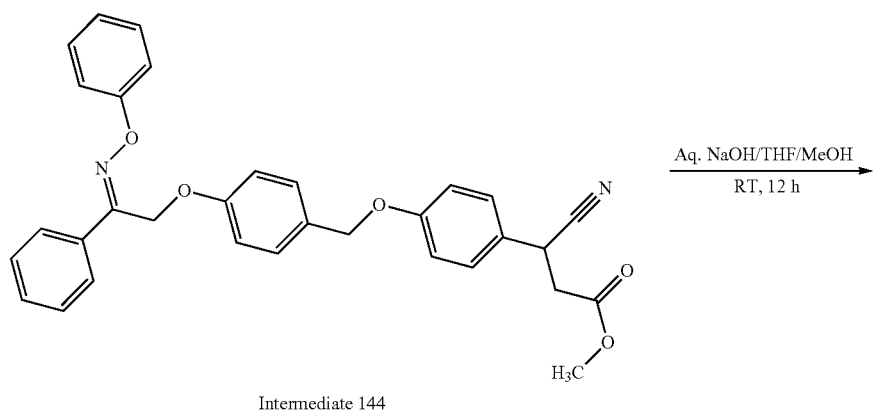
Intermediate 144
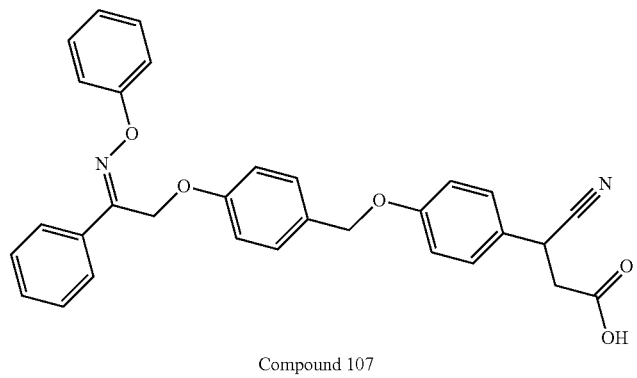 [SMILES: N#CC(CC(=O)O)c1ccc(OCc2ccc(OC/C(=N\Oc3ccccc3)c3ccccc3)cc2)cc1]
Compound 107

Example 107

3-Cyano-3-{4-[(4-{[(2E,2Z)-2-(phenoxy imino)-2-phenylethyl]oxy}benzyl)oxy]phenyl}propanoic acid (107)

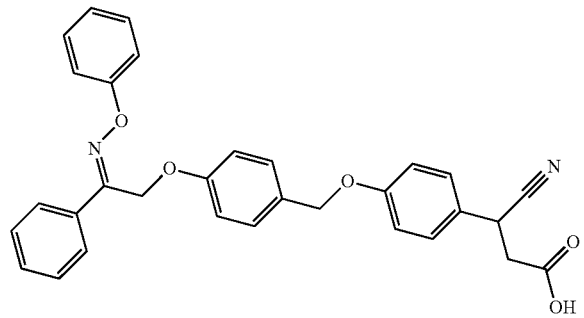

Compound 107 was synthesized from O-phenyl hydroxylamine (Amino oxy)benzene (0.15 g, 1.4 mmol) and methyl 3-cyano-3-(4-{[4-(2-oxo-2-phenylethoxy)benzyl]oxy}phenyl)propanoate (0.2 g, 0.46 mmol) by following the procedure described in scheme 35. (0.008 g, yield: 10%); purity: 69.92% and 26.24%.

Intermediate 139: 2-Hydroxy-1H-isoindole-1,3(2H)-Dione

To a 250 mL RB flask fitted with magnetic stirrer was charged with hydroxylamine hydrochloride (5 g, 73 mmol) in water, then slowly added 50% of NaOH solution. To this stirred solution, added phthalic anhydride (11.26 g, 76 mmol), stirred at 90° C. for 40 min. Then cooled to RT, yellowish solid was removed by filtration. The filtrate was neutralized with 30% of $H_2SO_4$ and solid was precipitated. The solid was filtered off on Buchner flask and dried under line vacuum to obtain the title compound (6.5 g, Yield: 55.34%); $^1$H NMR (300 MHz, DMSO-$d_6$): δ 10.80 (s, 1H), 7.84 (s, 4H).

Intermediate 140: 2-Phenoxy-1H-isoindole-1,3(2H)-Dione

To a 50 mL single neck RB flask wash charged with 2-hydroxy-1H-isoindole-1,3(2H)-dione (1 g, 6.13 mmol), 4 A° molecular sieves (1 g) and copper (I) chloride (0.61 g, 0.06 mmol) in DCE under open atmosphere. To the stirred reaction mixture, was added phenyl boronic acid (1.5 g, 12.2 mmol) followed by pyridine (0.53 g, 6.7 mmol) drop wise. Resulting mixture was stirred at RT for 12 h. The Reaction mixture was diluted with DCM and then filtered through celite pad. The organic layer was washed with saturated brine solution (50 mL) and dried over anhydrous $Na_2SO_4$. The solvent was removed under reduced pressure to afford off white solid. $^1$H NMR (300 MHz, CDCl$_3$): δ 7.83-7.86 (q, 2H), 7.73-7.77 (m, 2H), 7.28-7.30 (m, 2H), 7.07-7.11 (m, 3H).

Intermediate 141: O-Phenyl hydroxylamine(aminooxy)benzene

A 50 mL RB flask was charged with 2-phenoxy-1H-isoindole-1,3(2H)-dione (0.6 g, 2.5 mmol) and 10% of MeOH in CHCl$_3$ (15 mL). To the stirred solution was added hydrazine hydrate (0.37 mL, 7.53 mmol) in drop wise at RT and continued stirring for 3 h. phthalzine [by product] thrown out as solid, was filtered off and washed the solid with 10% of MeOH in CHCl$_3$. Filtrate was dried over anhydrous $Na_2SO_4$ and concentrated to afford crude product which was taken to next step immediately.

Intermediate 142: 2-[4-(Hydroxymethyl)phenoxy]-1-phenylethanone

To a 100 mL RB flask fitted with magnetic stirrer was charged 20 mL of acetonitrile. To the stirred solvent was added 4-Hydroxy-benzylalcohol (6.74 g, 25.1 mmol) and $K_2CO_3$ (10.4 g, 75.3 mmol). Then it was stirred for 5 min. 2-bromo-1-phenylethanone (5 g, 25.1 mmol) was added. Then RM heated 80° C. for 2 h. After completion of the reaction (reaction monitored by TLC), the RM was concentrated in vacuum to remove the acetonitrile. To the residue was then added 10 mL of water and extracted with ethyl acetate (15 mL×2). The organic layer was washed with saturated brine solution (15 mL), dried over anhydrous $Na_2SO_4$ and evaporated to dryness gave the titled compound (5 g, yield: 82.2%); $^1$H NMR (300 MHz, CDCl$_3$): δ 7.92-7.94 (d, 2H), 7.53-7.58 (t, 1H), 7.41-7.46 (t, 2H), 7.21-7.24 (d, 2H), 6.85-6.86 (d, 2H), 5.22 (s, 2H), 4.55 (s, 2H).

Intermediate 143: Methyl 3-cyano-3-(4-{[4-(2-oxo-2-phenylethoxy)benzyl]oxy}phenyl)propanoate To a 100 mL of two neck RB flask was charged with 2-[4-(hydroxy methyl)phenoxy]-1-phenylethanone (2.5 g, 10.3 mmol) and methyl 3-cyano-3-(4-hydroxyphenyl)propanoate (2.5 g, 12.4 mmol) in 50 mL of toluene. To this added tributylphosphine (3.33 g, 16.5 mmol) at 0° C. and added 1,1'-(Azodicarbonyl)dipiperidine (4.165 g, 16.5 mmol) portion wise over a period of 15 min at 0° C. After 12 h of stirring at RT, the mixture was diluted with n-hexane and stirred for 10 min. Solid formed was filtered off and the filtrate was concentrated to afford crude product which on trituration with ethyl acetate and pet ether gave pure product. (2.5 g yield: 56.1%); $^1$H NMR (300 MHz, DMSO-$d_6$): δ 8.01-8.03 (d, 2H), 7.67-7.72 (t, 1H), 7.55-7.60 (t, 2H), 7.34-7.37 (d, 4H), 6.96-7.02 (t, 4H), 5.59 (s, 2H), 5.01 (s, 2H), 4.37-4.46 (m, 1H), 3.61 (s, 3H), 3.07-3.16 (m, 1H), 2.90-2.97 (m, 1H).

Intermediate 144: Methyl 3-cyano-3-{4-[(4-{[(2E,2Z)-2-(phenoxyimino)-2-phenylethyl]oxy}benzyl)oxy]phenyl}propanoate To a 50 mL single neck RB flask charged with methyl 3-cyano-3-(4-{[4-(2-oxo-2-phenylethoxy)benzyl]oxy}phenyl)propanoate (0.2 g, 0.466 mmol) in acetic acid (2 mL) was added O-phenyl hydroxylamine (0.15 g, 1.4 mmol) followed by sodium acetate (0.076 g, 9.32 mmol). Reaction mixture was stirred at RT under nitrogen atmosphere for 3 h. Then, the RM was diluted with ethyl acetate (25 mL) and the organic layer was washed with water (20 mL). The organic layer was dried over anhydrous $Na_2SO_4$ and the solvent was removed under reduced pressure. The product was obtained as oil. (0.12 g, yield: 42.95%); MS (ESI, 120 eV): m/z=521.2 (M+H)$^+$; $^1$H NMR (300 MHz, CDCl$_3$): δ 7.70-7.74 (m, 2H), 7.34-7.35 (d, 4H), 7.23-7.29 (m, 8H), 6.86-6.94 (m, 4H), 5.36 (s, 2H), 4.89 (s, 2H), 4.14-4.19 (t, 1H), 3.65 (s, 3H), 2.88-2.96 (dd, 1H), 2.70-2.78 (dd, 1H)

Compound 107: 3-Cyano-3-{4-[(4-{[(2E,2Z)-2-(phenoxyimino)-2-phenylethyl]oxy}benzyl)oxy]phenyl}propanoic acid To a 10 mL RB flask fitted with magnetic stirrer was charged 3 mL of THF. To the stirred solvent was added methyl 3-cyano-3-{4-[(4-{[(2Z)-2-(phenoxy imino)-2-phenylethyl]oxy}benzyl)oxy]phenyl}propanoate (0.11 g, 0.211 mmol) and methanol (3 mL). The RM was brought to 0° C. and sodium hydroxide (0.03 g) in water (1 mL) was added drop wise. Then the reaction was stirred at RT for 12 h. Then, the solvents were evaporated and the crude was dissolved in minimum amount of water (2 mL) and the aqueous layer was washed with ether (5 mL×2). The aqueous layer was acidified to pH 3 with 1N hydrochloric acid. The aqueous layer was extracted with ethyl acetate (5 mL×2). The organic layer was washed with saturated brine solution (5 mL) and dried over anhydrous $Na_2SO_4$. The solvent was removed under reduced pressure, solid obtained as semi-solid. (0.008 g, yield: 8.0%); purity: 69.92% and 26.24%

Example 108

3-(4-{[4-({(2E,2Z)-2-[(Benzyloxy)imino]-2-phenylethyl}oxy)benzyl]oxy}phenyl) propanoic acid (108)

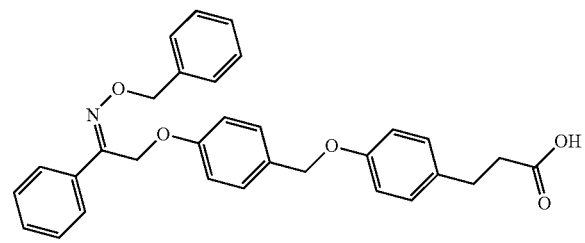

Compound 108 was synthesized from O-benzyl hydroxylamine[(aminooxy)methyl]benzene (0.07 g, 0.4 mmol) and methyl 3-(4-{[4-(2-oxo-2-phenylethoxy)benzyl]oxy}phenyl)propanoate (0.15 g, 0.4 mmol) by following the procedure described in scheme 35 (0.06 g, yield: 32.5%); purity: 84.22% and 10.16%.

Example 109

3-Cyano-3-{4-[(4-{[(2Z)-2-(hydroxy imino)-2-phenylethyl]oxy}benzyl)oxy]phenyl}propanoic acid (109)

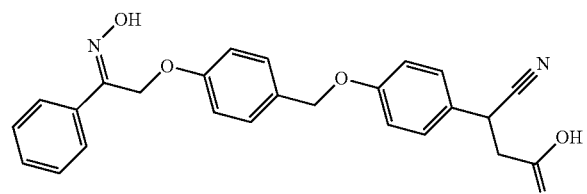

Compound 109 was synthesized from O-hydroxylamine HCl (0.34 g, 1.15 mmol) and methyl 3-cyano-3-(4-{[4-(2-oxo-2-phenylethoxy)benzyl]oxy}phenyl)propanoate (1.4 g, 3.26 mmol) by following the procedure described in scheme 35. (0.26 g, yield: 14.8%); purity: 92.16%.

Example 110

3-(4-{[4-({(2E,2Z)-2-Phenyl-2-[(prop-2-en-1-yloxy)imino]ethyl}oxy)benzyl]oxy}phenyl)propanoic acid (110)

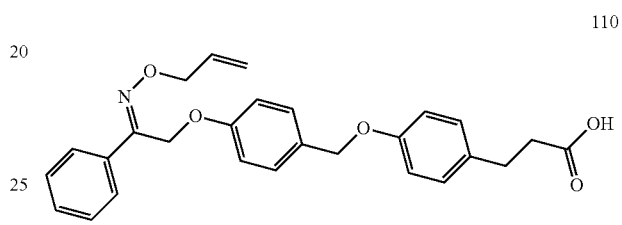

Compound 110 was synthesized from O-prop-2-en-1-yl-hydroxylamine 3-(aminooxy)prop-1-ene (0.2 g, 1.8 mmol) methyl 3-(4-{[4-(2-oxo-2-phenylethoxy)benzyl]oxy}phenyl)propanoate (0.37 g, 0.09 mmol) by following the procedure described in scheme 35 (0.08 g, yield: 12%); purity: 86.5% and 9.06%.

Example 111

3-Cyano-3-(4-{[4-({(2Z)-2-[(cyclohexyloxy)imino]-2-phenylethyl}oxy)benzyl]oxy}phenyl)propanoic acid (111)

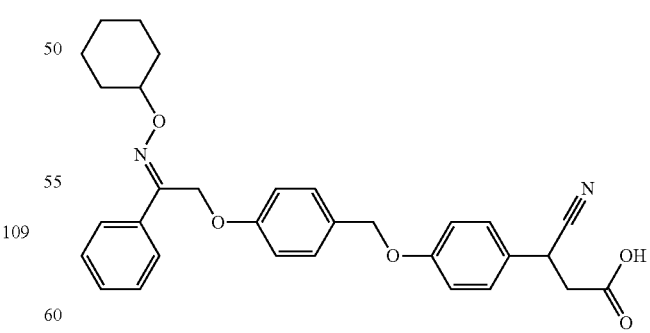

Compound 111 was synthesized from O-hydroxylamine HCl (0.16 g, 1.4 mmol) and methyl 3-cyano-3-(4-{[4-(2-oxo-2-phenylethoxy)benzyl]oxy}phenyl)propanoate (0.2 g, 0.46 mmol) by following the procedure described in scheme 35. (0.06 g, yield: 24%); purity: 95%.

Scheme 36:

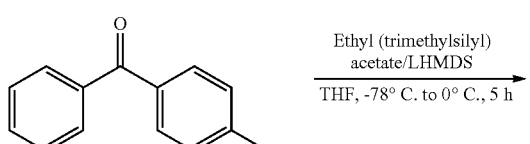

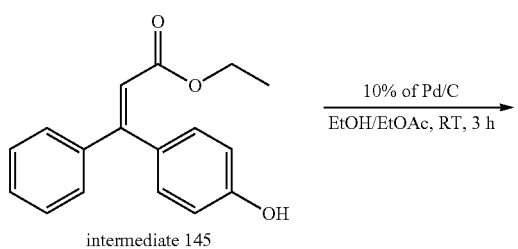
intermediate 145

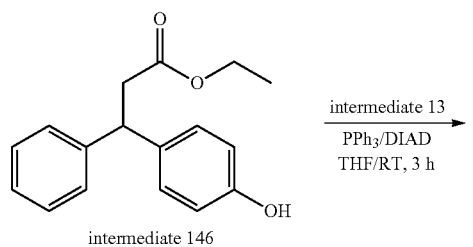
intermediate 146

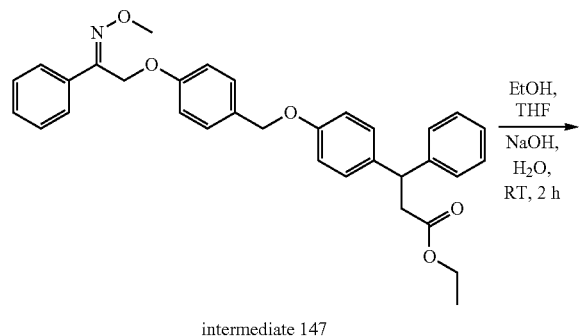
intermediate 147

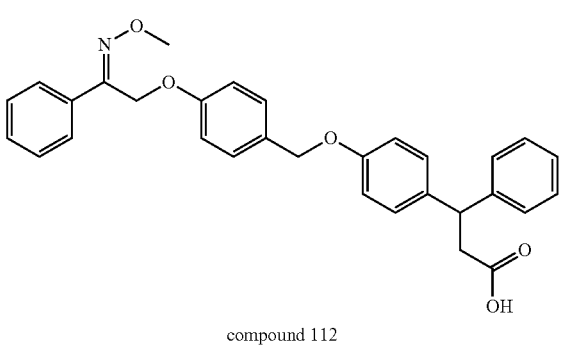
compound 112

Example 112

3-{4-[(4-{[(2Z)-2-(Methoxyimino)-2-phenylethyl]oxy}benzyl)oxy]phenyl}-3-phenylpropanoic acid (112)

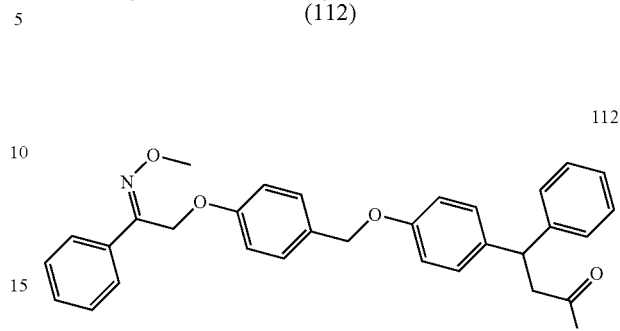

Compound 112 was synthesized from ethyl 3-(4-hydroxyphenyl)-3-phenylpropanoate (0.6 g, 2.2 mmol) and (4-{[(2Z)-2-(methoxyimino)-2-phenylethyl]oxy}phenyl)methanol (0.6 g, 2.2 mmol) by following the procedure described in scheme 36. (0.2 g, yield: 18.2%); purity: 98.55%.

Intermediate 145: Ethyl (2Z)-3-(4-hydroxyphenyl)-3-phenylprop-2-enoate

To a solution of HMDS (21.17 g, 131.1 mmol) in THF (200 mL) was cooled to −40° C. Then it was added with n-BuLi (56.7 mL, 136.22 mmol) and stirred at same temperature for 45 min. After that (4-hydroxyphenyl)(phenyl)methanone (2 g, 10 mmol) in THF was added slowly over a period of 10 min and stirred at −40° C. to −30° C. for one hour. Then Ethyl (trimethylsilyl)acetate (2.42 g, 15.1 mmol) was added drop wise and stirred at 0° C. to 15° C. for completion of starting material (4 h). After reaction completed reaction was quenched with ammonium chloride and then THF was evaporated under vacuum and the resulted solution was partitioned between water and Ethyl acetate. The combined organic layer was dried and evaporated to get crude. The crude was purified through chromatography and triturated with n-Hexane to afford red color oil as product (1.5 g, Yield: 55.9%); $^1$H NMR (300 MHz, CDCl$_3$): δ 7.31-7.33 (m, 4H), 7.01-7.74 (d, 1H), 6.7-7.16 (m, 4H), 6.25 (s, 1H), 3.94-3.99 (q, 2H), 1.07-1.10 (t, 3H)

Intermediate 146: Ethyl 3-(4-hydroxyphenyl)-3-phenylpropanoate

A 500 mL par shaker charged with ethyl (2Z)-3-(4-hydroxyphenyl)-3-phenylprop-2-enoate (1 g, 3.7 mmol) in Ethanol/Ethyl acetate was degasified with nitrogen for 2 min. Added 10% of Pd/C (0.4 g, 10%) and applied 50 psi of H$_2$ pressure for 3 h. Reaction mixture was filtered through celite pad and washed the pad with excess Ethanol. Organic phase was dried over anhydrous Na$_2$SO$_4$ and concentrated to afford oil as product. (0.6 g, Yield: 60.1%); $^1$H NMR (300 MHz, DMSO-d$_6$): δ 9.21 (s, 1H), 7.07-7.29 (m, 7H), 6.63-6.66 (d, 2H), 4.29-4.34 (t, 1H), 3.89-3.96 (q, 2H), 3.02-3.03 (d, 2H), 0.99-1.04 (t, 3H)

Intermediate 147: Ethyl 3-{4-[(4-{[(2Z)-2-(methoxyimino)-2-phenylethyl]oxy}benzyl)oxy]phenyl}-3-phenylpropanoate To a 100 mL of two neck RB flask was charged ethyl 3-(4-hydroxyphenyl)-3-phenylpropanoate (0.6 g, 2.2 mmol)

and (4-{[(2Z)-2-(methoxyimino)-2-phenylethyl]oxy}phenyl)methanol (0.6 g, 2.2 mmol) in 20 mL of THF. To this added triphenyl phosphine (0.755 g, 2.88 mmol) at 0° C. and added DIAD (0.59 g, 2.88 mmol) portion wise over a period of 15 min at 0° C. After 12 h of stirring at RT, the mixture was diluted with Ethyl acetate, washed with water and brine solution successively. Organic phase was dried over anhydrous $Na_2SO_4$ and concentrated to afford yellow oil as product (0.6 g, yield: 52.17%); $^1$H NMR (300 MHz, DMSO-$d_6$): δ 7.57-7.60 (m, 2H), 7.06-7.31 (m, 12H), 6.84-6.86 (m, 4H), 5.12 (s, 2H), 4.84 (s, 2H), 4.39-4.45 (t, 1H), 3.86-4.01 (m, 5H), 2.92-2.95 (d, 2H), 1.00-1.05 (t, 3H).

Compound 112: 3-{4-[(4-{[(2Z)-2-(Methoxyimino)-2-phenylethyl]oxy}benzyl)oxy]phenyl}-3-phenyl-propanoic acid To a 50 mL RB flask fitted with magnetic stirrer was charged 3 mL of THF. To the stirred solvent was added methyl ethyl 3-{4-[(4-{[(2Z)-2-(methoxyimino)-2-phenylethyl]oxy}benzyl)oxy]phenyl}-3-phenylpropanoate (0.6 g, 1.1 mmol) and methanol (3 mL). The RM was brought to 0° C. and sodium hydroxide (0.09 g) in water (1 mL) was added drop wise. Then the reaction was stirred at RT for 12 h. Then, the solvents were evaporated and the crude was dissolved in minimum amount of water (2 mL) and the aqueous layer was washed with ether (5 mL×2). The aqueous layer was acidified to pH 3 with 1N hydrochloric acid. The aqueous layer was extracted with ethyl acetate (5 mL×2). The organic layer was washed with saturated brine solution (5 mL) and dried over anhydrous $Na_2SO_4$. The solvent was removed under reduced pressure, solid obtained as a semi-solid. (0.2 g, yield: 35.71%); purity: 35.7%.

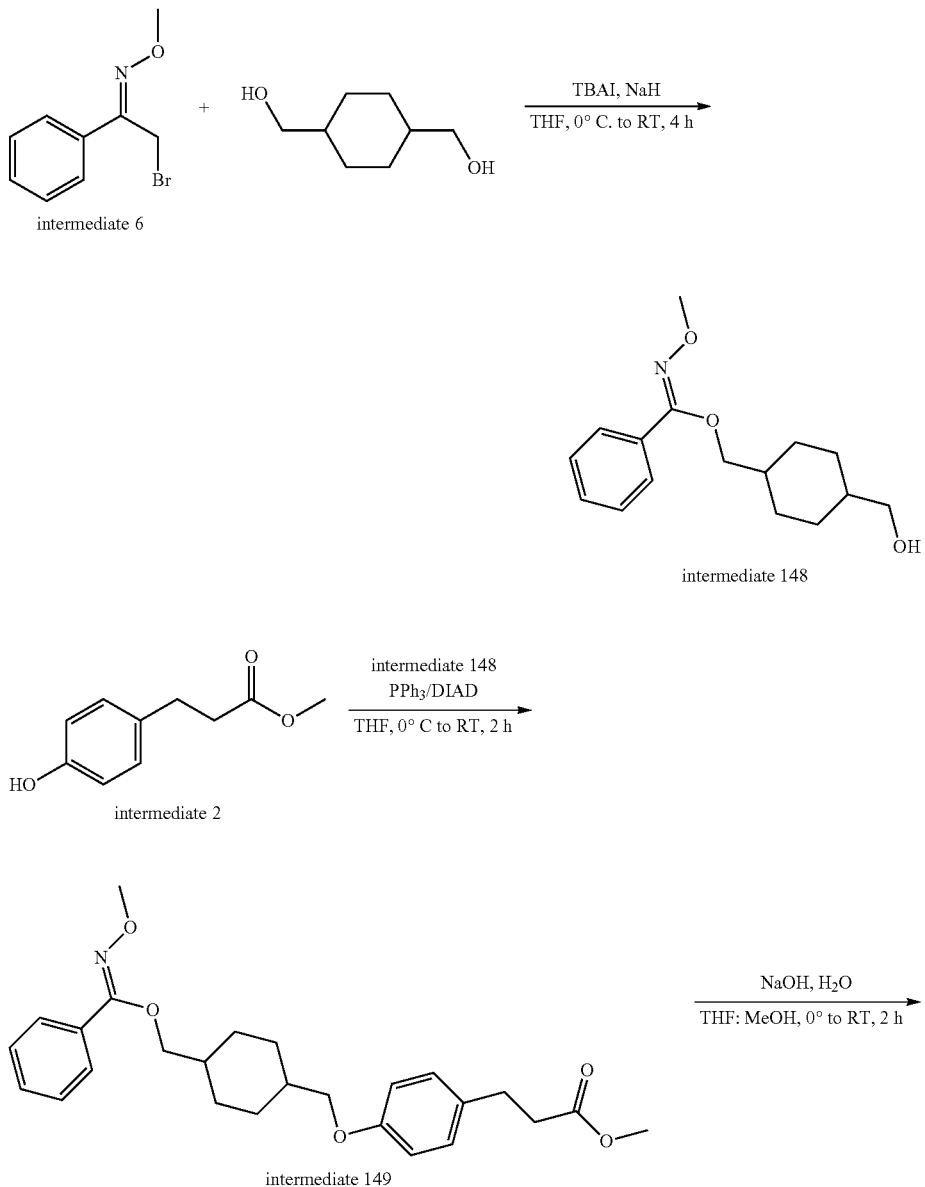

Scheme 37

-continued

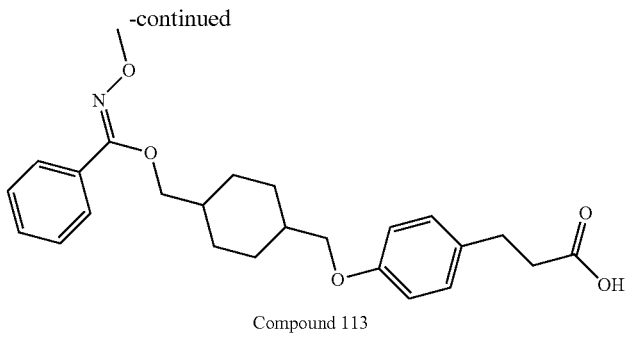

Compound 113

Example 113

3-(4-{[4-({[(2E,2Z)-2-(Methoxyimino)-2-phenylethyl]oxy}methyl)cyclohexyl]methyl}phenyl)propionic acid (113)

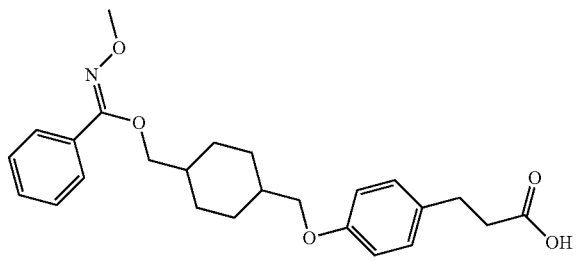

Compound 113 was synthesized from [4-({[(2E,2Z)-2-(methoxyimino)-2-phenylethyl]oxy}methyl)cyclohexyl]methanol (0.7 g, 2.4 mmol) and methyl 3-(4-hydroxyphenyl)propanoate (0.43 g, 2.4 mmol) by following the procedure described in scheme 37. (0.4 g, yield: 38.5%); purity: 49.3% and 50.04%.

Intermediate 148: [4-({[(2E,2Z)-2-(Methoxyimino)-2-phenylethyl]oxy}methyl)cyclohexyl]methanol To A 100 mL 2 necked RB flask charged with a suspension of NaH (0.33 g, 13.8 mmol) in THF (50 mL) under Nitrogen atmosphere was added cyclohexane-1,4-diyldimethanol (1 g, 6.93 mmol) in THF drop wise at 0° C. This solution was stirred at the same temperature for 5 min followed by the addition of (1Z)-2-bromo-N-methoxy-1-phenylethanimine (1.72 g, 9.5 mmol) and TBAI (0.128 g, 0.34 mmol) slowly. Reaction mixture was stirred at RT for 4 h. Excess NaH was quenched with ice and stirred for 5 min. Then, the RM was diluted with Ethyl acetate (50 mL) and the organic layer was washed with water (20 mL). The organic layer was dried over anhydrous $Na_2SO_4$ and the solvent was removed under reduced pressure. The product was obtained as oil (0.7 g, Yield: 35%); $^1$H NMR (300 MHz, $CDCl_3$): δ 7.59-7.93 (m, 2H), 7.27-7.29 (m, 3H), 4.57 (s, 2H), 3.92 (s, 3H), 3.34-3.41 (dd, 2H), 3.13-3.23 (dd, 2H), 1.19-1.40 (m, 8H)

Intermediate 149: Methyl3-(4-{[4-({[2E,2Z)-2-(methoxyimino)-2-phenylethyl]oxy}methyl)cyclohexyl]methoxy}phenyl)propanoate To a 100 mL of two neck RB flask was charged [4-({[(2E,2Z)-2-(methoxyimino)-2-phenylethyl]oxy}methyl)cyclohexyl]methanol (0.7 g, 2.4 mmol) and (methyl 3-(4-hydroxyphenyl)propanoate (0.43 g, 2.4 mmol) in 20 mL of THF. To this added triphenyl phosphine (0.82 g, 3.12 mmol) at 0° C. and added DIAD (0.63 g, 3.12 mmol) portion wise over a period of 15 min at 0° C. After 12 h of stirring at RT, the mixture was diluted with Ethyl acetate, washed with water and brine solution successively. Organic phase was dried over anhydrous $Na_2SO_4$ and concentrated to afford yellow oil as product (0.6 g yield: 55.17%); $^1$H NMR (300 MHz, $CDCl_3$): δ 7.60-7.62 (t, 2H), 7.19-7.29 (t, 3H), 7.02-7.04 (m, 2H), 6.70-6.74 (m, 2H), 4.57 (s, 2H), 3.92 (s, 3H), 3.59-3.69 (m, 5H), 3.14-3.25 (m, 2H), 2.81-2.82 (dd, 2H), 2.52-2.55 (dd, 2H), 1.19-1.54 (m, 8H).

Compound 113: 3-(4-{[4-({[(2E,2Z)-2-(Methoxyimino)-2-phenylethyl]oxy}methyl)cyclohexyl]methoxy}phenyl)propanoicacid To a 50 mL RB flask fitted with magnetic stirrer was charged 3 mL of THF. To the stirred solvent was added methyl 3-(4-{[4-({[2E, 2Z)-2-(methoxyimino)-2-phenylethyl]oxy}methyl)cyclohexyl]methoxy}phenyl)propanoate (0.6 g, 1.32 mmol) and methanol (3 mL). The RM was brought to 0° C. and sodium hydroxide (0.09 g) in water (1 mL) was added drop wise. Then the reaction was stirred at RT for 12 h. Then, the solvents were evaporated and the crude was dissolved in minimum amount of water (2 mL) and the aqueous layer was washed with ether (5 mL×2). The aqueous layer was acidified to pH 3 with 1N hydrochloric acid. The aqueous layer was extracted with ethyl acetate (5 mL×2). The organic layer was washed with saturated brine solution (5 mL) and dried over anhydrous $Na_2SO_4$. The solvent was removed under reduced pressure, solid obtained as oil. (0.2 g, yield: 70%); purity: 49.3% and 50.04%.

Scheme 38:
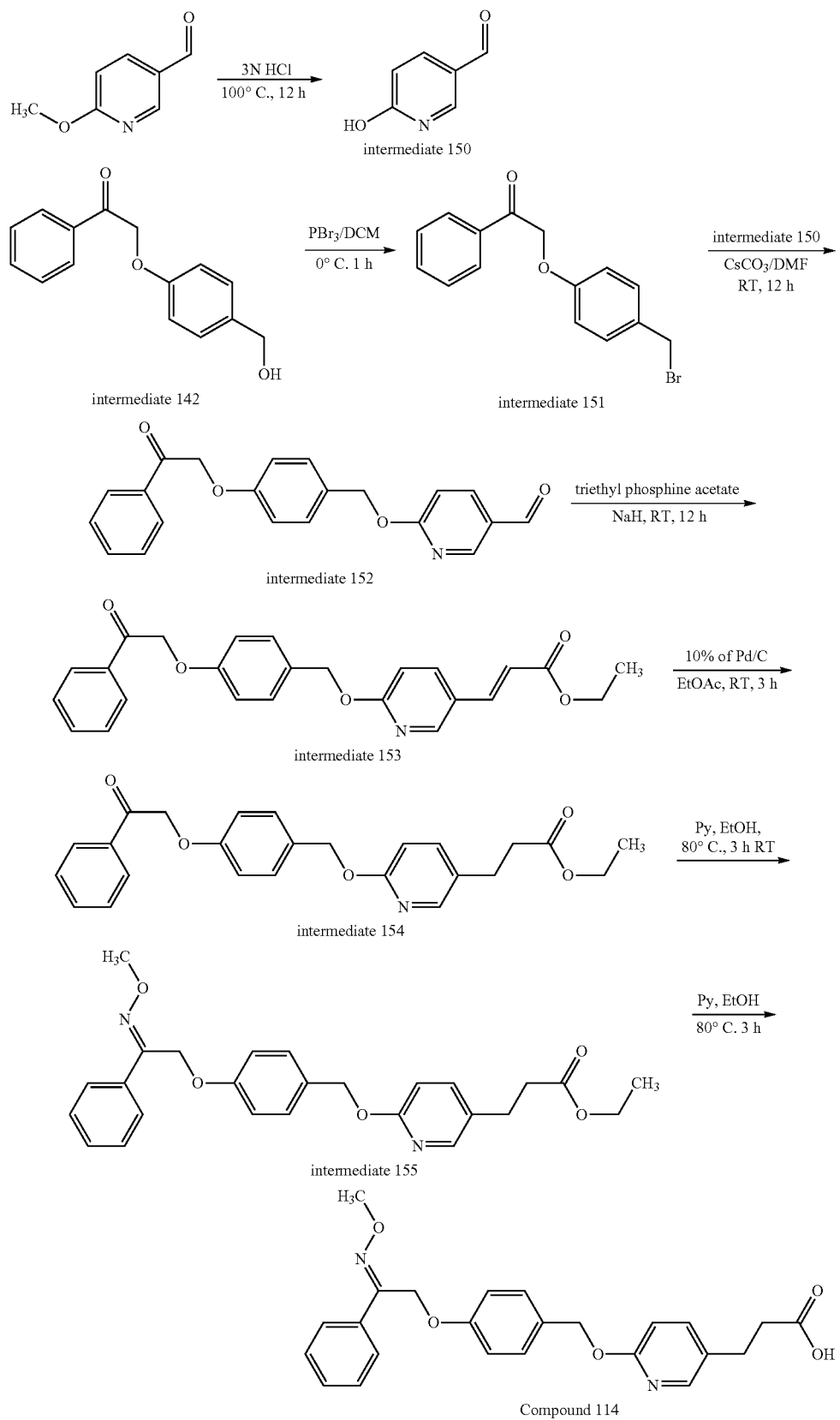

Example 114

3-{6-[(4-{[(2Z)-2-(Methoxyimino)-2-phenylethyl]oxy}benzyl)oxy]pyridin-3-yl}propanoic acid (114)

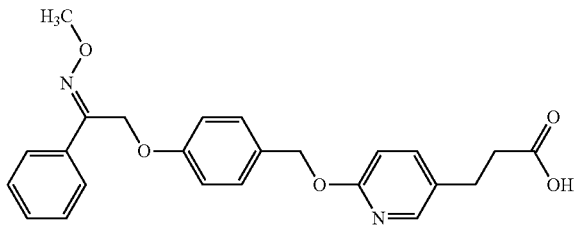

Compound 114 was synthesized from 2-[4-(bromomethyl)phenoxy]-1-phenylethanone (0.61 g, 2 mmol) and 6-hydroxypyridine-3-carbaldehyde (0.25 g, 2 mmol) by following the procedure described in scheme 38. (0.01 g, Yield: 21.8%) purity: 85%.

Intermediate 150:
6-Hydroxypyridine-3-carbaldehyde

To A 100 mL RB was charged with 6-methoxypyridine-3-carbaldehyde (1 g, 7 mmol) was added 3N HCl (20 mL) and then refluxed it at 100° C. for 12 h. RM was cooled slowly to RT. Solid was obtained up on cooling. It was filtered off on Buchner flask and dried under line vacuum to obtain the title compound as white crystals (0.3 g, Yield: 37%)

Intermediate 151:
2-[4-(Bromomethyl)phenoxy]-1-phenylethanone

To a 50 mL RB flask charged with 2-[4-(hydroxymethyl)phenoxy]-1-phenylethanone (10 g, 41.2 mmol) in DCM was added phosphorus tribromide (16.76 g, 61.9 mmol) in drops over period of 5 min at 0° C. Reaction mixture was stirred at RT for 1 h and then quenched with ice-water. Diluted it with excess DCM, washed with water, sat.NaHCO$_3$ solution and brine solution successively. Organic phase was dried over anhydrous Na$_2$SO$_4$ and concentrated to afford product (9 g, Yield: 71.4%); $^1$H NMR (300 MHz, DMSO-d$_6$): δ 7.90-7.93 (t, 2H), 7.53-7.58 (t, 1H), 7.41-7.46 (t, 2H), 7.23-7.26 (d, 2H), 6.81-6.84 (t, 2H), 5.20 (s, 2H), 4.40 (s, 2H).

Intermediate 152: 6-{[4-(2-Oxo-2-phenylethoxy)benzyl]oxy}pyridine-3-carbaldehyde To a solution of methyl 6-hydroxypyridine-3-carbaldehyde. (0.25 g, 2 mmol) in DMF (10 mL) was added cesium carbonate (0.97 g, 3 mmol) and stirred at RT for 30 min then added 2-[4-(bromomethyl)phenoxy]-1-phenylethanone (0.61 g, 2 mmol) this resulting mass was stirred at 80° C. for 12 h, reaction quenched with water and extracted with ethyl acetate, Organic layer was washed with water and brine solution dried over anhydrous Na$_2$SO$_4$ and concentrated to afford crude product which was purified by column chromatography to get pale brown solid as product (0.4 g, Yield: 60%); $^1$H NMR (300 MHz, CDCl$_3$): δ 9.59 (s, 1H) 7.95-8.02 (m, 2H), 7.67-7.78 (m, 3H), 7.54-7.59 (m, 2H), 7.30-7.33 (d, 2H), 6.93-6.96 (d, 2H), 6.49-6.53 (d, 1H), 5.57 (s, 2H), 5.11 (s, 2H).

Intermediate 153: Ethyl (2E)-3-(6-{[4-(2-oxo-2-phenylethoxy)benzyl]oxy}pyridin-3-yl)prop-2-enoate To a stirring suspension of NaH (0.025 g, 1 mmol) in dry THF (10 mL) at 0° C. was added Triethyl phosphonoacetate (0.224 g, 1 mmol) slowly and stirred for 30 min then added 6-{[4-(2-oxo-2-phenylethoxy)benzyl]oxy}pyridine-3-carbaldehyde (0.4 g, 1 mmol) dissolved in THF and stirred at RT for 12 h. RM quenched with ice and diluted with ethyl acetate, organic layer was washed with water and brine, dried over anhydrous Na$_2$SO$_4$ and concentrated. Crude product was purified by column chromatography to afford pale yellow oil as product (0.13 g, Yield: 31%); MS (ESI, 120 eV): m/z=418 (M+H)$^+$.

Intermediate 154: Ethyl 3-(6-{[4-(2-oxo-2-phenylethoxy)benzyl]oxy}pyridin-3-yl)propanoate A solution of ethyl (2E)-3-(6-{[4-(2-oxo-2-phenylethoxy)benzyl]oxy}pyridin-3-yl)prop-2-enoate (0.13 g, 0.31 mmol) in ethyl acetate ethanol mixture was degassed well and added palladium carbon (10 mg), and stirred under hydrogen bladder for 3 hrs. Reaction mass was filtered through celite pad and concentrated to a colourless oil (0.12 g, Yield: 95%); MS (ESI, 120 eV): m/z=420 (M+H)$^+$.

Intermediate 155: Ethyl 3-{6-[(4-{[(2Z)-2-(methoxyimino)-2-phenylethyl]oxy}benzyl)oxy]pyridin-3-yl}propanoate To a solution of ethyl (2E)-3-(6-{[4-(2-oxo-2-phenylethoxy)benzyl]oxy}pyridin-3-yl)prop-2-enoate (0.13 g, 0.3 mmol) in ethanol was added pyridine (0.038 g, 0.45 mmol) and O-Methoxylamine hydrochloride, the resulting mass was refluxed at 80° C. for 3 h. Reaction quenched with water and extracted with ethyl acetate, organic layer was washed with water and brine solution dried over anhydrous Na$_2$SO$_4$ and concentrated to colourless oil (0.03 g, Yield: 23%); MS (ESI, 120 eV): m/z=449 (M+H)$^+$.

Compound 114: 3-{6-[(4-{[(2Z)-2-(methoxyimino)-2-phenylethyl]oxy}benzyl)oxy]pyridin-3-yl}propanoic acid To a stirring solution of ethyl 3-{6-[(4-{[(2Z)-2-(methoxyimino)-2-phenylethyl]oxy}benzyl)oxy]pyridin-3-yl}propanoate (0.03 g, 0.067 mmol) in the mixture of THF and Ethanol was added aqueous NaOH (0.03 g, 0.067 mmol) at 0° C., then stirred at RT for 2 h. After the completion of the SM reaction mass was concentrated under vacuum at 25° C. to remove solvents and diluted with water. Aqueous portion was neutralized with citric acid up to neutral pH, then extracted with ethyl acetate organic layer was washed with water and brine, dried over Na$_2$SO$_4$ and concentrated. Crude product was purified by preparative TLC to afford colourless oil as product (0.01 g, Yield: 35%); purity: 85%.

Scheme 39:
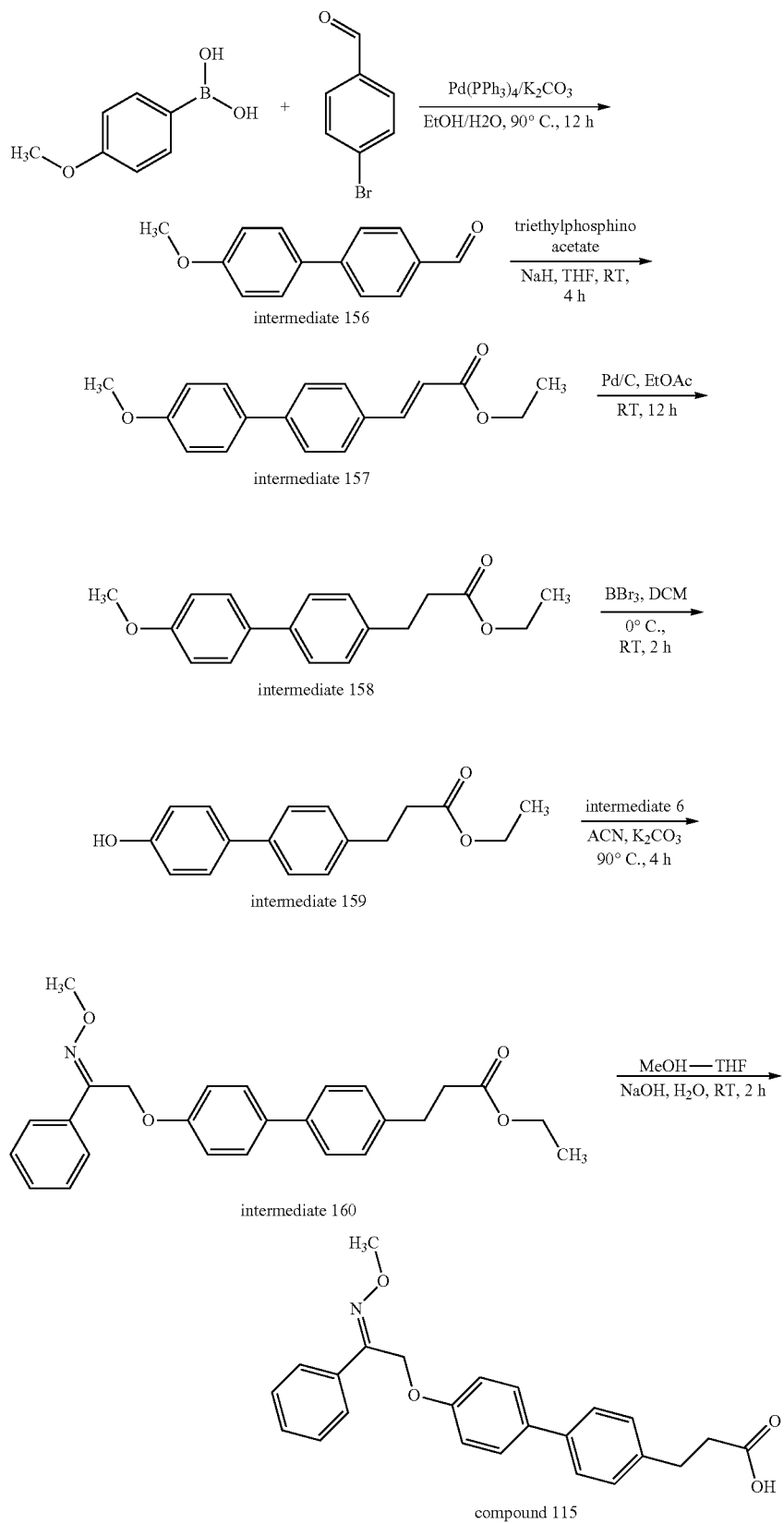

Example 115

3-(4'-{[(2Z)-2-(Methoxyimino)-2-phenylethyl]oxy}biphenyl-4-yl)propanoic acid (115)

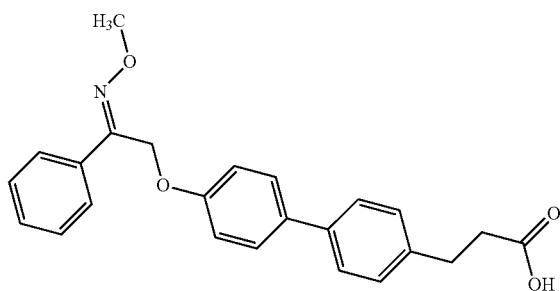

115

Compound 115 was synthesized from ethyl 3-(4'-hydroxybiphenyl-4-yl)propanoate (0.27 g, 1 mmol) and (1Z)-2-bromo-N-methoxy-1-phenylethanimine (0.23 g, 1 mmol) by following the procedure described in scheme 39. (0.2 g, 49.8%) purity: 99.5%.

Intermediate 156: 4'-Methoxybiphenyl-4-carbaldehyde

To a solution of (4-methoxyphenyl)boronic acid (1 g, 6.6 mmol) and 4-bromobenzaldehyde (1.2 g, 3.5 mmol) in ethanol water mixture was added potassium carbonate (1.7 g, 12.0 mmol) and degasified well and added tetrakis (0.7 g, 0.6 mmol) and stirred under argon for 12 h, reaction mass diluted with water and extracted with ethyl acetate, organic layer was washed with water and brine solutions, dried over anhydrous $Na_2SO_4$ and concentrated to brown solid as product (1 g, yield: 71.4%). $^1$H NMR (300 MHz, $CDCl_3$): δ 9.96 (s, 1H), 7.84 (d, 2H), 7.63-7.66 (d, 2H), 7.51-7.54 (s, 2H), 6.93-6.95 (d, 2H), 3.80 (s, 3H)

Intermediate 157: Ethyl (2Z)-3-(4'-methoxybiphenyl-4-yl)prop-2-enoate

To a stirring suspension of NaH (0.14 g, 5.8 mmol) in dry THF (10 mL) at 0° C. was added Triethyl phosphonoacetate (1.3 g, 5.8 mmol) slowly and stirred for 30 min then added 4'-methoxybiphenyl-4-carbaldehyde (1 g, 4.7 mmol) dissolved in THF and stirred at RT for overnight. RM quenched with ice and diluted with ethyl acetate, organic layer was washed with water and brine, dried over anhydrous sodium sulphate and concentrated to afford title compound as white solid (1 g, Yield: 74.4%): $^1$H NMR (300 MHz, $CDCl_3$): δ 7.47-7.61 (m, 8H), 6.90-6.93 (d, 2H), 4.17-4.24 (m, 2H), 3.78 (s, 3H), 1.25-1.30 (t, 3H).

Intermediate 158: Ethyl 3-(4'-methoxybiphenyl-4-yl)propanoate

To a solution of ethyl (2E)-3-(4'-methoxybiphenyl-4-yl)prop-2-enoate (1 g, 3.5 mmol) in ethyl acetate was added acetic acid and degassed well with argon and added palladium carbon (100 mg) and stirred under hydrogen for overnight, TLC shows a new spot, RM filtered through celite and washed with ethyl acetate and concentrated to afford white solid (0.7 g, Yield: 71.4%).

Intermediate 159: Ethyl 3-(4'-hydroxybiphenyl-4-yl)propanoate

To a solution of ethyl 3-(4'-methoxybiphenyl-4-yl)propanoate (0.35 g, 1.2 mmol) in dichloromethane was added borontribromide (0.4 g, 1.6 mmol) at 0° C. and stirred at RT for 30 min, Reaction quenched with ethanol and diluted with water and extracted with dichloromethane, organic layer was washed with $NaHCO_3$, water and brine solution and dried over sodium sulphate then concentrated to white solid (0.27 g, Yield: 83.3%): $^1$H NMR (300 MHz, $CDCl_3$): δ 9.49 (s, 1H), 7.43-7.48 (t, 4H), 7.23-7.26 (d, 2H), 6.81-6.84 (d, 2H), 4.01-4.08 (m, 2H), 2.83-2.88 (t, 2H), 2.59-2.64 (t, 2H), 1.13-1.18 (t, 3H).

Intermediate 160: Ethyl 3-(4'-{[(2Z)-2-(methoxyimino)-2-phenylethyl]oxy}biphenyl-4-yl)propanoate To a solution of ethyl 3-(4'-hydroxybiphenyl-4-yl)propanoate (0.27 g, 0.001 mmol) in acetonitrile was added potassium carbonate (0.27 g, 0.002 mmol) and (1Z)-2-bromo-N-methoxy-1-phenylethanimine (0.23 g, 0.001 mmol) and refluxed at 80° C. for 3 h. RM was diluted with water and extracted with ethyl acetate, Organic layer was washed with water and brine solution, dried over anhydrous $Na_2SO_4$ and concentrated to get crude product which was purified by comb flash to get white gummy solid as product (0.25 g, Yield: 60%): MS (ESI, 120 eV): m/z=418 (M+H)$^+$; $^1$H NMR (300 MHz, $CDCl_3$): δ 7.59-7.63 (m, 2H), 7.37-7.42 (m, 4H), 7.26-7.28 (m, 3H), 7.15 (d, 2H), 6.88-6.90 (d, 2H), 5.15 (s, 2H), 4.03-4.10 (m, 2H), 3.99 (s, 3H), 2.87-2.93 (t, 2H), 2.54-2.60 (t, 2H), 1.17-1.19 (t, 3H).

Compound 115: 3-(4'-{[(2Z)-2-(methoxyimino)-2-phenylethyl]oxy}biphenyl-4-yl)propanoic acid To a solution of ethyl 3-(4'-{[(2Z)-2-(methoxyimino)-2-phenylethyl]oxy}biphenyl-4-yl)propanoate (0.25 g, 0.6 mmol) in THF was added ethanol and aqueous solution of NaOH and stirred at RT for 2 h, reaction mass was concentrated to remove solvents and diluted with water and neutralized with 1 N HCl and extracted with ethyl acetate, organic layer was washed with water and brine solutions dried over anhydrous $Na_2SO_4$ and concentrated to white solid (0.2 g, 83.3%); purity: 99.5%

Scheme 40:

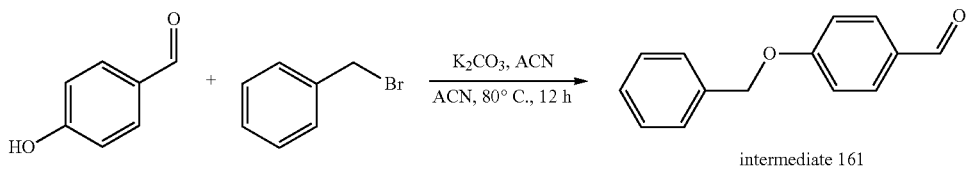

intermediate 161

-continued
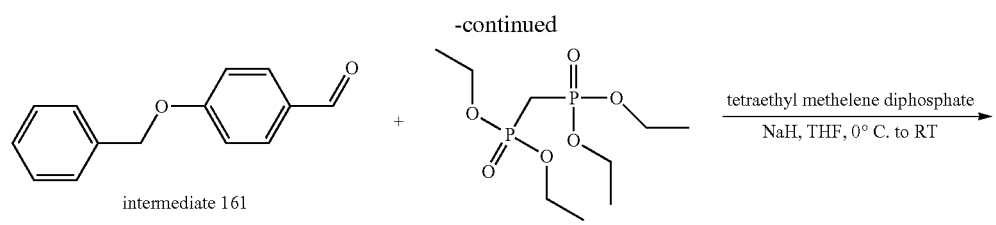
intermediate 161
tetraethyl methelene diphosphate
NaH, THF, 0° C. to RT
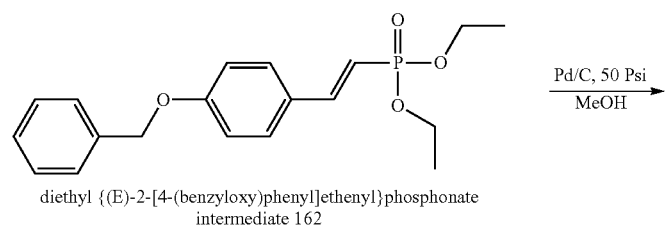
diethyl {(E)-2-[4-(benzyloxy)phenyl]ethenyl}phosphonate
intermediate 162
Pd/C, 50 Psi
MeOH
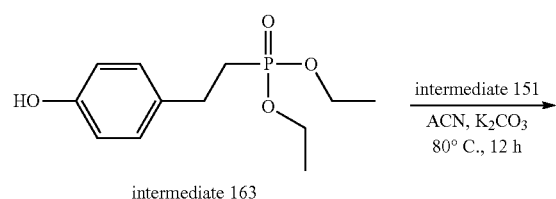
intermediate 163
intermediate 151
ACN, $K_2CO_3$
80° C., 12 h
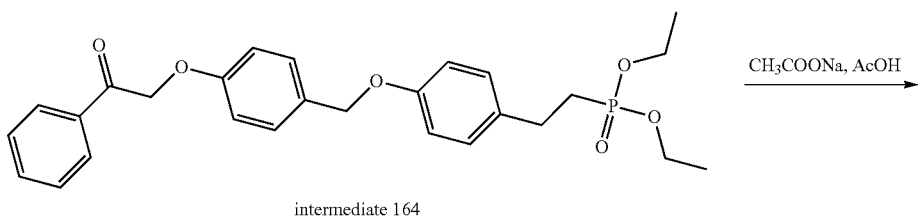
intermediate 164
$CH_3COONa$, AcOH
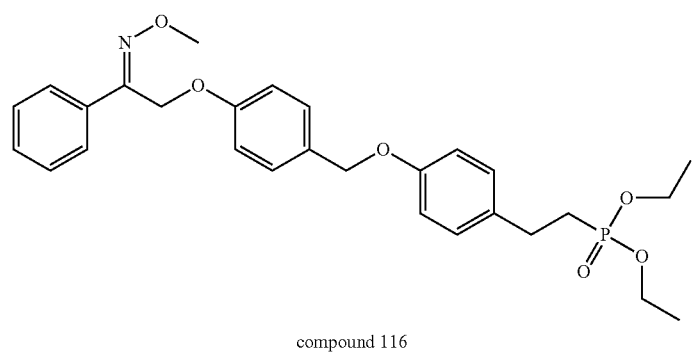
compound 116

Example 116

Dimethyl (2-{4-[(4-{[(2E,2Z)-2-(methoxyimino)-2-phenylethyl]oxy}benzyl)oxy]phenyl}ethyl)phosphonate (116)

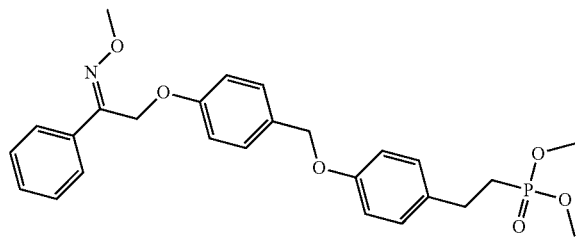

Compound 116 was synthesized from 2-[4-(bromomethyl)phenoxy]-1-phenylethanone (0.2 g, 0.657 mmol) and (Dimethyl [2-(4-hydroxyphenyl)ethyl]phosphonate (0.17 g, 0.657 mmol) by following the procedure described in scheme 40. (0.006 g, yield: 12.6%); purity; 79.9% and 12.52%

Intermediate 161: 4-(Benzyloxy)benzaldehyde

To a 100 mL RB flask fitted with magnetic stirrer was charged 80 mL of acetonitrile. To the stirred solvent was added 4-hydroxy benzaldehyde (4 g, 33 mmol) and $K_2CO_3$ (9 g, 65 mmol). Then it was stirred for 5 min. Benzyl bromide (6.7 g, 39 mmol) was added. Then RM heated 80° C. for 2 h. After completion of the reaction (reaction monitored by TLC), the RM was concentrated in vacuum to remove the acetonitrile. To the residue was then added 100 mL of water and extracted with ethyl acetate (150 mL×2). The organic layer was washed with saturated brine solution (50 mL), dried over anhydrous $Na_2SO_4$ and evaporated to dryness gave the titled compound (4.5 g, 64.75%).

Intermediate 162: Diethyl {(E)-2-[4-(benzyloxy)phenyl]ethenyl}phosphonate

To A 100 mL 2 necked RB flask charged with a suspension of NaH (0.14 g, 5.67 mmol) in THF (50 mL) under Nitrogen atmosphere was added tetraethyl methanediylbis(phosphonate) (1.63 g, 5.67 mmol) in THF drop wise at 0° C. This solution was stirred at the same temperature for 5 min followed by the addition of 4-(benzyloxy)benzaldehyde slowly. Reaction mixture was stirred at RT for 4 h. Excess NaH was quenched with ice and stirred for 5 min. Then the RM was diluted with ethyl acetate (50 mL) and the organic layer was washed with water (20 mL). The organic layer was dried over anhydrous $Na_2SO_4$ and the solvent was removed under reduced pressure. The product was obtained as oil (1.6 g, yield: 98%). $^1$H NMR (300 MHz, $CDCl_3$): δ 7.28-7.45 (m, 8H), 6.89-7.23 (d, 2H), 5.96-6.08 (t, 1H), 5.03 (s, 2H), 4.0-4.1 (m, 3H), 1.26-1.30 (t, 3H)

Intermediate 163: Diethyl [2-(4-hydroxyphenyl)ethyl]phosphonate

A 500 mL bar shaker charged with ethyl dimethyl {(E)-2-[4-(benzyloxy)phenyl]ethenyl}phosphonate (1.6 g, 4.62 mmol) in MeOH was degassed with nitrogen for 2 min. Added 10% of Pd/C (0.5 g, 10%) and applied 50 psi of $H_2$ pressure for 3 h. Reaction mixture was filtered through celite pad and washed the pad with excess MeOH. Organic phase was dried over sodium sulfate and concentrated to afford oil as product (1.01 g, yield: 84.16%).

Intermediate 164: Diethyl [2-(4-{[4-(2-oxo-2-phenylethoxy)benzyl]oxy}phenyl)ethyl]phosphonate To a 50 mL RB flask fitted with magnetic stirrer was charged 10 mL of acetonitrile. To the stirred solvent was added dimethyl [2-(4-hydroxyphenyl)ethyl]phosphonate (0.17 g, 0.66 mmol) and $K_2CO_3$ (0.27 g, 1.97 mmol). Then it was stirred for 5 min. 2-[4-(bromomethyl)phenoxy]-1-phenylethanone (0.2 g, 0.66 mmol) was added. Then RM heated 80° C. for 2 h. After completion of the reaction (reaction monitored by TLC), the RM was concentrated in vacuum to remove the acetonitrile. To the residue was then added 100 mL of water and extracted with ethyl acetate (30 mL×2). The organic layer was washed with saturated brine solution (20 mL), dried over anhydrous $Na_2SO_4$ and evaporated to dryness gave the titled compound (0.14 g, 45.2%); $^1$H NMR (300 MHz, DMSO-$d_6$): δ 8.01-8.04 (d, 2H), 7.68-7.70 (t, 1H), 7.55-7.60 (d, 2H), 7.33-7.36 (d, 2H), 7.14-7.17 (d, 2H), 6.96-6.98 (d, 2H), 6.89-6.92 (d, 2H), 5.59 (s, 2H), 4.98 (s, 2H), 3.92-4.04 (m, 4H), 2.66-2.75 (m, 2H), 1.94-2.05 (m, 2H), 1.18-1.91 (m, 6H)

Compound 116: Diethyl (2-{4-[(4-{[(2E,2Z)-2-(methoxyimino)-2-phenylethyl]oxy}benzyl)oxy]phenyl}ethyl)phosphonate To a 50 mL single neck RB flask charged with dimethyl [2-(4-{[4-(2-oxo-2-phenylethoxy)benzyl]oxy}phenyl)ethyl]phosphonate (0.02 g, 0.041 mmol) in acetic acid (2 mL) was added O-methoxylamine hydrochloride (0.007 g, 0.062 mmol) followed by sodium acetate (0.005 g, 0.083 mmol). Reaction mixture was stirred at RT under nitrogen atmosphere for 3 h. Then, the RM was diluted with ethyl acetate (15 mL) and the organic layer was washed with sat.$NaHCO_3$ solution (5 mL) and water (5 mL). The organic layer was dried over anhydrous $Na_2SO_4$ and the solvent was removed under reduced pressure. The product was obtained as oil. (0.006 g, yield: 28.57%) MS (ESI, 120 eV): m/z=512 (M+H)$^+$; Purity: 79.9% and 12.52%

Scheme 41

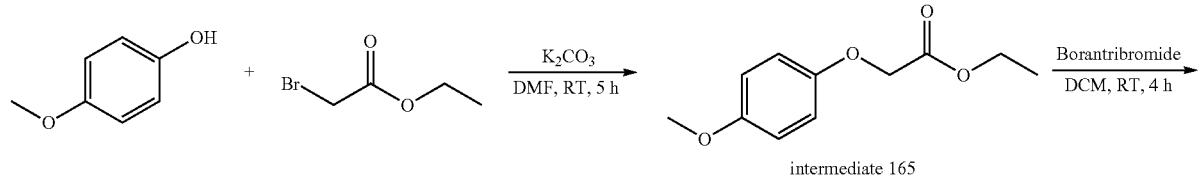

intermediate 165

-continued

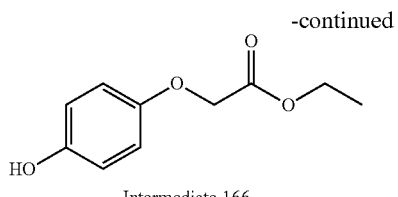
Intermediate 166

Intermediate 13
tributyl phospine
——————————————→
1,1'-(Azodicarbonyl)dipiperidine
Tolune, RT, 3 h

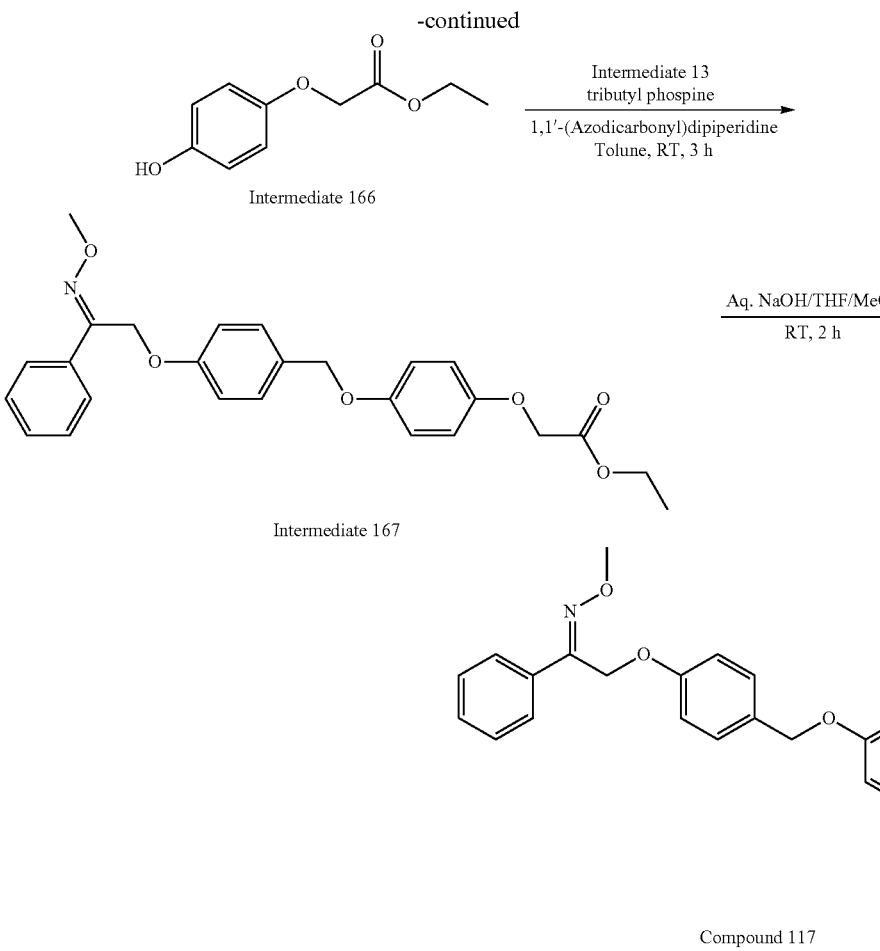
Intermediate 167

Aq. NaOH/THF/MeOH
————————————→
RT, 2 h

Compound 117

Example 117

{4-[(4-{[(2Z)-2-(Methoxyimino)-2-phenylethyl]oxy}benzyl)oxy]phenoxy}acetic acid (117)

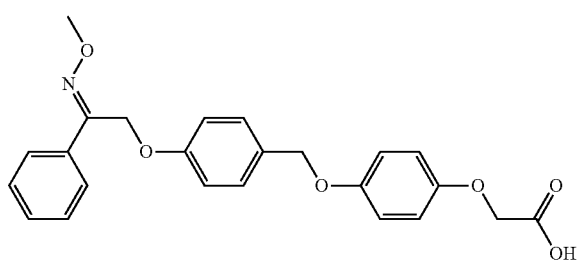
117

Compound 117 was synthesized from Intermediate 13 (0.22 g, 1.020 mmol) and ethyl (4-hydroxyphenoxy)acetate (0.20 g, 1.020 mmol) by following the procedure described in scheme 41 (0.060 g, yield: 13.72%); Purity: 97.98%.

Intermediate 165: Ethyl (4-methoxyphenoxy)acetate

To a 100 mL RB flask fitted with magnetic stirrer was charged 12 mL of DMF to the stirred solvent was added $K_2CO_3$ (2.2 g, 16 mmol), 4-methoxyphenol (1 g, 8 mmol) and ethyl bromoacetate (1.1 mL, 9.6 mmol) Then the reaction mixture was Stirred at RT for 5 h. After completion of the reaction (reaction monitored by TLC), reaction mixture was concentrated and extracted with ethyl acetate. Then the organic layer was dried over anhydrous $Na_2SO_4$. Solvent was removed under reduced pressure to get the compound (2 g, Yield: 90%).

Intermediate 166: Ethyl (4-hydroxyphenoxy)acetate

To a 100 mL RB flask fitted with magnetic stirrer was charged 20 mL of DCM to the stirred solvent was added ethyl (4-methoxyphenoxy)acetate (2 g, 9.5 mmol) and Borontribromide (1.85 g, 11.0 mmol) was added at 0° C. Then it was stirred at 0° C. for 30-45 min. After completion of the reaction (reaction monitored by TLC), reaction mass quenched with Sodium bicarbonate and concentrated the reaction mixture and extracted with ethyl acetate. The organic layer was washed with brine and dried by anhydrous $Na_2SO_4$ and evaporated to dryness, the resulting crude compound was purified by column chromatography on silica gel using petroleum ether and ethyl acetate as eluent to give the product (0.2 g Yield: 20%): $^1$H NMR (300 MHz, DMSO-$d_6$): δ 8.97 (s, 1H), 6.72-6.75 (d, 2H), 6.64-6.67 (d, 2H), 4.62 (s, 2H) 4.11-4.18 (q, 2H), 1.18-1.22 (t, 3H).

Intermediate 167: Ethyl {4-[(4-{[(2Z)-2-(methoxy-imino)-2-phenylethyl]oxy}benzyl)oxy]phenoxy}acetate To a 50 mL RB flask fitted with magnetic stirrer was charged 10 mL of Toluene. to the stirred solvent was added ethyl (4-hydroxyphenoxy)acetate (0.2 g, 1.030 mmol) and (4-{[(2Z)-2-(methoxyimino)-2-phenylethyl]oxy}phenyl) methanol (0.22 g, 0.810 mmol) was added Tributyl phosphine (0.268 g, 1.32 mmol) and 1,1'(Azodicarbonyl)di-piperidene (0.33 g, 1.326 mmol). Then the reaction mixture was Stirred at RT for 3 hrs. After completion of the reaction (reaction monitored by TLC), reaction mixture was extracted with ethyl acetate. Then the organic layer was dried over anhydrous $Na_2SO_4$. Solvent was removed under reduced pressure, and the resulting crude compound was purified by column chromatography on silica gel using petroleum ether and ethyl acetate as eluent (0.13 g Yield: 28.3%): $^1$H NMR (300 MHz, $CDCl_3$): δ 7.57-7.60 (m, 2H), 7.18-7.28 (m, 5H), 6.82-6.84 (d, 3H), 6.78-6.79 (d, 3H), 5.12 (s, 2H), 4.83 (s, 2H), 4.49 (s, 2H), 4.15-4.22 (m, 2H), 3.98 (s, 3H), 1.19-1.24 (t, 3H).

Compound 117: {4-[(4-{[(2Z)-2-(methoxyimino)-2-phenylethyl]oxy}benzyl)oxy]phenoxy}acetic acid To a 25 mL RB flask fitted with magnetic stirrer was charged 3 mL of ethanol and 3 mL of THF. To the stirred solvent was added ethyl {4-[(4-{[(2Z)-2-(methoxyimino)-2-phenylethyl]oxy}benzyl)oxy]phenoxy}acetate (0.13 g, 1.289 mmol) and NaOH was added followed by water (1 mL) at 0° C. Then it was stirred at RT for 5 h. After completion of the reaction (reaction monitored by TLC), reaction mixture was evaporated completely and the crude was washed with ether, and diluted with water and then neutralized with 1N HCl, then extracted with ethyl acetate, organic layer was washed with water and brine, dried over sodium sulphate. The organic layer was evaporated on rotavapor to give the product (0.06 g Yield: 49.5%). Purity: 97.98%

Scheme 42

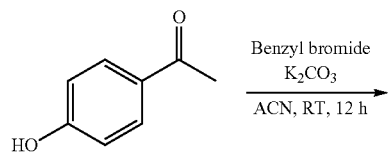

Benzyl bromide
$K_2CO_3$
———————→
ACN, RT, 12 h

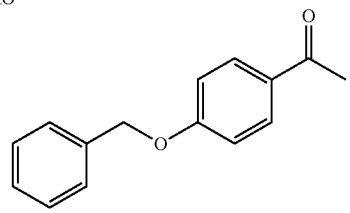

Intermediate 168

Dimethyl carbonate
NaH
———————→
DMF, RT, 12 h

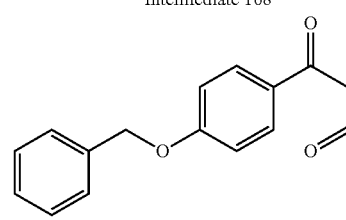

Intermediate 169

Pd/C 10%
———————→
Ethyl acetate

-continued

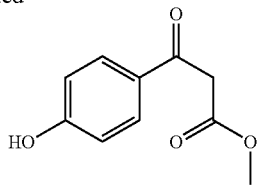

Intermediate 170

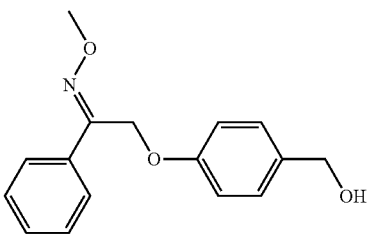

Intermediate 13

Intermediate 170
tributyl phospine
1.1'-(Azodicarbonyl)
dipiperidine
———————→
Tolune, RT, 12 h

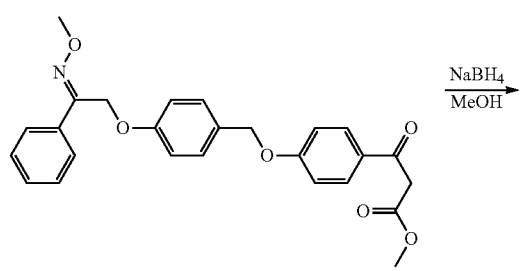

Intermediate 171

$NaBH_4$
———→
MeOH

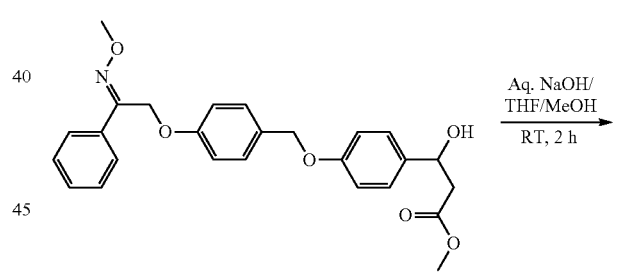

Intermediate 172

Aq. NaOH/
THF/MeOH
———————→
RT, 2 h

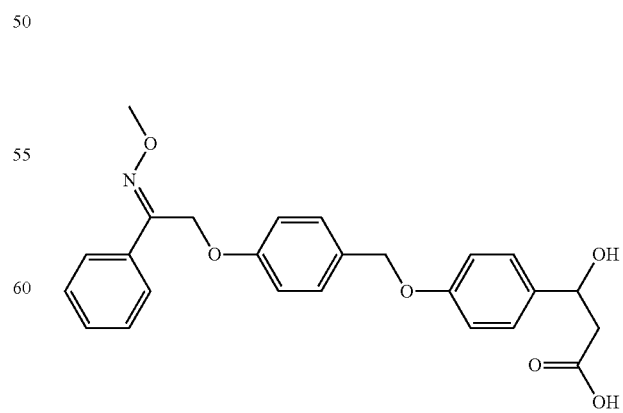

Compound 118

Example 118

3-Hydroxy-3-{4-[(4-{[(2Z)-2-(methoxyimino)-2-phenylethyl]oxy}benzyl)oxy]phenyl}propanoic acid (118)

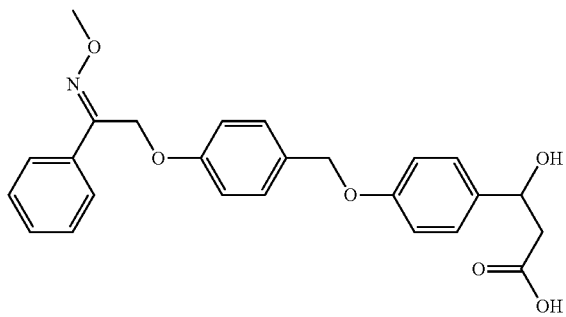

Compound 118 was synthesized from methyl 3-hydroxy-3-{4-[(4-{[(2Z)-2-(methoxyimino)-2-phenylethyl]oxy}benzyl)oxy]phenyl}propanoate by following the procedure described in scheme 42 (0.02 g, yield: 26.5%); Purity: 45.3% and 43.6%.

Intermediate 168: 1-[4-(Benzyloxy)phenyl]ethanone

To a stirring solution of 1-(4-hydroxyphenyl)ethanone (5 g, 36 mmol) in Acetonitrile 50 mL was added potassium carbonate (9.9 g, 72 mmol) and benzyl bromide (7.5 g, 44 mmol) and stirred at RT for overnight, reaction mass was diluted with water and extracted with ethyl acetate, organic layer was given water and brine washes, dried over $Na_2SO_4$, evaporation under reduced pressure yields titled compound as white solid (7 g Yield: 84.1%): $^1$H NMR (300 MHz, $CDCl_3$): δ 7.85-7.88 (d, 2H), 7.25-7.37 (m, 5H), 6.92-6.95 (d, 2H), 5.06 (s, 2H), 2.48 (s, 3H).

Intermediate 169: Methyl 3-[4-(benzyloxy)phenyl]-3-oxopropanoate

To a stirring suspension of NaH (3.7 g, 154.2 mmol) in DMF (25 mL) was added 1-[4-(benzyloxy)phenyl]ethanone (7 g, 31 mmol) at −5° C. and stirred for 30 min, then dim ethyl carbonate (13.5 g, 150 mmol, dissolved in DMF) was added at −5° C. slowly (exothermic) and warmed slowly to RT, stirred at RT for overnight. Reaction mass was quenched with ice cold water and extracted with ethyl acetate, organic layer was washed with water and brine dried over $Na_2SO_4$. The organic layer was concentrated to give the product (7 g, Yield: 92%): $^1$H NMR (300 MHz, $CDCl_3$): δ 7.84-7.87 (d, 2H), 7.28-7.35 (m, 5H), 6.94-6.96 (d, 2H), 5.07 (s, 2H), 3.89 (s, 2H), 3.68 (s, 3H)

Intermediate 170: Methyl 3-(4-hydroxyphenyl)-3-oxopropanoate

To a 50 mL RB flask fitted with magnetic stirrer were charged ethyl acetate (15 mL), to that stirred solvent was added methyl 3-[4-(benzyloxy)phenyl]-3-oxopropanoate (0.3 g, 1.05 mmol), and palladium carbon 10% (80 mg) was added. After addition, the hydrogen balloon was fixed to the reaction mixture and stirred at room temperature for 1 h. After 3 h, the reaction mixture was filtered through celite. Then the organic layer was concentrated and dried. The product was obtained as colourless liquid (0.2 g, Yield: 98%).

Intermediate 171: Methyl 3-{4-[(4-{[(2Z)-2-(methoxyimino)-2-phenylethyl]oxy}benzyl)oxy]phenyl}-3-oxopropanoate To a 50 mL RB flask fitted with magnetic stirrer was charged 10 mL of Toluene. to the stirred solvent was added methyl 3-(4-hydroxyphenyl)-3-oxopropanoate (0.2 g, 1.036 mmol) and (4-{[(2Z)-2-(methoxyimino)-2-phenylethyl]oxy}phenyl)methanol (0.22 g, 0.82 mmol) was added Tributyl phosphine (0.271 g, 1.324 mmol) and 1,1'-(Azodicarbonyl)di-Piperidine portion wise at 0° C. (0.339 g, 1.346 mmol). Then the reaction mixture was stirred at RT for 12 h. After completion of the reaction (reaction monitored by TLC), reaction mixture was concentrated and extracted with ethyl acetate. Then the organic layer was dried over anhydrous $Na_2SO_4$. Solvent was removed under reduced pressure, and the resulting crude compound was purified by column chromatography on silica gel using petroleum ether and ethyl acetate as eluent (0.05 g Yield: 14%) MS (ESI, 120 eV): m/z=448.1 $(M+H)^+$.

Intermediate 172: Methyl 3-hydroxy-3-{4-[(4-{[(2Z)-2-(methoxyimino)-2-phenylethyl]oxy}benzyl)oxy]phenyl}propanoate To a 25 mL RB flask fitted with magnetic stirrer was charged 4 mL of MeOH to the stirred solvent was added methyl 3-{4-[(4-{[(2Z)-2-(methoxyimino)-2-phenylethyl]oxy}benzyl)oxy]phenyl}-3-oxopropanoate (0.08 g, 0.178 mmol) and Sodium borohydride (0.008 g, 1.21 mmol) was added 0° C. Then it was stirred at RT for 6 h, after completion of the reaction (reaction monitored by TLC), reaction mass quenched with Ice water and concentrated the reaction mixture and extracted with ethyl acetate. The organic layer washed with brine and dried by anhydrous $Na_2SO_4$ and evaporated to dryness, and the resulting crude compound was purified by column chromatography on silica gel using petroleum ether and ethyl acetate as eluent (0.04 g, Yield: 50%) $^1$H NMR (300 MHz, DMSO-$d_6$): δ 7.62-7.65 (m, 2H), 7.32-7.40 (m, 5H), 7.23-7.26 (d, 2H), 6.90-6.93 (m, 4H), 5.36-5.38 (d, 1H) 5.22 (s, 2H), 4.92 (s, 2H), 4.85-4.89 (t, 1H), 4.04 (s, 3), 3.57 (s, 3H), 2.57-2.59 (d, 2H)

Compound 118: 3-hydroxy-3-{4-[(4-{[(2Z)-2-(methoxyimino)-2-phenylethyl]oxy}benzyl)oxy]phenyl}propanoic acid To a 25 mL RB flask fitted with magnetic stirrer was charged 2 mL of Methanol and 2 mL of THF. To the stirred solvent was added methyl 3-hydroxy-3-{4-[(4-{[(2Z)-2-(methoxyimino)-2-phenylethyl]oxy}benzyl)oxy]phenyl}propanoate (0.04 g, 0.08 mmol) and NaOH was added followed by water (0.5 mL). Then it was stirred at RT for 12 h, after completion of the reaction (reaction monitored by TLC), reaction mixture was evaporated completely and the crude was washed with ether, and diluted with water and then neutralized with 1N HCl, then extracted with ethyl acetate, organic layer was washed with water and brine, dried over $Na_2SO_4$. The organic layer was evaporated on rotavapor under reduced pressure to give the product as a white colour solid. (0.02 g, yield: 52.6%); Purity: 45.3% and 43.6%.

Scheme 43
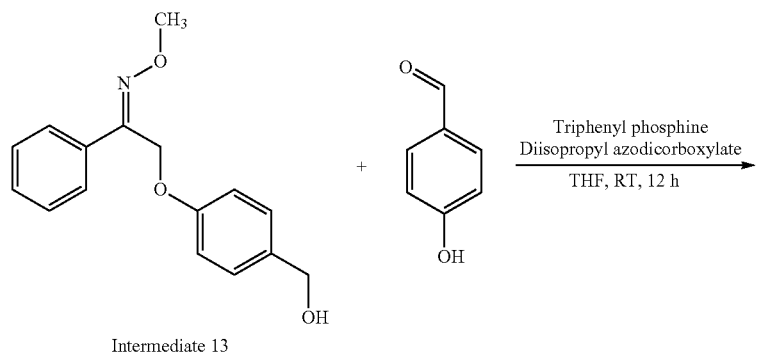
Intermediate 13
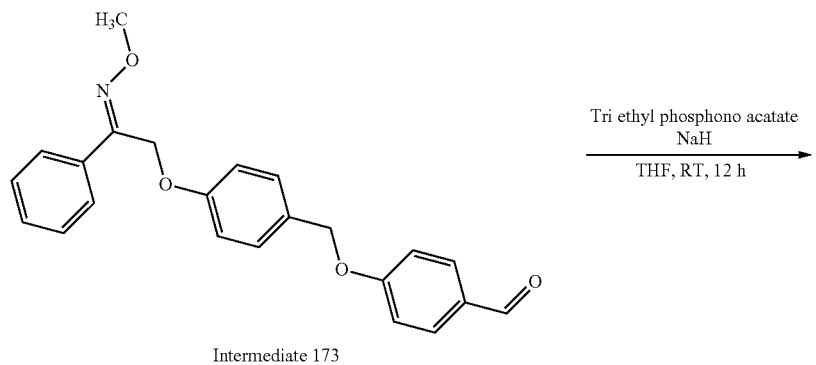
Intermediate 173
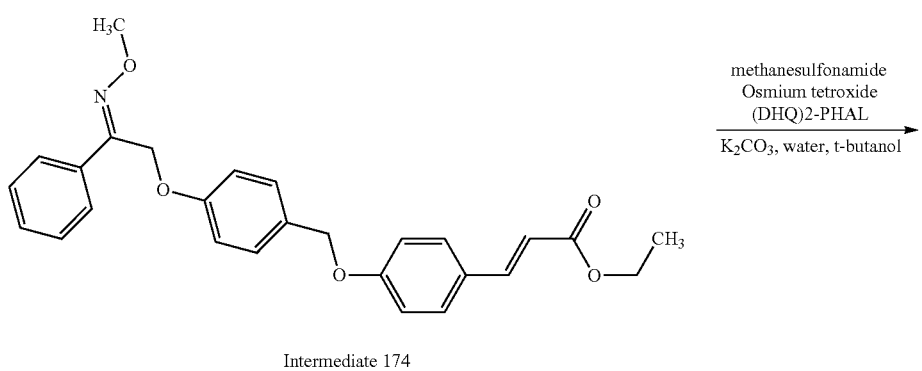
Intermediate 174
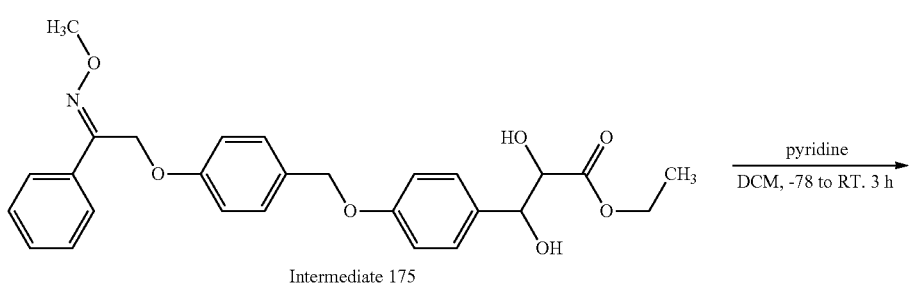
Intermediate 175

-continued
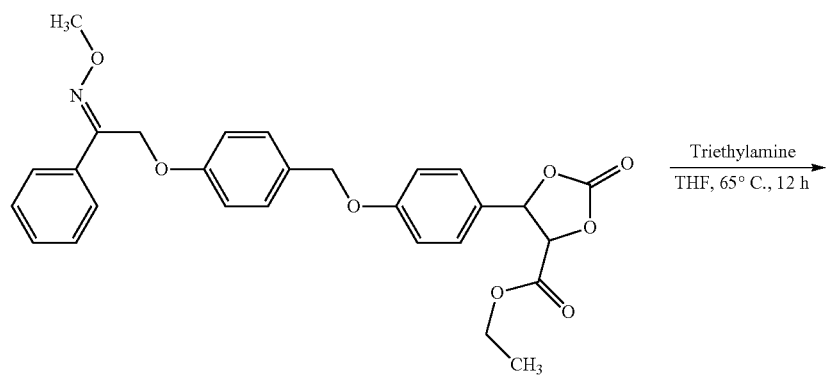
Intermediate 176
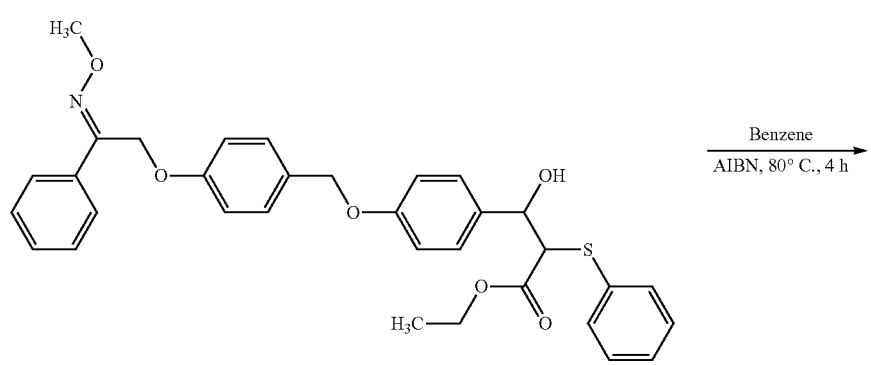
Intermediate 177
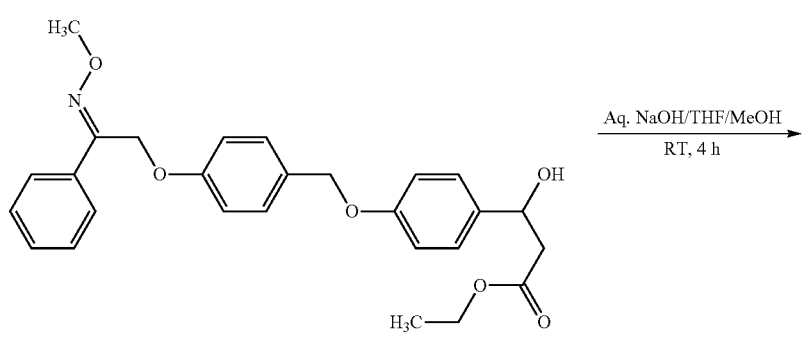
Intermediate 178
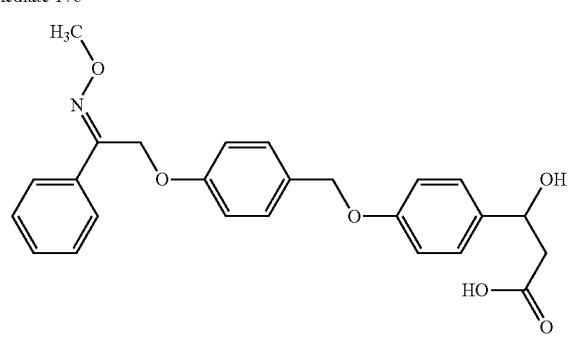
Compound 119

Example 119

3-Hydroxy-3-{4-[(4-{[(2Z)-2-(methoxyimino)-2-phenylethyl]oxy}benzyl)oxy]phenyl}propanoic acid (119)

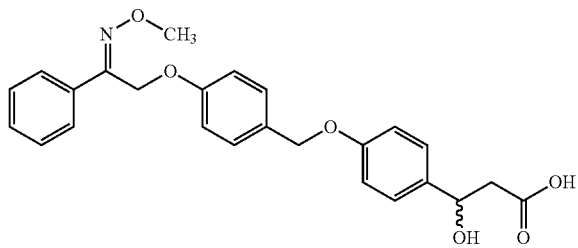

Compound 119 was synthesized from ethyl 3-hydroxy-3-{4-[(4-{[(2Z)-2-(methoxyimino)-2-phenylethyl]oxy}benzyl)oxy]phenyl}propanoate by following the procedure described in scheme 43 (0.008 g, yield: 5.1%); Purity: 96.8%.

Intermediate 173: 4-[(4-{[(2Z)-2-(Methoxyimino)-2-phenylethyl]oxy}benzyl)oxy]benzaldehyde To a stirring solution of (4-{[(2Z)-2-(methoxyimino)-2-phenylethyl]oxy}phenyl)methanol (10 g, 37 mmol) and 4-hydroxybenzaldehyde (4.5 g, 37 mmol) in THF (100 mL) was added triphenylphosphine (12.2 g, 46.5 mmol) and Diisopropyl azodicarboxylate (11.2 g, 55 mmol) at 0° C., then stirred at RT for 12 h. RM diluted with water and extracted with ethyl acetate. The organic layer was washed with brine solution, dried over Na$_2$SO$_4$ and concentrated to pale brown oil. Crude was purified by column (100-200 silica) using 8% ethyl acetate to get the titled compound as white solid (5 g, Yield: 36.2%). $^1$H NMR (300 MHz, CDCl3): δ 9.81 (s, 1H), 7.74-7.77 (d, 2H), 7.58-7.61 (m, 2H), 7.24-7.29 (m, 5H), 6.97-6.99 (d, 2H), 6.85-6.87 (d, 2H), 5.13 (s, 2H), 4.98 (s, 2H), 3.98 (s, 3H).

Intermediate 174: Ethyl (2E)-3-{4-[(4-{[(2Z)-2-(methoxyimino)-2-phenylethyl]oxy}benzyl)oxy]phenyl}prop-2-enoate To a stirring suspension of NaH (0.63 g, 26 mmol) in dry THF (25 mL) at 0° C. was added Triethyl phosphonoacetate (3.8 g, 16.9 mmol) slowly and stirred for 30 min then added 4-(4-{[(2Z)-2-(methoxyimino)-2-phenylethyl]oxy}phenoxy)benzaldehyde (5 g, 13 mmol) dissolved in THF and stirred at RT for 12 h. RM quenched with ice cold 1N HCl and diluted with ethyl acetate, organic layer was washed with water and brine, dried over sodium sulphate and concentrated (Note: Hydrolysis happened during the reaction and the acid obtained was made ester using methanol and methanesulfonic acid) (5 g, Yield: 83.7%) $^1$H NMR (300 MHz, CDCl$_3$): δ 7.54-7.60 (m, 3H), 7.38-7.41 (d, 2H), 7.23-7.29 (m, 4H), 6.83-6.89 (m, 4H), 6.21-6.26 (d, 1H), 5.13 (s, 2H), 4.92 (s, 2H), 3.98 (s, 3H), 3.7 (s, 3H).

Intermediate 175: Ethyl 2,3-dihydroxy-3-{4-[(4-{[(2Z)-2-(methoxyimino)-2-phenylethyl]oxy}benzyl)oxy]phenyl}propanoate To a 500 mL RB was charged with potassium ferricyanide (4.7 g, 14 mmol), potassium carbonate (1.98 g, 14 mmol), (DHQ)$_2$PHAL (0.075 g, 0.09 mmol) and methane sulfonamide (0.45 g, 4.8 mmol) in 1:1 t-butanol and water mixture and stirred at RT for 5 min, then cooled to 0° C., then added osmiumtetroxide (25 mg dissolved in 0.5 mL of toluene) followed by methyl (2{Z})-3-{4-[(4-{[(2%{Z})-2-(methoxyimino)-2-phenylethyl]oxy}benzyl)oxy]phenyl}prop-2-enoate (2 g, 4.8 mmol) then stirred at RT for 12 h. Reaction mass was quenched with sodium sulfite and extracted with ethyl acetate, organic layer was washed with water and brine dried over sodium sulphate and concentrated to a pale brown oil, which was purified by Column (60-120 silica) using 40% ethyl acetate in pet ether to get the titled compound as white solid (1.3 g, Yield: 60.7%) $^1$H NMR (300 MHz, CDCl3): δ 7.62-7.64 (m, 2H), 7.32-7.39 (m, 5H), 7.21-7.24 (d, 2H), 6.9-6.91 (m, 4H), 5.38-5.40 (d, 1H), 5.30-5.33 (d, 1H), 5.22 (s, 2H), 4.97 (s, 2H), 4.72-4.75 (t, 1H), 4.05-4.08 (m, 1H), 3.99 (s, 3H), 3.55 (s, 3H).

Intermediate 176: Ethyl 5-{4-[(4-{[(2Z)-2-(methoxyimino)-2-phenylethyl]oxy}benzyl)oxy]phenyl}-2-oxo-1,3-dioxolane-4-carboxylate To a stirring solution of methyl 2,3-dihydroxy-3-{4-[(4-{[(2Z)-2-(methoxyimino)-2-phenylethyl]oxy}benzyl)oxy]phenyl}propanoate (1.3 g, 2.8 mmol) in dichloromethane (20 mL) was added pyridine (1.4 g, 17.7 mmol) at −78° C. followed by solution of triphosgene (0.44 g, 15 mmol) in dichloromethane, and gradually warmed to RT then stirred at RT for 4 h. RM quenched with 1N HCl and extracted with dichloromethane. Organic layer was washed with water, NaHCO$_3$ and brine, dried over anhydrous Na$_2$SO$_4$ and concentrated to colourless oil which was purified by column (60-120 silica) using 20% ethyl acetate in pet ether to get the titled compound as colourless oil. (0.8 g, Yield: 58%) $^1$H NMR (300 MHz, CDCl3): δ 7.62-7.64 (m, 2H), 7.34-7.45 (m, 8H), 7.06-7.09 (d, 2H), 6.91-6.94 (d, 2H), 5.88-5.91 (d, 1H), 5.41-5.44 (d, 1H), 5.23 (s, 2H), 5.04 (s, 2H), 3.99 (s, 3H), 3.76 (s, 3H).

Intermediate 177: Ethyl 3-hydroxy-3-{4-[(4-{[(2Z)-2-(methoxyimino)-2-phenylethyl]oxy}benzyl)oxy]phenyl}-2-(phenylsulfanyl)propanoate To a solution of methyl 5-{4-[(4-{[(2Z)-2-(methoxyimino)-2-phenylethyl]oxy}benzyl)oxy]phenyl}-2-oxo-1,3-dioxolane-4-carboxylate (0.8 g, 1.6 mmol) in THF was added Triethylamine (0.32 g, 3.2 mmol) and Thiophenol (0.34 g, 3.2 mmol) at 0° C. under argon then slowly warmed to RT, then stirring continued at 60° C. for 12 h. Reaction mass quenched with water and extracted with ethyl acetate, organic layer was washed with water and brine, dried over sodium sulphate and concentrated to yellow oil which was further purified by column (60-120 silica) using 20% ethyl acetate in pet ether to get the titled compound as yellow oil. (0.55 g, Yield: 61%) $^1$H NMR (300 MHz, DMSO): δ 7.62-7.65 (m, 2H), 7.27-7.40 (m, 8H), 7.22-7.24 (m, 2H), 7.11-7.14 (m, 2H), 6.90-6.93 (d, 4H), 5.21 (s, 2H), 5.01 (s, 2H), 4.63-4.73 (m, 1H), 4.01 (s, 3H), 3.89-3.91 (d, 1H), 3.59 (s, 3H).

Intermediate 178: Ethyl 3-hydroxy-3-{4-[(4-{[(2Z)-2-(methoxyimino)-2-phenylethyl]oxy}benzyl)oxy]phenyl}propanoate To a solution of methyl 3-hydroxy-3-{4-[(4-{[(2Z)-2-(methoxyimino)-2-phenylethyl]oxy}benzyl)oxy]phenyl}-2-(phenylsulfanyl)propanoate (0.05 g, 0.09 mmol) in benzene was added AIBN (catalytic amount) and tributyl tin hydride, the resulting mass was refluxed at 80° C. for 4 h. RM quenched with water extracted with ethyl acetate, Organic layer was washed with water and brine, dried over anhydrous Na$_2$SO$_4$ and concentrated to yellow oil which was further purified by Preparative TLC using 10% ethyl acetate in chloroform to get the titled compound as yellow oil (0.015 g, Yield: 37.5%) $^1$H NMR (300 MHz, CDCl3): δ 7.63-7.65 (m, 2H), 7.32-740 (m, 5H), 7.23-7.26 (d, 2H), 6.9-6.93 (m, 4H), 5.37-5.38 (d, 1H), 5.22 (s, 2H), 4.98 (s, 2H), 4.85-4.92 (t, 1H), 3.99 (s, 3H), 3.57 (s, 3H), 3.15-3.17 (d, 1H), 2.57-2.59 (d, 2H).

Compound 119: 3-hydroxy-3-{4-[(4-{[(2Z)-2-(methoxyimino)-2-phenylethyl]oxy}benzyl)oxy]phenyl}propanoic acid To a stirring solution of methyl 3-hydroxy-3-{4-[(4-{[(2Z)-2-(methoxyimino)-2-phenylethyl]oxy}benzyl)oxy]phenyl}propanoate (0.015 g, 0.0334 mmol) in the mixture of THF and Ethanol was added NaOH (0.003 g, 0.075 mmol) in 0.5 mL of water at 0° C., then stirred at RT for 2 h. After the completion of the SM reaction mass was concentrated under vacuum to remove solvents and diluted with water. Aqueous portion was neutralized with 1N HCl up to neutral pH, then extracted with ethyl acetate organic layer was washed with water and brine, dried over anhydrous Na$_2$SO$_4$. Evaporation under vacuum yields the titled compound as white solid (0.008 g, yield: 13.70%). Purity: 96.8%.

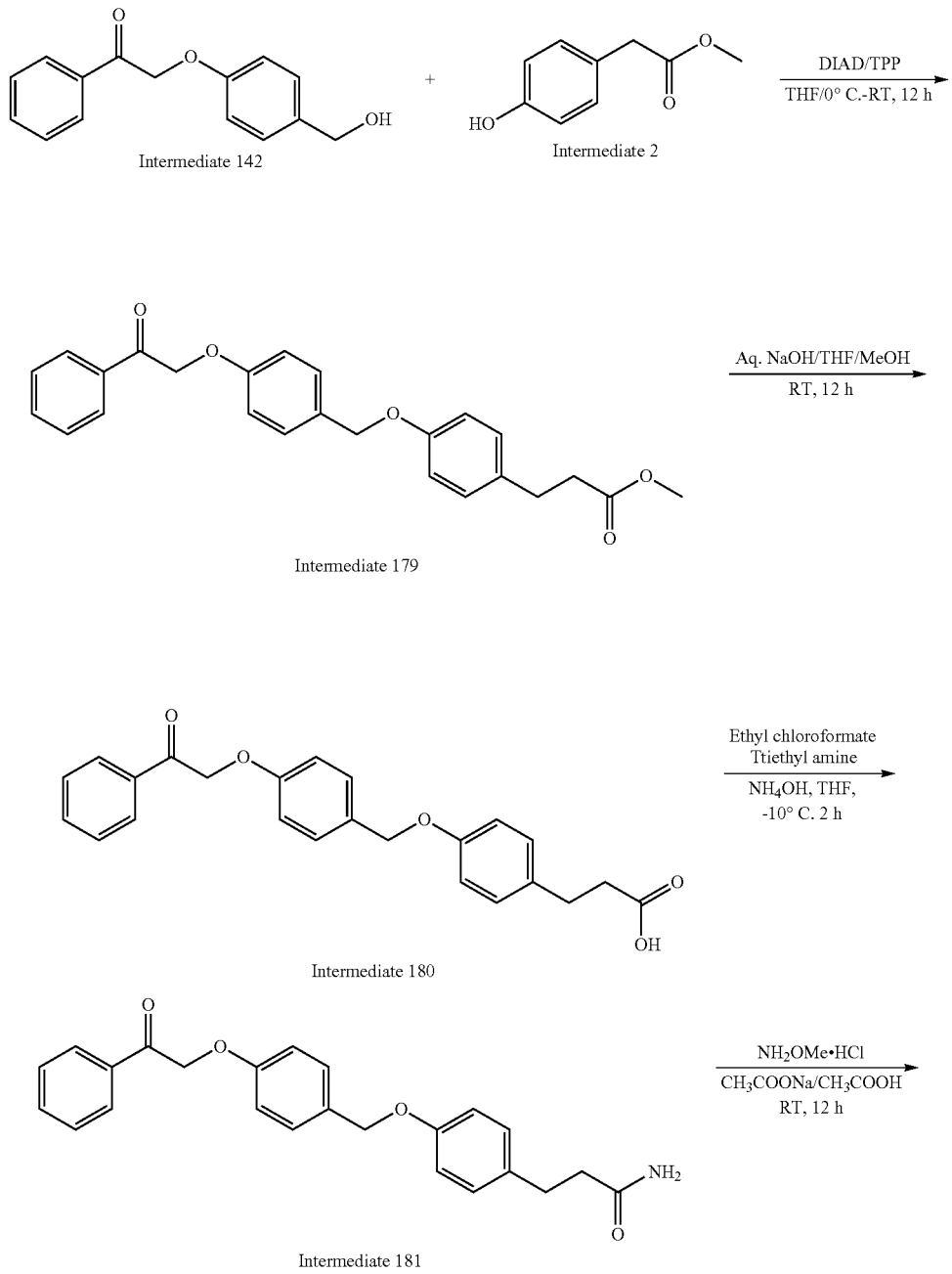

Scheme 44

-continued

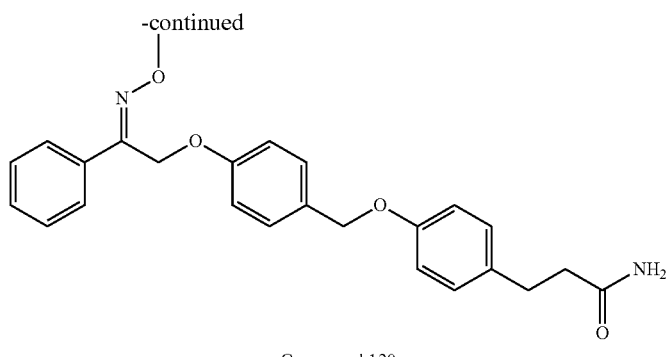

Compound 120

Example 120

3-{4-[(4-{[(2Z)-2-(Methoxyimino)-2-phenylethyl]oxy}benzyl)oxy]phenyl}propanamide (120)

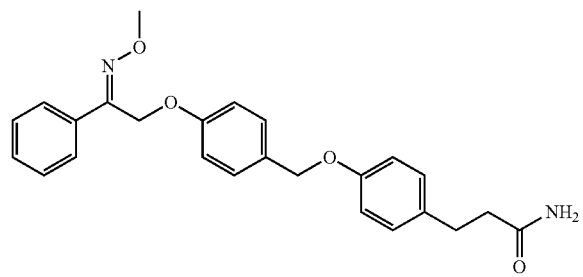

Compound 120 was synthesized from 3-(4-{[4-(2-oxo-2-henylethoxy)benzyl]oxy}phenyl)propanamide by following the procedure described in scheme 44 (0.02 g, yield: 19.8%); Purity: 91.0%.

Intermediate 179: Methyl 3-(4-{[4-(2-oxo-2-phenylethoxy)benzyl]oxy}phenyl)propanoate To a 250 mL RB flask fitted with magnetic stirrer was charged Dry THF, to this 2-[4-(hydroxymethyl)phenoxy]-1-phenylethanone (10.5 g, 43 mmol) and methyl 3-(4-hydroxyphenyl)propanoate (10.1 g, 56 mmol) were added, stirred at 0° C. for 5 min then added triphenyl phosphine (18.1 g, 39 mmol) stirred at 0° C. for 15 min then added diethylazadicarboxylate (14 g, 69 mmol), this resulting mass stirred at RT for overnight, RM evaporated to remove the THF then added water extracted with ethyl acetate. The organic layer washed by brine solution and dried over anhydrous $Na_2SO_4$ and evaporated, purified by 100-200 silica column using pet-ether and ethyl acetate (8 g, Yield: 45%)

Intermediate 180: 3-(4-{[4-(2-Oxo-2-phenylethoxy)benzyl]oxy}phenyl)propanoic acid To a 100 mL RB flask fitted with magnetic stirrer was charged 5 mL of Methanol and 5 mL of THF. To the stirred solvent was added 4-{[4-(3-methoxy-3-oxopropyl)phenoxy]methyl}phenyl benzoate (1 g, 2.4 mmol) and NaOH was added followed by water (1 mL). Then it was stirred at RT for 12 h. After completion of the reaction (reaction monitored by TLC), reaction mixture was evaporated completely and the crude was washed with ether, and diluted with water and then neutralized with 1NHCl, then extracted with ethyl acetate, organic layer was washed with water and brine, dried over $Na_2SO_4$. The organic layer was evaporated on rotavapor to give the product (1 g, Yield: 99%) MS (ESI, 120 eV): m/z=389.2 (M–H)$^+$

Intermediate 181: 3-(4-{[4-(2-Oxo-2-phenylethoxy)benzyl]oxy}phenyl)propanamide To a 100 mL RB flask fitted with magnetic stirrer was charged 12 mL THF to the stirred solvent was added 3-(4-{[4-(benzoyloxy)benzyl]oxy}phenyl)propanoic acid (1 g, 2.4 mmol), Ethyl chloroformate (0.36 mL, 38 mmol) and Tri ethyl amine (1.4 mL, 10 mmol) was added –10° C. Then it was stirred at same temp. 45 min then added NH$_4$OH, continued the stirring at same temperature for 1 h. After completion of the reaction (reaction monitored by TLC), reaction mass was extracted with ethyl acetate and water. The organic layer washed with brine and dried by $Na_2SO_4$ and evaporated to dryness to get the compound (1 g, Yield: 99%). MS (ESI, 120 eV): m/z=390.2 (M–H)$^+$.

Compound 120: 3-{4-[(4-{[(2Z)-2-(methoxyimino)-2-phenylethyl]oxy}benzyl)oxy]phenyl}propanamide To a 100 mL RB flask fitted with magnetic stirrer was charged 15 mL of Acetic acid to the stirred solvent was added 3-(4-{[4-(2-oxo-2-phenylethoxy)benzyl]oxy}phenyl)propanamide (1 g, 2.5 mmol) and O-methoxylamine hydrochloride (0.32 g, 3.8 mmol) and sodium acetate (0.311 g, 3.8 mmol). Then the reaction mixture was Stirred at RT for 12 h. After completion of the reaction (reaction monitored by TLC), reaction mixture was basify using Sodium carbonate, then extracted with ethyl acetate. Then the organic layer was dried over anhydrous $Na_2SO_4$. Solvent was removed under reduced pressure; the resulting crude compound was purified by column chromatography on silica gel using petroleum ether and ethyl acetate as eluent to get the titled compound as white solid, (0.02 g, Yield: 20%).

Scheme 45:

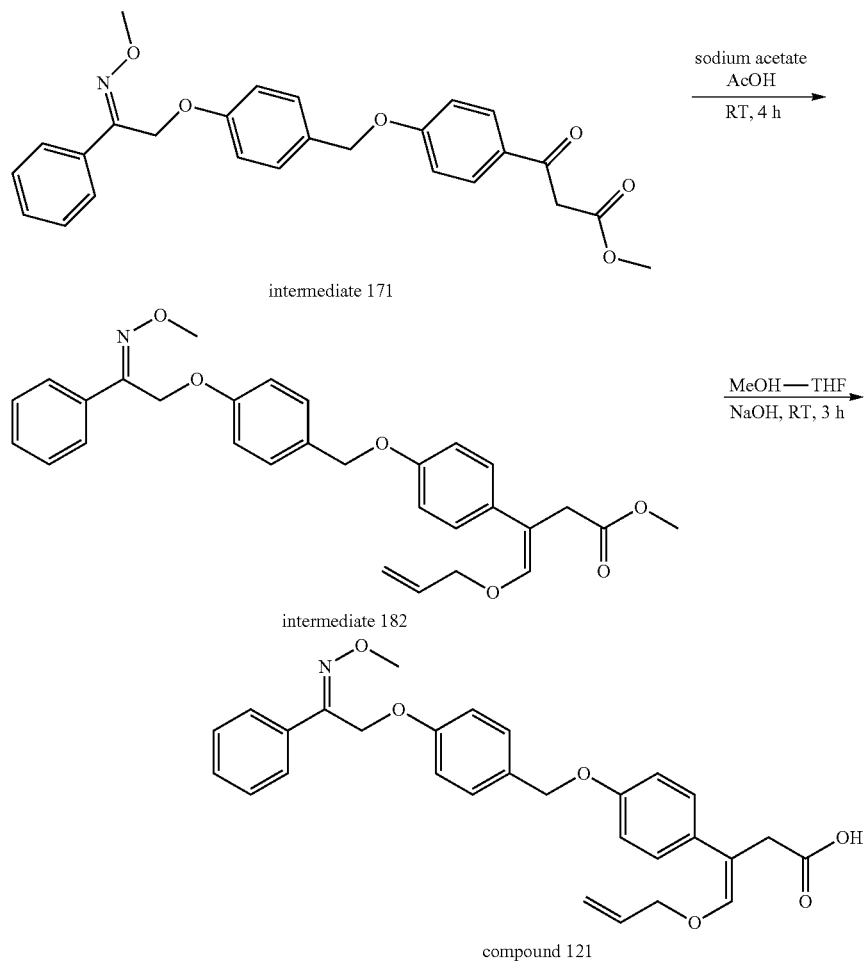

Example 121

(3Z)-3-{4-[(4-{[(2E,2Z)-2-(Methoxyimino)-2-phenylethyl]oxy}benzyl)oxy]phenyl}-3-[(prop-2-en-1-yloxy)imino]propanoic acid (121)

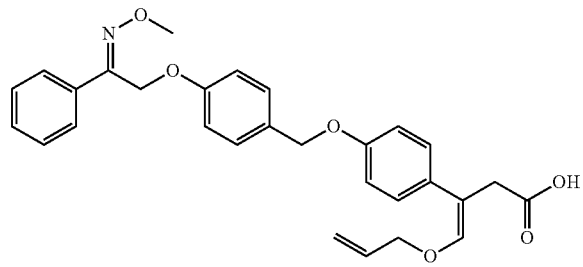

Compound 121 was synthesized from methyl 3-{4-[(4-{[(2E,2Z)-2-(methoxyimino)-2-phenylethyl]oxy}benzyl)oxy]phenyl}-3-oxopropanoate (1.2 g, 2.74 mmol) and O-allylhydroxylamine hydrochloride (0.2 g, 1.8 mmol) by the procedure described in scheme 46. (0.09 g, Yield: 11%); Purity: 57.5% and 29.89%

Intermediate 182: Methyl (3Z)-3-{4-[(4-{[(2Z)-2-(methoxyimino)-2-phenylethyl]oxy}benzyl)oxy]phenyl}-3-[(prop-2-en-1-yloxy)imino]propanoate To a 50 mL single neck RB flask charged with methyl 3-{4-[(4-{[(2E,2Z)-2-(methoxyimino)-2-phenylethyl]oxy}benzyl)oxy]phenyl}-3-oxopropanoate (1.2 g, 2.74 mmol) in acetic acid (2 mL) was added O-allylhydroxylamine hydrochloride (0.2 g, 1.8 mmol) followed by sodium acetate (0.14 g, 1.8 mmol). Reaction mixture was stirred at RT under nitrogen atmosphere for 2-3 h. Reaction mixture was diluted with ethyl acetate (40 mL), washed with (3×20 mL) of water, (2×20 mL) of sat.NaHCO$_3$ and (1×20 mL) of water successively. Organic phase was finally washed with (1×20 mL) of brine solution, then dried over sodium sulphate and concentrated to afford pale yellow gel (0.22 g, Yield: 24.32%). $^1$H NMR (300 MHz, CDCl$_3$): δ 7.58-7.61 (m, 4H), 7.23-7.29 (m, 5H), 6.83-6.89 (m, 4H), 5.92-6.03 (m, 1H), 5.13-5.33 (m, 5H), 4.9 (s, 2H), 4.64-4.70 (m, 3H), 3.98 (s, 3H), 3.67 (s, 3H).

Compound 121: (3Z)-3-{4-[(4-{[(2E,2Z)-2-(Methoxyimino)-2-phenylethyl]oxy}benzyl)oxy]phenyl}-3-[(prop-2-en-1-yloxy)imino]propanoic acid 2N NaOH (0.4 mL, 0.796 mmol) solution was added to a chilled solution of methyl (3E)-3-{4-[(4-{[(2Z)-2-(methoxyimino)-2-phenylethyl]oxy}benzyl)oxy]phenyl}-3-[(prop-2-en-1-yloxy)imino]propanoate (0.2 g, 0.39 mmol) in MeOH-THF mixture. Reaction mixture was stirred at RT for 12 h. Excess solvents were removed under reduced pressure and the resulting gummy mass was diluted with water, neutralized with 1N HCl and then extracted with ethyl acetate. Organic phase was dried over sodium sulphate and concentrated to afford solid (0.09 g, Yield: 46%); Purity: 57.5% and 29.89%.

Example 122

(3E,3Z)-3-[(Benzyloxy)imino]-3-{4-[(4-{[(2Z)-2-(methoxyimino)-2-phenylethyl]oxy}benzyl)oxy]phenyl}propanoic acid (122)

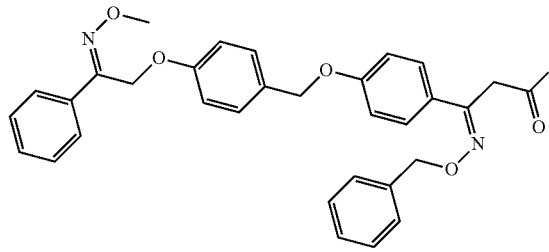

Compound 122 was synthesized from O-benzyl hydroxylamine. HCl (0.2 g, 1.25 mmol) and methyl 3-{4-[(4-{[(2Z)-2-(methoxyimino)-2-phenylethyl]oxy}benzyl)oxy]phenyl}-3-oxopropanoate (1.12 g, 2.5 mmol) by following the procedure described in scheme 46 (0.26 g, yield: 23.1%); Purity: 38%.

Example 123

(3E,3Z)-3-{4-[(4-{[(2Z)-2-(Methoxyimino)-2-phenylethyl]oxy}benzyl)oxy]phenyl}-3-(phenoxyimino)propanoic acid (123)

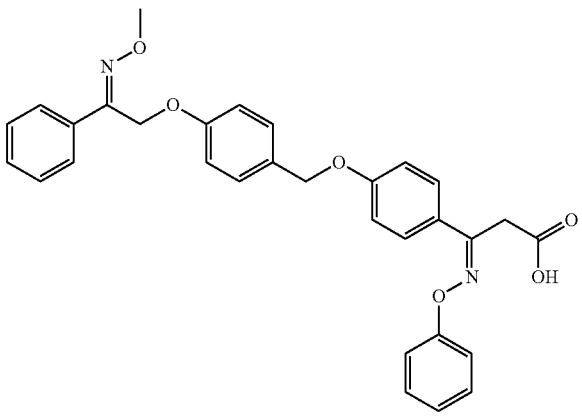

Compound 123 was synthesized from O-phenylhydroxylamine hydrochloride (0.12 g, 1.11 mmol) and methyl 3-{4-[(4-{[(2Z)-2-(methoxyimino)-2-phenylethyl]oxy}benzyl)oxy]phenyl}-3-oxopropanoate (0.25 g, 0.56 mmol) by following the procedure described in scheme 46 (0.03 g, yield: 1.05%); Purity: 87.35%.

Example 124

(3E,3Z)-3-[(Cyclohexyloxy)imino]-3-{4-[(4-{[(2Z)-2-(methoxyimino)-2-phenylethyl]oxy}benzyl)oxy]phenyl}propanoic acid (124)

Compound 124 was synthesized from O-Cyclohexylhydroxylamine hydrochloride (0.154 g, 1.34 mmol) and methyl 3-{4-[(4-{[(2Z)-2-(methoxyimino)-2-phenylethyl]oxy}benzyl)oxy]phenyl}-3-oxopropanoate (0.3 g, 0.67 mmol) by following the procedure described in scheme 46 (0.07 g, yield: 19.58%); Purity: 86.4% and 9%.

Note in the experimental procedures outlined above in many instances the product was geometrically pure meaning that only the E or Z isomer was made. In these instances this has been stated in the text of the experimental identifying the material as either the E or Z isomer. In these instances the structure shown is the correct. In other instances the material was a mixture of E and z isomers and this was also identified in the text of the experimental. In these instances for simplicity of the reader the structure shown is only one of the two geometric isomers (typically the Z isomer is shown) but a skilled addressee would understand from the text of the experimental that both isomers were present.

The compounds outlined in Table 1 or a geometric isomer thereof were synthesized following the procedures outlined above or variations thereof.

TABLE 1

| No | Structure | ¹H NMR | m/z |
|---|---|---|---|
| 1 | 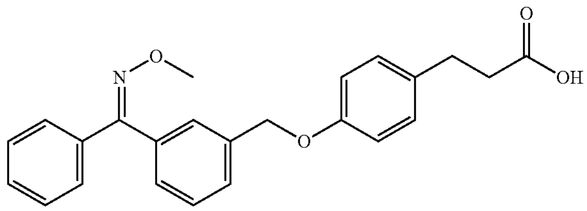 [SMILES: CO/N=C(/c1ccccc1)c1cccc(COc2ccc(CCC(=O)O)cc2)c1] | δ 12.1(s, 1H), 7.45-7.51(m, 4H), 7.36-7.42(m, 3H), 7.25-7.32(m, 2H), 7.11-7.14(m, 2H), 6.86-6.92(t, 2H), 5.05-5.10(d, 2H), 3.87-3.88(d, 3H), 2.71-2.77(t, 2H), 2.45-2.47(m, 2H). | 390.1 |
| 2 | 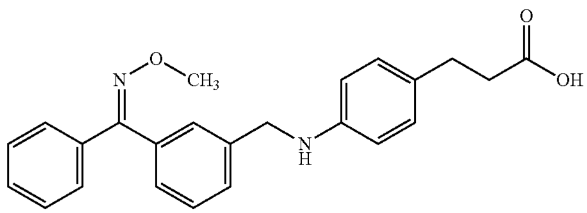 [SMILES: CO/N=C(/c1ccccc1)c1cccc(CNc2ccc(CCC(=O)O)cc2)c1] | δ 12.01(s, 1H), 7.30-7.46(m, 7H), 7.21(s, 1H), 7.13-7.16(d, 1H), 6.86-6.89(t, 2H), 6.43-6.48(t, 2H), 6.07-6.09(d, 1H), 4.19-4.26(m, 2H), 3.84-3.86(d, 3H), 2.85-2.89(t, 2H), 2.55-2.60(t, 2H). | 389.2 |
| 3 | 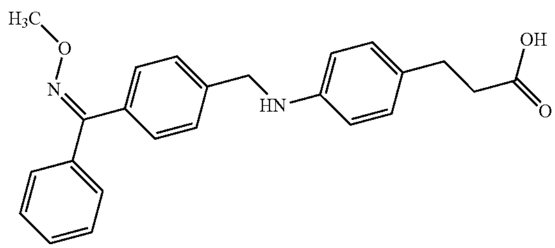 [SMILES: CO/N=C(/c1ccccc1)c1ccc(CNc2ccc(CCC(=O)O)cc2)cc1] | δ 7.25-7.44(m, 9H), 6.82-6.87(dd, 2H), 6.43-6.47(dd, 2H), 5.07-5.25(d, 1H), 4.83-4.87(d, 1H), 3.87(s, 3H), 2.65-2.71(t, 2H), 2.59-2.63(t, 2H). | 389.2 |
| 4 | 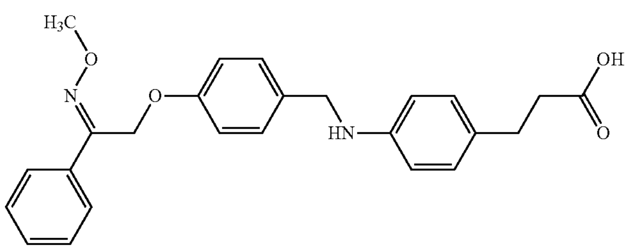 [SMILES: CO/N=C(\COc1ccc(CNc2ccc(CCC(=O)O)cc2)cc1)c1ccccc1] | δ 12.02(s, 1H), 7.61-7.64(2m, 2H), 7.38-7.40(m, 3H), 7.22-7.24(d, 2H), 6.83-6.88(m, 4H), 6.44-6.47(d, 2H), 5.96(s, 1H), 5.17(s, 2H), 4.11-4.13(d, 2H), 3.98(s, 3H), 2.60-2.65(t, 2H), 2.37-2.42(t, 2H). | 417.2 |
| 5 | 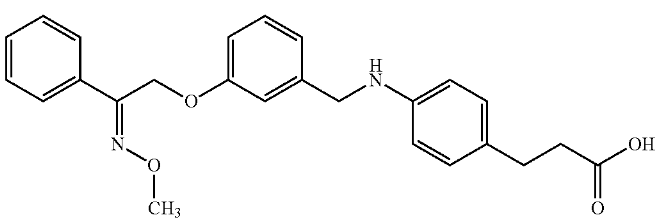 [SMILES: CO/N=C(\COc1cccc(CNc2ccc(CCC(=O)O)cc2)c1)c1ccccc1] | δ 7.60(s, 2H), 7.39(s, 3H), 7.16-7.21(t, 1H), 6.87-6.93(m, 4H), 6.74-6.77(d, 1H), 6.42-6.44(d, 2H), 5.98(s, 1H), 5.18(s, 2H), 4.16(s, 2H), 3.98(s, 3H), 2.57(t, 2H), 2.17(t, 2H). | 417.1 |
| 6 | 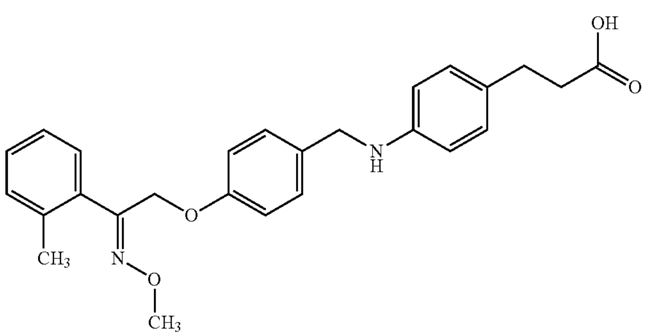 [SMILES: CO/N=C(\COc1ccc(CNc2ccc(CCC(=O)O)cc2)cc1)c1ccccc1C] | : δ 7.12-7.27(m, 6H), 6.82-6.85(d, 2H), 6.70-6.73(d, 2H), 6.40-6.42(d, 2H), 5.88(s, 1H), 5.13(s, 2H), 4.09-4.10(d, 2H), 3.93(s, 3H), 2.53-2.59(t, 2H), 2.22(s, 3H), 2.11(t, 2H). | 431.2 (M − H)⁺; |

TABLE 1-continued

| No | Structure | ¹H NMR | m/z |
|---|---|---|---|
| 7 | 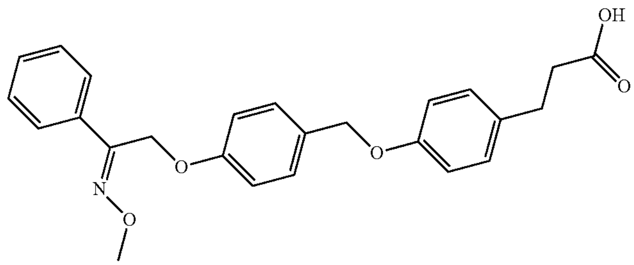 [SMILES: CO/N=C(\COc1ccc(COc2ccc(CCC(=O)O)cc2)cc1)c1ccccc1] | δ 12.08(s, 1H) 7.63-7.65(m, 2H), 7.38-7.40(m, 3H), 7.32-7.35(d, 2H), 7.10-7.13(d, 2H), 6.86-6.92(m, 4H), 5.22(s, 2H), 4.95(s, 2H), 3.98(s, 3H), 2.60-2.76(t, 2H), 2.47-2.52(t, 2H). | 420.2 |
| 8 | 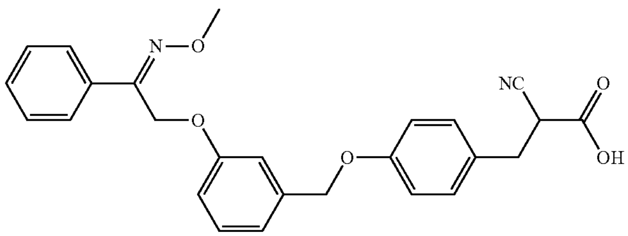 [SMILES: CO/N=C(\COc1cccc(COc2ccc(CC(C#N)C(=O)O)cc2)c1)c1ccccc1] | δ 7.57-7.64(m, 2H), 7.40(s, 3H), 6.99-7.17(m, 3H), 6.58-6.88(m, 5H), 5.16(s, 2H), 3.96-3.99(d, 3H), 3.83-3.84(d, 1H), 3.01-3.11(m, 2H), 2.59-2.65(m, 2H). | 445.1 |
| 9 | 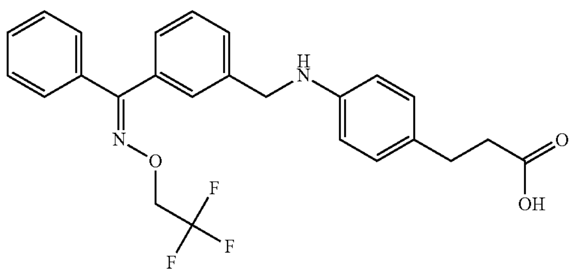 [SMILES: O=C(O)CCc1ccc(NCc2cccc(/C(=N\OCC(F)(F)F)c3ccccc3)c2)cc1] | δ 7.26-7.52(m, 9H), 6.81-6.83(d, 2H), 6.44-6.46(d, 2H), 5.10(d, 2H), 4.73-4.85(m, 3H), 2.55-2.67(m, 4H). | 457.2 |
| 10 | 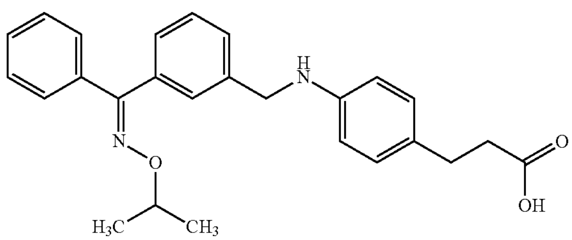 [SMILES: CC(C)O/N=C(/c1ccccc1)c1cccc(CNc2ccc(CCC(=O)O)cc2)c1] | δ 7.21-7.30(m, 9H), 6.87-6.90(d, 2H), 6.50-6.55(d, 2H), 5.03(d, 2H), 4.37-4.46(m, 3H), 2.73-2.80(m, 4H), 2.50-2.57(m, 2H). | 417.2 |
| 11 | 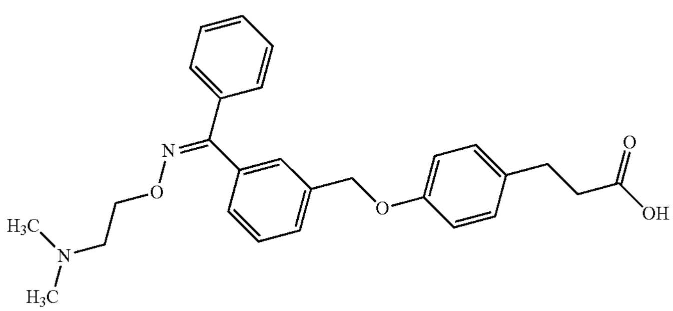 [SMILES: CN(C)CCO/N=C(/c1ccccc1)c1cccc(COc2ccc(CCC(=O)O)cc2)c1] | δ 11.00(s, 1H), 7.47-7.52(m, 4H), 7.40-7.41(m, 3H), 7.32-7.35(m, 2H), 7.11-7.18(m, 2H), 6.86-6.92(m, 2H), 5.06-5.10(d, 2H), 4.49-4.50(d, 2H), 2.80-2.81(d, 2H), 2.72-2.76(m, 4H), 2.67-2.68(d, 6H). | 447.2 |
| 12 | 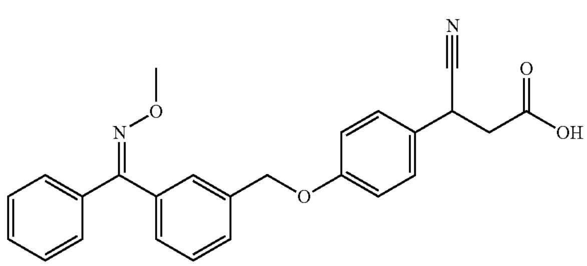 [SMILES: CO/N=C(/c1ccccc1)c1cccc(COc2ccc(C(C#N)CC(=O)O)cc2)c1] | δ 7.39-7.52(m, 7H), 7.24-7.34(m, 4H), 6.94-6.97(t, J = 9.0 Hz, 2H), 5.09-5.13(d, J = 12.6 Hz, 2H), 4.25(t, J = 7.2 Hz, 7.5 Hz, 1H), 3.88(d, J = 1.8 Hz, 3H), 2.44-2.51(m, 2H), 2.25-2.32(m, 1H). | 415.1 |

TABLE 1-continued

| No | Structure | ¹H NMR | m/z |
|---|---|---|---|
| 13 | 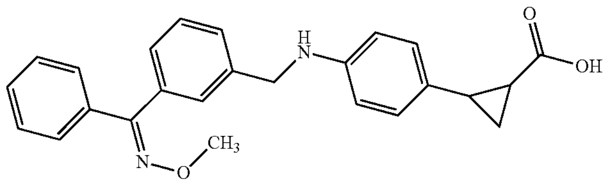 [SMILES: CO/N=C(/c1ccccc1)c1cccc(CNc2ccc(C3CC3C(=O)O)cc2)c1] | δ 7.45(s, 2H), 7.33-7.38(m, 8H), 7.23-7.28(m, 8H), 6.84-6.86(d, 4H), 6.45-6.49(m, 4H), 4.26(s, 2H), 4.21(s, 2H), 3.90(s, 3H), 3.89(s, 3H), 2.40-2.47(m, 2H), 1.68-1.73(m, 2H), 1.52-1.53(m, 2H), 1.23-1.27(m, 2H). | 401.2 |
| 14 | 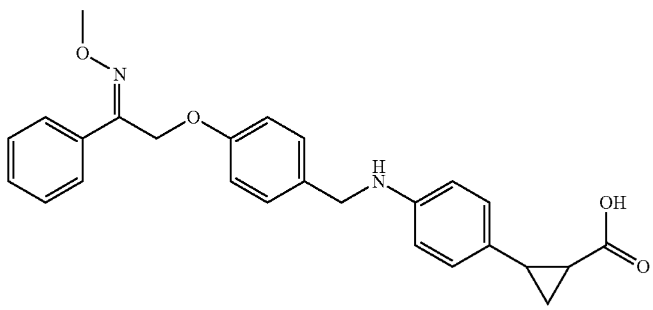 [SMILES: CO/N=C(/COc1ccc(CNc2ccc(C3CC3C(=O)O)cc2)cc1)c1ccccc1] | δ 7.57-7.61(dd, 2H), 7.27-7.29(m, 4H), 7.15-7.18(d, 1H), 6.78-6.87(q, 5H), 6.48(d, 2H), 5.10(s, 2H), 4.14(s, 2H), 3.97(s, 3H), 2.45(m, 1H), 1.71(m, 1H), 1.52(m, 1H), 1.25(m, 1H). | 429.1 |
| 15 | 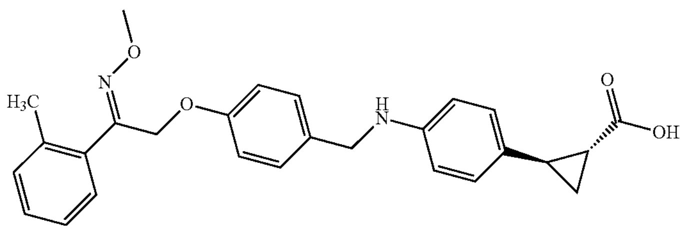 [SMILES: CO/N=C(\COc1ccc(CNc2ccc([C@@H]3C[C@H]3C(=O)O)cc2)cc1)c1ccccc1C] | δ 7.57-7.61(d, 1H), 7.27-7.29(m, 4H), 7.15-7.18(d, 1H), 6.78-6.87(q, 5H), 6.48(d, 2H), 5.10(s, 2H), 4.14(s, 2H), 3.97(s, 3H), 2.45(m, 1H), 2.31(s, 3H) 1.71(m, 1H), 1.52(m, 1H), 1.25(m, 1H). | 443.1 |
| 16 | 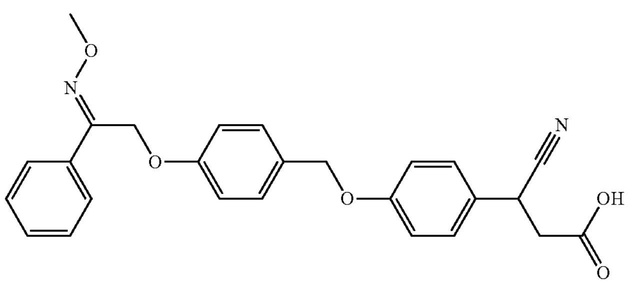 [SMILES: CO/N=C(\COc1ccc(COc2ccc(C(C#N)CC(=O)O)cc2)cc1)c1ccccc1] | δ 7.57-7.60(dd, 2H), 7.22-7.29(m, 7H), 6.83-6.90(m, 4H), 5.13(s, 2H), 4.89(s, 2H), 4.12-4.17(t, 1H), 3.84(s, 3H), 2.94-3.02(dd, 1H), 2.75-2.83(dd, 1H). | 445.1 |
| 17 | 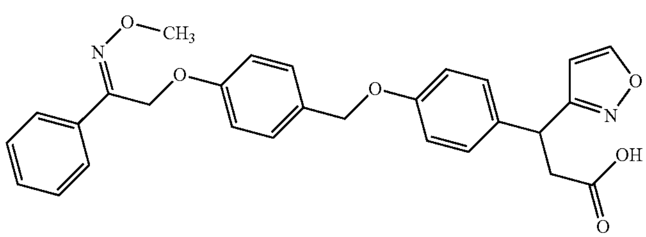 [SMILES: CO/N=C(\COc1ccc(COc2ccc(C(CC(=O)O)c3ccon3)cc2)cc1)c1ccccc1] | δ 8.19(d, 1H), 7.57-7.60(t, 2H), 7.21-7.28(m, 5H), 7.07-7.10(d, 2H), 6.80-6.84(m, 4H), 5.98(d, 1H), 5.11(s, 2H), 4.85(s, 2H), 4.44-4.49(t, 1H), 3.97(s, 3H), 3.22-3.30(q, 1H), 2.84-2.92(q, 1H). | 487.1 |
| 18 | 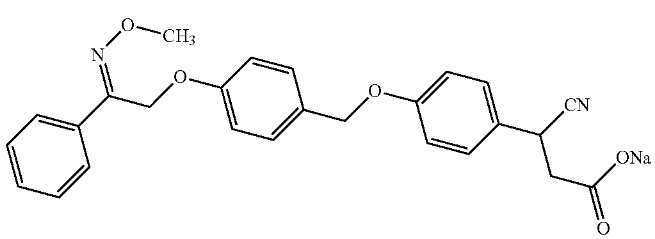 | : δ 7.62-7.65(q, 2H), 7.26-7.40(m, 7H), 6.90-6.97(m, 4H), 5.22(s, 2H), 4.98(s, 2H), 4.21-4.26(t, 1H), 3.99(s, 3H), 2.43-2.50(dd, 1H), 2.24-2.31(dd, 1H). | 445.1 |

TABLE 1-continued

| No | Structure | $^1$H NMR | m/z |
|---|---|---|---|
| 19 | 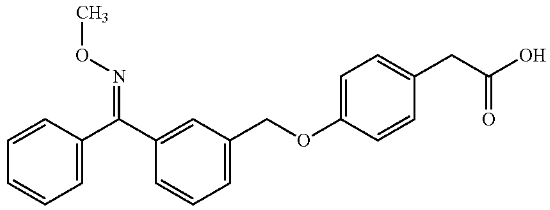 [SMILES: CO/N=C(\c1ccccc1)c1cccc(COc2ccc(CC(=O)O)cc2)c1] | δ 9.31-9.32(d, 1H), 7.44-7.48(t, 2H), 7.37-7.41(m, 5H), 7.22-7.28(m, 2H), 7.00-7.04(m, 2H), 6.65-6.69(m, 2H), 5.08-5.12(d, 2H), 3.87-3.88(d, 3H), 3.55-3.58(d, 2H) | 376.2 |
| 20 | 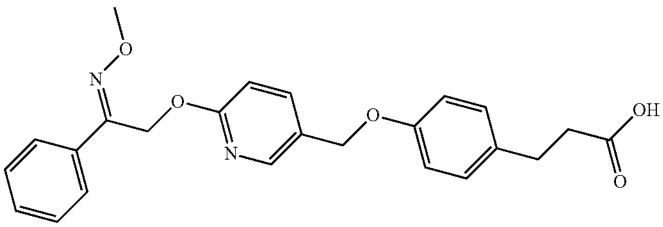 [SMILES: CO/N=C(\COc1ccc(COc2ccc(CCC(=O)O)cc2)cn1)c1ccccc1] | δ 12.07(s, 1H), 7.34-7.74(d, 1H), 7.48-7.50(d, 2H), 7.37-7.41(dd, 1H), 7.28-7.34(m, 3H), 7.12-7.14(d, 2H), 6.84-6.87(d, 2H), 6.29-6.32(d, 1H), 5.16(s, 2H), 4.75(s, 2H), 3.93(s, 3H), 2.73-2.78(2H, t), 2.46-2.51(t, 2H) | 421.1 |
| 21 | 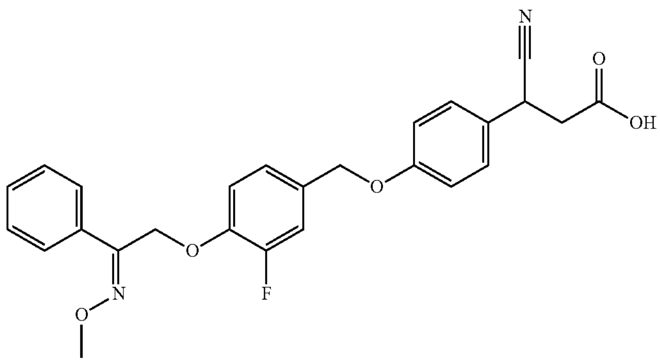 [SMILES: CO/N=C(/COc1ccc(COc2ccc(C(C#N)CC(=O)O)cc2)cc1F)c1ccccc1] | δ 7.54-7.61(m, 2H), 7.23-7.28(m, 4H), 6.82-7.04(m, 6H), 5.12(s, 2H), 4.81-4.91(t, 3H), 4.13-4.17(t, 1H), 3.98(s, 2H), 3.88(s, 1H), 2.95-3.03(q, 1H), 2.77-2.84(q, 1H) | 463.1 |
| 22 | 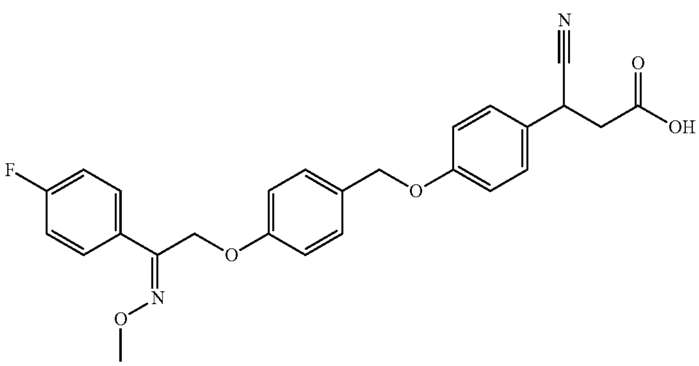 [SMILES: CO/N=C(/COc1ccc(COc2ccc(C(C#N)CC(=O)O)cc2)cc1)c1ccc(F)cc1] | δ 12.67(s, 1H), 7.64-7.67(q, 2H), 7.35-7.41(m, 5H), 7.18-7.28(m, 3H), 6.99-7.02(d, 2H), 5.31(s, 2H), 5.01(s, 2H), 4.35-4.40(q, 1H), 3.99(s, 3H), 2.95-3.04(q, 1H), 2.78-2.86(q, 1H) | 463.1 |
| 23 | 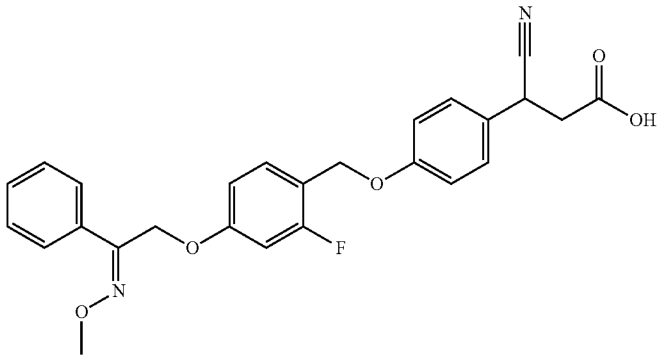 [SMILES: CO/N=C(/COc1ccc(COc2ccc(C(C#N)CC(=O)O)cc2)c(F)c1)c1ccccc1] | δ 12.7(s, 1H), 7.57-7.66(m, 3H), 7.36-7.47(m, 5H), 7.00-7.04(d, 2H), 6.77-6.97(m, 2H), 4.36-4.41(q, 1H), 4.00(s, 3H), 2.96-3.04(q, 1H), 2.79-2.86(q, 1H) | 463.1 |

TABLE 1-continued

| No | Structure | ¹H NMR | m/z |
|---|---|---|---|
| 24 | 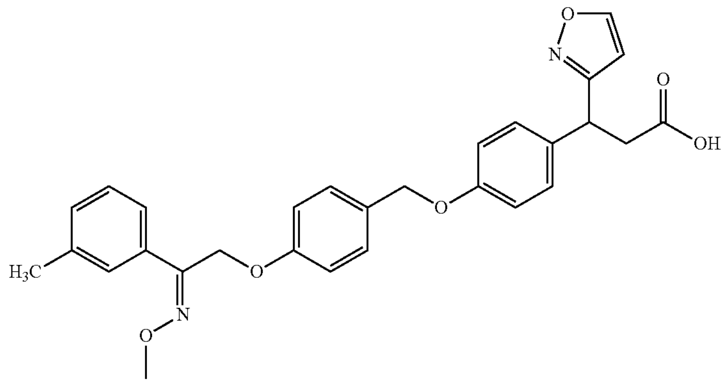 [SMILES: CO/N=C(/COc1ccc(COc2ccc(C(CC(=O)O)c3ccon3)cc2)cc1)c1cccc(C)c1] | δ 8.67(s, 1H), 7.38-7.46(s, 2H), 7.30-7.34(m, 2H), 7.15-7.28(m, 4H), 6.85-6.96(m, 4H), 6.43(s, 1H), 5.19(s, 2H), 4.94(s, 2H), 4.45(t, 1H), 3.98(s, 2H), 3.83(s, 1H), 3.39(t, J = 7.2 Hz, 1H), 2.64-2.71(m, 1H), 2.54-2.57(m, 1H), 2.31(s, 3H) | 501 |
| 25 | 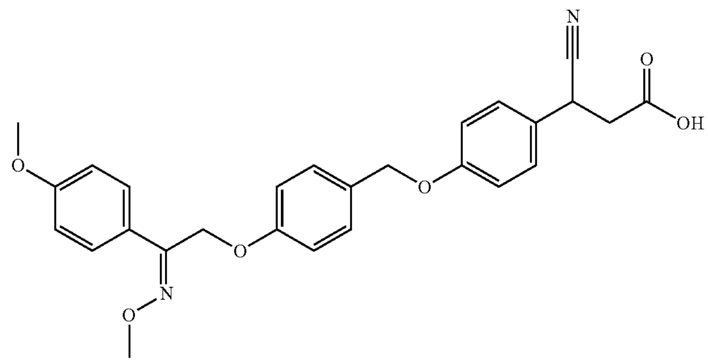 [SMILES: CO/N=C(/COc1ccc(COc2ccc(C(C#N)CC(=O)O)cc2)cc1)c1ccc(OC)cc1] | δ 7.48(d, 2H), 7.07(d, 2H), 7.01(m, 2H), 6.72(d, 4H), 6.66(d, 2H), 4.97(s, 2H), 4.59(s, 2H), 3.87(s, 3H), 3.64(s, 3H), 3.04(s, 2H), 2.59-2.70(m, 2H) | 475 |
| 26 | 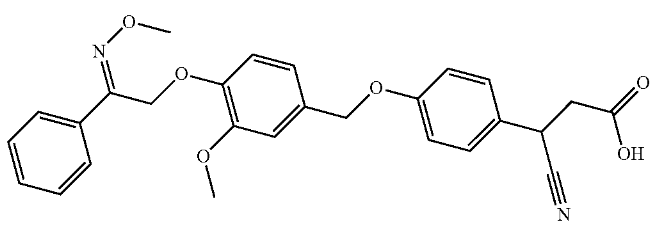 [SMILES: CO/N=C(\COc1ccc(COc2ccc(C(C#N)CC(=O)O)cc2)cc1OC)c1ccccc1] | δ 7.67-7.68(t, 2H), 7.34-7.48(m, 5H), 6.97-7.03(t, 5H), 5.18(s, 2H), 4.99(s, 2H), 4.35-4.40(t, 1H), 3.97(s, 3H), 3.68(s, 3H), 2.94-3.03(q, 3H), 2.83-2.85(q, 1H) | 475.1 |
| 27 | 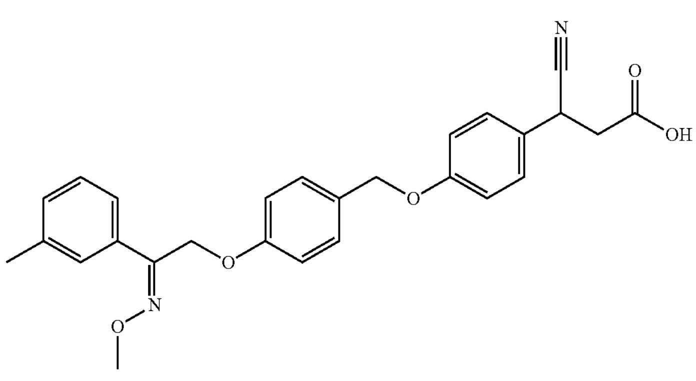 [SMILES: CO/N=C(/COc1ccc(COc2ccc(C(C#N)CC(=O)O)cc2)cc1)c1cccc(C)c1] | δ 7.42-7.47(m, 2H), 7.34-7.36(m, 2H), 7.26-7.31(m, 3H), 7.20-7.23(m, 1H), 6.91-6.97(m, 4H), 5.20(s, 2H), 4.93-4.99(d, 2H), 4.21-4.26(t, 4H), 3.99(s, 3H), 2.43-2.46(m, 1H), 2.31(s, 3H), 2.24-2.29(q, 1H) | 459.1 |

TABLE 1-continued

| No | Structure | ¹H NMR | m/z |
|---|---|---|---|
| 28 | 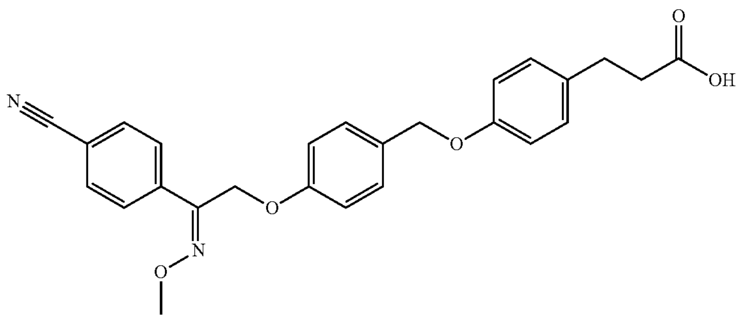 [SMILES: CO/N=C(/COc1ccc(COc2ccc(CCC(=O)O)cc2)cc1)c1ccc(C#N)cc1] | δ 12.08(s, 1H), 7.72-7.93(m, 4H), 7.33-7.35(d, 2H), 7.11-7.13(d, 2H), 6.87-6.95(q, 4H), 5.27(s, 2H), 4.96-5.00(d, 2H), 3.87-4.04(t, 3H), 2.71-2.76(t, 2H), 2.45-2.50(t, 2H) | 443 |
| 29 | 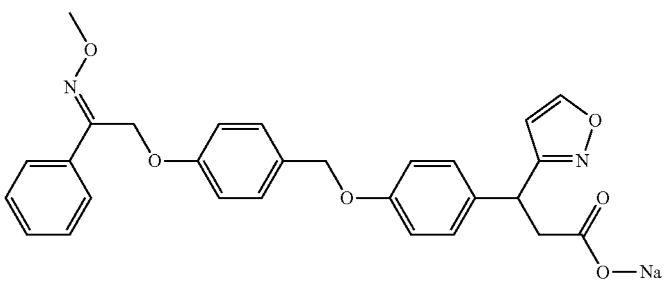 | δ 8.67(s, 1H), 7.62-7.65(q, 2H), 7.31-7.40(m, 5H), 7.14-7.17(d, 2H), 6.85-6.92(q, 4H), 6.43(s, 1H), 5.21(s, 2H), 4.94(s, 2H), 4.47-4.52(t, 1H), 3.99(s, 3H), 2.66-2.72(t, 1H), 2.54-2.64(t, 1H) | 487.1 |
| 30 | 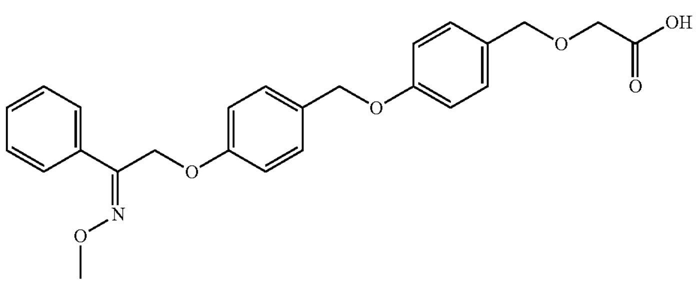 [SMILES: CO/N=C(/COc1ccc(COc2ccc(COCC(=O)O)cc2)cc1)c1ccccc1] | No data | 434.0 |
| 31 | 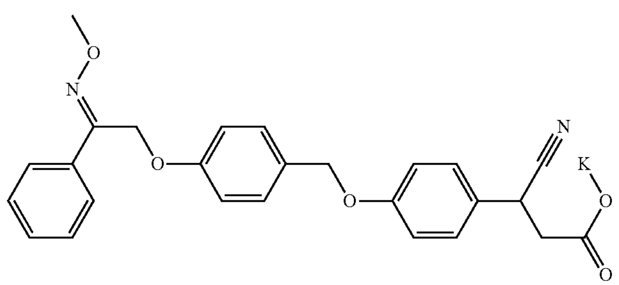 | δ 7.63-7.65(t, 2H), 7.35-7.41(m, 7H), 6.92-7.00(dd, 4H), 5.23(s, 2H), 4.96-5.02(d, 2H), 4.00(s, 3H), 2.38(s, 3H) | 445.1 |
| 32 | 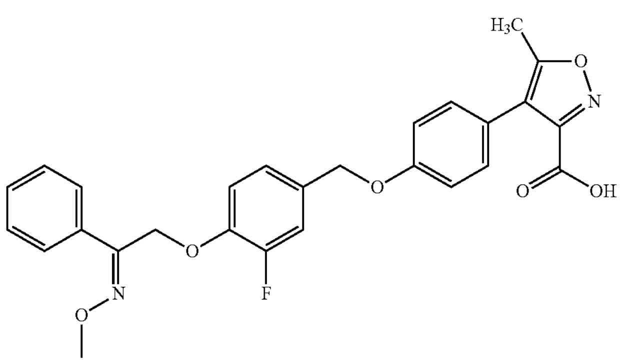 [SMILES: CO/N=C(/COc1ccc(COc2ccc(-c3c(C(=O)O)noc3C)cc2)cc1F)c1ccccc1] | δ 7.63-7.65(t, 2H), 7.33-7.41(m, 5H), 7.27-7.30(d, 2H), 6.91-6.97(t, 4H), 5.23(s, 2H), 4.96-4.99(d, 2H), 4.22-4.27(t, 2H), 4.00(s, 3H), 2.44-2.47(q, 1H), 2.25-2.32(q, 1H) | 473.1 |

TABLE 1-continued

| No | Structure | ¹H NMR | m/z |
|---|---|---|---|
| 33 | 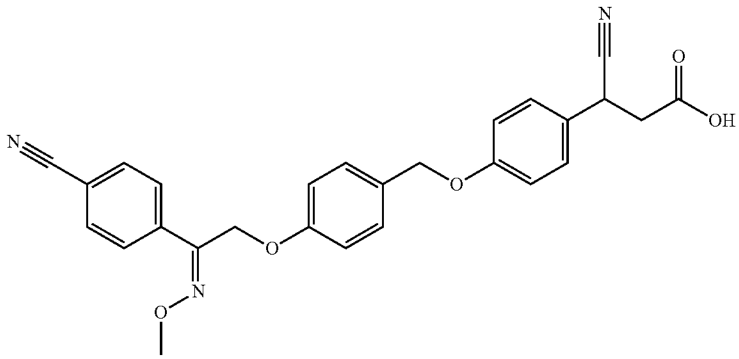 [SMILES: CO/N=C(/COc1ccc(COc2ccc(C(C#N)CC(=O)O)cc2)cc1)c1ccc(C#N)cc1] | δ 7.89-7.99(m, 2H), 7.21-7.83(m, 2H), 7.34-7.36(d, 4H), 6.98-7.01(d, 2H), 6.90-6.93(d, 2H), 5.28(s, 2H), 5.00(s, 2H), 4.34-4.39(t, 1H), 4.04(s, 3H), 2.92-3.01(q, 1H), 2.73-2.82(q, 1H) | 468.1 |
| 34 | 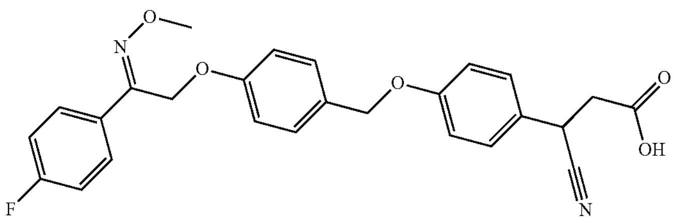 [SMILES: CO/N=C(\COc1ccc(COc2ccc(C(C#N)CC(=O)O)cc2)cc1)c1ccc(F)cc1] | ¹H(300 MHz, DMSO-d₆): δ 12.64(s, 1H), 7.66-7.71(m, 2H), 7.34-7.37(d, 4H), 7.21-7.26(m, 2H), 6.98-7.01(d, 2H), 6.90-6.93(d, 2H), 5.23(s, 2H), 5.00(s, 2H), 4.35-4.40(m, 1H), 3.99(s, 3H), 2.95-2.98(m, 1H), 2.77-2.85(m, 1). | 463.1 (M + H)⁺ |
| 35 | 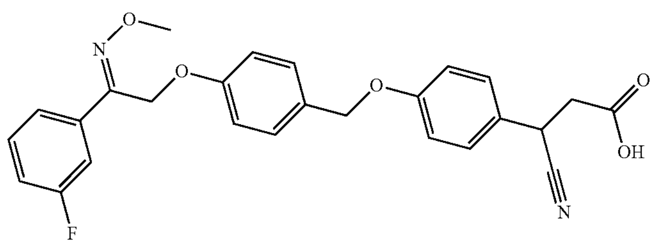 [SMILES: CO/N=C(\COc1ccc(COc2ccc(C(C#N)CC(=O)O)cc2)cc1)c1cccc(F)c1] | 1H(300 MHz, DMSO-d6): δ 7.43-7.48(m, 3H), 7.34-7.37(d, 2H), 7.26-7.29(d, 3H), 6.91-6.97(m, 4H), 5.23(s, 2H), 4.99(s, 2H), 4.24-4.27(m, 1H), 4.01(s, 3H), 2.43(s, 1H), 2.24-2.31(m, 1H). | 463.1 (M + H)⁺ |
| 36 | 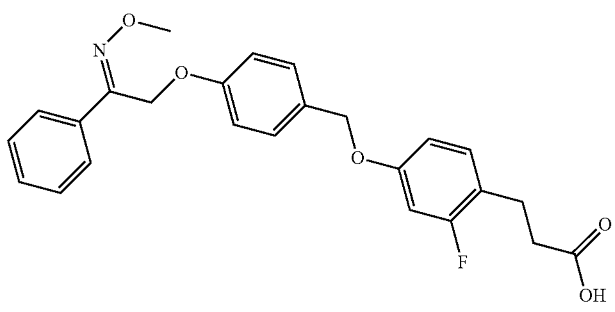 [SMILES: CO/N=C(\COc1ccc(COc2ccc(CCC(=O)O)c(F)c2)cc1)c1ccccc1] | 1H(300 MHz, DMSO-d6): δ 12.17(s, 1H), 7.62-7.66(m, 2H), 7.33-7.41(m, 5H), 7.16-7.22(t, 1H), 6.91-6.94(d, 2H), 6.74-6.85(m, 2H), 5.23(s, 2H), 4.98(s, 2H), 4.00(s, 3H), 2.73-2.78(t, 2H), 2.45-2.47(d, 2H). | 438.1 (M + H)⁺ |
| 37 | 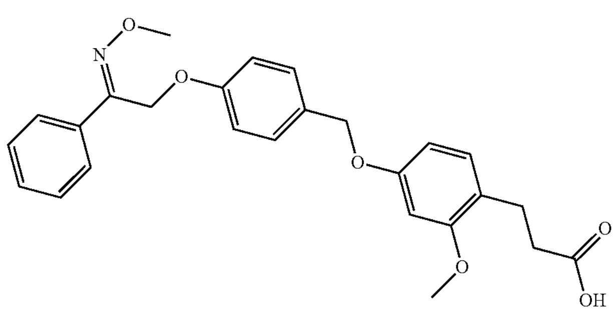 [SMILES: CO/N=C(\COc1ccc(COc2ccc(CCC(=O)O)c(OC)c2)cc1)c1ccccc1] | 1H(300 MHz, DMSO-d6): δ 12.05(s, 1H), 7.63-7.66(m, 2H), 7.33-7.41(m, 5H), 6.99-7.02(d, 1H), 6.91-6.93(d, 2H), 6.56-6.57(d, 1H), 6.47-6.50(dd, 1H), 5.23(s, 2H), 4.96(s, 2H), 3.99(s, 3H), 3.75(s, 3H), 2.66-2.71(t, 2H), 2.37-2.43(t, 2H) | 450.1 ((M + H)⁺ |

TABLE 1-continued
| No | Structure | ¹H NMR | m/z |
|---|---|---|---|
| 38 | 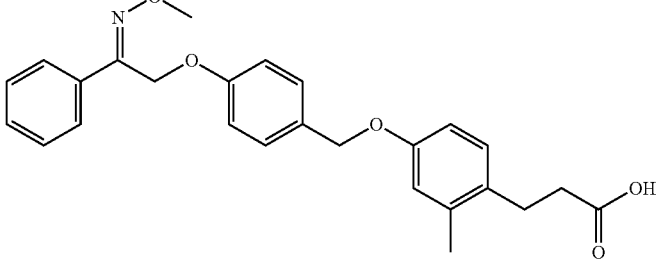 | 1H(300 MHz, DMSO-d6): δ 7.58-7.61(q, 2H), 7.23-7.29(m, 5H), 6.97-7.00(d, 1H), 6.83-6.86(d, 2H), 6.66-6.71(m, 2H), 5.13(s, 2H), 4.86(s, 2H), 3.98(s, 3H), 2.80-2.85(t, 2H), 2.51-2.56(t, 2H), 2.22(s, 3H) | 432.1 (M − H)+ |
| 39 | 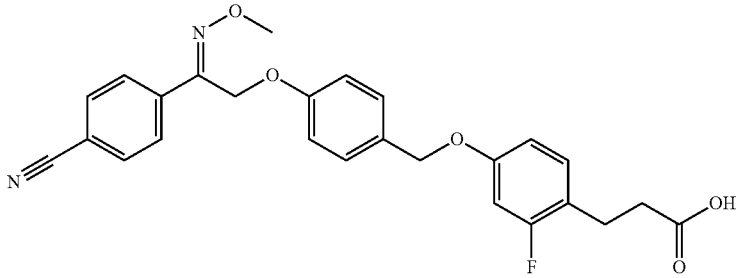 [SMILES: CO/N=C(\COc1ccc(COc2ccc(CCC(=O)O)c(F)c2)cc1)c1ccc(C#N)cc1] | 1H(300 MHz, DMSO-d6): δ 12.15(s, 1H), 7.80-7.89(m, 4H), 7.33-7.36(d, 2H), 7.16-7.22(m, 1H), 6.90-6.92(m, 2H), 6.80-6.85(m, 1H), 6.74-6.77(m, 1H), 5.28(s, 2H), 4.98(s, 2H), 4.04(s, 3H), 2.73-2.78(t, 2H), 2.44-2.47(d, 2H). | 461.1 ((M + H)+ |
| 40 | 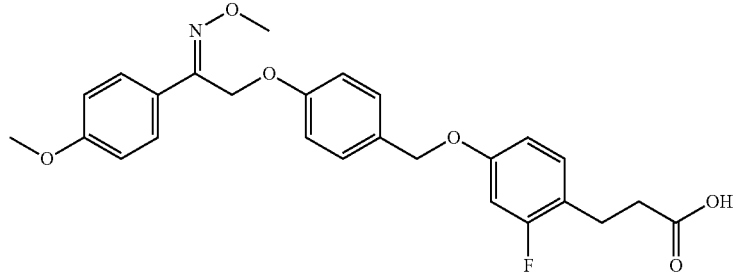 [SMILES: CO/N=C(\COc1ccc(COc2ccc(CCC(=O)O)c(F)c2)cc1)c1ccc(OC)cc1] | 1H(300 MHz, DMSO-d6): δ 12.15(s, 1H), 7.57-7.60(d, 2H), 7.33-7.36(d, 2H), 7.16-7.22(t, 1H), 6.91-6.96(t, 4H), 6.80-6.85(m, 1H), 6.74-6.77(m, 1H), 5.19(s, 2H), 4.98(s, 2H), 3.97(s, 3H), 3.77(s, 3H), 2.73-2.78(t, 2H), 2.44-2.47(d, 2H). | 468.1 ((M + H)+ |
| 41 | 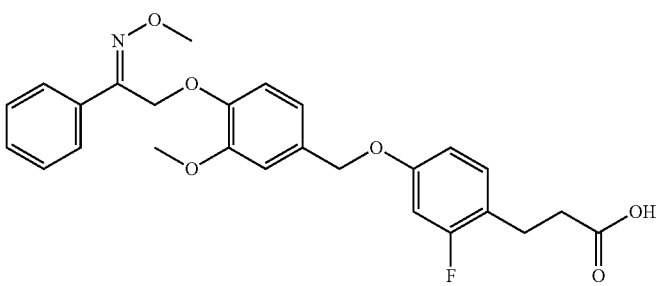 [SMILES: CO/N=C(\COc1ccc(COc2ccc(CCC(=O)O)c(F)c2)cc1OC)c1ccccc1] | 1H(300 MHz, DMSO-d6): δ 7.67-7.68(d, 2H), 7.41(s, 3H), 7.16-7.22(t, 1H), 6.96-7.02(m, 3H), 6.73-6.83(m, 2H), 5.18(s, 2H), 4.96(s, 2H), 3.97(s, 3H), 3.68(s, 3H), 2.70-2.73(d, 2H), 2.32-2.37(t, 2H). | 466.1 (M − H)+ |
| 42 | 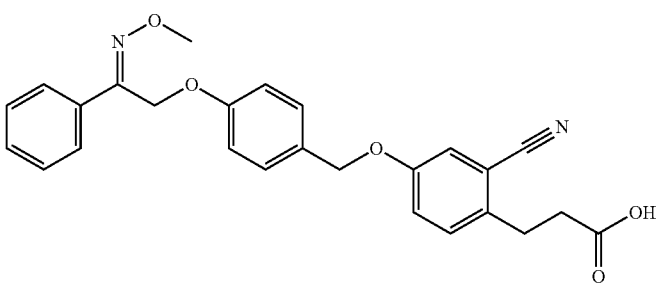 [SMILES: CO/N=C(\COc1ccc(COc2ccc(CCC(=O)O)c(C#N)c2)cc1)c1ccccc1] | No data | 443.1 (M − H)+ |

TABLE 1-continued

| No | Structure | ¹H NMR | m/z |
|---|---|---|---|
| 43 | 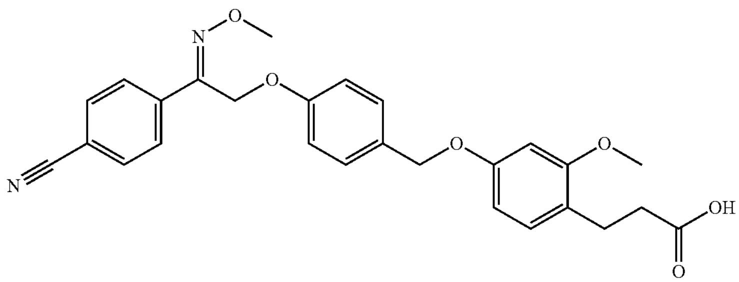 [SMILES: CO/N=C(\COc1ccc(COc2ccc(CCC(=O)O)c(OC)c2)cc1)c1ccc(C#N)cc1] | 1H(300 MHz, DMSO-d6): δ 12.05(s, 1H), 7.80-7.89(q, 4H), 7.34-7.37(d, 2H), 7.00-7.02(d, 1H), 6.90-6.92(d, 2H), 6.57(d, 1H), 6.46-6.50(m, 1H), 5.28(s, 2H), 4.96(s, 2H), 4.05(s, 3H), 3.75(s, 3H), 2.66-2.71(t, 2H), 2.38-2.43(t, 2H). | 473.1 (M − H)+ |
| 44 | 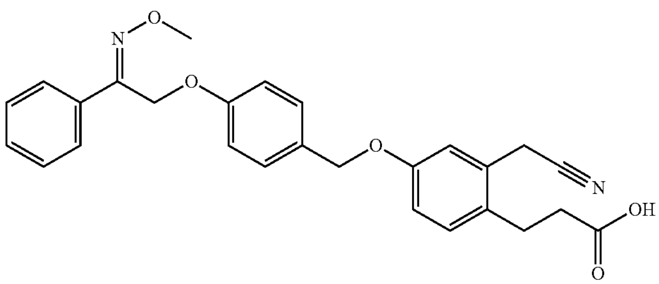 [SMILES: CO/N=C(\COc1ccc(COc2ccc(CCC(=O)O)c(CC#N)c2)cc1)c1ccccc1] | 1H(300 MHz, DMSO-d6): δ 12.20(s, 1H), 7.63-7.66(m, 2H), 7.34-7.41(m, 5H), 7.15-7.18(d, 1H), 6.99(s, 1H), 6.91-6.99(m, 3H), 5.23(s, 2H), 4.98(s, 2H), 4.01(s, 2H), 4.00(s, 3H), 2.74-2.79(m, 2H), 3.35(m, 2H). | 459.2 (M + H)+ |
| 45 | 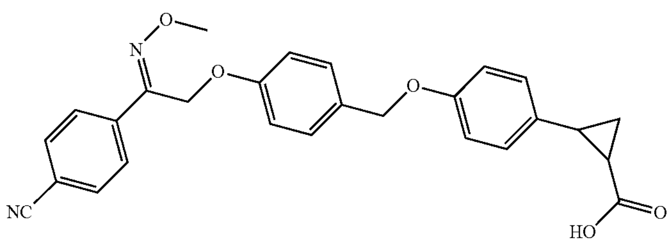 [SMILES: CO/N=C(\COc1ccc(COc2ccc(C3CC3C(=O)O)cc2)cc1)c1ccc(C#N)cc1] | 1H(300 MHz, DMSO-d6): δ 7.80-7.89(m, 4H), 7.32-7.35(d, 2H), 7.05-7.08(d, 2H), 6.87-6.91(m, 4H), 5.27(s, 2H), 4.97(s, 2H), 4.04(s, 3H), 2.27-2.35(m, 1H), 1.67-1.73(m, 1H), 1.23-1.41(m, 2H). | 455.1 (M − H)+ |
| 46 | 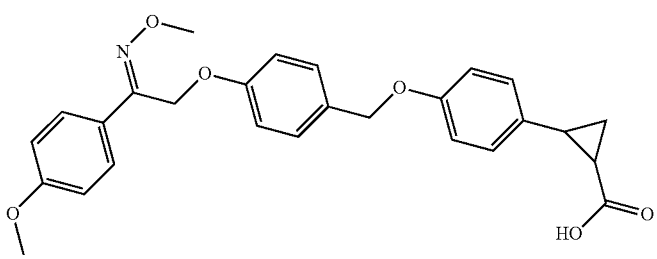 [SMILES: CO/N=C(\COc1ccc(COc2ccc(C3CC3C(=O)O)cc2)cc1)c1ccc(OC)cc1] | No data | 462.1 (M + H)+ |
| 47 | 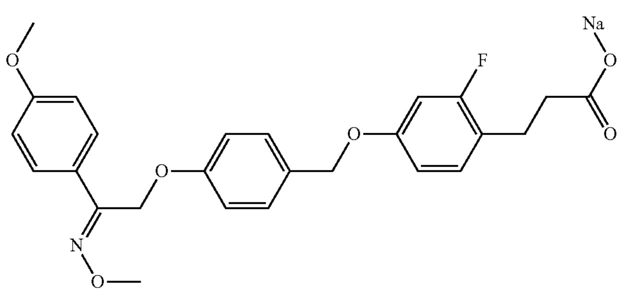 | 1H(300 MHz, DMSO-d6): δ 7.57-7.60(d, 2H), 7.32-7.35(d, 2H), 7.13-7.19(t, 1H), 6.90-6.96(t, 4H), 6.73-6.78(m, 1H), 6.68-6.73(m, 1H), 5.19(s, 2H), 4.96(s, 2H), 3.97(s, 3H), 3.77(s, 3H), 2.61-2.66(t, 2H), 1.99-2.04(t, 2H). | 468.1 (M + H)+ |
| 48 | 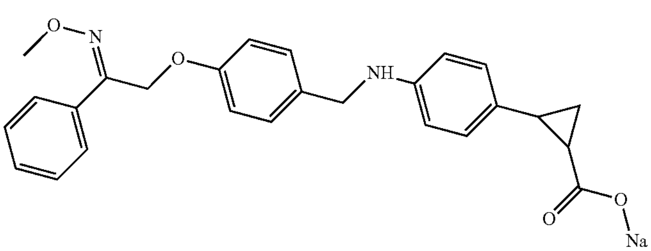 | 1H(300 MHz, DMSO-d6): δ 7.62-7.65(m, 2H), 7.38-7.40(m, 3H), 7.21-7.24(d, 2H), 6.83-6.86(d, 2H), 6.70-6.72(d, 2H), 6.42-6.45(d, 2H), 5.88-5.92(t, 1H), 5.18(s, 2H), 4.11-4.13(d, 2H), 3.98(s, 3H), 1.86-1.92(m, 1H), 1.24-1.32(m, 1H), 1.04-1.07(m, 1H), 0.90-0.95(m, 1H) | 431.3 (M + H)+ |

TABLE 1-continued

| No | Structure | ¹H NMR | m/z |
|---|---|---|---|
| 49 | 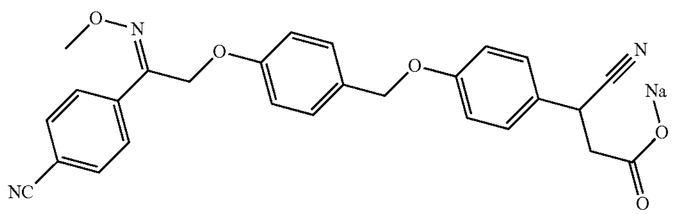 | 1H(300 MHz, CDCl3): δ 7.65-7.68(d, 2H), 7.48-7.55(t, 2H), 7.13-7.16(d, 2H), 7.07-7.09(d, 2H), 6.72-6.79(t, 4H), 5.06(S, 2H), 4.71(s, 2H), 4.10(s, 1H), 3.98(s, 3H), 2.66-2.78(m, 2H) | 468.1 ((M + H)+ |
| 50 | 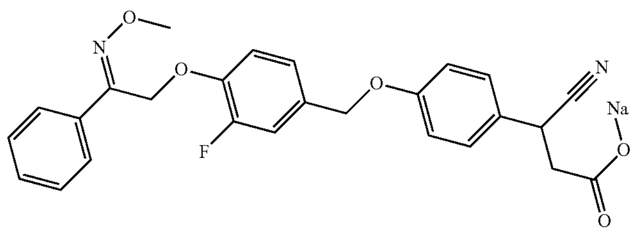 | 1H(300 MHz, DMSO-d6): δ 7.64-7.67(m, 2H), 7.40-7.42(m, 3H), 7.16-7.30(m, 5H), 6.95-6.98(d, 2H), 5.31(s, 2H), 4.96-5.04(m, 2H), 4.22-4.26(m, 1H), 3.99(s, 3H), 2.42-2.45(m, 1H), 2.23-2.30(m, 1H). | 461.1 (M − H)+ |
| 51 | 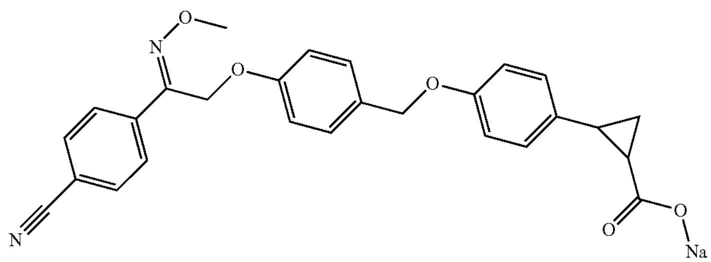 | 1H(300 MHz, DMSO-d6): δ 7.80-7.89(m, 4H), 7.32-7.35(d, 2H), 7.04-7.07(d, 2H), 6.86-6.91(m, 4H), 5.27(s, 2H), 4.96(s, 2H), 4.04(s, 3H), 2.28-2.33(m, 2H), 1.65-1.71(m, 1H), 1.32-1.38(m, 1H). | 455.1 (M − H)+ |
| 52 | 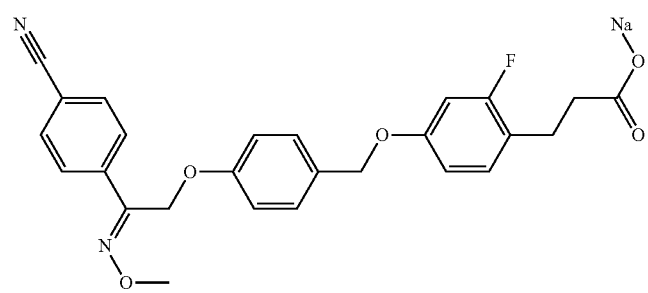 | 1H(300 MHz, DMSO-d6): δ 7.80-7.89(m, 4H), 7.33-7.35(d, 2H), 7.14-7.20(t, 1H), 6.89-6.92(d, 2H), 6.68-6.78(m, 2H), 5.27(s, 2H), 4.96(s, 2H), 4.04(s, 3H), 2.63-2.66(m, 2H), 2.04-2.09(m, 2H). | 461.1 (M − H)+ |
| 53 | 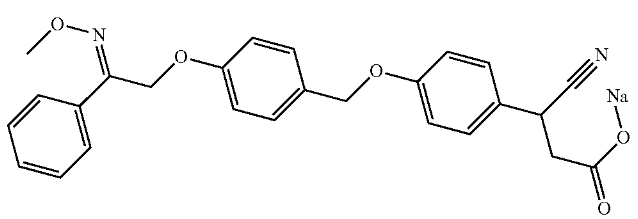 | 1H(300 MHz, DMSO-d6): δ 7.56-7.58(d, 2H), 7.41-7.43(m, 3H), 7.34-7.37(d, 2H), 7.26-7.29(d, 2H), 6.94-6.97(m, 4H), 4.99(s, 2H), 4.95(s, 2H), 4.21-4.25(t, 1H), 3.84(s, 3H), 2.40-2.46(m, 1H), 2.23-2.28(m, 1H). | 445.1 (M + H)+ |
| 54 | 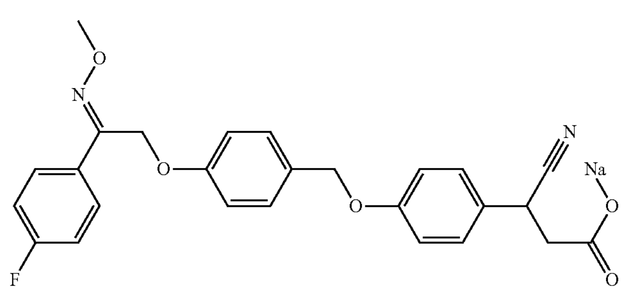 | 1H(300 MHz, DMSO-d6): δ 7.66-7.71(m, 2H), 7.34-7.37(d, 4H), 7.21-7.26(t, 2H), 6.98-7.01(d, 2H), 6.90-6.93(d, 2H), 5.23(s, 2H), 5.00(s, 2H), 4.35-4.40(m, 1H), 3.99(s, 3H), 2.95-2.98(m, 1H), 2.77-2.85(m, 1H). | 463.1 (M + H)+ |

TABLE 1-continued

| No | Structure | ¹H NMR | m/z |
|---|---|---|---|
| 55 | 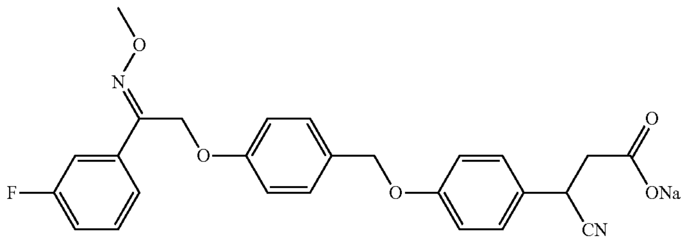 | 1H(300 MHz, DMSO-d6): δ 7.43-7.48(m, 3H), 7.34-7.37(d, 2H), 7.26-7.29(d, 3H), 6.91-6.97(m, 4H), 5.23(s, 2H), 4.99(s, 2H), 4.24-4.27(d, 1H), 4.01(s, 3H), 2.43(s, 1H), 2.24-2.31(m, 1H). | 463.1 (M + H)⁺ |
| 56 | 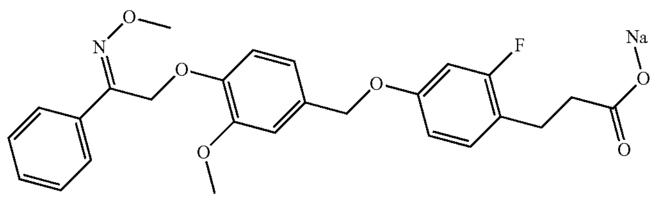 | No data | 468.1 (M + H)⁺ |
| 57 | 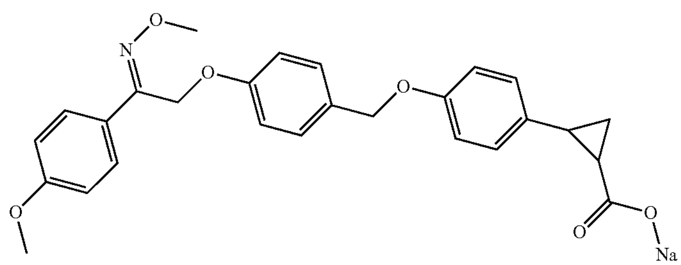 | No data | 462.1 (M + H)⁺ |
| 58 | 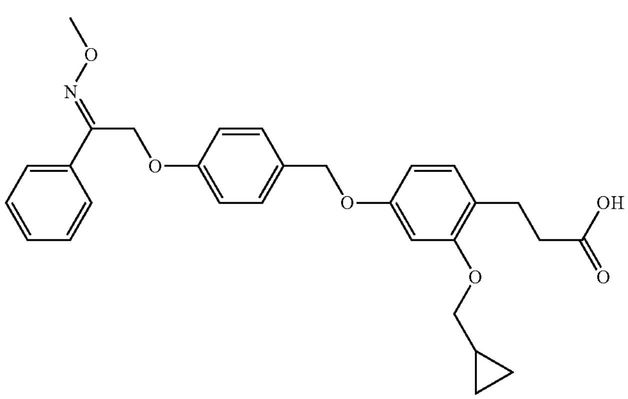 [SMILES: CO/N=C(\COc1ccc(COc2ccc(CCC(=O)O)c(OCC3CC3)c2)cc1)c1ccccc1] | 1H(300 MHz, DMSO-d6): δ 12.03(s, 1H), 7.62-7.65(m, 2H), 7.39-7.41(m, 3H), 7.32-7.35(d, 2H), 6.99-7.02(d, 1H), 6.90-6.93(m, 2H), 6.53-6.54(d, 1H), 6.45-6.48(d, 1H), 5.23(s, 2H), 4.94(s, 2H), 4.00(s, 3H), 3.80-3.82(d, 2H), 2.68-2.73(t, 2H), 2.42-2.47(t, 2H), 1.25(m, 1H), 0.52-0.58(m, 2H), 0.32-0.34(m, 2H) | 490.2 (M + H)⁺ |
| 59 | 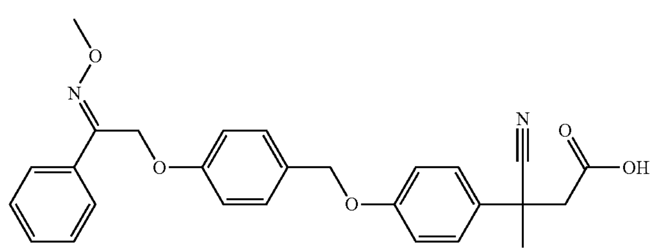 [SMILES: CO/N=C(\COc1ccc(COc2ccc(C(C)(C#N)CC(=O)O)cc2)cc1)c1ccccc1] | 1H(300 MHz, DMSO-d6): δ 7.63-7.65(m, 2H), 7.34-7.41(m, 7H), 6.91-6.98(m, 4H), 5.23(s, 2H), 4.98(s, 2H), 4.00(s, 3H), 2.63-2.65(s, 2H), 1.65(s, 3H). | 459.2 (M + H)⁺ |

TABLE 1-continued

| No | Structure | ¹H NMR | m/z |
|---|---|---|---|
| 60 | 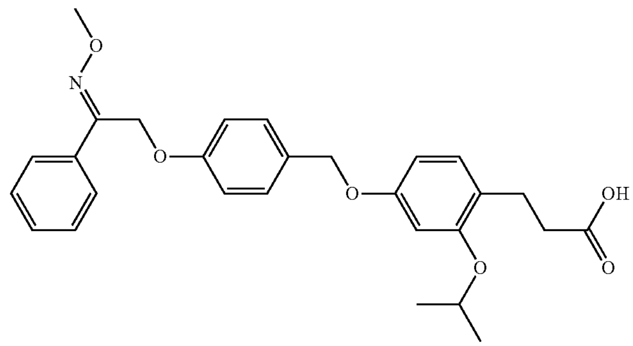 [SMILES: CO/N=C(\COc1ccc(COc2ccc(CCC(=O)O)c(OC(C)C)c2)cc1)c1ccccc1] | 1H(300 MHz, DMSO-d6): δ 12.01(s, 1H), 7.62-7.65(m, 2H), 7.33-7.41(m, 6H), 6.98-7.01(d, 1H), 6.90-6.93(d, 2H), 6.55-6.56(d, 1H), 6.43-6.47(m, 1H), 5.23(s, 2H), 4.95(s, 2H), 4.54-4.62(m, 1H), 4.00(s, 3H), 2.64-2.69(t, 2H), 2.38-2.43(t, 2H), 1.23-1.25(d, 6H). | 478.2 (M + H)⁺ |
| 61 | 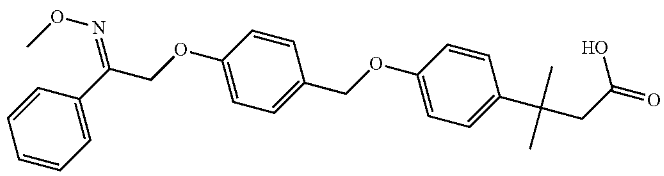 [SMILES: CO/N=C(/COc1ccc(COc2ccc(C(C)(C)CC(=O)O)cc2)cc1)c1ccccc1] | No data | 447.2 (M − H)⁺ |
| 62 | 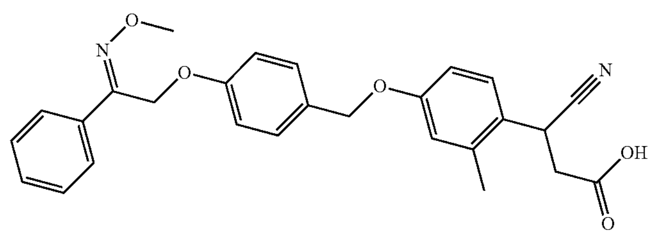 [SMILES: CO/N=C(\COc1ccc(COc2ccc(C(C#N)CC(=O)O)c(C)c2)cc1)c1ccccc1] | 1H(300 MHz, DMSO-d6): δ 12.67(s, 1H), 7.63-7.66(m, 2H), 7.31-7.41(m, 6H), 6.86-6.95(m, 4H), 5.23(s, 2H), 4.99(s, 2H), 4.37-4.42(m, 1H), 4.00(s, 3H), 2.93-3.02(m, 1H), 2.78-2.86(m, 1H), 2.32(s, 3H) | 457.1 (M − H)⁺ |
| 63 | 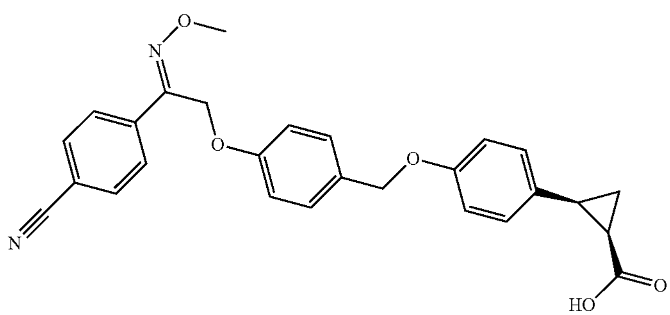 [SMILES: CO/N=C(\COc1ccc(COc2ccc([C@H]3C[C@H]3C(=O)O)cc2)cc1)c1ccc(C#N)cc1] | 1H(300 MHz, DMSO-d6): δ 12.11(br s, 1H), 7.80-7.89(m, 4H), 7.32-7.35(d, 2H), 7.05-7.08(d, 2H), 6.87-6.91(m, 4H), 5.27(s, 2H), 4.97(s, 2H), 4.03(s, 3H), 2.27-2.35(m, 1H), 1.67-1.73(m, 1H), 1.33-1.39(m, 1H) | 455.1 (M − H)⁺ |
| 64 | 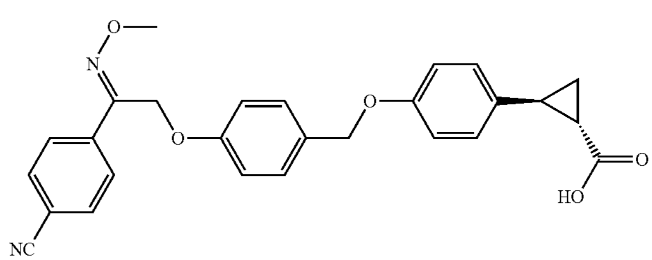 [SMILES: CO/N=C(\COc1ccc(COc2ccc([C@H]3C[C@@H]3C(=O)O)cc2)cc1)c1ccc(C#N)cc1] | 1H(300 MHz, DMSO-d6): δ 12.22(br s, 1H), 7.72-7.89(m, 4H), 7.32-7.35(d, 2H), 7.05-7.08(d, 2H), 6.87-6.91(m, 4H), 5.27(s, 2H), 4.97(s, 2H), 4.03(s, 3H) 2.29-2.35(m, 1H), 1.67-1.73(m, 1H), 1.33-1.39(m, 1H), 1.24-1.29(m, 1H) | 455.1 (M − H)⁺ |
| 65 | 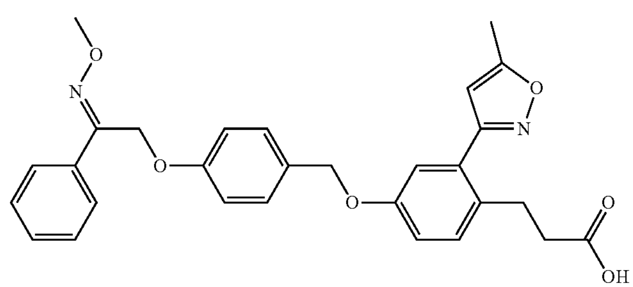 [SMILES: CO/N=C(\COc1ccc(COc2ccc(CCC(=O)O)c(-c3cc(C)on3)c2)cc1)c1ccccc1] | 1H(300 MHz, CDCl3): δ 8.02(s, 1H), 7.57-7.60(t, 2H), 7.27-7.29(m, 2H), 7.22-7.25(m, 3H), 6.96 (br, 1H), 6.83-6.85(m, 2H), 6.05(s, 1H), 5.12(s, 2H), 4.86(s, 2H), 3.98(s, 3H) 2.98(t, 2H), 2.53(t, 2H), 2.38(s, 3H). | 501 (M + H)⁺ |

TABLE 1-continued

| No | Structure | ¹H NMR | m/z |
|---|---|---|---|
| 66 | 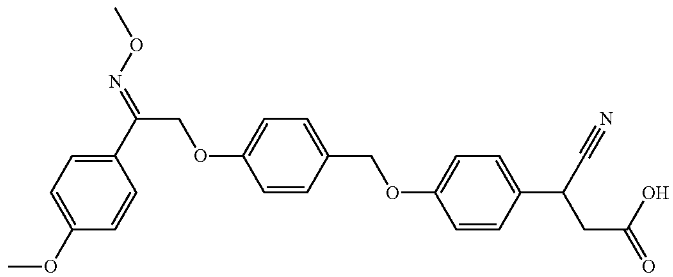 [SMILES: CO/N=C(\COc1ccc(COc2ccc(C(C#N)CC(=O)O)cc2)cc1)c1ccc(OC)cc1] | 1H(300 MHz, DMSO-d6): δ 7.48(d, 2H), 7.07(d, 2H), 7.01(m, 2H), 6.72(d, 4H), 6.66(d, 2H), 4.97(s, 2H), 4.59(s, 2H), 4.12-4.17(m, 1H) 3.87(s, 3H), 3.64(s, 3H), 3.04(s, 2H), 2.59-2.70 (m, 2H) | 475.1 (M + H)⁺ |
| 67 | 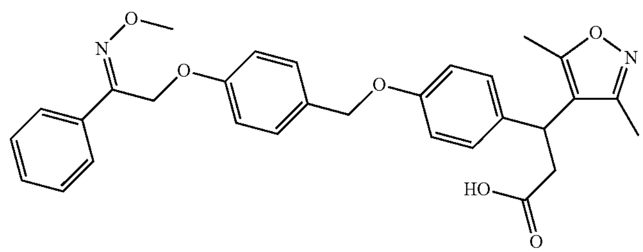 [SMILES: CO/N=C(\COc1ccc(COc2ccc(C(CC(=O)O)c3c(C)noc3C)cc2)cc1)c1ccccc1] | NO data | 515.1 (M + H)⁺ |
| 68 | 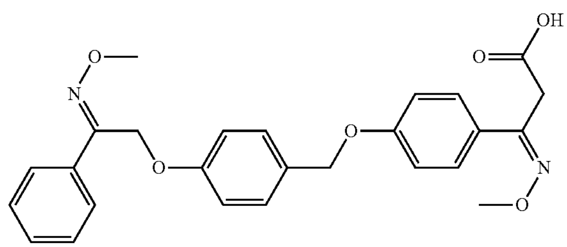 [SMILES: CO/N=C(\COc1ccc(COc2ccc(/C(CC(=O)O)=N\OC)cc2)cc1)c1ccccc1] | 1H(300 MHz, DMSO-d6): δ 7.63-7.65(m, 2H), 7.58(d, 2H), 7.34-7.41(m, 5H), 6.91-6.94(m, 4H), 5.22(s, 2H), 5.01(s, 2H), 4.00(s, 3H), 3.79(s, 3H), 3.26(s, 2H) | 463.1 (M + H)⁺ |
| 69 | 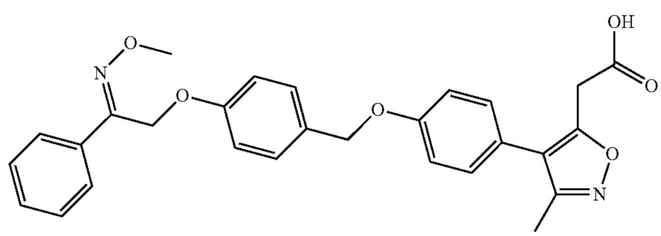 [SMILES: CO/N=C(\COc1ccc(COc2ccc(-c3c(C)noc3CC(=O)O)cc2)cc1)c1ccccc1] | 1H(300 MHz, DMSO-d6): δ 12.88(s, 1H), 7.63-7.66(m, 2H), 7.37-7.41(m, 5H), 7.28-7.31(d, 2H), 7.07-7.10(d, 2H), 6.93-6.95(d, 2H), 5.24(s, 2H), 5.03(s, 2H), 4.00(s, 3H), 3.77(s, 2H), 2.22(s, 3H) | 487.1 (M + H)⁺ |
| 70 | 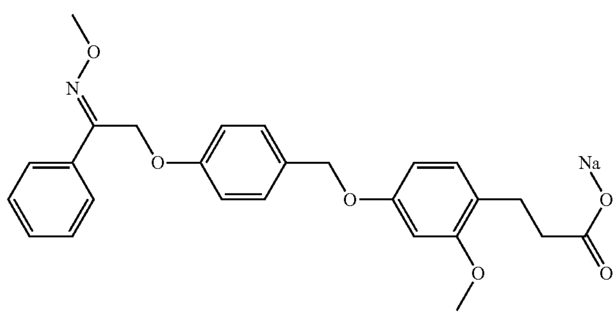 | 1H(300 MHz, DMSO-d6): δ 7.64-7.65(d, 2H), 7.33-7.40(m, 5H), 6.90-7.00(m, 3H), 6.43-6.52(m, 2H), 5.23 (s, 2H), 4.95(s, 2H), 3.99(s, 3H), 3.72(s, 3H), 2.58-2.63(t, 2H), 2.00-2.05(t, 2H) | 448.1 (M − H)⁺ |

TABLE 1-continued

| No | Structure | ¹H NMR | m/z |
|---|---|---|---|
| 71 | 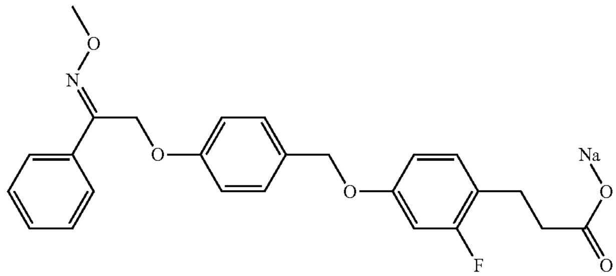 | 1H(300 MHz, DMSO-d6): δ 7.64(m, 2H), 7.33-7.40(m, 5H), 7.14-7.19(t, 1H), 6.91-6.93(d, 2H), 6.69-6.78(m, 2H), 5.23(s, 2H), 4.95(s, 2H) 3.99(s, 3H), 2.63-2.68(t, 2H), 2.04-2.09(t, 2H) | 436.1 (M − H)⁺ |
| 72 | 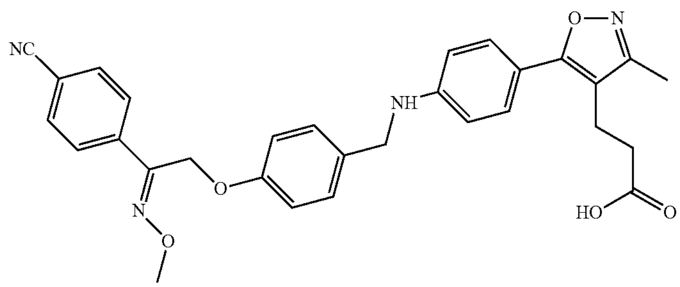 [SMILES: CO/N=C(\COc1ccc(CNc2ccc(-c3onc(C)c3CCC(=O)O)cc2)cc1)c1ccc(C#N)cc1] | 1H(300 MHz, DMSO-d6): δ 12.27(s, 1H), 7.80-7.89(q, 4H), 7.37-7.40(d, 2H), 7.26-7.29(d, 2H), 6.86-6.89(d, 2H), 6.74-6.78(t, 1H), 6.66-6.69(d, 2H), 5.24(s, 2H), 4.23-4.25(d, 2H), 4.03-4.06(d, 3H), 2.72-2.77(t, 2H), 2.40-2.45(t, 2H), 2.20(s, 3H) | 525.2 (M + H)⁺ |
| 73 | 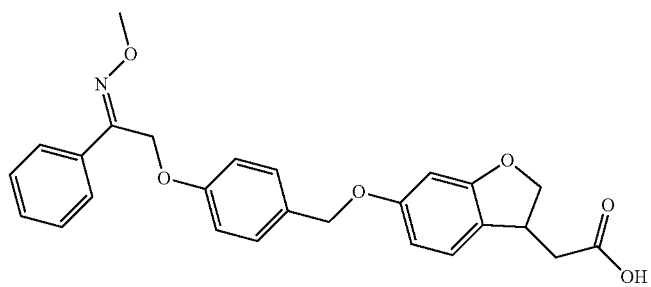 [SMILES: CO/N=C(\COc1ccc(COc2ccc3c(c2)OCC3CC(=O)O)cc1)c1ccccc1] | 1H(300 MHz, CDCl3): δ 7.59 (s, 1H), 7.20-7.29(m, 6H), 6.97-6.70 (d, 1H), 6.83-6.86(d, 2H), 6.39-6.42(d, 2H), 5.13(s, 2H), 4.85(s, 2H), 4.66-4.72(t, 1H), 4.20-4.22(t, 1H), 3.99(s, 3H), 3.74(s, 1H), 2.70-2.76(d, 1H), 2.50-2.59(m, 1H). | 446.1 (M − H)⁺ |
| 74 | 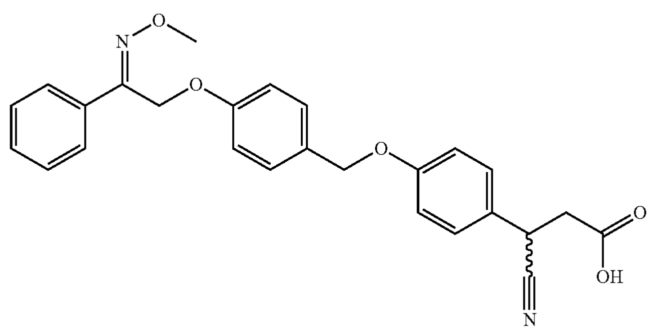 [SMILES: CO/N=C(\COc1ccc(COc2ccc(C(C#N)CC(=O)O)cc2)cc1)c1ccccc1] | 1H(300 MHz, DMSO-d6): δ 7.62-7.65(t, 2H), 7.33-7.40(m, 7H), 6.98-7.01(d, 2H), 6.90-6.94(d, 2H), 5.22(s, 2H), 4.98(s, 2H), 4.35-4.39(t, 1H), 3.98(s, 3H), 2.94-3.03(dd, 1H), 2.77-2.85(dd, 1H) | — |
| 75 | 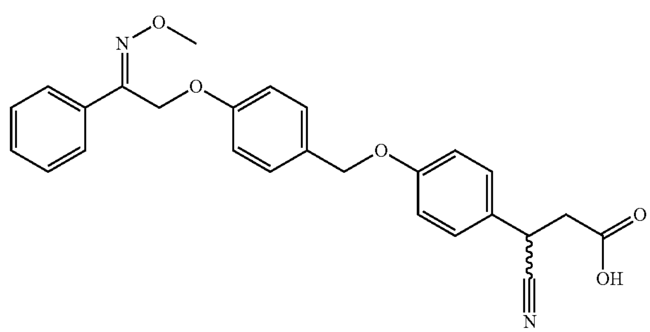 [SMILES: CO/N=C(\COc1ccc(COc2ccc(C(C#N)CC(=O)O)cc2)cc1)c1ccccc1] | 1H(300 MHz, DMSO-d6): δ 7.63-7.65(t, 2H), 7.26-7.40(m, 7H), 6.90-6.97(m, 4H), 5.22(s, 2H), 4.98(s, 2H), 4.21-4.26(t, 1H), 3.99(s, 3H), 2.45-2.53(dd, 1H), 2.24-2.31(dd, 1H) | 445.2 (M + H)⁺ |

TABLE 1-continued

| No | Structure | ¹H NMR | m/z |
|---|---|---|---|
| 76 | 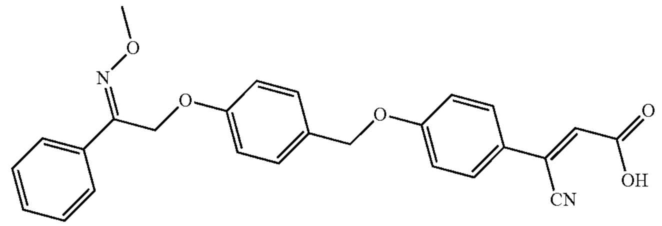 [SMILES: CO/N=C(\COc1ccc(COc2ccc(/C(C#N)=C/C(=O)O)cc2)cc1)c1ccccc1] | 1H(300 MHz, DMSO-d6): δ 7.62-7.66(q, 2H), 7.51-7.55(d, 2H), 7.37-7.41(m, 4H), 7.34(s, 1H), 7.02-7.05(d, 2H), 6.94-6.96(d, 2H), 6.91(s, 1H), 5.23(s, 2H), 5.03(s, 2H), 3.99(s, 3H) | 443.2 (M + H)⁺ |
| 77 | 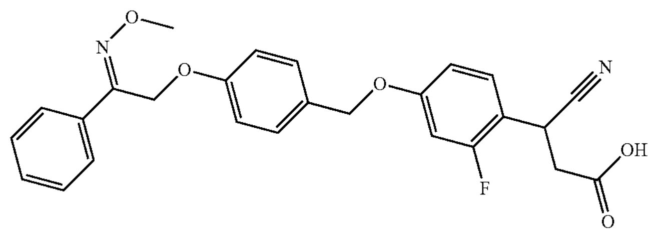 | 1H(300 MHz, CDCl3): δ 7.57-7.60(m, 2H), 7.18-7.29(m, 6H), 6.83-6.86(d, 2H), 6.61-6.72(m, 2H), 5.13(s, 2H), 4.88(s, 2H), 4.32-4.37(m, 1H), 3.98(s, 3H), 2.92-3.01(m, 1H), 2.80-2.88(m, 1H) | 463.2 (M − H)⁺ |
| 78 | 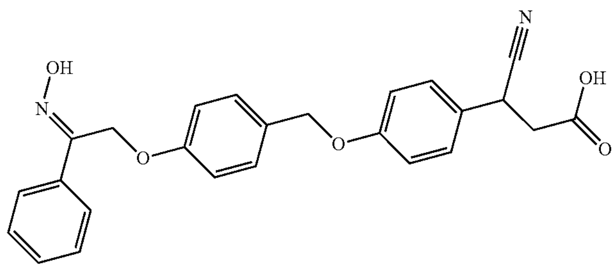 [SMILES: N#CC(CC(=O)O)c1ccc(OCc2ccc(OC/C(=N\O)c3ccccc3)cc2)cc1] | 1H(300 MHz, DMSO-d6): 12.65(s, 1H), 11.90(s, 1H), 7.66-7.63(t, 2H), 7.38-7.33(t, 7H), 7.01-6.93 (q, 4H), 5.25(s, 2H), 4.99(s, 2H), 4.39-4.34(q, 1H), 3.02-2.94(q, 1H), 2.84-2.77(q, 1H) | 429.0 (M − H)⁺ |
| 79 | 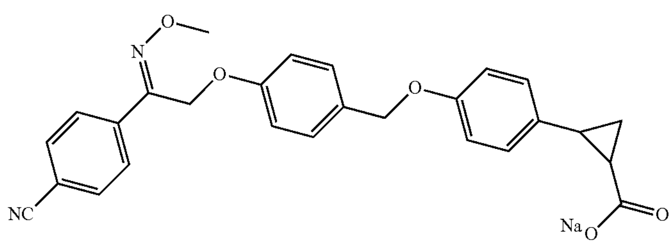 | No data | 455.1 (M − H)⁺ |
| 80 | 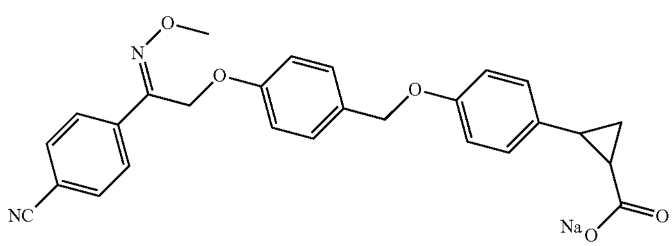 | 1H(300 MHz, DMSO-d6): δ 7.80-7.89(q, 4H), 7.31-7.35(d, 2H), 6.88-6.93(m, 4H), 6.81-6.84(m, 2H), 5.27(s, 2H), 4.94(s, 2H), 4.04(s, 3H), 1.92-1.98(m, 1H), 1.29-1.35(m, 2H), 1.05-1.10(m, 1H) | 455.1 (M − H)⁺ |
| 81 | 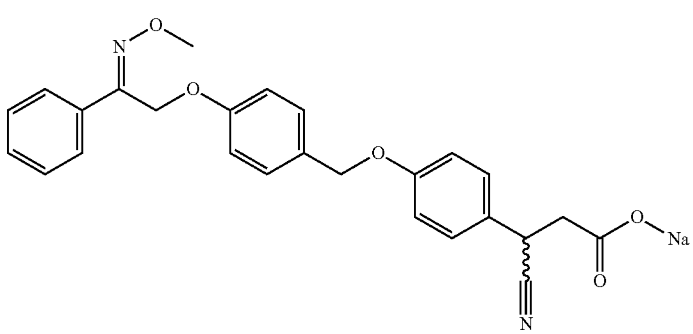 | 1H(300 MHz, DMSO-d6): δ 7.63-7.66(m, 2H), 7.33-7.41(m, 5H), 7.26-7.15(d, 2H), 6.91-6.97(m, 2H), 5.21(s, 2H), 4.99(s, 2H), 4.21-4.26(t, 1H), 4.0(s, 3H), 2.41-2.48(m, 1H), 2.23-2.30(m, 1H) | 445.2 (M + H)⁺ |

TABLE 1-continued

| No | Structure | ¹H NMR | m/z |
|---|---|---|---|
| 82 | 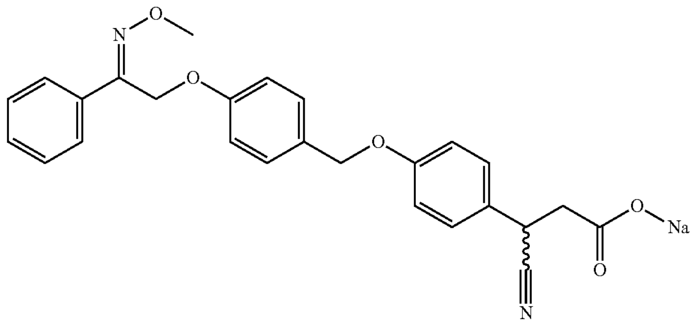 | No data | (M − H)⁺ |
| 83 | 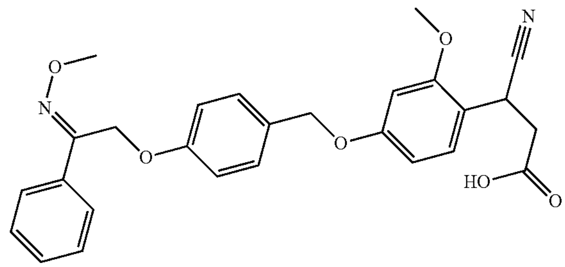 [SMILES: CO/N=C(\COc1ccc(COc2ccc(C(C#N)CC(=O)O)c(OC)c2)cc1)c1ccccc1] | 1H(300 MHz, CDCl3): δ 7.57-7.6(m, 2H), 7.20-7.29(m, 6H), 6.84-6.86(d, 2H), 6.45-6.47(d, 2H), 5.13(s, 2H), 4.87(s, 2H), 4.37-4.39(m, 1H), 3.98(s, 3H), 3.74(s, 3H), 2.85(m, 2H) | 473.1 (M − H)⁺ |
| 84 | 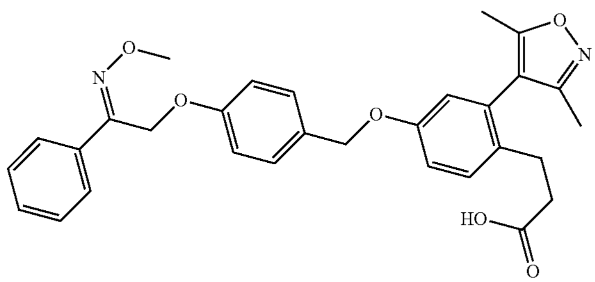 [SMILES: CO/N=C(\COc1ccc(COc2ccc(CCC(=O)O)c(-c3c(C)noc3C)c2)cc1)c1ccccc1] | 1H(300 MHz, CDCl3): δ 8.02-8.04(m, 1H), 7.58-7.61(m, 1H), 7.25-7.29(m, 3H), 7.14-7.25(m, 3H), 6.83-6.90(m, 3H), 6.58-6.59(m, 1H), 5.13(s, 2H(, 4.88(s, 2H), 3.98(s, 3H), 2.59-2.63(t, 2H), 2.32-2.37(t, 2H), 2.16(s, 3H), 2.00(s, 3H) | 513.2 (M − H)⁺ |
| 85 | 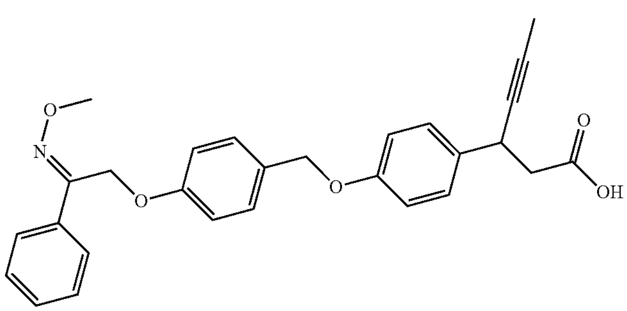 [SMILES: CC#CC(CC(=O)O)c1ccc(OCc2ccc(OC/C(=N\OC)c3ccccc3)cc2)cc1] | 1H(300 MHz, CDCl3): δ 7.56-7.59(m, 2H), 7.18-7.27(m, 7H), 6.78-6.83(m, 4H), 5.11(s, 2H), 4.82(s, 2H), 3.97(s, 4H), 2.55-2.72(m, 2H), 1.71(s, 3H) | 456.1 (M − H)⁺ |
| 86 | 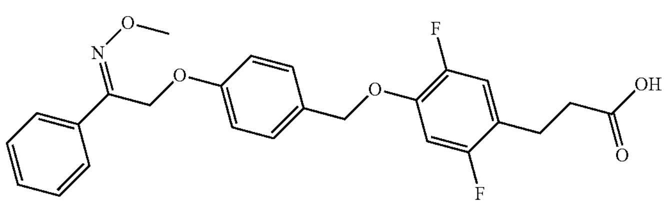 [SMILES: CO/N=C(\COc1ccc(COc2cc(F)c(CCC(=O)O)cc2F)cc1)c1ccccc1] | (300 MHz, DMSO-d6): δ 7.64-7.65(d, 2H) 7.34-, 7.41(m, 5H), 7.06-7.19(m, 2H), 6.92-6.95(m, 2H), 5.23(s, 2H), 5.03(s, 2H), 3.99(s, 3H) 2.65-2.67(t, 2H), 2.18-2.23(t, 2H) | 454.1 (M − H)⁺ |

TABLE 1-continued

| No | Structure | ¹H NMR | m/z |
|----|-----------|--------|-----|
| 87 | 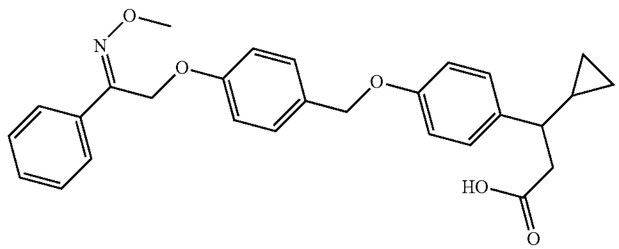 [SMILES: CO/N=C(\COc1ccc(COc2ccc(C(CC(=O)O)C3CC3)cc2)cc1)c1ccccc1] | 1H(300 MHz, DMSO-d6): δ 11.93(s, 1H), 7.57-7.65(m, 2H), 7.26-7.40(m, 5H), 7.06-7.16(m, 2H), 6.80-6.93(m, 4H), 5.22(s, 2H), 4.95(s, 2H), 3.99(s, 3H), 2.52-2.63(m, 2H), 2.14-2.26(m, 1H), 0.93-0.96(m, 1H), 0.43-0.49(m, 1H), 0.09-0.31(m, 2H), 0.05-0.08(m, 1H) | 460.2 (M + H)⁺ |
| 88 | 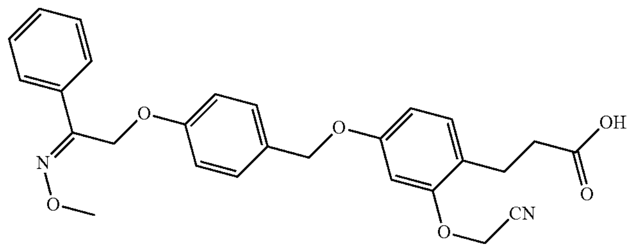 [SMILES: CO/N=C(\COc1ccc(COc2ccc(CCC(=O)O)c(OCC#N)c2)cc1)c1ccccc1] | No data | 475.2 (M + H)⁺ |
| 89 | 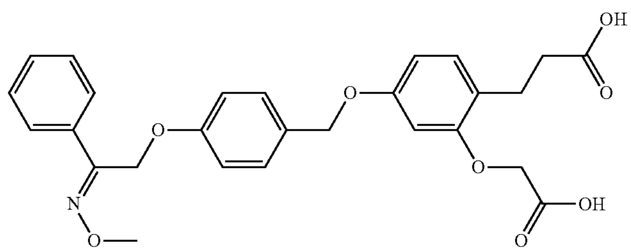 [SMILES: CO/N=C(\COc1ccc(COc2ccc(CCC(=O)O)c(OCC(=O)O)c2)cc1)c1ccccc1] | 1H(300 MHz, MeOD): 7.54-7.56(t, 2H), 7.20-7.26(m, 5H), 6.95-6.81(m, 1H), 6.78-6.81(m, 2h), 6.34-6.46(m, 2H), 5.15(s, 2H), 4.85(s, 2H), 4.37(d, 2H), 3.22-3.23(t, 3H), 2.79-2.84(t, 2H), 2.30-2.35(t, 2H) | 493.2 (M + H)⁺ |
| 90 | 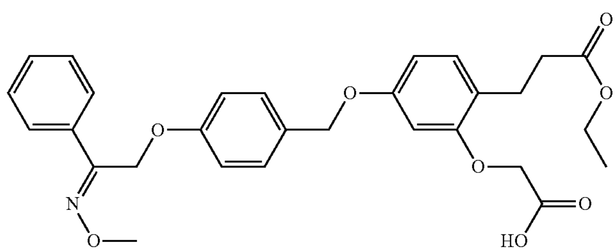 [SMILES: CCOC(=O)CCc1ccc(OCc2ccc(OC/C(=N\OC)c3ccccc3)cc2)cc1OCC(=O)O] | 1H(300 MHz, CDCl3): δ 7.52-7.59(m, 2H), 7.24-7.26(m, 3H), 7.09-7.19(m, 2H), 6.80-6.89(m, 1H), 6.72-6.77(m, 2H), 6.14-6.31(m, 2H), 5.07(s, 2H), 4.70(s, 2H), 4.38(s, 2H), 4.02-4.07(q, 2H), 3.95(s, 3H), 2.75(br, 2H), 2.43(br, 2H), 1.04-1.12(q, 3H) | 522.2 (M + H)⁺ |
| 91 | 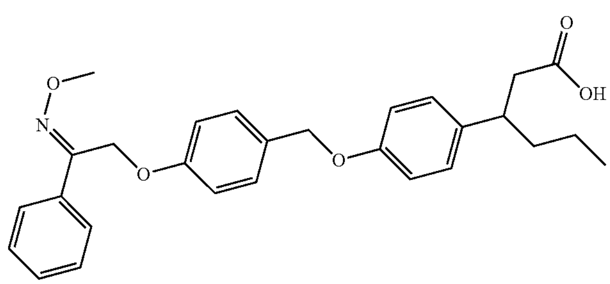 [SMILES: CCCC(CC(=O)O)c1ccc(OCc2ccc(OC/C(=N\OC)c3ccccc3)cc2)cc1] | 1H(300 MHz, CDCl3): δ 7.57-7.60(m, 2H), 7.22-7.28(m, 5H), 7.00-7.03(d, 2H), 6.79-6.85(t, 4H), 5.12(s, 2H), 4.85(s, 2H), 3.97(s, 3H), 2.94-2.98(m, 1H), 2.43-2.59(m, 2H), 1.42-1.55(m, 2H), 1.05-1.12(m, 2H), 0.74-0.79(t, 3H) | 460.1 (M − H)⁺ |
| 92 | 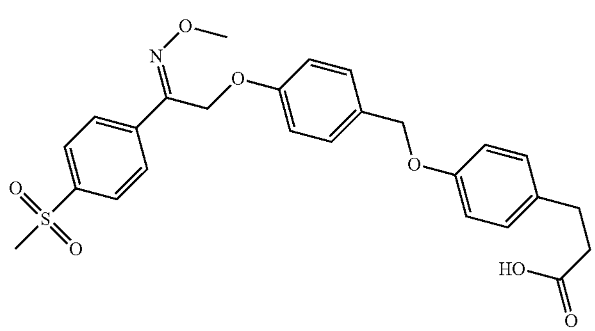 [SMILES: CO/N=C(\COc1ccc(COc2ccc(CCC(=O)O)cc2)cc1)c1ccc(S(C)(=O)=O)cc1] | 1H(300 MHz, DMSO-d6): δ 12.09(bs, 1H), 7.88-7.97(q, 4H), 7.33-7.36(d, 2H), 7.11-7.13(2H, d), 6.87-6.94(m, 4H), 5.29(2H, s), 4.96(s, 2H) 4.05 (3H, s), 3.23(3H, s), 2.72-2.76(2H, t), 2.45-2.47(2H, t) | 496.1 (M − H)⁺ |

TABLE 1-continued

| No | Structure | ¹H NMR | m/z |
|---|---|---|---|
| 93 | 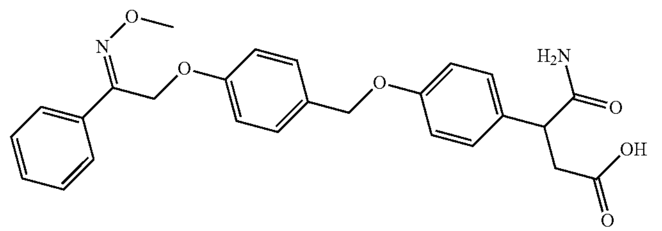 [SMILES: CO/N=C(\COc1ccc(COc2ccc(C(CC(=O)O)C(N)=O)cc2)cc1)c1ccccc1] | 1H(300 MHz, DMSO-d6): δ 12.11(s, 1H), 7.63-7.66(m, 2H), 7.32-7.41(m, 6H), 7.19-7.22(d, 2H), 6.89-6.93(m, 4H), 6.80(s, 1H), 5.23(s, 2H), 4.96(s, 2H), 4.00(s, 3H), 3.75-3.80(m, 1H), 2.86-2.95(m, 1H), 2.39-2.46(m, 1H) | 463.2 (M + H)⁺ |
| 94 | 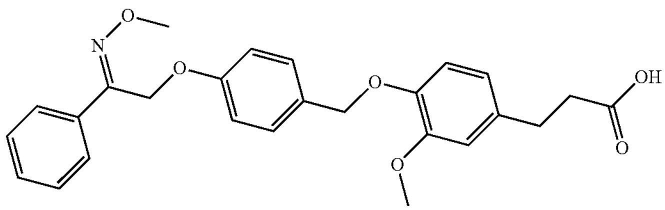 [SMILES: CO/N=C(\COc1ccc(COc2ccc(CCC(=O)O)cc2OC)cc1)c1ccccc1] | 1H NMR(300 MHz, CDCl3): δ 7.58(s, 2H), 7.26-7.28(t, 5H), 7.23 (s, 2H), 6.80-6.83(d, 2H), 6.71-6.74 (d, 1H), 6.67(s, 1H), 6.59-6.62(t, 1H), 5.11(s, 2H), 4.95(s, 2H), 3.98-3.98(d, 2H), 3.86(s, 3H) 3.78(s, 3H), 2.80-2.85(t, 2H), 2.56-2.61(t, 2H) | 448.4 (M − H)⁺ |
| 95 | 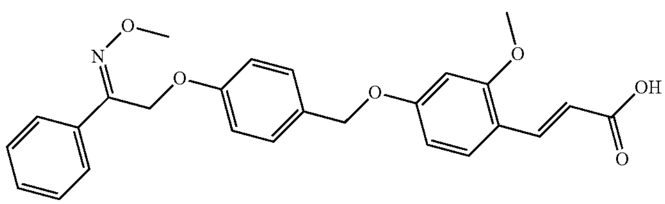 [SMILES: CO/N=C(\COc1ccc(COc2ccc(/C=C/C(=O)O)c(OC)c2)cc1)c1ccccc1] | 1H(300 MHz, DMSO-d6): δ 12.14(s, 1H), 7.72-7.77(d, 1H), 7.59-7.65(m, 3H), 7.36-7.41(m, 5H), 6.92-6.95(d, 2H), 6.62-6.68(m, 2H), 6.35-6.40(d, 1H), 5.24(s, 2H), 5.07(s, 2H), 3.99(s, 3H), 3.84(s, 3H) | 448.2 (M + H)⁺ |
| 96 | 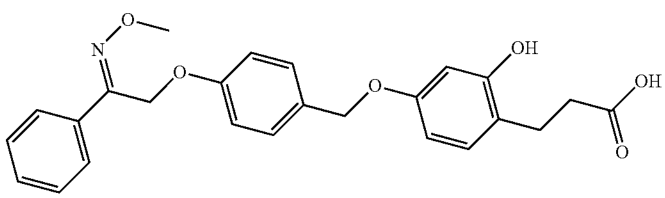 [SMILES: CO/N=C(\COc1ccc(COc2ccc(CCC(=O)O)c(O)c2)cc1)c1ccccc1] | 1H(300 MHz, CDCl3): δ 8.02(s, 1H), 7.58(s, 2H), 7.28-7.24(d, 4H), 6.806-6.88(t, 3H), 6.37-6.42(d, 2H), 5.11(s, 2H), 4.82(s, 2H), 4.61(s, 1H), 3.98(s, 3H), 2.71(s, 2H), 2.54(s, 2H)) | ((M − H)⁺ |
| 97 | 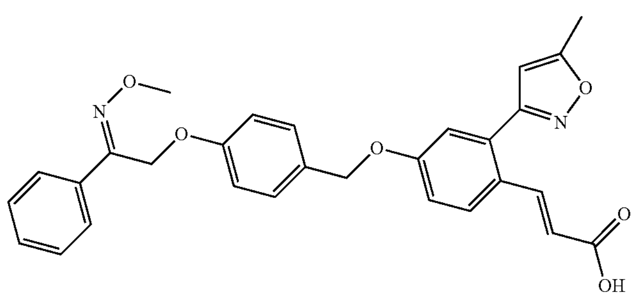 [SMILES: CO/N=C(\COc1ccc(COc2ccc(/C=C/C(=O)O)c(-c3cc(C)on3)c2)cc1)c1ccccc1] | 1H(300 MHz, CDCl3): δ 7.89-7.94(d, 1H), 7.57-7.60(t, 2H) 7.16-7.28 (m, 4H), 7.09-7.12(m, 4H), 6.93-6.95 (d, 1H), 6.83-6.86(d, 1H), 6.22-6.28, (d, 1H), 6.03(s, 1H), 5.12(s, 2H) 4.92(s, 2H), 3.98(s, 3H), 2.28(s, 3H) | 499.1 (M + H)⁺ |
| 98 | (Racemate) | 1H(300 MHz, CDCl3): δ 7.49-7.53(m, 2H), 7.31-7.33(m, 3H), 7.23-7.23(m, 4H), 6.88-6.91(d, 4H), 4.91(s, 2H), 4.82(s, 2H), 4.12-4.18(t, 1H), 3.86(s, 3H), 2.95-3.03(m, 1H), 2.76-2.84(m, 1H) | 445.1 (M + H)⁺ |

TABLE 1-continued

| No | Structure | ¹H NMR | m/z |
|---|---|---|---|
| 99 | (Enantiomer-1) | 1H(300 MHz, CDCl3): δ 7.49-7.53(m, 2H), 7.31-7.33(m, 3H), 7.23-7.23(m, 4H), 6.88-6.91(d, 4H), 4.91(s, 2H), 4.82(s, 2H), 4.13-4.18(t, 1H), 3.87(s, 3H), 2.95-3.03(m, 1H), 2.76-2.84(m, 1H) | 445.1 (M + H)⁺ |
| 100 | (Enantiomer-2) | 1H(300 MHz, CDCl3): δ 7.49-7.53(m, 2H), 7.31-7.33(m, 3H), 7.23-7.23(m, 4H), 6.88-6.91(d, 4H), 4.91(s, 2H), 4.82(s, 2H), 4.13-4.18(t, 1H), 3.87(s, 3H), 2.95-3.03(m, 1H), 2.76-2.84(m, 1H) | 445.1 (M + H)⁺ |
| 101 | 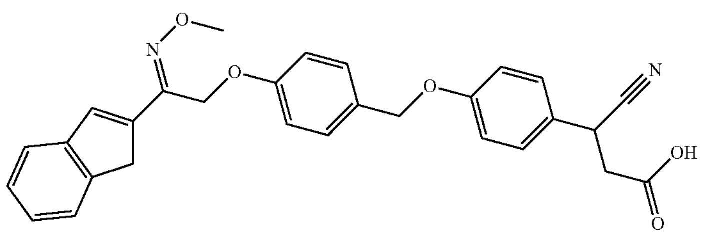 [SMILES: CO/N=C(\COc1ccc(COc2ccc(C(C#N)CC(=O)O)cc2)cc1)C1=Cc2ccccc2C1] | 1H(300 MHz, DMSO-d6): δ 7.44-7.46(m, 2H), 7.38-7.40(m, 3H), 7.22-7.29(m, 4H), 6.95-7.03(m, 4H), 5.08(s, 2H), 5.01(s, 2H), 4.21-4.26(t, 1H), 3.98(s, 3H), 3.66(s, 2H), 2.422-2.48(m, 1H), 2.23-2.30(m, 1H) | 481.1 (M + H)⁺ |
| 102 | 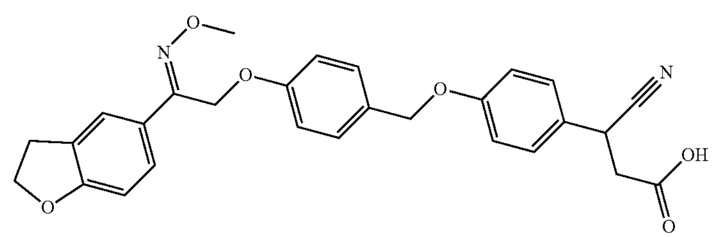 [SMILES: CO/N=C(\COc1ccc(COc2ccc(C(C#N)CC(=O)O)cc2)cc1)c1ccc2c(c1)CCO2] | 1H(300 MHz, DMSO-d6): δ 12.67(bro, 1H), 7.53(s, 1H), 7.41-7.41(d, 1H), 7.38(s, 1H), 7.34(s, 4H), 6.99-7.02(d, 2H), 6.92-6.94(d, 2H), 6.75-6.78(d, 1H), 5.17(s, 2H), 5.00 (s, 2H), 4.52-4.57(t, 2H), 3.95(s, 3H), 3.35-3.42(q, 1H), 3.15-3.20(t, 1H), 2.91-3.03(m, 1H), 2.74-2.85(m, 1H) | 487.3 (M + H)⁺ |
| 103 | 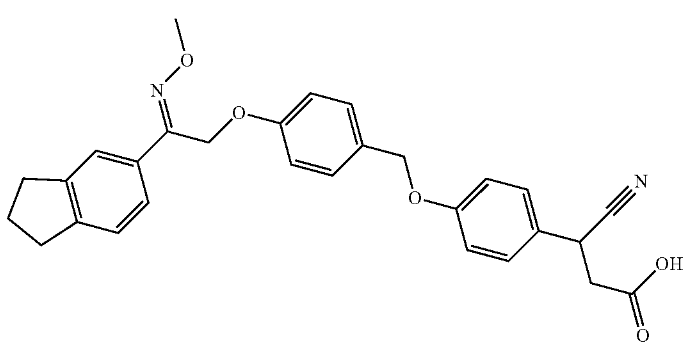 [SMILES: CO/N=C(\COc1ccc(COc2ccc(C(C#N)CC(=O)O)cc2)cc1)c1ccc2c(c1)CCC2] | 1H(300 MHz, DMSO-d6): δ 12.57(s, 1H), 7.51(s, 1H), 7.40-7.42(m, 4H), 7.22-7.25(m, 2H), 6.99-7.02(d, 2H), 6.91-6.94(d, 2H), 5.19(s, 2H), 5.0(s, 2H), 4.34-4.41(t, 1H), 3.96(s, 3H), 2.95-3.03(m, 1H), 2.77-2.88(m, 5H), 1.91-2.06(m, 2H) | 485.1 (M + H)⁺ |
| 104 | 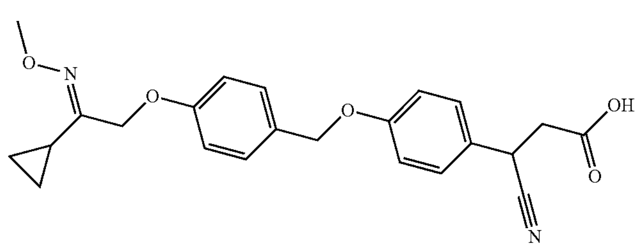 [SMILES: CO/N=C(/COc1ccc(COc2ccc(C(C#N)CC(=O)O)cc2)cc1)C1CC1] | 1H(300 MHz, CDCl3): δ 7.26-7.29(d, 2H), 7.19-7.23(d, 2H), 6.85-6.92(m, 4H), 4.92(s, 2H), 4.79(s, 2H), 4.13-4.18(m, 1H), 3.76(s, 3H), 2.95-3.03(m, 1H), 2.77-2.85(m, 1H), 1.57-1.67(m, 1H), 0.71-0.76(m, 2H), 0.62-0.68(m, 2H) | 409.1 (M + H)⁺ |

TABLE 1-continued

| No | Structure | ¹H NMR | m/z |
|---|---|---|---|
| 105 | 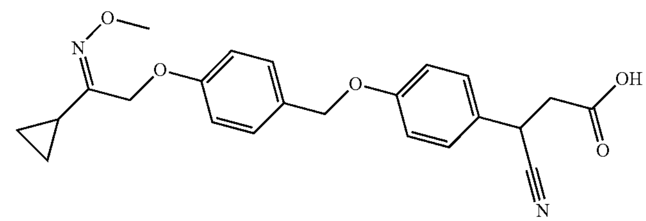 [SMILES: CO/N=C(\COc1ccc(COc2ccc(C(C#N)CC(=O)O)cc2)cc1)C1CC1] | 1H(300 MHz, CDCl3): δ 7.25-7.27(d, 2H), 7.19-7.23(d, 2H), 6.85-6.91(m, 4H), 4.90(s, 2H), 4.30(s, 2H), 4.13-4.17(m, 1H), 3.86(s, 3H), 2.94-3.02(m, 1H), 2.76-2.84(m, 1H), 2.12-2.19(m, 1H), 0.88-0.91(m, 2H), 0.79-0.83(m, 2H) | 409.1 (M + H)⁺ |
| 106 | 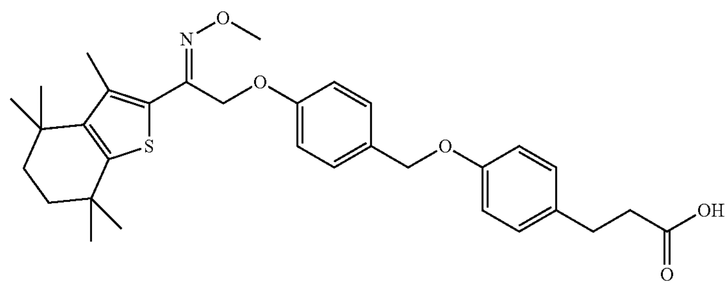 [SMILES: CO/N=C(\COc1ccc(COc2ccc(CCC(=O)O)cc2)cc1)c1sc2c(c1C)C(C)(C)CCC2(C)C] | 1H(300 MHz, CDCl3): δ 7.19-7.27(t, 2H), 7.03-7.06(d, 2H), 6.79-6.87(q, 4H), 4.97(s, 2H), 4.87(s, 2H), 3.95(s, 3H), 2.8-2.86(t, 2H), 2.55-2.60(t, 2H), 2.20(s, 3H), 1.20-1.28(m, 16H) | 550.2 (M + H)⁺ |
| 107 | 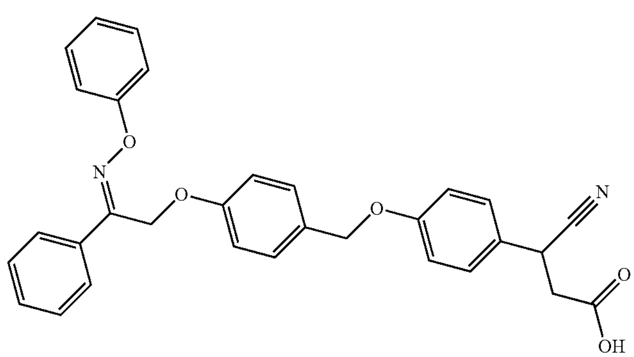 [SMILES: N#CC(CC(=O)O)c1ccc(OCc2ccc(OC/C(=N\Oc3ccccc3)c3ccccc3)cc2)cc1] | 1H(300 MHz, DMSO-d6): δ 7.78-7.80(m, 1H), 7.67-7.69(m, 1H), 7.46-7.51(m, 3H), 7.28-7.42(m, 7H), 7.05-7.21(m, 5H), 6.88-6.91(m, 1H), 5.51(s, 1H) 5.19(s, 1H), 4.97-4.99(m, 2H), 3.75-3.84(m, 1H), 2.83-2.92(m, 1H), 2.37-2.45(m, 1H). | 507.1 (M + H)⁺ |
| 108 | 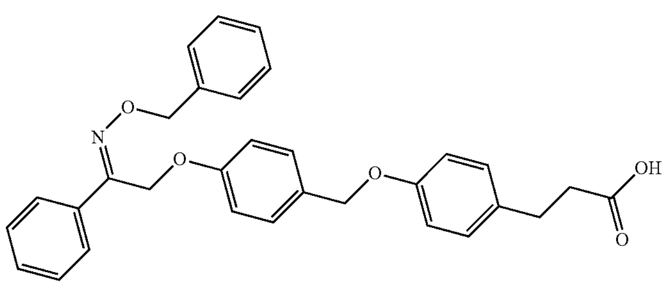 [SMILES: O=C(O)CCc1ccc(OCc2ccc(OC/C(=N\OCc3ccccc3)c3ccccc3)cc2)cc1] | 1H(300 MHz, DMSO-d6): δ 12.06(s, 1H), 9.14(s, 1H) 7.61-7.63(m, 2H), 7.34-7.46(m, 5H), 7.25-7.28(d, 2H) 7.11-.7.14(d, 2H), 6.98-7.01(d, 2H), 6.86-6.89(m, 3H), 6.64-6.66(d, 2H) 5.28(s, 4H), 4.97(s, 2H), 2.69-2.71(m, 2H), 2.45(m, 2H) | 496.2 (M + H)⁺ |
| 109 | 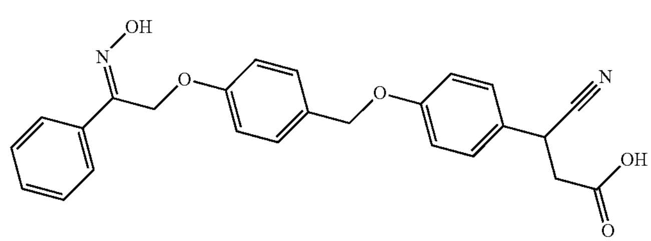 [SMILES: N#CC(CC(=O)O)c1ccc(OCc2ccc(OC/C(=N\O)c3ccccc3)cc2)cc1] | 1H(300 MHz, DMSO-d6): δ 12.65(s, 1H), 11.90(s, 1H), 7.63-7.67(m, 2H), 7.33-7.38(t, 7H), 6.93-7.01(q, 4H), 5.25(s, 2H), 4.99(s, 2H), 4.34-4.39(t, 1H), 2.94-3.036(m, 1H), 2.79-2.85(m, 1H). | 429.1 (M − H)⁺ |

TABLE 1-continued
| No | Structure | ¹H NMR | m/z |
|---|---|---|---|
| 110 | 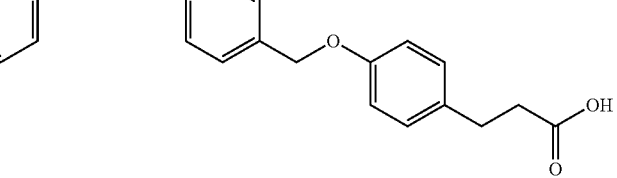 | 1H(300 MHz, DMSO-d6): δ 12.09(s, 1H), 7.62-7.65(m, 2H), 7.39-7.41(m, 3H), 7.32-7.35(d, 2H), 7.10-7.13(d, 2H), 6.91-6.94(d, 2H), 6.87-6.89(d, 2H), 6.03-6.13(m, 1H), 5.39-5.40(d, 1H), 5.24-5.27(m, 3H), 4.95(s, 2H), 4.73-4.75(d, 2H), 2.71-2.76(t, 2H), 2.45-2.47(t, 2H). | 446.2 (M + H)⁺ |
| 111 | 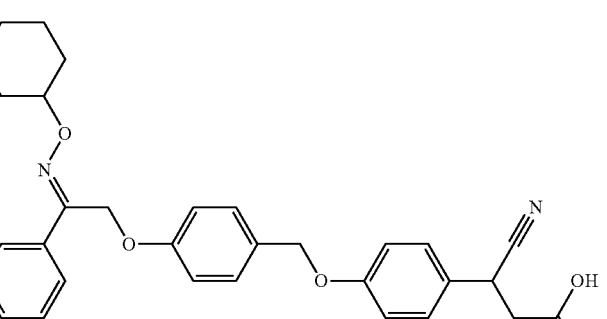 | 1H(300 MHz, DMSO-d6): δ 7.64-7.66(m, 2H), 7.33-7.39(m, 7H), 7.19-7.22(d, 1H), 6.89-7.00(m, 3H), 5.26(s, 2H), 4.95-4.99(d, 2H), 4.26-4.37(t, 1H), 4.22-4.24(m, 1H), 3.71-3.82(m, 1H), 2.93-2.96(m, 2H), 1.95-1.99(m, 2H), 1.69(s, 2H), 1.38-1.53(m, 3H), 1.244-1.35(m, 2H) | 513.2 (M + H)⁺ |
| 112 | 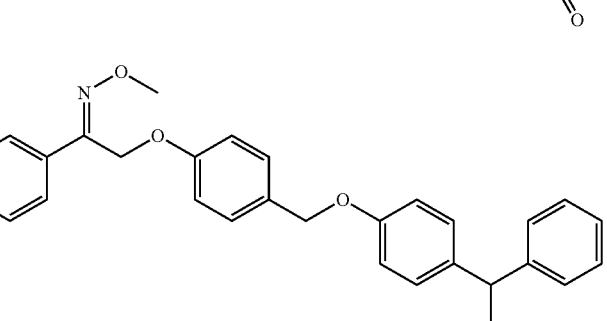 | 1H(300 MHz, DMSO-d6): δ 7.62-7.65(q, 2H), 7.38-7.40(q, 4H), 7.14-7.33(m, 8H), 6.85-6.91(q, 4H), 5.21(s, 2H), 4.92(s, 2H), 4.35-4.37(t, 1H), 3.90(s, 3H), 2.93-2.96(d, 2H) | 496 (M + H)⁺ |
| 113 | 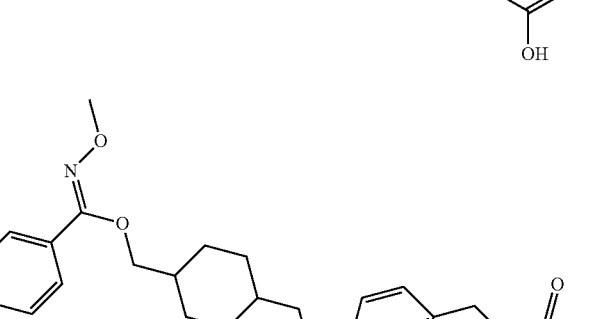 | 1H NMR(300 MHz, CDCl3): δ 7.60-7.61(d, 2H), 7.26-7.28(m, 3H), 7.02-7.06(q, 2H), 6.71-6.75(q, 2H), 4.56-4.57(d, 2H), 3.92(s, 3H), 3.62-3.70(dd, 2H), 3.14-3.25(dd, 2H), 2.81-2.83(m, 2H), 2.54-2.60(m, 2H), 1.77-1.82(d, 2H), 1.65-1.68(d, 2H), 0.81-0.87(m | 440 (M + H)⁺ |
| 114 | 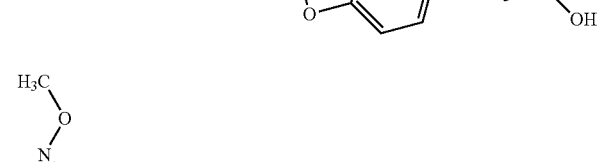 | 1H NMR(300 MHz, CDCl3): δ 8.02(d, 1H) 7.56-7.59(m, 2H), 7.25-7.27(m, 3H), 7.12-7.15(m, 2H), 7.02(s, 1H), 6.78-6.80(d, 2H), 6.46-6.49(d, 1H), 5.09(s, 2H), 4.95(s, 2H), 3.97(s, 3H) 2.54-2.2.58(t, 3H), 2.43-2.48(t, 3H). | 421 (M + H)⁺ |

TABLE 1-continued

| No | Structure | ¹H NMR | m/z |
|---|---|---|---|
| 115 | 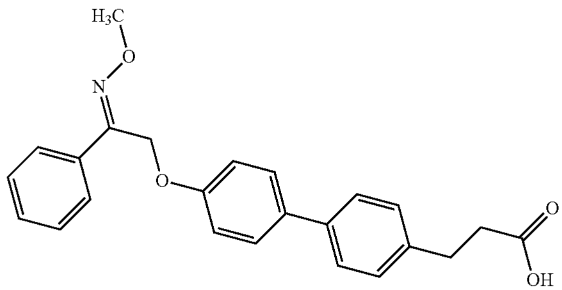 [SMILES: CO/N=C(\COc1ccc(-c2ccc(CCC(=O)O)cc2)cc1)c1ccccc1] | 1H NMR(300 MHz, DMSO-d6): 12.12(s, 1H), 7.64-7.67(m, 2H), 7.49-7.56(m, 4H), 7.39-7.42(m, 3H), 7.25-7.28(d, 2H), 6.96-6.99(d, 2H), 5.26(s, 2H), 4.01(s, 3H), 2.81-2.86(t, 2H), 2.56-2.57(t, 2H). | 390 (M + H)⁺ |
| 116 | 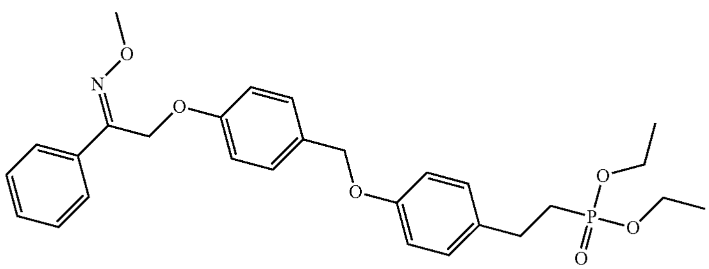 [SMILES: CCOP(=O)(CCc1ccc(OCc2ccc(OC/C(=N\OC)c3ccccc3)cc2)cc1)OCC] | | 512 (M + H)⁺ |
| 117 | 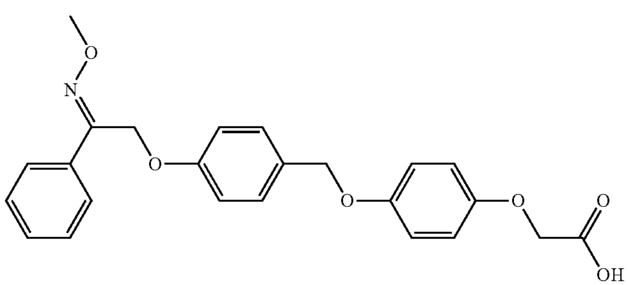 [SMILES: CO/N=C(\COc1ccc(COc2ccc(OCC(=O)O)cc2)cc1)c1ccccc1] | 1H(300 MHz, CDCl3-d6): δ 7.57-7.61(q, 2H), 7.25-7.29(m, 5H), 6.77-6.85(m, 6H), 5.13(s, 2H), 4.85(s, 2H), 4.55(s, 2H), 3.98(s, 3H) | 422.1 (M + H)⁺ |
| 118 | 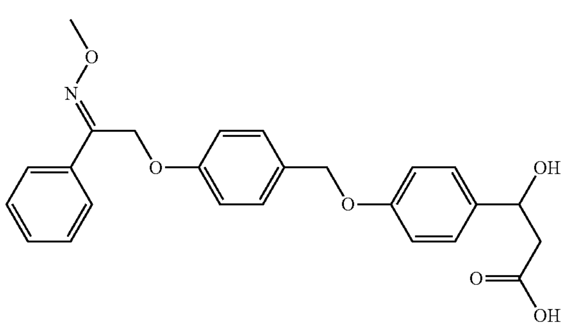 [SMILES: CO/N=C(\COc1ccc(COc2ccc(C(O)CC(=O)O)cc2)cc1)c1ccccc1] | 1H(300 MHz, CDCl3-d6): δ 7.57-7.61(q, 2H), 7.23-7.29(m, 7H), 6.83-6.89(t, 4H), 5.13(s, 2H), 5.01-5.05(q, 1H), 4.89(s, 2H), 3.98(s, 3H), 2.68-2.75(q, 2H), | 434.1 (M − H)⁺ |

| No | Structure | ¹H NMR | m/z |
|---|---|---|---|
| 119 | 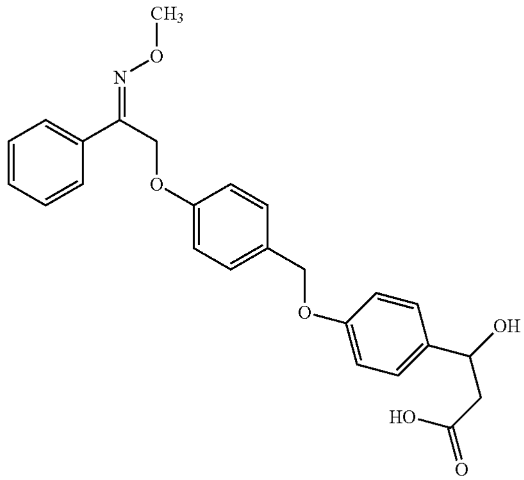 [SMILES: CO/N=C(\COc1ccc(COc2ccc(C(O)CC(=O)O)cc2)cc1)c1ccccc1] | 1H(300 MHz, DMSO-d6): δ 7.62-7.65(m, 2H), 7.38-7.40(m, 3H), 7.32-7.35(d, 2H) 7.23-7.25(d, 2H), 6.90-6.93(d, 4H), 5.28(m, 1H), 5.24(s, 2H), 4.97(s, 2H), 4.84-4.88(t, 1H), 3.99(s, 3H), 3.39(m, 2H). | 434.1 (M − H)⁺ |
| 120 | 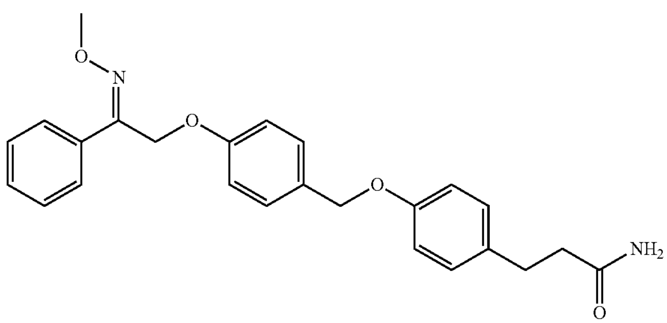 [SMILES: CO/N=C(/COc1ccc(COc2ccc(CCC(N)=O)cc2)cc1)c1ccccc1] | 1H(300 MHz, DMSO-d6): δ 7.62-7.64(t, 2H), 7.39-7.40(d, 3H), 7.32-7.35(d, 2H), 7.25(s, 1H), 7.08-7.11(d, 2H), 6.86-6.63(q, 4H), 6.73(s, 1H), 5.22(s, 2H), 4.95(s, 2H), 3.99(s, 3H), 2.69-2.74(t, 2H), 2.26-2.32(t, 2H) | 419 (M + H)⁺ |
| 121 | 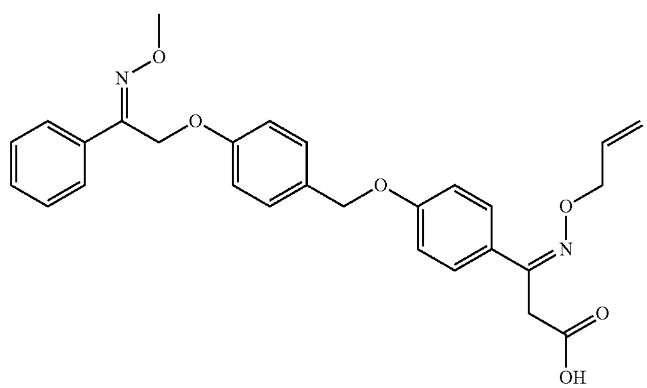 [SMILES: C=CCO/N=C(/CC(=O)O)c1ccc(OCc2ccc(OC/C(=N\OC)c3ccccc3)cc2)cc1] | 1H(300 MHz, CDCl3-d6): δ 7.58-7.61(m, 4H), 7.23-7.29(m, 5H), 6.83-6.89(m, 4H), 5.92-6.03(m, 1H), 5.13-5.33(m, 5H), 4.9(s, 2H), 4.64-4.70(m, 3H), 3.98(s, 3H) | 489.5 (M + H)⁺ |
| 122 | 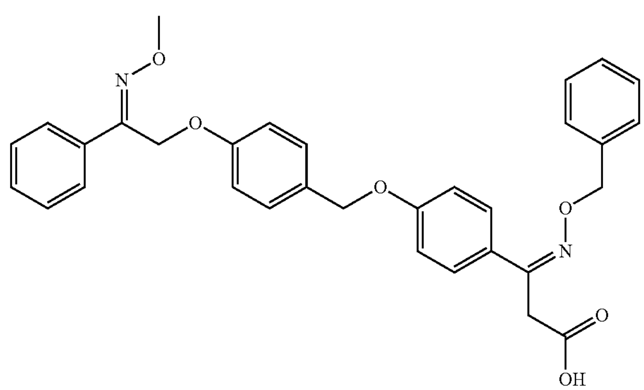 [SMILES: CO/N=C(\COc1ccc(COc2ccc(/C(CC(=O)O)=N\OCc3ccccc3)cc2)cc1)c1ccccc1] | 1H(300 MHz, DMSO-d6): δ 7.55-7.65(m, 4H), 7.27-7.4(m, 5H), 6.9-7.01(m, 4H), 5.22(s, 2H), 5.15-5.16(d, 2H), 5.07-5.03(d, 2H), 3.99(s, 3H), 3.6(s, 2H) | 539.5 (M + H)⁺ |

TABLE 1-continued

| No | Structure | ¹H NMR | m/z |
|---|---|---|---|
| 123 | 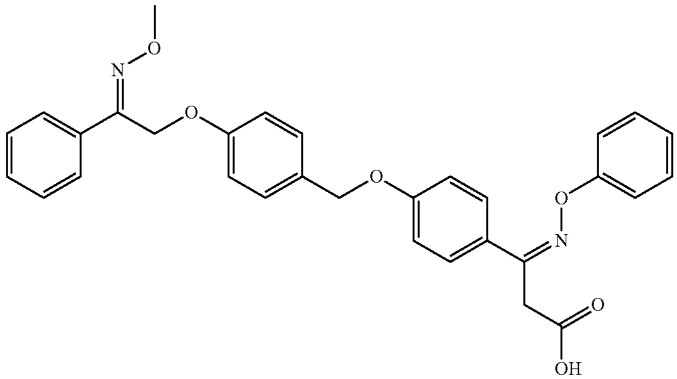 [SMILES: CO/N=C(\COc1ccc(COc2ccc(/C(CC(=O)O)=N\Oc3ccccc3)cc2)cc1)c1ccccc1] | 1H(300 MHz, CDCl3-d6): δ 7.98-8.04(m, 2H), 7.59-7.61(m, 4H), 7.21-7.29(m, 6H), 5.12-5.14(d, 2H), 4.88-4.98(d, 2H), 4.61(s, 2H), 3.98(s, 3H) | 525.5 (M + H)⁺ |
| 124 | 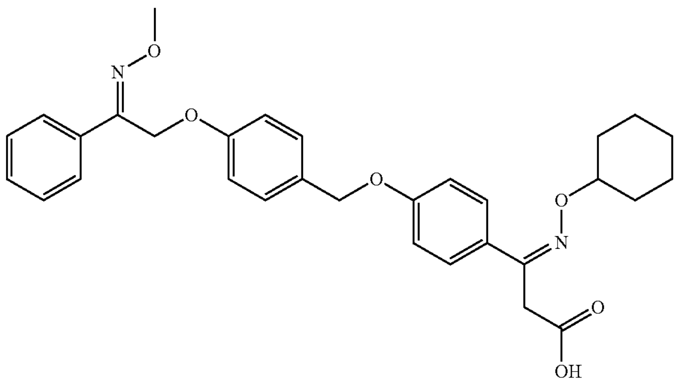 [SMILES: CO/N=C(\COc1ccc(COc2ccc(/C(CC(=O)O)=N\OC3CCCCC3)cc2)cc1)c1ccccc1] | 1H(300 MHz, CDCl3-d6): δ 7.52-7.62(m, 4H), 7.22-7.29(m, 5H), 6.83-6.91(m, 4H), 5.13-5.17(d, 2H), 4.91(s, 2H), 4.06-4.21(m, 1H), 3.96(s, 3H), 3.72(s, 2H), 1.26-1.95(m, 10H) | 531 (M + H)⁺ |

Employing modified procedures used in making the above compounds the following compounds or a geometric isomer thereof could also be made.

TABLE 2

| No | Structure |
|---|---|
| 125 | 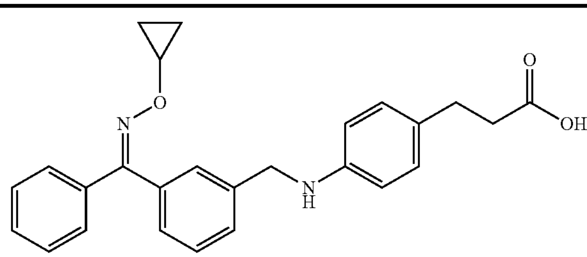 |
| 126 | 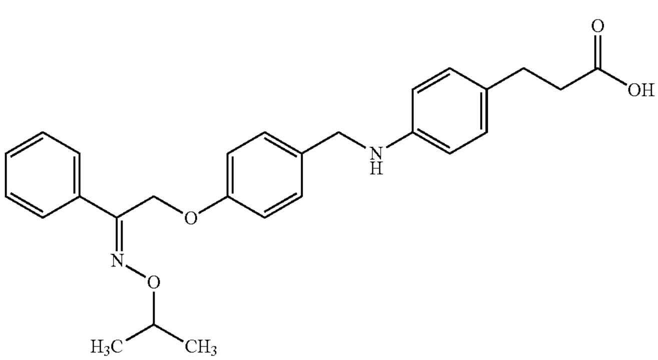 [SMILES: CC(C)O/N=C(\COc1ccc(CNc2ccc(CCC(=O)O)cc2)cc1)c1ccccc1] |

TABLE 2-continued

| No | Structure |
|---|---|
| 127 | 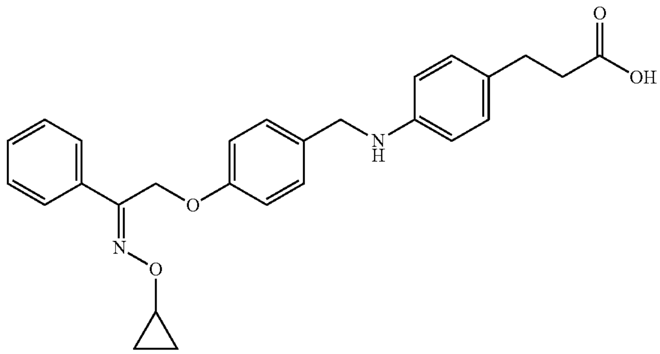 [SMILES: O=C(O)CCc1ccc(NCc2ccc(OC/C(=N\OC3CC3)c3ccccc3)cc2)cc1] |
| 128 | 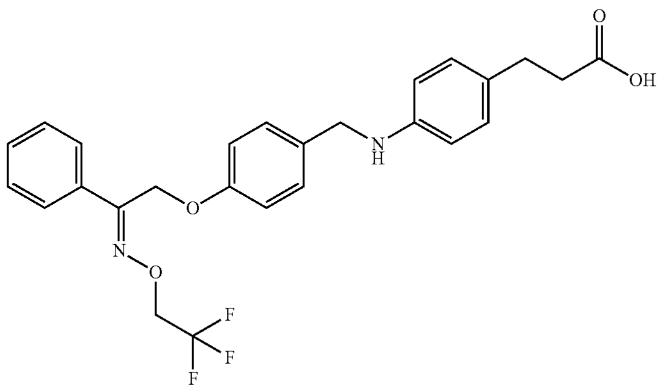 [SMILES: O=C(O)CCc1ccc(NCc2ccc(OC/C(=N\OCC(F)(F)F)c3ccccc3)cc2)cc1] |
| 129 | 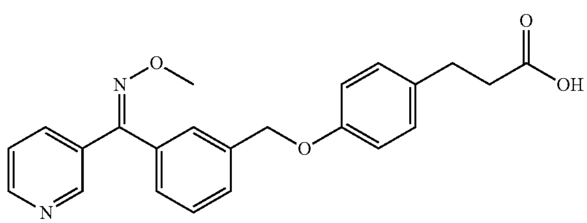 [SMILES: CO/N=C(/c1cccnc1)c1cccc(COc2ccc(CCC(=O)O)cc2)c1] |
| 130 | 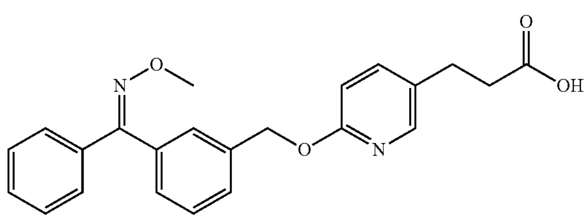 |
| 131 | 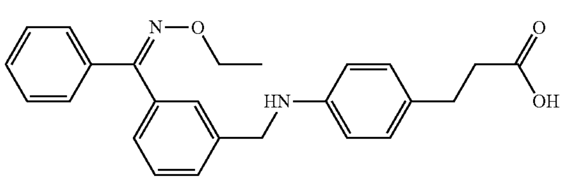 [SMILES: CCO/N=C(/c1ccccc1)c1cccc(CNc2ccc(CCC(=O)O)cc2)c1] |
| 132 | 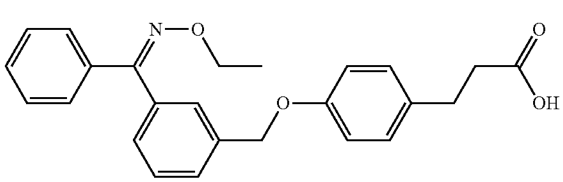 [SMILES: CCO/N=C(/c1ccccc1)c1cccc(COc2ccc(CCC(=O)O)cc2)c1] |

TABLE 2-continued

| No | Structure |
|---|---|
| 133 | 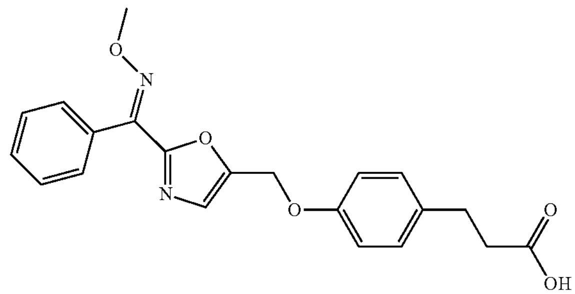 [SMILES: CO/N=C(\c1ccccc1)c1ncc(COc2ccc(CCC(=O)O)cc2)o1] |
| 134 | 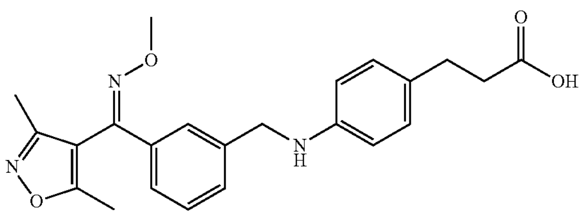 [SMILES: CO/N=C(\c1cccc(CNc2ccc(CCC(=O)O)cc2)c1)c1c(C)noc1C] |
| 135 | 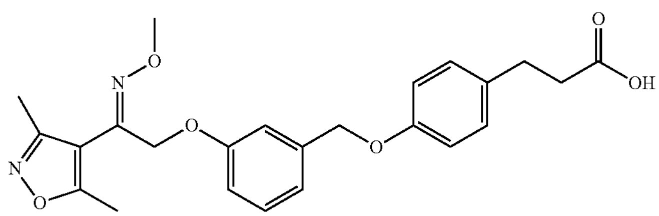 [SMILES: CO/N=C(\COc1cccc(COc2ccc(CCC(=O)O)cc2)c1)c1c(C)noc1C] |
| 136 | 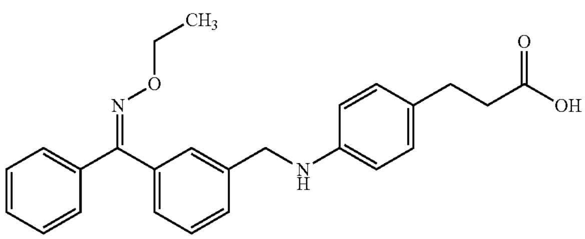 [SMILES: CCO/N=C(/c1ccccc1)c1cccc(CNc2ccc(CCC(=O)O)cc2)c1] |
| 137 | 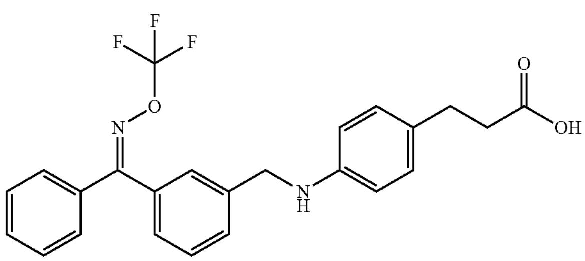 [SMILES: O=C(O)CCc1ccc(NCc2cccc(/C(=N\OC(F)(F)F)c3ccccc3)c2)cc1] |
| 138 | 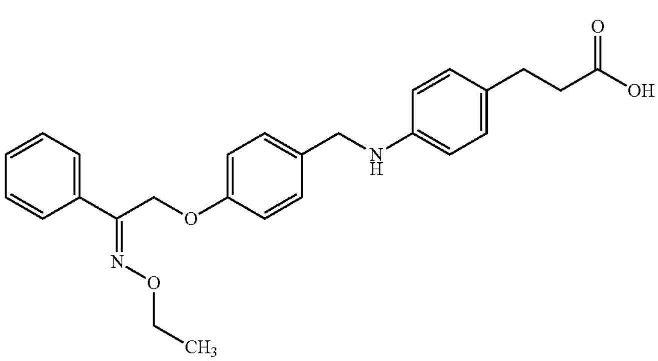 [SMILES: CCO/N=C(\COc1ccc(CNc2ccc(CCC(=O)O)cc2)cc1)c1ccccc1] |

TABLE 2-continued
| No | Structure |
|---|---|
| 139 | 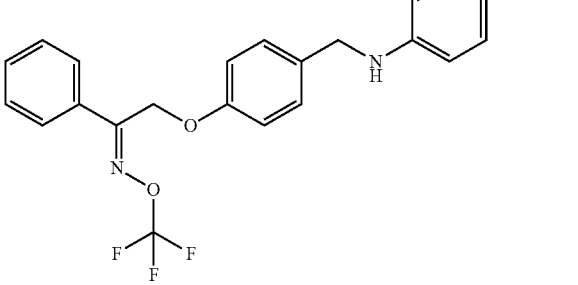 |
| 140 | 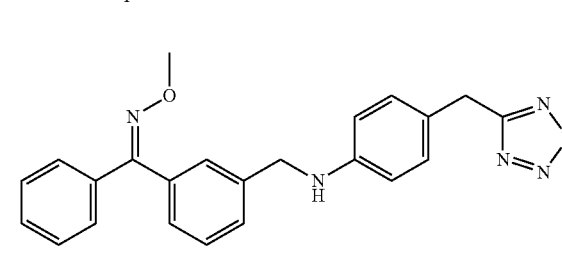 |
| 141 | 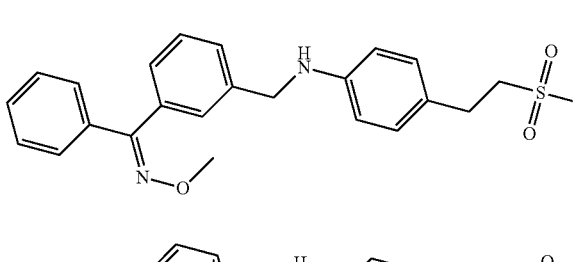 |
| 142 | 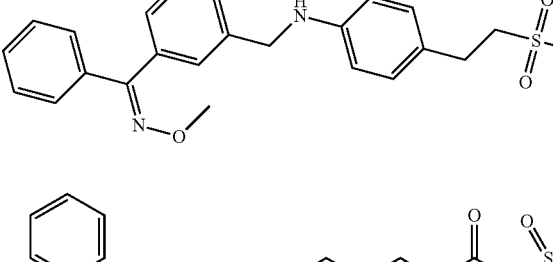 |
| 143 | 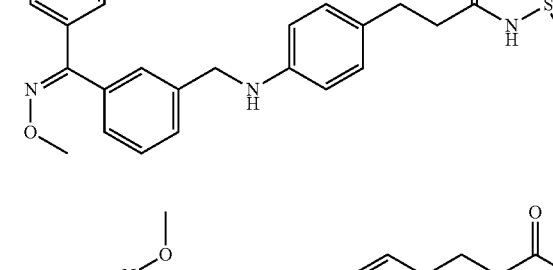 |
| 144 | 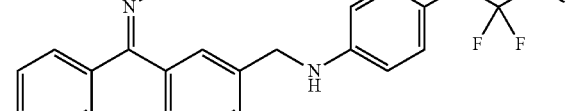 |

TABLE 2-continued
| No | Structure |
|----|-----------|
| 145 | 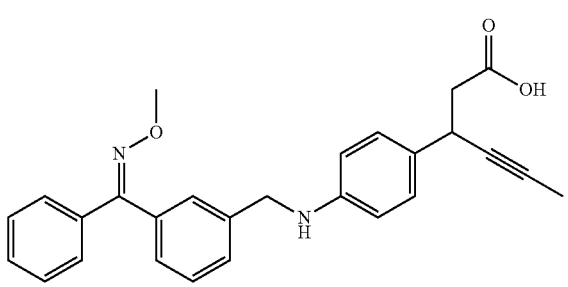 [SMILES: CC#CC(CC(=O)O)c1ccc(NCc2cccc(/C(=N\OC)c3ccccc3)c2)cc1] |
| 146 | 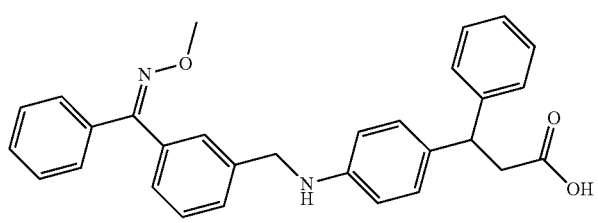 [SMILES: CO/N=C(/c1ccccc1)c1cccc(CNc2ccc(C(CC(=O)O)c3ccccc3)cc2)c1] |
| 147 | 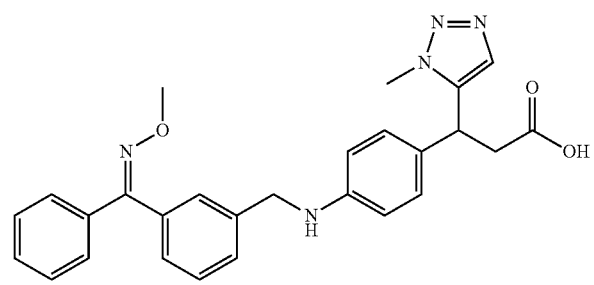 [SMILES: CO/N=C(/c1ccccc1)c1cccc(CNc2ccc(C(CC(=O)O)c3cnnn3C)cc2)c1] |
| 148 | 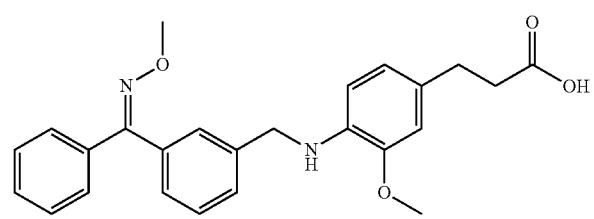 [SMILES: CO/N=C(/c1ccccc1)c1cccc(CNc2ccc(CCC(=O)O)cc2OC)c1] |
| 149 | 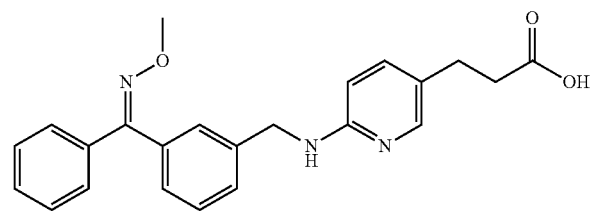 [SMILES: CO/N=C(/c1ccccc1)c1cccc(CNc2ccc(CCC(=O)O)cn2)c1] |
| 150 | 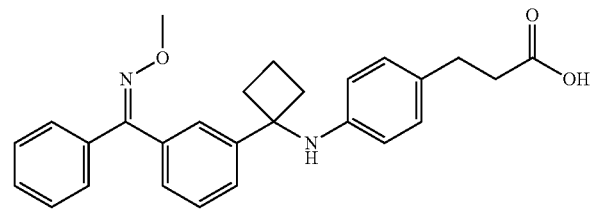 [SMILES: CO/N=C(/c1ccccc1)c1cccc(C2(Nc3ccc(CCC(=O)O)cc3)CCC2)c1] |

TABLE 2-continued
| No | Structure |
|---|---|
| 151 | 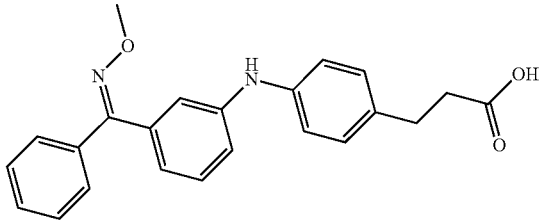 [SMILES: CO/N=C(/c1ccccc1)c1cccc(Nc2ccc(CCC(=O)O)cc2)c1] |
| 152 | 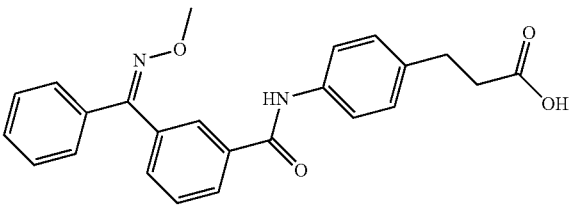 [SMILES: CO/N=C(/c1ccccc1)c1cccc(C(=O)Nc2ccc(CCC(=O)O)cc2)c1] |
| 153 | 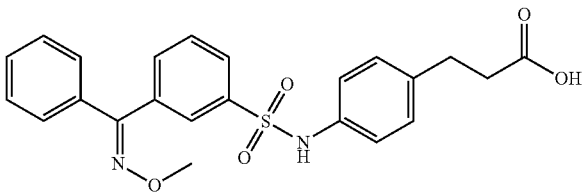 [SMILES: CO/N=C(/c1ccccc1)c1cccc(S(=O)(=O)Nc2ccc(CCC(=O)O)cc2)c1] |
| 154 | 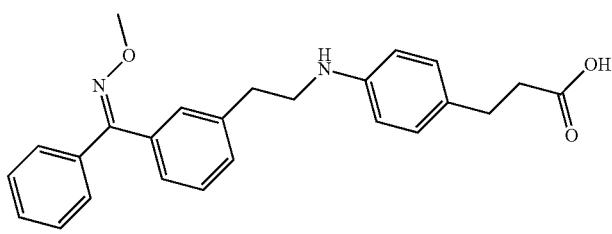 [SMILES: CO/N=C(/c1ccccc1)c1cccc(CCNc2ccc(CCC(=O)O)cc2)c1] |
| 155 | 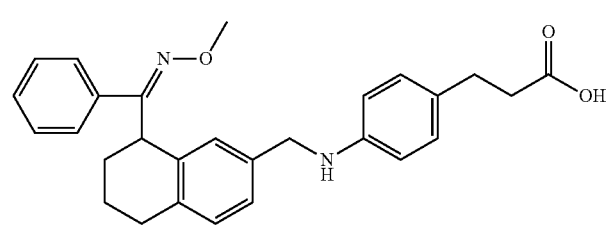 [SMILES: CO/N=C(/c1ccccc1)C1CCCc2ccc(CNc3ccc(CCC(=O)O)cc3)cc21] |
| 156 | 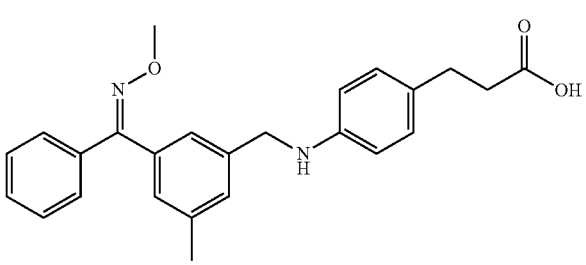 [SMILES: CO/N=C(/c1ccccc1)c1cc(C)cc(CNc2ccc(CCC(=O)O)cc2)c1] |

TABLE 2-continued

| No | Structure |
|---|---|
| 157 | (structure: phenyl-C(=N-OMe)-[3-fluoro-5-substituted phenyl]-CH2-NH-[4-(CH2CH2COOH)phenyl]) |
| 158 | (structure: phenyl-C(=N-OMe)-CH2-NH-[phenyl]-CH2-NH-[4-(CH2CH2COOH)phenyl]) |
| 159 | (structure: phenyl-C(=N-OMe)-CH2-O-[3-substituted phenyl]-CH2-NH-[4-(CH2CH2COOH)phenyl]) |
| 160 | (structure: phenyl-C(=N-OMe)-CH(CH3)-O-[4-substituted phenyl]-CH2-NH-[4-(CH2CH2COOH)phenyl]) |
| 161 | (structure: phenyl-C(=N-OCHF2)-[3-substituted phenyl]-CH2-NH-[4-(CH2CH2COOH)phenyl]) |
| 162 | (structure: phenyl-C(=N-O-CH2-C≡CH)-[3-substituted phenyl]-CH2-NH-[4-(CH2CH2COOH)phenyl]) |

TABLE 2-continued

| No | Structure |
|---|---|
| 163 | 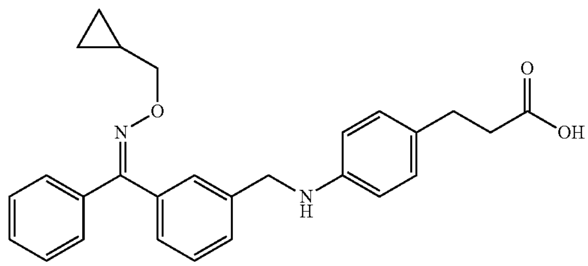 [SMILES: O=C(O)CCc1ccc(NCc2cccc(/C(=N\OCC3CC3)c3ccccc3)c2)cc1] |
| 164 | 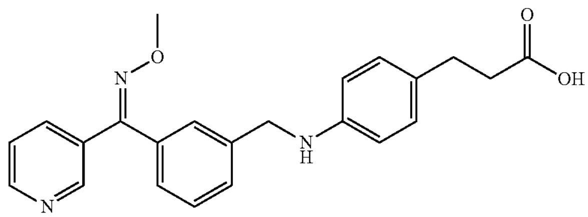 [SMILES: CO/N=C(/c1cccnc1)c1cccc(CNc2ccc(CCC(=O)O)cc2)c1] |
| 165 | 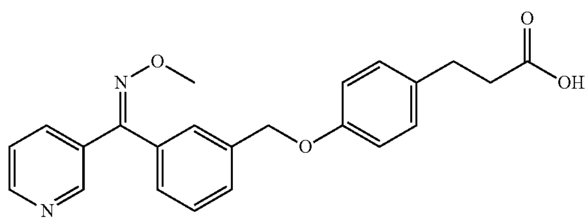 [SMILES: CO/N=C(/c1cccnc1)c1cccc(COc2ccc(CCC(=O)O)cc2)c1] |
| 166 | 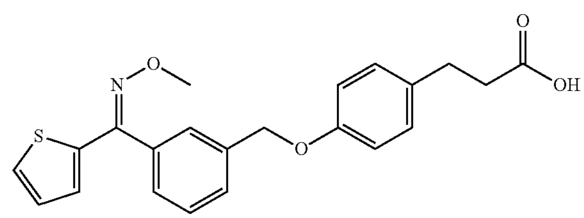 |
| 167 | 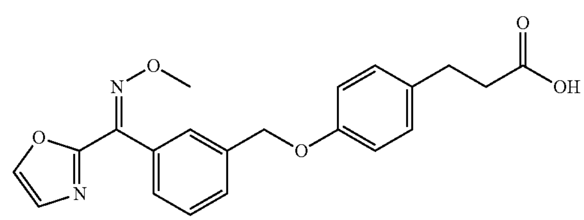 [SMILES: CO/N=C(\c1cccc(COc2ccc(CCC(=O)O)cc2)c1)c1ncco1] |
| 168 | 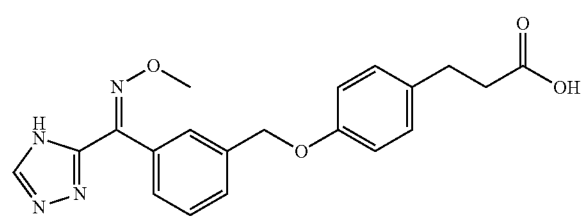 [SMILES: CO/N=C(\c1cccc(COc2ccc(CCC(=O)O)cc2)c1)c1nnc[nH]1] |
| 169 | 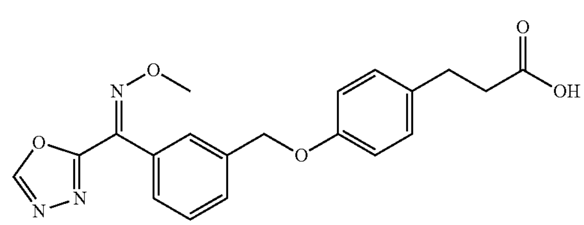 [SMILES: CO/N=C(\c1cccc(COc2ccc(CCC(=O)O)cc2)c1)c1nnco1] |

TABLE 2-continued

| No | Structure |
|---|---|
| 170 | *(structure: indole-C(=N-OMe)-phenyl-CH2-O-phenyl-CH2CH2-COOH)* |
| 171 | *(structure: benzothiazole-C(=N-OMe)-phenyl-CH2-O-phenyl-CH2CH2-COOH)* |
| 172 | *(structure: pyrrolopyrimidine-C(=N-OMe)-phenyl-CH2-O-phenyl-CH2CH2-COOH)* |
| 173 | *(structure: phenyl-C(=N-OMe)-CH2-O-phenyl-CH2-O-phenyl-CH(CN)-CH2-COOH)* |

Biological Activity

Calium Flux Assay to Detect GPR40 Activation:

CHO-K cells stably expressing hGPR40 were selected in a media containing Neomycin/G418. The cells were plated at a concentration of 20,000 cells per well in black 96-well clear bottom tissue culture treated plates. The cells were cultured for 24 h at 37° C. in a humidified 5% $CO_2$ air environment to allow for protein expression.

The next day, after removal of media from wells, Fluo-4 NW (Invitrogen) is added at 100 ul/well and the cells were incubated for 30 min at 37° C. and for a further 30 min at RT. All test compounds were diluted to appropriate concentrations in HEPES buffer. Compounds were added to the cells and the wells were read in the BioTEK synergy reader and readings were taken for 4 min with an interval of 5 s. The results are shown in table 3.

TABLE 3

| Compound | EC 50 |
|---|---|
| 1 | ** |
| 2 | ** |
| 3 | * |
| 4 | ** |
| 5 | * |
| 6 | ** |
| 7 | *** |
| 8 | * |
| 9 | * |
| 10 | * |
| 11 | * |
| 12 | * |
| 13 | ** |
| 14 | ** |
| 15 | ** |
| 16 | ** |

TABLE 3-continued

| Compound | EC 50 |
|---|---|
| 17 | ** |
| 18 | *** |
| 19 | * |
| 20 | * |
| 21 | ** |
| 22 | *** |
| 23 | *** |
| 24 | ** |
| 25 | *** |
| 26 | ** |
| 27 | ** |
| 28 | ** |
| 29 | *** |
| 30 | * |
| 31 | *** |
| 32 | * |
| 33 | *** |
| 34 | *** |
| 35 | ** |
| 36 | *** |
| 37 | * |
| 38 | * |
| 39 | *** |
| 40 | *** |
| 41 | ** |
| 42 | * |
| 43 | * |
| 44 | * |
| 45 | ** |
| 46 | ** |
| 47 | *** |
| 48 | ** |
| 49 | *** |
| 50 | *** |
| 51 | *** |
| 52 | *** |
| 53 | ** |
| 54 | ** |
| 55 | *** |
| 56 | ** |
| 57 | ** |
| 58 | * |
| 59 | * |
| 60 | * |
| 61 | * |
| 62 | ** |
| 63 | * |
| 64 | ** |
| 65 | * |
| 66 | *** |
| 67 | * |
| 68 | * |
| 69 | * |
| 70 | * |
| 71 | * |
| 72 | * |
| 73 | ** |
| 74 | * |
| 75 | *** |
| 76 | ** |
| 77 | *** |
| 78 | ** |
| 79 | * |
| 80 | *** |
| 81 | ** |
| 82 | *** |
| 83 | ** |
| 84 | * |
| 85 | *** |
| 86 | * |
| 87 | * |
| 88 | * |
| 89 | * |
| 90 | * |
| 91 | * |
| 92 | * |
| 93 | * |
| 94 | * |

TABLE 3-continued

| Compound | EC 50 |
|---|---|
| 95 | * |
| 96 | * |
| 97 | * |
| 98 | ** |
| 99 | ** |
| 100 | ** |
| 101 | ** |
| 102 | ** |
| 103 | ** |
| 104 | * |
| 105 | * |
| 106 | * |
| 107 | ** |
| 108 | ** |
| 109 | * |
| 110 | *** |
| 111 | ** |
| 112 | * |
| 113 | * |
| 114 | * |
| 115 | * |
| 116 | NT |
| 117 | * |
| 118 | * |
| 119 | * |
| 120 | * |
| 121 | * |
| 122 | * |
| 123 | * |
| 124 | * |

\* = >100 nm
\*\* = >10 nm but <100 nm
\*\*\* = <10 nm

We claim:

1. A compound of formula (I):

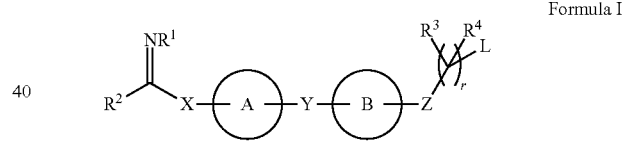

Formula I wherein:
ring A is an optionally substituted phenyl group;
ring B is an optionally substituted phenyl group;
X is a bond or —CH$_2$O—;
Y is —CH$_2$O—;
Z is a bond or is CR$^5$R$^6$;
L is selected from the group consisting of —CO$_2$H, —SO$_3$H, —PO$_3$H, —SO$_2$NH$_2$, —CONHSO$_2$CH$_3$, and tetrazol-5-yl;
R$^1$ is selected from the group consisting of H, OR$^7$, optionally substituted C$_1$-C$_{12}$alkyl, optionally substituted C$_1$-C$_{12}$haloalkyl optionally substituted C$_2$-C$_{12}$alkenyl, optionally substituted C$_2$-C$_{12}$alkynyl, optionally substituted C$_1$-C$_{12}$alkyloxy, optionally substituted C$_1$-C$_{12}$haloalkyloxy, optionally substituted C$_2$-C$_{10}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$heterocycloalkenyl, optionally substituted C$_6$-C$_{12}$aryl, and optionally substituted C$_1$-C$_{18}$heteroaryl;
R$^2$ is H or a ring selected from the group consisting of an optionally substituted C$_3$-C$_{12}$cycloalkyl, optionally substituted C$_2$-C$_{12}$heterocycloalkyl, an optionally substituted C₆-C₁₀arylfusedC₃-C₆cycloalkyl, an optionally substituted C₁-C₁₈heteroarylfusedC₃-C₆cycloalkyl, optionally substituted C₆-C₁₀arylfusedC₂-C₁₂heterocycloalkyl, optionally substituted C₁-C₁₈heteroarylfusedC₂-C₁₂heterocycloalkyl, optionally substituted C₆-C₁₈aryl and optionally substituted C₁-C₁₈heteroaryl;

each R³, R⁴, R⁵ and R⁶ is independently selected from the group consisting of H, halogen, CN, —NO₂, SH, CF₃, OH, CO₂H, CONH₂, OCF₃, optionally substituted C₁-C₁₂alkyl, optionally substituted isoxazol-3-yl and optionally substituted isoxazol-4-yl, R⁷ is selected from the group consisting of H, optionally substituted C₁-C₁₂alkyl, optionally substituted C₂-C₁₂alkenyl, optionally substituted C₂-C₁₀heteroalkyl, optionally substituted C₁-C₁₂haloalkyl, optionally substituted C₃-C₁₂cycloalkyl, optionally substituted C₆-C₁₈aryl, and optionally substituted C₁-C₁₈heteroaryl;

r is an integer selected from the group consisting of 0, 1 and 2;

or a pharmaceutically acceptable salt or N-oxide thereof.

2. The compound according to claim 1, wherein L is —CO₂H.

3. The compound according to claim 1, wherein R³ and R⁴ are each H.

4. The compound according to claim 1, wherein Z is CR⁵R⁶.

5. The compound according to claim 3, wherein R⁵ is H.

6. The compound according to claim 5, wherein R⁶ is selected from the group consisting of H, cyano and isoxazol-3-yl.

7. The compound according to claim 1 wherein ring B is an optionally substituted phenyl group of the formula:

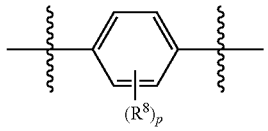

each R⁸ is independently selected from the group consisting of H, halogen, OH, NO₂, CN, C₁-C₁₂alkyl, C₁-C₁₂haloalkyl, C₁-C₁₂alkoxyl, and C₁-C₁₂haloalkoxyl; and wherein p is an integer selected from the group consisting of 0, 1, 2, 3 and 4.

8. The compound according to claim 1, wherein ring A is an optionally substituted phenyl group selected from the group consisting of:

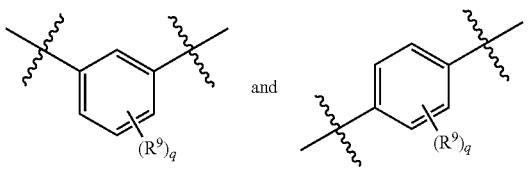

each R⁹ is independently selected from the group consisting of H, halogen, OH, NO₂, CN, C₁-C₁₂alkyl, C₁-C₁₂haloalkyl, C₁-C₁₂alkoxyl, and C₁-C₁₂haloalkoxyl; and wherein q is an integer selected from the group consisting of 0, 1, 2, 3 and 4.

9. The compound according to claim 1, wherein X is —CH₂O—.

10. The compound according to claim 1, wherein R¹ is OR⁷.

11. The compound according to claim 10, wherein R⁷ is selected from the group consisting of H, optionally substituted C₁-C₁₂alkyl, optionally substituted C₂-C₁₀heteroalkyl and optionally substituted C₁-C₁₂haloalkyl.

12. The compound according to claim 10, wherein R⁷ is methyl.

13. The compound according to claim 1, wherein R² is optionally substituted phenyl.

14. The compound according to claim 13, wherein R² is an optionally substituted phenyl of the formula;

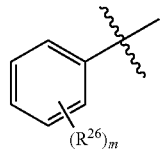

Formula (IIX)

wherein each R²⁶ is independently selected from the group consisting of H, halogen, OH, NO₂, CN, SH, NH₂, CF₃, OCF₃, optionally substituted C₁-C₁₂alkyl, optionally substituted C₁-C₁₂haloalkyl optionally substituted C₂-C₁₂alkenyl, optionally substituted C₂-C₁₂alkynyl, optionally substituted C₂-C₁₂heteroalkyl, optionally substituted C₃-C₁₂cycloalkyl, optionally substituted C₃-C₁₂cycloalkenyl, optionally substituted C₂-C₁₂heterocycloalkyl, optionally substituted C₂-C₁₂heterocycloalkenyl, optionally substituted C₆-C₁₈aryl, optionally substituted C₁-C₁₈heteroaryl, optionally substituted C₁-C₁₂alkyloxy, optionally substituted C₂-C₁₂alkenyloxy, optionally substituted C₂-C₁₂alkynyloxy, optionally substituted C₂-C₁₀heteroalkyloxy, optionally substituted C₃-C₁₂cycloalkyloxy, optionally substituted C₃-C₁₂cycloalkenyloxy, optionally substituted C₂-C₁₂heterocycloalkyloxy, optionally substituted C₂-C₁₂ heterocycloalkenyloxy, optionally substituted C₆-C₁₈aryloxy, optionally substituted C₁-C₁₈heteroaryloxy, optionally substituted C₁-C₁₂alkylamino, SR⁷, SO₃H, SO₂NR⁷R⁷, SO₂R⁷, SONR⁷R⁷, SOR⁷, COR⁷, COOH, COOR⁷, CONR⁷R⁷, NR⁷COR⁷, NR⁷COOR⁷, NR⁷SO₂R⁷, NR⁷CONR⁷R⁷, NR⁷R⁷, and acyl; and m is an integer selected from the group consisting of 0, 1, 2, 3, 4 and 5.

15. The compound according to claim 1 selected from the group consisting of:

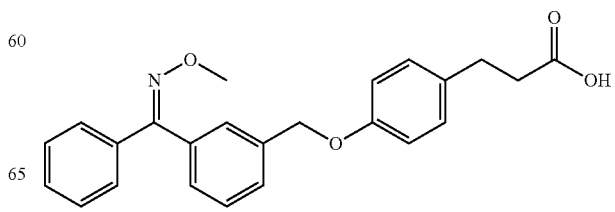

303
-continued
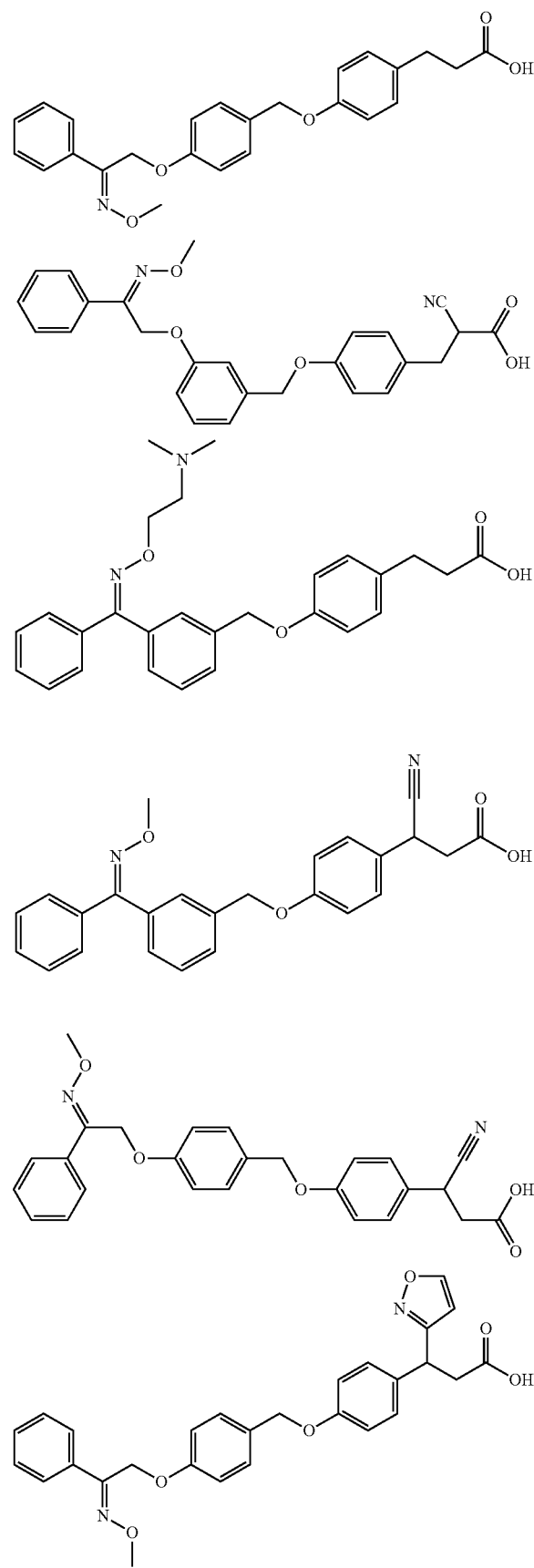
304
-continued
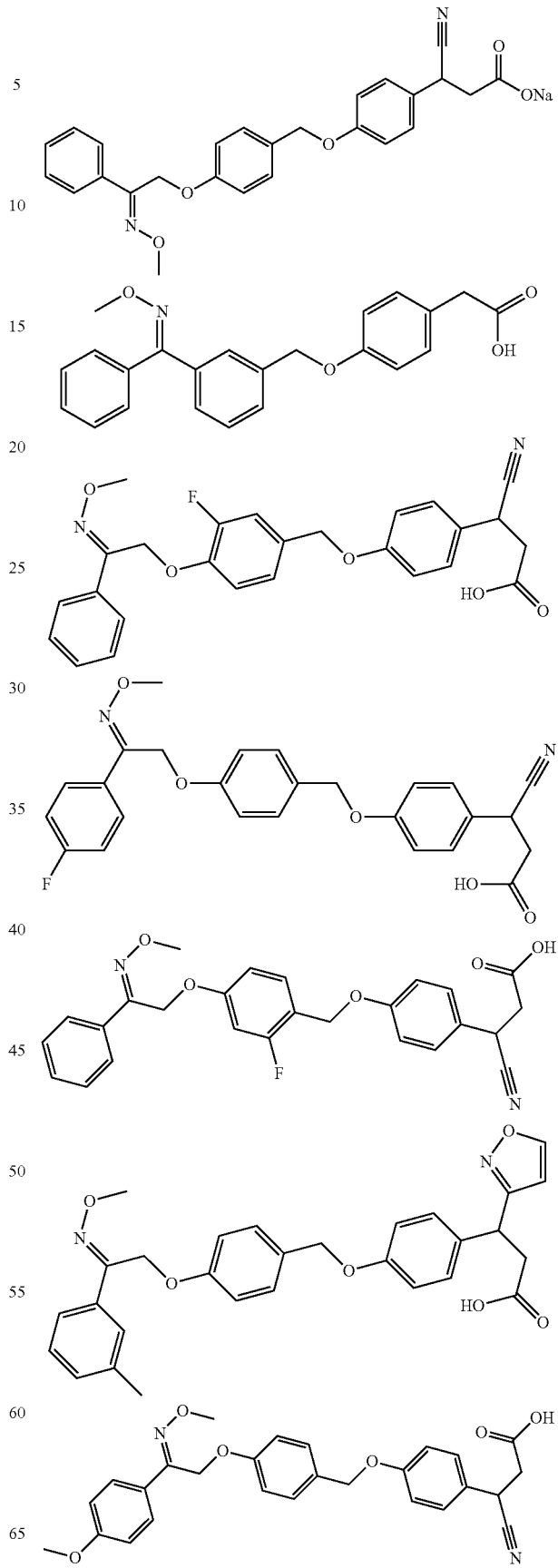

305
-continued
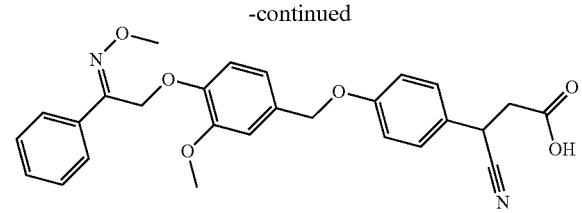
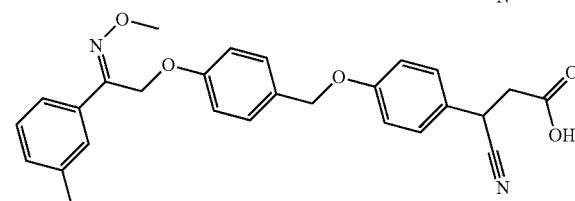
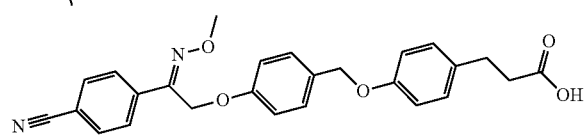
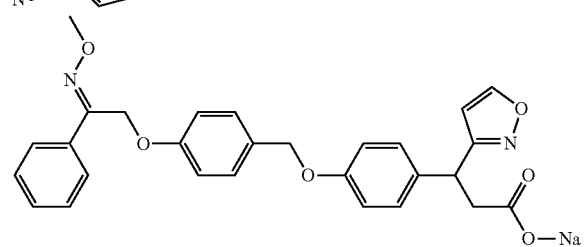
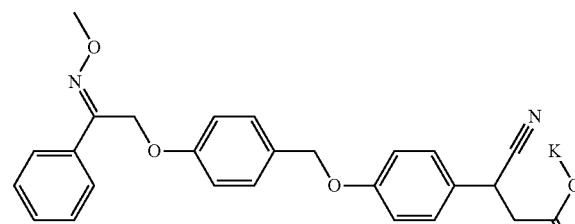
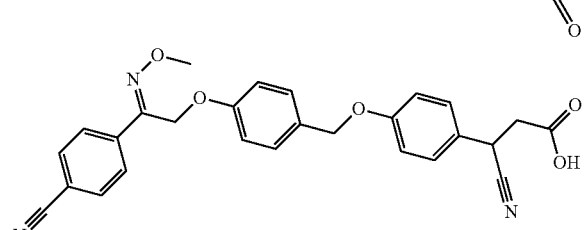
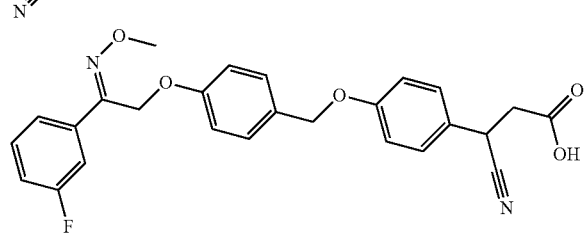
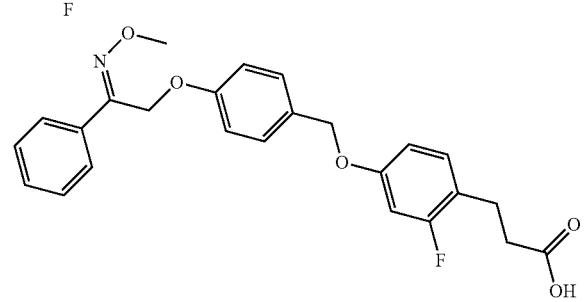
306
-continued
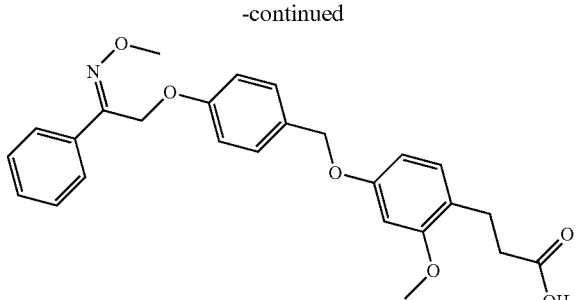
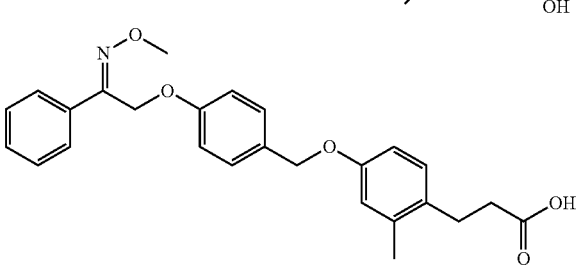
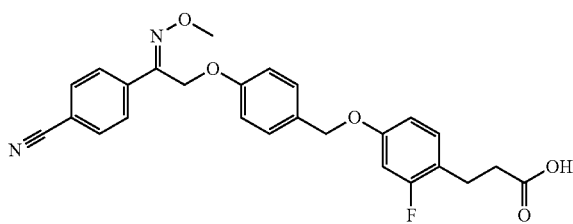
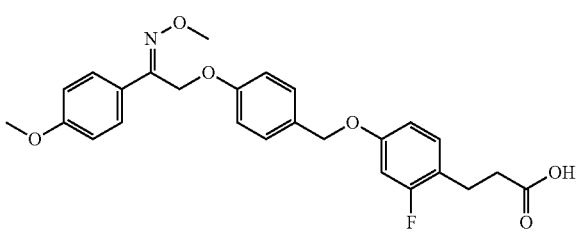
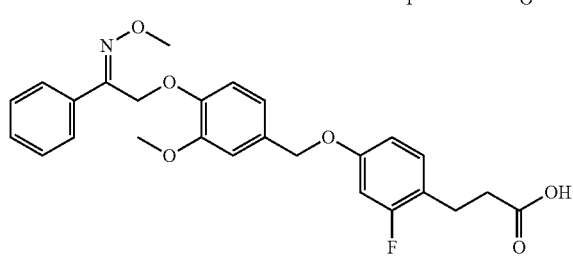
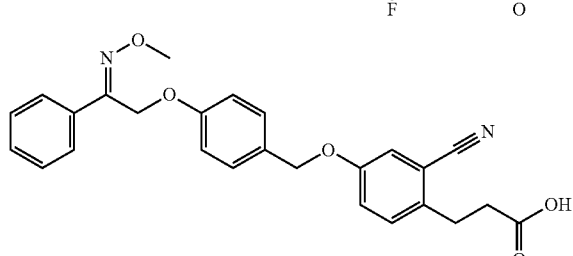
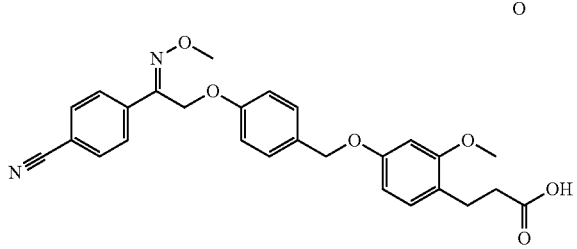

| 307 -continued | 308 -continued |
|---|---|
| 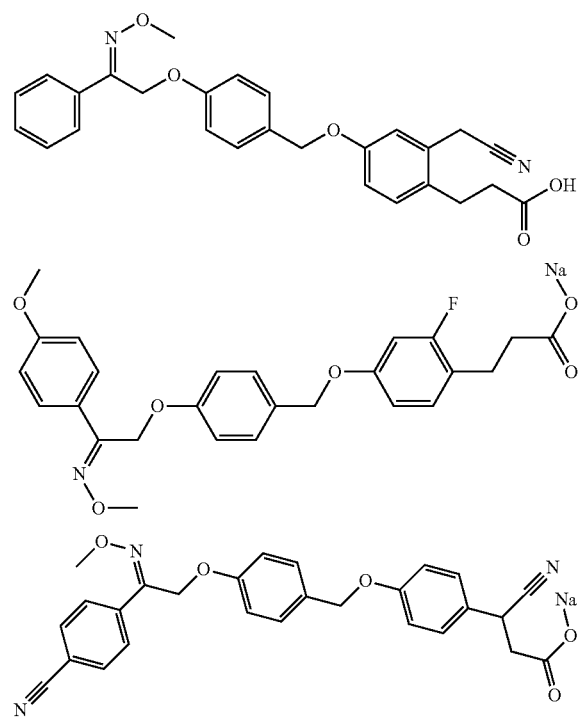 | 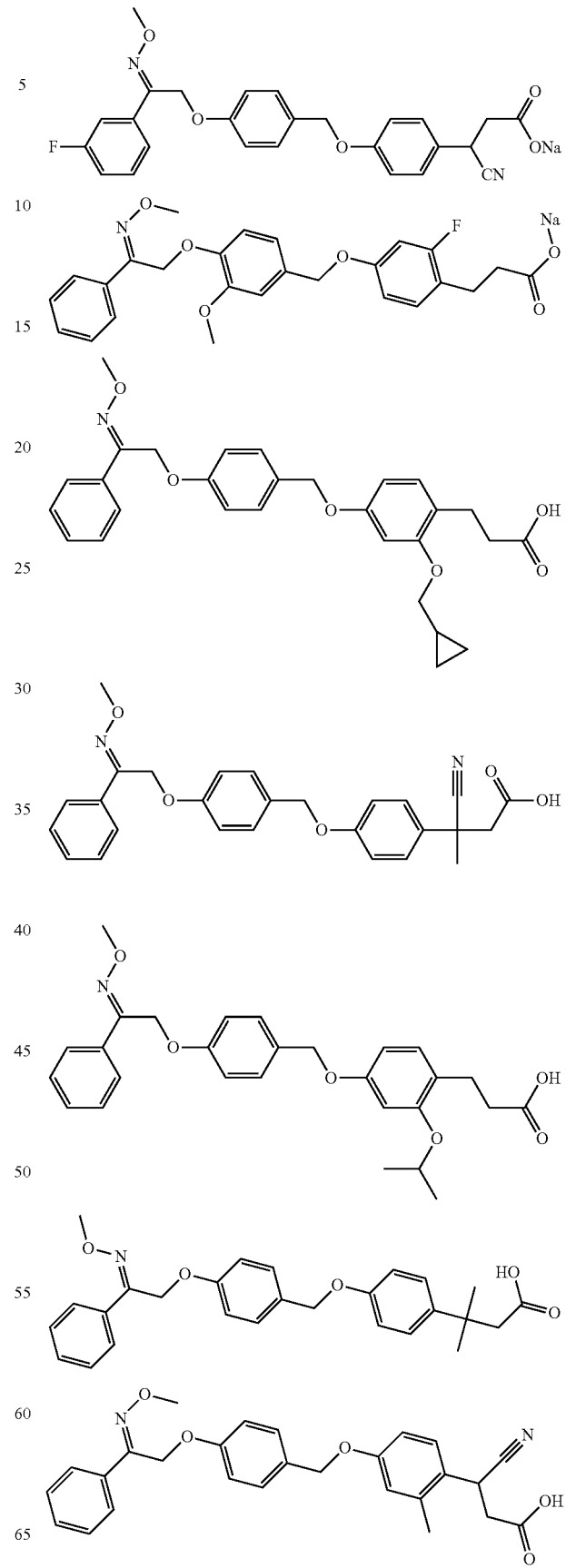 |

309
-continued
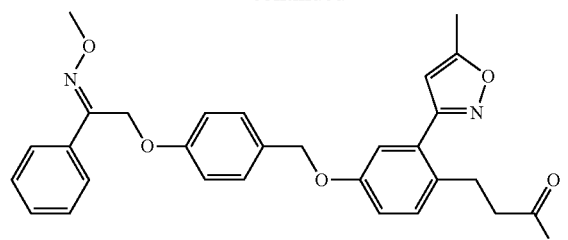
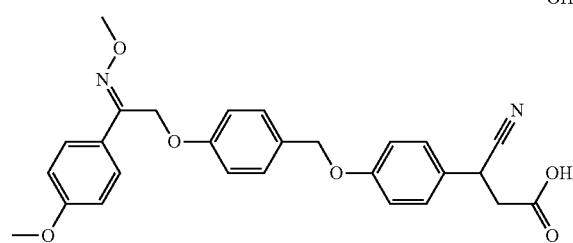
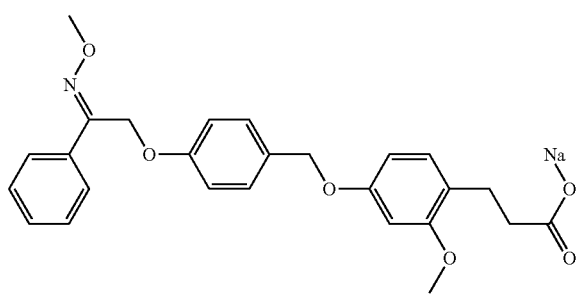
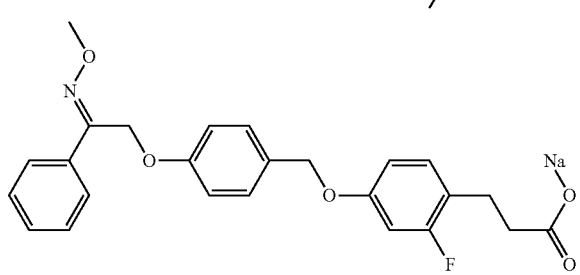
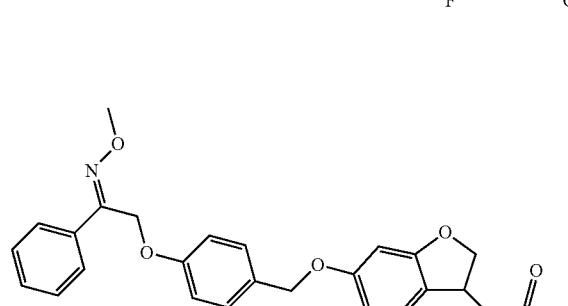
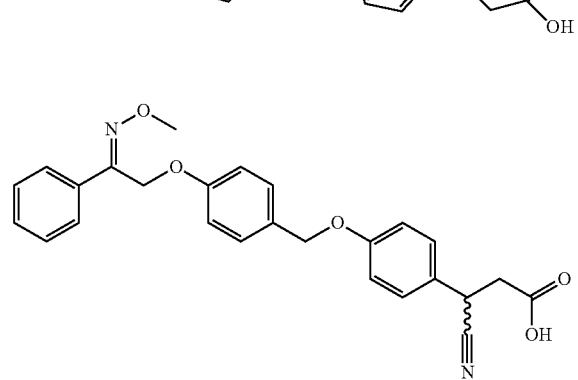
310
-continued
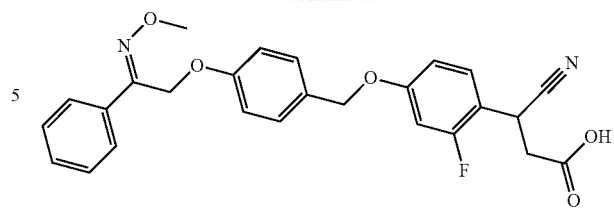
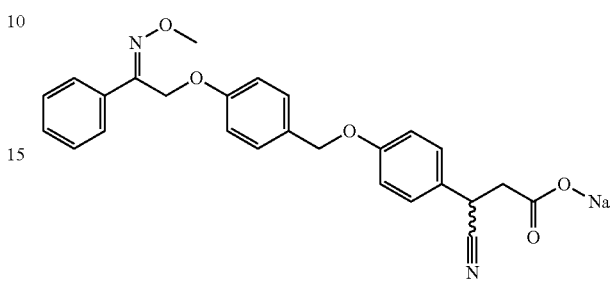
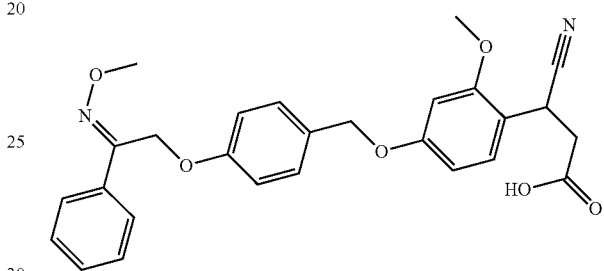
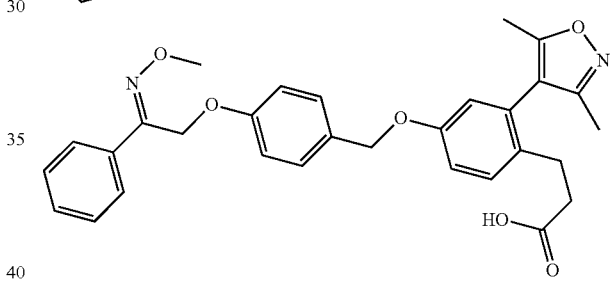
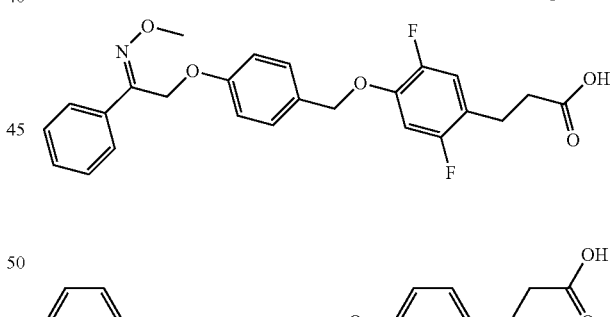
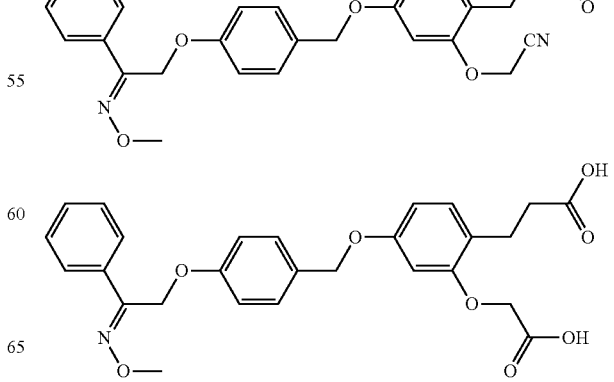

311
-continued
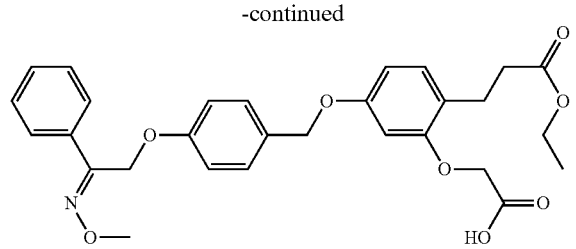
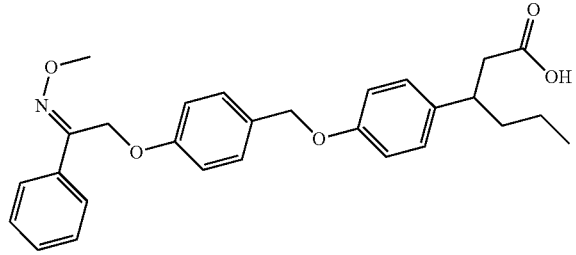
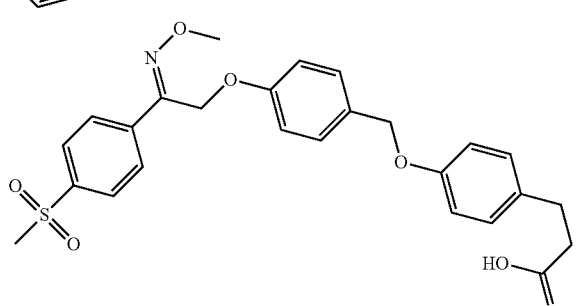
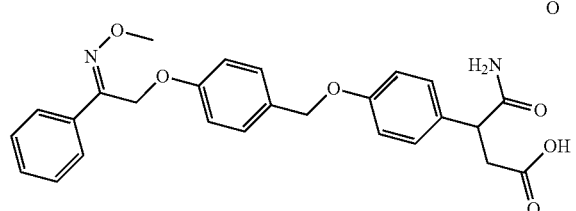
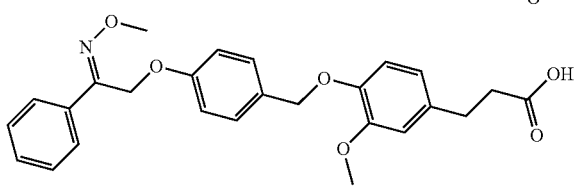
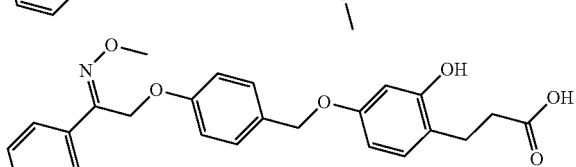
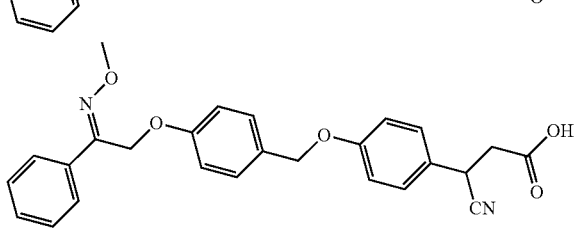
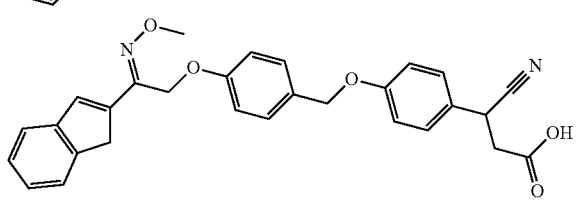
312
-continued
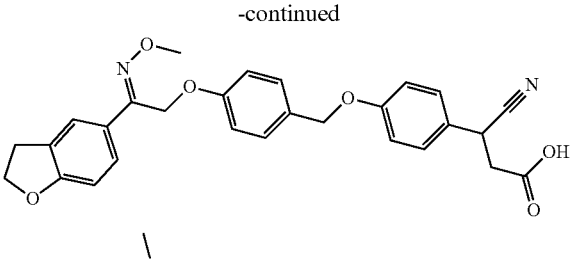
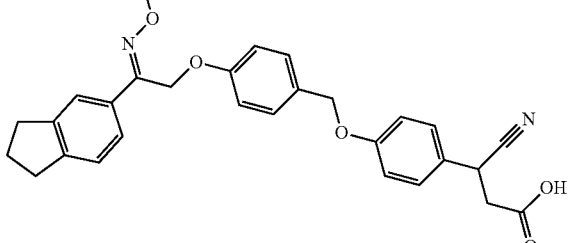
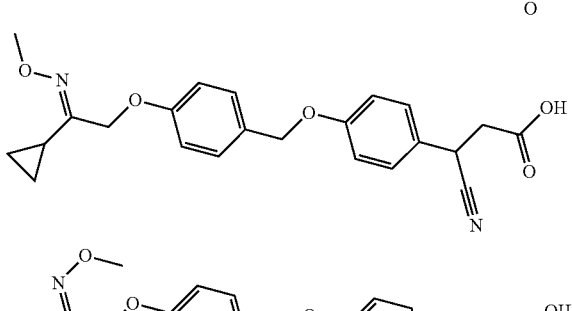
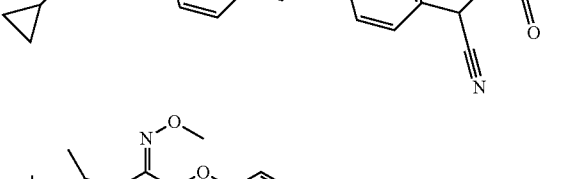
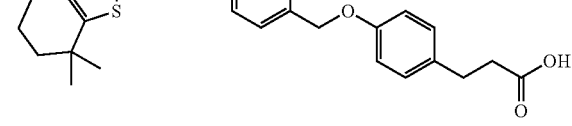
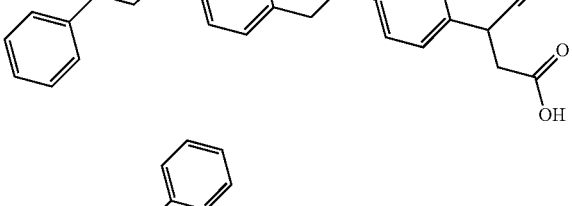
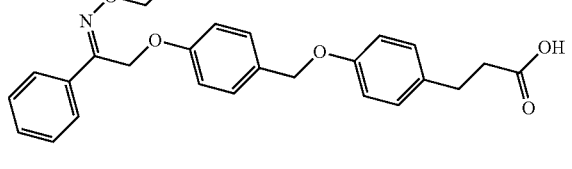

313
-continued
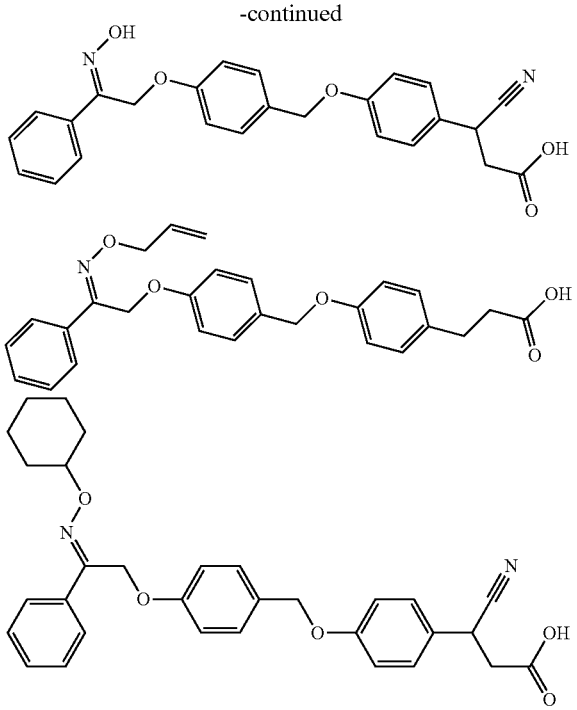
314
-continued
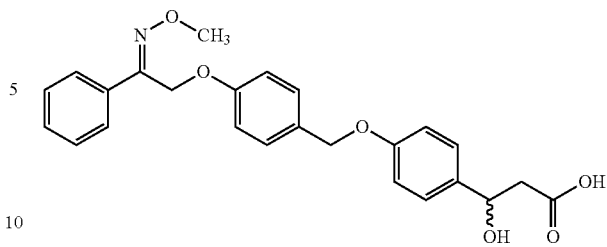
or a pharmaceutically acceptable salt or prodrug thereof.
16. A pharmaceutical composition including a compound according claim 15 and a pharmaceutically acceptable diluent, excipient or carrier.
17. The pharmaceutical composition including a compound according claim 1 and a pharmaceutically acceptable diluent, excipient or carrier.
* * * * *